US007534592B1

(12) United States Patent
Dougan et al.

(10) Patent No.: US 7,534,592 B1
(45) Date of Patent: May 19, 2009

(54) CRYSTALLIZATION OF CARBOXYLTRANSFERASE DOMAIN OF ACETYL-COENZYME A CARBOXYLASE 2 WITH A LIGAND

(75) Inventors: Douglas R. Dougan, Calgary (CA); Clifford D. Mol, San Diego, CA (US); Bi Ching Sang, San Diego, CA (US); Gyorgy Snell, Richmond, CA (US); Hua Zou, San Diego, CA (US)

(73) Assignee: Takeda San Diego, Inc., San Diego, CA (US)

(*) Notice: Subject to any disclaimer, the term of this patent is extended or adjusted under 35 U.S.C. 154(b) by 0 days.

(21) Appl. No.: 11/392,483

(22) Filed: Mar. 28, 2006

(51) Int. Cl.
- *C12N 9/00* (2006.01)
- *C08H 1/00* (2006.01)
- *C12P 19/34* (2006.01)
- *C12N 15/09* (2006.01)

(52) U.S. Cl. ...................... 435/183; 530/402; 435/91.1; 435/69.2

(58) Field of Classification Search .................. None
See application file for complete search history.

(56) References Cited

U.S. PATENT DOCUMENTS

2004/0137518 A1   7/2004   Lambert et al.

OTHER PUBLICATIONS

Giege et al. (1994) Acta Cryst., D50, 339-350.*
Branden et al (1999) Introduction to Protein Structure, Second Edition, Garland Publishing Inc., New York, pp. 374-375 and 382.*
Drenth (1995) Principles of X-ray Crystallography, Springer, New York, p. 1.*
Kierzek et al. (2001) Biophys Chem, 91:1-20.*
Wiencek (1999) Ann Rev Biomed Eng., 1:505-534.*
Zhang et al., Molecular basis for the inhibition of the carboxyltransferase domain of acetyl-coenzyme-A carboxylase by haloxfop and diclofop, PNAS, 2004, 101(16): 5910-5915.
Tong, Acetyl-coenzyme A carboxlase: crucial metabolic enzyme and attrative target for drug discovery, Cell. Mol. Life Sci, 2005, 62: 1784-1803.
Hopkins et al., Biochemistry, 2000, 39(10): 2805-14.
Hegyi et al., J Mol Biol (1999) 288: 147-164.

\* cited by examiner

*Primary Examiner*—Suzanne M. Noakes
*Assistant Examiner*—Alexander D Kim
(74) *Attorney, Agent, or Firm*—David J. Weitz

(57) ABSTRACT

Provided are crystals relating to the carboxyltransferase domain of human Acetyl-Coenzyme A Carboxylase 2 and its various uses.

7 Claims, 133 Drawing Sheets

```
Amino acid sequence for full-length human wild type ACC2 [SEQ. ID No. 1]
                    (Residues 1715-2483 are underlined)
   1 MVLLLCLSCLIFSCLTFSWLKIWEKMTDSKPITKSKSEANLIPSQEFFPASDNSGETPQRNGEGH
  66 TLHKDTQPGRACPPTKAQRSGRRRNSLPPSRQKPPRNPLSSSDAAPSPELQANGTGTQGLEATDT
 131 NGLSSSARPQGSKLVPSKEDKKQANIKRQLMTNFILGSFDDYSSDEDSVAGSSRESTRKGSRASL
 196 GALSLEAYLTTGEAETRVPTMRPSMSGLHLVKRGREHKKLDLHRDFTVASPAEFVTRFGGDRVIE
 261 KVLIANNGIAAVKCMRSIRRWAYEMFRNERAIRFVRMVTPEDLKANAEYIKMADHYGPAPGGPNN
 326 NNYANVELIVDIAKRIPLQAVWAGWGHALENPKLPELLCKNGVAFLGPPRLRPMVGLGDKIASTV
 391 VAQTLQVPTLPRSGSALTVEWTEDDLQQGKRISVPEDVYDKGCVKDVDECLEAAERIGFPLMIKA
 456 SEGGGGKGIRETESAEDFPILFRQVQSEIPGSPIFLMKLAQHARHLEVQILADQYGNAVSLFGRD
 521 CSIQRRHQKIVEEAPATIAPLAIFEFMEQCAIRLAKTVGYVSAGTVEYLYSQDGSFHFLELNPRL
 586 QVEHPCTEMIADVNLPAAQLQIAMGAPLHRLKDIRLLYGESPWGDSPISFENSAHLPCPRGHVIA
 651 TRITSENPDEGFKFSSGTVQELNFRSSKNVWGYFTVAATGGLHEFAISQFGHCFSWGENRKEAIS
 716 NMVVALKELSLRGDFRTTVEYLINLLETESFQNNYIDTGWLDYLIAEKVQKKPNIMLGVVCGALE
 781 RGDAMFRTCMTDFLHSLERGQVLPADSLLNLVDVELIYEGVKYILKVTRQSLTMFVLIMNGCHIE
 846 IDAHRLNDGGLLLSYNGNSYTTYMKEEVDSYRTIGNKTCVFEKENDPTVLRSPSAGKLTQITVED
 911 GGHVEAGRRYAEMEVMKMIMTLNVQERGRVKYIKRPGAVLEAGCVVARLELDDPSKVHPAEPFTG
 976 ELPAQQNTADLGKKLHRVPHSVLGSLTNVMSGFCLPZPFFSIKLKEWVQKLMMTLRHPSLLLDVQ
1041 EIMTSRAGRIPPPVEKSVRKVMAQYASNITSVLCQFPSQQIATILDCHAATLQRKADREVFFINT
1106 QSMVQLVQRYRSGIRGHMKTVVIDLLRRYLRVETIPGKARDADANSSGMVGCVRSLSFTSVMVVL
1171 SPPAHYDKCVINLREQFKPDMSQVLDCIFSHAQVTKKNQLVIMLIDELCGPDPSLSDELISILNE
1236 LTQLSKSEHCKVALRARQILIASPSYELRHNQVESIFLSAIDMYGHQFCPENLQKLILSETTIFD
1301 VLNTFFYHANKVVCMASLEVYVGGAYIAYVLNSLQHRQLPDGTCVVEFQFMLPSSHPNRMTVPIS
1366 ITNPDLLRHTTELFMDSGFSPLCQRMGAMVAFRRFEDFTRNFDEVISCFANVPKDPPLFSEARTS
1431 LYSEDDCKSLREEPTHILNVSIQCADHLEDEALVPILRTFVQSKKNILVDYGLRRIPFLIAQEKE
1496 FPKFFTFRARDEFAEDRIYRHLEPALAFQLELNRMRNFDLTAVPCANHKMHLYLGAAKVEGRYEV
1561 TDHRFFIRAIIRHSDLITKEASFEYLQNEGERLLLEAMDELEVAFNNTNVRTDCNHIPLNFVPTV
1626 IMDPNKIEESVRYMVMRYGSRLWKLRVLQAEVKINIRQTTTGSAVPIRLFITNESGYYLDISLYK
1691 EVTDSRSGNIMFHSFGNKQGPQHGMLINTPYVTKDLLQAKKFQAQTLGTTYIYDFPBMFRQALFK
1756 LWGSPDKYPKDILTYTELVLDSQGQLVEMNRLPGGNEVGMVAFKMRFKTQEYPBGRDVIVIGNDI
1821 TFRIGSFGPGEDLLYLRASEMARAEAIPKIYVAANSGARIGMAEEIKHMFHVAWVDPEDPHKGFK
1886 YLYLTPQDYTRISSLNSVHCKHIEEGGESRYMITDIIGKDDGLGVENLRGSGMIAGESSLAYEEI
1951 VTISLVTCRAIGIGAYLVRLGQRVIQVENSHIILTGASALNKVLGREVYTSNNQLGGVQIMHYNG
2016 VSHITVPDDFBGVYTILEWLSYMPKDNHSPVPIITPTDPIDREIEFLPSRAPYDPRWMLAGRPHP
2081 TLKGTWQSGFFDHGSFKEIMAPWAQTVVTGRARLGGIPVGVIAVETRTVEVAVPADPANLDSEAK
2146 IIQQAGQVWFPDSAYKTAQAIKDFNREKLPLMIFANWRGFSGGMKDMYDQVLKFGAYIVDGLRQY
2211 KQPILIYIRPMRELRGGSWVVIDATINPLCIEMYADKESRGGVLEPEGTVEIKFRKEDLIKSMRR
2276 IDPAYKKLMEQLGEPDLSDKDRKDLEGRLKAREDLLLPIYHQVAVQFADFHDTPGRMLEKGVISD
2341 ILEWKTARTFLYWRLRRLLLEDQVKQEILQASGELSHVHIQSMLRRWFVETEGAVKAYLWDNNQV
2406 VVQWLEQHWQAGDGPRSTIRENITYLKHDSVLKTIRGLVEENPEVAVDCVIYLSQHISPAERAQV
2471 VHLLSTMDSPAST Human cDNA sequence encoding residues 1715-2483 of ACC2
                                [SEQ. ID No. 2]
   1 ATGCTGATCAATACTCCCTACGTCACCAAGGATCTGCTCCAGGCCAAGCGATTCCAGGCC
  61 CAGACCCTGGGAACCACCTACATCTATGACTTCCCGGAAATGTTCAGGCAGGCTCTCTTT
 121 AAACTGTGGGGCTCCCCAGACAAGTATCCCAAAGACATCCTGACATACACTGAATTAGTG
 181 TTGGACTCTCAGGGCCAGCTGGTGGAGATGAACCGACTTCCTGGTGGAAATGAGGTGGGC
 241 ATGGTGGCCTTCAAAATGAGGTTTAAGACCCAGGAGTACCCGGAAGGACGGGATGTGATC
```

FIGURE 1A

Amino acid sequence for full-length human wild type ACC2 [SEQ. ID No. 1]
(Residues 1715-2483 are underlined)

```
   1 MVLLLCLSCLIFSCLTFSWLKIWEKMTDSKPITKSKSEANLIPSQEPFPASDNSGETPQRNGEGH
  66 TLHKDTQPGRAQPPTKAQRSGRRRNSLPPSRQKPPRNPLSSSDAAPSPELQANGTGTQGLEATDT
 131 NGLSSSARPQGSKLVPSKEDKKQANIKRQLMTNFILGSFDDYSSDEDSVAGSSRESTRKGSRASL
 196 GALSLEAYLTTGEAETRVPTMRPSMSGLHLVKRGREHKKLDLHRDFTVASPAEFVTRFGGDRVIE
 261 KVLIANNGIAAVKCMRSIRRWAYEMFRNERAIRFVRMVTPEDLKANAEYIKMADHYGPAPGGPNN
 326 NNYANVELIVDIAKRIPLQAVWAGWGHALENPKLPELLCKNGVAFLGPPRLRPMVGLGDKIASTV
 391 VAQTLQVPTLPRSGSALTVEWTEDDLQQGKRISVPEDVYDKGCVKDVDEGLEAAERIGFPLMIKA
 456 SEGGGGKGIRETESAEDFPILFRQVQSEIPGSPIFLMKLAQHARHLEVQILADQYGNAVSLFGRD
 521 CSIQRRHQKIVEEAPATIAPLAIFEFMEQCAIRLAKTVGYVSAGTVEYLYSQDGSFHFLELNPRL
 586 QVEHPCTEMIADVNLPAAQLQIAMGAPLHRLKDIRLLYGESPWGDSPISFENSAHLPCPRGHVIA
 651 TRITSENPDEGFKPSSGTVQELNFRSSKNVWGYFTVAATGGLHEFAISQFGHCFSWGENRKEAIS
 716 NMVVALKELSLRGDFRTTVEYLINLLETESFQNNYIDTGWLDYLIAEKVQKKPNIMLGVVCGALE
 781 RGDAMFRTCMTDFLHSLERGQVLPADSLLNLVDVELIYEGVKYILKVTRQSLTMFVLIMNGCHIE
 846 IDAHRLNDGGLLLSYNGNSYTTYMKEEVDSYRTIGNKTCVFEKENDPTVLRSPSAGKLTQITVED
 911 GGHVEAGRRYAEMEVMKMIMTLNVQERGRVKYIKRPGAVLEAGCVVARLELDDPSKVHPAEPFTG
 976 ELPAQQNTADLGKKLHRVFHSVLGSLTNVMSGFCLPEPFFSIKLKEWVQKLMMTLRHPSLLLDVQ
1041 EIMTSRAGRIPPPVEKSVRKVMAQYASNITSVLCQFPSQQIATILDCHAATLQRKADREVFFINT
1106 QSMVQLVQRYRSGIRGHMKTVVIDLLRRYLRVETIFGKARDADANSSGMVGGVRSLSFTSVWVVL
1171 SPPAHYDKCVINLREQFKPDMSQVLDCIFSHAQVTKKNQLVIMLIDELCGPDPSLSDELISILNE
1236 LTQLSKSEHCKVALRARQILIASPSYELRHNQVESIFLSAIDMYGHQFCPENLQKLILSETTIFD
1301 VLNTFFYHANKVVCMASLEVYVGGAYIAYVLNSLQHRQLPDGTCVVEFQFMLPSSHPNRMTVPIS
1366 ITNPDLLRHTTELPMDSGFSPLCQRMGAMVAFRRFEDFTRNFDEVISCFANVPKDPPLFSEARTS
1431 LYSEDDCKSLREEPIHILNVSIQCADHLEDEALVPILRTFVQSKKNILVDYGLRRIPFLIAQEKE
1496 FPKFFTFRARDEFAEDRIYRHLEPALAFQLELNRMRNFDLTAVPCANHKMHLYLGAAKVEGRYEV
1561 TDHRFFIRAIIRHSDLITKEASFEYLQNEGERLLLEAMDELEVAFNNTNVRTDCNHIFLNFVPTV
1626 IMDPNKIEESVRYMVMRYGSRLWKLRVLQAEVKINIRQTTTGSAVPIRLFITNESGYYLDISLYK
1691 EVTDSRSGNIMFHSFGNKQGPQHGMLINTPYVTKDLLQAKRFQAQTLGTTYIYDFPEMFRQALFK
1756 LWGSPDKYPKDILTYTELVLDSQGQLVEMNRLPGGNEVGMVAFKMRFKTQEYPEGRDVIVIGNDI
1821 TFRIGSFGPGEDLLYLRASEMAREAIPKIYVAANSGARIGMAEEIKHMFHVAWVDPEDPHKGFK
1886 YLYLTPQDYTRISSLNSVHCKHIEEGGESRYMITDIIGKDDGLGVENLRGSGMIAGESSLAYEEI
1951 VTISLVTCRAIGIGAYLVRLGQRVIQVENSHIILTGASALNKVLGREVYTSNNQLGGVQIMHYNG
2016 VSHITVPDDFEGVYTILEWLSYMPKDNHSPVPIITPTDPIDREIEFLPSRAPYDPRWMLAGRPHP
2081 TLKGTWQSGFFDHGSPKEIMAPWAQTVVTGRARLGGIPVGVIAVETRTVEVAVPADPANLDSEAK
2146 IIQQAGQVWFPDSAYKTAQAIKDFNREKLPLMIFANWRGFSGGMKDMYDQVLKFGAYIVDGLRQY
2211 KQPILIYIRPMRELRGGSWVVIDATINPLCIEMYADKESRGGVLEPEGTVEIKFRKEDLIKSMRR
2276 IDPAYKKLMEQLGEPDLSDKDRKDLEGRLKAREDLLLPIYHQVAVQFADFHDTPGRMLEKGVISD
2341 ILEWKTARTFLYWRLRRLLLEDQVKQEILQASGELSHVHIQSMLRRWFVETEGAVKAYLWDNNQV
2406 VVQWLEQHWQAGDGPRSTIRENITYLKHDSVLKTIRGLVEENPEVAVDCVIYLSQHISPAERAQV
2471 VHLLSTMDSPAST
```

Human cDNA sequence encoding residues 1715-2483 of ACC2
[SEQ. ID No. 2]

```
   1 ATGCTGATCAATACTCCCTACGTCACCAAGGATCTGCTCCAGGCCAAGCGATTCCAGGCC
  61 CAGACCCTGGGAACCACCTACATCTATGACTTCCCGGAAATGTTCAGGCAGGCTCTCTTT
 121 AAACTGTGGGGCTCCCCAGACAAGTATCCCAAAGACATCCTGACATACACTGAATTAGTG
 181 TTGGACTCTCAGGGCCAGCTGGTGGAGATGAACCGACTTCCTGGTGGAAATGAGGTGGGC
 241 ATGGTGGCCTTCAAAATGAGGTTTAAGACCCAGGAGTACCCGGAAGGACGGGATGTGATC
```

FIGURE 1B

```
 301 GTCATCGGCAATGACATCACCTTTCGCATTGGATCCTTTGGCCCTGGAGAGGACCTTCTG
 361 TACCTGCGGGCATCCGAGATGGCCCGGGCAGAGGGCATTCCCAAAATTTACGTGGCAGCC
 421 AACAGTGGCGCCCGTATTGGCATGGCAGAGGAGATCAAACACATGTTCCACGTGGCTTGG
 481 GTGGACCCAGAAGACCCCCACAAAGGATTTAAATACCTGTACCTGACTCCCCAAGACTAC
 541 ACCAGAATCAGCTCCCTGAACTCCGTCCACTGTAAACACATCGAGGAAGGAGGAGAGTCC
 601 AGATACATGATCACGGATATCATCGGGAAGGATGATGGCTTGGGCGTGGAGAATCTGAGG
 661 GGCTCAGGCATGATTGCTGGGGAGTCCTCTCTGGCTTACGAAGAGATCGTCACCATTAGC
 721 TTGGTGACCTGCCGAGCCATTGGGATTGGGGCCTACTTGGTGAGGCTGGGCCAGCGAGTG
 781 ATCCAGGTGGAGAATTCCCACATCATCCTCACAGGAGCAAGTGCTCTCAACAAGGTCCTG
 841 GGAAGAGAGGTCTACACATCCAACAACCAGCTGGGTGGCGTTCAGATCATGCATTACAAT
 901 GGTGTCTCCCACATCACCGTGCCAGATGACTTTGAGGGGGTTTATACCATCCTGGAGTGG
 961 CTGTCCTATATGCCAAAGGATAATCACAGCCCTGTCCCTATCATCACACCCACTGACCCC
1021 ATTGACAGAGAAATTGAATTCCTCCCATCCAGAGCTCCCTACGACCCCGGTGGATGCTT
1081 GCAGGAAGCCCTCACCCAACTCTGAAGGGAACGTGGCAGAGCGGATTCTTTGACCATGGC
1141 AGTTTCAAGGAAATCATGGCACCCTGGGCGCAGACCGTGGTGACAGGACGAGCAAGGCTT
1201 GGGGGGATTCCCGTGGGAGTGATTGCTGTGGAGACACGGACTGTGGAGGTGGCAGTCCCT
1261 GCAGACCCTGCCAACCTGGATTCTGAGGCCAAGATAATTCAGCAGGCAGGACAGGTGTGG
1321 TTCCCAGACTCAGCCTACAAAACCGCCCAGGCCATCAAGGACTTCAACCGGGAGAAGTTG
1381 CCCCTGATGATCTTTGCCAACTGGAGGGGGTTCTCCGGTGGCATGAAAGACATGTATGAC
1441 CAGGTGCTGAAGTTTGGAGCCTACATCGTGGACGGCTTAGACAATACAAACAGCCCATC
1501 CTGATCTATATCCCGCCCTATGCGGAGCTCCGGGGAGGCTCCTGGGTGGTCATAGATGCC
1561 ACCATCAACCCGCTGTGCATAGAAATGTATGCAGACAAAGAGAGCAGGGGTGGTGTTCTG
1621 GAACCAGAGGGGACAGTGGAGATTAAGTTCCGAAAGAAAGATCTGATAAAGTCCATGAGA
1681 AGGATCGATCCAGCTTACAAGAAGCTCATGGAACAGCTAGGGGAACCTGATCTCTCCGAC
1741 AAGGACCGAAAGGACCTGGAGGGCCGGCTAAAGGCTCGCGAGGACCTGCTGCTCCCCATC
1801 TACCACCAGGTGGCGGTGCAGTTCGCCGACTTCATGACACACCCGGCCGGATGCTGGAG
1861 AAGGGCGTCATATCTGACATCCTGGAGTGGAAGACCGCACGCACCTTCCTGTATTGGCGT
1921 CTGCGCCGCCTCCTCCTGGAGGACCAGGTCAAGCAGGAGATCCTGCAGGCCAGCGGGGAG
1981 CTGAGTCACGTGCATATCCAGTCCATGCTGCGTCGCTGGTTCGTGGAGACGGAGGGGGCT
2041 GTCAAGGCCTACTTGTGGGACAACAACCAGGTGGTTGTGCAGTGGCTGGAACAGCACTGG
2101 CAGGCAGGGGATGGCCCCGCGCTCCACCATCCGTGGAACATCACGTACCTGAAGCACGAC
2161 TCTGTCCTCAAGACCATCCGAGGCCTGGTTGAAGAAAACCCCGAGGTGGCCGTGGACTGT
2221 GTGATATACCTGAGCCAGCACATCAGCCCAGCTGAGCGGGCGCAGGTCGTTCACCTGCTG
2281 TCTACCATGGACAGCCCGGCCTCCACC
```

Amino acid sequence for residues 1715-2483 of ACC2 with a C-terminal 6x-histidine tag [SEQ. ID No. 3]

```
  1 MLINTPYVTKDLLQAKRFQAQTLGTTYIYDFPEMFRQALFKLWGSPDKYPKDILTYTELV
 61 LDSQGQLVEMNRLPGGNEVGMVAFKMRFKTQEYPEGRDVIVIGNDITFRIGSFGPGEDLL
121 YLRASEMARAEGIPKIYVAANSGARIGMAEEIKHMFHVAWVDPEDPHKGFKYLYLTPQDY
181 TRISSLNSVHCKHIEEGGESRYMITDIIGKDDGLGVENLRGSGMIAGESSLAYEEIVTIS
241 LVTCRAIGIGAYLVRLGQRVIQVENSHIILTGASALNKVLGREVYTSNNQLGGVQIMHYN
301 GVSHITVPDDFEGVYTILEWLSYMPKDNHSPVPIITPTDPIDREIEFLPSRAPYDPRWML
361 AGRPHPTLKGTWQSGFFDHGSFKEIMAPWAQTVVTGRARLGGIPVGVIAVETRTVEVAVP
421 ADPANLDSEAKIIQQAGQVWFPDSAYKTAQAIKDFNREKLPLMIFANWRGFSGGMKDMYD
481 QVLKFGAYIVDGLRQYKQPILIYIPPYAELRGGSWVVIDATINPLCIEMYADKESRGGVL
541 EPEGTVEIKFRKKDLIKSMRRIDPAYKKLMEQLGEPDLSDKDRKDLEGRLKAREDLLLPI
601 YHQVAVQFADFHDTPGRMLEKGVISDILEWKTARTFLYWRLRRLLLEDQVKQEILQASGE
661 LSHVHIQSMLRRWFVETEGAVKAYLWDNNQVVVQWLEQHWQAGDGPRSTIRENITYLKHD
721 SVLKTIRGLVEENPEVAVDCVIYLSQHISPAERAQVVHLLSTMDSPASTHHHHHH
```

FIGURE 3A

LEGEND

Column headings from left to right are (A)'Atom Number', (B)'Atom Type', (C)'Amino Acid', (D)'Chain Identifier', (E)'Amino Acid Number', (F)'X Coordinate', (G)'Y Coordinate', (H)'Z Coordinate', (I)'Occupancy' (OCC) and (J)'B factor'.

ACC2 Coordinates corresponding to amino acid residues 1719 – 2414 and 2427-2451 of SEQ ID NO: 3

|      | A  | B   | C   | D | E    | F      | G      | H      | I    | J     |
|------|----|-----|-----|---|------|--------|--------|--------|------|-------|
| ATOM | 1  | N   | THR | A | 1719 | 25.009 | 19.500 | 33.149 | 1.00 | 39.73 |
| ATOM | 2  | CA  | THR | A | 1719 | 24.320 | 18.182 | 32.977 | 1.00 | 39.89 |
| ATOM | 3  | CB  | THR | A | 1719 | 24.623 | 17.220 | 34.168 | 1.00 | 39.43 |
| ATOM | 4  | OG1 | THR | A | 1719 | 23.406 | 16.623 | 34.631 | 1.00 | 38.21 |
| ATOM | 5  | CG2 | THR | A | 1719 | 25.129 | 17.979 | 35.393 | 1.00 | 39.53 |
| ATOM | 6  | C   | THR | A | 1719 | 22.806 | 18.351 | 32.780 | 1.00 | 40.17 |
| ATOM | 7  | O   | THR | A | 1719 | 22.194 | 19.224 | 33.404 | 1.00 | 39.97 |
| ATOM | 8  | N   | PRO | A | 1720 | 22.207 | 17.517 | 31.923 | 1.00 | 40.61 |
| ATOM | 9  | CA  | PRO | A | 1720 | 20.770 | 17.601 | 31.627 | 1.00 | 40.83 |
| ATOM | 10 | CB  | PRO | A | 1720 | 20.676 | 16.984 | 30.225 | 1.00 | 40.81 |
| ATOM | 11 | CG  | PRO | A | 1720 | 21.809 | 15.990 | 30.163 | 1.00 | 40.52 |
| ATOM | 12 | CD  | PRO | A | 1720 | 22.857 | 16.436 | 31.156 | 1.00 | 40.55 |
| ATOM | 13 | C   | PRO | A | 1720 | 19.875 | 16.825 | 32.606 | 1.00 | 40.63 |
| ATOM | 14 | O   | PRO | A | 1720 | 18.669 | 16.719 | 32.369 | 1.00 | 41.10 |
| ATOM | 15 | N   | TYR | A | 1721 | 20.453 | 16.307 | 33.687 | 1.00 | 39.87 |
| ATOM | 16 | CA  | TYR | A | 1721 | 19.720 | 15.441 | 34.608 | 1.00 | 39.54 |
| ATOM | 17 | CB  | TYR | A | 1721 | 20.442 | 14.100 | 34.770 | 1.00 | 37.68 |
| ATOM | 18 | CG  | TYR | A | 1721 | 20.778 | 13.445 | 33.450 | 1.00 | 35.88 |
| ATOM | 19 | CD1 | TYR | A | 1721 | 22.100 | 13.202 | 33.087 | 1.00 | 35.29 |
| ATOM | 20 | CE1 | TYR | A | 1721 | 22.411 | 12.603 | 31.867 | 1.00 | 34.47 |
| ATOM | 21 | CZ  | TYR | A | 1721 | 21.391 | 12.247 | 31.001 | 1.00 | 34.56 |
| ATOM | 22 | OH  | TYR | A | 1721 | 21.685 | 11.654 | 29.795 | 1.00 | 34.67 |
| ATOM | 23 | CE2 | TYR | A | 1721 | 20.071 | 12.486 | 31.337 | 1.00 | 34.97 |
| ATOM | 24 | CD2 | TYR | A | 1721 | 19.770 | 13.083 | 32.556 | 1.00 | 35.61 |
| ATOM | 25 | C   | TYR | A | 1721 | 19.441 | 16.075 | 35.957 | 1.00 | 40.65 |
| ATOM | 26 | O   | TYR | A | 1721 | 18.515 | 15.662 | 36.666 | 1.00 | 40.87 |
| ATOM | 27 | N   | VAL | A | 1722 | 20.240 | 17.074 | 36.334 | 1.00 | 42.02 |
| ATOM | 28 | CA  | VAL | A | 1722 | 19.981 | 17.857 | 37.541 | 1.00 | 43.87 |
| ATOM | 29 | CB  | VAL | A | 1722 | 21.268 | 18.522 | 38.120 | 1.00 | 43.95 |
| ATOM | 30 | CG1 | VAL | A | 1722 | 22.179 | 17.479 | 38.764 | 1.00 | 43.62 |
| ATOM | 31 | CG2 | VAL | A | 1722 | 22.019 | 19.329 | 37.056 | 1.00 | 43.89 |
| ATOM | 32 | C   | VAL | A | 1722 | 18.920 | 18.920 | 37.257 | 1.00 | 45.40 |
| ATOM | 33 | O   | VAL | A | 1722 | 18.797 | 19.400 | 36.126 | 1.00 | 45.50 |
| ATOM | 34 | N   | THR | A | 1723 | 18.148 | 19.267 | 38.285 | 1.00 | 47.18 |
| ATOM | 35 | CA  | THR | A | 1723 | 17.133 | 20.309 | 38.176 | 1.00 | 48.52 |
| ATOM | 36 | CB  | THR | A | 1723 | 15.956 | 20.033 | 39.139 | 1.00 | 48.48 |
| ATOM | 37 | OG1 | THR | A | 1723 | 15.400 | 18.741 | 38.857 | 1.00 | 48.15 |

FIGURE 3B

| | A | B | C | D | E | F | G | H | I | J |
|---|---|---|---|---|---|---|---|---|---|---|
| ATOM | 38 | CG2 | THR | A1723 | 14.792 | 20.980 | 38.859 | 1.00 | 48.40 |
| ATOM | 39 | C | THR | A1723 | 17.764 | 21.668 | 38.454 | 1.00 | 49.84 |
| ATOM | 40 | O | THR | A1723 | 18.344 | 21.892 | 39.521 | 1.00 | 50.13 |
| ATOM | 41 | N | LYS | A1724 | 17.646 | 22.568 | 37.482 | 1.00 | 51.32 |
| ATOM | 42 | CA | LYS | A1724 | 18.286 | 23.880 | 37.559 | 1.00 | 53.33 |
| ATOM | 43 | CB | LYS | A1724 | 19.570 | 23.907 | 36.713 | 1.00 | 54.11 |
| ATOM | 44 | CG | LYS | A1724 | 19.429 | 23.332 | 35.300 | 1.00 | 54.81 |
| ATOM | 45 | CD | LYS | A1724 | 19.386 | 24.430 | 34.244 | 1.00 | 55.29 |
| ATOM | 46 | CE | LYS | A1724 | 18.211 | 24.241 | 33.295 | 1.00 | 55.61 |
| ATOM | 47 | NZ | LYS | A1724 | 18.312 | 25.122 | 32.096 | 1.00 | 55.79 |
| ATOM | 48 | C | LYS | A1724 | 17.363 | 25.022 | 37.137 | 1.00 | 53.81 |
| ATOM | 49 | O | LYS | A1724 | 16.511 | 24.856 | 36.259 | 1.00 | 54.01 |
| ATOM | 50 | N | ASP | A1725 | 17.541 | 26.176 | 37.777 | 1.00 | 54.59 |
| ATOM | 51 | CA | ASP | A1725 | 16.891 | 27.412 | 37.348 | 1.00 | 54.90 |
| ATOM | 52 | CB | ASP | A1725 | 16.514 | 28.294 | 38.551 | 1.00 | 56.63 |
| ATOM | 53 | CG | ASP | A1725 | 17.631 | 28.405 | 39.584 | 1.00 | 57.95 |
| ATOM | 54 | OD1 | ASP | A1725 | 18.615 | 29.135 | 39.330 | 1.00 | 58.49 |
| ATOM | 55 | OD2 | ASP | A1725 | 17.605 | 27.808 | 40.682 | 1.00 | 58.48 |
| ATOM | 56 | C | ASP | A1725 | 17.794 | 28.165 | 36.364 | 1.00 | 54.05 |
| ATOM | 57 | O | ASP | A1725 | 18.935 | 27.758 | 36.120 | 1.00 | 54.39 |
| ATOM | 58 | N | LEU | A1726 | 17.278 | 29.251 | 35.793 | 1.00 | 52.55 |
| ATOM | 59 | CA | LEU | A1726 | 18.044 | 30.068 | 34.853 | 1.00 | 51.04 |
| ATOM | 60 | CB | LEU | A1726 | 17.142 | 30.568 | 33.719 | 1.00 | 51.41 |
| ATOM | 61 | CG | LEU | A1726 | 16.499 | 29.504 | 32.826 | 1.00 | 51.26 |
| ATOM | 62 | CD1 | LEU | A1726 | 15.013 | 29.371 | 33.132 | 1.00 | 51.29 |
| ATOM | 63 | CD2 | LEU | A1726 | 16.727 | 29.824 | 31.354 | 1.00 | 51.69 |
| ATOM | 64 | C | LEU | A1726 | 18.729 | 31.239 | 35.567 | 1.00 | 50.01 |
| ATOM | 65 | O | LEU | A1726 | 18.887 | 32.324 | 34.997 | 1.00 | 50.49 |
| ATOM | 66 | N | LEU | A1727 | 19.143 | 31.003 | 36.811 | 1.00 | 48.01 |
| ATOM | 67 | CA | LEU | A1727 | 19.750 | 32.035 | 37.649 | 1.00 | 46.22 |
| ATOM | 68 | CB | LEU | A1727 | 18.831 | 32.372 | 38.831 | 1.00 | 46.45 |
| ATOM | 69 | CG | LEU | A1727 | 17.445 | 32.953 | 38.552 | 1.00 | 46.60 |
| ATOM | 70 | CD1 | LEU | A1727 | 16.581 | 32.804 | 39.788 | 1.00 | 46.42 |
| ATOM | 71 | CD2 | LEU | A1727 | 17.529 | 34.414 | 38.118 | 1.00 | 47.05 |
| ATOM | 72 | C | LEU | A1727 | 21.133 | 31.644 | 38.171 | 1.00 | 44.49 |
| ATOM | 73 | O | LEU | A1727 | 21.603 | 32.196 | 39.171 | 1.00 | 43.83 |
| ATOM | 74 | N | GLN | A1728 | 21.780 | 30.696 | 37.493 | 1.00 | 41.74 |
| ATOM | 75 | CA | GLN | A1728 | 23.117 | 30.242 | 37.879 | 1.00 | 39.29 |
| ATOM | 76 | CB | GLN | A1728 | 23.537 | 28.996 | 37.084 | 1.00 | 40.14 |
| ATOM | 77 | CG | GLN | A1728 | 23.783 | 29.230 | 35.593 | 1.00 | 41.63 |
| ATOM | 78 | CD | GLN | A1728 | 25.259 | 29.193 | 35.222 | 1.00 | 42.63 |
| ATOM | 79 | OE1 | GLN | A1728 | 26.022 | 30.094 | 35.586 | 1.00 | 42.34 |
| ATOM | 80 | NE2 | GLN | A1728 | 25.663 | 28.154 | 34.494 | 1.00 | 42.16 |
| ATOM | 81 | C | GLN | A1728 | 24.158 | 31.355 | 37.744 | 1.00 | 36.33 |
| ATOM | 82 | O | GLN | A1728 | 25.103 | 31.422 | 38.533 | 1.00 | 36.17 |
| ATOM | 83 | N | ALA | A1729 | 23.975 | 32.215 | 36.742 | 1.00 | 32.82 |
| ATOM | 84 | CA | ALA | A1729 | 24.844 | 33.370 | 36.528 | 1.00 | 31.60 |
| ATOM | 85 | CB | ALA | A1729 | 24.527 | 34.037 | 35.195 | 1.00 | 30.71 |
| ATOM | 86 | C | ALA | A1729 | 24.728 | 34.375 | 37.682 | 1.00 | 30.20 |
| ATOM | 87 | O | ALA | A1729 | 25.733 | 34.918 | 38.137 | 1.00 | 29.43 |
| ATOM | 88 | N | LYS | A1730 | 23.500 | 34.604 | 38.147 | 1.00 | 29.39 |
| ATOM | 89 | CA | LYS | A1730 | 23.238 | 35.488 | 39.287 | 1.00 | 29.32 |

FIGURE 3C

| | A | B | C | D | E | F | G | H | I | J |
|---|---|---|---|---|---|---|---|---|---|---|
| ATOM | 90 | CB | LYS | | A1730 | 21.733 | 35.721 | 39.466 | 1.00 | 29.02 |
| ATOM | 91 | CG | LYS | | A1730 | 21.010 | 36.209 | 38.220 | 1.00 | 29.45 |
| ATOM | 92 | CD | LYS | | A1730 | 20.696 | 37.687 | 38.287 | 1.00 | 29.96 |
| ATOM | 93 | CE | LYS | | A1730 | 19.749 | 38.092 | 37.166 | 1.00 | 31.80 |
| ATOM | 94 | NZ | LYS | | A1730 | 18.419 | 38.545 | 37.671 | 1.00 | 31.49 |
| ATOM | 95 | C | LYS | | A1730 | 23.831 | 34.899 | 40.562 | 1.00 | 29.11 |
| ATOM | 96 | O | LYS | | A1730 | 24.434 | 35.616 | 41.361 | 1.00 | 28.57 |
| ATOM | 97 | N | ARG | | A1731 | 23.658 | 33.588 | 40.734 | 1.00 | 29.70 |
| ATOM | 98 | CA | ARG | | A1731 | 24.256 | 32.841 | 41.838 | 1.00 | 30.25 |
| ATOM | 99 | CB | ARG | | A1731 | 23.908 | 31.356 | 41.725 | 1.00 | 33.07 |
| ATOM | 100 | CG | ARG | | A1731 | 22.949 | 30.856 | 42.775 | 1.00 | 35.61 |
| ATOM | 101 | CD | ARG | | A1731 | 21.565 | 30.588 | 42.236 | 1.00 | 38.05 |
| ATOM | 102 | NE | ARG | | A1731 | 20.993 | 29.363 | 42.788 | 1.00 | 40.38 |
| ATOM | 103 | CZ | ARG | | A1731 | 19.694 | 29.094 | 42.821 | 1.00 | 41.71 |
| ATOM | 104 | NH1 | ARG | | A1731 | 19.270 | 27.952 | 43.345 | 1.00 | 42.69 |
| ATOM | 105 | NH2 | ARG | | A1731 | 18.814 | 29.964 | 42.336 | 1.00 | 41.91 |
| ATOM | 106 | C | ARG | | A1731 | 25.771 | 32.992 | 41.847 | 1.00 | 29.09 |
| ATOM | 107 | O | ARG | | A1731 | 26.369 | 33.198 | 42.902 | 1.00 | 28.49 |
| ATOM | 108 | N | PHE | | A1732 | 26.375 | 32.873 | 40.664 | 1.00 | 27.04 |
| ATOM | 109 | CA | PHE | | A1732 | 27.817 | 33.008 | 40.490 | 1.00 | 26.53 |
| ATOM | 110 | CB | PHE | | A1732 | 28.233 | 32.578 | 39.075 | 1.00 | 26.36 |
| ATOM | 111 | CG | PHE | | A1732 | 29.711 | 32.683 | 38.812 | 1.00 | 27.27 |
| ATOM | 112 | CD1 | PHE | | A1732 | 30.563 | 31.624 | 39.118 | 1.00 | 28.08 |
| ATOM | 113 | CE1 | PHE | | A1732 | 31.934 | 31.717 | 38.873 | 1.00 | 28.62 |
| ATOM | 114 | CZ | PHE | | A1732 | 32.464 | 32.881 | 38.312 | 1.00 | 28.83 |
| ATOM | 115 | CE2 | PHE | | A1732 | 31.623 | 33.945 | 38.002 | 1.00 | 28.13 |
| ATOM | 116 | CD2 | PHE | | A1732 | 30.254 | 33.841 | 38.251 | 1.00 | 27.97 |
| ATOM | 117 | C | PHE | | A1732 | 28.282 | 34.433 | 40.775 | 1.00 | 25.04 |
| ATOM | 118 | O | PHE | | A1732 | 29.344 | 34.633 | 41.362 | 1.00 | 25.00 |
| ATOM | 119 | N | GLN | | A1733 | 27.487 | 35.411 | 40.344 | 1.00 | 25.15 |
| ATOM | 120 | CA | GLN | | A1733 | 27.744 | 36.819 | 40.634 | 1.00 | 26.28 |
| ATOM | 121 | CB | GLN | | A1733 | 26.660 | 37.696 | 40.009 | 1.00 | 29.49 |
| ATOM | 122 | CG | GLN | | A1733 | 27.116 | 38.529 | 38.826 | 1.00 | 33.05 |
| ATOM | 123 | CD | GLN | | A1733 | 26.092 | 39.576 | 38.437 | 1.00 | 34.85 |
| ATOM | 124 | OE1 | GLN | | A1733 | 26.284 | 40.769 | 38.699 | 1.00 | 36.74 |
| ATOM | 125 | NE2 | GLN | | A1733 | 24.996 | 39.137 | 37.821 | 1.00 | 34.16 |
| ATOM | 126 | C | GLN | | A1733 | 27.783 | 37.061 | 42.142 | 1.00 | 24.00 |
| ATOM | 127 | O | GLN | | A1733 | 28.742 | 37.635 | 42.661 | 1.00 | 22.66 |
| ATOM | 128 | N | ALA | | A1734 | 26.737 | 36.614 | 42.834 | 1.00 | 22.35 |
| ATOM | 129 | CA | ALA | | A1734 | 26.645 | 36.774 | 44.284 | 1.00 | 22.77 |
| ATOM | 130 | CB | ALA | | A1734 | 25.299 | 36.303 | 44.783 | 1.00 | 22.15 |
| ATOM | 131 | C | ALA | | A1734 | 27.779 | 36.026 | 44.980 | 1.00 | 22.98 |
| ATOM | 132 | O | ALA | | A1734 | 28.426 | 36.569 | 45.878 | 1.00 | 22.17 |
| ATOM | 133 | N | GLN | | A1735 | 28.026 | 34.793 | 44.535 | 1.00 | 23.79 |
| ATOM | 134 | CA | GLN | | A1735 | 29.145 | 33.977 | 45.010 | 1.00 | 25.24 |
| ATOM | 135 | CB | GLN | | A1735 | 29.181 | 32.639 | 44.264 | 1.00 | 27.17 |
| ATOM | 136 | CG | GLN | | A1735 | 30.237 | 31.661 | 44.757 | 1.00 | 30.75 |
| ATOM | 137 | CD | GLN | | A1735 | 30.033 | 30.261 | 44.205 | 1.00 | 32.21 |
| ATOM | 138 | OE1 | GLN | | A1735 | 29.416 | 29.418 | 44.858 | 1.00 | 33.47 |
| ATOM | 139 | NE2 | GLN | | A1735 | 30.546 | 30.012 | 43.003 | 1.00 | 31.63 |
| ATOM | 140 | C | GLN | | A1735 | 30.493 | 34.691 | 44.871 | 1.00 | 24.61 |
| ATOM | 141 | O | GLN | | A1735 | 31.323 | 34.633 | 45.782 | 1.00 | 24.31 |

FIGURE 3D

|      | A    | B   | C   | D E     | F      | G      | H      | I    | J     |
|------|------|-----|-----|---------|--------|--------|--------|------|-------|
| ATOM | 142  | N   | THR | A1736   | 30.699 | 35.359 | 43.735 | 1.00 | 23.10 |
| ATOM | 143  | CA  | THR | A1736   | 31.924 | 36.117 | 43.479 | 1.00 | 24.71 |
| ATOM | 144  | CB  | THR | A1736   | 31.939 | 36.643 | 42.021 | 1.00 | 25.19 |
| ATOM | 145  | OG1 | THR | A1736   | 32.093 | 35.539 | 41.122 | 1.00 | 27.07 |
| ATOM | 146  | CG2 | THR | A1736   | 33.182 | 37.488 | 41.740 | 1.00 | 25.00 |
| ATOM | 147  | C   | THR | A1736   | 32.085 | 37.260 | 44.479 | 1.00 | 24.41 |
| ATOM | 148  | O   | THR | A1736   | 33.197 | 37.557 | 44.928 | 1.00 | 24.50 |
| ATOM | 149  | N   | LEU | A1737   | 30.967 | 37.883 | 44.835 | 1.00 | 24.53 |
| ATOM | 150  | CA  | LEU | A1737   | 30.971 | 38.976 | 45.797 | 1.00 | 24.94 |
| ATOM | 151  | CB  | LEU | A1737   | 29.747 | 39.875 | 45.585 | 1.00 | 25.76 |
| ATOM | 152  | CG  | LEU | A1737   | 29.809 | 40.724 | 44.309 | 1.00 | 26.24 |
| ATOM | 153  | CD1 | LEU | A1737   | 28.419 | 41.006 | 43.768 | 1.00 | 26.29 |
| ATOM | 154  | CD2 | LEU | A1737   | 30.562 | 42.027 | 44.549 | 1.00 | 27.12 |
| ATOM | 155  | C   | LEU | A1737   | 31.053 | 38.471 | 47.239 | 1.00 | 24.42 |
| ATOM | 156  | O   | LEU | A1737   | 31.187 | 39.259 | 48.173 | 1.00 | 25.94 |
| ATOM | 157  | N   | GLY | A1738   | 30.987 | 37.153 | 47.407 | 1.00 | 24.16 |
| ATOM | 158  | CA  | GLY | A1738   | 31.121 | 36.531 | 48.712 | 1.00 | 23.61 |
| ATOM | 159  | C   | GLY | A1738   | 29.839 | 36.609 | 49.509 | 1.00 | 22.40 |
| ATOM | 160  | O   | GLY | A1738   | 29.861 | 36.763 | 50.733 | 1.00 | 23.93 |
| ATOM | 161  | N   | THR | A1739   | 28.717 | 36.497 | 48.806 | 1.00 | 20.56 |
| ATOM | 162  | CA  | THR | A1739   | 27.398 | 36.610 | 49.419 | 1.00 | 19.58 |
| ATOM | 163  | CB  | THR | A1739   | 26.908 | 38.093 | 49.387 | 1.00 | 18.80 |
| ATOM | 164  | OG1 | THR | A1739   | 25.719 | 38.233 | 50.174 | 1.00 | 19.10 |
| ATOM | 165  | CG2 | THR | A1739   | 26.468 | 38.514 | 47.986 | 1.00 | 19.51 |
| ATOM | 166  | C   | THR | A1739   | 26.409 | 35.642 | 48.756 | 1.00 | 18.60 |
| ATOM | 167  | O   | THR | A1739   | 26.789 | 34.873 | 47.872 | 1.00 | 18.43 |
| ATOM | 168  | N   | THR | A1740   | 25.154 | 35.674 | 49.196 | 1.00 | 18.17 |
| ATOM | 169  | CA  | THR | A1740   | 24.125 | 34.774 | 48.685 | 1.00 | 17.37 |
| ATOM | 170  | CB  | THR | A1740   | 23.360 | 34.128 | 49.857 | 1.00 | 17.81 |
| ATOM | 171  | OG1 | THR | A1740   | 24.279 | 33.399 | 50.678 | 1.00 | 19.81 |
| ATOM | 172  | CG2 | THR | A1740   | 22.392 | 33.055 | 49.362 | 1.00 | 16.15 |
| ATOM | 173  | C   | THR | A1740   | 23.150 | 35.533 | 47.804 | 1.00 | 17.77 |
| ATOM | 174  | O   | THR | A1740   | 22.707 | 36.634 | 48.156 | 1.00 | 16.81 |
| ATOM | 175  | N   | TYR | A1741   | 22.807 | 34.935 | 46.668 | 1.00 | 17.43 |
| ATOM | 176  | CA  | TYR | A1741   | 21.780 | 35.487 | 45.794 | 1.00 | 17.24 |
| ATOM | 177  | CB  | TYR | A1741   | 21.536 | 34.569 | 44.595 | 1.00 | 17.12 |
| ATOM | 178  | CG  | TYR | A1741   | 20.569 | 35.140 | 43.578 | 1.00 | 16.78 |
| ATOM | 179  | CD1 | TYR | A1741   | 19.578 | 34.341 | 43.012 | 1.00 | 15.75 |
| ATOM | 180  | CE1 | TYR | A1741   | 18.688 | 34.856 | 42.075 | 1.00 | 16.66 |
| ATOM | 181  | CZ  | TYR | A1741   | 18.780 | 36.190 | 41.699 | 1.00 | 16.53 |
| ATOM | 182  | OH  | TYR | A1741   | 17.895 | 36.693 | 40.774 | 1.00 | 15.00 |
| ATOM | 183  | CE2 | TYR | A1741   | 19.755 | 37.010 | 42.248 | 1.00 | 16.65 |
| ATOM | 184  | CD2 | TYR | A1741   | 20.646 | 36.481 | 43.183 | 1.00 | 15.90 |
| ATOM | 185  | C   | TYR | A1741   | 20.505 | 35.657 | 46.600 | 1.00 | 16.33 |
| ATOM | 186  | O   | TYR | A1741   | 20.080 | 34.731 | 47.288 | 1.00 | 18.16 |
| ATOM | 187  | N   | ILE | A1742   | 19.907 | 36.841 | 46.520 | 1.00 | 16.14 |
| ATOM | 188  | CA  | ILE | A1742   | 18.792 | 37.203 | 47.399 | 1.00 | 14.84 |
| ATOM | 189  | CB  | ILE | A1742   | 18.356 | 38.683 | 47.187 | 1.00 | 14.41 |
| ATOM | 190  | CG1 | ILE | A1742   | 17.353 | 39.125 | 48.265 | 1.00 | 13.66 |
| ATOM | 191  | CD1 | ILE | A1742   | 17.909 | 39.075 | 49.676 | 1.00 | 15.15 |
| ATOM | 192  | CG2 | ILE | A1742   | 17.795 | 38.908 | 45.782 | 1.00 | 15.49 |
| ATOM | 193  | C   | ILE | A1742   | 17.605 | 36.236 | 47.333 | 1.00 | 14.24 |

FIGURE 3E

|  | A | B | C | D | E | F | G | H | I | J |
|---|---|---|---|---|---|---|---|---|---|---|
| ATOM | 194 | O | | ILE | A1742 | 16.972 | 35.965 | 48.352 | 1.00 | 13.44 |
| ATOM | 195 | N | | TYR | A1743 | 17.326 | 35.699 | 46.147 | 1.00 | 13.94 |
| ATOM | 196 | CA | | TYR | A1743 | 16.244 | 34.727 | 45.981 | 1.00 | 15.79 |
| ATOM | 197 | CB | | TYR | A1743 | 15.847 | 34.596 | 44.508 | 1.00 | 14.52 |
| ATOM | 198 | CG | | TYR | A1743 | 14.995 | 35.746 | 44.031 | 1.00 | 14.85 |
| ATOM | 199 | CD1 | | TYR | A1743 | 15.567 | 36.817 | 43.335 | 1.00 | 14.29 |
| ATOM | 200 | CE1 | | TYR | A1743 | 14.796 | 37.889 | 42.900 | 1.00 | 13.72 |
| ATOM | 201 | CZ | | TYR | A1743 | 13.433 | 37.903 | 43.156 | 1.00 | 14.45 |
| ATOM | 202 | OH | | TYR | A1743 | 12.676 | 38.964 | 42.710 | 1.00 | 13.74 |
| ATOM | 203 | CE2 | | TYR | A1743 | 12.834 | 36.852 | 43.852 | 1.00 | 14.24 |
| ATOM | 204 | CD2 | | TYR | A1743 | 13.621 | 35.778 | 44.288 | 1.00 | 13.52 |
| ATOM | 205 | C | | TYR | A1743 | 16.546 | 33.351 | 46.583 | 1.00 | 15.21 |
| ATOM | 206 | O | | TYR | A1743 | 15.684 | 32.467 | 46.583 | 1.00 | 15.89 |
| ATOM | 207 | N | | ASP | A1744 | 17.763 | 33.176 | 47.097 | 1.00 | 15.34 |
| ATOM | 208 | CA | | ASP | A1744 | 18.133 | 31.942 | 47.792 | 1.00 | 15.48 |
| ATOM | 209 | CB | | ASP | A1744 | 19.552 | 31.506 | 47.412 | 1.00 | 17.19 |
| ATOM | 210 | CG | | ASP | A1744 | 19.633 | 30.960 | 46.002 | 1.00 | 19.45 |
| ATOM | 211 | OD1 | | ASP | A1744 | 20.746 | 30.961 | 45.436 | 1.00 | 20.71 |
| ATOM | 212 | OD2 | | ASP | A1744 | 18.642 | 30.509 | 45.386 | 1.00 | 18.54 |
| ATOM | 213 | C | | ASP | A1744 | 17.995 | 32.042 | 49.315 | 1.00 | 14.26 |
| ATOM | 214 | O | | ASP | A1744 | 18.157 | 31.052 | 50.023 | 1.00 | 14.00 |
| ATOM | 215 | N | | PHE | A1745 | 17.678 | 33.227 | 49.825 | 1.00 | 14.46 |
| ATOM | 216 | CA | | PHE | A1745 | 17.510 | 33.375 | 51.269 | 1.00 | 13.77 |
| ATOM | 217 | CB | | PHE | A1745 | 17.489 | 34.853 | 51.685 | 1.00 | 15.56 |
| ATOM | 218 | CG | | PHE | A1745 | 18.849 | 35.405 | 51.978 | 1.00 | 15.66 |
| ATOM | 219 | CD1 | | PHE | A1745 | 19.644 | 35.903 | 50.956 | 1.00 | 16.02 |
| ATOM | 220 | CE1 | | PHE | A1745 | 20.909 | 36.409 | 51.222 | 1.00 | 16.12 |
| ATOM | 221 | CZ | | PHE | A1745 | 21.399 | 36.399 | 52.523 | 1.00 | 16.55 |
| ATOM | 222 | CE2 | | PHE | A1745 | 20.617 | 35.892 | 53.552 | 1.00 | 16.46 |
| ATOM | 223 | CD2 | | PHE | A1745 | 19.352 | 35.391 | 53.274 | 1.00 | 16.50 |
| ATOM | 224 | C | | PHE | A1745 | 16.326 | 32.598 | 51.859 | 1.00 | 15.27 |
| ATOM | 225 | O | | PHE | A1745 | 16.483 | 31.981 | 52.911 | 1.00 | 16.06 |
| ATOM | 226 | N | | PRO | A1746 | 15.160 | 32.590 | 51.204 | 1.00 | 15.60 |
| ATOM | 227 | CA | | PRO | A1746 | 14.024 | 31.817 | 51.723 | 1.00 | 17.04 |
| ATOM | 228 | CB | | PRO | A1746 | 12.967 | 31.966 | 50.625 | 1.00 | 16.42 |
| ATOM | 229 | CG | | PRO | A1746 | 13.312 | 33.273 | 49.966 | 1.00 | 16.20 |
| ATOM | 230 | CD | | PRO | A1746 | 14.809 | 33.296 | 49.954 | 1.00 | 15.03 |
| ATOM | 231 | C | | PRO | A1746 | 14.373 | 30.341 | 51.956 | 1.00 | 18.24 |
| ATOM | 232 | O | | PRO | A1746 | 13.986 | 29.791 | 52.986 | 1.00 | 18.91 |
| ATOM | 233 | N | | GLU | A1747 | 15.101 | 29.723 | 51.026 | 1.00 | 18.42 |
| ATOM | 234 | CA | | GLU | A1747 | 15.582 | 28.349 | 51.202 | 1.00 | 16.31 |
| ATOM | 235 | CB | B | GLU | A1747 | 16.232 | 27.829 | 49.918 | 0.50 | 17.29 |
| ATOM | 236 | CB | A | GLU | A1747 | 16.234 | 27.836 | 49.909 | 0.50 | 15.84 |
| ATOM | 237 | CG | B | GLU | A1747 | 15.362 | 26.874 | 49.111 | 0.50 | 19.15 |
| ATOM | 238 | CG | A | GLU | A1747 | 17.046 | 26.554 | 50.065 | 0.50 | 16.03 |
| ATOM | 239 | CD | B | GLU | A1747 | 14.722 | 25.787 | 49.956 | 0.50 | 20.02 |
| ATOM | 240 | CD | A | GLU | A1747 | 17.845 | 26.190 | 48.826 | 0.50 | 16.46 |
| ATOM | 241 | OE1 | B | GLU | A1747 | 13.476 | 25.714 | 49.975 | 0.50 | 20.79 |
| ATOM | 242 | OE1 | A | GLU | A1747 | 17.824 | 25.003 | 48.444 | 0.50 | 16.85 |
| ATOM | 243 | OE2 | B | GLU | A1747 | 15.458 | 25.005 | 50.599 | 0.50 | 20.49 |
| ATOM | 244 | OE2 | A | GLU | A1747 | 18.501 | 27.078 | 48.237 | 0.50 | 16.52 |
| ATOM | 245 | C | | GLU | A1747 | 16.561 | 28.231 | 52.378 | 1.00 | 16.08 |

FIGURE 3F

|      | A    | B   | C   | D    | E     | F      | G      | H      | I    | J     |
|------|------|-----|-----|------|-------|--------|--------|--------|------|-------|
| ATOM | 246  | O   | GLU | A1747 |       | 16.563 | 27.225 | 53.097 | 1.00 | 13.93 |
| ATOM | 247  | N   | MET | A1748 |       | 17.396 | 29.252 | 52.558 | 1.00 | 16.02 |
| ATOM | 248  | CA  | MET | A1748 |       | 18.301 | 29.312 | 53.706 | 1.00 | 18.29 |
| ATOM | 249  | CB  | MET | A1748 |       | 19.211 | 30.534 | 53.614 | 1.00 | 20.36 |
| ATOM | 250  | CG  | MET | A1748 |       | 20.571 | 30.244 | 53.033 | 1.00 | 24.58 |
| ATOM | 251  | SD  | MET | A1748 |       | 21.772 | 31.496 | 53.508 | 1.00 | 29.37 |
| ATOM | 252  | CE  | MET | A1748 |       | 23.141 | 30.933 | 52.542 | 1.00 | 28.00 |
| ATOM | 253  | C   | MET | A1748 |       | 17.515 | 29.351 | 55.011 | 1.00 | 16.73 |
| ATOM | 254  | O   | MET | A1748 |       | 17.871 | 28.663 | 55.969 | 1.00 | 15.49 |
| ATOM | 255  | N   | PHE | A1749 |       | 16.450 | 30.156 | 55.038 | 1.00 | 15.16 |
| ATOM | 256  | CA  | PHE | A1749 |       | 15.549 | 30.219 | 56.191 | 1.00 | 16.39 |
| ATOM | 257  | CB  | PHE | A1749 |       | 14.458 | 31.283 | 55.998 | 1.00 | 15.61 |
| ATOM | 258  | CG  | PHE | A1749 |       | 14.866 | 32.665 | 56.446 | 1.00 | 15.74 |
| ATOM | 259  | CD1 | PHE | A1749 |       | 15.311 | 33.605 | 55.521 | 1.00 | 15.58 |
| ATOM | 260  | CE1 | PHE | A1749 |       | 15.689 | 34.886 | 55.927 | 1.00 | 14.79 |
| ATOM | 261  | CZ  | PHE | A1749 |       | 15.618 | 35.235 | 57.278 | 1.00 | 15.67 |
| ATOM | 262  | CE2 | PHE | A1749 |       | 15.172 | 34.302 | 58.210 | 1.00 | 15.09 |
| ATOM | 263  | CD2 | PHE | A1749 |       | 14.801 | 33.027 | 57.790 | 1.00 | 15.24 |
| ATOM | 264  | C   | PHE | A1749 |       | 14.923 | 28.853 | 56.476 | 1.00 | 16.04 |
| ATOM | 265  | O   | PHE | A1749 |       | 14.862 | 28.436 | 57.627 | 1.00 | 16.97 |
| ATOM | 266  | N   | ARG | A1750 |       | 14.473 | 28.167 | 55.425 | 1.00 | 16.68 |
| ATOM | 267  | CA  | ARG | A1750 |       | 13.920 | 26.815 | 55.546 | 1.00 | 17.44 |
| ATOM | 268  | CB  | ARG | A1750 |       | 13.477 | 26.283 | 54.177 | 1.00 | 19.78 |
| ATOM | 269  | CG  | ARG | A1750 |       | 12.474 | 25.131 | 54.237 | 1.00 | 24.86 |
| ATOM | 270  | CD  | ARG | A1750 |       | 11.899 | 24.722 | 52.875 | 1.00 | 28.27 |
| ATOM | 271  | NE  | ARG | A1750 |       | 10.607 | 25.359 | 52.611 | 1.00 | 31.28 |
| ATOM | 272  | CZ  | ARG | A1750 |       | 10.402 | 26.341 | 51.731 | 1.00 | 32.77 |
| ATOM | 273  | NH1 | ARG | A1750 |       | 11.401 | 26.825 | 51.002 | 1.00 | 33.96 |
| ATOM | 274  | NH2 | ARG | A1750 |       | 9.184  | 26.846 | 51.575 | 1.00 | 33.28 |
| ATOM | 275  | C   | ARG | A1750 |       | 14.927 | 25.861 | 56.185 | 1.00 | 16.31 |
| ATOM | 276  | O   | ARG | A1750 |       | 14.586 | 25.127 | 57.122 | 1.00 | 15.92 |
| ATOM | 277  | N   | GLN | A1751 |       | 16.162 | 25.885 | 55.679 | 1.00 | 15.19 |
| ATOM | 278  | CA  | GLN | A1751 |       | 17.234 | 25.019 | 56.168 | 1.00 | 16.25 |
| ATOM | 279  | CB  | GLN | A1751 |       | 18.482 | 25.144 | 55.290 | 1.00 | 17.99 |
| ATOM | 280  | CG  | GLN | A1751 |       | 18.440 | 24.323 | 54.008 | 1.00 | 20.32 |
| ATOM | 281  | CD  | GLN | A1751 |       | 19.294 | 24.918 | 52.898 | 1.00 | 22.49 |
| ATOM | 282  | OE1 | GLN | A1751 |       | 19.868 | 26.001 | 53.053 | 1.00 | 23.90 |
| ATOM | 283  | NE2 | GLN | A1751 |       | 19.377 | 24.214 | 51.777 | 1.00 | 23.83 |
| ATOM | 284  | C   | GLN | A1751 |       | 17.585 | 25.351 | 57.614 | 1.00 | 14.93 |
| ATOM | 285  | O   | GLN | A1751 |       | 17.826 | 24.456 | 58.420 | 1.00 | 13.15 |
| ATOM | 286  | N   | ALA | A1752 |       | 17.608 | 26.643 | 57.935 | 1.00 | 13.25 |
| ATOM | 287  | CA  | ALA | A1752 |       | 17.875 | 27.084 | 59.300 | 1.00 | 14.22 |
| ATOM | 288  | CB  | ALA | A1752 |       | 18.070 | 28.595 | 59.346 | 1.00 | 12.69 |
| ATOM | 289  | C   | ALA | A1752 |       | 16.773 | 26.642 | 60.265 | 1.00 | 15.21 |
| ATOM | 290  | O   | ALA | A1752 |       | 17.065 | 26.214 | 61.380 | 1.00 | 15.55 |
| ATOM | 291  | N   | LEU | A1753 |       | 15.517 | 26.736 | 59.826 | 1.00 | 16.58 |
| ATOM | 292  | CA  | LEU | A1753 |       | 14.364 | 26.334 | 60.636 | 1.00 | 18.81 |
| ATOM | 293  | CB  | LEU | A1753 |       | 13.049 | 26.646 | 59.910 | 1.00 | 19.20 |
| ATOM | 294  | CG  | LEU | A1753 |       | 12.573 | 28.099 | 59.944 | 1.00 | 20.32 |
| ATOM | 295  | CD1 | LEU | A1753 |       | 11.615 | 28.359 | 58.807 | 1.00 | 19.77 |
| ATOM | 296  | CD2 | LEU | A1753 |       | 11.941 | 28.457 | 61.291 | 1.00 | 21.92 |
| ATOM | 297  | C   | LEU | A1753 |       | 14.410 | 24.856 | 60.985 | 1.00 | 20.17 |

FIGURE 3G

| | A | B | C | D E | F | G | H | I | J |
|---|---|---|---|---|---|---|---|---|---|
| ATOM | 298 | O | LEU | A1753 | 14.196 | 24.479 | 62.140 | 1.00 | 19.44 |
| ATOM | 299 | N | PHE | A1754 | 14.694 | 24.030 | 59.978 | 1.00 | 22.01 |
| ATOM | 300 | CA | PHE | A1754 | 14.847 | 22.592 | 60.159 | 1.00 | 24.57 |
| ATOM | 301 | CB | PHE | A1754 | 15.204 | 21.915 | 58.829 | 1.00 | 27.01 |
| ATOM | 302 | CG | PHE | A1754 | 14.026 | 21.681 | 57.920 | 1.00 | 27.93 |
| ATOM | 303 | CD1 | PHE | A1754 | 12.834 | 21.157 | 58.412 | 1.00 | 28.65 |
| ATOM | 304 | CE1 | PHE | A1754 | 11.748 | 20.931 | 57.567 | 1.00 | 28.42 |
| ATOM | 305 | CZ | PHE | A1754 | 11.853 | 21.225 | 56.213 | 1.00 | 28.80 |
| ATOM | 306 | CE2 | PHE | A1754 | 13.039 | 21.743 | 55.707 | 1.00 | 28.87 |
| ATOM | 307 | CD2 | PHE | A1754 | 14.119 | 21.965 | 56.560 | 1.00 | 29.22 |
| ATOM | 308 | C | PHE | A1754 | 15.906 | 22.274 | 61.213 | 1.00 | 25.66 |
| ATOM | 309 | O | PHE | A1754 | 15.677 | 21.439 | 62.088 | 1.00 | 26.76 |
| ATOM | 310 | N | LYS | A1755 | 17.052 | 22.951 | 61.129 | 1.00 | 27.11 |
| ATOM | 311 | CA | LYS | A1755 | 18.147 | 22.765 | 62.086 | 1.00 | 29.05 |
| ATOM | 312 | CB | LYS | A1755 | 19.421 | 23.459 | 61.589 | 1.00 | 30.13 |
| ATOM | 313 | CG | LYS | A1755 | 20.685 | 23.074 | 62.346 | 1.00 | 31.84 |
| ATOM | 314 | CD | LYS | A1755 | 21.796 | 24.097 | 62.144 | 1.00 | 33.51 |
| ATOM | 315 | CE | LYS | A1755 | 23.142 | 23.541 | 62.594 | 1.00 | 33.96 |
| ATOM | 316 | NZ | LYS | A1755 | 24.016 | 23.158 | 61.446 | 1.00 | 34.61 |
| ATOM | 317 | C | LYS | A1755 | 17.787 | 23.266 | 63.488 | 1.00 | 29.83 |
| ATOM | 318 | O | LYS | A1755 | 18.147 | 22.640 | 64.487 | 1.00 | 28.67 |
| ATOM | 319 | N | LEU | A1756 | 17.082 | 24.396 | 63.550 | 1.00 | 31.22 |
| ATOM | 320 | CA | LEU | A1756 | 16.637 | 24.969 | 64.818 | 1.00 | 32.67 |
| ATOM | 321 | CB | LEU | A1756 | 16.019 | 26.352 | 64.594 | 1.00 | 32.37 |
| ATOM | 322 | CG | LEU | A1756 | 15.850 | 27.268 | 65.808 | 1.00 | 33.65 |
| ATOM | 323 | CD1 | LEU | A1756 | 17.168 | 27.503 | 66.545 | 1.00 | 33.68 |
| ATOM | 324 | CD2 | LEU | A1756 | 15.237 | 28.591 | 65.378 | 1.00 | 34.14 |
| ATOM | 325 | C | LEU | A1756 | 15.647 | 24.049 | 65.529 | 1.00 | 34.21 |
| ATOM | 326 | O | LEU | A1756 | 15.676 | 23.921 | 66.756 | 1.00 | 33.54 |
| ATOM | 327 | N | TRP | A1757 | 14.785 | 23.406 | 64.743 | 1.00 | 35.79 |
| ATOM | 328 | CA | TRP | A1757 | 13.801 | 22.459 | 65.257 | 1.00 | 38.42 |
| ATOM | 329 | CB | TRP | A1757 | 12.824 | 22.058 | 64.156 | 1.00 | 37.43 |
| ATOM | 330 | CG | TRP | A1757 | 11.564 | 22.848 | 64.180 | 1.00 | 37.46 |
| ATOM | 331 | CD1 | TRP | A1757 | 11.229 | 23.883 | 63.357 | 1.00 | 37.19 |
| ATOM | 332 | NE1 | TRP | A1757 | 9.984 | 24.366 | 63.680 | 1.00 | 37.21 |
| ATOM | 333 | CE2 | TRP | A1757 | 9.488 | 23.646 | 64.735 | 1.00 | 37.22 |
| ATOM | 334 | CD2 | TRP | A1757 | 10.462 | 22.679 | 65.078 | 1.00 | 37.82 |
| ATOM | 335 | CE3 | TRP | A1757 | 10.193 | 21.806 | 66.143 | 1.00 | 38.34 |
| ATOM | 336 | CZ3 | TRP | A1757 | 8.981 | 21.925 | 66.820 | 1.00 | 38.87 |
| ATOM | 337 | CH2 | TRP | A1757 | 8.037 | 22.900 | 66.451 | 1.00 | 38.21 |
| ATOM | 338 | CZ2 | TRP | A1757 | 8.271 | 23.764 | 65.413 | 1.00 | 37.06 |
| ATOM | 339 | C | TRP | A1757 | 14.450 | 21.218 | 65.861 | 1.00 | 40.49 |
| ATOM | 340 | O | TRP | A1757 | 13.857 | 20.561 | 66.714 | 1.00 | 40.60 |
| ATOM | 341 | N | GLY | A1758 | 15.664 | 20.906 | 65.411 | 1.00 | 43.77 |
| ATOM | 342 | CA | GLY | A1758 | 16.437 | 19.807 | 65.960 | 1.00 | 47.77 |
| ATOM | 343 | C | GLY | A1758 | 16.480 | 18.588 | 65.062 | 1.00 | 50.91 |
| ATOM | 344 | O | GLY | A1758 | 17.225 | 18.557 | 64.080 | 1.00 | 51.73 |
| ATOM | 345 | N | SER | A1759 | 15.669 | 17.589 | 65.401 | 1.00 | 53.75 |
| ATOM | 346 | CA | SER | A1759 | 15.673 | 16.300 | 64.710 | 1.00 | 56.53 |
| ATOM | 347 | CB | SER | A1759 | 15.674 | 15.158 | 65.732 | 1.00 | 56.77 |
| ATOM | 348 | OG | SER | A1759 | 16.997 | 14.768 | 66.059 | 1.00 | 57.41 |
| ATOM | 349 | C | SER | A1759 | 14.496 | 16.136 | 63.740 | 1.00 | 58.23 |

FIGURE 3H

| | A | B | C | D | E | F | G | H | I | J |
|---|---|---|---|---|---|---|---|---|---|---|
| ATOM | 350 | O | SER | A1759 | | 13.381 | 16.576 | 64.038 | 1.00 | 58.44 |
| ATOM | 351 | N | PRO | A1760 | | 14.746 | 15.508 | 62.586 | 1.00 | 59.73 |
| ATOM | 352 | CA | PRO | A1760 | | 13.687 | 15.191 | 61.613 | 1.00 | 60.68 |
| ATOM | 353 | CB | PRO | A1760 | | 14.474 | 14.717 | 60.382 | 1.00 | 60.66 |
| ATOM | 354 | CG | PRO | A1760 | | 15.764 | 14.216 | 60.923 | 1.00 | 60.62 |
| ATOM | 355 | CD | PRO | A1760 | | 16.075 | 15.081 | 62.107 | 1.00 | 60.31 |
| ATOM | 356 | C | PRO | A1760 | | 12.704 | 14.106 | 62.080 | 1.00 | 61.90 |
| ATOM | 357 | O | PRO | A1760 | | 12.261 | 13.279 | 61.273 | 1.00 | 61.73 |
| ATOM | 358 | N | ASP | A1761 | | 12.370 | 14.122 | 63.369 | 1.00 | 63.01 |
| ATOM | 359 | CA | ASP | A1761 | | 11.384 | 13.207 | 63.937 | 1.00 | 63.91 |
| ATOM | 360 | CB | ASP | A1761 | | 11.868 | 12.663 | 65.286 | 1.00 | 64.67 |
| ATOM | 361 | CG | ASP | A1761 | | 11.951 | 11.146 | 65.309 | 1.00 | 65.39 |
| ATOM | 362 | OD1 | ASP | A1761 | | 12.862 | 10.586 | 64.659 | 1.00 | 65.62 |
| ATOM | 363 | OD2 | ASP | A1761 | | 11.151 | 10.430 | 65.951 | 1.00 | 65.58 |
| ATOM | 364 | C | ASP | A1761 | | 10.034 | 13.905 | 64.097 | 1.00 | 63.63 |
| ATOM | 365 | O | ASP | A1761 | | 8.982 | 13.295 | 63.891 | 1.00 | 64.06 |
| ATOM | 366 | N | LYS | A1762 | | 10.078 | 15.186 | 64.461 | 1.00 | 62.95 |
| ATOM | 367 | CA | LYS | A1762 | | 8.874 | 15.997 | 64.616 | 1.00 | 62.16 |
| ATOM | 368 | CB | LYS | A1762 | | 8.564 | 16.225 | 66.100 | 1.00 | 62.48 |
| ATOM | 369 | CG | LYS | A1762 | | 7.613 | 15.197 | 66.695 | 1.00 | 62.47 |
| ATOM | 370 | CD | LYS | A1762 | | 8.331 | 14.270 | 67.663 | 1.00 | 62.45 |
| ATOM | 371 | CE | LYS | A1762 | | 7.808 | 12.846 | 67.557 | 1.00 | 62.41 |
| ATOM | 372 | NZ | LYS | A1762 | | 6.601 | 12.635 | 68.402 | 1.00 | 62.31 |
| ATOM | 373 | C | LYS | A1762 | | 8.991 | 17.325 | 63.857 | 1.00 | 61.25 |
| ATOM | 374 | O | LYS | A1762 | | 8.979 | 18.409 | 64.454 | 1.00 | 61.42 |
| ATOM | 375 | N | TYR | A1763 | | 9.115 | 17.220 | 62.535 | 1.00 | 59.75 |
| ATOM | 376 | CA | TYR | A1763 | | 9.146 | 18.380 | 61.649 | 1.00 | 57.99 |
| ATOM | 377 | CB | TYR | A1763 | | 9.966 | 18.074 | 60.386 | 1.00 | 58.91 |
| ATOM | 378 | CG | TYR | A1763 | | 11.472 | 18.268 | 60.506 | 1.00 | 59.56 |
| ATOM | 379 | CD1 | TYR | A1763 | | 12.321 | 17.893 | 59.461 | 1.00 | 59.61 |
| ATOM | 380 | CE1 | TYR | A1763 | | 13.705 | 18.067 | 59.552 | 1.00 | 59.40 |
| ATOM | 381 | CZ | TYR | A1763 | | 14.252 | 18.616 | 60.701 | 1.00 | 59.64 |
| ATOM | 382 | OH | TYR | A1763 | | 15.615 | 18.783 | 60.794 | 1.00 | 59.67 |
| ATOM | 383 | CE2 | TYR | A1763 | | 13.432 | 18.997 | 61.756 | 1.00 | 59.62 |
| ATOM | 384 | CD2 | TYR | A1763 | | 12.049 | 18.823 | 61.655 | 1.00 | 59.67 |
| ATOM | 385 | C | TYR | A1763 | | 7.717 | 18.765 | 61.256 | 1.00 | 55.92 |
| ATOM | 386 | O | TYR | A1763 | | 6.914 | 17.892 | 60.912 | 1.00 | 55.78 |
| ATOM | 387 | N | PRO | A1764 | | 7.400 | 20.060 | 61.313 | 1.00 | 53.72 |
| ATOM | 388 | CA | PRO | A1764 | | 6.075 | 20.560 | 60.915 | 1.00 | 51.75 |
| ATOM | 389 | CB | PRO | A1764 | | 6.155 | 22.057 | 61.236 | 1.00 | 52.49 |
| ATOM | 390 | CG | PRO | A1764 | | 7.292 | 22.191 | 62.193 | 1.00 | 52.79 |
| ATOM | 391 | CD | PRO | A1764 | | 8.278 | 21.149 | 61.779 | 1.00 | 53.46 |
| ATOM | 392 | C | PRO | A1764 | | 5.788 | 20.357 | 59.424 | 1.00 | 49.54 |
| ATOM | 393 | O | PRO | A1764 | | 6.726 | 20.289 | 58.626 | 1.00 | 49.17 |
| ATOM | 394 | N | LYS | A1765 | | 4.505 | 20.279 | 59.069 | 1.00 | 47.24 |
| ATOM | 395 | CA | LYS | A1765 | | 4.065 | 19.973 | 57.702 | 1.00 | 44.85 |
| ATOM | 396 | CB | LYS | A1765 | | 2.550 | 19.736 | 57.667 | 1.00 | 45.78 |
| ATOM | 397 | CG | LYS | A1765 | | 2.133 | 18.428 | 56.988 | 1.00 | 46.67 |
| ATOM | 398 | CD | LYS | A1765 | | 2.217 | 17.238 | 57.943 | 1.00 | 46.77 |
| ATOM | 399 | CE | LYS | A1765 | | 0.985 | 16.353 | 57.844 | 1.00 | 47.00 |
| ATOM | 400 | NZ | LYS | A1765 | | 0.839 | 15.473 | 59.038 | 1.00 | 46.84 |
| ATOM | 401 | C | LYS | A1765 | | 4.466 | 21.010 | 56.645 | 1.00 | 42.89 |

FIGURE 3I

| | A | B | C | D | E | F | G | H | I | J |
|---|---|---|---|---|---|---|---|---|---|---|
| ATOM | 402 | O | | LYS | A1765 | 4.872 | 20.645 | 55.535 | 1.00 | 43.96 |
| ATOM | 403 | N | | ASP | A1766 | 4.336 | 22.290 | 56.987 | 1.00 | 37.75 |
| ATOM | 404 | CA | | ASP | A1766 | 4.765 | 23.378 | 56.111 | 1.00 | 34.08 |
| ATOM | 405 | CB | | ASP | A1766 | 3.565 | 24.045 | 55.434 | 1.00 | 34.81 |
| ATOM | 406 | CG | | ASP | A1766 | 3.308 | 23.507 | 54.038 | 1.00 | 35.03 |
| ATOM | 407 | OD1 | | ASP | A1766 | 3.375 | 24.296 | 53.072 | 1.00 | 35.18 |
| ATOM | 408 | OD2 | | ASP | A1766 | 3.030 | 22.312 | 53.810 | 1.00 | 36.01 |
| ATOM | 409 | C | | ASP | A1766 | 5.558 | 24.387 | 56.930 | 1.00 | 29.75 |
| ATOM | 410 | O | | ASP | A1766 | 5.042 | 25.436 | 57.319 | 1.00 | 31.02 |
| ATOM | 411 | N | | ILE | A1767 | 6.819 | 24.046 | 57.182 | 1.00 | 25.26 |
| ATOM | 412 | CA | | ILE | A1767 | 7.686 | 24.769 | 58.111 | 1.00 | 22.83 |
| ATOM | 413 | CB | | ILE | A1767 | 9.029 | 24.005 | 58.287 | 1.00 | 22.99 |
| ATOM | 414 | CG1 | | ILE | A1767 | 9.749 | 24.453 | 59.561 | 1.00 | 23.09 |
| ATOM | 415 | CD1 | | ILE | A1767 | 10.781 | 23.461 | 60.043 | 1.00 | 23.55 |
| ATOM | 416 | CG2 | | ILE | A1767 | 9.929 | 24.152 | 57.049 | 1.00 | 22.73 |
| ATOM | 417 | C | | ILE | A1767 | 7.930 | 26.225 | 57.712 | 1.00 | 21.17 |
| ATOM | 418 | O | | ILE | A1767 | 8.140 | 27.079 | 58.572 | 1.00 | 19.80 |
| ATOM | 419 | N | | LEU | A1768 | 7.904 | 26.491 | 56.410 | 1.00 | 18.92 |
| ATOM | 420 | CA | | LEU | A1768 | 8.122 | 27.824 | 55.878 | 1.00 | 18.56 |
| ATOM | 421 | CB | | LEU | A1768 | 9.614 | 28.061 | 55.593 | 1.00 | 19.19 |
| ATOM | 422 | CG | | LEU | A1768 | 10.167 | 29.442 | 55.183 | 1.00 | 19.91 |
| ATOM | 423 | CD1 | | LEU | A1768 | 10.301 | 29.565 | 53.668 | 1.00 | 19.83 |
| ATOM | 424 | CD2 | | LEU | A1768 | 9.360 | 30.605 | 55.736 | 1.00 | 20.51 |
| ATOM | 425 | C | | LEU | A1768 | 7.309 | 27.989 | 54.607 | 1.00 | 18.85 |
| ATOM | 426 | O | | LEU | A1768 | 7.448 | 27.209 | 53.662 | 1.00 | 15.84 |
| ATOM | 427 | N | | THR | A1769 | 6.438 | 28.994 | 54.609 | 1.00 | 17.27 |
| ATOM | 428 | CA | | THR | A1769 | 5.749 | 29.418 | 53.398 | 1.00 | 17.75 |
| ATOM | 429 | CB | | THR | A1769 | 4.221 | 29.149 | 53.466 | 1.00 | 19.05 |
| ATOM | 430 | OG1 | | THR | A1769 | 3.624 | 29.958 | 54.484 | 1.00 | 20.77 |
| ATOM | 431 | CG2 | | THR | A1769 | 3.921 | 27.716 | 53.922 | 1.00 | 20.67 |
| ATOM | 432 | C | | THR | A1769 | 6.024 | 30.899 | 53.214 | 1.00 | 16.98 |
| ATOM | 433 | O | | THR | A1769 | 6.178 | 31.637 | 54.193 | 1.00 | 16.76 |
| ATOM | 434 | N | | TYR | A1770 | 6.105 | 31.334 | 51.964 | 1.00 | 15.51 |
| ATOM | 435 | CA | | TYR | A1770 | 6.398 | 32.727 | 51.680 | 1.00 | 16.34 |
| ATOM | 436 | CB | | TYR | A1770 | 7.910 | 32.995 | 51.765 | 1.00 | 16.93 |
| ATOM | 437 | CG | | TYR | A1770 | 8.700 | 32.481 | 50.583 | 1.00 | 18.39 |
| ATOM | 438 | CD1 | | TYR | A1770 | 8.986 | 31.119 | 50.445 | 1.00 | 18.46 |
| ATOM | 439 | CE1 | | TYR | A1770 | 9.708 | 30.645 | 49.352 | 1.00 | 19.93 |
| ATOM | 440 | CZ | | TYR | A1770 | 10.148 | 31.543 | 48.388 | 1.00 | 20.36 |
| ATOM | 441 | OH | | TYR | A1770 | 10.862 | 31.091 | 47.305 | 1.00 | 22.51 |
| ATOM | 442 | CE2 | | TYR | A1770 | 9.874 | 32.897 | 48.506 | 1.00 | 19.34 |
| ATOM | 443 | CD2 | | TYR | A1770 | 9.153 | 33.356 | 49.596 | 1.00 | 17.78 |
| ATOM | 444 | C | | TYR | A1770 | 5.851 | 33.164 | 50.333 | 1.00 | 16.33 |
| ATOM | 445 | O | | TYR | A1770 | 5.597 | 32.339 | 49.453 | 1.00 | 14.90 |
| ATOM | 446 | N | | THR | A1771 | 5.662 | 34.473 | 50.197 | 1.00 | 15.28 |
| ATOM | 447 | CA | | THR | A1771 | 5.303 | 35.090 | 48.927 | 1.00 | 16.03 |
| ATOM | 448 | CB | | THR | A1771 | 3.888 | 35.721 | 48.988 | 1.00 | 16.99 |
| ATOM | 449 | OG1 | | THR | A1771 | 3.844 | 36.716 | 50.025 | 1.00 | 17.91 |
| ATOM | 450 | CG2 | | THR | A1771 | 2.834 | 34.702 | 49.419 | 1.00 | 17.20 |
| ATOM | 451 | C | | THR | A1771 | 6.332 | 36.180 | 48.659 | 1.00 | 15.10 |
| ATOM | 452 | O | | THR | A1771 | 6.940 | 36.704 | 49.596 | 1.00 | 14.31 |
| ATOM | 453 | N | | GLU | A1772 | 6.539 | 36.512 | 47.390 | 1.00 | 15.25 |

FIGURE 3J

| | A | B | C | D | E | F | G | H | I | J |
|---|---|---|---|---|---|---|---|---|---|---|
| ATOM | 454 | CA | GLU | A1772 | | 7.342 | 37.678 | 47.057 | 1.00 | 15.82 |
| ATOM | 455 | CB | GLU | A1772 | | 8.036 | 37.523 | 45.701 | 1.00 | 15.19 |
| ATOM | 456 | CG | GLU | A1772 | | 9.095 | 38.594 | 45.469 | 1.00 | 14.03 |
| ATOM | 457 | CD | GLU | A1772 | | 9.704 | 38.565 | 44.078 | 1.00 | 14.28 |
| ATOM | 458 | OE1 | GLU | A1772 | | 9.567 | 37.549 | 43.373 | 1.00 | 12.60 |
| ATOM | 459 | OE2 | GLU | A1772 | | 10.334 | 39.571 | 43.693 | 1.00 | 14.09 |
| ATOM | 460 | C | GLU | A1772 | | 6.455 | 38.913 | 47.059 | 1.00 | 15.61 |
| ATOM | 461 | O | GLU | A1772 | | 5.327 | 38.880 | 46.555 | 1.00 | 16.54 |
| ATOM | 462 | N | LEU | A1773 | | 6.969 | 39.990 | 47.643 | 1.00 | 15.62 |
| ATOM | 463 | CA | LEU | A1773 | | 6.302 | 41.285 | 47.625 | 1.00 | 15.98 |
| ATOM | 464 | CB | LEU | A1773 | | 6.507 | 42.020 | 48.957 | 1.00 | 16.41 |
| ATOM | 465 | CG | LEU | A1773 | | 6.084 | 41.237 | 50.209 | 1.00 | 18.25 |
| ATOM | 466 | CD1 | LEU | A1773 | | 6.660 | 41.871 | 51.463 | 1.00 | 16.78 |
| ATOM | 467 | CD2 | LEU | A1773 | | 4.561 | 41.126 | 50.309 | 1.00 | 17.66 |
| ATOM | 468 | C | LEU | A1773 | | 6.834 | 42.102 | 46.456 | 1.00 | 14.92 |
| ATOM | 469 | O | LEU | A1773 | | 8.038 | 42.358 | 46.357 | 1.00 | 12.93 |
| ATOM | 470 | N | VAL | A1774 | | 5.926 | 42.484 | 45.561 | 1.00 | 15.12 |
| ATOM | 471 | CA | VAL | A1774 | | 6.286 | 43.111 | 44.293 | 1.00 | 13.70 |
| ATOM | 472 | CB | VAL | A1774 | | 6.041 | 42.139 | 43.097 | 1.00 | 15.17 |
| ATOM | 473 | CG1 | VAL | A1774 | | 6.470 | 42.765 | 41.769 | 1.00 | 15.69 |
| ATOM | 474 | CG2 | VAL | A1774 | | 6.755 | 40.801 | 43.318 | 1.00 | 13.75 |
| ATOM | 475 | C | VAL | A1774 | | 5.461 | 44.379 | 44.112 | 1.00 | 15.86 |
| ATOM | 476 | O | VAL | A1774 | | 4.248 | 44.372 | 44.321 | 1.00 | 16.46 |
| ATOM | 477 | N | LEU | A1775 | | 6.122 | 45.466 | 43.724 | 1.00 | 15.64 |
| ATOM | 478 | CA | LEU | A1775 | | 5.434 | 46.721 | 43.460 | 1.00 | 16.41 |
| ATOM | 479 | CB | LEU | A1775 | | 6.434 | 47.866 | 43.293 | 1.00 | 17.31 |
| ATOM | 480 | CG | LEU | A1775 | | 7.298 | 48.256 | 44.492 | 1.00 | 16.59 |
| ATOM | 481 | CD1 | LEU | A1775 | | 8.440 | 49.125 | 44.003 | 1.00 | 18.28 |
| ATOM | 482 | CD2 | LEU | A1775 | | 6.479 | 48.989 | 45.540 | 1.00 | 16.97 |
| ATOM | 483 | C | LEU | A1775 | | 4.586 | 46.616 | 42.204 | 1.00 | 17.05 |
| ATOM | 484 | O | LEU | A1775 | | 5.042 | 46.098 | 41.181 | 1.00 | 15.97 |
| ATOM | 485 | N | ASP | A1776 | | 3.352 | 47.102 | 42.297 | 1.00 | 18.40 |
| ATOM | 486 | CA | ASP | A1776 | | 2.493 | 47.249 | 41.127 | 1.00 | 19.02 |
| ATOM | 487 | CB | ASP | A1776 | | 1.023 | 46.987 | 41.487 | 1.00 | 19.89 |
| ATOM | 488 | CG | ASP | A1776 | | 0.443 | 48.027 | 42.442 | 1.00 | 20.59 |
| ATOM | 489 | OD1 | ASP | A1776 | | -0.607 | 47.735 | 43.051 | 1.00 | 20.55 |
| ATOM | 490 | OD2 | ASP | A1776 | | 0.946 | 49.156 | 42.652 | 1.00 | 20.61 |
| ATOM | 491 | C | ASP | A1776 | | 2.684 | 48.634 | 40.497 | 1.00 | 19.62 |
| ATOM | 492 | O | ASP | A1776 | | 3.604 | 49.374 | 40.865 | 1.00 | 15.92 |
| ATOM | 493 | N | SER | A1777 | | 1.805 | 48.981 | 39.559 | 1.00 | 19.88 |
| ATOM | 494 | CA | SER | A1777 | | 1.909 | 50.234 | 38.810 | 1.00 | 20.57 |
| ATOM | 495 | CB | BSER | A1777 | | 0.989 | 50.198 | 37.590 | 0.50 | 19.88 |
| ATOM | 496 | CB | ASER | A1777 | | 0.967 | 50.207 | 37.605 | 0.50 | 20.35 |
| ATOM | 497 | OG | BSER | A1777 | | 1.343 | 49.122 | 36.741 | 0.50 | 18.45 |
| ATOM | 498 | OG | ASER | A1777 | | -0.368 | 49.957 | 38.011 | 0.50 | 19.76 |
| ATOM | 499 | C | SER | A1777 | | 1.629 | 51.475 | 39.656 | 1.00 | 21.97 |
| ATOM | 500 | O | SER | A1777 | | 2.121 | 52.561 | 39.344 | 1.00 | 23.61 |
| ATOM | 501 | N | GLN | A1778 | | 0.847 | 51.304 | 40.721 | 1.00 | 24.25 |
| ATOM | 502 | CA | GLN | A1778 | | 0.525 | 52.388 | 41.650 | 1.00 | 25.19 |
| ATOM | 503 | CB | GLN | A1778 | | -0.871 | 52.178 | 42.257 | 1.00 | 27.37 |
| ATOM | 504 | CG | GLN | A1778 | | -2.030 | 52.314 | 41.266 | 1.00 | 30.83 |
| ATOM | 505 | CD | GLN | A1778 | | -2.358 | 53.763 | 40.937 | 1.00 | 32.93 |

FIGURE 3K

|  | A | B | C | D | E | F | G | H | I | J |
|---|---|---|---|---|---|---|---|---|---|---|
| ATOM | 506 | OE1 | GLN | A1778 | | -2.986 | 54.465 | 41.736 | 1.00 | 33.90 |
| ATOM | 507 | NE2 | GLN | A1778 | | -1.933 | 54.214 | 39.762 | 1.00 | 33.42 |
| ATOM | 508 | C | GLN | A1778 | | 1.566 | 52.534 | 42.770 | 1.00 | 24.41 |
| ATOM | 509 | O | GLN | A1778 | | 1.419 | 53.384 | 43.654 | 1.00 | 24.24 |
| ATOM | 510 | N | GLY | A1779 | | 2.610 | 51.709 | 42.729 | 1.00 | 23.19 |
| ATOM | 511 | CA | GLY | A1779 | | 3.653 | 51.725 | 43.741 | 1.00 | 21.36 |
| ATOM | 512 | C | GLY | A1779 | | 3.226 | 51.080 | 45.048 | 1.00 | 21.57 |
| ATOM | 513 | O | GLY | A1779 | | 3.706 | 51.453 | 46.120 | 1.00 | 19.42 |
| ATOM | 514 | N | GLN | A1780 | | 2.311 | 50.118 | 44.953 | 1.00 | 20.13 |
| ATOM | 515 | CA | GLN | A1780 | | 1.857 | 49.357 | 46.108 | 1.00 | 21.19 |
| ATOM | 516 | CB | GLN | A1780 | | 0.333 | 49.455 | 46.269 | 1.00 | 22.51 |
| ATOM | 517 | CG | GLN | A1780 | | -0.202 | 50.868 | 46.536 | 1.00 | 23.95 |
| ATOM | 518 | CD | GLN | A1780 | | 0.332 | 51.488 | 47.827 | 1.00 | 25.49 |
| ATOM | 519 | OE1 | GLN | A1780 | | 0.459 | 50.808 | 48.850 | 1.00 | 27.23 |
| ATOM | 520 | NE2 | GLN | A1780 | | 0.638 | 52.780 | 47.780 | 1.00 | 23.97 |
| ATOM | 521 | C | GLN | A1780 | | 2.282 | 47.902 | 45.956 | 1.00 | 20.64 |
| ATOM | 522 | O | GLN | A1780 | | 2.347 | 47.380 | 44.843 | 1.00 | 21.88 |
| ATOM | 523 | N | LEU | A1781 | | 2.570 | 47.256 | 47.079 | 1.00 | 20.73 |
| ATOM | 524 | CA | LEU | A1781 | | 3.036 | 45.876 | 47.069 | 1.00 | 21.47 |
| ATOM | 525 | CB | LEU | A1781 | | 3.713 | 45.521 | 48.388 | 1.00 | 21.46 |
| ATOM | 526 | CG | LEU | A1781 | | 5.100 | 46.071 | 48.689 | 1.00 | 21.99 |
| ATOM | 527 | CD1 | LEU | A1781 | | 5.488 | 45.614 | 50.080 | 1.00 | 22.28 |
| ATOM | 528 | CD2 | LEU | A1781 | | 6.135 | 45.626 | 47.661 | 1.00 | 21.64 |
| ATOM | 529 | C | LEU | A1781 | | 1.902 | 44.903 | 46.828 | 1.00 | 21.22 |
| ATOM | 530 | O | LEU | A1781 | | 0.819 | 45.046 | 47.393 | 1.00 | 21.67 |
| ATOM | 531 | N | VAL | A1782 | | 2.170 | 43.918 | 45.978 | 1.00 | 21.37 |
| ATOM | 532 | CA | VAL | A1782 | | 1.260 | 42.806 | 45.746 | 1.00 | 22.04 |
| ATOM | 533 | CB | VAL | A1782 | | 0.784 | 42.740 | 44.267 | 1.00 | 22.60 |
| ATOM | 534 | CG1 | VAL | A1782 | | -0.199 | 41.588 | 44.054 | 1.00 | 22.69 |
| ATOM | 535 | CG2 | VAL | A1782 | | 0.150 | 44.056 | 43.835 | 1.00 | 23.32 |
| ATOM | 536 | C | VAL | A1782 | | 2.023 | 41.539 | 46.097 | 1.00 | 22.39 |
| ATOM | 537 | O | VAL | A1782 | | 3.194 | 41.397 | 45.738 | 1.00 | 21.18 |
| ATOM | 538 | N | GLU | A1783 | | 1.360 | 40.634 | 46.811 | 1.00 | 23.99 |
| ATOM | 539 | CA | GLU | A1783 | | 1.940 | 39.343 | 47.151 | 1.00 | 26.36 |
| ATOM | 540 | CB | GLU | A1783 | | 1.207 | 38.716 | 48.343 | 1.00 | 27.91 |
| ATOM | 541 | CG | GLU | A1783 | | 1.650 | 39.296 | 49.681 | 1.00 | 30.05 |
| ATOM | 542 | CD | GLU | A1783 | | 0.806 | 38.847 | 50.862 | 1.00 | 31.80 |
| ATOM | 543 | OE1 | GLU | A1783 | | 0.523 | 37.636 | 50.981 | 1.00 | 32.76 |
| ATOM | 544 | OE2 | GLU | A1783 | | 0.442 | 39.711 | 51.691 | 1.00 | 33.10 |
| ATOM | 545 | C | GLU | A1783 | | 1.883 | 38.446 | 45.922 | 1.00 | 26.84 |
| ATOM | 546 | O | GLU | A1783 | | 0.820 | 38.260 | 45.331 | 1.00 | 26.82 |
| ATOM | 547 | N | MET | A1784 | | 3.038 | 37.918 | 45.531 | 1.00 | 26.91 |
| ATOM | 548 | CA | MET | A1784 | | 3.154 | 37.129 | 44.312 | 1.00 | 28.01 |
| ATOM | 549 | CB | MET | A1784 | | 3.920 | 37.911 | 43.246 | 1.00 | 28.45 |
| ATOM | 550 | CG | MET | A1784 | | 3.121 | 39.007 | 42.574 | 1.00 | 29.34 |
| ATOM | 551 | SD | MET | A1784 | | 3.956 | 39.603 | 41.107 | 1.00 | 31.11 |
| ATOM | 552 | CE | MET | A1784 | | 3.202 | 38.554 | 39.831 | 1.00 | 30.55 |
| ATOM | 553 | C | MET | A1784 | | 3.852 | 35.798 | 44.541 | 1.00 | 29.45 |
| ATOM | 554 | O | MET | A1784 | | 4.833 | 35.709 | 45.291 | 1.00 | 29.25 |
| ATOM | 555 | N | ASN | A1785 | | 3.323 | 34.764 | 43.895 | 1.00 | 30.15 |
| ATOM | 556 | CA | ASN | A1785 | | 4.019 | 33.496 | 43.752 | 1.00 | 30.98 |
| ATOM | 557 | CB | ASN | A1785 | | 3.113 | 32.323 | 44.137 | 1.00 | 34.07 |

FIGURE 3L

| | A | B | C | D E | F | G | H | I | J |
|---|---|---|---|---|---|---|---|---|---|
| ATOM | 558 | CG | ASN | A1785 | 2.797 | 32.290 | 45.624 | 1.00 | 36.49 |
| ATOM | 559 | OD1 | ASN | A1785 | 1.634 | 32.357 | 46.023 | 1.00 | 38.79 |
| ATOM | 560 | ND2 | ASN | A1785 | 3.833 | 32.180 | 46.451 | 1.00 | 36.50 |
| ATOM | 561 | C | ASN | A1785 | 4.500 | 33.380 | 42.310 | 1.00 | 29.95 |
| ATOM | 562 | O | ASN | A1785 | 3.766 | 32.927 | 41.428 | 1.00 | 29.79 |
| ATOM | 563 | N | ARG | A1786 | 5.729 | 33.833 | 42.076 | 1.00 | 28.59 |
| ATOM | 564 | CA | ARG | A1786 | 6.316 | 33.851 | 40.739 | 1.00 | 26.97 |
| ATOM | 565 | CB | ARG | A1786 | 6.333 | 35.283 | 40.176 | 1.00 | 28.27 |
| ATOM | 566 | CG | ARG | A1786 | 7.558 | 36.119 | 40.555 | 1.00 | 28.92 |
| ATOM | 567 | CD | ARG | A1786 | 7.252 | 37.544 | 40.996 | 1.00 | 30.10 |
| ATOM | 568 | NE | ARG | A1786 | 7.523 | 38.522 | 39.944 | 1.00 | 31.51 |
| ATOM | 569 | CZ | ARG | A1786 | 8.372 | 39.545 | 40.041 | 1.00 | 31.03 |
| ATOM | 570 | NH1 | ARG | A1786 | 9.076 | 39.755 | 41.146 | 1.00 | 30.07 |
| ATOM | 571 | NH2 | ARG | A1786 | 8.522 | 40.367 | 39.012 | 1.00 | 31.78 |
| ATOM | 572 | C | ARG | A1786 | 7.719 | 33.247 | 40.761 | 1.00 | 25.42 |
| ATOM | 573 | O | ARG | A1786 | 8.306 | 33.062 | 41.833 | 1.00 | 24.36 |
| ATOM | 574 | N | LEU | A1787 | 8.244 | 32.940 | 39.579 | 1.00 | 23.80 |
| ATOM | 575 | CA | LEU | A1787 | 9.594 | 32.407 | 39.445 | 1.00 | 23.25 |
| ATOM | 576 | CB | LEU | A1787 | 9.897 | 32.082 | 37.978 | 1.00 | 24.13 |
| ATOM | 577 | CG | LEU | A1787 | 9.808 | 30.616 | 37.515 | 1.00 | 25.53 |
| ATOM | 578 | CD1 | LEU | A1787 | 8.460 | 29.975 | 37.844 | 1.00 | 26.43 |
| ATOM | 579 | CD2 | LEU | A1787 | 10.097 | 30.505 | 36.023 | 1.00 | 24.69 |
| ATOM | 580 | C | LEU | A1787 | 10.611 | 33.409 | 39.994 | 1.00 | 22.79 |
| ATOM | 581 | O | LEU | A1787 | 10.492 | 34.611 | 39.746 | 1.00 | 22.08 |
| ATOM | 582 | N | PRO | A1788 | 11.592 | 32.921 | 40.753 | 1.00 | 21.74 |
| ATOM | 583 | CA | PRO | A1788 | 12.638 | 33.788 | 41.311 | 1.00 | 21.58 |
| ATOM | 584 | CB | PRO | A1788 | 13.536 | 32.810 | 42.078 | 1.00 | 21.06 |
| ATOM | 585 | CG | PRO | A1788 | 13.227 | 31.464 | 41.493 | 1.00 | 21.75 |
| ATOM | 586 | CD | PRO | A1788 | 11.772 | 31.511 | 41.151 | 1.00 | 21.58 |
| ATOM | 587 | C | PRO | A1788 | 13.436 | 34.501 | 40.222 | 1.00 | 20.34 |
| ATOM | 588 | O | PRO | A1788 | 13.538 | 33.993 | 39.105 | 1.00 | 18.40 |
| ATOM | 589 | N | GLY | A1789 | 13.971 | 35.672 | 40.551 | 1.00 | 19.90 |
| ATOM | 590 | CA | GLY | A1789 | 14.816 | 36.426 | 39.641 | 1.00 | 19.10 |
| ATOM | 591 | C | GLY | A1789 | 14.079 | 37.398 | 38.745 | 1.00 | 19.25 |
| ATOM | 592 | O | GLY | A1789 | 14.657 | 37.904 | 37.784 | 1.00 | 19.52 |
| ATOM | 593 | N | GLY | A1790 | 12.811 | 37.664 | 39.057 | 1.00 | 18.75 |
| ATOM | 594 | CA | GLY | A1790 | 11.985 | 38.544 | 38.245 | 1.00 | 18.28 |
| ATOM | 595 | C | GLY | A1790 | 11.947 | 39.992 | 38.713 | 1.00 | 17.54 |
| ATOM | 596 | O | GLY | A1790 | 11.135 | 40.785 | 38.226 | 1.00 | 16.45 |
| ATOM | 597 | N | ASN | A1791 | 12.824 | 40.342 | 39.651 | 1.00 | 16.15 |
| ATOM | 598 | CA | ASN | A1791 | 12.861 | 41.697 | 40.197 | 1.00 | 16.21 |
| ATOM | 599 | CB | ASN | A1791 | 13.752 | 41.774 | 41.446 | 1.00 | 14.87 |
| ATOM | 600 | CG | ASN | A1791 | 15.177 | 41.310 | 41.194 | 1.00 | 15.32 |
| ATOM | 601 | OD1 | ASN | A1791 | 15.411 | 40.232 | 40.637 | 1.00 | 15.17 |
| ATOM | 602 | ND2 | ASN | A1791 | 16.141 | 42.117 | 41.623 | 1.00 | 14.32 |
| ATOM | 603 | C | ASN | A1791 | 13.257 | 42.753 | 39.164 | 1.00 | 16.11 |
| ATOM | 604 | O | ASN | A1791 | 14.257 | 42.603 | 38.456 | 1.00 | 16.67 |
| ATOM | 605 | N | GLU | A1792 | 12.446 | 43.806 | 39.075 | 1.00 | 16.16 |
| ATOM | 606 | CA | GLU | A1792 | 12.679 | 44.896 | 38.123 | 1.00 | 17.95 |
| ATOM | 607 | CB | GLU | A1792 | 11.367 | 45.320 | 37.459 | 1.00 | 21.57 |
| ATOM | 608 | CG | GLU | A1792 | 10.916 | 44.369 | 36.354 | 1.00 | 26.65 |
| ATOM | 609 | CD | GLU | A1792 | 9.432 | 44.470 | 36.039 | 1.00 | 29.09 |

FIGURE 3M

| | A | B | C | D | E | F | G | H | I | J |
|---|---|---|---|---|---|---|---|---|---|---|
| ATOM | 610 | OE1 | GLU | A1792 | | 8.956 | 45.574 | 35.694 | 1.00 | 30.46 |
| ATOM | 611 | OE2 | GLU | A1792 | | 8.740 | 43.436 | 36.119 | 1.00 | 32.22 |
| ATOM | 612 | C | GLU | A1792 | | 13.382 | 46.082 | 38.788 | 1.00 | 16.48 |
| ATOM | 613 | O | GLU | A1792 | | 13.726 | 47.067 | 38.134 | 1.00 | 15.53 |
| ATOM | 614 | N | VAL | A1793 | | 13.576 | 45.974 | 40.100 | 1.00 | 14.63 |
| ATOM | 615 | CA | VAL | A1793 | | 14.417 | 46.895 | 40.859 | 1.00 | 13.89 |
| ATOM | 616 | CB | VAL | A1793 | | 13.582 | 47.814 | 41.805 | 1.00 | 14.05 |
| ATOM | 617 | CG1 | VAL | A1793 | | 12.687 | 48.758 | 40.988 | 1.00 | 14.75 |
| ATOM | 618 | CG2 | VAL | A1793 | | 12.738 | 46.992 | 42.783 | 1.00 | 13.08 |
| ATOM | 619 | C | VAL | A1793 | | 15.427 | 46.059 | 41.648 | 1.00 | 13.64 |
| ATOM | 620 | O | VAL | A1793 | | 15.217 | 44.855 | 41.848 | 1.00 | 13.55 |
| ATOM | 621 | N | GLY | A1794 | | 16.520 | 46.688 | 42.083 | 1.00 | 13.08 |
| ATOM | 622 | CA | GLY | A1794 | | 17.574 | 45.999 | 42.816 | 1.00 | 13.37 |
| ATOM | 623 | C | GLY | A1794 | | 17.296 | 45.803 | 44.294 | 1.00 | 14.14 |
| ATOM | 624 | O | GLY | A1794 | | 18.208 | 45.874 | 45.126 | 1.00 | 13.56 |
| ATOM | 625 | N | MET | A1795 | | 16.029 | 45.568 | 44.615 | 1.00 | 14.85 |
| ATOM | 626 | CA | MET | A1795 | | 15.591 | 45.294 | 45.976 | 1.00 | 14.53 |
| ATOM | 627 | CB | MET | A1795 | | 15.047 | 46.561 | 46.634 | 1.00 | 13.96 |
| ATOM | 628 | CG | MET | A1795 | | 14.809 | 46.442 | 48.144 | 1.00 | 13.92 |
| ATOM | 629 | SD | MET | A1795 | | 16.310 | 46.645 | 49.119 | 1.00 | 14.98 |
| ATOM | 630 | CE | MET | A1795 | | 16.651 | 48.415 | 48.895 | 1.00 | 12.55 |
| ATOM | 631 | C | MET | A1795 | | 14.507 | 44.228 | 45.911 | 1.00 | 14.81 |
| ATOM | 632 | O | MET | A1795 | | 13.638 | 44.274 | 45.037 | 1.00 | 15.19 |
| ATOM | 633 | N | VAL | A1796 | | 14.567 | 43.266 | 46.828 | 1.00 | 14.09 |
| ATOM | 634 | CA | VAL | A1796 | | 13.615 | 42.160 | 46.843 | 1.00 | 13.82 |
| ATOM | 635 | CB | VAL | A1796 | | 14.285 | 40.829 | 46.411 | 1.00 | 15.33 |
| ATOM | 636 | CG1 | VAL | A1796 | | 13.291 | 39.671 | 46.461 | 1.00 | 15.03 |
| ATOM | 637 | CG2 | VAL | A1796 | | 14.865 | 40.945 | 45.000 | 1.00 | 14.85 |
| ATOM | 638 | C | VAL | A1796 | | 13.004 | 42.025 | 48.237 | 1.00 | 14.26 |
| ATOM | 639 | O | VAL | A1796 | | 13.670 | 42.279 | 49.242 | 1.00 | 12.02 |
| ATOM | 640 | N | ALA | A1797 | | 11.734 | 41.632 | 48.292 | 1.00 | 14.72 |
| ATOM | 641 | CA | ALA | A1797 | | 11.037 | 41.490 | 49.566 | 1.00 | 13.89 |
| ATOM | 642 | CB | ALA | A1797 | | 10.242 | 42.755 | 49.886 | 1.00 | 14.46 |
| ATOM | 643 | C | ALA | A1797 | | 10.133 | 40.270 | 49.591 | 1.00 | 13.98 |
| ATOM | 644 | O | ALA | A1797 | | 9.509 | 39.925 | 48.589 | 1.00 | 14.12 |
| ATOM | 645 | N | PHE | A1798 | | 10.083 | 39.618 | 50.747 | 1.00 | 13.63 |
| ATOM | 646 | CA | PHE | A1798 | | 9.257 | 38.440 | 50.951 | 1.00 | 14.61 |
| ATOM | 647 | CB | PHE | A1798 | | 10.124 | 37.187 | 51.116 | 1.00 | 14.16 |
| ATOM | 648 | CG | PHE | A1798 | | 11.124 | 36.971 | 50.008 | 1.00 | 14.41 |
| ATOM | 649 | CD1 | PHE | A1798 | | 12.466 | 37.304 | 50.192 | 1.00 | 15.45 |
| ATOM | 650 | CE1 | PHE | A1798 | | 13.400 | 37.094 | 49.181 | 1.00 | 15.26 |
| ATOM | 651 | CZ | PHE | A1798 | | 12.993 | 36.541 | 47.963 | 1.00 | 14.94 |
| ATOM | 652 | CE2 | PHE | A1798 | | 11.656 | 36.200 | 47.771 | 1.00 | 14.86 |
| ATOM | 653 | CD2 | PHE | A1798 | | 10.732 | 36.413 | 48.794 | 1.00 | 13.71 |
| ATOM | 654 | C | PHE | A1798 | | 8.440 | 38.623 | 52.218 | 1.00 | 15.84 |
| ATOM | 655 | O | PHE | A1798 | | 8.913 | 39.221 | 53.185 | 1.00 | 15.68 |
| ATOM | 656 | N | LYS | A1799 | | 7.206 | 38.129 | 52.200 | 1.00 | 15.36 |
| ATOM | 657 | CA | LYS | A1799 | | 6.478 | 37.898 | 53.436 | 1.00 | 17.71 |
| ATOM | 658 | CB | LYS | A1799 | | 5.015 | 38.342 | 53.337 | 1.00 | 19.63 |
| ATOM | 659 | CG | LYS | A1799 | | 4.296 | 38.295 | 54.686 | 1.00 | 23.85 |
| ATOM | 660 | CD | LYS | A1799 | | 2.923 | 38.937 | 54.645 | 1.00 | 25.85 |
| ATOM | 661 | CE | LYS | A1799 | | 2.054 | 38.397 | 55.769 | 1.00 | 27.59 |

FIGURE 3N

|  | A | B | C | D | E | F | G | H | I | J |
|---|---|---|---|---|---|---|---|---|---|---|
| ATOM | 662 | NZ | LYS | A1799 | 0.750 | 39.110 | 55.859 | 1.00 | 28.76 |
| ATOM | 663 | C | LYS | A1799 | 6.573 | 36.405 | 53.731 | 1.00 | 16.36 |
| ATOM | 664 | O | LYS | A1799 | 6.138 | 35.582 | 52.923 | 1.00 | 15.92 |
| ATOM | 665 | N | MET | A1800 | 7.162 | 36.069 | 54.875 | 1.00 | 15.75 |
| ATOM | 666 | CA | MET | A1800 | 7.386 | 34.676 | 55.256 | 1.00 | 15.87 |
| ATOM | 667 | CB | MET | A1800 | 8.870 | 34.403 | 55.516 | 1.00 | 16.94 |
| ATOM | 668 | CG | MET | A1800 | 9.797 | 34.711 | 54.353 | 1.00 | 18.24 |
| ATOM | 669 | SD | MET | A1800 | 11.464 | 34.145 | 54.692 | 1.00 | 20.89 |
| ATOM | 670 | CE | MET | A1800 | 12.288 | 34.697 | 53.251 | 1.00 | 20.80 |
| ATOM | 671 | C | MET | A1800 | 6.604 | 34.310 | 56.501 | 1.00 | 17.10 |
| ATOM | 672 | O | MET | A1800 | 6.539 | 35.086 | 57.459 | 1.00 | 13.75 |
| ATOM | 673 | N | ARG | A1801 | 6.008 | 33.124 | 56.473 | 1.00 | 16.55 |
| ATOM | 674 | CA | ARG | A1801 | 5.401 | 32.538 | 57.655 | 1.00 | 18.29 |
| ATOM | 675 | CB | ARG | A1801 | 3.923 | 32.213 | 57.418 | 1.00 | 20.70 |
| ATOM | 676 | CG | ARG | A1801 | 3.229 | 31.543 | 58.612 | 1.00 | 23.31 |
| ATOM | 677 | CD | ARG | A1801 | 1.710 | 31.552 | 58.554 | 1.00 | 26.48 |
| ATOM | 678 | NE | ARG | A1801 | 1.159 | 32.871 | 58.862 | 1.00 | 30.71 |
| ATOM | 679 | CZ | ARG | A1801 | 0.156 | 33.449 | 58.204 | 1.00 | 33.19 |
| ATOM | 680 | NH1 | ARG | A1801 | -0.433 | 32.830 | 57.183 | 1.00 | 34.55 |
| ATOM | 681 | NH2 | ARG | A1801 | -0.262 | 34.655 | 58.568 | 1.00 | 33.88 |
| ATOM | 682 | C | ARG | A1801 | 6.174 | 31.275 | 57.990 | 1.00 | 17.85 |
| ATOM | 683 | O | ARG | A1801 | 6.281 | 30.367 | 57.162 | 1.00 | 18.59 |
| ATOM | 684 | N | PHE | A1802 | 6.734 | 31.218 | 59.189 | 1.00 | 18.36 |
| ATOM | 685 | CA | PHE | A1802 | 7.377 | 29.980 | 59.607 | 1.00 | 19.45 |
| ATOM | 686 | CB | PHE | A1802 | 8.899 | 30.029 | 59.464 | 1.00 | 20.96 |
| ATOM | 687 | CG | PHE | A1802 | 9.518 | 31.329 | 59.862 | 1.00 | 22.12 |
| ATOM | 688 | CD1 | PHE | A1802 | 9.739 | 31.629 | 61.197 | 1.00 | 23.31 |
| ATOM | 689 | CE1 | PHE | A1802 | 10.332 | 32.834 | 61.562 | 1.00 | 22.42 |
| ATOM | 690 | CZ | PHE | A1802 | 10.724 | 33.735 | 60.589 | 1.00 | 20.93 |
| ATOM | 691 | CE2 | PHE | A1802 | 10.526 | 33.440 | 59.255 | 1.00 | 23.53 |
| ATOM | 692 | CD2 | PHE | A1802 | 9.927 | 32.236 | 58.893 | 1.00 | 22.61 |
| ATOM | 693 | C | PHE | A1802 | 6.979 | 29.462 | 60.978 | 1.00 | 16.68 |
| ATOM | 694 | O | PHE | A1802 | 6.603 | 30.225 | 61.872 | 1.00 | 14.10 |
| ATOM | 695 | N | LYS | A1803 | 7.077 | 28.145 | 61.115 | 1.00 | 14.62 |
| ATOM | 696 | CA | LYS | A1803 | 6.718 | 27.453 | 62.340 | 1.00 | 13.57 |
| ATOM | 697 | CB | LYS | A1803 | 5.974 | 26.156 | 62.014 | 1.00 | 13.95 |
| ATOM | 698 | CG | LYS | A1803 | 4.797 | 26.366 | 61.065 | 1.00 | 15.68 |
| ATOM | 699 | CD | LYS | A1803 | 4.089 | 25.063 | 60.693 | 1.00 | 14.89 |
| ATOM | 700 | CE | LYS | A1803 | 2.825 | 25.354 | 59.893 | 1.00 | 15.61 |
| ATOM | 701 | NZ | LYS | A1803 | 2.053 | 24.119 | 59.582 | 1.00 | 18.82 |
| ATOM | 702 | C | LYS | A1803 | 7.963 | 27.190 | 63.177 | 1.00 | 12.35 |
| ATOM | 703 | O | LYS | A1803 | 8.979 | 26.708 | 62.670 | 1.00 | 12.62 |
| ATOM | 704 | N | THR | A1804 | 7.874 | 27.539 | 64.458 | 1.00 | 11.09 |
| ATOM | 705 | CA | THR | A1804 | 8.970 | 27.392 | 65.408 | 1.00 | 11.80 |
| ATOM | 706 | CB | THR | A1804 | 9.625 | 28.761 | 65.703 | 1.00 | 11.85 |
| ATOM | 707 | OG1 | THR | A1804 | 8.661 | 29.623 | 66.319 | 1.00 | 11.46 |
| ATOM | 708 | CG2 | THR | A1804 | 10.000 | 29.506 | 64.412 | 1.00 | 11.71 |
| ATOM | 709 | C | THR | A1804 | 8.394 | 26.828 | 66.700 | 1.00 | 12.86 |
| ATOM | 710 | O | THR | A1804 | 7.179 | 26.744 | 66.835 | 1.00 | 11.57 |
| ATOM | 711 | N | GLN | A1805 | 9.252 | 26.464 | 67.653 | 1.00 | 13.94 |
| ATOM | 712 | CA | GLN | A1805 | 8.777 | 25.976 | 68.954 | 1.00 | 14.59 |
| ATOM | 713 | CB | BGLN | A1805 | 9.924 | 25.523 | 69.872 | 0.50 | 16.11 |

FIGURE 3O

| | A | B | C | D E | F | G | H | I | J |
|---|---|---|---|---|---|---|---|---|---|
| ATOM | 714 | CB | AGLN | A1805 | 9.956 | 25.578 | 69.846 | 0.50 | 14.71 |
| ATOM | 715 | CG | BGLN | A1805 | 11.320 | 25.961 | 69.457 | 0.50 | 18.33 |
| ATOM | 716 | CG | AGLN | A1805 | 9.605 | 24.550 | 70.914 | 0.50 | 15.31 |
| ATOM | 717 | CD | BGLN | A1805 | 12.210 | 24.797 | 69.050 | 0.50 | 18.73 |
| ATOM | 718 | CD | AGLN | A1805 | 10.524 | 24.606 | 72.121 | 0.50 | 15.09 |
| ATOM | 719 | OE1 | BGLN | A1805 | 11.883 | 23.636 | 69.299 | 0.50 | 19.01 |
| ATOM | 720 | OE1 | AGLN | A1805 | 11.707 | 24.929 | 71.998 | 0.50 | 16.16 |
| ATOM | 721 | NE2 | BGLN | A1805 | 13.340 | 25.108 | 68.423 | 0.50 | 19.04 |
| ATOM | 722 | NE2 | AGLN | A1805 | 9.983 | 24.284 | 73.289 | 0.50 | 14.25 |
| ATOM | 723 | C | GLN | A1805 | 7.915 | 27.005 | 69.672 | 1.00 | 13.94 |
| ATOM | 724 | O | GLN | A1805 | 6.944 | 26.650 | 70.335 | 1.00 | 13.27 |
| ATOM | 725 | N | GLU | A1806 | 8.282 | 28.278 | 69.533 | 1.00 | 12.29 |
| ATOM | 726 | CA | GLU | A1806 | 7.536 | 29.380 | 70.124 | 1.00 | 12.05 |
| ATOM | 727 | CB | GLU | A1806 | 8.332 | 30.682 | 70.006 | 1.00 | 11.54 |
| ATOM | 728 | CG | GLU | A1806 | 9.536 | 30.761 | 70.930 | 1.00 | 13.47 |
| ATOM | 729 | CD | GLU | A1806 | 10.724 | 29.949 | 70.445 | 1.00 | 14.39 |
| ATOM | 730 | OE1 | GLU | A1806 | 10.941 | 29.847 | 69.218 | 1.00 | 14.85 |
| ATOM | 731 | OE2 | GLU | A1806 | 11.446 | 29.409 | 71.301 | 1.00 | 18.06 |
| ATOM | 732 | C | GLU | A1806 | 6.184 | 29.550 | 69.446 | 1.00 | 12.16 |
| ATOM | 733 | O | GLU | A1806 | 5.193 | 29.856 | 70.102 | 1.00 | 14.60 |
| ATOM | 734 | N | TYR | A1807 | 6.157 | 29.357 | 68.128 | 1.00 | 13.02 |
| ATOM | 735 | CA | TYR | A1807 | 4.932 | 29.495 | 67.341 | 1.00 | 12.08 |
| ATOM | 736 | CB | TYR | A1807 | 4.912 | 30.850 | 66.622 | 1.00 | 11.49 |
| ATOM | 737 | CG | TYR | A1807 | 4.948 | 32.005 | 67.590 | 1.00 | 11.40 |
| ATOM | 738 | CD1 | TYR | A1807 | 6.138 | 32.688 | 67.845 | 1.00 | 10.06 |
| ATOM | 739 | CE1 | TYR | A1807 | 6.181 | 33.742 | 68.755 | 1.00 | 11.08 |
| ATOM | 740 | CZ | TYR | A1807 | 5.024 | 34.112 | 69.421 | 1.00 | 11.24 |
| ATOM | 741 | OH | TYR | A1807 | 5.057 | 35.152 | 70.314 | 1.00 | 11.33 |
| ATOM | 742 | CE2 | TYR | A1807 | 3.833 | 33.443 | 69.190 | 1.00 | 10.16 |
| ATOM | 743 | CD2 | TYR | A1807 | 3.799 | 32.394 | 68.282 | 1.00 | 10.42 |
| ATOM | 744 | C | TYR | A1807 | 4.755 | 28.339 | 66.356 | 1.00 | 12.93 |
| ATOM | 745 | O | TYR | A1807 | 5.049 | 28.484 | 65.161 | 1.00 | 12.77 |
| ATOM | 746 | N | PRO | A1808 | 4.293 | 27.188 | 66.859 | 1.00 | 14.04 |
| ATOM | 747 | CA | PRO | A1808 | 4.132 | 25.993 | 66.019 | 1.00 | 14.59 |
| ATOM | 748 | CB | PRO | A1808 | 3.675 | 24.908 | 67.011 | 1.00 | 14.42 |
| ATOM | 749 | CG | PRO | A1808 | 3.125 | 25.649 | 68.178 | 1.00 | 14.83 |
| ATOM | 750 | CD | PRO | A1808 | 3.919 | 26.923 | 68.263 | 1.00 | 14.15 |
| ATOM | 751 | C | PRO | A1808 | 3.111 | 26.177 | 64.899 | 1.00 | 15.39 |
| ATOM | 752 | O | PRO | A1808 | 3.216 | 25.481 | 63.892 | 1.00 | 16.39 |
| ATOM | 753 | N | GLU | A1809 | 2.156 | 27.090 | 65.068 | 1.00 | 16.27 |
| ATOM | 754 | CA | GLU | A1809 | 1.175 | 27.383 | 64.021 | 1.00 | 17.17 |
| ATOM | 755 | CB | GLU | A1809 | -0.215 | 27.642 | 64.619 | 1.00 | 20.47 |
| ATOM | 756 | CG | GLU | A1809 | -0.949 | 26.394 | 65.102 | 1.00 | 24.58 |
| ATOM | 757 | CD | GLU | A1809 | -1.152 | 25.358 | 64.009 | 1.00 | 27.13 |
| ATOM | 758 | OE1 | GLU | A1809 | -0.651 | 24.226 | 64.169 | 1.00 | 28.82 |
| ATOM | 759 | OE2 | GLU | A1809 | -1.807 | 25.672 | 62.986 | 1.00 | 28.60 |
| ATOM | 760 | C | GLU | A1809 | 1.613 | 28.552 | 63.128 | 1.00 | 14.98 |
| ATOM | 761 | O | GLU | A1809 | 0.894 | 28.939 | 62.201 | 1.00 | 12.94 |
| ATOM | 762 | N | GLY | A1810 | 2.787 | 29.114 | 63.414 | 1.00 | 12.67 |
| ATOM | 763 | CA | GLY | A1810 | 3.405 | 30.080 | 62.522 | 1.00 | 11.70 |
| ATOM | 764 | C | GLY | A1810 | 3.550 | 31.492 | 63.062 | 1.00 | 12.71 |
| ATOM | 765 | O | GLY | A1810 | 2.702 | 31.982 | 63.815 | 1.00 | 14.02 |

FIGURE 3P

|  | A | B | C | D | E | F | G | H | I | J |
|---|---|---|---|---|---|---|---|---|---|---|
| ATOM | 766 | N | ARG | A1811 | 4.642 | 32.139 | 62.663 | 1.00 | 10.21 |
| ATOM | 767 | CA | ARG | A1811 | 4.870 | 33.562 | 62.913 | 1.00 | 11.66 |
| ATOM | 768 | CB | ARG | A1811 | 5.940 | 33.771 | 63.994 | 1.00 | 11.49 |
| ATOM | 769 | CG | ARG | A1811 | 7.341 | 33.279 | 63.618 | 1.00 | 12.04 |
| ATOM | 770 | CD | ARG | A1811 | 8.390 | 33.455 | 64.709 | 1.00 | 11.91 |
| ATOM | 771 | NE | ARG | A1811 | 8.543 | 34.852 | 65.120 | 1.00 | 12.67 |
| ATOM | 772 | CZ | ARG | A1811 | 9.055 | 35.247 | 66.281 | 1.00 | 11.93 |
| ATOM | 773 | NH1 | ARG | A1811 | 9.137 | 36.539 | 66.559 | 1.00 | 13.46 |
| ATOM | 774 | NH2 | ARG | A1811 | 9.474 | 34.356 | 67.170 | 1.00 | 12.84 |
| ATOM | 775 | C | ARG | A1811 | 5.304 | 34.209 | 61.604 | 1.00 | 12.20 |
| ATOM | 776 | O | ARG | A1811 | 5.992 | 33.577 | 60.793 | 1.00 | 12.42 |
| ATOM | 777 | N | ASP | A1812 | 4.886 | 35.455 | 61.397 | 1.00 | 11.10 |
| ATOM | 778 | CA | ASP | A1812 | 5.184 | 36.179 | 60.168 | 1.00 | 11.66 |
| ATOM | 779 | CB | ASP | A1812 | 3.966 | 36.983 | 59.700 | 1.00 | 13.31 |
| ATOM | 780 | CG | ASP | A1812 | 2.780 | 36.110 | 59.323 | 1.00 | 16.37 |
| ATOM | 781 | OD1 | ASP | A1812 | 2.954 | 34.891 | 59.105 | 1.00 | 16.39 |
| ATOM | 782 | OD2 | ASP | A1812 | 1.624 | 36.571 | 59.216 | 1.00 | 18.35 |
| ATOM | 783 | C | ASP | A1812 | 6.361 | 37.131 | 60.339 | 1.00 | 11.90 |
| ATOM | 784 | O | ASP | A1812 | 6.566 | 37.699 | 61.418 | 1.00 | 9.77 |
| ATOM | 785 | N | VAL | A1813 | 7.133 | 37.290 | 59.268 | 1.00 | 11.66 |
| ATOM | 786 | CA | VAL | A1813 | 8.143 | 38.348 | 59.174 | 1.00 | 12.42 |
| ATOM | 787 | CB | VAL | A1813 | 9.580 | 37.856 | 59.515 | 1.00 | 12.99 |
| ATOM | 788 | CG1 | VAL | A1813 | 9.650 | 37.230 | 60.914 | 1.00 | 12.38 |
| ATOM | 789 | CG2 | VAL | A1813 | 10.112 | 36.893 | 58.448 | 1.00 | 11.95 |
| ATOM | 790 | C | VAL | A1813 | 8.151 | 38.909 | 57.756 | 1.00 | 12.79 |
| ATOM | 791 | O | VAL | A1813 | 7.697 | 38.247 | 56.814 | 1.00 | 13.96 |
| ATOM | 792 | N | ILE | A1814 | 8.666 | 40.124 | 57.610 | 1.00 | 13.44 |
| ATOM | 793 | CA | ILE | A1814 | 8.979 | 40.662 | 56.290 | 1.00 | 15.14 |
| ATOM | 794 | CB | ILE | A1814 | 8.447 | 42.111 | 56.106 | 1.00 | 14.35 |
| ATOM | 795 | CG1 | ILE | A1814 | 6.929 | 42.200 | 56.344 | 1.00 | 16.75 |
| ATOM | 796 | CD1 | ILE | A1814 | 6.047 | 41.593 | 55.258 | 1.00 | 16.71 |
| ATOM | 797 | CG2 | ILE | A1814 | 8.853 | 42.675 | 54.732 | 1.00 | 12.54 |
| ATOM | 798 | C | ILE | A1814 | 10.491 | 40.634 | 56.110 | 1.00 | 13.67 |
| ATOM | 799 | O | ILE | A1814 | 11.236 | 41.112 | 56.966 | 1.00 | 14.50 |
| ATOM | 800 | N | VAL | A1815 | 10.934 | 40.062 | 54.998 | 1.00 | 13.63 |
| ATOM | 801 | CA | VAL | A1815 | 12.350 | 40.071 | 54.649 | 1.00 | 13.82 |
| ATOM | 802 | CB | VAL | A1815 | 12.868 | 38.650 | 54.314 | 1.00 | 13.41 |
| ATOM | 803 | CG1 | VAL | A1815 | 14.336 | 38.688 | 53.874 | 1.00 | 15.45 |
| ATOM | 804 | CG2 | VAL | A1815 | 12.714 | 37.731 | 55.515 | 1.00 | 12.01 |
| ATOM | 805 | C | VAL | A1815 | 12.536 | 41.005 | 53.462 | 1.00 | 14.55 |
| ATOM | 806 | O | VAL | A1815 | 11.841 | 40.874 | 52.451 | 1.00 | 15.44 |
| ATOM | 807 | N | ILE | A1816 | 13.446 | 41.965 | 53.608 | 1.00 | 13.80 |
| ATOM | 808 | CA | ILE | A1816 | 13.808 | 42.882 | 52.526 | 1.00 | 12.98 |
| ATOM | 809 | CB | ILE | A1816 | 13.515 | 44.362 | 52.900 | 1.00 | 12.43 |
| ATOM | 810 | CG1 | ILE | A1816 | 12.124 | 44.515 | 53.522 | 1.00 | 12.78 |
| ATOM | 811 | CD1 | ILE | A1816 | 11.919 | 45.840 | 54.242 | 1.00 | 13.57 |
| ATOM | 812 | CG2 | ILE | A1816 | 13.683 | 45.295 | 51.676 | 1.00 | 12.69 |
| ATOM | 813 | C | ILE | A1816 | 15.296 | 42.712 | 52.299 | 1.00 | 15.04 |
| ATOM | 814 | O | ILE | A1816 | 16.058 | 42.611 | 53.255 | 1.00 | 12.75 |
| ATOM | 815 | N | GLY | A1817 | 15.714 | 42.667 | 51.040 | 1.00 | 14.63 |
| ATOM | 816 | CA | GLY | A1817 | 17.129 | 42.602 | 50.746 | 1.00 | 15.18 |
| ATOM | 817 | C | GLY | A1817 | 17.489 | 43.301 | 49.461 | 1.00 | 15.29 |

FIGURE 3Q

|      | A | B | C | D | E | F | G | H | I | J |
|---|---|---|---|---|---|---|---|---|---|---|
| ATOM | 818 | O | GLY | A1817 | | 16.725 | 43.253 | 48.493 | 1.00 | 14.88 |
| ATOM | 819 | N | ASN | A1818 | | 18.651 | 43.951 | 49.449 | 1.00 | 14.07 |
| ATOM | 820 | CA | ASN | A1818 | | 19.221 | 44.426 | 48.194 | 1.00 | 14.92 |
| ATOM | 821 | CB | ASN | A1818 | | 20.532 | 45.174 | 48.399 | 1.00 | 14.37 |
| ATOM | 822 | CG | ASN | A1818 | | 20.395 | 46.347 | 49.320 | 1.00 | 15.30 |
| ATOM | 823 | OD1 | ASN | A1818 | | 20.018 | 47.450 | 48.903 | 1.00 | 17.18 |
| ATOM | 824 | ND2 | ASN | A1818 | | 20.719 | 46.132 | 50.581 | 1.00 | 12.77 |
| ATOM | 825 | C | ASN | A1818 | | 19.521 | 43.225 | 47.331 | 1.00 | 16.69 |
| ATOM | 826 | O | ASN | A1818 | | 19.859 | 42.155 | 47.844 | 1.00 | 15.90 |
| ATOM | 827 | N | ASP | A1819 | | 19.393 | 43.410 | 46.023 | 1.00 | 16.45 |
| ATOM | 828 | CA | ASP | A1819 | | 19.922 | 42.453 | 45.068 | 1.00 | 15.12 |
| ATOM | 829 | CB | ASP | A1819 | | 18.945 | 42.259 | 43.916 | 1.00 | 14.08 |
| ATOM | 830 | CG | ASP | A1819 | | 19.449 | 41.269 | 42.879 | 1.00 | 14.03 |
| ATOM | 831 | OD1 | ASP | A1819 | | 20.511 | 40.638 | 43.090 | 1.00 | 12.44 |
| ATOM | 832 | OD2 | ASP | A1819 | | 18.836 | 41.067 | 41.816 | 1.00 | 12.95 |
| ATOM | 833 | C | ASP | A1819 | | 21.248 | 43.009 | 44.556 | 1.00 | 15.86 |
| ATOM | 834 | O | ASP | A1819 | | 21.271 | 43.869 | 43.672 | 1.00 | 14.00 |
| ATOM | 835 | N | ILE | A1820 | | 22.346 | 42.516 | 45.122 | 1.00 | 14.88 |
| ATOM | 836 | CA | ILE | A1820 | | 23.677 | 42.991 | 44.756 | 1.00 | 15.77 |
| ATOM | 837 | CB | ILE | A1820 | | 24.743 | 42.487 | 45.778 | 1.00 | 16.32 |
| ATOM | 838 | CG1 | ILE | A1820 | | 26.020 | 43.328 | 45.679 | 1.00 | 17.56 |
| ATOM | 839 | CD1 | ILE | A1820 | | 26.718 | 43.586 | 46.995 | 1.00 | 18.11 |
| ATOM | 840 | CG2 | ILE | A1820 | | 25.019 | 40.989 | 45.589 | 1.00 | 16.30 |
| ATOM | 841 | C | ILE | A1820 | | 24.065 | 42.648 | 43.309 | 1.00 | 15.43 |
| ATOM | 842 | O | ILE | A1820 | | 25.047 | 43.175 | 42.791 | 1.00 | 16.12 |
| ATOM | 843 | N | THR | A1821 | | 23.297 | 41.769 | 42.666 | 1.00 | 15.38 |
| ATOM | 844 | CA | THR | A1821 | | 23.533 | 41.436 | 41.261 | 1.00 | 14.83 |
| ATOM | 845 | CB | THR | A1821 | | 23.092 | 39.988 | 40.918 | 1.00 | 15.19 |
| ATOM | 846 | OG1 | THR | A1821 | | 21.659 | 39.909 | 40.889 | 1.00 | 14.45 |
| ATOM | 847 | CG2 | THR | A1821 | | 23.500 | 39.003 | 42.015 | 1.00 | 13.58 |
| ATOM | 848 | C | THR | A1821 | | 22.837 | 42.425 | 40.329 | 1.00 | 15.34 |
| ATOM | 849 | O | THR | A1821 | | 23.129 | 42.467 | 39.129 | 1.00 | 14.47 |
| ATOM | 850 | N | PHE | A1822 | | 21.921 | 43.215 | 40.889 | 1.00 | 15.14 |
| ATOM | 851 | CA | PHE | A1822 | | 21.140 | 44.186 | 40.126 | 1.00 | 14.72 |
| ATOM | 852 | CB | PHE | A1822 | | 19.676 | 44.153 | 40.582 | 1.00 | 14.93 |
| ATOM | 853 | CG | PHE | A1822 | | 18.734 | 44.941 | 39.703 | 1.00 | 16.06 |
| ATOM | 854 | CD1 | PHE | A1822 | | 17.766 | 44.287 | 38.951 | 1.00 | 16.74 |
| ATOM | 855 | CE1 | PHE | A1822 | | 16.883 | 45.007 | 38.138 | 1.00 | 18.29 |
| ATOM | 856 | CZ | PHE | A1822 | | 16.962 | 46.396 | 38.086 | 1.00 | 16.86 |
| ATOM | 857 | CE2 | PHE | A1822 | | 17.917 | 47.061 | 38.844 | 1.00 | 15.49 |
| ATOM | 858 | CD2 | PHE | A1822 | | 18.795 | 46.338 | 39.647 | 1.00 | 15.79 |
| ATOM | 859 | C | PHE | A1822 | | 21.725 | 45.575 | 40.334 | 1.00 | 15.30 |
| ATOM | 860 | O | PHE | A1822 | | 21.571 | 46.158 | 41.411 | 1.00 | 14.34 |
| ATOM | 861 | N | ARG | A1823 | | 22.388 | 46.098 | 39.299 | 1.00 | 13.60 |
| ATOM | 862 | CA | ARG | A1823 | | 23.067 | 47.394 | 39.364 | 1.00 | 15.18 |
| ATOM | 863 | CB | ARG | A1823 | | 22.066 | 48.553 | 39.237 | 1.00 | 16.29 |
| ATOM | 864 | CG | ARG | A1823 | | 21.257 | 48.554 | 37.942 | 1.00 | 19.90 |
| ATOM | 865 | CD | ARG | A1823 | | 21.375 | 49.841 | 37.168 | 1.00 | 24.13 |
| ATOM | 866 | NE | ARG | A1823 | | 20.080 | 50.446 | 36.888 | 1.00 | 27.45 |
| ATOM | 867 | CZ | ARG | A1823 | | 19.912 | 51.689 | 36.447 | 1.00 | 28.04 |
| ATOM | 868 | NH1 | ARG | A1823 | | 20.959 | 52.483 | 36.242 | 1.00 | 27.13 |
| ATOM | 869 | NH2 | ARG | A1823 | | 18.687 | 52.143 | 36.217 | 1.00 | 28.95 |

FIGURE 3R

|  | A | B | C | D | E | F | G | H | I | J |
|---|---|---|---|---|---|---|---|---|---|---|
| ATOM | 870 | C | ARG | A1823 | | 23.886 | 47.516 | 40.651 | 1.00 | 15.47 |
| ATOM | 871 | O | ARG | A1823 | | 23.764 | 48.495 | 41.392 | 1.00 | 13.98 |
| ATOM | 872 | N | ILE | A1824 | | 24.700 | 46.488 | 40.903 | 1.00 | 15.92 |
| ATOM | 873 | CA | ILE | A1824 | | 25.572 | 46.369 | 42.084 | 1.00 | 16.59 |
| ATOM | 874 | CB | ILE | A1824 | | 26.937 | 47.114 | 41.868 | 1.00 | 16.95 |
| ATOM | 875 | CG1 | ILE | A1824 | | 26.772 | 48.638 | 41.861 | 1.00 | 18.97 |
| ATOM | 876 | CD1 | ILE | A1824 | | 28.038 | 49.373 | 42.204 | 1.00 | 19.21 |
| ATOM | 877 | CG2 | ILE | A1824 | | 27.603 | 46.649 | 40.566 | 1.00 | 19.89 |
| ATOM | 878 | C | ILE | A1824 | | 24.918 | 46.674 | 43.455 | 1.00 | 15.68 |
| ATOM | 879 | O | ILE | A1824 | | 25.585 | 47.087 | 44.404 | 1.00 | 15.92 |
| ATOM | 880 | N | GLY | A1825 | | 23.613 | 46.444 | 43.558 | 1.00 | 15.13 |
| ATOM | 881 | CA | GLY | A1825 | | 22.898 | 46.695 | 44.800 | 1.00 | 14.50 |
| ATOM | 882 | C | GLY | A1825 | | 22.852 | 48.166 | 45.181 | 1.00 | 14.48 |
| ATOM | 883 | O | GLY | A1825 | | 22.754 | 48.511 | 46.360 | 1.00 | 14.36 |
| ATOM | 884 | N | SER | A1826 | | 22.939 | 49.035 | 44.181 | 1.00 | 13.99 |
| ATOM | 885 | CA | SER | A1826 | | 22.818 | 50.467 | 44.402 | 1.00 | 13.28 |
| ATOM | 886 | CB | SER | A1826 | | 23.321 | 51.249 | 43.187 | 1.00 | 11.63 |
| ATOM | 887 | OG | SER | A1826 | | 22.637 | 50.863 | 42.006 | 1.00 | 12.56 |
| ATOM | 888 | C | SER | A1826 | | 21.366 | 50.817 | 44.701 | 1.00 | 13.01 |
| ATOM | 889 | O | SER | A1826 | | 20.455 | 50.076 | 44.311 | 1.00 | 13.03 |
| ATOM | 890 | N | PHE | A1827 | | 21.160 | 51.932 | 45.403 | 1.00 | 11.18 |
| ATOM | 891 | CA | PHE | A1827 | | 19.825 | 52.369 | 45.798 | 1.00 | 11.90 |
| ATOM | 892 | CB | PHE | A1827 | | 19.823 | 52.961 | 47.212 | 1.00 | 10.30 |
| ATOM | 893 | CG | PHE | A1827 | | 19.998 | 51.960 | 48.322 | 1.00 | 11.80 |
| ATOM | 894 | CD1 | PHE | A1827 | | 21.254 | 51.444 | 48.627 | 1.00 | 11.89 |
| ATOM | 895 | CE1 | PHE | A1827 | | 21.427 | 50.553 | 49.695 | 1.00 | 13.81 |
| ATOM | 896 | CZ | PHE | A1827 | | 20.331 | 50.183 | 50.477 | 1.00 | 14.14 |
| ATOM | 897 | CE2 | PHE | A1827 | | 19.074 | 50.703 | 50.186 | 1.00 | 14.13 |
| ATOM | 898 | CD2 | PHE | A1827 | | 18.915 | 51.592 | 49.113 | 1.00 | 12.84 |
| ATOM | 899 | C | PHE | A1827 | | 19.369 | 53.468 | 44.856 | 1.00 | 10.84 |
| ATOM | 900 | O | PHE | A1827 | | 19.830 | 54.606 | 44.967 | 1.00 | 10.27 |
| ATOM | 901 | N | GLY | A1828 | | 18.483 | 53.125 | 43.925 | 1.00 | 11.02 |
| ATOM | 902 | CA | GLY | A1828 | | 17.810 | 54.115 | 43.104 | 1.00 | 9.63 |
| ATOM | 903 | C | GLY | A1828 | | 16.408 | 54.321 | 43.645 | 1.00 | 11.19 |
| ATOM | 904 | O | GLY | A1828 | | 16.049 | 53.724 | 44.663 | 1.00 | 12.35 |
| ATOM | 905 | N | PRO | A1829 | | 15.606 | 55.151 | 42.987 | 1.00 | 11.94 |
| ATOM | 906 | CA | PRO | A1829 | | 14.257 | 55.449 | 43.486 | 1.00 | 14.56 |
| ATOM | 907 | CB | PRO | A1829 | | 13.734 | 56.464 | 42.468 | 1.00 | 14.50 |
| ATOM | 908 | CG | PRO | A1829 | | 14.993 | 57.080 | 41.909 | 1.00 | 14.46 |
| ATOM | 909 | CD | PRO | A1829 | | 15.910 | 55.901 | 41.753 | 1.00 | 12.55 |
| ATOM | 910 | C | PRO | A1829 | | 13.339 | 54.218 | 43.592 | 1.00 | 14.71 |
| ATOM | 911 | O | PRO | A1829 | | 12.565 | 54.138 | 44.546 | 1.00 | 14.54 |
| ATOM | 912 | N | GLY | A1830 | | 13.442 | 53.279 | 42.652 | 1.00 | 14.89 |
| ATOM | 913 | CA | GLY | A1830 | | 12.629 | 52.073 | 42.676 | 1.00 | 13.08 |
| ATOM | 914 | C | GLY | A1830 | | 12.983 | 51.148 | 43.830 | 1.00 | 14.02 |
| ATOM | 915 | O | GLY | A1830 | | 12.105 | 50.552 | 44.465 | 1.00 | 13.63 |
| ATOM | 916 | N | GLU | A1831 | | 14.277 | 51.027 | 44.104 | 1.00 | 12.44 |
| ATOM | 917 | CA | GLU | A1831 | | 14.753 | 50.218 | 45.223 | 1.00 | 12.58 |
| ATOM | 918 | CB | GLU | A1831 | | 16.286 | 50.142 | 45.211 | 1.00 | 11.46 |
| ATOM | 919 | CG | GLU | A1831 | | 16.871 | 49.301 | 44.083 | 1.00 | 11.30 |
| ATOM | 920 | CD | GLU | A1831 | | 16.842 | 49.989 | 42.721 | 1.00 | 12.31 |
| ATOM | 921 | OE1 | GLU | A1831 | | 16.842 | 49.287 | 41.689 | 1.00 | 12.29 |

FIGURE 3S

|  | A | B | C | D | E | F | G | H | I | J |
|---|---|---|---|---|---|---|---|---|---|---|
| ATOM | 922 | OE2 | GLU | A1831 | 16.825 | 51.231 | 42.669 | 1.00 | 12.19 |
| ATOM | 923 | C | GLU | A1831 | 14.257 | 50.811 | 46.543 | 1.00 | 12.30 |
| ATOM | 924 | O | GLU | A1831 | 13.826 | 50.082 | 47.445 | 1.00 | 10.71 |
| ATOM | 925 | N | ASP | A1832 | 14.309 | 52.138 | 46.641 | 1.00 | 11.76 |
| ATOM | 926 | CA | ASP | A1832 | 13.867 | 52.843 | 47.842 | 1.00 | 13.45 |
| ATOM | 927 | CB | ASP | A1832 | 14.204 | 54.334 | 47.744 | 1.00 | 14.92 |
| ATOM | 928 | CG | ASP | A1832 | 15.700 | 54.590 | 47.630 | 1.00 | 16.09 |
| ATOM | 929 | OD1 | ASP | A1832 | 16.074 | 55.669 | 47.132 | 1.00 | 17.38 |
| ATOM | 930 | OD2 | ASP | A1832 | 16.577 | 53.774 | 47.998 | 1.00 | 14.79 |
| ATOM | 931 | C | ASP | A1832 | 12.366 | 52.642 | 48.071 | 1.00 | 13.40 |
| ATOM | 932 | O | ASP | A1832 | 11.934 | 52.406 | 49.200 | 1.00 | 12.96 |
| ATOM | 933 | N | LEU | A1833 | 11.591 | 52.713 | 46.991 | 1.00 | 11.72 |
| ATOM | 934 | CA | LEU | A1833 | 10.141 | 52.524 | 47.052 | 1.00 | 12.98 |
| ATOM | 935 | CB | LEU | A1833 | 9.512 | 52.718 | 45.668 | 1.00 | 13.17 |
| ATOM | 936 | CG | LEU | A1833 | 8.180 | 53.464 | 45.464 | 1.00 | 18.24 |
| ATOM | 937 | CD1 | LEU | A1833 | 7.374 | 52.871 | 44.290 | 1.00 | 16.03 |
| ATOM | 938 | CD2 | LEU | A1833 | 7.311 | 53.592 | 46.727 | 1.00 | 16.24 |
| ATOM | 939 | C | LEU | A1833 | 9.778 | 51.139 | 47.591 | 1.00 | 10.74 |
| ATOM | 940 | O | LEU | A1833 | 8.915 | 51.014 | 48.453 | 1.00 | 11.12 |
| ATOM | 941 | N | LEU | A1834 | 10.425 | 50.101 | 47.071 | 1.00 | 13.14 |
| ATOM | 942 | CA | LEU | A1834 | 10.140 | 48.744 | 47.535 | 1.00 | 13.75 |
| ATOM | 943 | CB | LEU | A1834 | 10.813 | 47.675 | 46.668 | 1.00 | 15.38 |
| ATOM | 944 | CG | LEU | A1834 | 10.328 | 46.279 | 47.084 | 1.00 | 17.93 |
| ATOM | 945 | CD1 | LEU | A1834 | 9.698 | 45.527 | 45.950 | 1.00 | 19.15 |
| ATOM | 946 | CD2 | LEU | A1834 | 11.456 | 45.471 | 47.712 | 1.00 | 18.55 |
| ATOM | 947 | C | LEU | A1834 | 10.518 | 48.565 | 49.005 | 1.00 | 12.61 |
| ATOM | 948 | O | LEU | A1834 | 9.729 | 48.036 | 49.782 | 1.00 | 14.07 |
| ATOM | 949 | N | TYR | A1835 | 11.713 | 49.009 | 49.385 | 1.00 | 12.00 |
| ATOM | 950 | CA | TYR | A1835 | 12.103 | 48.972 | 50.792 | 1.00 | 12.00 |
| ATOM | 951 | CB | TYR | A1835 | 13.482 | 49.604 | 51.023 | 1.00 | 11.53 |
| ATOM | 952 | CG | TYR | A1835 | 13.917 | 49.559 | 52.479 | 1.00 | 12.91 |
| ATOM | 953 | CD1 | TYR | A1835 | 14.840 | 48.620 | 52.924 | 1.00 | 14.42 |
| ATOM | 954 | CE1 | TYR | A1835 | 15.234 | 48.573 | 54.271 | 1.00 | 15.87 |
| ATOM | 955 | CZ | TYR | A1835 | 14.693 | 49.476 | 55.171 | 1.00 | 15.32 |
| ATOM | 956 | OH | TYR | A1835 | 15.073 | 49.449 | 56.498 | 1.00 | 16.37 |
| ATOM | 957 | CE2 | TYR | A1835 | 13.768 | 50.415 | 54.748 | 1.00 | 15.26 |
| ATOM | 958 | CD2 | TYR | A1835 | 13.390 | 50.455 | 53.411 | 1.00 | 13.42 |
| ATOM | 959 | C | TYR | A1835 | 11.043 | 49.675 | 51.649 | 1.00 | 11.59 |
| ATOM | 960 | O | TYR | A1835 | 10.556 | 49.114 | 52.626 | 1.00 | 12.42 |
| ATOM | 961 | N | LEU | A1836 | 10.687 | 50.895 | 51.261 | 1.00 | 12.28 |
| ATOM | 962 | CA | LEU | A1836 | 9.710 | 51.694 | 51.989 | 1.00 | 10.47 |
| ATOM | 963 | CB | LEU | A1836 | 9.457 | 53.011 | 51.243 | 1.00 | 11.33 |
| ATOM | 964 | CG | LEU | A1836 | 8.386 | 53.939 | 51.812 | 1.00 | 11.48 |
| ATOM | 965 | CD1 | LEU | A1836 | 8.827 | 54.541 | 53.153 | 1.00 | 11.51 |
| ATOM | 966 | CD2 | LEU | A1836 | 8.054 | 55.036 | 50.820 | 1.00 | 11.24 |
| ATOM | 967 | C | LEU | A1836 | 8.392 | 50.944 | 52.170 | 1.00 | 11.33 |
| ATOM | 968 | O | LEU | A1836 | 7.861 | 50.853 | 53.285 | 1.00 | 10.22 |
| ATOM | 969 | N | ARG | A1837 | 7.865 | 50.415 | 51.065 | 1.00 | 9.44 |
| ATOM | 970 | CA | ARG | A1837 | 6.568 | 49.755 | 51.083 | 1.00 | 11.21 |
| ATOM | 971 | CB | ARG | A1837 | 6.092 | 49.439 | 49.656 | 1.00 | 11.01 |
| ATOM | 972 | CG | ARG | A1837 | 5.681 | 50.664 | 48.852 | 1.00 | 14.84 |
| ATOM | 973 | CD | ARG | A1837 | 4.540 | 51.460 | 49.459 | 1.00 | 15.75 |

FIGURE 3T

| | A | B | C | D E | F | G | H | I | J |
|---|---|---|---|---|---|---|---|---|---|
| ATOM | 974 | NE | ARG | A1837 | 4.186 | 52.605 | 48.627 | 1.00 | 18.08 |
| ATOM | 975 | CZ | ARG | A1837 | 4.137 | 53.858 | 49.055 | 1.00 | 18.32 |
| ATOM | 976 | NH1 | ARG | A1837 | 4.421 | 54.147 | 50.320 | 1.00 | 18.05 |
| ATOM | 977 | NH2 | ARG | A1837 | 3.802 | 54.828 | 48.215 | 1.00 | 16.60 |
| ATOM | 978 | C | ARG | A1837 | 6.587 | 48.490 | 51.936 | 1.00 | 10.42 |
| ATOM | 979 | O | ARG | A1837 | 5.657 | 48.246 | 52.702 | 1.00 | 11.29 |
| ATOM | 980 | N | ALA | A1838 | 7.653 | 47.701 | 51.810 | 1.00 | 10.11 |
| ATOM | 981 | CA | ALA | A1838 | 7.793 | 46.471 | 52.588 | 1.00 | 12.44 |
| ATOM | 982 | CB | ALA | A1838 | 8.988 | 45.657 | 52.105 | 1.00 | 10.94 |
| ATOM | 983 | C | ALA | A1838 | 7.914 | 46.775 | 54.077 | 1.00 | 12.84 |
| ATOM | 984 | O | ALA | A1838 | 7.344 | 46.076 | 54.916 | 1.00 | 11.81 |
| ATOM | 985 | N | SER | A1839 | 8.658 | 47.830 | 54.393 | 1.00 | 12.49 |
| ATOM | 986 | CA | SER | A1839 | 8.833 | 48.262 | 55.769 | 1.00 | 11.52 |
| ATOM | 987 | CB | SER | A1839 | 9.924 | 49.329 | 55.853 | 1.00 | 13.06 |
| ATOM | 988 | OG | SER | A1839 | 10.174 | 49.688 | 57.202 | 1.00 | 15.67 |
| ATOM | 989 | C | SER | A1839 | 7.515 | 48.776 | 56.353 | 1.00 | 10.24 |
| ATOM | 990 | O | SER | A1839 | 7.172 | 48.456 | 57.484 | 1.00 | 11.28 |
| ATOM | 991 | N | GLU | A1840 | 6.773 | 49.549 | 55.566 | 1.00 | 11.72 |
| ATOM | 992 | CA | GLU | A1840 | 5.461 | 50.047 | 55.977 | 1.00 | 12.49 |
| ATOM | 993 | CB | GLU | A1840 | 4.864 | 50.965 | 54.903 | 1.00 | 12.12 |
| ATOM | 994 | CG | GLU | A1840 | 5.377 | 52.395 | 54.972 | 1.00 | 13.98 |
| ATOM | 995 | CD | GLU | A1840 | 4.970 | 53.238 | 53.772 | 1.00 | 15.75 |
| ATOM | 996 | OE1 | GLU | A1840 | 4.975 | 54.477 | 53.903 | 1.00 | 17.22 |
| ATOM | 997 | OE2 | GLU | A1840 | 4.656 | 52.678 | 52.700 | 1.00 | 15.96 |
| ATOM | 998 | C | GLU | A1840 | 4.495 | 48.904 | 56.267 | 1.00 | 12.45 |
| ATOM | 999 | O | GLU | A1840 | 3.698 | 48.983 | 57.205 | 1.00 | 11.55 |
| ATOM | 1000 | N | MET | A1841 | 4.575 | 47.855 | 55.450 | 1.00 | 11.85 |
| ATOM | 1001 | CA | MET | A1841 | 3.753 | 46.664 | 55.618 | 1.00 | 13.30 |
| ATOM | 1002 | CB | MET | A1841 | 3.890 | 45.735 | 54.413 | 1.00 | 14.09 |
| ATOM | 1003 | CG | MET | A1841 | 3.005 | 44.498 | 54.493 | 1.00 | 15.47 |
| ATOM | 1004 | SD | MET | A1841 | 3.202 | 43.412 | 53.082 | 1.00 | 18.36 |
| ATOM | 1005 | CE | MET | A1841 | 2.230 | 44.297 | 51.838 | 1.00 | 19.21 |
| ATOM | 1006 | C | MET | A1841 | 4.109 | 45.911 | 56.892 | 1.00 | 12.95 |
| ATOM | 1007 | O | MET | A1841 | 3.217 | 45.450 | 57.599 | 1.00 | 12.68 |
| ATOM | 1008 | N | ALA | A1842 | 5.405 | 45.785 | 57.181 | 1.00 | 11.69 |
| ATOM | 1009 | CA | ALA | A1842 | 5.841 | 45.177 | 58.442 | 1.00 | 12.81 |
| ATOM | 1010 | CB | ALA | A1842 | 7.370 | 45.108 | 58.521 | 1.00 | 10.73 |
| ATOM | 1011 | C | ALA | A1842 | 5.258 | 45.941 | 59.638 | 1.00 | 12.09 |
| ATOM | 1012 | O | ALA | A1842 | 4.714 | 45.341 | 60.561 | 1.00 | 13.97 |
| ATOM | 1013 | N | ARG | A1843 | 5.348 | 47.267 | 59.597 | 1.00 | 11.20 |
| ATOM | 1014 | CA | ARG | A1843 | 4.782 | 48.106 | 60.650 | 1.00 | 12.43 |
| ATOM | 1015 | CB | ARG | A1843 | 5.184 | 49.562 | 60.446 | 1.00 | 12.98 |
| ATOM | 1016 | CG | ARG | A1843 | 6.657 | 49.838 | 60.661 | 1.00 | 12.13 |
| ATOM | 1017 | CD | ARG | A1843 | 6.991 | 51.326 | 60.772 | 1.00 | 12.14 |
| ATOM | 1018 | NE | ARG | A1843 | 6.685 | 52.082 | 59.556 | 1.00 | 11.33 |
| ATOM | 1019 | CZ | ARG | A1843 | 5.613 | 52.856 | 59.384 | 1.00 | 11.57 |
| ATOM | 1020 | NH1 | ARG | A1843 | 4.698 | 52.984 | 60.343 | 1.00 | 9.71 |
| ATOM | 1021 | NH2 | ARG | A1843 | 5.457 | 53.512 | 58.242 | 1.00 | 10.47 |
| ATOM | 1022 | C | ARG | A1843 | 3.251 | 47.999 | 60.738 | 1.00 | 12.34 |
| ATOM | 1023 | O | ARG | A1843 | 2.695 | 47.929 | 61.827 | 1.00 | 12.01 |
| ATOM | 1024 | N | ALA | A1844 | 2.576 | 47.979 | 59.594 | 1.00 | 13.00 |
| ATOM | 1025 | CA | ALA | A1844 | 1.120 | 47.887 | 59.574 | 1.00 | 13.85 |

FIGURE 3U

| | A | B | C | D | E | F | G | H | I | J |
|---|---|---|---|---|---|---|---|---|---|---|
| ATOM | 1026 | CB | ALA | A1844 | | 0.588 | 48.045 | 58.155 | 1.00 | 15.22 |
| ATOM | 1027 | C | ALA | A1844 | | 0.650 | 46.566 | 60.189 | 1.00 | 15.32 |
| ATOM | 1028 | O | ALA | A1844 | | -0.355 | 46.521 | 60.900 | 1.00 | 13.62 |
| ATOM | 1029 | N | GLU | A1845 | | 1.402 | 45.502 | 59.933 | 1.00 | 13.18 |
| ATOM | 1030 | CA | GLU | A1845 | | 1.093 | 44.192 | 60.490 | 1.00 | 14.80 |
| ATOM | 1031 | CB | GLU | A1845 | | 1.487 | 43.099 | 59.493 | 1.00 | 15.58 |
| ATOM | 1032 | CG | GLU | A1845 | | 0.782 | 43.245 | 58.148 | 1.00 | 19.14 |
| ATOM | 1033 | CD | GLU | A1845 | | 1.020 | 42.075 | 57.214 | 1.00 | 22.31 |
| ATOM | 1034 | OE1 | GLU | A1845 | | 0.707 | 42.209 | 56.009 | 1.00 | 24.21 |
| ATOM | 1035 | OE2 | GLU | A1845 | | 1.506 | 41.017 | 57.679 | 1.00 | 24.08 |
| ATOM | 1036 | C | GLU | A1845 | | 1.729 | 43.956 | 61.864 | 1.00 | 14.27 |
| ATOM | 1037 | O | GLU | A1845 | | 1.397 | 42.991 | 62.552 | 1.00 | 14.09 |
| ATOM | 1038 | N | GLY | A1846 | | 2.632 | 44.848 | 62.267 | 1.00 | 14.26 |
| ATOM | 1039 | CA | GLY | A1846 | | 3.300 | 44.742 | 63.554 | 1.00 | 12.58 |
| ATOM | 1040 | C | GLY | A1846 | | 4.365 | 43.662 | 63.647 | 1.00 | 11.27 |
| ATOM | 1041 | O | GLY | A1846 | | 4.845 | 43.350 | 64.739 | 1.00 | 10.88 |
| ATOM | 1042 | N | ILE | A1847 | | 4.763 | 43.115 | 62.503 | 1.00 | 12.90 |
| ATOM | 1043 | CA | ILE | A1847 | | 5.681 | 41.970 | 62.458 | 1.00 | 11.78 |
| ATOM | 1044 | CB | ILE | A1847 | | 5.219 | 40.939 | 61.392 | 1.00 | 11.22 |
| ATOM | 1045 | CG1 | ILE | A1847 | | 5.312 | 41.533 | 59.971 | 1.00 | 11.13 |
| ATOM | 1046 | CD1 | ILE | A1847 | | 4.886 | 40.565 | 58.844 | 1.00 | 10.96 |
| ATOM | 1047 | CG2 | ILE | A1847 | | 3.814 | 40.444 | 61.722 | 1.00 | 10.71 |
| ATOM | 1048 | C | ILE | A1847 | | 7.131 | 42.395 | 62.214 | 1.00 | 10.79 |
| ATOM | 1049 | O | ILE | A1847 | | 7.380 | 43.485 | 61.711 | 1.00 | 12.29 |
| ATOM | 1050 | N | PRO | A1848 | | 8.087 | 41.546 | 62.589 | 1.00 | 12.96 |
| ATOM | 1051 | CA | PRO | A1848 | | 9.508 | 41.870 | 62.411 | 1.00 | 12.04 |
| ATOM | 1052 | CB | PRO | A1848 | | 10.220 | 40.617 | 62.927 | 1.00 | 11.29 |
| ATOM | 1053 | CG | PRO | A1848 | | 9.251 | 40.038 | 63.898 | 1.00 | 12.75 |
| ATOM | 1054 | CD | PRO | A1848 | | 7.906 | 40.243 | 63.260 | 1.00 | 11.21 |
| ATOM | 1055 | C | PRO | A1848 | | 9.896 | 42.149 | 60.968 | 1.00 | 13.29 |
| ATOM | 1056 | O | PRO | A1848 | | 9.414 | 41.499 | 60.032 | 1.00 | 12.78 |
| ATOM | 1057 | N | LYS | A1849 | | 10.753 | 43.149 | 60.812 | 1.00 | 12.50 |
| ATOM | 1058 | CA | LYS | A1849 | | 11.352 | 43.484 | 59.534 | 1.00 | 15.50 |
| ATOM | 1059 | CB | LYS | A1849 | | 11.285 | 44.997 | 59.306 | 1.00 | 14.68 |
| ATOM | 1060 | CG | LYS | A1849 | | 12.097 | 45.482 | 58.117 | 1.00 | 15.11 |
| ATOM | 1061 | CD | LYS | A1849 | | 11.866 | 46.960 | 57.860 | 1.00 | 17.15 |
| ATOM | 1062 | CE | LYS | A1849 | | 12.757 | 47.836 | 58.723 | 1.00 | 17.76 |
| ATOM | 1063 | NZ | LYS | A1849 | | 12.810 | 49.216 | 58.182 | 1.00 | 21.25 |
| ATOM | 1064 | C | LYS | A1849 | | 12.804 | 43.022 | 59.533 | 1.00 | 14.21 |
| ATOM | 1065 | O | LYS | A1849 | | 13.607 | 43.470 | 60.361 | 1.00 | 14.11 |
| ATOM | 1066 | N | ILE | A1850 | | 13.126 | 42.124 | 58.607 | 1.00 | 15.81 |
| ATOM | 1067 | CA | ILE | A1850 | | 14.476 | 41.578 | 58.459 | 1.00 | 15.48 |
| ATOM | 1068 | CB | ILE | A1850 | | 14.459 | 40.016 | 58.337 | 1.00 | 15.90 |
| ATOM | 1069 | CG1 | ILE | A1850 | | 13.702 | 39.345 | 59.496 | 1.00 | 17.10 |
| ATOM | 1070 | CD1 | ILE | A1850 | | 14.189 | 39.712 | 60.884 | 1.00 | 18.06 |
| ATOM | 1071 | CG2 | ILE | A1850 | | 15.879 | 39.459 | 58.234 | 1.00 | 14.69 |
| ATOM | 1072 | C | ILE | A1850 | | 15.094 | 42.188 | 57.215 | 1.00 | 16.04 |
| ATOM | 1073 | O | ILE | A1850 | | 14.558 | 42.040 | 56.116 | 1.00 | 17.71 |
| ATOM | 1074 | N | TYR | A1851 | | 16.216 | 42.880 | 57.380 | 1.00 | 14.54 |
| ATOM | 1075 | CA | TYR | A1851 | | 16.865 | 43.517 | 56.241 | 1.00 | 13.49 |
| ATOM | 1076 | CB | TYR | A1851 | | 17.026 | 45.033 | 56.479 | 1.00 | 13.39 |
| ATOM | 1077 | CG | TYR | A1851 | | 17.862 | 45.748 | 55.438 | 1.00 | 13.71 |

FIGURE 3V

| | A | B | C | D | E | F | G | H | I | J |
|---|---|---|---|---|---|---|---|---|---|---|
| ATOM | 1078 | CD1 | TYR | A1851 | | 18.860 | 46.649 | 55.819 | 1.00 | 14.58 |
| ATOM | 1079 | CE1 | TYR | A1851 | | 19.632 | 47.311 | 54.867 | 1.00 | 15.24 |
| ATOM | 1080 | CZ | TYR | A1851 | | 19.413 | 47.065 | 53.520 | 1.00 | 14.16 |
| ATOM | 1081 | OH | TYR | A1851 | | 20.178 | 47.706 | 52.583 | 1.00 | 16.60 |
| ATOM | 1082 | CE2 | TYR | A1851 | | 18.432 | 46.177 | 53.114 | 1.00 | 13.79 |
| ATOM | 1083 | CD2 | TYR | A1851 | | 17.659 | 45.528 | 54.072 | 1.00 | 13.31 |
| ATOM | 1084 | C | TYR | A1851 | | 18.199 | 42.844 | 55.925 | 1.00 | 13.76 |
| ATOM | 1085 | O | TYR | A1851 | | 19.094 | 42.790 | 56.765 | 1.00 | 11.22 |
| ATOM | 1086 | N | VAL | A1852 | | 18.313 | 42.316 | 54.710 | 1.00 | 14.27 |
| ATOM | 1087 | CA | VAL | A1852 | | 19.564 | 41.730 | 54.236 | 1.00 | 12.96 |
| ATOM | 1088 | CB | VAL | A1852 | | 19.319 | 40.461 | 53.386 | 1.00 | 13.90 |
| ATOM | 1089 | CG1 | VAL | A1852 | | 20.637 | 39.890 | 52.865 | 1.00 | 13.60 |
| ATOM | 1090 | CG2 | VAL | A1852 | | 18.565 | 39.409 | 54.187 | 1.00 | 12.82 |
| ATOM | 1091 | C | VAL | A1852 | | 20.307 | 42.791 | 53.423 | 1.00 | 13.36 |
| ATOM | 1092 | O | VAL | A1852 | | 19.902 | 43.132 | 52.315 | 1.00 | 12.90 |
| ATOM | 1093 | N | ALA | A1853 | | 21.384 | 43.320 | 53.996 | 1.00 | 12.27 |
| ATOM | 1094 | CA | ALA | A1853 | | 22.108 | 44.431 | 53.401 | 1.00 | 13.05 |
| ATOM | 1095 | CB | ALA | A1853 | | 22.525 | 45.440 | 54.476 | 1.00 | 13.12 |
| ATOM | 1096 | C | ALA | A1853 | | 23.324 | 43.935 | 52.635 | 1.00 | 15.42 |
| ATOM | 1097 | O | ALA | A1853 | | 24.271 | 43.411 | 53.222 | 1.00 | 14.93 |
| ATOM | 1098 | N | ALA | A1854 | | 23.271 | 44.108 | 51.317 | 1.00 | 14.99 |
| ATOM | 1099 | CA | ALA | A1854 | | 24.358 | 43.760 | 50.415 | 1.00 | 15.01 |
| ATOM | 1100 | CB | ALA | A1854 | | 24.179 | 42.341 | 49.876 | 1.00 | 12.68 |
| ATOM | 1101 | C | ALA | A1854 | | 24.251 | 44.781 | 49.302 | 1.00 | 13.65 |
| ATOM | 1102 | O | ALA | A1854 | | 23.448 | 44.624 | 48.387 | 1.00 | 12.55 |
| ATOM | 1103 | N | ASN | A1855 | | 25.037 | 45.848 | 49.392 | 1.00 | 13.94 |
| ATOM | 1104 | CA | ASN | A1855 | | 24.744 | 47.022 | 48.575 | 1.00 | 16.11 |
| ATOM | 1105 | CB | ASN | A1855 | | 23.568 | 47.802 | 49.191 | 1.00 | 13.83 |
| ATOM | 1106 | CG | ASN | A1855 | | 23.865 | 48.305 | 50.588 | 1.00 | 14.08 |
| ATOM | 1107 | OD1 | ASN | A1855 | | 24.703 | 49.181 | 50.778 | 1.00 | 15.64 |
| ATOM | 1108 | ND2 | ASN | A1855 | | 23.165 | 47.762 | 51.574 | 1.00 | 14.06 |
| ATOM | 1109 | C | ASN | A1855 | | 25.916 | 47.951 | 48.305 | 1.00 | 15.79 |
| ATOM | 1110 | O | ASN | A1855 | | 27.009 | 47.760 | 48.834 | 1.00 | 17.65 |
| ATOM | 1111 | N | SER | A1856 | | 25.668 | 48.972 | 47.485 | 1.00 | 15.17 |
| ATOM | 1112 | CA | SER | A1856 | | 26.702 | 49.924 | 47.109 | 1.00 | 14.47 |
| ATOM | 1113 | CB | SER | A1856 | | 27.069 | 49.745 | 45.636 | 1.00 | 15.05 |
| ATOM | 1114 | OG | SER | A1856 | | 27.462 | 48.409 | 45.384 | 1.00 | 15.39 |
| ATOM | 1115 | C | SER | A1856 | | 26.298 | 51.369 | 47.374 | 1.00 | 14.90 |
| ATOM | 1116 | O | SER | A1856 | | 26.876 | 52.287 | 46.804 | 1.00 | 16.41 |
| ATOM | 1117 | N | GLY | A1857 | | 25.312 | 51.565 | 48.246 | 1.00 | 14.62 |
| ATOM | 1118 | CA | GLY | A1857 | | 24.850 | 52.899 | 48.587 | 1.00 | 13.12 |
| ATOM | 1119 | C | GLY | A1857 | | 24.011 | 53.533 | 47.499 | 1.00 | 12.52 |
| ATOM | 1120 | O | GLY | A1857 | | 23.617 | 52.871 | 46.528 | 1.00 | 11.94 |
| ATOM | 1121 | N | ALA | A1858 | | 23.731 | 54.823 | 47.670 | 1.00 | 11.50 |
| ATOM | 1122 | CA | ALA | A1858 | | 22.937 | 55.575 | 46.710 | 1.00 | 11.90 |
| ATOM | 1123 | CB | ALA | A1858 | | 22.927 | 57.058 | 47.081 | 1.00 | 10.46 |
| ATOM | 1124 | C | ALA | A1858 | | 23.486 | 55.380 | 45.297 | 1.00 | 11.79 |
| ATOM | 1125 | O | ALA | A1858 | | 24.697 | 55.355 | 45.092 | 1.00 | 11.72 |
| ATOM | 1126 | N | ARG | A1859 | | 22.587 | 55.223 | 44.330 | 1.00 | 12.90 |
| ATOM | 1127 | CA | ARG | A1859 | | 22.987 | 55.089 | 42.933 | 1.00 | 11.68 |
| ATOM | 1128 | CB | ARG | A1859 | | 21.774 | 54.729 | 42.080 | 1.00 | 11.08 |
| ATOM | 1129 | CG | ARG | A1859 | | 22.062 | 54.438 | 40.616 | 1.00 | 12.90 |

FIGURE 3W

| | A | B | C | D | E | F | G | H | I | J |
|---|---|---|---|---|---|---|---|---|---|---|
| ATOM | 1130 | CD | ARG | A1859 | | 20.898 | 53.774 | 39.899 | 1.00 | 11.87 |
| ATOM | 1131 | NE | ARG | A1859 | | 20.609 | 52.460 | 40.473 | 1.00 | 11.91 |
| ATOM | 1132 | CZ | ARG | A1859 | | 19.463 | 51.798 | 40.315 | 1.00 | 11.71 |
| ATOM | 1133 | NH1 | ARG | A1859 | | 18.471 | 52.315 | 39.596 | 1.00 | 9.96 |
| ATOM | 1134 | NH2 | ARG | A1859 | | 19.316 | 50.605 | 40.870 | 1.00 | 10.52 |
| ATOM | 1135 | C | ARG | A1859 | | 23.626 | 56.400 | 42.454 | 1.00 | 12.20 |
| ATOM | 1136 | O | ARG | A1859 | | 23.176 | 57.486 | 42.821 | 1.00 | 12.40 |
| ATOM | 1137 | N | ILE | A1860 | | 24.689 | 56.275 | 41.663 | 1.00 | 10.83 |
| ATOM | 1138 | CA | ILE | A1860 | | 25.377 | 57.412 | 41.064 | 1.00 | 11.50 |
| ATOM | 1139 | CB | ILE | A1860 | | 26.874 | 57.428 | 41.475 | 1.00 | 12.06 |
| ATOM | 1140 | CG1 | ILE | A1860 | | 27.017 | 57.591 | 42.991 | 1.00 | 11.88 |
| ATOM | 1141 | CD1 | ILE | A1860 | | 28.207 | 56.870 | 43.581 | 1.00 | 12.89 |
| ATOM | 1142 | CG2 | ILE | A1860 | | 27.633 | 58.539 | 40.749 | 1.00 | 10.60 |
| ATOM | 1143 | C | ILE | A1860 | | 25.243 | 57.280 | 39.553 | 1.00 | 11.29 |
| ATOM | 1144 | O | ILE | A1860 | | 25.561 | 56.238 | 38.985 | 1.00 | 12.07 |
| ATOM | 1145 | N | GLY | A1861 | | 24.748 | 58.331 | 38.912 | 1.00 | 10.40 |
| ATOM | 1146 | CA | GLY | A1861 | | 24.613 | 58.343 | 37.470 | 1.00 | 9.83 |
| ATOM | 1147 | C | GLY | A1861 | | 24.988 | 59.692 | 36.895 | 1.00 | 11.02 |
| ATOM | 1148 | O | GLY | A1861 | | 25.037 | 60.697 | 37.609 | 1.00 | 10.31 |
| ATOM | 1149 | N | MET | A1862 | | 25.282 | 59.693 | 35.600 | 1.00 | 11.20 |
| ATOM | 1150 | CA | MET | A1862 | | 25.476 | 60.909 | 34.831 | 1.00 | 11.92 |
| ATOM | 1151 | CB | MET | A1862 | | 26.929 | 61.026 | 34.376 | 1.00 | 13.83 |
| ATOM | 1152 | CG | MET | A1862 | | 27.953 | 60.880 | 35.502 | 1.00 | 15.46 |
| ATOM | 1153 | SD | MET | A1862 | | 29.588 | 61.439 | 34.994 | 1.00 | 16.52 |
| ATOM | 1154 | CE | MET | A1862 | | 29.474 | 63.069 | 35.505 | 1.00 | 15.95 |
| ATOM | 1155 | C | MET | A1862 | | 24.541 | 60.836 | 33.629 | 1.00 | 12.27 |
| ATOM | 1156 | O | MET | A1862 | | 24.043 | 59.758 | 33.289 | 1.00 | 10.77 |
| ATOM | 1157 | N | ALA | A1863 | | 24.286 | 61.978 | 32.997 | 1.00 | 13.78 |
| ATOM | 1158 | CA | ALA | A1863 | | 23.424 | 62.004 | 31.824 | 1.00 | 15.60 |
| ATOM | 1159 | CB | ALA | A1863 | | 22.961 | 63.420 | 31.530 | 1.00 | 15.62 |
| ATOM | 1160 | C | ALA | A1863 | | 24.191 | 61.415 | 30.648 | 1.00 | 16.23 |
| ATOM | 1161 | O | ALA | A1863 | | 25.008 | 62.090 | 30.021 | 1.00 | 16.02 |
| ATOM | 1162 | N | GLU | A1864 | | 23.937 | 60.139 | 30.375 | 1.00 | 18.43 |
| ATOM | 1163 | CA | GLU | A1864 | | 24.689 | 59.388 | 29.369 | 1.00 | 20.17 |
| ATOM | 1164 | CB | GLU | A1864 | | 24.313 | 57.903 | 29.411 | 1.00 | 22.17 |
| ATOM | 1165 | CG | GLU | A1864 | | 24.687 | 57.177 | 30.701 | 1.00 | 26.20 |
| ATOM | 1166 | CD | GLU | A1864 | | 26.181 | 57.170 | 30.986 | 1.00 | 27.56 |
| ATOM | 1167 | OE1 | GLU | A1864 | | 26.983 | 57.070 | 30.034 | 1.00 | 28.58 |
| ATOM | 1168 | OE2 | GLU | A1864 | | 26.557 | 57.260 | 32.173 | 1.00 | 28.71 |
| ATOM | 1169 | C | GLU | A1864 | | 24.506 | 59.937 | 27.950 | 1.00 | 21.03 |
| ATOM | 1170 | O | GLU | A1864 | | 25.377 | 59.766 | 27.098 | 1.00 | 19.83 |
| ATOM | 1171 | N | GLU | A1865 | | 23.376 | 60.601 | 27.714 | 1.00 | 19.14 |
| ATOM | 1172 | CA | GLU | A1865 | | 23.061 | 61.178 | 26.408 | 1.00 | 20.57 |
| ATOM | 1173 | CB | GLU | A1865 | | 21.535 | 61.305 | 26.237 | 1.00 | 20.85 |
| ATOM | 1174 | CG | GLU | A1865 | | 20.885 | 62.480 | 26.966 | 1.00 | 20.87 |
| ATOM | 1175 | CD | GLU | A1865 | | 20.606 | 62.216 | 28.445 | 1.00 | 21.08 |
| ATOM | 1176 | OE1 | GLU | A1865 | | 19.830 | 62.988 | 29.040 | 1.00 | 21.63 |
| ATOM | 1177 | OE2 | GLU | A1865 | | 21.145 | 61.252 | 29.024 | 1.00 | 19.76 |
| ATOM | 1178 | C | GLU | A1865 | | 23.770 | 62.518 | 26.184 | 1.00 | 20.55 |
| ATOM | 1179 | O | GLU | A1865 | | 23.782 | 63.036 | 25.070 | 1.00 | 21.98 |
| ATOM | 1180 | N | ILE | A1866 | | 24.372 | 63.067 | 27.240 | 1.00 | 18.91 |
| ATOM | 1181 | CA | ILE | A1866 | | 25.118 | 64.321 | 27.137 | 1.00 | 17.56 |

FIGURE 3X

| | A | B | C | D | E | F | G | H | I | J |
|---|---|---|---|---|---|---|---|---|---|---|
| ATOM | 1182 | CB | | ILE | A1866 | 24.640 | 65.345 | 28.208 | 1.00 | 17.70 |
| ATOM | 1183 | CG1 | | ILE | A1866 | 23.115 | 65.549 | 28.147 | 1.00 | 16.94 |
| ATOM | 1184 | CD1 | | ILE | A1866 | 22.566 | 65.925 | 26.761 | 1.00 | 15.41 |
| ATOM | 1185 | CG2 | | ILE | A1866 | 25.377 | 66.683 | 28.061 | 1.00 | 17.44 |
| ATOM | 1186 | C | | ILE | A1866 | 26.629 | 64.081 | 27.243 | 1.00 | 18.39 |
| ATOM | 1187 | O | | ILE | A1866 | 27.433 | 64.828 | 26.666 | 1.00 | 17.55 |
| ATOM | 1188 | N | | LYS | A1867 | 26.994 | 63.026 | 27.967 | 1.00 | 17.73 |
| ATOM | 1189 | CA | | LYS | A1867 | 28.386 | 62.697 | 28.273 | 1.00 | 20.73 |
| ATOM | 1190 | CB | | LYS | A1867 | 28.459 | 61.367 | 29.029 | 1.00 | 21.70 |
| ATOM | 1191 | CG | | LYS | A1867 | 29.867 | 60.890 | 29.349 | 1.00 | 23.08 |
| ATOM | 1192 | CD | | LYS | A1867 | 29.886 | 60.107 | 30.645 | 1.00 | 23.00 |
| ATOM | 1193 | CE | | LYS | A1867 | 31.124 | 59.252 | 30.741 | 1.00 | 23.23 |
| ATOM | 1194 | NZ | | LYS | A1867 | 30.829 | 57.979 | 31.448 | 1.00 | 22.08 |
| ATOM | 1195 | C | | LYS | A1867 | 29.294 | 62.663 | 27.044 | 1.00 | 21.13 |
| ATOM | 1196 | O | | LYS | A1867 | 30.440 | 63.101 | 27.108 | 1.00 | 21.72 |
| ATOM | 1197 | N | | HIS | A1868 | 28.788 | 62.148 | 25.931 | 1.00 | 20.93 |
| ATOM | 1198 | CA | | HIS | A1868 | 29.600 | 62.071 | 24.721 | 1.00 | 22.50 |
| ATOM | 1199 | CB | | HIS | A1868 | 29.784 | 60.614 | 24.283 | 1.00 | 24.82 |
| ATOM | 1200 | CG | | HIS | A1868 | 30.426 | 59.754 | 25.329 | 1.00 | 26.77 |
| ATOM | 1201 | ND1 | | HIS | A1868 | 29.778 | 58.690 | 25.918 | 1.00 | 27.85 |
| ATOM | 1202 | CE1 | | HIS | A1868 | 30.577 | 58.131 | 26.810 | 1.00 | 27.75 |
| ATOM | 1203 | NE2 | | HIS | A1868 | 31.717 | 58.799 | 26.826 | 1.00 | 27.51 |
| ATOM | 1204 | CD2 | | HIS | A1868 | 31.646 | 59.823 | 25.913 | 1.00 | 27.04 |
| ATOM | 1205 | C | | HIS | A1868 | 29.063 | 62.951 | 23.589 | 1.00 | 22.03 |
| ATOM | 1206 | O | | HIS | A1868 | 29.208 | 62.622 | 22.414 | 1.00 | 20.99 |
| ATOM | 1207 | N | | MET | A1869 | 28.459 | 64.081 | 23.947 | 1.00 | 21.71 |
| ATOM | 1208 | CA | | MET | A1869 | 28.004 | 65.033 | 22.934 | 1.00 | 21.79 |
| ATOM | 1209 | CB | B | MET | A1869 | 26.471 | 65.041 | 22.874 | 0.50 | 23.77 |
| ATOM | 1210 | CB | A | MET | A1869 | 26.490 | 64.946 | 22.699 | 0.50 | 21.29 |
| ATOM | 1211 | CG | B | MET | A1869 | 25.835 | 63.701 | 22.516 | 0.50 | 25.23 |
| ATOM | 1212 | CG | A | MET | A1869 | 25.603 | 65.640 | 23.709 | 0.50 | 19.76 |
| ATOM | 1213 | SD | B | MET | A1869 | 25.671 | 63.455 | 20.737 | 0.50 | 27.64 |
| ATOM | 1214 | SD | A | MET | A1869 | 24.110 | 66.319 | 22.935 | 0.50 | 18.78 |
| ATOM | 1215 | CE | B | MET | A1869 | 24.037 | 64.155 | 20.459 | 0.50 | 28.14 |
| ATOM | 1216 | CE | A | MET | A1869 | 23.491 | 64.908 | 22.007 | 0.50 | 17.66 |
| ATOM | 1217 | C | | MET | A1869 | 28.493 | 66.455 | 23.177 | 1.00 | 21.41 |
| ATOM | 1218 | O | | MET | A1869 | 28.592 | 67.244 | 22.237 | 1.00 | 22.32 |
| ATOM | 1219 | N | | PHE | A1870 | 28.818 | 66.778 | 24.427 | 1.00 | 19.49 |
| ATOM | 1220 | CA | | PHE | A1870 | 29.220 | 68.135 | 24.774 | 1.00 | 19.30 |
| ATOM | 1221 | CB | | PHE | A1870 | 29.237 | 68.345 | 26.299 | 1.00 | 19.39 |
| ATOM | 1222 | CG | | PHE | A1870 | 30.402 | 67.706 | 26.996 | 1.00 | 18.77 |
| ATOM | 1223 | CD1 | | PHE | A1870 | 31.619 | 68.371 | 27.098 | 1.00 | 19.09 |
| ATOM | 1224 | CE1 | | PHE | A1870 | 32.699 | 67.784 | 27.740 | 1.00 | 19.19 |
| ATOM | 1225 | CZ | | PHE | A1870 | 32.568 | 66.522 | 28.303 | 1.00 | 19.69 |
| ATOM | 1226 | CE2 | | PHE | A1870 | 31.354 | 65.850 | 28.219 | 1.00 | 17.82 |
| ATOM | 1227 | CD2 | | PHE | A1870 | 30.279 | 66.445 | 27.569 | 1.00 | 18.60 |
| ATOM | 1228 | C | | PHE | A1870 | 30.556 | 68.528 | 24.143 | 1.00 | 20.07 |
| ATOM | 1229 | O | | PHE | A1870 | 31.404 | 67.678 | 23.855 | 1.00 | 19.46 |
| ATOM | 1230 | N | | HIS | A1871 | 30.727 | 69.825 | 23.928 | 1.00 | 19.09 |
| ATOM | 1231 | CA | | HIS | A1871 | 31.985 | 70.356 | 23.446 | 1.00 | 18.14 |
| ATOM | 1232 | CB | | HIS | A1871 | 31.783 | 71.069 | 22.113 | 1.00 | 20.02 |
| ATOM | 1233 | CG | | HIS | A1871 | 31.533 | 70.135 | 20.971 | 1.00 | 22.46 |

FIGURE 3Y

|  | A | B | C | D | E | F | G | H | I | J |
|---|---|---|---|---|---|---|---|---|---|---|
| ATOM | 1234 | ND1 | HIS | A1871 |  | 30.270 | 69.704 | 20.624 | 1.00 | 23.19 |
| ATOM | 1235 | CE1 | HIS | A1871 |  | 30.356 | 68.880 | 19.595 | 1.00 | 23.43 |
| ATOM | 1236 | NE2 | HIS | A1871 |  | 31.629 | 68.756 | 19.266 | 1.00 | 24.10 |
| ATOM | 1237 | CD2 | HIS | A1871 |  | 32.386 | 69.529 | 20.113 | 1.00 | 23.76 |
| ATOM | 1238 | C | HIS | A1871 |  | 32.565 | 71.289 | 24.498 | 1.00 | 18.98 |
| ATOM | 1239 | O | HIS | A1871 |  | 31.864 | 71.711 | 25.430 | 1.00 | 17.07 |
| ATOM | 1240 | N | VAL | A1872 |  | 33.849 | 71.595 | 24.352 | 1.00 | 15.99 |
| ATOM | 1241 | CA | VAL | A1872 |  | 34.542 | 72.449 | 25.302 | 1.00 | 15.44 |
| ATOM | 1242 | CB | VAL | A1872 |  | 35.775 | 71.741 | 25.895 | 1.00 | 14.51 |
| ATOM | 1243 | CG1 | VAL | A1872 |  | 36.450 | 72.622 | 26.932 | 1.00 | 12.55 |
| ATOM | 1244 | CG2 | VAL | A1872 |  | 35.374 | 70.415 | 26.518 | 1.00 | 13.02 |
| ATOM | 1245 | C | VAL | A1872 |  | 34.966 | 73.746 | 24.636 | 1.00 | 15.92 |
| ATOM | 1246 | O | VAL | A1872 |  | 35.582 | 73.730 | 23.576 | 1.00 | 16.14 |
| ATOM | 1247 | N | ALA | A1873 |  | 34.618 | 74.869 | 25.260 | 1.00 | 16.42 |
| ATOM | 1248 | CA | ALA | A1873 |  | 35.121 | 76.161 | 24.823 | 1.00 | 16.43 |
| ATOM | 1249 | CB | ALA | A1873 |  | 34.100 | 77.239 | 25.066 | 1.00 | 14.66 |
| ATOM | 1250 | C | ALA | A1873 |  | 36.426 | 76.477 | 25.548 | 1.00 | 17.71 |
| ATOM | 1251 | O | ALA | A1873 |  | 36.426 | 76.993 | 26.670 | 1.00 | 18.40 |
| ATOM | 1252 | N | TRP | A1874 |  | 37.535 | 76.160 | 24.894 | 1.00 | 17.94 |
| ATOM | 1253 | CA | TRP | A1874 |  | 38.858 | 76.328 | 25.481 | 1.00 | 18.48 |
| ATOM | 1254 | CB | TRP | A1874 |  | 39.899 | 75.594 | 24.633 | 1.00 | 17.77 |
| ATOM | 1255 | CG | TRP | A1874 |  | 39.655 | 74.116 | 24.535 | 1.00 | 16.75 |
| ATOM | 1256 | CD1 | TRP | A1874 |  | 39.167 | 73.436 | 23.457 | 1.00 | 17.12 |
| ATOM | 1257 | NE1 | TRP | A1874 |  | 39.085 | 72.093 | 23.741 | 1.00 | 16.23 |
| ATOM | 1258 | CE2 | TRP | A1874 |  | 39.523 | 71.881 | 25.022 | 1.00 | 16.25 |
| ATOM | 1259 | CD2 | TRP | A1874 |  | 39.891 | 73.136 | 25.553 | 1.00 | 15.61 |
| ATOM | 1260 | CE3 | TRP | A1874 |  | 40.376 | 73.190 | 26.868 | 1.00 | 16.44 |
| ATOM | 1261 | CZ3 | TRP | A1874 |  | 40.472 | 72.006 | 27.600 | 1.00 | 16.67 |
| ATOM | 1262 | CH2 | TRP | A1874 |  | 40.096 | 70.776 | 27.041 | 1.00 | 15.76 |
| ATOM | 1263 | CZ2 | TRP | A1874 |  | 39.621 | 70.692 | 25.757 | 1.00 | 16.62 |
| ATOM | 1264 | C | TRP | A1874 |  | 39.240 | 77.802 | 25.616 | 1.00 | 19.46 |
| ATOM | 1265 | O | TRP | A1874 |  | 38.825 | 78.634 | 24.805 | 1.00 | 17.90 |
| ATOM | 1266 | N | VAL | A1875 |  | 40.016 | 78.119 | 26.651 | 1.00 | 21.03 |
| ATOM | 1267 | CA | VAL | A1875 |  | 40.631 | 79.440 | 26.769 | 1.00 | 24.04 |
| ATOM | 1268 | CB | VAL | A1875 |  | 41.545 | 79.550 | 28.021 | 1.00 | 24.25 |
| ATOM | 1269 | CG1 | VAL | A1875 |  | 42.401 | 80.825 | 27.982 | 1.00 | 24.73 |
| ATOM | 1270 | CG2 | VAL | A1875 |  | 40.718 | 79.524 | 29.288 | 1.00 | 24.48 |
| ATOM | 1271 | C | VAL | A1875 |  | 41.426 | 79.691 | 25.488 | 1.00 | 26.06 |
| ATOM | 1272 | O | VAL | A1875 |  | 41.307 | 80.750 | 24.868 | 1.00 | 26.68 |
| ATOM | 1273 | N | ASP | A1876 |  | 42.212 | 78.690 | 25.092 | 1.00 | 28.08 |
| ATOM | 1274 | CA | ASP | A1876 |  | 42.938 | 78.696 | 23.827 | 1.00 | 29.24 |
| ATOM | 1275 | CB | ASP | A1876 |  | 44.323 | 79.329 | 24.008 | 1.00 | 29.64 |
| ATOM | 1276 | CG | ASP | A1876 |  | 45.268 | 79.019 | 22.861 | 1.00 | 29.58 |
| ATOM | 1277 | OD1 | ASP | A1876 |  | 46.481 | 78.890 | 23.124 | 1.00 | 30.33 |
| ATOM | 1278 | OD2 | ASP | A1876 |  | 44.898 | 78.887 | 21.674 | 1.00 | 29.47 |
| ATOM | 1279 | C | ASP | A1876 |  | 43.048 | 77.262 | 23.298 | 1.00 | 30.29 |
| ATOM | 1280 | O | ASP | A1876 |  | 43.734 | 76.430 | 23.897 | 1.00 | 30.72 |
| ATOM | 1281 | N | PRO | A1877 |  | 42.381 | 76.974 | 22.178 | 1.00 | 31.53 |
| ATOM | 1282 | CA | PRO | A1877 |  | 42.322 | 75.605 | 21.637 | 1.00 | 33.06 |
| ATOM | 1283 | CB | PRO | A1877 |  | 41.474 | 75.759 | 20.367 | 1.00 | 32.45 |
| ATOM | 1284 | CG | PRO | A1877 |  | 41.541 | 77.212 | 20.031 | 1.00 | 33.04 |
| ATOM | 1285 | CD | PRO | A1877 |  | 41.632 | 77.930 | 21.342 | 1.00 | 32.10 |

FIGURE 3Z

|      | A    | B   | C    | D   | E      | F      | G      | H      | I    | J     |
|------|------|-----|------|-----|--------|--------|--------|--------|------|-------|
| ATOM | 1286 | C   |      | PRO | A1877  | 43.694 | 75.009 | 21.301 | 1.00 | 34.04 |
| ATOM | 1287 | O   |      | PRO | A1877  | 43.816 | 73.786 | 21.206 | 1.00 | 33.96 |
| ATOM | 1288 | N   |      | GLU | A1878  | 44.701 | 75.864 | 21.134 | 1.00 | 34.40 |
| ATOM | 1289 | CA  |      | GLU | A1878  | 46.062 | 75.416 | 20.844 | 1.00 | 35.32 |
| ATOM | 1290 | CB  |      | GLU | A1878  | 46.802 | 76.437 | 19.964 | 1.00 | 35.73 |
| ATOM | 1291 | CG  |      | GLU | A1878  | 45.965 | 77.053 | 18.845 | 1.00 | 36.60 |
| ATOM | 1292 | CD  |      | GLU | A1878  | 45.733 | 76.109 | 17.675 | 1.00 | 37.47 |
| ATOM | 1293 | OE1 |      | GLU | A1878  | 46.714 | 75.749 | 16.987 | 1.00 | 38.13 |
| ATOM | 1294 | OE2 |      | GLU | A1878  | 44.565 | 75.732 | 17.434 | 1.00 | 37.30 |
| ATOM | 1295 | C   |      | GLU | A1878  | 46.858 | 75.124 | 22.124 | 1.00 | 35.32 |
| ATOM | 1296 | O   |      | GLU | A1878  | 47.929 | 74.513 | 22.069 | 1.00 | 35.80 |
| ATOM | 1297 | N   |      | ASP | A1879  | 46.330 | 75.560 | 23.267 | 1.00 | 34.92 |
| ATOM | 1298 | CA  |      | ASP | A1879  | 46.959 | 75.319 | 24.566 | 1.00 | 34.78 |
| ATOM | 1299 | CB  |      | ASP | A1879  | 47.730 | 76.560 | 25.033 | 1.00 | 35.98 |
| ATOM | 1300 | CG  |      | ASP | A1879  | 48.825 | 76.230 | 26.033 | 1.00 | 36.83 |
| ATOM | 1301 | OD1 |      | ASP | A1879  | 50.016 | 76.295 | 25.656 | 1.00 | 37.87 |
| ATOM | 1302 | OD2 |      | ASP | A1879  | 48.593 | 75.904 | 27.217 | 1.00 | 37.17 |
| ATOM | 1303 | C   |      | ASP | A1879  | 45.919 | 74.896 | 25.611 | 1.00 | 33.82 |
| ATOM | 1304 | O   |      | ASP | A1879  | 45.418 | 75.726 | 26.372 | 1.00 | 33.20 |
| ATOM | 1305 | N   |      | PRO | A1880  | 45.600 | 73.601 | 25.647 | 1.00 | 33.28 |
| ATOM | 1306 | CA  |      | PRO | A1880  | 44.549 | 73.079 | 26.532 | 1.00 | 32.41 |
| ATOM | 1307 | CB  |      | PRO | A1880  | 44.519 | 71.587 | 26.195 | 1.00 | 32.48 |
| ATOM | 1308 | CG  |      | PRO | A1880  | 45.141 | 71.497 | 24.844 | 1.00 | 33.38 |
| ATOM | 1309 | CD  |      | PRO | A1880  | 46.218 | 72.531 | 24.842 | 1.00 | 33.14 |
| ATOM | 1310 | C   |      | PRO | A1880  | 44.835 | 73.282 | 28.020 | 1.00 | 31.91 |
| ATOM | 1311 | O   |      | PRO | A1880  | 43.883 | 73.409 | 28.792 | 1.00 | 31.64 |
| ATOM | 1312 | N   |      | HIS | A1881  | 46.110 | 73.321 | 28.407 | 1.00 | 31.65 |
| ATOM | 1313 | CA  |      | HIS | A1881  | 46.492 | 73.561 | 29.800 | 1.00 | 31.57 |
| ATOM | 1314 | CB  | B    | HIS | A1881  | 48.016 | 73.503 | 29.953 | 0.50 | 32.51 |
| ATOM | 1315 | CB  | A    | HIS | A1881  | 48.010 | 73.473 | 29.991 | 0.50 | 32.17 |
| ATOM | 1316 | CG  | B    | HIS | A1881  | 48.578 | 72.114 | 29.940 | 0.50 | 33.40 |
| ATOM | 1317 | CG  | A    | HIS | A1881  | 48.443 | 73.600 | 31.421 | 0.50 | 32.74 |
| ATOM | 1318 | ND1 | B    | HIS | A1881  | 48.216 | 71.152 | 30.859 | 0.50 | 33.82 |
| ATOM | 1319 | ND1 | A    | HIS | A1881  | 48.732 | 74.815 | 32.005 | 0.50 | 33.05 |
| ATOM | 1320 | CE1 | B    | HIS | A1881  | 48.873 | 70.034 | 30.607 | 0.50 | 33.83 |
| ATOM | 1321 | CE1 | A    | HIS | A1881  | 49.074 | 74.624 | 33.267 | 0.50 | 33.24 |
| ATOM | 1322 | NE2 | B    | HIS | A1881  | 49.651 | 70.237 | 29.559 | 0.50 | 33.87 |
| ATOM | 1323 | NE2 | A    | HIS | A1881  | 49.013 | 73.330 | 33.524 | 0.50 | 33.10 |
| ATOM | 1324 | CD2 | B    | HIS | A1881  | 49.487 | 71.529 | 29.124 | 0.50 | 33.64 |
| ATOM | 1325 | CD2 | A    | HIS | A1881  | 48.617 | 72.668 | 32.387 | 0.50 | 32.92 |
| ATOM | 1326 | C   |      | HIS | A1881  | 45.973 | 74.906 | 30.316 | 1.00 | 30.35 |
| ATOM | 1327 | O   |      | HIS | A1881  | 45.730 | 75.063 | 31.516 | 1.00 | 30.13 |
| ATOM | 1328 | N   |      | LYS | A1882  | 45.801 | 75.862 | 29.403 | 1.00 | 28.52 |
| ATOM | 1329 | CA  |      | LYS | A1882  | 45.310 | 77.200 | 29.743 | 1.00 | 28.05 |
| ATOM | 1330 | CB  |      | LYS | A1882  | 45.350 | 78.122 | 28.517 | 1.00 | 28.77 |
| ATOM | 1331 | CG  |      | LYS | A1882  | 46.736 | 78.658 | 28.185 | 1.00 | 29.17 |
| ATOM | 1332 | CD  |      | LYS | A1882  | 46.655 | 80.020 | 27.511 | 1.00 | 30.28 |
| ATOM | 1333 | CE  |      | LYS | A1882  | 48.007 | 80.716 | 27.505 | 1.00 | 31.04 |
| ATOM | 1334 | NZ  |      | LYS | A1882  | 48.110 | 81.715 | 26.403 | 1.00 | 31.60 |
| ATOM | 1335 | C   |      | LYS | A1882  | 43.904 | 77.186 | 30.349 | 1.00 | 26.64 |
| ATOM | 1336 | O   |      | LYS | A1882  | 43.495 | 78.151 | 30.998 | 1.00 | 27.56 |
| ATOM | 1337 | N   |      | GLY | A1883  | 43.176 | 76.090 | 30.135 | 1.00 | 24.33 |

FIGURE 3AA

|  | A | B | C | D E | F | G | H | I | J |
|---|---|---|---|---|---|---|---|---|---|
| ATOM | 1338 | CA | GLY | A1883 | 41.857 | 75.904 | 30.714 | 1.00 | 21.39 |
| ATOM | 1339 | C | GLY | A1883 | 40.725 | 76.010 | 29.711 | 1.00 | 19.79 |
| ATOM | 1340 | O | GLY | A1883 | 40.954 | 76.100 | 28.504 | 1.00 | 19.53 |
| ATOM | 1341 | N | PHE | A1884 | 39.497 | 76.004 | 30.222 | 1.00 | 19.19 |
| ATOM | 1342 | CA | PHE | A1884 | 38.302 | 76.133 | 29.394 | 1.00 | 19.75 |
| ATOM | 1343 | CB | PHE | A1884 | 37.654 | 74.766 | 29.153 | 1.00 | 20.46 |
| ATOM | 1344 | CG | PHE | A1884 | 37.347 | 74.003 | 30.410 | 1.00 | 21.43 |
| ATOM | 1345 | CD1 | PHE | A1884 | 38.299 | 73.160 | 30.976 | 1.00 | 21.79 |
| ATOM | 1346 | CE1 | PHE | A1884 | 38.025 | 72.454 | 32.136 | 1.00 | 22.10 |
| ATOM | 1347 | CZ | PHE | A1884 | 36.783 | 72.584 | 32.751 | 1.00 | 23.21 |
| ATOM | 1348 | CE2 | PHE | A1884 | 35.820 | 73.424 | 32.197 | 1.00 | 22.68 |
| ATOM | 1349 | CD2 | PHE | A1884 | 36.107 | 74.125 | 31.029 | 1.00 | 22.63 |
| ATOM | 1350 | C | PHE | A1884 | 37.305 | 77.102 | 30.024 | 1.00 | 19.44 |
| ATOM | 1351 | O | PHE | A1884 | 37.295 | 77.292 | 31.241 | 1.00 | 19.38 |
| ATOM | 1352 | N | LYS | A1885 | 36.475 | 77.712 | 29.184 | 1.00 | 19.68 |
| ATOM | 1353 | CA | LYS | A1885 | 35.563 | 78.767 | 29.617 | 1.00 | 20.05 |
| ATOM | 1354 | CB | LYS | A1885 | 35.372 | 79.805 | 28.506 | 1.00 | 20.34 |
| ATOM | 1355 | CG | LYS | A1885 | 36.666 | 80.332 | 27.900 | 1.00 | 22.04 |
| ATOM | 1356 | CD | LYS | A1885 | 36.446 | 81.662 | 27.195 | 1.00 | 22.42 |
| ATOM | 1357 | CE | LYS | A1885 | 36.182 | 81.471 | 25.709 | 1.00 | 23.17 |
| ATOM | 1358 | NZ | LYS | A1885 | 35.976 | 82.783 | 25.031 | 1.00 | 25.34 |
| ATOM | 1359 | C | LYS | A1885 | 34.214 | 78.208 | 30.038 | 1.00 | 19.18 |
| ATOM | 1360 | O | LYS | A1885 | 33.656 | 78.620 | 31.054 | 1.00 | 19.23 |
| ATOM | 1361 | N | TYR | A1886 | 33.694 | 77.275 | 29.241 | 1.00 | 18.64 |
| ATOM | 1362 | CA | TYR | A1886 | 32.378 | 76.682 | 29.467 | 1.00 | 16.69 |
| ATOM | 1363 | CB | TYR | A1886 | 31.253 | 77.672 | 29.104 | 1.00 | 16.31 |
| ATOM | 1364 | CG | TYR | A1886 | 31.311 | 78.216 | 27.682 | 1.00 | 16.86 |
| ATOM | 1365 | CD1 | TYR | A1886 | 30.750 | 77.509 | 26.614 | 1.00 | 16.56 |
| ATOM | 1366 | CE1 | TYR | A1886 | 30.798 | 78.006 | 25.315 | 1.00 | 15.52 |
| ATOM | 1367 | CZ | TYR | A1886 | 31.418 | 79.227 | 25.077 | 1.00 | 17.07 |
| ATOM | 1368 | OH | TYR | A1886 | 31.477 | 79.724 | 23.797 | 1.00 | 17.76 |
| ATOM | 1369 | CE2 | TYR | A1886 | 31.976 | 79.948 | 26.119 | 1.00 | 15.51 |
| ATOM | 1370 | CD2 | TYR | A1886 | 31.921 | 79.441 | 27.411 | 1.00 | 17.14 |
| ATOM | 1371 | C | TYR | A1886 | 32.242 | 75.409 | 28.645 | 1.00 | 17.46 |
| ATOM | 1372 | O | TYR | A1886 | 33.074 | 75.125 | 27.782 | 1.00 | 16.12 |
| ATOM | 1373 | N | LEU | A1887 | 31.192 | 74.646 | 28.928 | 1.00 | 17.45 |
| ATOM | 1374 | CA | LEU | A1887 | 30.831 | 73.489 | 28.120 | 1.00 | 16.39 |
| ATOM | 1375 | CB | LEU | A1887 | 30.552 | 72.272 | 29.008 | 1.00 | 16.73 |
| ATOM | 1376 | CG | LEU | A1887 | 31.655 | 71.782 | 29.951 | 1.00 | 17.24 |
| ATOM | 1377 | CD1 | LEU | A1887 | 31.236 | 70.461 | 30.595 | 1.00 | 17.05 |
| ATOM | 1378 | CD2 | LEU | A1887 | 32.995 | 71.634 | 29.234 | 1.00 | 16.70 |
| ATOM | 1379 | C | LEU | A1887 | 29.600 | 73.827 | 27.298 | 1.00 | 15.75 |
| ATOM | 1380 | O | LEU | A1887 | 28.732 | 74.585 | 27.745 | 1.00 | 14.38 |
| ATOM | 1381 | N | TYR | A1888 | 29.515 | 73.261 | 26.098 | 1.00 | 14.28 |
| ATOM | 1382 | CA | TYR | A1888 | 28.443 | 73.630 | 25.185 | 1.00 | 14.50 |
| ATOM | 1383 | CB | TYR | A1888 | 28.823 | 74.889 | 24.384 | 1.00 | 14.35 |
| ATOM | 1384 | CG | TYR | A1888 | 29.891 | 74.702 | 23.324 | 1.00 | 14.60 |
| ATOM | 1385 | CD1 | TYR | A1888 | 31.247 | 74.808 | 23.642 | 1.00 | 15.69 |
| ATOM | 1386 | CE1 | TYR | A1888 | 32.231 | 74.659 | 22.657 | 1.00 | 15.27 |
| ATOM | 1387 | CZ | TYR | A1888 | 31.850 | 74.412 | 21.341 | 1.00 | 16.21 |
| ATOM | 1388 | OH | TYR | A1888 | 32.806 | 74.255 | 20.367 | 1.00 | 15.57 |

FIGURE 3AB

| | A | B | C | D | E | F | G | H | I | J |
|---|---|---|---|---|---|---|---|---|---|---|
| ATOM | 1389 | CE2 | TYR | A1888 | | 30.508 | 74.309 | 21.007 | 1.00 | 15.45 |
| ATOM | 1390 | CD2 | TYR | A1888 | | 29.542 | 74.460 | 21.994 | 1.00 | 15.01 |
| ATOM | 1391 | C | TYR | A1888 | | 27.997 | 72.521 | 24.250 | 1.00 | 13.45 |
| ATOM | 1392 | O | TYR | A1888 | | 28.728 | 71.565 | 24.007 | 1.00 | 12.57 |
| ATOM | 1393 | N | LEU | A1889 | | 26.780 | 72.681 | 23.737 | 1.00 | 14.26 |
| ATOM | 1394 | CA | LEU | A1889 | | 26.257 | 71.853 | 22.661 | 1.00 | 14.65 |
| ATOM | 1395 | CB | LEU | A1889 | | 24.874 | 71.304 | 23.034 | 1.00 | 15.86 |
| ATOM | 1396 | CG | LEU | A1889 | | 24.768 | 70.560 | 24.374 | 1.00 | 15.76 |
| ATOM | 1397 | CD1 | LEU | A1889 | | 23.334 | 70.182 | 24.664 | 1.00 | 16.67 |
| ATOM | 1398 | CD2 | LEU | A1889 | | 25.641 | 69.324 | 24.365 | 1.00 | 17.47 |
| ATOM | 1399 | C | LEU | A1889 | | 26.161 | 72.667 | 21.380 | 1.00 | 14.04 |
| ATOM | 1400 | O | LEU | A1889 | | 25.858 | 73.861 | 21.414 | 1.00 | 12.14 |
| ATOM | 1401 | N | THR | A1890 | | 26.422 | 72.016 | 20.249 | 1.00 | 14.76 |
| ATOM | 1402 | CA | THR | A1890 | | 26.167 | 72.627 | 18.947 | 1.00 | 15.39 |
| ATOM | 1403 | CB | THR | A1890 | | 26.781 | 71.789 | 17.806 | 1.00 | 16.49 |
| ATOM | 1404 | OG1 | THR | A1890 | | 26.182 | 70.491 | 17.790 | 1.00 | 15.58 |
| ATOM | 1405 | CG2 | THR | A1890 | | 28.257 | 71.510 | 18.057 | 1.00 | 17.09 |
| ATOM | 1406 | C | THR | A1890 | | 24.655 | 72.727 | 18.760 | 1.00 | 14.87 |
| ATOM | 1407 | O | THR | A1890 | | 23.909 | 71.959 | 19.372 | 1.00 | 12.37 |
| ATOM | 1408 | N | PRO | A1891 | | 24.195 | 73.677 | 17.946 | 1.00 | 16.45 |
| ATOM | 1409 | CA | PRO | A1891 | | 22.770 | 73.768 | 17.614 | 1.00 | 18.46 |
| ATOM | 1410 | CB | PRO | A1891 | | 22.730 | 74.845 | 16.529 | 1.00 | 18.60 |
| ATOM | 1411 | CG | PRO | A1891 | | 23.923 | 75.685 | 16.799 | 1.00 | 18.27 |
| ATOM | 1412 | CD | PRO | A1891 | | 24.980 | 74.746 | 17.300 | 1.00 | 17.20 |
| ATOM | 1413 | C | PRO | A1891 | | 22.228 | 72.439 | 17.083 | 1.00 | 20.14 |
| ATOM | 1414 | O | PRO | A1891 | | 21.100 | 72.077 | 17.417 | 1.00 | 19.95 |
| ATOM | 1415 | N | GLN | A1892 | | 23.026 | 71.724 | 16.291 | 1.00 | 22.90 |
| ATOM | 1416 | CA | GLN | A1892 | | 22.625 | 70.420 | 15.769 | 1.00 | 25.03 |
| ATOM | 1417 | CB | GLN | A1892 | | 23.642 | 69.897 | 14.746 | 1.00 | 26.97 |
| ATOM | 1418 | CG | GLN | A1892 | | 23.228 | 68.591 | 14.059 | 1.00 | 30.30 |
| ATOM | 1419 | CD | GLN | A1892 | | 21.982 | 68.745 | 13.198 | 1.00 | 31.27 |
| ATOM | 1420 | OE1 | GLN | A1892 | | 22.055 | 69.246 | 12.075 | 1.00 | 32.58 |
| ATOM | 1421 | NE2 | GLN | A1892 | | 20.839 | 68.321 | 13.725 | 1.00 | 31.95 |
| ATOM | 1422 | C | GLN | A1892 | | 22.420 | 69.402 | 16.892 | 1.00 | 25.00 |
| ATOM | 1423 | O | GLN | A1892 | | 21.415 | 68.692 | 16.909 | 1.00 | 24.59 |
| ATOM | 1424 | N | ASP | A1893 | | 23.368 | 69.342 | 17.826 | 1.00 | 24.86 |
| ATOM | 1425 | CA | ASP | A1893 | | 23.266 | 68.420 | 18.955 | 1.00 | 26.93 |
| ATOM | 1426 | CB | ASP | A1893 | | 24.592 | 68.326 | 19.717 | 1.00 | 28.84 |
| ATOM | 1427 | CG | ASP | A1893 | | 25.593 | 67.411 | 19.032 | 1.00 | 30.71 |
| ATOM | 1428 | OD1 | ASP | A1893 | | 25.166 | 66.449 | 18.360 | 1.00 | 33.23 |
| ATOM | 1429 | OD2 | ASP | A1893 | | 26.829 | 67.570 | 19.106 | 1.00 | 32.05 |
| ATOM | 1430 | C | ASP | A1893 | | 22.124 | 68.799 | 19.892 | 1.00 | 26.06 |
| ATOM | 1431 | O | ASP | A1893 | | 21.412 | 67.926 | 20.387 | 1.00 | 24.90 |
| ATOM | 1432 | N | TYR | A1894 | | 21.949 | 70.104 | 20.109 | 1.00 | 25.17 |
| ATOM | 1433 | CA | TYR | A1894 | | 20.863 | 70.623 | 20.933 | 1.00 | 26.70 |
| ATOM | 1434 | CB | TYR | A1894 | | 20.962 | 72.144 | 21.071 | 1.00 | 27.01 |
| ATOM | 1435 | CG | TYR | A1894 | | 19.985 | 72.748 | 22.064 | 1.00 | 28.47 |
| ATOM | 1436 | CD1 | TYR | A1894 | | 20.139 | 72.545 | 23.436 | 1.00 | 30.20 |
| ATOM | 1437 | CE1 | TYR | A1894 | | 19.246 | 73.098 | 24.352 | 1.00 | 31.39 |
| ATOM | 1438 | CZ | TYR | A1894 | | 18.188 | 73.872 | 23.897 | 1.00 | 31.62 |
| ATOM | 1439 | OH | TYR | A1894 | | 17.307 | 74.423 | 24.807 | 1.00 | 32.21 |
| ATOM | 1440 | CE2 | TYR | A1894 | | 18.015 | 74.090 | 22.537 | 1.00 | 29.86 |

FIGURE 3AC

| | A | B | C | D | E | F | G | H | I | J |
|---|---|---|---|---|---|---|---|---|---|---|
| ATOM | 1441 | CD2 | TYR | A1894 | | 18.913 | 73.527 | 21.630 | 1.00 | 29.16 |
| ATOM | 1442 | C | TYR | A1894 | | 19.496 | 70.232 | 20.370 | 1.00 | 27.36 |
| ATOM | 1443 | O | TYR | A1894 | | 18.594 | 69.892 | 21.124 | 1.00 | 25.01 |
| ATOM | 1444 | N | THR | A1895 | | 19.362 | 70.280 | 19.046 | 1.00 | 28.45 |
| ATOM | 1445 | CA | THR | A1895 | | 18.139 | 69.857 | 18.367 | 1.00 | 30.87 |
| ATOM | 1446 | CB | THR | A1895 | | 18.280 | 70.050 | 16.839 | 1.00 | 31.72 |
| ATOM | 1447 | OG1 | THR | A1895 | | 18.605 | 71.419 | 16.553 | 1.00 | 32.07 |
| ATOM | 1448 | CG2 | THR | A1895 | | 16.940 | 69.863 | 16.138 | 1.00 | 32.70 |
| ATOM | 1449 | C | THR | A1895 | | 17.796 | 68.403 | 18.706 | 1.00 | 31.55 |
| ATOM | 1450 | O | THR | A1895 | | 16.627 | 68.063 | 18.876 | 1.00 | 32.18 |
| ATOM | 1451 | N | ARG | A1896 | | 18.823 | 67.564 | 18.825 | 1.00 | 32.54 |
| ATOM | 1452 | CA | ARG | A1896 | | 18.654 | 66.144 | 19.142 | 1.00 | 33.30 |
| ATOM | 1453 | CB | ARG | A1896 | | 19.974 | 65.394 | 18.940 | 1.00 | 35.48 |
| ATOM | 1454 | CG | ARG | A1896 | | 20.099 | 64.703 | 17.595 | 1.00 | 37.61 |
| ATOM | 1455 | CD | ARG | A1896 | | 21.064 | 65.374 | 16.643 | 1.00 | 39.12 |
| ATOM | 1456 | NE | ARG | A1896 | | 22.427 | 64.862 | 16.783 | 1.00 | 41.09 |
| ATOM | 1457 | CZ | ARG | A1896 | | 23.283 | 64.696 | 15.776 | 1.00 | 41.75 |
| ATOM | 1458 | NH1 | ARG | A1896 | | 22.937 | 64.993 | 14.529 | 1.00 | 41.15 |
| ATOM | 1459 | NH2 | ARG | A1896 | | 24.500 | 64.228 | 16.020 | 1.00 | 42.68 |
| ATOM | 1460 | C | ARG | A1896 | | 18.118 | 65.867 | 20.551 | 1.00 | 32.67 |
| ATOM | 1461 | O | ARG | A1896 | | 17.412 | 64.875 | 20.764 | 1.00 | 33.34 |
| ATOM | 1462 | N | ILE | A1897 | | 18.445 | 66.732 | 21.508 | 1.00 | 30.76 |
| ATOM | 1463 | CA | ILE | A1897 | | 18.076 | 66.478 | 22.906 | 1.00 | 31.06 |
| ATOM | 1464 | CB | ILE | A1897 | | 19.342 | 66.201 | 23.783 | 1.00 | 30.56 |
| ATOM | 1465 | CG1 | ILE | A1897 | | 20.411 | 67.280 | 23.584 | 1.00 | 29.51 |
| ATOM | 1466 | CD1 | ILE | A1897 | | 20.234 | 68.483 | 24.469 | 1.00 | 28.31 |
| ATOM | 1467 | CG2 | ILE | A1897 | | 19.916 | 64.823 | 23.483 | 1.00 | 31.24 |
| ATOM | 1468 | C | ILE | A1897 | | 17.176 | 67.529 | 23.570 | 1.00 | 31.03 |
| ATOM | 1469 | O | ILE | A1897 | | 16.766 | 67.351 | 24.722 | 1.00 | 29.55 |
| ATOM | 1470 | N | SER | A1898 | | 16.866 | 68.608 | 22.849 | 1.00 | 30.90 |
| ATOM | 1471 | CA | SER | A1898 | | 16.110 | 69.737 | 23.413 | 1.00 | 31.63 |
| ATOM | 1472 | CB | SER | A1898 | | 16.088 | 70.928 | 22.447 | 1.00 | 31.51 |
| ATOM | 1473 | OG | SER | A1898 | | 15.303 | 70.649 | 21.301 | 1.00 | 32.89 |
| ATOM | 1474 | C | SER | A1898 | | 14.684 | 69.381 | 23.832 | 1.00 | 32.15 |
| ATOM | 1475 | O | SER | A1898 | | 14.086 | 70.073 | 24.657 | 1.00 | 32.82 |
| ATOM | 1476 | N | SER | A1899 | | 14.145 | 68.308 | 23.262 | 1.00 | 32.17 |
| ATOM | 1477 | CA | SER | A1899 | | 12.807 | 67.838 | 23.610 | 1.00 | 33.13 |
| ATOM | 1478 | CB | SER | A1899 | | 12.120 | 67.246 | 22.380 | 1.00 | 34.84 |
| ATOM | 1479 | OG | SER | A1899 | | 12.960 | 66.300 | 21.739 | 1.00 | 37.38 |
| ATOM | 1480 | C | SER | A1899 | | 12.830 | 66.813 | 24.745 | 1.00 | 32.44 |
| ATOM | 1481 | O | SER | A1899 | | 11.777 | 66.397 | 25.238 | 1.00 | 32.88 |
| ATOM | 1482 | N | LEU | A1900 | | 14.030 | 66.414 | 25.160 | 1.00 | 31.01 |
| ATOM | 1483 | CA | LEU | A1900 | | 14.190 | 65.371 | 26.172 | 1.00 | 31.23 |
| ATOM | 1484 | CB | LEU | A1900 | | 15.353 | 64.440 | 25.804 | 1.00 | 31.01 |
| ATOM | 1485 | CG | LEU | A1900 | | 15.304 | 63.684 | 24.471 | 1.00 | 32.21 |
| ATOM | 1486 | CD1 | LEU | A1900 | | 16.668 | 63.083 | 24.169 | 1.00 | 32.73 |
| ATOM | 1487 | CD2 | LEU | A1900 | | 14.227 | 62.602 | 24.472 | 1.00 | 31.97 |
| ATOM | 1488 | C | LEU | A1900 | | 14.404 | 65.942 | 27.571 | 1.00 | 31.36 |
| ATOM | 1489 | O | LEU | A1900 | | 14.551 | 65.189 | 28.536 | 1.00 | 31.57 |
| ATOM | 1490 | N | ASN | A1901 | | 14.402 | 67.271 | 27.664 | 1.00 | 31.71 |
| ATOM | 1491 | CA | ASN | A1901 | | 14.783 | 68.011 | 28.875 | 1.00 | 31.67 |
| ATOM | 1492 | CB | ASN | A1901 | | 13.564 | 68.357 | 29.757 | 1.00 | 33.89 |

FIGURE 3AD

|      |      |     |      |       | A      | B    | C   | D   | E     | F      | G      | H      | I    | J     |
|------|------|-----|------|-------|--------|------|-----|-----|-------|--------|--------|--------|------|-------|
| ATOM | 1493 | CG  |      | ASN   | A1901  |      |     |     |       | 13.117 | 67.213 | 30.638 | 1.00 | 35.58 |
| ATOM | 1494 | OD1 |      | ASN   | A1901  |      |     |     |       | 12.552 | 66.229 | 30.162 | 1.00 | 38.60 |
| ATOM | 1495 | ND2 |      | ASN   | A1901  |      |     |     |       | 13.346 | 67.348 | 31.940 | 1.00 | 37.00 |
| ATOM | 1496 | C   |      | ASN   | A1901  |      |     |     |       | 15.968 | 67.405 | 29.643 | 1.00 | 28.92 |
| ATOM | 1497 | O   |      | ASN   | A1901  |      |     |     |       | 15.894 | 67.101 | 30.840 | 1.00 | 30.67 |
| ATOM | 1498 | N   |      | SER   | A1902  |      |     |     |       | 17.057 | 67.221 | 28.906 | 1.00 | 24.56 |
| ATOM | 1499 | CA  |      | SER   | A1902  |      |     |     |       | 18.285 | 66.653 | 29.437 | 1.00 | 22.58 |
| ATOM | 1500 | CB  | BSER | A1902 |        |      |     |     |       | 19.043 | 65.921 | 28.328 | 0.50 | 21.37 |
| ATOM | 1501 | CB  | ASER | A1902 |        |      |     |     |       | 19.023 | 65.857 | 28.361 | 0.50 | 22.38 |
| ATOM | 1502 | OG  | BSER | A1902 |        |      |     |     |       | 18.234 | 64.936 | 27.714 | 0.50 | 20.87 |
| ATOM | 1503 | OG  | ASER | A1902 |        |      |     |     |       | 19.403 | 66.683 | 27.282 | 0.50 | 23.59 |
| ATOM | 1504 | C   |      | SER   | A1902  |      |     |     |       | 19.177 | 67.743 | 30.008 | 1.00 | 20.72 |
| ATOM | 1505 | O   |      | SER   | A1902  |      |     |     |       | 19.964 | 67.489 | 30.914 | 1.00 | 18.40 |
| ATOM | 1506 | N   |      | VAL   | A1903  |      |     |     |       | 19.060 | 68.949 | 29.457 | 1.00 | 19.99 |
| ATOM | 1507 | CA  |      | VAL   | A1903  |      |     |     |       | 19.922 | 70.061 | 29.837 | 1.00 | 19.07 |
| ATOM | 1508 | CB  |      | VAL   | A1903  |      |     |     |       | 21.096 | 70.270 | 28.829 | 1.00 | 18.96 |
| ATOM | 1509 | CG1 |      | VAL   | A1903  |      |     |     |       | 22.012 | 69.065 | 28.782 | 1.00 | 17.88 |
| ATOM | 1510 | CG2 |      | VAL   | A1903  |      |     |     |       | 20.570 | 70.626 | 27.421 | 1.00 | 19.54 |
| ATOM | 1511 | C   |      | VAL   | A1903  |      |     |     |       | 19.157 | 71.373 | 29.923 | 1.00 | 18.96 |
| ATOM | 1512 | O   |      | VAL   | A1903  |      |     |     |       | 18.088 | 71.528 | 29.331 | 1.00 | 18.98 |
| ATOM | 1513 | N   |      | HIS   | A1904  |      |     |     |       | 19.721 | 72.311 | 30.674 | 1.00 | 19.07 |
| ATOM | 1514 | CA  |      | HIS   | A1904  |      |     |     |       | 19.332 | 73.702 | 30.587 | 1.00 | 18.01 |
| ATOM | 1515 | CB  |      | HIS   | A1904  |      |     |     |       | 19.095 | 74.310 | 31.970 | 1.00 | 19.25 |
| ATOM | 1516 | CG  |      | HIS   | A1904  |      |     |     |       | 17.893 | 73.768 | 32.687 | 1.00 | 20.80 |
| ATOM | 1517 | ND1 |      | HIS   | A1904  |      |     |     |       | 17.143 | 72.712 | 32.215 | 1.00 | 21.36 |
| ATOM | 1518 | CE1 |      | HIS   | A1904  |      |     |     |       | 16.159 | 72.460 | 33.059 | 1.00 | 21.01 |
| ATOM | 1519 | NE2 |      | HIS   | A1904  |      |     |     |       | 16.245 | 73.312 | 34.064 | 1.00 | 21.74 |
| ATOM | 1520 | CD2 |      | HIS   | A1904  |      |     |     |       | 17.322 | 74.138 | 33.858 | 1.00 | 19.93 |
| ATOM | 1521 | C   |      | HIS   | A1904  |      |     |     |       | 20.516 | 74.372 | 29.908 | 1.00 | 18.07 |
| ATOM | 1522 | O   |      | HIS   | A1904  |      |     |     |       | 21.663 | 74.220 | 30.345 | 1.00 | 15.77 |
| ATOM | 1523 | N   |      | CYS   | A1905  |      |     |     |       | 20.237 | 75.078 | 28.819 | 1.00 | 18.23 |
| ATOM | 1524 | CA  |      | CYS   | A1905  |      |     |     |       | 21.280 | 75.732 | 28.041 | 1.00 | 21.15 |
| ATOM | 1525 | CB  |      | CYS   | A1905  |      |     |     |       | 21.439 | 75.051 | 26.678 | 1.00 | 23.41 |
| ATOM | 1526 | SG  |      | CYS   | A1905  |      |     |     |       | 22.409 | 73.529 | 26.715 | 1.00 | 26.65 |
| ATOM | 1527 | C   |      | CYS   | A1905  |      |     |     |       | 20.971 | 77.204 | 27.832 | 1.00 | 21.25 |
| ATOM | 1528 | O   |      | CYS   | A1905  |      |     |     |       | 19.804 | 77.604 | 27.797 | 1.00 | 20.09 |
| ATOM | 1529 | N   |      | LYS   | A1906  |      |     |     |       | 22.029 | 77.999 | 27.689 | 1.00 | 22.41 |
| ATOM | 1530 | CA  |      | LYS   | A1906  |      |     |     |       | 21.906 | 79.399 | 27.302 | 1.00 | 22.60 |
| ATOM | 1531 | CB  |      | LYS   | A1906  |      |     |     |       | 22.637 | 80.299 | 28.303 | 1.00 | 24.07 |
| ATOM | 1532 | CG  |      | LYS   | A1906  |      |     |     |       | 22.189 | 81.758 | 28.281 | 1.00 | 28.33 |
| ATOM | 1533 | CD  |      | LYS   | A1906  |      |     |     |       | 23.370 | 82.706 | 28.426 | 1.00 | 29.22 |
| ATOM | 1534 | CE  |      | LYS   | A1906  |      |     |     |       | 22.951 | 84.159 | 28.241 | 1.00 | 30.31 |
| ATOM | 1535 | NZ  |      | LYS   | A1906  |      |     |     |       | 22.833 | 84.549 | 26.804 | 1.00 | 31.01 |
| ATOM | 1536 | C   |      | LYS   | A1906  |      |     |     |       | 22.484 | 79.579 | 25.899 | 1.00 | 21.90 |
| ATOM | 1537 | O   |      | LYS   | A1906  |      |     |     |       | 23.663 | 79.303 | 25.664 | 1.00 | 20.22 |
| ATOM | 1538 | N   |      | HIS   | A1907  |      |     |     |       | 21.644 | 80.028 | 24.970 | 1.00 | 21.80 |
| ATOM | 1539 | CA  |      | HIS   | A1907  |      |     |     |       | 22.076 | 80.274 | 23.601 | 1.00 | 22.28 |
| ATOM | 1540 | CB  |      | HIS   | A1907  |      |     |     |       | 20.874 | 80.484 | 22.672 | 1.00 | 22.00 |
| ATOM | 1541 | CG  |      | HIS   | A1907  |      |     |     |       | 21.249 | 80.891 | 21.281 | 1.00 | 22.57 |
| ATOM | 1542 | ND1 |      | HIS   | A1907  |      |     |     |       | 21.960 | 80.072 | 20.430 | 1.00 | 23.54 |
| ATOM | 1543 | CE1 |      | HIS   | A1907  |      |     |     |       | 22.149 | 80.694 | 19.280 | 1.00 | 22.51 |
| ATOM | 1544 | NE2 |      | HIS   | A1907  |      |     |     |       | 21.592 | 81.888 | 19.355 | 1.00 | 23.42 |

FIGURE 3AE

|  | A | B | C | D | E | F | G | H | I | J |
|---|---|---|---|---|---|---|---|---|---|---|
| ATOM | 1545 | CD2 | HIS | A1907 |  | 21.024 | 82.037 | 20.597 | 1.00 | 23.67 |
| ATOM | 1546 | C | HIS | A1907 |  | 23.001 | 81.482 | 23.564 | 1.00 | 23.13 |
| ATOM | 1547 | O | HIS | A1907 |  | 22.631 | 82.576 | 24.003 | 1.00 | 22.99 |
| ATOM | 1548 | N | ILE | A1908 |  | 24.208 | 81.260 | 23.052 | 1.00 | 23.75 |
| ATOM | 1549 | CA | ILE | A1908 |  | 25.223 | 82.300 | 22.917 | 1.00 | 24.36 |
| ATOM | 1550 | CB | ILE | A1908 |  | 26.298 | 82.180 | 24.031 | 1.00 | 24.97 |
| ATOM | 1551 | CG1 | ILE | A1908 |  | 26.884 | 80.767 | 24.075 | 1.00 | 25.78 |
| ATOM | 1552 | CD1 | ILE | A1908 |  | 28.380 | 80.734 | 23.969 | 1.00 | 25.62 |
| ATOM | 1553 | CG2 | ILE | A1908 |  | 25.732 | 82.588 | 25.395 | 1.00 | 25.03 |
| ATOM | 1554 | C | ILE | A1908 |  | 25.890 | 82.235 | 21.545 | 1.00 | 25.64 |
| ATOM | 1555 | O | ILE | A1908 |  | 25.786 | 81.227 | 20.829 | 1.00 | 24.48 |
| ATOM | 1556 | N | GLU | A1909 |  | 26.579 | 83.316 | 21.193 | 1.00 | 26.17 |
| ATOM | 1557 | CA | GLU | A1909 |  | 27.359 | 83.379 | 19.966 | 1.00 | 28.28 |
| ATOM | 1558 | CB | GLU | A1909 |  | 26.787 | 84.439 | 19.024 | 1.00 | 29.89 |
| ATOM | 1559 | CG | GLU | A1909 |  | 25.599 | 83.969 | 18.201 | 1.00 | 33.07 |
| ATOM | 1560 | CD | GLU | A1909 |  | 25.026 | 85.072 | 17.332 | 1.00 | 35.67 |
| ATOM | 1561 | OE1 | GLU | A1909 |  | 24.003 | 85.669 | 17.731 | 1.00 | 37.02 |
| ATOM | 1562 | OE2 | GLU | A1909 |  | 25.600 | 85.347 | 16.252 | 1.00 | 36.31 |
| ATOM | 1563 | C | GLU | A1909 |  | 28.815 | 83.694 | 20.292 | 1.00 | 27.28 |
| ATOM | 1564 | O | GLU | A1909 |  | 29.107 | 84.666 | 20.989 | 1.00 | 27.55 |
| ATOM | 1565 | N | GLU | A1910 |  | 29.722 | 82.855 | 19.803 | 1.00 | 26.53 |
| ATOM | 1566 | CA | GLU | A1910 |  | 31.149 | 83.093 | 19.973 | 1.00 | 25.73 |
| ATOM | 1567 | CB | GLU | A1910 |  | 31.696 | 82.339 | 21.184 | 1.00 | 28.23 |
| ATOM | 1568 | CG | GLU | A1910 |  | 32.932 | 82.991 | 21.785 | 1.00 | 30.38 |
| ATOM | 1569 | CD | GLU | A1910 |  | 33.605 | 82.119 | 22.820 | 1.00 | 31.71 |
| ATOM | 1570 | OE1 | GLU | A1910 |  | 32.998 | 81.900 | 23.889 | 1.00 | 30.46 |
| ATOM | 1571 | OE2 | GLU | A1910 |  | 34.741 | 81.662 | 22.565 | 1.00 | 32.88 |
| ATOM | 1572 | C | GLU | A1910 |  | 31.918 | 82.710 | 18.720 | 1.00 | 23.78 |
| ATOM | 1573 | O | GLU | A1910 |  | 31.628 | 81.694 | 18.090 | 1.00 | 22.08 |
| ATOM | 1574 | N | GLY | A1911 |  | 32.893 | 83.542 | 18.360 | 1.00 | 21.94 |
| ATOM | 1575 | CA | GLY | A1911 |  | 33.674 | 83.339 | 17.154 | 1.00 | 19.63 |
| ATOM | 1576 | C | GLY | A1911 |  | 32.807 | 83.123 | 15.931 | 1.00 | 18.64 |
| ATOM | 1577 | O | GLY | A1911 |  | 33.177 | 82.371 | 15.030 | 1.00 | 19.20 |
| ATOM | 1578 | N | GLY | A1912 |  | 31.642 | 83.767 | 15.917 | 1.00 | 17.83 |
| ATOM | 1579 | CA | GLY | A1912 |  | 30.720 | 83.689 | 14.798 | 1.00 | 19.47 |
| ATOM | 1580 | C | GLY | A1912 |  | 29.884 | 82.426 | 14.708 | 1.00 | 20.87 |
| ATOM | 1581 | O | GLY | A1912 |  | 29.200 | 82.212 | 13.705 | 1.00 | 21.00 |
| ATOM | 1582 | N | GLU | A1913 |  | 29.934 | 81.586 | 15.739 | 1.00 | 21.75 |
| ATOM | 1583 | CA | GLU | A1913 |  | 29.123 | 80.373 | 15.746 | 1.00 | 23.52 |
| ATOM | 1584 | CB | GLU | A1913 |  | 29.985 | 79.099 | 15.699 | 1.00 | 25.93 |
| ATOM | 1585 | CG | GLU | A1913 |  | 30.726 | 78.740 | 16.979 | 1.00 | 28.88 |
| ATOM | 1586 | CD | GLU | A1913 |  | 31.464 | 77.416 | 16.870 | 1.00 | 30.80 |
| ATOM | 1587 | OE1 | GLU | A1913 |  | 32.458 | 77.354 | 16.108 | 1.00 | 31.29 |
| ATOM | 1588 | OE2 | GLU | A1913 |  | 31.052 | 76.438 | 17.546 | 1.00 | 30.43 |
| ATOM | 1589 | C | GLU | A1913 |  | 28.112 | 80.338 | 16.887 | 1.00 | 22.34 |
| ATOM | 1590 | O | GLU | A1913 |  | 28.378 | 80.808 | 17.996 | 1.00 | 22.20 |
| ATOM | 1591 | N | SER | A1914 |  | 26.939 | 79.802 | 16.581 | 1.00 | 20.60 |
| ATOM | 1592 | CA | SER | A1914 |  | 25.887 | 79.625 | 17.562 | 1.00 | 20.73 |
| ATOM | 1593 | CB | SER | A1914 |  | 24.555 | 79.385 | 16.847 | 1.00 | 21.59 |
| ATOM | 1594 | OG | SER | A1914 |  | 23.569 | 78.875 | 17.720 | 1.00 | 25.18 |
| ATOM | 1595 | C | SER | A1914 |  | 26.267 | 78.453 | 18.470 | 1.00 | 19.00 |
| ATOM | 1596 | O | SER | A1914 |  | 26.731 | 77.412 | 17.993 | 1.00 | 19.22 |

FIGURE 3AF

|  | A | B | C | D | E | F | G | H | I | J |
|---|---|---|---|---|---|---|---|---|---|---|
| ATOM | 1597 | N | ARG | A1915 | | 26.108 | 78.651 | 19.775 | 1.00 | 17.84 |
| ATOM | 1598 | CA | ARG | A1915 | | 26.447 | 77.640 | 20.771 | 1.00 | 17.30 |
| ATOM | 1599 | CB | ARG | A1915 | | 27.809 | 77.930 | 21.404 | 1.00 | 18.20 |
| ATOM | 1600 | CG | ARG | A1915 | | 28.996 | 77.687 | 20.497 | 1.00 | 19.90 |
| ATOM | 1601 | CD | ARG | A1915 | | 30.317 | 77.968 | 21.160 | 1.00 | 20.51 |
| ATOM | 1602 | NE | ARG | A1915 | | 31.437 | 77.764 | 20.250 | 1.00 | 21.29 |
| ATOM | 1603 | CZ | ARG | A1915 | | 32.711 | 77.918 | 20.590 | 1.00 | 22.39 |
| ATOM | 1604 | NH1 | ARG | A1915 | | 33.038 | 78.280 | 21.825 | 1.00 | 21.67 |
| ATOM | 1605 | NH2 | ARG | A1915 | | 33.661 | 77.713 | 19.690 | 1.00 | 23.06 |
| ATOM | 1606 | C | ARG | A1915 | | 25.403 | 77.607 | 21.870 | 1.00 | 17.13 |
| ATOM | 1607 | O | ARG | A1915 | | 24.888 | 78.648 | 22.285 | 1.00 | 17.07 |
| ATOM | 1608 | N | TYR | A1916 | | 25.100 | 76.407 | 22.350 | 1.00 | 15.46 |
| ATOM | 1609 | CA | TYR | A1916 | | 24.211 | 76.264 | 23.491 | 1.00 | 15.46 |
| ATOM | 1610 | CB | TYR | A1916 | | 23.116 | 75.232 | 23.198 | 1.00 | 15.13 |
| ATOM | 1611 | CG | TYR | A1916 | | 22.055 | 75.777 | 22.261 | 1.00 | 17.00 |
| ATOM | 1612 | CD1 | TYR | A1916 | | 22.188 | 75.656 | 20.873 | 1.00 | 18.21 |
| ATOM | 1613 | CE1 | TYR | A1916 | | 21.223 | 76.171 | 20.006 | 1.00 | 17.90 |
| ATOM | 1614 | CZ | TYR | A1916 | | 20.111 | 76.819 | 20.529 | 1.00 | 19.50 |
| ATOM | 1615 | OH | TYR | A1916 | | 19.150 | 77.334 | 19.684 | 1.00 | 20.31 |
| ATOM | 1616 | CE2 | TYR | A1916 | | 19.964 | 76.963 | 21.899 | 1.00 | 18.25 |
| ATOM | 1617 | CD2 | TYR | A1916 | | 20.936 | 76.440 | 22.758 | 1.00 | 16.15 |
| ATOM | 1618 | C | TYR | A1916 | | 25.028 | 75.934 | 24.736 | 1.00 | 15.08 |
| ATOM | 1619 | O | TYR | A1916 | | 25.395 | 74.784 | 24.970 | 1.00 | 15.20 |
| ATOM | 1620 | N | MET | A1917 | | 25.320 | 76.971 | 25.518 | 1.00 | 14.83 |
| ATOM | 1621 | CA | MET | A1917 | | 26.152 | 76.847 | 26.708 | 1.00 | 15.00 |
| ATOM | 1622 | CB | MET | A1917 | | 26.621 | 78.223 | 27.181 | 1.00 | 15.82 |
| ATOM | 1623 | CG | MET | A1917 | | 27.434 | 78.201 | 28.473 | 1.00 | 18.39 |
| ATOM | 1624 | SD | MET | A1917 | | 28.090 | 79.826 | 28.896 | 1.00 | 23.21 |
| ATOM | 1625 | CE | MET | A1917 | | 26.587 | 80.706 | 29.324 | 1.00 | 22.84 |
| ATOM | 1626 | C | MET | A1917 | | 25.401 | 76.129 | 27.824 | 1.00 | 13.63 |
| ATOM | 1627 | O | MET | A1917 | | 24.296 | 76.519 | 28.191 | 1.00 | 14.36 |
| ATOM | 1628 | N | ILE | A1918 | | 26.010 | 75.081 | 28.354 | 1.00 | 12.00 |
| ATOM | 1629 | CA | ILE | A1918 | | 25.380 | 74.292 | 29.402 | 1.00 | 13.33 |
| ATOM | 1630 | CB | ILE | A1918 | | 26.017 | 72.894 | 29.472 | 1.00 | 13.79 |
| ATOM | 1631 | CG1 | ILE | A1918 | | 25.765 | 72.131 | 28.160 | 1.00 | 14.12 |
| ATOM | 1632 | CD1 | ILE | A1918 | | 26.784 | 71.038 | 27.874 | 1.00 | 14.03 |
| ATOM | 1633 | CG2 | ILE | A1918 | | 25.495 | 72.123 | 30.693 | 1.00 | 13.07 |
| ATOM | 1634 | C | ILE | A1918 | | 25.473 | 75.010 | 30.749 | 1.00 | 14.27 |
| ATOM | 1635 | O | ILE | A1918 | | 26.562 | 75.431 | 31.156 | 1.00 | 16.00 |
| ATOM | 1636 | N | THR | A1919 | | 24.323 | 75.160 | 31.410 | 1.00 | 14.85 |
| ATOM | 1637 | CA | THR | A1919 | | 24.248 | 75.688 | 32.776 | 1.00 | 16.33 |
| ATOM | 1638 | CB | THR | A1919 | | 23.244 | 76.862 | 32.874 | 1.00 | 16.23 |
| ATOM | 1639 | OG1 | THR | A1919 | | 21.938 | 76.412 | 32.486 | 1.00 | 17.27 |
| ATOM | 1640 | CG2 | THR | A1919 | | 23.571 | 77.961 | 31.867 | 1.00 | 18.06 |
| ATOM | 1641 | C | THR | A1919 | | 23.842 | 74.599 | 33.768 | 1.00 | 16.48 |
| ATOM | 1642 | O | THR | A1919 | | 24.213 | 74.650 | 34.942 | 1.00 | 18.76 |
| ATOM | 1643 | N | ASP | A1920 | | 23.050 | 73.640 | 33.294 | 1.00 | 17.79 |
| ATOM | 1644 | CA | ASP | A1920 | | 22.556 | 72.538 | 34.116 | 1.00 | 17.77 |
| ATOM | 1645 | CB | ASP | A1920 | | 21.173 | 72.851 | 34.697 | 1.00 | 18.40 |
| ATOM | 1646 | CG | ASP | A1920 | | 21.116 | 74.197 | 35.378 | 1.00 | 19.82 |
| ATOM | 1647 | OD1 | ASP | A1920 | | 21.201 | 74.235 | 36.623 | 1.00 | 20.02 |
| ATOM | 1648 | OD2 | ASP | A1920 | | 20.995 | 75.270 | 34.753 | 1.00 | 19.41 |

FIGURE 3AG

| | A | B | C | D | E | F | G | H | I | J |
|---|---|---|---|---|---|---|---|---|---|---|
| ATOM | 1649 | C | | ASP | A1920 | 22.441 | 71.284 | 33.274 | 1.00 | 17.16 |
| ATOM | 1650 | O | | ASP | A1920 | 22.031 | 71.341 | 32.117 | 1.00 | 17.03 |
| ATOM | 1651 | N | | ILE | A1921 | 22.790 | 70.150 | 33.865 | 1.00 | 16.09 |
| ATOM | 1652 | CA | | ILE | A1921 | 22.558 | 68.873 | 33.225 | 1.00 | 17.01 |
| ATOM | 1653 | CB | | ILE | A1921 | 23.881 | 68.093 | 33.036 | 1.00 | 16.22 |
| ATOM | 1654 | CG1 | | ILE | A1921 | 24.811 | 68.866 | 32.098 | 1.00 | 15.45 |
| ATOM | 1655 | CD1 | | ILE | A1921 | 26.197 | 68.264 | 31.932 | 1.00 | 15.17 |
| ATOM | 1656 | CG2 | | ILE | A1921 | 23.597 | 66.713 | 32.459 | 1.00 | 15.63 |
| ATOM | 1657 | C | | ILE | A1921 | 21.554 | 68.101 | 34.060 | 1.00 | 17.66 |
| ATOM | 1658 | O | | ILE | A1921 | 21.832 | 67.757 | 35.211 | 1.00 | 17.45 |
| ATOM | 1659 | N | | ILE | A1922 | 20.377 | 67.857 | 33.484 | 1.00 | 15.52 |
| ATOM | 1660 | CA | | ILE | A1922 | 19.313 | 67.151 | 34.192 | 1.00 | 15.18 |
| ATOM | 1661 | CB | | ILE | A1922 | 17.904 | 67.665 | 33.758 | 1.00 | 16.55 |
| ATOM | 1662 | CG1 | | ILE | A1922 | 17.823 | 69.209 | 33.761 | 1.00 | 16.94 |
| ATOM | 1663 | CD1 | | ILE | A1922 | 18.079 | 69.885 | 35.126 | 1.00 | 15.20 |
| ATOM | 1664 | CG2 | | ILE | A1922 | 16.801 | 67.013 | 34.603 | 1.00 | 15.31 |
| ATOM | 1665 | C | | ILE | A1922 | 19.415 | 65.651 | 33.945 | 1.00 | 15.83 |
| ATOM | 1666 | O | | ILE | A1922 | 19.367 | 64.853 | 34.876 | 1.00 | 16.42 |
| ATOM | 1667 | N | | GLY | A1923 | 19.545 | 65.278 | 32.679 | 1.00 | 15.38 |
| ATOM | 1668 | CA | | GLY | A1923 | 19.477 | 63.886 | 32.283 | 1.00 | 16.73 |
| ATOM | 1669 | C | | GLY | A1923 | 18.039 | 63.464 | 32.077 | 1.00 | 17.07 |
| ATOM | 1670 | O | | GLY | A1923 | 17.194 | 63.664 | 32.952 | 1.00 | 16.90 |
| ATOM | 1671 | N | | LYS | A1924 | 17.759 | 62.878 | 30.918 | 1.00 | 17.51 |
| ATOM | 1672 | CA | | LYS | A1924 | 16.424 | 62.362 | 30.629 | 1.00 | 18.60 |
| ATOM | 1673 | CB | | LYS | A1924 | 16.266 | 62.032 | 29.136 | 1.00 | 19.55 |
| ATOM | 1674 | CG | | LYS | A1924 | 17.194 | 60.936 | 28.631 | 1.00 | 20.37 |
| ATOM | 1675 | CD | | LYS | A1924 | 16.939 | 60.615 | 27.162 | 1.00 | 20.92 |
| ATOM | 1676 | CE | | LYS | A1924 | 17.705 | 59.369 | 26.727 | 1.00 | 22.30 |
| ATOM | 1677 | NZ | | LYS | A1924 | 17.295 | 58.165 | 27.511 | 1.00 | 22.16 |
| ATOM | 1678 | C | | LYS | A1924 | 16.082 | 61.139 | 31.479 | 1.00 | 19.13 |
| ATOM | 1679 | O | | LYS | A1924 | 14.904 | 60.829 | 31.660 | 1.00 | 19.63 |
| ATOM | 1680 | N | | ASP | A1925 | 17.101 | 60.442 | 31.988 | 1.00 | 18.73 |
| ATOM | 1681 | CA | | ASP | A1925 | 16.860 | 59.230 | 32.775 | 1.00 | 19.23 |
| ATOM | 1682 | CB | | ASP | A1925 | 17.947 | 58.184 | 32.549 | 1.00 | 20.68 |
| ATOM | 1683 | CG | | ASP | A1925 | 17.957 | 57.632 | 31.137 | 1.00 | 22.06 |
| ATOM | 1684 | OD1 | | ASP | A1925 | 16.900 | 57.604 | 30.467 | 1.00 | 21.55 |
| ATOM | 1685 | OD2 | | ASP | A1925 | 19.000 | 57.191 | 30.619 | 1.00 | 23.77 |
| ATOM | 1686 | C | | ASP | A1925 | 16.790 | 59.566 | 34.252 | 1.00 | 19.68 |
| ATOM | 1687 | O | | ASP | A1925 | 17.581 | 60.363 | 34.756 | 1.00 | 19.77 |
| ATOM | 1688 | N | | ASP | A1926 | 15.835 | 58.958 | 34.942 | 1.00 | 20.20 |
| ATOM | 1689 | CA | | ASP | A1926 | 15.676 | 59.190 | 36.369 | 1.00 | 20.02 |
| ATOM | 1690 | CB | | ASP | A1926 | 14.241 | 58.887 | 36.797 | 1.00 | 21.64 |
| ATOM | 1691 | CG | | ASP | A1926 | 13.911 | 59.455 | 38.161 | 1.00 | 21.78 |
| ATOM | 1692 | OD1 | | ASP | A1926 | 14.150 | 60.663 | 38.382 | 1.00 | 22.03 |
| ATOM | 1693 | OD2 | | ASP | A1926 | 13.419 | 58.767 | 39.077 | 1.00 | 24.25 |
| ATOM | 1694 | C | | ASP | A1926 | 16.674 | 58.353 | 37.167 | 1.00 | 18.82 |
| ATOM | 1695 | O | | ASP | A1926 | 17.190 | 57.356 | 36.668 | 1.00 | 18.74 |
| ATOM | 1696 | N | | GLY | A1927 | 16.961 | 58.786 | 38.392 | 1.00 | 18.38 |
| ATOM | 1697 | CA | | GLY | A1927 | 17.788 | 58.032 | 39.315 | 1.00 | 17.15 |
| ATOM | 1698 | C | | GLY | A1927 | 19.273 | 58.281 | 39.170 | 1.00 | 18.34 |
| ATOM | 1699 | O | | GLY | A1927 | 20.074 | 57.353 | 39.305 | 1.00 | 18.65 |
| ATOM | 1700 | N | | LEU | A1928 | 19.643 | 59.535 | 38.921 | 1.00 | 16.51 |

FIGURE 3AH

| | A | B | C | D | E | F | G | H | I | J |
|---|---|---|---|---|---|---|---|---|---|---|
| ATOM | 1701 | CA | LEU | A1928 | | 21.036 | 59.897 | 38.665 | 1.00 | 18.14 |
| ATOM | 1702 | CB | LEU | A1928 | | 21.112 | 60.909 | 37.511 | 1.00 | 18.09 |
| ATOM | 1703 | CG | LEU | A1928 | | 21.454 | 60.500 | 36.074 | 1.00 | 21.48 |
| ATOM | 1704 | CD1 | LEU | A1928 | | 20.865 | 59.155 | 35.672 | 1.00 | 20.38 |
| ATOM | 1705 | CD2 | LEU | A1928 | | 21.026 | 61.615 | 35.096 | 1.00 | 20.33 |
| ATOM | 1706 | C | LEU | A1928 | | 21.739 | 60.495 | 39.878 | 1.00 | 17.86 |
| ATOM | 1707 | O | LEU | A1928 | | 22.886 | 60.149 | 40.166 | 1.00 | 17.71 |
| ATOM | 1708 | N | GLY | A1929 | | 21.060 | 61.410 | 40.570 | 1.00 | 17.92 |
| ATOM | 1709 | CA | GLY | A1929 | | 21.709 | 62.238 | 41.572 | 1.00 | 17.24 |
| ATOM | 1710 | C | GLY | A1929 | | 20.937 | 62.476 | 42.854 | 1.00 | 17.14 |
| ATOM | 1711 | O | GLY | A1929 | | 20.655 | 61.536 | 43.602 | 1.00 | 17.23 |
| ATOM | 1712 | N | VAL | A1930 | | 20.599 | 63.737 | 43.108 | 1.00 | 15.14 |
| ATOM | 1713 | CA | VAL | A1930 | | 19.967 | 64.138 | 44.372 | 1.00 | 15.08 |
| ATOM | 1714 | CB | VAL | A1930 | | 19.750 | 65.671 | 44.478 | 1.00 | 15.48 |
| ATOM | 1715 | CG1 | VAL | A1930 | | 21.068 | 66.385 | 44.680 | 1.00 | 16.34 |
| ATOM | 1716 | CG2 | VAL | A1930 | | 19.012 | 66.211 | 43.259 | 1.00 | 12.89 |
| ATOM | 1717 | C | VAL | A1930 | | 18.640 | 63.447 | 44.664 | 1.00 | 13.19 |
| ATOM | 1718 | O | VAL | A1930 | | 18.255 | 63.327 | 45.829 | 1.00 | 14.35 |
| ATOM | 1719 | N | GLU | A1931 | | 17.944 | 62.998 | 43.617 | 1.00 | 12.94 |
| ATOM | 1720 | CA | GLU | A1931 | | 16.691 | 62.268 | 43.809 | 1.00 | 13.98 |
| ATOM | 1721 | CB | GLU | A1931 | | 15.941 | 62.049 | 42.476 | 1.00 | 14.16 |
| ATOM | 1722 | CG | GLU | A1931 | | 16.594 | 61.073 | 41.500 | 1.00 | 16.29 |
| ATOM | 1723 | CD | GLU | A1931 | | 17.551 | 61.754 | 40.539 | 1.00 | 16.59 |
| ATOM | 1724 | OE1 | GLU | A1931 | | 17.520 | 61.426 | 39.333 | 1.00 | 19.29 |
| ATOM | 1725 | OE2 | GLU | A1931 | | 18.330 | 62.627 | 40.982 | 1.00 | 17.84 |
| ATOM | 1726 | C | GLU | A1931 | | 16.967 | 60.946 | 44.518 | 1.00 | 12.42 |
| ATOM | 1727 | O | GLU | A1931 | | 16.101 | 60.409 | 45.209 | 1.00 | 10.78 |
| ATOM | 1728 | N | ASN | A1932 | | 18.183 | 60.429 | 44.347 | 1.00 | 13.10 |
| ATOM | 1729 | CA | ASN | A1932 | | 18.587 | 59.204 | 45.026 | 1.00 | 12.45 |
| ATOM | 1730 | CB | ASN | A1932 | | 19.812 | 58.588 | 44.349 | 1.00 | 14.12 |
| ATOM | 1731 | CG | ASN | A1932 | | 19.520 | 58.120 | 42.928 | 1.00 | 15.34 |
| ATOM | 1732 | OD1 | ASN | A1932 | | 18.362 | 57.992 | 42.531 | 1.00 | 16.14 |
| ATOM | 1733 | ND2 | ASN | A1932 | | 20.569 | 57.867 | 42.160 | 1.00 | 14.11 |
| ATOM | 1734 | C | ASN | A1932 | | 18.846 | 59.454 | 46.506 | 1.00 | 13.12 |
| ATOM | 1735 | O | ASN | A1932 | | 18.603 | 58.585 | 47.342 | 1.00 | 12.54 |
| ATOM | 1736 | N | LEU | A1933 | | 19.330 | 60.653 | 46.825 | 1.00 | 10.57 |
| ATOM | 1737 | CA | LEU | A1933 | | 19.528 | 61.047 | 48.216 | 1.00 | 11.02 |
| ATOM | 1738 | CB | LEU | A1933 | | 20.395 | 62.300 | 48.293 | 1.00 | 10.67 |
| ATOM | 1739 | CG | LEU | A1933 | | 21.768 | 62.161 | 47.641 | 1.00 | 11.32 |
| ATOM | 1740 | CD1 | LEU | A1933 | | 22.459 | 63.509 | 47.622 | 1.00 | 10.07 |
| ATOM | 1741 | CD2 | LEU | A1933 | | 22.615 | 61.094 | 48.356 | 1.00 | 9.25 |
| ATOM | 1742 | C | LEU | A1933 | | 18.195 | 61.269 | 48.930 | 1.00 | 10.75 |
| ATOM | 1743 | O | LEU | A1933 | | 18.049 | 60.897 | 50.093 | 1.00 | 9.38 |
| ATOM | 1744 | N | ARG | A1934 | | 17.229 | 61.866 | 48.226 | 1.00 | 10.16 |
| ATOM | 1745 | CA | ARG | A1934 | | 15.863 | 62.010 | 48.749 | 1.00 | 9.89 |
| ATOM | 1746 | CB | ARG | A1934 | | 14.992 | 62.810 | 47.768 | 1.00 | 10.04 |
| ATOM | 1747 | CG | ARG | A1934 | | 13.497 | 62.842 | 48.112 | 1.00 | 11.29 |
| ATOM | 1748 | CD | ARG | A1934 | | 12.698 | 63.834 | 47.259 | 1.00 | 12.22 |
| ATOM | 1749 | NE | ARG | A1934 | | 11.256 | 63.795 | 47.529 | 1.00 | 15.04 |
| ATOM | 1750 | CZ | ARG | A1934 | | 10.596 | 64.671 | 48.285 | 1.00 | 18.11 |
| ATOM | 1751 | NH1 | ARG | A1934 | | 11.242 | 65.667 | 48.903 | 1.00 | 17.45 |
| ATOM | 1752 | NH2 | ARG | A1934 | | 9.281 | 64.537 | 48.453 | 1.00 | 18.72 |

FIGURE 3AI

|  | A | B | C | D | E | F | G | H | I | J |
|---|---|---|---|---|---|---|---|---|---|---|
| ATOM | 1753 | C | | ARG | A1934 | 15.237 | 60.636 | 49.029 | 1.00 | 7.32 |
| ATOM | 1754 | O | | ARG | A1934 | 14.671 | 60.401 | 50.103 | 1.00 | 8.30 |
| ATOM | 1755 | N | | GLY | A1935 | 15.353 | 59.728 | 48.066 | 1.00 | 8.38 |
| ATOM | 1756 | CA | | GLY | A1935 | 14.885 | 58.364 | 48.248 | 1.00 | 5.78 |
| ATOM | 1757 | C | | GLY | A1935 | 15.565 | 57.655 | 49.405 | 1.00 | 6.26 |
| ATOM | 1758 | O | | GLY | A1935 | 14.919 | 56.906 | 50.138 | 1.00 | 7.24 |
| ATOM | 1759 | N | | SER | A1936 | 16.868 | 57.890 | 49.568 | 1.00 | 7.88 |
| ATOM | 1760 | CA | | SER | A1936 | 17.627 | 57.339 | 50.698 | 1.00 | 7.87 |
| ATOM | 1761 | CB | | SER | A1936 | 19.128 | 57.594 | 50.522 | 1.00 | 7.30 |
| ATOM | 1762 | OG | | SER | A1936 | 19.709 | 56.651 | 49.643 | 1.00 | 8.32 |
| ATOM | 1763 | C | | SER | A1936 | 17.143 | 57.926 | 52.029 | 1.00 | 7.64 |
| ATOM | 1764 | O | | SER | A1936 | 16.942 | 57.198 | 53.000 | 1.00 | 8.61 |
| ATOM | 1765 | N | | GLY | A1937 | 16.945 | 59.243 | 52.065 | 1.00 | 8.95 |
| ATOM | 1766 | CA | | GLY | A1937 | 16.403 | 59.906 | 53.242 | 1.00 | 7.94 |
| ATOM | 1767 | C | | GLY | A1937 | 15.064 | 59.305 | 53.642 | 1.00 | 8.73 |
| ATOM | 1768 | O | | GLY | A1937 | 14.821 | 59.028 | 54.813 | 1.00 | 7.89 |
| ATOM | 1769 | N | | MET | A1938 | 14.209 | 59.083 | 52.644 | 1.00 | 10.88 |
| ATOM | 1770 | CA | | MET | A1938 | 12.876 | 58.508 | 52.835 | 1.00 | 9.45 |
| ATOM | 1771 | CB | | MET | A1938 | 12.219 | 58.305 | 51.469 | 1.00 | 10.41 |
| ATOM | 1772 | CG | | MET | A1938 | 10.739 | 57.963 | 51.503 | 1.00 | 10.99 |
| ATOM | 1773 | SD | | MET | A1938 | 10.073 | 57.812 | 49.818 | 1.00 | 14.55 |
| ATOM | 1774 | CE | | MET | A1938 | 11.119 | 56.518 | 49.159 | 1.00 | 12.63 |
| ATOM | 1775 | C | | MET | A1938 | 12.920 | 57.181 | 53.574 | 1.00 | 8.84 |
| ATOM | 1776 | O | | MET | A1938 | 12.132 | 56.942 | 54.486 | 1.00 | 8.57 |
| ATOM | 1777 | N | | ILE | A1939 | 13.830 | 56.306 | 53.167 | 1.00 | 6.73 |
| ATOM | 1778 | CA | | ILE | A1939 | 13.896 | 54.994 | 53.794 | 1.00 | 7.27 |
| ATOM | 1779 | CB | | ILE | A1939 | 14.358 | 53.896 | 52.807 | 1.00 | 7.04 |
| ATOM | 1780 | CG1 | | ILE | A1939 | 15.709 | 54.240 | 52.168 | 1.00 | 6.25 |
| ATOM | 1781 | CD1 | | ILE | A1939 | 16.380 | 53.042 | 51.469 | 1.00 | 7.03 |
| ATOM | 1782 | CG2 | | ILE | A1939 | 13.276 | 53.659 | 51.747 | 1.00 | 7.13 |
| ATOM | 1783 | C | | ILE | A1939 | 14.698 | 55.006 | 55.086 | 1.00 | 6.94 |
| ATOM | 1784 | O | | ILE | A1939 | 14.524 | 54.128 | 55.924 | 1.00 | 8.02 |
| ATOM | 1785 | N | | ALA | A1940 | 15.557 | 56.011 | 55.250 | 1.00 | 6.95 |
| ATOM | 1786 | CA | | ALA | A1940 | 16.219 | 56.231 | 56.531 | 1.00 | 7.00 |
| ATOM | 1787 | CB | | ALA | A1940 | 17.319 | 57.313 | 56.413 | 1.00 | 7.13 |
| ATOM | 1788 | C | | ALA | A1940 | 15.179 | 56.630 | 57.573 | 1.00 | 7.95 |
| ATOM | 1789 | O | | ALA | A1940 | 15.173 | 56.094 | 58.677 | 1.00 | 9.42 |
| ATOM | 1790 | N | | GLY | A1941 | 14.306 | 57.574 | 57.212 | 1.00 | 7.12 |
| ATOM | 1791 | CA | | GLY | A1941 | 13.232 | 58.007 | 58.089 | 1.00 | 8.32 |
| ATOM | 1792 | C | | GLY | A1941 | 12.309 | 56.854 | 58.449 | 1.00 | 9.11 |
| ATOM | 1793 | O | | GLY | A1941 | 11.980 | 56.645 | 59.612 | 1.00 | 9.70 |
| ATOM | 1794 | N | | GLU | A1942 | 11.907 | 56.088 | 57.443 | 1.00 | 8.71 |
| ATOM | 1795 | CA | | GLU | A1942 | 11.076 | 54.909 | 57.660 | 1.00 | 8.91 |
| ATOM | 1796 | CB | | GLU | A1942 | 10.700 | 54.281 | 56.309 | 1.00 | 8.90 |
| ATOM | 1797 | CG | | GLU | A1942 | 10.157 | 52.857 | 56.390 | 1.00 | 9.80 |
| ATOM | 1798 | CD | | GLU | A1942 | 8.811 | 52.763 | 57.096 | 1.00 | 9.87 |
| ATOM | 1799 | OE1 | | GLU | A1942 | 8.493 | 51.681 | 57.627 | 1.00 | 12.15 |
| ATOM | 1800 | OE2 | | GLU | A1942 | 8.053 | 53.752 | 57.106 | 1.00 | 12.48 |
| ATOM | 1801 | C | | GLU | A1942 | 11.764 | 53.881 | 58.576 | 1.00 | 8.36 |
| ATOM | 1802 | O | | GLU | A1942 | 11.121 | 53.278 | 59.435 | 1.00 | 7.06 |
| ATOM | 1803 | N | | SER | A1943 | 13.071 | 53.698 | 58.404 | 1.00 | 8.36 |
| ATOM | 1804 | CA | | SER | A1943 | 13.818 | 52.754 | 59.235 | 1.00 | 9.36 |

FIGURE 3AJ

| | A | B | C | D E | F | G | H | I | J |
|---|---|---|---|---|---|---|---|---|---|
| ATOM | 1805 | CB | SER | A1943 | 15.219 | 52.527 | 58.672 | 1.00 | 10.25 |
| ATOM | 1806 | OG | SER | A1943 | 15.120 | 51.912 | 57.408 | 1.00 | 13.39 |
| ATOM | 1807 | C | SER | A1943 | 13.909 | 53.210 | 60.683 | 1.00 | 9.32 |
| ATOM | 1808 | O | SER | A1943 | 13.850 | 52.388 | 61.601 | 1.00 | 9.49 |
| ATOM | 1809 | N | SER | A1944 | 14.081 | 54.521 | 60.870 | 1.00 | 8.11 |
| ATOM | 1810 | CA | SER | A1944 | 14.059 | 55.147 | 62.193 | 1.00 | 9.30 |
| ATOM | 1811 | CB | SER | A1944 | 14.305 | 56.663 | 62.058 | 1.00 | 7.37 |
| ATOM | 1812 | OG | SER | A1944 | 14.106 | 57.354 | 63.285 | 1.00 | 8.84 |
| ATOM | 1813 | C | SER | A1944 | 12.715 | 54.878 | 62.886 | 1.00 | 7.65 |
| ATOM | 1814 | O | SER | A1944 | 12.665 | 54.528 | 64.069 | 1.00 | 8.53 |
| ATOM | 1815 | N | LEU | A1945 | 11.630 | 55.053 | 62.146 | 1.00 | 8.79 |
| ATOM | 1816 | CA | LEU | A1945 | 10.296 | 54.772 | 62.675 | 1.00 | 9.26 |
| ATOM | 1817 | CB | LEU | A1945 | 9.219 | 55.285 | 61.714 | 1.00 | 8.56 |
| ATOM | 1818 | CG | LEU | A1945 | 7.744 | 55.065 | 62.088 | 1.00 | 9.14 |
| ATOM | 1819 | CD1 | LEU | A1945 | 7.424 | 55.584 | 63.486 | 1.00 | 9.35 |
| ATOM | 1820 | CD2 | LEU | A1945 | 6.851 | 55.726 | 61.028 | 1.00 | 8.88 |
| ATOM | 1821 | C | LEU | A1945 | 10.082 | 53.283 | 62.981 | 1.00 | 8.19 |
| ATOM | 1822 | O | LEU | A1945 | 9.514 | 52.935 | 64.015 | 1.00 | 10.00 |
| ATOM | 1823 | N | ALA | A1946 | 10.537 | 52.413 | 62.083 | 1.00 | 8.71 |
| ATOM | 1824 | CA | ALA | A1946 | 10.346 | 50.971 | 62.241 | 1.00 | 7.26 |
| ATOM | 1825 | CB | ALA | A1946 | 10.941 | 50.225 | 61.053 | 1.00 | 6.07 |
| ATOM | 1826 | C | ALA | A1946 | 10.963 | 50.473 | 63.540 | 1.00 | 9.20 |
| ATOM | 1827 | O | ALA | A1946 | 10.384 | 49.638 | 64.234 | 1.00 | 9.73 |
| ATOM | 1828 | N | TYR | A1947 | 12.141 | 50.992 | 63.873 | 1.00 | 8.18 |
| ATOM | 1829 | CA | TYR | A1947 | 12.810 | 50.585 | 65.107 | 1.00 | 9.25 |
| ATOM | 1830 | CB | TYR | A1947 | 14.203 | 51.209 | 65.209 | 1.00 | 8.51 |
| ATOM | 1831 | CG | TYR | A1947 | 14.842 | 51.047 | 66.571 | 1.00 | 10.32 |
| ATOM | 1832 | CD1 | TYR | A1947 | 14.957 | 52.132 | 67.439 | 1.00 | 10.02 |
| ATOM | 1833 | CE1 | TYR | A1947 | 15.530 | 51.989 | 68.687 | 1.00 | 11.26 |
| ATOM | 1834 | CZ | TYR | A1947 | 15.994 | 50.740 | 69.085 | 1.00 | 9.87 |
| ATOM | 1835 | OH | TYR | A1947 | 16.560 | 50.588 | 70.322 | 1.00 | 10.56 |
| ATOM | 1836 | CE2 | TYR | A1947 | 15.876 | 49.646 | 68.254 | 1.00 | 9.60 |
| ATOM | 1837 | CD2 | TYR | A1947 | 15.311 | 49.806 | 66.996 | 1.00 | 8.66 |
| ATOM | 1838 | C | TYR | A1947 | 11.958 | 50.910 | 66.346 | 1.00 | 10.29 |
| ATOM | 1839 | O | TYR | A1947 | 12.018 | 50.196 | 67.348 | 1.00 | 9.11 |
| ATOM | 1840 | N | GLU | A1948 | 11.158 | 51.973 | 66.256 | 1.00 | 8.13 |
| ATOM | 1841 | CA | GLU | A1948 | 10.281 | 52.385 | 67.353 | 1.00 | 10.94 |
| ATOM | 1842 | CB | GLU | A1948 | 9.859 | 53.857 | 67.207 | 1.00 | 11.80 |
| ATOM | 1843 | CG | GLU | A1948 | 10.996 | 54.871 | 67.138 | 1.00 | 15.25 |
| ATOM | 1844 | CD | GLU | A1948 | 11.771 | 55.026 | 68.446 | 1.00 | 19.51 |
| ATOM | 1845 | OE1 | GLU | A1948 | 12.690 | 55.874 | 68.483 | 1.00 | 23.62 |
| ATOM | 1846 | OE2 | GLU | A1948 | 11.488 | 54.315 | 69.434 | 1.00 | 19.50 |
| ATOM | 1847 | C | GLU | A1948 | 9.025 | 51.519 | 67.486 | 1.00 | 11.01 |
| ATOM | 1848 | O | GLU | A1948 | 8.416 | 51.473 | 68.554 | 1.00 | 10.42 |
| ATOM | 1849 | N | GLU | A1949 | 8.647 | 50.836 | 66.408 | 1.00 | 9.42 |
| ATOM | 1850 | CA | GLU | A1949 | 7.346 | 50.170 | 66.340 | 1.00 | 10.71 |
| ATOM | 1851 | CB | GLU | A1949 | 6.550 | 50.690 | 65.134 | 1.00 | 12.39 |
| ATOM | 1852 | CG | GLU | A1949 | 6.160 | 52.162 | 65.258 | 1.00 | 14.69 |
| ATOM | 1853 | CD | GLU | A1949 | 5.145 | 52.614 | 64.217 | 1.00 | 16.45 |
| ATOM | 1854 | OE1 | GLU | A1949 | 4.579 | 53.710 | 64.398 | 1.00 | 17.31 |
| ATOM | 1855 | OE2 | GLU | A1949 | 4.918 | 51.894 | 63.217 | 1.00 | 15.54 |
| ATOM | 1856 | C | GLU | A1949 | 7.417 | 48.651 | 66.304 | 1.00 | 10.83 |

FIGURE 3AK

| | A | B | C | D | E | F | G | H | I | J |
|---|---|---|---|---|---|---|---|---|---|---|
| ATOM | 1857 | O | | GLU | A1949 | 6.566 | 47.978 | 66.879 | 1.00 | 12.03 |
| ATOM | 1858 | N | | ILE | A1950 | 8.417 | 48.109 | 65.615 | 1.00 | 10.00 |
| ATOM | 1859 | CA | | ILE | A1950 | 8.482 | 46.665 | 65.395 | 1.00 | 8.49 |
| ATOM | 1860 | CB | | ILE | A1950 | 8.049 | 46.295 | 63.937 | 1.00 | 9.17 |
| ATOM | 1861 | CG1 | | ILE | A1950 | 8.859 | 47.099 | 62.899 | 1.00 | 8.28 |
| ATOM | 1862 | CD1 | | ILE | A1950 | 8.687 | 46.619 | 61.470 | 1.00 | 6.97 |
| ATOM | 1863 | CG2 | | ILE | A1950 | 6.542 | 46.463 | 63.752 | 1.00 | 8.51 |
| ATOM | 1864 | C | | ILE | A1950 | 9.883 | 46.152 | 65.657 | 1.00 | 9.49 |
| ATOM | 1865 | O | | ILE | A1950 | 10.815 | 46.942 | 65.795 | 1.00 | 9.61 |
| ATOM | 1866 | N | | VAL | A1951 | 10.031 | 44.830 | 65.704 | 1.00 | 9.04 |
| ATOM | 1867 | CA | | VAL | A1951 | 11.356 | 44.210 | 65.745 | 1.00 | 8.61 |
| ATOM | 1868 | CB | | VAL | A1951 | 11.260 | 42.687 | 66.015 | 1.00 | 8.56 |
| ATOM | 1869 | CG1 | | VAL | A1951 | 12.589 | 41.984 | 65.741 | 1.00 | 7.73 |
| ATOM | 1870 | CG2 | | VAL | A1951 | 10.814 | 42.430 | 67.455 | 1.00 | 8.53 |
| ATOM | 1871 | C | | VAL | A1951 | 12.068 | 44.488 | 64.414 | 1.00 | 9.85 |
| ATOM | 1872 | O | | VAL | A1951 | 11.500 | 44.290 | 63.338 | 1.00 | 8.51 |
| ATOM | 1873 | N | | THR | A1952 | 13.300 | 44.979 | 64.495 | 1.00 | 8.24 |
| ATOM | 1874 | CA | | THR | A1952 | 14.097 | 45.224 | 63.303 | 1.00 | 7.27 |
| ATOM | 1875 | CB | | THR | A1952 | 14.299 | 46.730 | 63.059 | 1.00 | 7.78 |
| ATOM | 1876 | OG1 | | THR | A1952 | 14.757 | 47.357 | 64.262 | 1.00 | 8.21 |
| ATOM | 1877 | CG2 | | THR | A1952 | 12.967 | 47.425 | 62.768 | 1.00 | 7.27 |
| ATOM | 1878 | C | | THR | A1952 | 15.433 | 44.528 | 63.468 | 1.00 | 7.13 |
| ATOM | 1879 | O | | THR | A1952 | 16.083 | 44.661 | 64.502 | 1.00 | 6.43 |
| ATOM | 1880 | N | | ILE | A1953 | 15.813 | 43.752 | 62.461 | 1.00 | 6.90 |
| ATOM | 1881 | CA | | ILE | A1953 | 17.076 | 43.019 | 62.475 | 1.00 | 8.49 |
| ATOM | 1882 | CB | | ILE | A1953 | 16.864 | 41.513 | 62.806 | 1.00 | 8.32 |
| ATOM | 1883 | CG1 | | ILE | A1953 | 16.346 | 41.314 | 64.234 | 1.00 | 7.77 |
| ATOM | 1884 | CD1 | | ILE | A1953 | 15.622 | 39.955 | 64.439 | 1.00 | 8.81 |
| ATOM | 1885 | CG2 | | ILE | A1953 | 18.169 | 40.721 | 62.609 | 1.00 | 6.88 |
| ATOM | 1886 | C | | ILE | A1953 | 17.694 | 43.154 | 61.101 | 1.00 | 8.65 |
| ATOM | 1887 | O | | ILE | A1953 | 16.989 | 43.077 | 60.094 | 1.00 | 10.14 |
| ATOM | 1888 | N | | SER | A1954 | 19.006 | 43.364 | 61.057 | 1.00 | 8.58 |
| ATOM | 1889 | CA | | SER | A1954 | 19.715 | 43.403 | 59.783 | 1.00 | 9.20 |
| ATOM | 1890 | CB | | SER | A1954 | 20.298 | 44.782 | 59.496 | 1.00 | 9.70 |
| ATOM | 1891 | OG | | SER | A1954 | 19.275 | 45.742 | 59.422 | 1.00 | 14.10 |
| ATOM | 1892 | C | | SER | A1954 | 20.824 | 42.397 | 59.736 | 1.00 | 8.86 |
| ATOM | 1893 | O | | SER | A1954 | 21.448 | 42.087 | 60.752 | 1.00 | 10.54 |
| ATOM | 1894 | N | | LEU | A1955 | 21.057 | 41.891 | 58.534 | 1.00 | 8.54 |
| ATOM | 1895 | CA | | LEU | A1955 | 22.182 | 41.030 | 58.263 | 1.00 | 8.16 |
| ATOM | 1896 | CB | | LEU | A1955 | 21.698 | 39.677 | 57.730 | 1.00 | 7.18 |
| ATOM | 1897 | CG | | LEU | A1955 | 22.793 | 38.718 | 57.262 | 1.00 | 7.76 |
| ATOM | 1898 | CD1 | | LEU | A1955 | 23.754 | 38.371 | 58.404 | 1.00 | 5.30 |
| ATOM | 1899 | CD2 | | LEU | A1955 | 22.182 | 37.460 | 56.656 | 1.00 | 6.80 |
| ATOM | 1900 | C | | LEU | A1955 | 23.054 | 41.723 | 57.232 | 1.00 | 9.14 |
| ATOM | 1901 | O | | LEU | A1955 | 22.597 | 42.014 | 56.126 | 1.00 | 9.69 |
| ATOM | 1902 | N | | VAL | A1956 | 24.307 | 41.989 | 57.590 | 1.00 | 9.17 |
| ATOM | 1903 | CA | | VAL | A1956 | 25.237 | 42.578 | 56.637 | 1.00 | 8.73 |
| ATOM | 1904 | CB | | VAL | A1956 | 26.138 | 43.666 | 57.262 | 1.00 | 7.34 |
| ATOM | 1905 | CG1 | | VAL | A1956 | 27.114 | 44.196 | 56.221 | 1.00 | 8.27 |
| ATOM | 1906 | CG2 | | VAL | A1956 | 25.285 | 44.808 | 57.815 | 1.00 | 6.93 |
| ATOM | 1907 | C | | VAL | A1956 | 26.072 | 41.489 | 55.987 | 1.00 | 9.77 |
| ATOM | 1908 | O | | VAL | A1956 | 26.793 | 40.749 | 56.661 | 1.00 | 9.89 |

FIGURE 3AL

|  | A | B | C | D | E | F | G | H | I | J |
|---|---|---|---|---|---|---|---|---|---|---|
| ATOM | 1909 | N | THR | A1957 | 25.957 | 41.392 | 54.668 | 1.00 | 9.18 |
| ATOM | 1910 | CA | THR | A1957 | 26.670 | 40.363 | 53.923 | 1.00 | 9.63 |
| ATOM | 1911 | CB | THR | A1957 | 25.731 | 39.177 | 53.577 | 1.00 | 9.47 |
| ATOM | 1912 | OG1 | THR | A1957 | 26.395 | 38.269 | 52.685 | 1.00 | 10.86 |
| ATOM | 1913 | CG2 | THR | A1957 | 24.474 | 39.636 | 52.814 | 1.00 | 10.11 |
| ATOM | 1914 | C | THR | A1957 | 27.312 | 41.011 | 52.702 | 1.00 | 10.49 |
| ATOM | 1915 | O | THR | A1957 | 26.690 | 41.842 | 52.033 | 1.00 | 10.65 |
| ATOM | 1916 | N | CYS | A1958 | 28.572 | 40.657 | 52.456 | 1.00 | 10.06 |
| ATOM | 1917 | CA | CYS | A1958 | 29.437 | 41.354 | 51.499 | 1.00 | 10.28 |
| ATOM | 1918 | CB | CYS | A1958 | 28.847 | 41.364 | 50.078 | 1.00 | 12.59 |
| ATOM | 1919 | SG | CYS | A1958 | 29.804 | 42.336 | 48.880 | 1.00 | 15.66 |
| ATOM | 1920 | C | CYS | A1958 | 29.760 | 42.776 | 51.990 | 1.00 | 10.63 |
| ATOM | 1921 | O | CYS | A1958 | 30.879 | 43.032 | 52.442 | 1.00 | 9.47 |
| ATOM | 1922 | N | ARG | A1959 | 28.788 | 43.689 | 51.912 | 1.00 | 9.38 |
| ATOM | 1923 | CA | ARG | A1959 | 29.010 | 45.076 | 52.328 | 1.00 | 9.47 |
| ATOM | 1924 | CB | ARG | A1959 | 29.992 | 45.772 | 51.375 | 1.00 | 10.71 |
| ATOM | 1925 | CG | ARG | A1959 | 29.420 | 45.981 | 49.976 | 1.00 | 11.40 |
| ATOM | 1926 | CD | ARG | A1959 | 30.435 | 46.350 | 48.925 | 1.00 | 14.11 |
| ATOM | 1927 | NE | ARG | A1959 | 29.773 | 46.627 | 47.649 | 1.00 | 14.01 |
| ATOM | 1928 | CZ | ARG | A1959 | 30.120 | 46.083 | 46.495 | 1.00 | 15.97 |
| ATOM | 1929 | NH1 | ARG | A1959 | 31.140 | 45.226 | 46.435 | 1.00 | 14.74 |
| ATOM | 1930 | NH2 | ARG | A1959 | 29.455 | 46.404 | 45.393 | 1.00 | 16.39 |
| ATOM | 1931 | C | ARG | A1959 | 27.724 | 45.901 | 52.424 | 1.00 | 9.88 |
| ATOM | 1932 | O | ARG | A1959 | 26.731 | 45.595 | 51.773 | 1.00 | 10.92 |
| ATOM | 1933 | N | ALA | A1960 | 27.765 | 46.937 | 53.258 | 1.00 | 9.35 |
| ATOM | 1934 | CA | ALA | A1960 | 26.703 | 47.938 | 53.351 | 1.00 | 10.20 |
| ATOM | 1935 | CB | ALA | A1960 | 25.898 | 47.769 | 54.632 | 1.00 | 9.73 |
| ATOM | 1936 | C | ALA | A1960 | 27.373 | 49.307 | 53.307 | 1.00 | 9.95 |
| ATOM | 1937 | O | ALA | A1960 | 28.250 | 49.600 | 54.121 | 1.00 | 11.69 |
| ATOM | 1938 | N | ILE | A1961 | 26.977 | 50.124 | 52.336 | 1.00 | 9.49 |
| ATOM | 1939 | CA | ILE | A1961 | 27.638 | 51.404 | 52.069 | 1.00 | 10.00 |
| ATOM | 1940 | CB | ILE | A1961 | 28.293 | 51.388 | 50.655 | 1.00 | 10.53 |
| ATOM | 1941 | CG1 | ILE | A1961 | 29.320 | 50.252 | 50.542 | 1.00 | 9.99 |
| ATOM | 1942 | CD1 | ILE | A1961 | 29.972 | 50.150 | 49.157 | 1.00 | 12.89 |
| ATOM | 1943 | CG2 | ILE | A1961 | 28.914 | 52.768 | 50.300 | 1.00 | 8.32 |
| ATOM | 1944 | C | ILE | A1961 | 26.652 | 52.557 | 52.158 | 1.00 | 10.22 |
| ATOM | 1945 | O | ILE | A1961 | 25.531 | 52.462 | 51.644 | 1.00 | 9.94 |
| ATOM | 1946 | N | GLY | A1962 | 27.077 | 53.644 | 52.802 | 1.00 | 10.36 |
| ATOM | 1947 | CA | GLY | A1962 | 26.315 | 54.884 | 52.819 | 1.00 | 9.35 |
| ATOM | 1948 | C | GLY | A1962 | 24.945 | 54.676 | 53.419 | 1.00 | 9.53 |
| ATOM | 1949 | O | GLY | A1962 | 24.832 | 54.274 | 54.575 | 1.00 | 9.53 |
| ATOM | 1950 | N | ILE | A1963 | 23.902 | 54.919 | 52.629 | 1.00 | 10.45 |
| ATOM | 1951 | CA | ILE | A1963 | 22.537 | 54.652 | 53.079 | 1.00 | 10.50 |
| ATOM | 1952 | CB | ILE | A1963 | 21.485 | 54.960 | 51.963 | 1.00 | 11.13 |
| ATOM | 1953 | CG1 | ILE | A1963 | 20.059 | 54.639 | 52.441 | 1.00 | 11.14 |
| ATOM | 1954 | CD1 | ILE | A1963 | 19.610 | 55.416 | 53.697 | 1.00 | 10.37 |
| ATOM | 1955 | CG2 | ILE | A1963 | 21.806 | 54.206 | 50.660 | 1.00 | 10.87 |
| ATOM | 1956 | C | ILE | A1963 | 22.391 | 53.220 | 53.600 | 1.00 | 9.10 |
| ATOM | 1957 | O | ILE | A1963 | 21.640 | 52.972 | 54.541 | 1.00 | 7.38 |
| ATOM | 1958 | N | GLY | A1964 | 23.110 | 52.286 | 52.980 | 1.00 | 8.45 |
| ATOM | 1959 | CA | GLY | A1964 | 23.106 | 50.900 | 53.417 | 1.00 | 8.92 |
| ATOM | 1960 | C | GLY | A1964 | 23.565 | 50.765 | 54.859 | 1.00 | 9.17 |

FIGURE 3AM

|      | A    | B   | C   | D   | E      | F      | G      | H      | I    | J     |
|------|------|-----|-----|-----|--------|--------|--------|--------|------|-------|
| ATOM | 1961 | O   |     | GLY | A1964  | 22.975 | 50.017 | 55.628 | 1.00 | 8.68  |
| ATOM | 1962 | N   |     | ALA | A1965  | 24.623 | 51.492 | 55.215 | 1.00 | 9.37  |
| ATOM | 1963 | CA  |     | ALA | A1965  | 25.152 | 51.512 | 56.583 | 1.00 | 7.81  |
| ATOM | 1964 | CB  |     | ALA | A1965  | 26.453 | 52.281 | 56.621 | 1.00 | 8.96  |
| ATOM | 1965 | C   |     | ALA | A1965  | 24.156 | 52.131 | 57.555 | 1.00 | 8.40  |
| ATOM | 1966 | O   |     | ALA | A1965  | 23.982 | 51.648 | 58.679 | 1.00 | 8.44  |
| ATOM | 1967 | N   |     | TYR | A1966  | 23.506 | 53.210 | 57.125 | 1.00 | 7.89  |
| ATOM | 1968 | CA  |     | TYR | A1966  | 22.546 | 53.885 | 57.987 | 1.00 | 9.49  |
| ATOM | 1969 | CB  |     | TYR | A1966  | 22.237 | 55.304 | 57.487 | 1.00 | 8.83  |
| ATOM | 1970 | CG  |     | TYR | A1966  | 23.263 | 56.279 | 58.015 | 1.00 | 10.78 |
| ATOM | 1971 | CD1 |     | TYR | A1966  | 23.384 | 56.492 | 59.385 | 1.00 | 11.78 |
| ATOM | 1972 | CE1 |     | TYR | A1966  | 24.328 | 57.356 | 59.902 | 1.00 | 13.41 |
| ATOM | 1973 | CZ  |     | TYR | A1966  | 25.184 | 58.014 | 59.051 | 1.00 | 12.23 |
| ATOM | 1974 | OH  |     | TYR | A1966  | 26.110 | 58.860 | 59.613 | 1.00 | 13.79 |
| ATOM | 1975 | CE2 |     | TYR | A1966  | 25.101 | 57.825 | 57.673 | 1.00 | 11.80 |
| ATOM | 1976 | CD2 |     | TYR | A1966  | 24.141 | 56.944 | 57.161 | 1.00 | 10.71 |
| ATOM | 1977 | C   |     | TYR | A1966  | 21.298 | 53.055 | 58.214 | 1.00 | 7.62  |
| ATOM | 1978 | O   |     | TYR | A1966  | 20.777 | 53.025 | 59.320 | 1.00 | 7.89  |
| ATOM | 1979 | N   |     | LEU | A1967  | 20.841 | 52.357 | 57.177 | 1.00 | 9.26  |
| ATOM | 1980 | CA  |     | LEU | A1967  | 19.699 | 51.454 | 57.323 | 1.00 | 8.87  |
| ATOM | 1981 | CB  |     | LEU | A1967  | 19.325 | 50.812 | 55.984 | 1.00 | 8.45  |
| ATOM | 1982 | CG  |     | LEU | A1967  | 18.757 | 51.719 | 54.884 | 1.00 | 9.94  |
| ATOM | 1983 | CD1 |     | LEU | A1967  | 18.414 | 50.894 | 53.662 | 1.00 | 7.68  |
| ATOM | 1984 | CD2 |     | LEU | A1967  | 17.553 | 52.508 | 55.364 | 1.00 | 9.53  |
| ATOM | 1985 | C   |     | LEU | A1967  | 19.948 | 50.376 | 58.378 | 1.00 | 8.35  |
| ATOM | 1986 | O   |     | LEU | A1967  | 19.095 | 50.135 | 59.232 | 1.00 | 9.68  |
| ATOM | 1987 | N   |     | VAL | A1968  | 21.116 | 49.738 | 58.340 | 1.00 | 8.37  |
| ATOM | 1988 | CA  |     | VAL | A1968  | 21.407 | 48.700 | 59.336 | 1.00 | 9.12  |
| ATOM | 1989 | CB  |     | VAL | A1968  | 22.601 | 47.766 | 58.954 | 1.00 | 10.27 |
| ATOM | 1990 | CG1 |     | VAL | A1968  | 22.423 | 47.211 | 57.536 | 1.00 | 10.54 |
| ATOM | 1991 | CG2 |     | VAL | A1968  | 23.943 | 48.455 | 59.089 | 1.00 | 12.09 |
| ATOM | 1992 | C   |     | VAL | A1968  | 21.543 | 49.270 | 60.750 | 1.00 | 7.88  |
| ATOM | 1993 | O   |     | VAL | A1968  | 21.068 | 48.669 | 61.713 | 1.00 | 7.91  |
| ATOM | 1994 | N   |     | ARG | A1969  | 22.150 | 50.449 | 60.866 | 1.00 | 8.17  |
| ATOM | 1995 | CA  |     | ARG | A1969  | 22.292 | 51.089 | 62.169 | 1.00 | 8.04  |
| ATOM | 1996 | CB  |     | ARG | A1969  | 23.234 | 52.308 | 62.104 | 1.00 | 6.43  |
| ATOM | 1997 | CG  |     | ARG | A1969  | 23.319 | 53.118 | 63.423 | 1.00 | 7.13  |
| ATOM | 1998 | CD  |     | ARG | A1969  | 23.632 | 52.260 | 64.661 | 1.00 | 6.96  |
| ATOM | 1999 | NE  |     | ARG | A1969  | 23.308 | 52.930 | 65.919 | 1.00 | 7.42  |
| ATOM | 2000 | CZ  |     | ARG | A1969  | 23.538 | 52.412 | 67.127 | 1.00 | 8.17  |
| ATOM | 2001 | NH1 |     | ARG | A1969  | 24.077 | 51.199 | 67.262 | 1.00 | 5.93  |
| ATOM | 2002 | NH2 |     | ARG | A1969  | 23.207 | 53.099 | 68.210 | 1.00 | 7.74  |
| ATOM | 2003 | C   |     | ARG | A1969  | 20.923 | 51.480 | 62.738 | 1.00 | 8.10  |
| ATOM | 2004 | O   |     | ARG | A1969  | 20.650 | 51.252 | 63.917 | 1.00 | 8.70  |
| ATOM | 2005 | N   |     | LEU | A1970  | 20.071 | 52.056 | 61.897 | 1.00 | 7.35  |
| ATOM | 2006 | CA  |     | LEU | A1970  | 18.752 | 52.514 | 62.335 | 1.00 | 8.81  |
| ATOM | 2007 | CB  |     | LEU | A1970  | 18.052 | 53.312 | 61.225 | 1.00 | 7.24  |
| ATOM | 2008 | CG  |     | LEU | A1970  | 18.600 | 54.729 | 61.046 | 1.00 | 7.51  |
| ATOM | 2009 | CD1 |     | LEU | A1970  | 18.248 | 55.263 | 59.662 | 1.00 | 5.58  |
| ATOM | 2010 | CD2 |     | LEU | A1970  | 18.049 | 55.632 | 62.134 | 1.00 | 6.64  |
| ATOM | 2011 | C   |     | LEU | A1970  | 17.861 | 51.377 | 62.823 | 1.00 | 7.82  |
| ATOM | 2012 | O   |     | LEU | A1970  | 17.052 | 51.579 | 63.734 | 1.00 | 9.97  |

FIGURE 3AN

| | A | B | C | D | E | F | G | H | I | J |
|---|---|---|---|---|---|---|---|---|---|---|
| ATOM | 2013 | N | GLY | A1971 | | 18.029 | 50.197 | 62.229 | 1.00 | 8.15 |
| ATOM | 2014 | CA | GLY | A1971 | | 17.392 | 48.972 | 62.703 | 1.00 | 8.01 |
| ATOM | 2015 | C | GLY | A1971 | | 18.031 | 48.402 | 63.969 | 1.00 | 8.05 |
| ATOM | 2016 | O | GLY | A1971 | | 17.453 | 47.519 | 64.625 | 1.00 | 7.70 |
| ATOM | 2017 | N | GLN | A1972 | | 19.235 | 48.893 | 64.282 | 1.00 | 8.23 |
| ATOM | 2018 | CA | GLN | A1972 | | 19.960 | 48.638 | 65.542 | 1.00 | 7.54 |
| ATOM | 2019 | CB | GLN | A1972 | | 19.106 | 49.017 | 66.771 | 1.00 | 8.27 |
| ATOM | 2020 | CG | GLN | A1972 | | 18.780 | 50.507 | 66.857 | 1.00 | 8.87 |
| ATOM | 2021 | CD | GLN | A1972 | | 19.951 | 51.354 | 67.324 | 1.00 | 10.98 |
| ATOM | 2022 | OE1 | GLN | A1972 | | 20.953 | 50.830 | 67.818 | 1.00 | 10.49 |
| ATOM | 2023 | NE2 | GLN | A1972 | | 19.828 | 52.667 | 67.162 | 1.00 | 8.99 |
| ATOM | 2024 | C | GLN | A1972 | | 20.555 | 47.248 | 65.714 | 1.00 | 7.86 |
| ATOM | 2025 | O | GLN | A1972 | | 21.763 | 47.110 | 65.969 | 1.00 | 9.14 |
| ATOM | 2026 | N | ARG | A1973 | | 19.714 | 46.227 | 65.590 | 1.00 | 7.91 |
| ATOM | 2027 | CA | ARG | A1973 | | 20.128 | 44.845 | 65.843 | 1.00 | 9.32 |
| ATOM | 2028 | CB | ARG | A1973 | | 18.917 | 43.989 | 66.232 | 1.00 | 8.38 |
| ATOM | 2029 | CG | ARG | A1973 | | 18.192 | 44.459 | 67.490 | 1.00 | 8.00 |
| ATOM | 2030 | CD | ARG | A1973 | | 16.815 | 43.818 | 67.687 | 1.00 | 9.06 |
| ATOM | 2031 | NE | ARG | A1973 | | 16.016 | 44.613 | 68.610 | 1.00 | 7.11 |
| ATOM | 2032 | CZ | ARG | A1973 | | 15.235 | 45.622 | 68.253 | 1.00 | 6.76 |
| ATOM | 2033 | NH1 | ARG | A1973 | | 15.123 | 45.972 | 66.976 | 1.00 | 6.11 |
| ATOM | 2034 | NH2 | ARG | A1973 | | 14.573 | 46.292 | 69.183 | 1.00 | 6.21 |
| ATOM | 2035 | C | ARG | A1973 | | 20.777 | 44.312 | 64.576 | 1.00 | 8.75 |
| ATOM | 2036 | O | ARG | A1973 | | 20.086 | 44.003 | 63.607 | 1.00 | 10.21 |
| ATOM | 2037 | N | VAL | A1974 | | 22.104 | 44.223 | 64.590 | 1.00 | 7.03 |
| ATOM | 2038 | CA | VAL | A1974 | | 22.887 | 43.979 | 63.386 | 1.00 | 7.27 |
| ATOM | 2039 | CB | VAL | A1974 | | 23.818 | 45.184 | 63.071 | 1.00 | 8.80 |
| ATOM | 2040 | CG1 | VAL | A1974 | | 24.760 | 44.874 | 61.907 | 1.00 | 9.20 |
| ATOM | 2041 | CG2 | VAL | A1974 | | 23.001 | 46.452 | 62.784 | 1.00 | 7.53 |
| ATOM | 2042 | C | VAL | A1974 | | 23.735 | 42.723 | 63.531 | 1.00 | 8.04 |
| ATOM | 2043 | O | VAL | A1974 | | 24.447 | 42.555 | 64.517 | 1.00 | 7.61 |
| ATOM | 2044 | N | ILE | A1975 | | 23.642 | 41.854 | 62.532 | 1.00 | 7.62 |
| ATOM | 2045 | CA | ILE | A1975 | | 24.498 | 40.684 | 62.421 | 1.00 | 7.89 |
| ATOM | 2046 | CB | ILE | A1975 | | 23.675 | 39.414 | 62.144 | 1.00 | 8.41 |
| ATOM | 2047 | CG1 | ILE | A1975 | | 22.630 | 39.194 | 63.235 | 1.00 | 7.48 |
| ATOM | 2048 | CD1 | ILE | A1975 | | 21.431 | 38.365 | 62.771 | 1.00 | 8.03 |
| ATOM | 2049 | CG2 | ILE | A1975 | | 24.605 | 38.187 | 62.011 | 1.00 | 5.36 |
| ATOM | 2050 | C | ILE | A1975 | | 25.402 | 40.961 | 61.243 | 1.00 | 7.73 |
| ATOM | 2051 | O | ILE | A1975 | | 24.927 | 41.309 | 60.153 | 1.00 | 8.06 |
| ATOM | 2052 | N | GLN | A1976 | | 26.703 | 40.848 | 61.471 | 1.00 | 9.00 |
| ATOM | 2053 | CA | GLN | A1976 | | 27.677 | 41.165 | 60.441 | 1.00 | 8.18 |
| ATOM | 2054 | CB | GLN | A1976 | | 28.657 | 42.236 | 60.922 | 1.00 | 8.34 |
| ATOM | 2055 | CG | GLN | A1976 | | 29.630 | 42.677 | 59.820 | 1.00 | 8.10 |
| ATOM | 2056 | CD | GLN | A1976 | | 30.492 | 43.858 | 60.196 | 1.00 | 9.47 |
| ATOM | 2057 | OE1 | GLN | A1976 | | 30.502 | 44.294 | 61.351 | 1.00 | 9.17 |
| ATOM | 2058 | NE2 | GLN | A1976 | | 31.243 | 44.369 | 59.223 | 1.00 | 10.22 |
| ATOM | 2059 | C | GLN | A1976 | | 28.431 | 39.901 | 60.066 | 1.00 | 9.62 |
| ATOM | 2060 | O | GLN | A1976 | | 29.049 | 39.268 | 60.919 | 1.00 | 10.50 |
| ATOM | 2061 | N | VAL | A1977 | | 28.379 | 39.531 | 58.791 | 1.00 | 9.08 |
| ATOM | 2062 | CA | VAL | A1977 | | 29.161 | 38.394 | 58.323 | 1.00 | 9.36 |
| ATOM | 2063 | CB | VAL | A1977 | | 28.741 | 37.943 | 56.897 | 1.00 | 9.17 |
| ATOM | 2064 | CG1 | VAL | A1977 | | 29.601 | 36.757 | 56.413 | 1.00 | 9.94 |

FIGURE 3AO

|  | A | B | C | D | E | F | G | H | I | J |
|---|---|---|---|---|---|---|---|---|---|---|
| ATOM | 2065 | CG2 | VAL | A1977 | | 27.269 | 37.564 | 56.879 | 1.00 | 7.56 |
| ATOM | 2066 | C | VAL | A1977 | | 30.641 | 38.763 | 58.374 | 1.00 | 9.99 |
| ATOM | 2067 | O | VAL | A1977 | | 31.026 | 39.882 | 58.012 | 1.00 | 8.91 |
| ATOM | 2068 | N | GLU | A1978 | | 31.460 | 37.828 | 58.850 | 1.00 | 10.90 |
| ATOM | 2069 | CA | GLU | A1978 | | 32.911 | 37.979 | 58.826 | 1.00 | 12.29 |
| ATOM | 2070 | CB | BGLU | A1978 | | 33.589 | 36.676 | 59.250 | 0.50 | 12.89 |
| ATOM | 2071 | CB | AGLU | A1978 | | 33.583 | 36.673 | 59.281 | 0.50 | 13.35 |
| ATOM | 2072 | CG | BGLU | A1978 | | 33.840 | 36.566 | 60.744 | 0.50 | 13.25 |
| ATOM | 2073 | CG | AGLU | A1978 | | 35.107 | 36.693 | 59.319 | 0.50 | 14.26 |
| ATOM | 2074 | CD | BGLU | A1978 | | 34.401 | 35.212 | 61.136 | 0.50 | 13.87 |
| ATOM | 2075 | CD | AGLU | A1978 | | 35.677 | 37.299 | 60.592 | 0.50 | 15.14 |
| ATOM | 2076 | OE1 | BGLU | A1978 | | 33.736 | 34.494 | 61.907 | 0.50 | 12.47 |
| ATOM | 2077 | OE1 | AGLU | A1978 | | 36.508 | 38.230 | 60.486 | 0.50 | 15.45 |
| ATOM | 2078 | OE2 | BGLU | A1978 | | 35.508 | 34.865 | 60.670 | 0.50 | 14.54 |
| ATOM | 2079 | OE2 | AGLU | A1978 | | 35.310 | 36.844 | 61.698 | 0.50 | 16.63 |
| ATOM | 2080 | C | GLU | A1978 | | 33.362 | 38.366 | 57.417 | 1.00 | 12.32 |
| ATOM | 2081 | O | GLU | A1978 | | 32.812 | 37.881 | 56.428 | 1.00 | 10.62 |
| ATOM | 2082 | N | ASN | A1979 | | 34.345 | 39.259 | 57.337 | 1.00 | 14.82 |
| ATOM | 2083 | CA | ASN | A1979 | | 34.855 | 39.769 | 56.055 | 1.00 | 15.39 |
| ATOM | 2084 | CB | ASN | A1979 | | 35.412 | 38.637 | 55.169 | 1.00 | 20.01 |
| ATOM | 2085 | CG | ASN | A1979 | | 36.537 | 39.108 | 54.251 | 1.00 | 24.47 |
| ATOM | 2086 | OD1 | ASN | A1979 | | 37.313 | 40.000 | 54.604 | 1.00 | 27.03 |
| ATOM | 2087 | ND2 | ASN | A1979 | | 36.627 | 38.508 | 53.067 | 1.00 | 26.05 |
| ATOM | 2088 | C | ASN | A1979 | | 33.905 | 40.687 | 55.263 | 1.00 | 14.19 |
| ATOM | 2089 | O | ASN | A1979 | | 34.212 | 41.077 | 54.131 | 1.00 | 15.53 |
| ATOM | 2090 | N | SER | A1980 | | 32.755 | 41.030 | 55.840 | 1.00 | 10.90 |
| ATOM | 2091 | CA | SER | A1980 | | 31.918 | 42.074 | 55.247 | 1.00 | 9.43 |
| ATOM | 2092 | CB | SER | A1980 | | 30.431 | 41.840 | 55.536 | 1.00 | 8.61 |
| ATOM | 2093 | OG | SER | A1980 | | 30.148 | 42.053 | 56.912 | 1.00 | 6.25 |
| ATOM | 2094 | C | SER | A1980 | | 32.375 | 43.413 | 55.811 | 1.00 | 9.33 |
| ATOM | 2095 | O | SER | A1980 | | 33.145 | 43.452 | 56.776 | 1.00 | 10.16 |
| ATOM | 2096 | N | HIS | A1981 | | 31.919 | 44.507 | 55.210 | 1.00 | 9.37 |
| ATOM | 2097 | CA | HIS | A1981 | | 32.191 | 45.822 | 55.777 | 1.00 | 8.67 |
| ATOM | 2098 | CB | HIS | A1981 | | 33.431 | 46.487 | 55.145 | 1.00 | 8.74 |
| ATOM | 2099 | CG | HIS | A1981 | | 33.418 | 46.518 | 53.648 | 1.00 | 8.36 |
| ATOM | 2100 | ND1 | HIS | A1981 | | 33.930 | 45.496 | 52.876 | 1.00 | 8.86 |
| ATOM | 2101 | CE1 | HIS | A1981 | | 33.796 | 45.801 | 51.597 | 1.00 | 8.83 |
| ATOM | 2102 | NE2 | HIS | A1981 | | 33.221 | 46.988 | 51.511 | 1.00 | 10.12 |
| ATOM | 2103 | CD2 | HIS | A1981 | | 32.978 | 47.459 | 52.780 | 1.00 | 8.50 |
| ATOM | 2104 | C | HIS | A1981 | | 30.979 | 46.743 | 55.745 | 1.00 | 10.15 |
| ATOM | 2105 | O | HIS | A1981 | | 30.150 | 46.685 | 54.826 | 1.00 | 8.53 |
| ATOM | 2106 | N | ILE | A1982 | | 30.891 | 47.575 | 56.778 | 1.00 | 8.54 |
| ATOM | 2107 | CA | ILE | A1982 | | 29.867 | 48.599 | 56.896 | 1.00 | 9.29 |
| ATOM | 2108 | CB | ILE | A1982 | | 29.132 | 48.476 | 58.251 | 1.00 | 9.30 |
| ATOM | 2109 | CG1 | ILE | A1982 | | 28.513 | 47.082 | 58.421 | 1.00 | 8.62 |
| ATOM | 2110 | CD1 | ILE | A1982 | | 28.068 | 46.792 | 59.853 | 1.00 | 9.37 |
| ATOM | 2111 | CG2 | ILE | A1982 | | 28.077 | 49.582 | 58.399 | 1.00 | 7.95 |
| ATOM | 2112 | C | ILE | A1982 | | 30.618 | 49.917 | 56.831 | 1.00 | 9.32 |
| ATOM | 2113 | O | ILE | A1982 | | 31.362 | 50.254 | 57.749 | 1.00 | 7.77 |
| ATOM | 2114 | N | ILE | A1983 | | 30.446 | 50.648 | 55.736 | 1.00 | 7.73 |
| ATOM | 2115 | CA | ILE | A1983 | | 31.259 | 51.832 | 55.494 | 1.00 | 8.32 |
| ATOM | 2116 | CB | ILE | A1983 | | 32.391 | 51.539 | 54.473 | 1.00 | 9.17 |

FIGURE 3AP

| | A | B | C | D E | F | G | H | I | J |
|---|---|---|---|---|---|---|---|---|---|
| ATOM | 2117 | CG1 | ILE | A1983 | 31.809 | 51.099 | 53.118 | 1.00 | 8.74 |
| ATOM | 2118 | CD1 | ILE | A1983 | 32.779 | 51.188 | 51.940 | 1.00 | 8.21 |
| ATOM | 2119 | CG2 | ILE | A1983 | 33.394 | 50.532 | 55.052 | 1.00 | 9.38 |
| ATOM | 2120 | C | ILE | A1983 | 30.440 | 53.024 | 55.021 | 1.00 | 9.91 |
| ATOM | 2121 | O | ILE | A1983 | 29.303 | 52.873 | 54.571 | 1.00 | 7.33 |
| ATOM | 2122 | N | LEU | A1984 | 31.040 | 54.203 | 55.130 | 1.00 | 10.00 |
| ATOM | 2123 | CA | LEU | A1984 | 30.507 | 55.393 | 54.488 | 1.00 | 14.37 |
| ATOM | 2124 | CB | LEU | A1984 | 30.529 | 56.586 | 55.448 | 1.00 | 14.59 |
| ATOM | 2125 | CG | LEU | A1984 | 29.699 | 56.390 | 56.723 | 1.00 | 15.44 |
| ATOM | 2126 | CD1 | LEU | A1984 | 29.856 | 57.574 | 57.667 | 1.00 | 14.99 |
| ATOM | 2127 | CD2 | LEU | A1984 | 28.225 | 56.159 | 56.387 | 1.00 | 16.92 |
| ATOM | 2128 | C | LEU | A1984 | 31.330 | 55.647 | 53.235 | 1.00 | 16.79 |
| ATOM | 2129 | O | LEU | A1984 | 30.815 | 55.560 | 52.124 | 1.00 | 21.21 |
| ATOM | 2130 | N | THR | A1985 | 32.616 | 55.923 | 53.420 | 1.00 | 17.67 |
| ATOM | 2131 | CA | THR | A1985 | 33.549 | 56.069 | 52.312 | 1.00 | 18.51 |
| ATOM | 2132 | CB | THR | A1985 | 34.354 | 57.379 | 52.455 | 1.00 | 19.70 |
| ATOM | 2133 | OG1 | THR | A1985 | 33.455 | 58.460 | 52.719 | 1.00 | 22.30 |
| ATOM | 2134 | CG2 | THR | A1985 | 34.981 | 57.786 | 51.124 | 1.00 | 20.25 |
| ATOM | 2135 | C | THR | A1985 | 34.477 | 54.863 | 52.274 | 1.00 | 16.20 |
| ATOM | 2136 | O | THR | A1985 | 34.856 | 54.336 | 53.320 | 1.00 | 14.55 |
| ATOM | 2137 | N | GLY | A1986 | 34.825 | 54.429 | 51.065 | 1.00 | 15.67 |
| ATOM | 2138 | CA | GLY | A1986 | 35.756 | 53.329 | 50.868 | 1.00 | 14.52 |
| ATOM | 2139 | C | GLY | A1986 | 37.198 | 53.735 | 51.101 | 1.00 | 15.54 |
| ATOM | 2140 | O | GLY | A1986 | 37.539 | 54.920 | 51.035 | 1.00 | 14.43 |
| ATOM | 2141 | N | ALA | A1987 | 38.040 | 52.742 | 51.378 | 1.00 | 15.95 |
| ATOM | 2142 | CA | ALA | A1987 | 39.456 | 52.952 | 51.676 | 1.00 | 17.54 |
| ATOM | 2143 | CB | ALA | A1987 | 40.147 | 51.618 | 51.920 | 1.00 | 18.70 |
| ATOM | 2144 | C | ALA | A1987 | 40.197 | 53.733 | 50.594 | 1.00 | 17.73 |
| ATOM | 2145 | O | ALA | A1987 | 40.936 | 54.673 | 50.898 | 1.00 | 15.11 |
| ATOM | 2146 | N | SER | A1988 | 39.982 | 53.350 | 49.341 | 1.00 | 19.68 |
| ATOM | 2147 | CA | SER | A1988 | 40.712 | 53.945 | 48.221 | 1.00 | 22.85 |
| ATOM | 2148 | CB | SER | A1988 | 40.565 | 53.090 | 46.954 | 1.00 | 24.35 |
| ATOM | 2149 | OG | SER | A1988 | 39.565 | 53.591 | 46.089 | 1.00 | 28.20 |
| ATOM | 2150 | C | SER | A1988 | 40.335 | 55.414 | 47.986 | 1.00 | 22.53 |
| ATOM | 2151 | O | SER | A1988 | 41.206 | 56.243 | 47.731 | 1.00 | 22.83 |
| ATOM | 2152 | N | ALA | A1989 | 39.046 | 55.732 | 48.105 | 1.00 | 22.70 |
| ATOM | 2153 | CA | ALA | A1989 | 38.582 | 57.117 | 48.021 | 1.00 | 22.01 |
| ATOM | 2154 | CB | ALA | A1989 | 37.066 | 57.175 | 48.005 | 1.00 | 23.21 |
| ATOM | 2155 | C | ALA | A1989 | 39.144 | 57.987 | 49.151 | 1.00 | 23.09 |
| ATOM | 2156 | O | ALA | A1989 | 39.502 | 59.148 | 48.924 | 1.00 | 23.06 |
| ATOM | 2157 | N | LEU | A1990 | 39.227 | 57.421 | 50.357 | 1.00 | 21.79 |
| ATOM | 2158 | CA | LEU | A1990 | 39.843 | 58.108 | 51.494 | 1.00 | 23.08 |
| ATOM | 2159 | CB | LEU | A1990 | 39.565 | 57.370 | 52.804 | 1.00 | 22.23 |
| ATOM | 2160 | CG | LEU | A1990 | 38.167 | 57.484 | 53.417 | 1.00 | 21.52 |
| ATOM | 2161 | CD1 | LEU | A1990 | 38.044 | 56.502 | 54.559 | 1.00 | 20.20 |
| ATOM | 2162 | CD2 | LEU | A1990 | 37.874 | 58.901 | 53.897 | 1.00 | 21.25 |
| ATOM | 2163 | C | LEU | A1990 | 41.348 | 58.259 | 51.311 | 1.00 | 23.90 |
| ATOM | 2164 | O | LEU | A1990 | 41.943 | 59.238 | 51.768 | 1.00 | 24.22 |
| ATOM | 2165 | N | ASN | A1991 | 41.956 | 57.277 | 50.653 | 1.00 | 24.98 |
| ATOM | 2166 | CA | ASN | A1991 | 43.378 | 57.319 | 50.343 | 1.00 | 27.42 |
| ATOM | 2167 | CB | ASN | A1991 | 43.841 | 55.984 | 49.757 | 1.00 | 25.90 |
| ATOM | 2168 | CG | ASN | A1991 | 44.062 | 54.927 | 50.820 | 1.00 | 25.12 |

FIGURE 3AQ

|      | A    | B   | C   | D | E     | F      | G      | H      | I    | J     |
|------|------|-----|-----|---|-------|--------|--------|--------|------|-------|
| ATOM | 2169 | OD1 | ASN | A | 1991  | 44.225 | 53.748 | 50.512 | 1.00 | 24.97 |
| ATOM | 2170 | ND2 | ASN | A | 1991  | 44.068 | 55.345 | 52.080 | 1.00 | 23.46 |
| ATOM | 2171 | C   | ASN | A | 1991  | 43.718 | 58.465 | 49.398 | 1.00 | 29.25 |
| ATOM | 2172 | O   | ASN | A | 1991  | 44.748 | 59.120 | 49.558 | 1.00 | 29.04 |
| ATOM | 2173 | N   | LYS | A | 1992  | 42.835 | 58.705 | 48.429 | 1.00 | 32.38 |
| ATOM | 2174 | CA  | LYS | A | 1992  | 42.998 | 59.793 | 47.469 | 1.00 | 35.72 |
| ATOM | 2175 | CB  | LYS | A | 1992  | 42.008 | 59.645 | 46.312 | 1.00 | 36.75 |
| ATOM | 2176 | CG  | LYS | A | 1992  | 42.458 | 58.654 | 45.241 | 1.00 | 38.55 |
| ATOM | 2177 | CD  | LYS | A | 1992  | 41.366 | 58.395 | 44.207 | 1.00 | 39.68 |
| ATOM | 2178 | CE  | LYS | A | 1992  | 40.949 | 56.925 | 44.182 | 1.00 | 39.92 |
| ATOM | 2179 | NZ  | LYS | A | 1992  | 41.915 | 56.065 | 43.435 | 1.00 | 39.81 |
| ATOM | 2180 | C   | LYS | A | 1992  | 42.863 | 61.164 | 48.134 | 1.00 | 37.24 |
| ATOM | 2181 | O   | LYS | A | 1992  | 43.635 | 62.078 | 47.837 | 1.00 | 38.37 |
| ATOM | 2182 | N   | VAL | A | 1993  | 41.895 | 61.293 | 49.041 | 1.00 | 38.72 |
| ATOM | 2183 | CA  | VAL | A | 1993  | 41.680 | 62.530 | 49.797 | 1.00 | 40.08 |
| ATOM | 2184 | CB  | VAL | A | 1993  | 40.400 | 62.448 | 50.682 | 1.00 | 40.13 |
| ATOM | 2185 | CG1 | VAL | A | 1993  | 40.323 | 63.610 | 51.668 | 1.00 | 40.14 |
| ATOM | 2186 | CG2 | VAL | A | 1993  | 39.150 | 62.412 | 49.815 | 1.00 | 39.66 |
| ATOM | 2187 | C   | VAL | A | 1993  | 42.912 | 62.898 | 50.638 | 1.00 | 41.32 |
| ATOM | 2188 | O   | VAL | A | 1993  | 43.396 | 64.032 | 50.576 | 1.00 | 43.11 |
| ATOM | 2189 | N   | LEU | A | 1994  | 43.430 | 61.929 | 51.392 | 1.00 | 41.47 |
| ATOM | 2190 | CA  | LEU | A | 1994  | 44.572 | 62.157 | 52.282 | 1.00 | 41.27 |
| ATOM | 2191 | CB  | LEU | A | 1994  | 44.619 | 61.088 | 53.384 | 1.00 | 41.26 |
| ATOM | 2192 | CG  | LEU | A | 1994  | 43.522 | 61.154 | 54.455 | 1.00 | 41.84 |
| ATOM | 2193 | CD1 | LEU | A | 1994  | 43.120 | 59.756 | 54.907 | 1.00 | 41.41 |
| ATOM | 2194 | CD2 | LEU | A | 1994  | 43.950 | 62.003 | 55.650 | 1.00 | 41.50 |
| ATOM | 2195 | C   | LEU | A | 1994  | 45.920 | 62.245 | 51.550 | 1.00 | 41.70 |
| ATOM | 2196 | O   | LEU | A | 1994  | 46.923 | 62.657 | 52.139 | 1.00 | 41.61 |
| ATOM | 2197 | N   | GLY | A | 1995  | 45.935 | 61.856 | 50.276 | 1.00 | 41.52 |
| ATOM | 2198 | CA  | GLY | A | 1995  | 47.119 | 61.962 | 49.437 | 1.00 | 41.64 |
| ATOM | 2199 | C   | GLY | A | 1995  | 48.209 | 60.950 | 49.742 | 1.00 | 41.30 |
| ATOM | 2200 | O   | GLY | A | 1995  | 49.383 | 61.198 | 49.463 | 1.00 | 42.30 |
| ATOM | 2201 | N   | ARG | A | 1996  | 47.815 | 59.814 | 50.314 | 1.00 | 40.85 |
| ATOM | 2202 | CA  | ARG | A | 1996  | 48.735 | 58.732 | 50.663 | 1.00 | 39.97 |
| ATOM | 2203 | CB  | ARG | A | 1996  | 49.526 | 59.082 | 51.928 | 1.00 | 42.20 |
| ATOM | 2204 | CG  | ARG | A | 1996  | 51.028 | 59.209 | 51.702 | 1.00 | 44.95 |
| ATOM | 2205 | CD  | ARG | A | 1996  | 51.573 | 60.624 | 51.860 | 1.00 | 46.46 |
| ATOM | 2206 | NE  | ARG | A | 1996  | 51.870 | 60.948 | 53.256 | 1.00 | 48.16 |
| ATOM | 2207 | CZ  | ARG | A | 1996  | 52.924 | 61.653 | 53.661 | 1.00 | 48.87 |
| ATOM | 2208 | NH1 | ARG | A | 1996  | 53.104 | 61.891 | 54.955 | 1.00 | 48.99 |
| ATOM | 2209 | NH2 | ARG | A | 1996  | 53.800 | 62.122 | 52.781 | 1.00 | 49.22 |
| ATOM | 2210 | C   | ARG | A | 1996  | 47.975 | 57.422 | 50.866 | 1.00 | 37.85 |
| ATOM | 2211 | O   | ARG | A | 1996  | 46.758 | 57.429 | 51.087 | 1.00 | 37.05 |
| ATOM | 2212 | N   | GLU | A | 1997  | 48.694 | 56.303 | 50.794 | 1.00 | 35.03 |
| ATOM | 2213 | CA  | GLU | A | 1997  | 48.098 | 54.980 | 50.995 | 1.00 | 33.02 |
| ATOM | 2214 | CB  | GLU | A | 1997  | 48.915 | 53.883 | 50.284 | 1.00 | 34.67 |
| ATOM | 2215 | CG  | GLU | A | 1997  | 50.421 | 53.920 | 50.540 | 1.00 | 37.04 |
| ATOM | 2216 | CD  | GLU | A | 1997  | 51.261 | 53.701 | 49.288 | 1.00 | 38.33 |
| ATOM | 2217 | OE1 | GLU | A | 1997  | 50.730 | 53.208 | 48.266 | 1.00 | 38.95 |
| ATOM | 2218 | OE2 | GLU | A | 1997  | 52.469 | 54.022 | 49.328 | 1.00 | 39.06 |
| ATOM | 2219 | C   | GLU | A | 1997  | 47.893 | 54.676 | 52.489 | 1.00 | 30.46 |
| ATOM | 2220 | O   | GLU | A | 1997  | 48.545 | 53.796 | 53.065 | 1.00 | 29.92 |

FIGURE 3AR

|  | A | B | C | D E | F | G | H | I | J |
|---|---|---|---|---|---|---|---|---|---|
| ATOM | 2221 | N | VAL | A1998 | 46.975 | 55.420 | 53.105 | 1.00 | 26.75 |
| ATOM | 2222 | CA | VAL | A1998 | 46.702 | 55.310 | 54.537 | 1.00 | 24.20 |
| ATOM | 2223 | CB | VAL | A1998 | 45.777 | 56.452 | 55.026 | 1.00 | 24.64 |
| ATOM | 2224 | CG1 | VAL | A1998 | 45.376 | 56.238 | 56.479 | 1.00 | 25.22 |
| ATOM | 2225 | CG2 | VAL | A1998 | 46.449 | 57.810 | 54.850 | 1.00 | 25.32 |
| ATOM | 2226 | C | VAL | A1998 | 46.080 | 53.956 | 54.880 | 1.00 | 21.72 |
| ATOM | 2227 | O | VAL | A1998 | 46.557 | 53.250 | 55.771 | 1.00 | 20.67 |
| ATOM | 2228 | N | TYR | A1999 | 45.023 | 53.605 | 54.154 | 1.00 | 19.65 |
| ATOM | 2229 | CA | TYR | A1999 | 44.259 | 52.392 | 54.413 | 1.00 | 18.83 |
| ATOM | 2230 | CB | TYR | A1999 | 42.766 | 52.711 | 54.396 | 1.00 | 17.06 |
| ATOM | 2231 | CG | TYR | A1999 | 42.364 | 53.773 | 55.390 | 1.00 | 16.23 |
| ATOM | 2232 | CD1 | TYR | A1999 | 42.077 | 55.073 | 54.974 | 1.00 | 15.07 |
| ATOM | 2233 | CE1 | TYR | A1999 | 41.706 | 56.055 | 55.895 | 1.00 | 15.95 |
| ATOM | 2234 | CZ | TYR | A1999 | 41.623 | 55.734 | 57.242 | 1.00 | 16.01 |
| ATOM | 2235 | OH | TYR | A1999 | 41.257 | 56.695 | 58.156 | 1.00 | 17.13 |
| ATOM | 2236 | CE2 | TYR | A1999 | 41.913 | 54.456 | 57.678 | 1.00 | 15.72 |
| ATOM | 2237 | CD2 | TYR | A1999 | 42.280 | 53.481 | 56.754 | 1.00 | 16.52 |
| ATOM | 2238 | C | TYR | A1999 | 44.568 | 51.305 | 53.397 | 1.00 | 19.65 |
| ATOM | 2239 | O | TYR | A1999 | 44.826 | 51.598 | 52.233 | 1.00 | 20.70 |
| ATOM | 2240 | N | THR | A2000 | 44.544 | 50.052 | 53.843 | 1.00 | 19.69 |
| ATOM | 2241 | CA | THR | A2000 | 44.766 | 48.916 | 52.948 | 1.00 | 20.81 |
| ATOM | 2242 | CB | THR | A2000 | 45.893 | 47.993 | 53.474 | 1.00 | 21.33 |
| ATOM | 2243 | OG1 | THR | A2000 | 45.673 | 47.695 | 54.858 | 1.00 | 24.22 |
| ATOM | 2244 | CG2 | THR | A2000 | 47.232 | 48.721 | 53.469 | 1.00 | 22.76 |
| ATOM | 2245 | C | THR | A2000 | 43.498 | 48.107 | 52.687 | 1.00 | 19.46 |
| ATOM | 2246 | O | THR | A2000 | 43.437 | 47.334 | 51.728 | 1.00 | 19.37 |
| ATOM | 2247 | N | SER | A2001 | 42.487 | 48.290 | 53.533 | 1.00 | 18.94 |
| ATOM | 2248 | CA | SER | A2001 | 41.261 | 47.500 | 53.442 | 1.00 | 17.37 |
| ATOM | 2249 | CB | SER | A2001 | 41.425 | 46.207 | 54.248 | 1.00 | 18.20 |
| ATOM | 2250 | OG | SER | A2001 | 40.215 | 45.479 | 54.330 | 1.00 | 19.05 |
| ATOM | 2251 | C | SER | A2001 | 40.023 | 48.259 | 53.924 | 1.00 | 17.67 |
| ATOM | 2252 | O | SER | A2001 | 40.092 | 49.058 | 54.858 | 1.00 | 14.38 |
| ATOM | 2253 | N | ASN | A2002 | 38.893 | 47.984 | 53.276 | 1.00 | 16.50 |
| ATOM | 2254 | CA | ASN | A2002 | 37.590 | 48.453 | 53.733 | 1.00 | 17.18 |
| ATOM | 2255 | CB | ASN | A2002 | 36.512 | 48.120 | 52.698 | 1.00 | 17.78 |
| ATOM | 2256 | CG | ASN | A2002 | 36.405 | 49.175 | 51.600 | 1.00 | 19.11 |
| ATOM | 2257 | OD1 | ASN | A2002 | 36.955 | 50.269 | 51.711 | 1.00 | 20.47 |
| ATOM | 2258 | ND2 | ASN | A2002 | 35.685 | 48.847 | 50.538 | 1.00 | 20.45 |
| ATOM | 2259 | C | ASN | A2002 | 37.222 | 47.877 | 55.104 | 1.00 | 16.85 |
| ATOM | 2260 | O | ASN | A2002 | 36.419 | 48.467 | 55.837 | 1.00 | 13.13 |
| ATOM | 2261 | N | ASN | A2003 | 37.827 | 46.734 | 55.445 | 1.00 | 14.87 |
| ATOM | 2262 | CA | ASN | A2003 | 37.670 | 46.123 | 56.761 | 1.00 | 16.42 |
| ATOM | 2263 | CB | ASN | A2003 | 38.298 | 44.724 | 56.804 | 1.00 | 20.29 |
| ATOM | 2264 | CG | ASN | A2003 | 37.444 | 43.681 | 56.116 | 1.00 | 22.44 |
| ATOM | 2265 | OD1 | ASN | A2003 | 36.221 | 43.807 | 56.058 | 1.00 | 23.80 |
| ATOM | 2266 | ND2 | ASN | A2003 | 38.084 | 42.642 | 55.587 | 1.00 | 23.34 |
| ATOM | 2267 | C | ASN | A2003 | 38.265 | 46.977 | 57.861 | 1.00 | 16.35 |
| ATOM | 2268 | O | ASN | A2003 | 37.811 | 46.927 | 59.001 | 1.00 | 16.63 |
| ATOM | 2269 | N | GLN | A2004 | 39.284 | 47.762 | 57.515 | 1.00 | 16.89 |
| ATOM | 2270 | CA | GLN | A2004 | 39.898 | 48.685 | 58.462 | 1.00 | 16.96 |
| ATOM | 2271 | CB | GLN | A2004 | 41.110 | 49.358 | 57.834 | 1.00 | 19.04 |
| ATOM | 2272 | CG | GLN | A2004 | 42.424 | 48.718 | 58.160 | 1.00 | 21.44 |

FIGURE 3AS

|  | A | B | C | D E | F | G | H | I | J |
|---|---|---|---|---|---|---|---|---|---|
| ATOM | 2273 | CD | GLN | A2004 | 43.578 | 49.451 | 57.511 | 1.00 | 23.06 |
| ATOM | 2274 | OE1 | GLN | A2004 | 43.558 | 49.705 | 56.306 | 1.00 | 23.81 |
| ATOM | 2275 | NE2 | GLN | A2004 | 44.582 | 49.797 | 58.304 | 1.00 | 23.38 |
| ATOM | 2276 | C | GLN | A2004 | 38.920 | 49.766 | 58.885 | 1.00 | 15.06 |
| ATOM | 2277 | O | GLN | A2004 | 39.050 | 50.348 | 59.960 | 1.00 | 13.58 |
| ATOM | 2278 | N | LEU | A2005 | 37.950 | 50.041 | 58.018 | 1.00 | 13.10 |
| ATOM | 2279 | CA | LEU | A2005 | 36.987 | 51.104 | 58.258 | 1.00 | 11.33 |
| ATOM | 2280 | CB | LEU | A2005 | 36.676 | 51.853 | 56.957 | 1.00 | 11.77 |
| ATOM | 2281 | CG | LEU | A2005 | 37.902 | 52.342 | 56.180 | 1.00 | 11.68 |
| ATOM | 2282 | CD1 | LEU | A2005 | 37.510 | 52.716 | 54.772 | 1.00 | 12.65 |
| ATOM | 2283 | CD2 | LEU | A2005 | 38.553 | 53.514 | 56.891 | 1.00 | 10.57 |
| ATOM | 2284 | C | LEU | A2005 | 35.710 | 50.566 | 58.863 | 1.00 | 10.71 |
| ATOM | 2285 | O | LEU | A2005 | 35.186 | 51.138 | 59.810 | 1.00 | 11.20 |
| ATOM | 2286 | N | GLY | A2006 | 35.208 | 49.465 | 58.314 | 1.00 | 9.81 |
| ATOM | 2287 | CA | GLY | A2006 | 33.917 | 48.956 | 58.727 | 1.00 | 7.91 |
| ATOM | 2288 | C | GLY | A2006 | 33.810 | 47.451 | 58.814 | 1.00 | 7.45 |
| ATOM | 2289 | O | GLY | A2006 | 32.707 | 46.918 | 58.821 | 1.00 | 7.06 |
| ATOM | 2290 | N | GLY | A2007 | 34.950 | 46.768 | 58.899 | 1.00 | 7.47 |
| ATOM | 2291 | CA | GLY | A2007 | 34.962 | 45.331 | 59.102 | 1.00 | 6.04 |
| ATOM | 2292 | C | GLY | A2007 | 34.577 | 45.001 | 60.526 | 1.00 | 6.88 |
| ATOM | 2293 | O | GLY | A2007 | 34.408 | 45.902 | 61.351 | 1.00 | 8.09 |
| ATOM | 2294 | N | VAL | A2008 | 34.446 | 43.714 | 60.825 | 1.00 | 6.76 |
| ATOM | 2295 | CA | VAL | A2008 | 34.050 | 43.279 | 62.165 | 1.00 | 8.07 |
| ATOM | 2296 | CB | VAL | A2008 | 33.842 | 41.741 | 62.250 | 1.00 | 8.03 |
| ATOM | 2297 | CG1 | VAL | A2008 | 32.727 | 41.309 | 61.302 | 1.00 | 9.10 |
| ATOM | 2298 | CG2 | VAL | A2008 | 35.135 | 40.962 | 61.947 | 1.00 | 7.34 |
| ATOM | 2299 | C | VAL | A2008 | 35.003 | 43.777 | 63.253 | 1.00 | 9.64 |
| ATOM | 2300 | O | VAL | A2008 | 34.581 | 44.027 | 64.386 | 1.00 | 8.11 |
| ATOM | 2301 | N | GLN | A2009 | 36.276 | 43.947 | 62.893 | 1.00 | 9.99 |
| ATOM | 2302 | CA | GLN | A2009 | 37.292 | 44.472 | 63.811 | 1.00 | 11.07 |
| ATOM | 2303 | CB | GLN | A2009 | 38.671 | 44.525 | 63.133 | 1.00 | 13.14 |
| ATOM | 2304 | CG | GLN | A2009 | 38.811 | 45.607 | 62.047 | 1.00 | 17.22 |
| ATOM | 2305 | CD | GLN | A2009 | 40.027 | 45.402 | 61.162 | 1.00 | 19.93 |
| ATOM | 2306 | OE1 | GLN | A2009 | 41.056 | 46.060 | 61.344 | 1.00 | 21.83 |
| ATOM | 2307 | NE2 | GLN | A2009 | 39.914 | 44.496 | 60.204 | 1.00 | 19.38 |
| ATOM | 2308 | C | GLN | A2009 | 36.923 | 45.853 | 64.356 | 1.00 | 10.16 |
| ATOM | 2309 | O | GLN | A2009 | 37.386 | 46.245 | 65.426 | 1.00 | 10.21 |
| ATOM | 2310 | N | ILE | A2010 | 36.109 | 46.588 | 63.604 | 1.00 | 10.04 |
| ATOM | 2311 | CA | ILE | A2010 | 35.620 | 47.896 | 64.038 | 1.00 | 9.21 |
| ATOM | 2312 | CB | ILE | A2010 | 35.587 | 48.900 | 62.842 | 1.00 | 9.88 |
| ATOM | 2313 | CG1 | ILE | A2010 | 37.001 | 49.210 | 62.322 | 1.00 | 10.49 |
| ATOM | 2314 | CD1 | ILE | A2010 | 37.945 | 49.891 | 63.329 | 1.00 | 12.34 |
| ATOM | 2315 | CG2 | ILE | A2010 | 34.779 | 50.183 | 63.194 | 1.00 | 9.26 |
| ATOM | 2316 | C | ILE | A2010 | 34.228 | 47.751 | 64.652 | 1.00 | 10.98 |
| ATOM | 2317 | O | ILE | A2010 | 34.020 | 48.067 | 65.829 | 1.00 | 10.62 |
| ATOM | 2318 | N | MET | A2011 | 33.292 | 47.242 | 63.855 | 1.00 | 10.25 |
| ATOM | 2319 | CA | MET | A2011 | 31.868 | 47.315 | 64.175 | 1.00 | 8.30 |
| ATOM | 2320 | CB | MET | A2011 | 31.024 | 47.146 | 62.906 | 1.00 | 9.26 |
| ATOM | 2321 | CG | MET | A2011 | 31.262 | 48.237 | 61.859 | 1.00 | 9.72 |
| ATOM | 2322 | SD | MET | A2011 | 30.805 | 49.875 | 62.453 | 1.00 | 11.71 |
| ATOM | 2323 | CE | MET | A2011 | 31.629 | 50.907 | 61.241 | 1.00 | 9.83 |
| ATOM | 2324 | C | MET | A2011 | 31.407 | 46.358 | 65.266 | 1.00 | 7.59 |

FIGURE 3AT

|      | A    | B   | C   | D    | E     | F      | G      | H     | I    | J     |
|------|------|-----|-----|------|-------|--------|--------|-------|------|-------|
| ATOM | 2325 | O   |     | MET  | A2011 | 30.495 | 46.683 | 66.015 | 1.00 | 7.74  |
| ATOM | 2326 | N   |     | HIS  | A2012 | 32.040 | 45.191 | 65.365 | 1.00 | 7.87  |
| ATOM | 2327 | CA  |     | HIS  | A2012 | 31.762 | 44.276 | 66.472 | 1.00 | 7.50  |
| ATOM | 2328 | CB  |     | HIS  | A2012 | 32.335 | 42.884 | 66.187 | 1.00 | 10.13 |
| ATOM | 2329 | CG  |     | HIS  | A2012 | 31.749 | 41.800 | 67.039 | 1.00 | 9.36  |
| ATOM | 2330 | ND1 |     | HIS  | A2012 | 32.406 | 40.612 | 67.282 | 1.00 | 10.51 |
| ATOM | 2331 | CE1 |     | HIS  | A2012 | 31.658 | 39.848 | 68.061 | 1.00 | 9.37  |
| ATOM | 2332 | NE2 |     | HIS  | A2012 | 30.538 | 40.498 | 68.329 | 1.00 | 10.52 |
| ATOM | 2333 | CD2 |     | HIS  | A2012 | 30.568 | 41.720 | 67.699 | 1.00 | 8.35  |
| ATOM | 2334 | C   |     | HIS  | A2012 | 32.334 | 44.820 | 67.781 | 1.00 | 8.13  |
| ATOM | 2335 | O   |     | HIS  | A2012 | 31.882 | 44.449 | 68.871 | 1.00 | 7.16  |
| ATOM | 2336 | N   |     | TYR  | A2013 | 33.314 | 45.720 | 67.667 | 1.00 | 7.52  |
| ATOM | 2337 | CA  |     | TYR  | A2013 | 34.024 | 46.247 | 68.837 | 1.00 | 7.38  |
| ATOM | 2338 | CB  |     | TYR  | A2013 | 35.533 | 46.263 | 68.570 | 1.00 | 6.75  |
| ATOM | 2339 | CG  |     | TYR  | A2013 | 36.131 | 44.880 | 68.684 | 1.00 | 9.29  |
| ATOM | 2340 | CD1 |     | TYR  | A2013 | 36.810 | 44.495 | 69.834 | 1.00 | 8.44  |
| ATOM | 2341 | CE1 |     | TYR  | A2013 | 37.355 | 43.213 | 69.955 | 1.00 | 12.41 |
| ATOM | 2342 | CZ  |     | TYR  | A2013 | 37.196 | 42.303 | 68.923 | 1.00 | 12.61 |
| ATOM | 2343 | OH  |     | TYR  | A2013 | 37.735 | 41.040 | 69.051 | 1.00 | 17.44 |
| ATOM | 2344 | CE2 |     | TYR  | A2013 | 36.507 | 42.656 | 67.771 | 1.00 | 10.75 |
| ATOM | 2345 | CD2 |     | TYR  | A2013 | 35.974 | 43.942 | 67.657 | 1.00 | 8.67  |
| ATOM | 2346 | C   |     | TYR  | A2013 | 33.527 | 47.615 | 69.312 | 1.00 | 8.30  |
| ATOM | 2347 | O   |     | TYR  | A2013 | 33.983 | 48.135 | 70.341 | 1.00 | 6.43  |
| ATOM | 2348 | N   |     | ASN  | A2014 | 32.582 | 48.192 | 68.580 | 1.00 | 8.04  |
| ATOM | 2349 | CA  |     | ASN  | A2014 | 32.014 | 49.478 | 68.983 | 1.00 | 7.44  |
| ATOM | 2350 | CB  |     | ASN  | A2014 | 32.419 | 50.584 | 67.999 | 1.00 | 7.71  |
| ATOM | 2351 | CG  |     | ASN  | A2014 | 31.718 | 50.461 | 66.647 | 1.00 | 7.56  |
| ATOM | 2352 | OD1 |     | ASN  | A2014 | 30.898 | 49.572 | 66.443 | 1.00 | 5.61  |
| ATOM | 2353 | ND2 |     | ASN  | A2014 | 32.055 | 51.350 | 65.718 | 1.00 | 7.12  |
| ATOM | 2354 | C   |     | ASN  | A2014 | 30.498 | 49.452 | 69.184 | 1.00 | 7.46  |
| ATOM | 2355 | O   |     | ASN  | A2014 | 29.884 | 50.492 | 69.391 | 1.00 | 9.14  |
| ATOM | 2356 | N   |     | GLY  | A2015 | 29.902 | 48.266 | 69.115 | 1.00 | 8.06  |
| ATOM | 2357 | CA  |     | GLY  | A2015 | 28.476 | 48.114 | 69.357 | 1.00 | 6.98  |
| ATOM | 2358 | C   |     | GLY  | A2015 | 27.546 | 48.259 | 68.168 | 1.00 | 7.91  |
| ATOM | 2359 | O   |     | GLY  | A2015 | 26.340 | 48.043 | 68.301 | 1.00 | 9.41  |
| ATOM | 2360 | N   |     | VAL  | A2016 | 28.077 | 48.628 | 67.007 | 1.00 | 8.27  |
| ATOM | 2361 | CA  |     | VAL  | A2016 | 27.237 | 48.735 | 65.814 | 1.00 | 6.89  |
| ATOM | 2362 | CB  |     | VAL  | A2016 | 27.956 | 49.491 | 64.684 | 1.00 | 7.20  |
| ATOM | 2363 | CG1 |     | VAL  | A2016 | 27.203 | 49.358 | 63.368 | 1.00 | 6.67  |
| ATOM | 2364 | CG2 |     | VAL  | A2016 | 28.122 | 50.975 | 65.070 | 1.00 | 6.45  |
| ATOM | 2365 | C   |     | VAL  | A2016 | 26.755 | 47.345 | 65.363 | 1.00 | 9.08  |
| ATOM | 2366 | O   |     | VAL  | A2016 | 25.580 | 47.159 | 65.052 | 1.00 | 9.28  |
| ATOM | 2367 | N   |     | SER  | A2017 | 27.665 | 46.372 | 65.346 | 1.00 | 8.27  |
| ATOM | 2368 | CA  |     | SER  | A2017 | 27.300 | 44.993 | 65.038 | 1.00 | 8.25  |
| ATOM | 2369 | CB  |     | SER  | A2017 | 28.363 | 44.325 | 64.165 | 1.00 | 6.71  |
| ATOM | 2370 | OG  |     | SER  | A2017 | 28.432 | 44.961 | 62.905 | 1.00 | 8.76  |
| ATOM | 2371 | C   |     | SER  | A2017 | 27.134 | 44.228 | 66.338 | 1.00 | 8.59  |
| ATOM | 2372 | O   |     | SER  | A2017 | 28.087 | 44.099 | 67.117 | 1.00 | 11.17 |
| ATOM | 2373 | N   |     | HIS  | A2018 | 25.922 | 43.734 | 66.566 | 1.00 | 8.93  |
| ATOM | 2374 | CA  |     | HIS  | A2018 | 25.596 | 43.001 | 67.788 | 1.00 | 9.44  |
| ATOM | 2375 | CB  |     | HIS  | A2018 | 24.086 | 42.791 | 67.884 | 1.00 | 8.57  |
| ATOM | 2376 | CG  |     | HIS  | A2018 | 23.329 | 44.024 | 68.280 | 1.00 | 7.79  |

FIGURE 3AU

|      | A    | B    | C   | D    | E      | F      | G      | H      | I    | J     |
|------|------|------|-----|------|--------|--------|--------|--------|------|-------|
| ATOM | 2377 | ND1  | HIS | A2018 |       | 22.118 | 43.973 | 68.931 | 1.00 | 6.76  |
| ATOM | 2378 | CE1  | HIS | A2018 |       | 21.689 | 45.203 | 69.159 | 1.00 | 7.23  |
| ATOM | 2379 | NE2  | HIS | A2018 |       | 22.587 | 46.051 | 68.692 | 1.00 | 8.57  |
| ATOM | 2380 | CD2  | HIS | A2018 |       | 23.623 | 45.340 | 68.133 | 1.00 | 8.49  |
| ATOM | 2381 | C    | HIS | A2018 |       | 26.328 | 41.663 | 67.873 | 1.00 | 9.94  |
| ATOM | 2382 | O    | HIS | A2018 |       | 26.673 | 41.207 | 68.963 | 1.00 | 11.23 |
| ATOM | 2383 | N    | ILE | A2019 |       | 26.568 | 41.049 | 66.716 | 1.00 | 9.01  |
| ATOM | 2384 | CA   | ILE | A2019 |       | 27.212 | 39.742 | 66.638 | 1.00 | 9.00  |
| ATOM | 2385 | CB   | ILE | A2019 |       | 26.200 | 38.613 | 66.999 | 1.00 | 9.30  |
| ATOM | 2386 | CG1  | ILE | A2019 |       | 26.929 | 37.344 | 67.464 | 1.00 | 11.59 |
| ATOM | 2387 | CD1  | ILE | A2019 |       | 26.119 | 36.470 | 68.422 | 1.00 | 11.20 |
| ATOM | 2388 | CG2  | ILE | A2019 |       | 25.264 | 38.318 | 65.824 | 1.00 | 9.26  |
| ATOM | 2389 | C    | ILE | A2019 |       | 27.789 | 39.534 | 65.237 | 1.00 | 8.72  |
| ATOM | 2390 | O    | ILE | A2019 |       | 27.369 | 40.180 | 64.266 | 1.00 | 8.65  |
| ATOM | 2391 | N    | THR | A2020 |       | 28.760 | 38.640 | 65.141 | 1.00 | 8.03  |
| ATOM | 2392 | CA   | THR | A2020 |       | 29.330 | 38.248 | 63.857 | 1.00 | 8.61  |
| ATOM | 2393 | CB   | CTHR| A2020 |       | 30.858 | 38.428 | 63.818 | 0.50 | 7.47  |
| ATOM | 2394 | CB   | BTHR| A2020 |       | 30.857 | 38.474 | 63.899 | 0.50 | 10.59 |
| ATOM | 2395 | OG1  | CTHR| A2020 |       | 31.474 | 37.499 | 64.716 | 0.50 | 3.38  |
| ATOM | 2396 | OG1  | BTHR| A2020 |       | 31.114 | 39.879 | 64.024 | 0.50 | 11.99 |
| ATOM | 2397 | CG2  | CTHR| A2020 |       | 31.257 | 39.787 | 64.353 | 0.50 | 8.20  |
| ATOM | 2398 | CG2  | BTHR| A2020 |       | 31.519 | 38.113 | 62.573 | 0.50 | 11.84 |
| ATOM | 2399 | C    | THR | A2020 |       | 28.993 | 36.792 | 63.588 | 1.00 | 9.89  |
| ATOM | 2400 | O    | THR | A2020 |       | 28.781 | 36.014 | 64.527 | 1.00 | 10.79 |
| ATOM | 2401 | N    | VAL | A2021 |       | 28.924 | 36.443 | 62.304 | 1.00 | 8.65  |
| ATOM | 2402 | CA   | VAL | A2021 |       | 28.739 | 35.063 | 61.862 | 1.00 | 10.56 |
| ATOM | 2403 | CB   | VAL | A2021 |       | 27.292 | 34.813 | 61.347 | 1.00 | 9.04  |
| ATOM | 2404 | CG1  | VAL | A2021 |       | 26.280 | 34.906 | 62.486 | 1.00 | 10.11 |
| ATOM | 2405 | CG2  | VAL | A2021 |       | 26.931 | 35.794 | 60.242 | 1.00 | 9.26  |
| ATOM | 2406 | C    | VAL | A2021 |       | 29.769 | 34.750 | 60.752 | 1.00 | 10.08 |
| ATOM | 2407 | O    | VAL | A2021 |       | 30.151 | 35.651 | 60.004 | 1.00 | 10.16 |
| ATOM | 2408 | N    | PRO | A2022 |       | 30.238 | 33.501 | 60.663 | 1.00 | 10.71 |
| ATOM | 2409 | CA   | PRO | A2022 |       | 31.194 | 33.114 | 59.609 | 1.00 | 9.58  |
| ATOM | 2410 | CB   | PRO | A2022 |       | 31.569 | 31.668 | 59.976 | 1.00 | 10.12 |
| ATOM | 2411 | CG   | PRO | A2022 |       | 30.484 | 31.185 | 60.870 | 1.00 | 10.00 |
| ATOM | 2412 | CD   | PRO | A2022 |       | 29.959 | 32.388 | 61.592 | 1.00 | 9.95  |
| ATOM | 2413 | C    | PRO | A2022 |       | 30.643 | 33.172 | 58.177 | 1.00 | 11.76 |
| ATOM | 2414 | O    | PRO | A2022 |       | 31.426 | 33.329 | 57.235 | 1.00 | 12.41 |
| ATOM | 2415 | N    | ASP | A2023 |       | 29.328 | 33.037 | 58.016 | 1.00 | 11.77 |
| ATOM | 2416 | CA   | ASP | A2023 |       | 28.714 | 32.998 | 56.687 | 1.00 | 12.72 |
| ATOM | 2417 | CB   | ASP | A2023 |       | 28.873 | 31.608 | 56.055 | 1.00 | 15.60 |
| ATOM | 2418 | CG   | ASP | A2023 |       | 28.370 | 30.491 | 56.957 | 1.00 | 18.02 |
| ATOM | 2419 | OD1  | ASP | A2023 |       | 27.179 | 30.506 | 57.334 | 1.00 | 17.85 |
| ATOM | 2420 | OD2  | ASP | A2023 |       | 29.100 | 29.550 | 57.336 | 1.00 | 21.33 |
| ATOM | 2421 | C    | ASP | A2023 |       | 27.242 | 33.389 | 56.723 | 1.00 | 11.42 |
| ATOM | 2422 | O    | ASP | A2023 |       | 26.678 | 33.627 | 57.794 | 1.00 | 11.53 |
| ATOM | 2423 | N    | ASP | A2024 |       | 26.625 | 33.425 | 55.546 | 1.00 | 10.86 |
| ATOM | 2424 | CA   | ASP | A2024 |       | 25.229 | 33.833 | 55.402 | 1.00 | 12.71 |
| ATOM | 2425 | CB   | ASP | A2024 |       | 24.853 | 33.931 | 53.925 | 1.00 | 13.32 |
| ATOM | 2426 | CG   | ASP | A2024 |       | 25.521 | 35.100 | 53.230 | 1.00 | 14.22 |
| ATOM | 2427 | OD1  | ASP | A2024 |       | 26.062 | 35.990 | 53.922 | 1.00 | 14.37 |
| ATOM | 2428 | OD2  | ASP | A2024 |       | 25.558 | 35.208 | 51.990 | 1.00 | 14.75 |

FIGURE 3AV

| | A | B | C | D | E | F | G | H | I | J |
|---|---|---|---|---|---|---|---|---|---|---|
| ATOM | 2429 | C | | ASP | A2024 | 24.248 | 32.921 | 56.131 | 1.00 | 11.50 |
| ATOM | 2430 | O | | ASP | A2024 | 23.335 | 33.405 | 56.791 | 1.00 | 9.11 |
| ATOM | 2431 | N | | PHE | A2025 | 24.442 | 31.608 | 56.016 | 1.00 | 11.21 |
| ATOM | 2432 | CA | | PHE | A2025 | 23.557 | 30.654 | 56.682 | 1.00 | 11.01 |
| ATOM | 2433 | CB | | PHE | A2025 | 23.929 | 29.197 | 56.365 | 1.00 | 11.22 |
| ATOM | 2434 | CG | | PHE | A2025 | 23.148 | 28.202 | 57.177 | 1.00 | 12.08 |
| ATOM | 2435 | CD1 | | PHE | A2025 | 23.676 | 27.668 | 58.347 | 1.00 | 12.59 |
| ATOM | 2436 | CE1 | | PHE | A2025 | 22.943 | 26.768 | 59.115 | 1.00 | 13.75 |
| ATOM | 2437 | CZ | | PHE | A2025 | 21.661 | 26.407 | 58.719 | 1.00 | 13.01 |
| ATOM | 2438 | CE2 | | PHE | A2025 | 21.120 | 26.939 | 57.558 | 1.00 | 12.63 |
| ATOM | 2439 | CD2 | | PHE | A2025 | 21.859 | 27.841 | 56.798 | 1.00 | 13.09 |
| ATOM | 2440 | C | | PHE | A2025 | 23.529 | 30.852 | 58.202 | 1.00 | 9.90 |
| ATOM | 2441 | O | | PHE | A2025 | 22.462 | 30.835 | 58.810 | 1.00 | 9.47 |
| ATOM | 2442 | N | | GLU | A2026 | 24.701 | 31.017 | 58.806 | 1.00 | 8.95 |
| ATOM | 2443 | CA | | GLU | A2026 | 24.790 | 31.253 | 60.246 | 1.00 | 11.39 |
| ATOM | 2444 | CB | | GLU | A2026 | 26.246 | 31.221 | 60.739 | 1.00 | 11.95 |
| ATOM | 2445 | CG | | GLU | A2026 | 26.952 | 29.859 | 60.668 | 1.00 | 16.72 |
| ATOM | 2446 | CD | | GLU | A2026 | 26.131 | 28.688 | 61.201 | 1.00 | 18.89 |
| ATOM | 2447 | OE1 | | GLU | A2026 | 25.355 | 28.866 | 62.164 | 1.00 | 20.81 |
| ATOM | 2448 | OE2 | | GLU | A2026 | 26.266 | 27.571 | 60.654 | 1.00 | 21.30 |
| ATOM | 2449 | C | | GLU | A2026 | 24.113 | 32.576 | 60.614 | 1.00 | 11.29 |
| ATOM | 2450 | O | | GLU | A2026 | 23.532 | 32.701 | 61.691 | 1.00 | 11.05 |
| ATOM | 2451 | N | | GLY | A2027 | 24.176 | 33.546 | 59.701 | 1.00 | 11.21 |
| ATOM | 2452 | CA | | GLY | A2027 | 23.468 | 34.808 | 59.853 | 1.00 | 11.94 |
| ATOM | 2453 | C | | GLY | A2027 | 21.967 | 34.599 | 59.914 | 1.00 | 11.87 |
| ATOM | 2454 | O | | GLY | A2027 | 21.291 | 35.137 | 60.789 | 1.00 | 12.23 |
| ATOM | 2455 | N | | VAL | A2028 | 21.454 | 33.796 | 58.986 | 1.00 | 11.00 |
| ATOM | 2456 | CA | | VAL | A2028 | 20.033 | 33.466 | 58.931 | 1.00 | 10.57 |
| ATOM | 2457 | CB | | VAL | A2028 | 19.709 | 32.651 | 57.651 | 1.00 | 10.48 |
| ATOM | 2458 | CG1 | | VAL | A2028 | 18.297 | 32.109 | 57.689 | 1.00 | 10.72 |
| ATOM | 2459 | CG2 | | VAL | A2028 | 19.927 | 33.503 | 56.411 | 1.00 | 9.61 |
| ATOM | 2460 | C | | VAL | A2028 | 19.615 | 32.688 | 60.179 | 1.00 | 10.52 |
| ATOM | 2461 | O | | VAL | A2028 | 18.533 | 32.912 | 60.741 | 1.00 | 9.23 |
| ATOM | 2462 | N | | TYR | A2029 | 20.481 | 31.772 | 60.601 | 1.00 | 10.53 |
| ATOM | 2463 | CA | | TYR | A2029 | 20.254 | 30.992 | 61.810 | 1.00 | 10.85 |
| ATOM | 2464 | CB | | TYR | A2029 | 21.369 | 29.964 | 61.989 | 1.00 | 12.78 |
| ATOM | 2465 | CG | | TYR | A2029 | 21.086 | 28.957 | 63.080 | 1.00 | 16.94 |
| ATOM | 2466 | CD1 | | TYR | A2029 | 20.342 | 27.804 | 62.818 | 1.00 | 18.15 |
| ATOM | 2467 | CE1 | | TYR | A2029 | 20.076 | 26.879 | 63.824 | 1.00 | 20.26 |
| ATOM | 2468 | CZ | | TYR | A2029 | 20.550 | 27.110 | 65.101 | 1.00 | 21.29 |
| ATOM | 2469 | OH | | TYR | A2029 | 20.297 | 26.206 | 66.108 | 1.00 | 25.66 |
| ATOM | 2470 | CE2 | | TYR | A2029 | 21.289 | 28.242 | 65.378 | 1.00 | 19.79 |
| ATOM | 2471 | CD2 | | TYR | A2029 | 21.551 | 29.158 | 64.374 | 1.00 | 16.80 |
| ATOM | 2472 | C | | TYR | A2029 | 20.168 | 31.905 | 63.039 | 1.00 | 9.60 |
| ATOM | 2473 | O | | TYR | A2029 | 19.315 | 31.711 | 63.907 | 1.00 | 8.48 |
| ATOM | 2474 | N | | THR | A2030 | 21.057 | 32.895 | 63.094 | 1.00 | 7.56 |
| ATOM | 2475 | CA | | THR | A2030 | 21.106 | 33.849 | 64.194 | 1.00 | 9.74 |
| ATOM | 2476 | CB | | THR | A2030 | 22.374 | 34.732 | 64.078 | 1.00 | 9.91 |
| ATOM | 2477 | OG1 | | THR | A2030 | 23.537 | 33.894 | 64.175 | 1.00 | 11.28 |
| ATOM | 2478 | CG2 | | THR | A2030 | 22.508 | 35.683 | 65.278 | 1.00 | 10.42 |
| ATOM | 2479 | C | | THR | A2030 | 19.836 | 34.703 | 64.232 | 1.00 | 9.13 |
| ATOM | 2480 | O | | THR | A2030 | 19.326 | 35.000 | 65.312 | 1.00 | 10.76 |

FIGURE 3AW

|      | A    | B   | C D  | E     | F      | G      | H      | I    | J     |
|------|------|-----|------|-------|--------|--------|--------|------|-------|
| ATOM | 2481 | N   | ILE  | A2031 | 19.335 | 35.085 | 63.060 | 1.00 | 9.81  |
| ATOM | 2482 | CA  | ILE  | A2031 | 18.072 | 35.824 | 62.955 | 1.00 | 10.92 |
| ATOM | 2483 | CB  | ILE  | A2031 | 17.698 | 36.100 | 61.477 | 1.00 | 10.17 |
| ATOM | 2484 | CG1 | ILE  | A2031 | 18.633 | 37.142 | 60.861 | 1.00 | 10.23 |
| ATOM | 2485 | CD1 | ILE  | A2031 | 18.599 | 37.163 | 59.335 | 1.00 | 10.37 |
| ATOM | 2486 | CG2 | ILE  | A2031 | 16.225 | 36.562 | 61.348 | 1.00 | 10.68 |
| ATOM | 2487 | C   | ILE  | A2031 | 16.958 | 35.041 | 63.652 | 1.00 | 11.44 |
| ATOM | 2488 | O   | ILE  | A2031 | 16.257 | 35.581 | 64.500 | 1.00 | 13.99 |
| ATOM | 2489 | N   | LEU  | A2032 | 16.823 | 33.766 | 63.296 | 1.00 | 11.98 |
| ATOM | 2490 | CA  | LEU  | A2032 | 15.802 | 32.887 | 63.873 | 1.00 | 11.00 |
| ATOM | 2491 | CB  | LEU  | A2032 | 15.823 | 31.527 | 63.172 | 1.00 | 10.46 |
| ATOM | 2492 | CG  | LEU  | A2032 | 15.381 | 31.544 | 61.704 | 1.00 | 11.63 |
| ATOM | 2493 | CD1 | LEU  | A2032 | 15.476 | 30.154 | 61.113 | 1.00 | 9.84  |
| ATOM | 2494 | CD2 | LEU  | A2032 | 13.960 | 32.087 | 61.542 | 1.00 | 10.43 |
| ATOM | 2495 | C   | LEU  | A2032 | 15.984 | 32.710 | 65.378 | 1.00 | 9.75  |
| ATOM | 2496 | O   | LEU  | A2032 | 15.016 | 32.713 | 66.146 | 1.00 | 8.79  |
| ATOM | 2497 | N   | GLU  | A2033 | 17.238 | 32.558 | 65.784 | 1.00 | 9.41  |
| ATOM | 2498 | CA  | GLU  | A2033 | 17.604 | 32.447 | 67.186 | 1.00 | 10.71 |
| ATOM | 2499 | CB  | BGLU | A2033 | 19.107 | 32.212 | 67.284 | 0.50 | 11.85 |
| ATOM | 2500 | CB  | AGLU | A2033 | 19.103 | 32.200 | 67.323 | 0.50 | 11.62 |
| ATOM | 2501 | CG  | BGLU | A2033 | 19.616 | 31.930 | 68.680 | 0.50 | 13.79 |
| ATOM | 2502 | CG  | AGLU | A2033 | 19.505 | 30.743 | 67.179 | 0.50 | 13.18 |
| ATOM | 2503 | CD  | BGLU | A2033 | 21.125 | 31.904 | 68.723 | 0.50 | 14.80 |
| ATOM | 2504 | CD  | AGLU | A2033 | 20.968 | 30.515 | 67.496 | 0.50 | 14.36 |
| ATOM | 2505 | OE1 | BGLU | A2033 | 21.700 | 30.811 | 68.564 | 0.50 | 15.25 |
| ATOM | 2506 | OE1 | AGLU | A2033 | 21.816 | 31.285 | 66.989 | 0.50 | 15.87 |
| ATOM | 2507 | OE2 | BGLU | A2033 | 21.731 | 32.978 | 68.909 | 0.50 | 16.68 |
| ATOM | 2508 | OE2 | AGLU | A2033 | 21.271 | 29.559 | 68.240 | 0.50 | 14.12 |
| ATOM | 2509 | C   | GLU  | A2033 | 17.206 | 33.697 | 67.981 | 1.00 | 9.95  |
| ATOM | 2510 | O   | GLU  | A2033 | 16.617 | 33.590 | 69.056 | 1.00 | 9.53  |
| ATOM | 2511 | N   | TRP  | A2034 | 17.531 | 34.872 | 67.450 | 1.00 | 8.88  |
| ATOM | 2512 | CA  | TRP  | A2034 | 17.109 | 36.133 | 68.063 | 1.00 | 9.73  |
| ATOM | 2513 | CB  | TRP  | A2034 | 17.641 | 37.319 | 67.259 | 1.00 | 10.11 |
| ATOM | 2514 | CG  | TRP  | A2034 | 19.074 | 37.664 | 67.545 | 1.00 | 9.81  |
| ATOM | 2515 | CD1 | TRP  | A2034 | 19.925 | 37.029 | 68.414 | 1.00 | 8.66  |
| ATOM | 2516 | NE1 | TRP  | A2034 | 21.158 | 37.639 | 68.394 | 1.00 | 9.36  |
| ATOM | 2517 | CE2 | TRP  | A2034 | 21.126 | 38.689 | 67.514 | 1.00 | 8.06  |
| ATOM | 2518 | CD2 | TRP  | A2034 | 19.826 | 38.737 | 66.963 | 1.00 | 9.21  |
| ATOM | 2519 | CE3 | TRP  | A2034 | 19.531 | 39.738 | 66.025 | 1.00 | 8.52  |
| ATOM | 2520 | CZ3 | TRP  | A2034 | 20.527 | 40.648 | 65.678 | 1.00 | 8.69  |
| ATOM | 2521 | CH2 | TRP  | A2034 | 21.808 | 40.568 | 66.242 | 1.00 | 9.94  |
| ATOM | 2522 | CZ2 | TRP  | A2034 | 22.126 | 39.603 | 67.166 | 1.00 | 8.58  |
| ATOM | 2523 | C   | TRP  | A2034 | 15.587 | 36.208 | 68.149 | 1.00 | 8.30  |
| ATOM | 2524 | O   | TRP  | A2034 | 15.038 | 36.530 | 69.202 | 1.00 | 8.43  |
| ATOM | 2525 | N   | LEU  | A2035 | 14.916 | 35.894 | 67.042 | 1.00 | 9.02  |
| ATOM | 2526 | CA  | LEU  | A2035 | 13.446 | 35.924 | 66.979 | 1.00 | 9.06  |
| ATOM | 2527 | CB  | LEU  | A2035 | 12.962 | 35.648 | 65.551 | 1.00 | 10.33 |
| ATOM | 2528 | CG  | LEU  | A2035 | 13.157 | 36.744 | 64.487 | 1.00 | 10.19 |
| ATOM | 2529 | CD1 | LEU  | A2035 | 12.763 | 36.191 | 63.139 | 1.00 | 8.37  |
| ATOM | 2530 | CD2 | LEU  | A2035 | 12.354 | 38.020 | 64.800 | 1.00 | 7.32  |
| ATOM | 2531 | C   | LEU  | A2035 | 12.771 | 34.961 | 67.963 | 1.00 | 8.36  |
| ATOM | 2532 | O   | LEU  | A2035 | 11.650 | 35.207 | 68.411 | 1.00 | 9.48  |

FIGURE 3AX

|      | A    | B   | C D E      | F      | G      | H      | I    | J     |
|------|------|-----|------------|--------|--------|--------|------|-------|
| ATOM | 2533 | N   | SER A2036  | 13.461 | 33.876 | 68.304 | 1.00 | 9.22  |
| ATOM | 2534 | CA  | SER A2036  | 12.942 | 32.893 | 69.259 | 1.00 | 9.36  |
| ATOM | 2535 | CB  | SER A2036  | 13.886 | 31.693 | 69.374 | 1.00 | 10.05 |
| ATOM | 2536 | OG  | SER A2036  | 15.022 | 31.996 | 70.164 | 1.00 | 11.51 |
| ATOM | 2537 | C   | SER A2036  | 12.643 | 33.483 | 70.643 | 1.00 | 9.73  |
| ATOM | 2538 | O   | SER A2036  | 11.837 | 32.931 | 71.384 | 1.00 | 9.04  |
| ATOM | 2539 | N   | TYR A2037  | 13.284 | 34.606 | 70.975 | 1.00 | 10.14 |
| ATOM | 2540 | CA  | TYR A2037  | 13.038 | 35.312 | 72.244 | 1.00 | 10.70 |
| ATOM | 2541 | CB  | TYR A2037  | 14.290 | 36.080 | 72.696 | 1.00 | 10.25 |
| ATOM | 2542 | CG  | TYR A2037  | 15.465 | 35.177 | 72.954 | 1.00 | 10.16 |
| ATOM | 2543 | CD1 | TYR A2037  | 16.406 | 34.932 | 71.951 | 1.00 | 10.29 |
| ATOM | 2544 | CE1 | TYR A2037  | 17.482 | 34.087 | 72.170 | 1.00 | 12.80 |
| ATOM | 2545 | CZ  | TYR A2037  | 17.628 | 33.473 | 73.403 | 1.00 | 13.58 |
| ATOM | 2546 | OH  | TYR A2037  | 18.696 | 32.628 | 73.616 | 1.00 | 15.96 |
| ATOM | 2547 | CE2 | TYR A2037  | 16.703 | 33.696 | 74.418 | 1.00 | 12.15 |
| ATOM | 2548 | CD2 | TYR A2037  | 15.629 | 34.551 | 74.187 | 1.00 | 10.28 |
| ATOM | 2549 | C   | TYR A2037  | 11.882 | 36.296 | 72.161 | 1.00 | 10.67 |
| ATOM | 2550 | O   | TYR A2037  | 11.385 | 36.774 | 73.182 | 1.00 | 9.64  |
| ATOM | 2551 | N   | MET A2038  | 11.455 | 36.590 | 70.940 | 1.00 | 10.89 |
| ATOM | 2552 | CA  | MET A2038  | 10.617 | 37.752 | 70.682 | 1.00 | 11.01 |
| ATOM | 2553 | CB  | MET A2038  | 11.246 | 38.593 | 69.569 | 1.00 | 11.51 |
| ATOM | 2554 | CG  | MET A2038  | 12.697 | 38.950 | 69.827 | 1.00 | 11.45 |
| ATOM | 2555 | SD  | MET A2038  | 13.413 | 39.833 | 68.447 | 1.00 | 11.10 |
| ATOM | 2556 | CE  | MET A2038  | 15.115 | 39.940 | 68.972 | 1.00 | 12.13 |
| ATOM | 2557 | C   | MET A2038  | 9.190  | 37.368 | 70.303 | 1.00 | 10.23 |
| ATOM | 2558 | O   | MET A2038  | 8.973  | 36.327 | 69.690 | 1.00 | 11.04 |
| ATOM | 2559 | N   | PRO A2039  | 8.221  | 38.201 | 70.688 | 1.00 | 10.37 |
| ATOM | 2560 | CA  | PRO A2039  | 6.825  | 38.006 | 70.289 | 1.00 | 9.41  |
| ATOM | 2561 | CB  | PRO A2039  | 6.136  | 39.271 | 70.813 | 1.00 | 9.28  |
| ATOM | 2562 | CG  | PRO A2039  | 6.983  | 39.739 | 71.930 | 1.00 | 10.41 |
| ATOM | 2563 | CD  | PRO A2039  | 8.384  | 39.393 | 71.542 | 1.00 | 9.78  |
| ATOM | 2564 | C   | PRO A2039  | 6.684  | 37.952 | 68.771 | 1.00 | 9.52  |
| ATOM | 2565 | O   | PRO A2039  | 7.431  | 38.627 | 68.054 | 1.00 | 11.10 |
| ATOM | 2566 | N   | LYS A2040  | 5.727  | 37.162 | 68.296 | 1.00 | 9.66  |
| ATOM | 2567 | CA  | LYS A2040  | 5.476  | 37.029 | 66.859 | 1.00 | 9.89  |
| ATOM | 2568 | CB  | LYS A2040  | 4.377  | 35.995 | 66.582 | 1.00 | 9.91  |
| ATOM | 2569 | CG  | LYS A2040  | 2.984  | 36.371 | 67.090 | 1.00 | 11.01 |
| ATOM | 2570 | CD  | LYS A2040  | 1.919  | 35.388 | 66.537 | 1.00 | 12.19 |
| ATOM | 2571 | CE  | LYS A2040  | 0.517  | 35.791 | 66.982 | 1.00 | 13.59 |
| ATOM | 2572 | NZ  | LYS A2040  | -0.544 | 35.035 | 66.243 | 1.00 | 17.81 |
| ATOM | 2573 | C   | LYS A2040  | 5.138  | 38.360 | 66.189 | 1.00 | 9.30  |
| ATOM | 2574 | O   | LYS A2040  | 5.376  | 38.531 | 64.994 | 1.00 | 9.21  |
| ATOM | 2575 | N   | ASP A2041  | 4.585  | 39.291 | 66.966 | 1.00 | 9.95  |
| ATOM | 2576 | CA  | ASP A2041  | 4.306  | 40.643 | 66.492 | 1.00 | 11.72 |
| ATOM | 2577 | CB  | ASP A2041  | 2.988  | 40.699 | 65.694 | 1.00 | 11.74 |
| ATOM | 2578 | CG  | ASP A2041  | 1.789  | 40.182 | 66.484 | 1.00 | 12.04 |
| ATOM | 2579 | OD1 | ASP A2041  | 1.605  | 40.595 | 67.643 | 1.00 | 13.09 |
| ATOM | 2580 | OD2 | ASP A2041  | 0.962  | 39.376 | 66.013 | 1.00 | 13.55 |
| ATOM | 2581 | C   | ASP A2041  | 4.297  | 41.626 | 67.669 | 1.00 | 12.20 |
| ATOM | 2582 | O   | ASP A2041  | 4.427  | 41.213 | 68.818 | 1.00 | 11.25 |
| ATOM | 2583 | N   | ASN A2042  | 4.140  | 42.916 | 67.378 | 1.00 | 12.65 |
| ATOM | 2584 | CA  | ASN A2042  | 4.170  | 43.966 | 68.413 | 1.00 | 13.13 |

FIGURE 3AY

| | A | B | C | D | E | F | G | H | I | J |
|---|---|---|---|---|---|---|---|---|---|---|
| ATOM | 2585 | CB | ASN | A2042 | | 4.580 | 45.325 | 67.807 | 1.00 | 12.44 |
| ATOM | 2586 | CG | ASN | A2042 | | 3.522 | 45.922 | 66.861 | 1.00 | 13.28 |
| ATOM | 2587 | OD1 | ASN | A2042 | | 3.767 | 46.951 | 66.208 | 1.00 | 13.87 |
| ATOM | 2588 | ND2 | ASN | A2042 | | 2.359 | 45.297 | 66.785 | 1.00 | 8.25 |
| ATOM | 2589 | C | ASN | A2042 | | 2.895 | 44.095 | 69.267 | 1.00 | 14.24 |
| ATOM | 2590 | O | ASN | A2042 | | 2.733 | 45.050 | 70.030 | 1.00 | 15.88 |
| ATOM | 2591 | N | HIS | A2043 | | 1.991 | 43.132 | 69.140 | 1.00 | 15.21 |
| ATOM | 2592 | CA | HIS | A2043 | | 0.786 | 43.127 | 69.961 | 1.00 | 15.33 |
| ATOM | 2593 | CB | HIS | A2043 | | -0.406 | 43.713 | 69.191 | 1.00 | 14.66 |
| ATOM | 2594 | CG | HIS | A2043 | | -0.581 | 43.156 | 67.811 | 1.00 | 15.11 |
| ATOM | 2595 | ND1 | HIS | A2043 | | 0.143 | 43.608 | 66.728 | 1.00 | 14.45 |
| ATOM | 2596 | CE1 | HIS | A2043 | | -0.228 | 42.947 | 65.645 | 1.00 | 14.91 |
| ATOM | 2597 | NE2 | HIS | A2043 | | -1.175 | 42.091 | 65.984 | 1.00 | 12.49 |
| ATOM | 2598 | CD2 | HIS | A2043 | | -1.419 | 42.206 | 67.333 | 1.00 | 13.89 |
| ATOM | 2599 | C | HIS | A2043 | | 0.495 | 41.730 | 70.510 | 1.00 | 15.08 |
| ATOM | 2600 | O | HIS | A2043 | | -0.656 | 41.308 | 70.607 | 1.00 | 16.66 |
| ATOM | 2601 | N | SER | A2044 | | 1.567 | 41.026 | 70.865 | 1.00 | 15.24 |
| ATOM | 2602 | CA | SER | A2044 | | 1.496 | 39.663 | 71.382 | 1.00 | 14.17 |
| ATOM | 2603 | CB | SER | A2044 | | 1.898 | 38.662 | 70.297 | 1.00 | 12.63 |
| ATOM | 2604 | OG | SER | A2044 | | 0.985 | 38.704 | 69.218 | 1.00 | 15.03 |
| ATOM | 2605 | C | SER | A2044 | | 2.428 | 39.523 | 72.582 | 1.00 | 14.22 |
| ATOM | 2606 | O | SER | A2044 | | 3.484 | 40.159 | 72.615 | 1.00 | 13.86 |
| ATOM | 2607 | N | PRO | A2045 | | 2.042 | 38.703 | 73.565 | 1.00 | 13.94 |
| ATOM | 2608 | CA | PRO | A2045 | | 2.907 | 38.419 | 74.723 | 1.00 | 14.72 |
| ATOM | 2609 | CB | PRO | A2045 | | 2.069 | 37.442 | 75.568 | 1.00 | 14.64 |
| ATOM | 2610 | CG | PRO | A2045 | | 0.984 | 36.942 | 74.663 | 1.00 | 16.09 |
| ATOM | 2611 | CD | PRO | A2045 | | 0.738 | 38.015 | 73.651 | 1.00 | 14.06 |
| ATOM | 2612 | C | PRO | A2045 | | 4.232 | 37.768 | 74.311 | 1.00 | 14.19 |
| ATOM | 2613 | O | PRO | A2045 | | 4.331 | 37.254 | 73.189 | 1.00 | 12.79 |
| ATOM | 2614 | N | VAL | A2046 | | 5.238 | 37.799 | 75.183 | 1.00 | 13.21 |
| ATOM | 2615 | CA | VAL | A2046 | | 6.485 | 37.089 | 74.884 | 1.00 | 14.46 |
| ATOM | 2616 | CB | VAL | A2046 | | 7.664 | 37.412 | 75.865 | 1.00 | 15.07 |
| ATOM | 2617 | CG1 | VAL | A2046 | | 8.129 | 38.848 | 75.691 | 1.00 | 14.78 |
| ATOM | 2618 | CG2 | VAL | A2046 | | 7.312 | 37.109 | 77.320 | 1.00 | 13.46 |
| ATOM | 2619 | C | VAL | A2046 | | 6.194 | 35.590 | 74.844 | 1.00 | 14.12 |
| ATOM | 2620 | O | VAL | A2046 | | 5.341 | 35.107 | 75.590 | 1.00 | 15.48 |
| ATOM | 2621 | N | PRO | A2047 | | 6.853 | 34.867 | 73.944 | 1.00 | 15.24 |
| ATOM | 2622 | CA | PRO | A2047 | | 6.608 | 33.430 | 73.809 | 1.00 | 15.15 |
| ATOM | 2623 | CB | PRO | A2047 | | 7.203 | 33.102 | 72.437 | 1.00 | 16.12 |
| ATOM | 2624 | CG | PRO | A2047 | | 8.277 | 34.132 | 72.221 | 1.00 | 14.60 |
| ATOM | 2625 | CD | PRO | A2047 | | 7.856 | 35.353 | 72.976 | 1.00 | 16.01 |
| ATOM | 2626 | C | PRO | A2047 | | 7.276 | 32.623 | 74.919 | 1.00 | 15.00 |
| ATOM | 2627 | O | PRO | A2047 | | 8.486 | 32.377 | 74.882 | 1.00 | 13.89 |
| ATOM | 2628 | N | ILE | A2048 | | 6.477 | 32.221 | 75.905 | 1.00 | 14.65 |
| ATOM | 2629 | CA | ILE | A2048 | | 6.957 | 31.344 | 76.971 | 1.00 | 14.25 |
| ATOM | 2630 | CB | ILE | A2048 | | 6.194 | 31.582 | 78.298 | 1.00 | 13.61 |
| ATOM | 2631 | CG1 | ILE | A2048 | | 6.307 | 33.054 | 78.725 | 1.00 | 13.04 |
| ATOM | 2632 | CD1 | ILE | A2048 | | 5.285 | 33.486 | 79.781 | 1.00 | 12.64 |
| ATOM | 2633 | CG2 | ILE | A2048 | | 6.727 | 30.646 | 79.403 | 1.00 | 12.59 |
| ATOM | 2634 | C | ILE | A2048 | | 6.845 | 29.887 | 76.530 | 1.00 | 14.99 |
| ATOM | 2635 | O | ILE | A2048 | | 5.750 | 29.384 | 76.251 | 1.00 | 16.82 |
| ATOM | 2636 | N | ILE | A2049 | | 7.988 | 29.217 | 76.462 | 1.00 | 14.37 |

FIGURE 3AZ

| | A | B | C | D | E | F | G | H | I | J |
|---|---|---|---|---|---|---|---|---|---|---|
| ATOM | 2637 | CA | ILE | A2049 | | 8.024 | 27.829 | 76.027 | 1.00 | 13.73 |
| ATOM | 2638 | CB | ILE | A2049 | | 9.192 | 27.589 | 75.035 | 1.00 | 14.62 |
| ATOM | 2639 | CG1 | ILE | A2049 | | 10.544 | 27.863 | 75.708 | 1.00 | 13.84 |
| ATOM | 2640 | CD1 | ILE | A2049 | | 11.738 | 27.353 | 74.928 | 1.00 | 15.75 |
| ATOM | 2641 | CG2 | ILE | A2049 | | 9.014 | 28.448 | 73.777 | 1.00 | 15.27 |
| ATOM | 2642 | C | ILE | A2049 | | 8.132 | 26.912 | 77.241 | 1.00 | 13.78 |
| ATOM | 2643 | O | ILE | A2049 | | 8.377 | 27.372 | 78.358 | 1.00 | 12.39 |
| ATOM | 2644 | N | THR | A2050 | | 7.928 | 25.620 | 77.012 | 1.00 | 14.70 |
| ATOM | 2645 | CA | THR | A2050 | | 8.127 | 24.607 | 78.043 | 1.00 | 16.51 |
| ATOM | 2646 | CB | THR | A2050 | | 7.430 | 23.285 | 77.635 | 1.00 | 16.84 |
| ATOM | 2647 | OG1 | THR | A2050 | | 6.046 | 23.547 | 77.362 | 1.00 | 19.38 |
| ATOM | 2648 | CG2 | THR | A2050 | | 7.376 | 22.299 | 78.807 | 1.00 | 16.80 |
| ATOM | 2649 | C | THR | A2050 | | 9.632 | 24.412 | 78.225 | 1.00 | 16.74 |
| ATOM | 2650 | O | THR | A2050 | | 10.331 | 24.041 | 77.281 | 1.00 | 17.86 |
| ATOM | 2651 | N | PRO | A2051 | | 10.131 | 24.676 | 79.430 | 1.00 | 19.01 |
| ATOM | 2652 | CA | PRO | A2051 | | 11.566 | 24.540 | 79.707 | 1.00 | 20.44 |
| ATOM | 2653 | CB | PRO | A2051 | | 11.734 | 25.296 | 81.025 | 1.00 | 19.98 |
| ATOM | 2654 | CG | PRO | A2051 | | 10.403 | 25.132 | 81.715 | 1.00 | 20.42 |
| ATOM | 2655 | CD | PRO | A2051 | | 9.370 | 25.092 | 80.624 | 1.00 | 18.77 |
| ATOM | 2656 | C | PRO | A2051 | | 11.947 | 23.073 | 79.892 | 1.00 | 20.52 |
| ATOM | 2657 | O | PRO | A2051 | | 11.140 | 22.298 | 80.407 | 1.00 | 20.53 |
| ATOM | 2658 | N | THR | A2052 | | 13.144 | 22.700 | 79.451 | 1.00 | 20.98 |
| ATOM | 2659 | CA | THR | A2052 | | 13.692 | 21.379 | 79.756 | 1.00 | 22.39 |
| ATOM | 2660 | CB | THR | A2052 | | 14.506 | 20.810 | 78.567 | 1.00 | 23.42 |
| ATOM | 2661 | OG1 | THR | A2052 | | 15.473 | 21.773 | 78.135 | 1.00 | 25.11 |
| ATOM | 2662 | CG2 | THR | A2052 | | 13.622 | 20.633 | 77.342 | 1.00 | 24.26 |
| ATOM | 2663 | C | THR | A2052 | | 14.552 | 21.471 | 81.014 | 1.00 | 20.66 |
| ATOM | 2664 | O | THR | A2052 | | 14.776 | 20.473 | 81.700 | 1.00 | 20.71 |
| ATOM | 2665 | N | ASP | A2053 | | 15.030 | 22.680 | 81.301 | 1.00 | 16.96 |
| ATOM | 2666 | CA | ASP | A2053 | | 15.769 | 22.966 | 82.522 | 1.00 | 16.23 |
| ATOM | 2667 | CB | ASP | A2053 | | 16.689 | 24.172 | 82.299 | 1.00 | 15.57 |
| ATOM | 2668 | CG | ASP | A2053 | | 17.822 | 24.247 | 83.302 | 1.00 | 15.87 |
| ATOM | 2669 | OD1 | ASP | A2053 | | 17.779 | 23.548 | 84.340 | 1.00 | 14.79 |
| ATOM | 2670 | OD2 | ASP | A2053 | | 18.803 | 24.998 | 83.138 | 1.00 | 16.86 |
| ATOM | 2671 | C | ASP | A2053 | | 14.764 | 23.261 | 83.638 | 1.00 | 16.51 |
| ATOM | 2672 | O | ASP | A2053 | | 14.030 | 24.250 | 83.559 | 1.00 | 19.14 |
| ATOM | 2673 | N | PRO | A2054 | | 14.718 | 22.413 | 84.668 | 1.00 | 16.45 |
| ATOM | 2674 | CA | PRO | A2054 | | 13.728 | 22.565 | 85.746 | 1.00 | 15.36 |
| ATOM | 2675 | CB | PRO | A2054 | | 14.125 | 21.471 | 86.744 | 1.00 | 15.34 |
| ATOM | 2676 | CG | PRO | A2054 | | 14.832 | 20.454 | 85.919 | 1.00 | 15.38 |
| ATOM | 2677 | CD | PRO | A2054 | | 15.583 | 21.234 | 84.883 | 1.00 | 15.02 |
| ATOM | 2678 | C | PRO | A2054 | | 13.759 | 23.930 | 86.429 | 1.00 | 13.62 |
| ATOM | 2679 | O | PRO | A2054 | | 14.833 | 24.436 | 86.748 | 1.00 | 11.02 |
| ATOM | 2680 | N | ILE | A2055 | | 12.577 | 24.502 | 86.639 | 1.00 | 14.02 |
| ATOM | 2681 | CA | ILE | A2055 | | 12.411 | 25.727 | 87.413 | 1.00 | 17.01 |
| ATOM | 2682 | CB | ILE | A2055 | | 10.933 | 26.192 | 87.358 | 1.00 | 18.19 |
| ATOM | 2683 | CG1 | ILE | A2055 | | 10.601 | 26.748 | 85.972 | 1.00 | 18.63 |
| ATOM | 2684 | CD1 | ILE | A2055 | | 9.358 | 26.141 | 85.361 | 1.00 | 19.03 |
| ATOM | 2685 | CG2 | ILE | A2055 | | 10.639 | 27.222 | 88.455 | 1.00 | 18.18 |
| ATOM | 2686 | C | ILE | A2055 | | 12.826 | 25.485 | 88.860 | 1.00 | 18.33 |
| ATOM | 2687 | O | ILE | A2055 | | 13.562 | 26.288 | 89.455 | 1.00 | 18.41 |
| ATOM | 2688 | N | ASP | A2056 | | 12.345 | 24.368 | 89.407 | 1.00 | 17.77 |

FIGURE 3BA

| | A | B | C | D E | F | G | H | I | J |
|---|---|---|---|---|---|---|---|---|---|
| ATOM | 2689 | CA | | ASP A2056 | 12.598 | 23.973 | 90.788 | 1.00 | 19.68 |
| ATOM | 2690 | CB | B | ASP A2056 | 11.440 | 23.106 | 91.306 | 0.50 | 20.51 |
| ATOM | 2691 | CB | A | ASP A2056 | 11.441 | 23.135 | 91.354 | 0.50 | 18.29 |
| ATOM | 2692 | CG | B | ASP A2056 | 11.028 | 22.018 | 90.318 | 0.50 | 21.40 |
| ATOM | 2693 | CG | A | ASP A2056 | 11.575 | 22.878 | 92.854 | 0.50 | 17.50 |
| ATOM | 2694 | OD1 | B | ASP A2056 | 10.727 | 22.340 | 89.144 | 0.50 | 22.55 |
| ATOM | 2695 | OD1 | A | ASP A2056 | 12.241 | 23.673 | 93.557 | 0.50 | 17.11 |
| ATOM | 2696 | OD2 | B | ASP A2056 | 10.973 | 20.809 | 90.628 | 0.50 | 22.32 |
| ATOM | 2697 | OD2 | A | ASP A2056 | 11.045 | 21.901 | 93.422 | 0.50 | 17.40 |
| ATOM | 2698 | C | | ASP A2056 | 13.930 | 23.224 | 90.904 | 1.00 | 20.66 |
| ATOM | 2699 | O | | ASP A2056 | 13.979 | 22.004 | 91.108 | 1.00 | 23.75 |
| ATOM | 2700 | N | | ARG A2057 | 15.008 | 23.976 | 90.747 | 1.00 | 18.10 |
| ATOM | 2701 | CA | | ARG A2057 | 16.354 | 23.472 | 90.965 | 1.00 | 17.56 |
| ATOM | 2702 | CB | | ARG A2057 | 16.969 | 22.944 | 89.662 | 1.00 | 15.60 |
| ATOM | 2703 | CG | | ARG A2057 | 17.324 | 24.032 | 88.632 | 1.00 | 15.45 |
| ATOM | 2704 | CD | | ARG A2057 | 18.542 | 23.713 | 87.787 | 1.00 | 14.79 |
| ATOM | 2705 | NE | | ARG A2057 | 18.700 | 24.630 | 86.660 | 1.00 | 13.53 |
| ATOM | 2706 | CZ | | ARG A2057 | 19.336 | 25.795 | 86.711 | 1.00 | 12.36 |
| ATOM | 2707 | NH1 | | ARG A2057 | 19.876 | 26.228 | 87.851 | 1.00 | 11.33 |
| ATOM | 2708 | NH2 | | ARG A2057 | 19.419 | 26.541 | 85.618 | 1.00 | 11.72 |
| ATOM | 2709 | C | | ARG A2057 | 17.192 | 24.610 | 91.525 | 1.00 | 17.82 |
| ATOM | 2710 | O | | ARG A2057 | 16.876 | 25.787 | 91.326 | 1.00 | 18.74 |
| ATOM | 2711 | N | | GLU A2058 | 18.262 | 24.256 | 92.219 | 1.00 | 17.42 |
| ATOM | 2712 | CA | | GLU A2058 | 19.202 | 25.249 | 92.702 | 1.00 | 18.23 |
| ATOM | 2713 | CB | | GLU A2058 | 19.993 | 24.710 | 93.892 | 1.00 | 19.61 |
| ATOM | 2714 | CG | | GLU A2058 | 19.153 | 24.458 | 95.135 | 1.00 | 22.58 |
| ATOM | 2715 | CD | | GLU A2058 | 19.988 | 24.219 | 96.381 | 1.00 | 25.45 |
| ATOM | 2716 | OE1 | | GLU A2058 | 21.197 | 23.915 | 96.262 | 1.00 | 26.38 |
| ATOM | 2717 | OE2 | | GLU A2058 | 19.429 | 24.332 | 97.491 | 1.00 | 28.19 |
| ATOM | 2718 | C | | GLU A2058 | 20.150 | 25.658 | 91.582 | 1.00 | 16.30 |
| ATOM | 2719 | O | | GLU A2058 | 20.244 | 24.988 | 90.550 | 1.00 | 15.48 |
| ATOM | 2720 | N | | ILE A2059 | 20.833 | 26.775 | 91.793 | 1.00 | 14.86 |
| ATOM | 2721 | CA | | ILE A2059 | 21.913 | 27.200 | 90.920 | 1.00 | 13.17 |
| ATOM | 2722 | CB | | ILE A2059 | 21.945 | 28.734 | 90.809 | 1.00 | 10.29 |
| ATOM | 2723 | CG1 | | ILE A2059 | 20.611 | 29.261 | 90.273 | 1.00 | 10.14 |
| ATOM | 2724 | CD1 | | ILE A2059 | 20.413 | 30.744 | 90.514 | 1.00 | 9.95 |
| ATOM | 2725 | CG2 | | ILE A2059 | 23.108 | 29.172 | 89.930 | 1.00 | 9.32 |
| ATOM | 2726 | C | | ILE A2059 | 23.209 | 26.694 | 91.536 | 1.00 | 12.81 |
| ATOM | 2727 | O | | ILE A2059 | 23.461 | 26.912 | 92.718 | 1.00 | 13.94 |
| ATOM | 2728 | N | | GLU A2060 | 24.023 | 26.022 | 90.733 | 1.00 | 12.12 |
| ATOM | 2729 | CA | | GLU A2060 | 25.235 | 25.390 | 91.238 | 1.00 | 12.46 |
| ATOM | 2730 | CB | A | GLU A2060 | 25.541 | 24.105 | 90.464 | 0.65 | 10.30 |
| ATOM | 2731 | CG | A | GLU A2060 | 24.461 | 23.048 | 90.609 | 0.65 | 9.78 |
| ATOM | 2732 | CD | A | GLU A2060 | 24.607 | 21.909 | 89.619 | 0.65 | 10.58 |
| ATOM | 2733 | OE1 | A | GLU A2060 | 24.527 | 20.739 | 90.061 | 0.65 | 11.39 |
| ATOM | 2734 | OE2 | A | GLU A2060 | 24.804 | 22.177 | 88.411 | 0.65 | 7.49 |
| ATOM | 2735 | C | | GLU A2060 | 26.422 | 26.338 | 91.216 | 1.00 | 11.95 |
| ATOM | 2736 | O | | GLU A2060 | 27.226 | 26.335 | 92.142 | 1.00 | 11.03 |
| ATOM | 2737 | N | | PHE A2061 | 26.539 | 27.146 | 90.164 | 1.00 | 13.30 |
| ATOM | 2738 | CA | | PHE A2061 | 27.579 | 28.160 | 90.151 | 1.00 | 13.58 |
| ATOM | 2739 | CB | | PHE A2061 | 27.777 | 28.825 | 88.784 | 1.00 | 12.91 |
| ATOM | 2740 | CG | | PHE A2061 | 28.847 | 29.880 | 88.808 | 1.00 | 14.32 |

FIGURE 3BB

| | A | B | C | D | E | F | G | H | I | J |
|---|---|---|---|---|---|---|---|---|---|---|
| ATOM | 2741 | CD1 | PHE | A2061 | 30.193 | 29.520 | 88.760 | 1.00 | 13.14 |
| ATOM | 2742 | CE1 | PHE | A2061 | 31.187 | 30.487 | 88.823 | 1.00 | 14.46 |
| ATOM | 2743 | CZ | PHE | A2061 | 30.843 | 31.827 | 88.963 | 1.00 | 13.79 |
| ATOM | 2744 | CE2 | PHE | A2061 | 29.503 | 32.195 | 89.043 | 1.00 | 13.20 |
| ATOM | 2745 | CD2 | PHE | A2061 | 28.517 | 31.221 | 88.975 | 1.00 | 13.11 |
| ATOM | 2746 | C | PHE | A2061 | 27.287 | 29.220 | 91.198 | 1.00 | 14.71 |
| ATOM | 2747 | O | PHE | A2061 | 26.183 | 29.773 | 91.254 | 1.00 | 14.40 |
| ATOM | 2748 | N | LEU | A2062 | 28.293 | 29.501 | 92.018 | 1.00 | 15.64 |
| ATOM | 2749 | CA | LEU | A2062 | 28.162 | 30.497 | 93.066 | 1.00 | 17.54 |
| ATOM | 2750 | CB | LEU | A2062 | 28.499 | 29.887 | 94.430 | 1.00 | 18.87 |
| ATOM | 2751 | CG | LEU | A2062 | 27.780 | 28.570 | 94.764 | 1.00 | 19.24 |
| ATOM | 2752 | CD1 | LEU | A2062 | 28.283 | 27.983 | 96.080 | 1.00 | 18.76 |
| ATOM | 2753 | CD2 | LEU | A2062 | 26.256 | 28.759 | 94.796 | 1.00 | 18.02 |
| ATOM | 2754 | C | LEU | A2062 | 29.035 | 31.708 | 92.771 | 1.00 | 18.42 |
| ATOM | 2755 | O | LEU | A2062 | 30.264 | 31.602 | 92.748 | 1.00 | 18.52 |
| ATOM | 2756 | N | PRO | A2063 | 28.398 | 32.850 | 92.513 | 1.00 | 19.37 |
| ATOM | 2757 | CA | PRO | A2063 | 29.109 | 34.127 | 92.436 | 1.00 | 20.56 |
| ATOM | 2758 | CB | PRO | A2063 | 27.974 | 35.151 | 92.402 | 1.00 | 21.08 |
| ATOM | 2759 | CG | PRO | A2063 | 26.838 | 34.418 | 91.760 | 1.00 | 20.19 |
| ATOM | 2760 | CD | PRO | A2063 | 26.954 | 33.008 | 92.261 | 1.00 | 19.50 |
| ATOM | 2761 | C | PRO | A2063 | 29.961 | 34.293 | 93.689 | 1.00 | 22.28 |
| ATOM | 2762 | O | PRO | A2063 | 29.552 | 33.862 | 94.770 | 1.00 | 23.55 |
| ATOM | 2763 | N | SER | A2064 | 31.141 | 34.880 | 93.534 | 1.00 | 22.34 |
| ATOM | 2764 | CA | SER | A2064 | 32.121 | 34.930 | 94.612 | 1.00 | 22.31 |
| ATOM | 2765 | CB | SER | A2064 | 33.266 | 33.960 | 94.320 | 1.00 | 21.93 |
| ATOM | 2766 | OG | SER | A2064 | 33.792 | 34.183 | 93.023 | 1.00 | 21.54 |
| ATOM | 2767 | C | SER | A2064 | 32.688 | 36.326 | 94.807 | 1.00 | 22.15 |
| ATOM | 2768 | O | SER | A2064 | 32.537 | 37.201 | 93.946 | 1.00 | 20.95 |
| ATOM | 2769 | N | ARG | A2065 | 33.344 | 36.512 | 95.949 | 1.00 | 21.95 |
| ATOM | 2770 | CA | ARG | A2065 | 34.082 | 37.730 | 96.253 | 1.00 | 23.93 |
| ATOM | 2771 | CB | ARG | A2065 | 34.606 | 37.678 | 97.694 | 1.00 | 27.55 |
| ATOM | 2772 | CG | ARG | A2065 | 35.292 | 38.957 | 98.174 | 1.00 | 31.74 |
| ATOM | 2773 | CD | ARG | A2065 | 34.741 | 39.529 | 99.478 | 1.00 | 35.55 |
| ATOM | 2774 | NE | ARG | A2065 | 34.390 | 38.493 | 100.454 | 1.00 | 38.21 |
| ATOM | 2775 | CZ | ARG | A2065 | 33.317 | 38.527 | 101.240 | 1.00 | 39.00 |
| ATOM | 2776 | NH1 | ARG | A2065 | 32.470 | 39.550 | 101.183 | 1.00 | 39.34 |
| ATOM | 2777 | NH2 | ARG | A2065 | 33.088 | 37.532 | 102.089 | 1.00 | 40.47 |
| ATOM | 2778 | C | ARG | A2065 | 35.236 | 37.889 | 95.267 | 1.00 | 21.76 |
| ATOM | 2779 | O | ARG | A2065 | 35.494 | 38.992 | 94.779 | 1.00 | 21.27 |
| ATOM | 2780 | N | ALA | A2066 | 35.921 | 36.781 | 94.978 | 1.00 | 19.02 |
| ATOM | 2781 | CA | ALA | A2066 | 36.941 | 36.759 | 93.940 | 1.00 | 18.36 |
| ATOM | 2782 | CB | ALA | A2066 | 37.717 | 35.447 | 93.973 | 1.00 | 17.60 |
| ATOM | 2783 | C | ALA | A2066 | 36.277 | 36.961 | 92.571 | 1.00 | 18.30 |
| ATOM | 2784 | O | ALA | A2066 | 35.235 | 36.346 | 92.288 | 1.00 | 17.27 |
| ATOM | 2785 | N | PRO | A2067 | 36.859 | 37.831 | 91.742 | 1.00 | 17.39 |
| ATOM | 2786 | CA | PRO | A2067 | 36.315 | 38.113 | 90.408 | 1.00 | 17.65 |
| ATOM | 2787 | CB | PRO | A2067 | 37.427 | 38.927 | 89.740 | 1.00 | 18.62 |
| ATOM | 2788 | CG | PRO | A2067 | 38.140 | 39.589 | 90.871 | 1.00 | 19.11 |
| ATOM | 2789 | CD | PRO | A2067 | 38.067 | 38.632 | 92.022 | 1.00 | 18.32 |
| ATOM | 2790 | C | PRO | A2067 | 36.046 | 36.834 | 89.622 | 1.00 | 17.76 |
| ATOM | 2791 | O | PRO | A2067 | 36.820 | 35.876 | 89.701 | 1.00 | 19.09 |
| ATOM | 2792 | N | TYR | A2068 | 34.941 | 36.832 | 88.887 | 1.00 | 15.87 |

FIGURE 3BC

| | A | B | C | D | E | F | G | H | I | J |
|---|---|---|---|---|---|---|---|---|---|---|
| ATOM | 2793 | CA | TYR | A2068 | | 34.507 | 35.688 | 88.100 | 1.00 | 14.47 |
| ATOM | 2794 | CB | TYR | A2068 | | 33.488 | 34.845 | 88.894 | 1.00 | 15.48 |
| ATOM | 2795 | CG | TYR | A2068 | | 32.228 | 35.599 | 89.275 | 1.00 | 16.48 |
| ATOM | 2796 | CD1 | TYR | A2068 | | 31.089 | 35.553 | 88.465 | 1.00 | 16.44 |
| ATOM | 2797 | CE1 | TYR | A2068 | | 29.936 | 36.257 | 88.804 | 1.00 | 16.77 |
| ATOM | 2798 | CZ | TYR | A2068 | | 29.915 | 37.021 | 89.959 | 1.00 | 16.29 |
| ATOM | 2799 | OH | TYR | A2068 | | 28.779 | 37.725 | 90.291 | 1.00 | 16.74 |
| ATOM | 2800 | CE2 | TYR | A2068 | | 31.029 | 37.083 | 90.780 | 1.00 | 16.28 |
| ATOM | 2801 | CD2 | TYR | A2068 | | 32.178 | 36.375 | 90.437 | 1.00 | 16.45 |
| ATOM | 2802 | C | TYR | A2068 | | 33.886 | 36.211 | 86.803 | 1.00 | 14.16 |
| ATOM | 2803 | O | TYR | A2068 | | 33.510 | 37.381 | 86.713 | 1.00 | 11.95 |
| ATOM | 2804 | N | ASP | A2069 | | 33.799 | 35.348 | 85.799 | 1.00 | 13.74 |
| ATOM | 2805 | CA | ASP | A2069 | | 33.122 | 35.681 | 84.555 | 1.00 | 11.39 |
| ATOM | 2806 | CB | ASP | A2069 | | 33.470 | 34.634 | 83.488 | 1.00 | 11.52 |
| ATOM | 2807 | CG | ASP | A2069 | | 32.970 | 35.005 | 82.092 | 1.00 | 12.12 |
| ATOM | 2808 | OD1 | ASP | A2069 | | 32.145 | 35.927 | 81.944 | 1.00 | 10.71 |
| ATOM | 2809 | OD2 | ASP | A2069 | | 33.356 | 34.409 | 81.070 | 1.00 | 14.69 |
| ATOM | 2810 | C | ASP | A2069 | | 31.619 | 35.685 | 84.843 | 1.00 | 10.30 |
| ATOM | 2811 | O | ASP | A2069 | | 31.071 | 34.662 | 85.240 | 1.00 | 7.34 |
| ATOM | 2812 | N | PRO | A2070 | | 30.956 | 36.831 | 84.665 | 1.00 | 10.31 |
| ATOM | 2813 | CA | PRO | A2070 | | 29.513 | 36.929 | 84.922 | 1.00 | 9.82 |
| ATOM | 2814 | CB | PRO | A2070 | | 29.190 | 38.380 | 84.546 | 1.00 | 10.41 |
| ATOM | 2815 | CG | PRO | A2070 | | 30.311 | 38.787 | 83.643 | 1.00 | 9.73 |
| ATOM | 2816 | CD | PRO | A2070 | | 31.516 | 38.115 | 84.202 | 1.00 | 10.45 |
| ATOM | 2817 | C | PRO | A2070 | | 28.696 | 35.949 | 84.069 | 1.00 | 8.84 |
| ATOM | 2818 | O | PRO | A2070 | | 27.614 | 35.560 | 84.481 | 1.00 | 9.85 |
| ATOM | 2819 | N | ARG | A2071 | | 29.228 | 35.540 | 82.919 | 1.00 | 8.71 |
| ATOM | 2820 | CA | ARG | A2071 | | 28.559 | 34.577 | 82.047 | 1.00 | 9.86 |
| ATOM | 2821 | CB | ARG | A2071 | | 29.326 | 34.417 | 80.736 | 1.00 | 9.25 |
| ATOM | 2822 | CG | ARG | A2071 | | 29.318 | 35.665 | 79.872 | 1.00 | 9.18 |
| ATOM | 2823 | CD | ARG | A2071 | | 30.434 | 35.699 | 78.838 | 1.00 | 10.15 |
| ATOM | 2824 | NE | ARG | A2071 | | 30.567 | 37.028 | 78.250 | 1.00 | 10.03 |
| ATOM | 2825 | CZ | ARG | A2071 | | 31.268 | 38.017 | 78.790 | 1.00 | 10.36 |
| ATOM | 2826 | NH1 | ARG | A2071 | | 31.922 | 37.837 | 79.937 | 1.00 | 8.51 |
| ATOM | 2827 | NH2 | ARG | A2071 | | 31.324 | 39.188 | 78.177 | 1.00 | 8.70 |
| ATOM | 2828 | C | ARG | A2071 | | 28.358 | 33.214 | 82.710 | 1.00 | 11.19 |
| ATOM | 2829 | O | ARG | A2071 | | 27.396 | 32.509 | 82.401 | 1.00 | 14.27 |
| ATOM | 2830 | N | TRP | A2072 | | 29.263 | 32.850 | 83.617 | 1.00 | 11.39 |
| ATOM | 2831 | CA | TRP | A2072 | | 29.140 | 31.605 | 84.374 | 1.00 | 12.98 |
| ATOM | 2832 | CB | TRP | A2072 | | 30.391 | 31.345 | 85.217 | 1.00 | 12.23 |
| ATOM | 2833 | CG | TRP | A2072 | | 31.653 | 31.235 | 84.425 | 1.00 | 12.87 |
| ATOM | 2834 | CD1 | TRP | A2072 | | 31.774 | 30.927 | 83.095 | 1.00 | 13.54 |
| ATOM | 2835 | NE1 | TRP | A2072 | | 33.099 | 30.926 | 82.729 | 1.00 | 14.32 |
| ATOM | 2836 | CE2 | TRP | A2072 | | 33.863 | 31.233 | 83.824 | 1.00 | 14.10 |
| ATOM | 2837 | CD2 | TRP | A2072 | | 32.982 | 31.435 | 84.911 | 1.00 | 13.79 |
| ATOM | 2838 | CE3 | TRP | A2072 | | 33.525 | 31.760 | 86.164 | 1.00 | 13.68 |
| ATOM | 2839 | CZ3 | TRP | A2072 | | 34.904 | 31.881 | 86.287 | 1.00 | 14.03 |
| ATOM | 2840 | CH2 | TRP | A2072 | | 35.749 | 31.679 | 85.186 | 1.00 | 14.60 |
| ATOM | 2841 | CZ2 | TRP | A2072 | | 35.251 | 31.354 | 83.950 | 1.00 | 14.29 |
| ATOM | 2842 | C | TRP | A2072 | | 27.919 | 31.649 | 85.280 | 1.00 | 13.48 |
| ATOM | 2843 | O | TRP | A2072 | | 27.253 | 30.638 | 85.487 | 1.00 | 12.83 |
| ATOM | 2844 | N | MET | A2073 | | 27.633 | 32.830 | 85.816 | 1.00 | 12.83 |

FIGURE 3BD

|      | A    | B   | C   | D    | E     | F      | G      | H      | I    | J     |
|------|------|-----|-----|------|-------|--------|--------|--------|------|-------|
| ATOM | 2845 | CA  | MET | A2073 |      | 26.464 | 33.022 | 86.662 | 1.00 | 15.49 |
| ATOM | 2846 | CB  | MET | A2073 |      | 26.603 | 34.343 | 87.431 | 1.00 | 18.63 |
| ATOM | 2847 | CG  | MET | A2073 |      | 25.327 | 35.117 | 87.645 | 1.00 | 22.88 |
| ATOM | 2848 | SD  | MET | A2073 |      | 25.665 | 36.699 | 88.396 | 1.00 | 25.15 |
| ATOM | 2849 | CE  | MET | A2073 |      | 25.689 | 37.688 | 86.920 | 1.00 | 23.01 |
| ATOM | 2850 | C   | MET | A2073 |      | 25.158 | 32.943 | 85.854 | 1.00 | 12.45 |
| ATOM | 2851 | O   | MET | A2073 |      | 24.130 | 32.498 | 86.362 | 1.00 | 13.05 |
| ATOM | 2852 | N   | LEU | A2074 |      | 25.215 | 33.354 | 84.590 | 1.00 | 12.35 |
| ATOM | 2853 | CA  | LEU | A2074 |      | 24.055 | 33.305 | 83.702 | 1.00 | 11.05 |
| ATOM | 2854 | CB  | LEU | A2074 |      | 24.172 | 34.380 | 82.609 | 1.00 | 11.17 |
| ATOM | 2855 | CG  | LEU | A2074 |      | 24.510 | 35.813 | 83.053 | 1.00 | 12.20 |
| ATOM | 2856 | CD1 | LEU | A2074 |      | 24.812 | 36.697 | 81.841 | 1.00 | 11.11 |
| ATOM | 2857 | CD2 | LEU | A2074 |      | 23.389 | 36.419 | 83.899 | 1.00 | 10.28 |
| ATOM | 2858 | C   | LEU | A2074 |      | 23.849 | 31.934 | 83.064 | 1.00 | 12.00 |
| ATOM | 2859 | O   | LEU | A2074 |      | 22.755 | 31.370 | 83.128 | 1.00 | 13.83 |
| ATOM | 2860 | N   | ALA | A2075 |      | 24.907 | 31.398 | 82.460 | 1.00 | 10.94 |
| ATOM | 2861 | CA  | ALA | A2075 |      | 24.802 | 30.202 | 81.625 | 1.00 | 11.55 |
| ATOM | 2862 | CB  | ALA | A2075 |      | 25.515 | 30.430 | 80.291 | 1.00 | 11.66 |
| ATOM | 2863 | C   | ALA | A2075 |      | 25.356 | 28.954 | 82.304 | 1.00 | 12.56 |
| ATOM | 2864 | O   | ALA | A2075 |      | 25.185 | 27.839 | 81.807 | 1.00 | 12.24 |
| ATOM | 2865 | N   | GLY | A2076 |      | 26.015 | 29.142 | 83.440 | 1.00 | 13.49 |
| ATOM | 2866 | CA  | GLY | A2076 |      | 26.757 | 28.062 | 84.054 | 1.00 | 13.57 |
| ATOM | 2867 | C   | GLY | A2076 |      | 28.089 | 27.893 | 83.348 | 1.00 | 15.65 |
| ATOM | 2868 | O   | GLY | A2076 |      | 28.483 | 28.732 | 82.527 | 1.00 | 12.16 |
| ATOM | 2869 | N   | ARG | A2077 |      | 28.779 | 26.803 | 83.667 | 1.00 | 14.98 |
| ATOM | 2870 | CA  | ARG | A2077 |      | 30.103 | 26.528 | 83.122 | 1.00 | 15.98 |
| ATOM | 2871 | CB  | ARG | A2077 |      | 31.160 | 27.407 | 83.810 | 1.00 | 15.98 |
| ATOM | 2872 | CG  | ARG | A2077 |      | 31.200 | 27.301 | 85.339 | 1.00 | 15.64 |
| ATOM | 2873 | CD  | BARG | A2077 |     | 32.535 | 27.710 | 85.953 | 0.50 | 16.31 |
| ATOM | 2874 | CD  | AARG | A2077 |     | 32.558 | 27.589 | 85.963 | 0.50 | 13.47 |
| ATOM | 2875 | NE  | BARG | A2077 |     | 33.618 | 26.846 | 85.490 | 0.50 | 17.71 |
| ATOM | 2876 | NE  | AARG | A2077 |     | 32.541 | 27.303 | 87.395 | 0.50 | 12.29 |
| ATOM | 2877 | CZ  | BARG | A2077 |     | 34.901 | 27.190 | 85.428 | 0.50 | 17.69 |
| ATOM | 2878 | CZ  | AARG | A2077 |     | 33.423 | 27.756 | 88.280 | 0.50 | 11.71 |
| ATOM | 2879 | NH1 | BARG | A2077 |     | 35.789 | 26.311 | 84.987 | 0.50 | 17.71 |
| ATOM | 2880 | NH1 | AARG | A2077 |     | 34.430 | 28.531 | 87.898 | 0.50 | 10.72 |
| ATOM | 2881 | NH2 | BARG | A2077 |     | 35.303 | 28.397 | 85.805 | 0.50 | 17.20 |
| ATOM | 2882 | NH2 | AARG | A2077 |     | 33.295 | 27.429 | 89.559 | 0.50 | 11.24 |
| ATOM | 2883 | C   | ARG | A2077 |      | 30.422 | 25.051 | 83.334 | 1.00 | 18.15 |
| ATOM | 2884 | O   | ARG | A2077 |      | 29.782 | 24.407 | 84.166 | 1.00 | 15.70 |
| ATOM | 2885 | N   | PRO | A2078 |      | 31.387 | 24.504 | 82.590 | 1.00 | 20.28 |
| ATOM | 2886 | CA  | PRO | A2078 |      | 31.897 | 23.162 | 82.893 | 1.00 | 21.89 |
| ATOM | 2887 | CB  | PRO | A2078 |      | 33.072 | 23.005 | 81.925 | 1.00 | 21.08 |
| ATOM | 2888 | CG  | PRO | A2078 |      | 32.749 | 23.907 | 80.795 | 1.00 | 20.83 |
| ATOM | 2889 | CD  | PRO | A2078 |      | 32.056 | 25.089 | 81.412 | 1.00 | 20.38 |
| ATOM | 2890 | C   | PRO | A2078 |      | 32.386 | 23.115 | 84.336 | 1.00 | 24.01 |
| ATOM | 2891 | O   | PRO | A2078 |      | 33.060 | 24.050 | 84.787 | 1.00 | 22.42 |
| ATOM | 2892 | N   | HIS | A2079 |      | 32.022 | 22.052 | 85.051 | 1.00 | 27.66 |
| ATOM | 2893 | CA  | HIS | A2079 |      | 32.452 | 21.858 | 86.431 | 1.00 | 31.00 |
| ATOM | 2894 | CB  | HIS | A2079 |      | 31.965 | 20.506 | 86.954 | 1.00 | 33.42 |
| ATOM | 2895 | CG  | HIS | A2079 |      | 31.583 | 20.520 | 88.400 | 1.00 | 35.17 |
| ATOM | 2896 | ND1 | HIS | A2079 |      | 32.504 | 20.365 | 89.414 | 1.00 | 36.07 |

FIGURE 3BE

|      | A    | B    | C   | D E     | F      | G      | H      | I    | J     |
|------|------|------|-----|---------|--------|--------|--------|------|-------|
| ATOM | 2897 | CE1  | HIS | A2079   | 31.885 | 20.423 | 90.580 | 1.00 | 36.66 |
| ATOM | 2898 | NE2  | HIS | A2079   | 30.595 | 20.607 | 90.358 | 1.00 | 36.53 |
| ATOM | 2899 | CD2  | HIS | A2079   | 30.380 | 20.670 | 89.003 | 1.00 | 35.75 |
| ATOM | 2900 | C    | HIS | A2079   | 33.975 | 21.957 | 86.529 | 1.00 | 32.27 |
| ATOM | 2901 | O    | HIS | A2079   | 34.685 | 21.399 | 85.692 | 1.00 | 32.29 |
| ATOM | 2902 | N    | PRO | A2080   | 34.473 | 22.682 | 87.531 | 1.00 | 34.49 |
| ATOM | 2903 | CA   | PRO | A2080   | 35.919 | 22.902 | 87.686 | 1.00 | 36.76 |
| ATOM | 2904 | CB   | PRO | A2080   | 36.006 | 23.868 | 88.873 | 1.00 | 36.39 |
| ATOM | 2905 | CG   | PRO | A2080   | 34.642 | 24.430 | 89.023 | 1.00 | 35.94 |
| ATOM | 2906 | CD   | PRO | A2080   | 33.700 | 23.357 | 88.588 | 1.00 | 34.93 |
| ATOM | 2907 | C    | PRO | A2080   | 36.705 | 21.625 | 87.994 | 1.00 | 39.00 |
| ATOM | 2908 | O    | PRO | A2080   | 37.899 | 21.576 | 87.690 | 1.00 | 39.86 |
| ATOM | 2909 | N    | THR | A2081   | 36.049 | 20.623 | 88.583 | 1.00 | 41.09 |
| ATOM | 2910 | CA   | THR | A2081   | 36.704 | 19.362 | 88.945 | 1.00 | 43.21 |
| ATOM | 2911 | CB   | THR | A2081   | 36.825 | 19.217 | 90.488 | 1.00 | 43.72 |
| ATOM | 2912 | OG1  | THR | A2081   | 35.577 | 19.549 | 91.108 | 1.00 | 44.56 |
| ATOM | 2913 | CG2  | THR | A2081   | 37.794 | 20.249 | 91.065 | 1.00 | 44.06 |
| ATOM | 2914 | C    | THR | A2081   | 35.999 | 18.139 | 88.347 | 1.00 | 44.12 |
| ATOM | 2915 | O    | THR | A2081   | 36.642 | 17.293 | 87.719 | 1.00 | 43.91 |
| ATOM | 2916 | N    | LEU | A2082   | 34.683 | 18.057 | 88.552 | 1.00 | 45.30 |
| ATOM | 2917 | CA   | LEU | A2082   | 33.855 | 16.959 | 88.047 | 1.00 | 45.56 |
| ATOM | 2918 | CB   | LEU | A2082   | 32.455 | 17.023 | 88.671 | 1.00 | 46.37 |
| ATOM | 2919 | CG   | LEU | A2082   | 31.998 | 15.923 | 89.630 | 1.00 | 47.16 |
| ATOM | 2920 | CD1  | LEU | A2082   | 32.059 | 16.409 | 91.069 | 1.00 | 47.20 |
| ATOM | 2921 | CD2  | LEU | A2082   | 30.588 | 15.465 | 89.280 | 1.00 | 47.10 |
| ATOM | 2922 | C    | LEU | A2082   | 33.746 | 17.008 | 86.524 | 1.00 | 45.88 |
| ATOM | 2923 | O    | LEU | A2082   | 32.800 | 17.582 | 85.978 | 1.00 | 46.68 |
| ATOM | 2924 | N    | LYS | A2083   | 34.719 | 16.405 | 85.844 | 1.00 | 45.63 |
| ATOM | 2925 | CA   | LYS | A2083   | 34.768 | 16.419 | 84.379 | 1.00 | 44.95 |
| ATOM | 2926 | CB   | LYS | A2083   | 36.070 | 15.792 | 83.855 | 1.00 | 46.63 |
| ATOM | 2927 | CG   | LYS | A2083   | 36.453 | 14.454 | 84.483 | 1.00 | 47.88 |
| ATOM | 2928 | CD   | LYS | A2083   | 37.632 | 14.610 | 85.438 | 1.00 | 49.31 |
| ATOM | 2929 | CE   | LYS | A2083   | 38.926 | 14.101 | 84.817 | 1.00 | 50.35 |
| ATOM | 2930 | NZ   | LYS | A2083   | 40.120 | 14.582 | 85.569 | 1.00 | 50.84 |
| ATOM | 2931 | C    | LYS | A2083   | 33.546 | 15.751 | 83.747 | 1.00 | 43.57 |
| ATOM | 2932 | O    | LYS | A2083   | 32.980 | 14.810 | 84.309 | 1.00 | 42.86 |
| ATOM | 2933 | N    | GLY | A2084   | 33.137 | 16.262 | 82.589 | 1.00 | 42.24 |
| ATOM | 2934 | CA   | GLY | A2084   | 32.006 | 15.718 | 81.859 | 1.00 | 40.93 |
| ATOM | 2935 | C    | GLY | A2084   | 30.659 | 16.343 | 82.183 | 1.00 | 40.34 |
| ATOM | 2936 | O    | GLY | A2084   | 29.719 | 16.217 | 81.395 | 1.00 | 41.30 |
| ATOM | 2937 | N    | THR | A2085   | 30.561 | 17.018 | 83.329 | 1.00 | 38.37 |
| ATOM | 2938 | CA   | THR | A2085   | 29.284 | 17.569 | 83.788 | 1.00 | 36.99 |
| ATOM | 2939 | CB   | THR | A2085   | 28.871 | 16.949 | 85.153 | 1.00 | 38.64 |
| ATOM | 2940 | OG1  | THR | A2085   | 27.476 | 17.187 | 85.383 | 1.00 | 40.76 |
| ATOM | 2941 | CG2  | THR | A2085   | 29.543 | 17.665 | 86.322 | 1.00 | 39.06 |
| ATOM | 2942 | C    | THR | A2085   | 29.227 | 19.107 | 83.823 | 1.00 | 34.01 |
| ATOM | 2943 | O    | THR | A2085   | 30.255 | 19.785 | 83.928 | 1.00 | 33.02 |
| ATOM | 2944 | N    | TRP | A2086   | 28.010 | 19.637 | 83.734 | 1.00 | 29.98 |
| ATOM | 2945 | CA   | TRP | A2086   | 27.784 | 21.077 | 83.710 | 1.00 | 26.25 |
| ATOM | 2946 | CB   | TRP | A2086   | 26.697 | 21.424 | 82.697 | 1.00 | 25.78 |
| ATOM | 2947 | CG   | TRP | A2086   | 26.678 | 22.867 | 82.300 | 1.00 | 24.81 |
| ATOM | 2948 | CD1  | TRP | A2086   | 25.843 | 23.838 | 82.773 | 1.00 | 25.15 |

FIGURE 3BF

|  | A | B | C | D E | F | G | H | I | J |
|---|---|---|---|---|---|---|---|---|---|
| ATOM | 2949 | NE1 | TRP | A2086 | 26.124 | 25.042 | 82.171 | 1.00 | 23.49 |
| ATOM | 2950 | CE2 | TRP | A2086 | 27.152 | 24.866 | 81.283 | 1.00 | 24.39 |
| ATOM | 2951 | CD2 | TRP | A2086 | 27.529 | 23.503 | 81.341 | 1.00 | 24.54 |
| ATOM | 2952 | CE3 | TRP | A2086 | 28.576 | 23.060 | 80.516 | 1.00 | 24.33 |
| ATOM | 2953 | CZ3 | TRP | A2086 | 29.202 | 23.976 | 79.675 | 1.00 | 24.56 |
| ATOM | 2954 | CH2 | TRP | A2086 | 28.803 | 25.327 | 79.645 | 1.00 | 24.52 |
| ATOM | 2955 | CZ2 | TRP | A2086 | 27.783 | 25.788 | 80.437 | 1.00 | 23.91 |
| ATOM | 2956 | C | TRP | A2086 | 27.391 | 21.607 | 85.082 | 1.00 | 24.03 |
| ATOM | 2957 | O | TRP | A2086 | 26.582 | 21.000 | 85.789 | 1.00 | 22.44 |
| ATOM | 2958 | N | GLN | A2087 | 27.977 | 22.745 | 85.441 | 1.00 | 20.47 |
| ATOM | 2959 | CA | GLN | A2087 | 27.641 | 23.457 | 86.664 | 1.00 | 18.40 |
| ATOM | 2960 | CB | GLN | A2087 | 28.907 | 24.050 | 87.280 | 1.00 | 19.54 |
| ATOM | 2961 | CG | GLN | A2087 | 28.754 | 24.564 | 88.694 | 1.00 | 22.96 |
| ATOM | 2962 | CD | GLN | A2087 | 30.085 | 24.951 | 89.316 | 1.00 | 24.46 |
| ATOM | 2963 | OE1 | GLN | A2087 | 30.786 | 25.821 | 88.798 | 1.00 | 24.81 |
| ATOM | 2964 | NE2 | GLN | A2087 | 30.436 | 24.306 | 90.427 | 1.00 | 24.79 |
| ATOM | 2965 | C | GLN | A2087 | 26.633 | 24.552 | 86.304 | 1.00 | 17.10 |
| ATOM | 2966 | O | GLN | A2087 | 26.984 | 25.543 | 85.664 | 1.00 | 13.52 |
| ATOM | 2967 | N | SER | A2088 | 25.384 | 24.345 | 86.713 | 1.00 | 14.87 |
| ATOM | 2968 | CA | SER | A2088 | 24.262 | 25.180 | 86.296 | 1.00 | 13.79 |
| ATOM | 2969 | CB | SER | A2088 | 22.951 | 24.608 | 86.834 | 1.00 | 13.96 |
| ATOM | 2970 | OG | SER | A2088 | 22.884 | 24.757 | 88.242 | 1.00 | 14.63 |
| ATOM | 2971 | C | SER | A2088 | 24.404 | 26.636 | 86.730 | 1.00 | 11.61 |
| ATOM | 2972 | O | SER | A2088 | 24.992 | 26.938 | 87.774 | 1.00 | 11.01 |
| ATOM | 2973 | N | GLY | A2089 | 23.865 | 27.527 | 85.906 | 1.00 | 12.57 |
| ATOM | 2974 | CA | GLY | A2089 | 23.760 | 28.931 | 86.241 | 1.00 | 10.95 |
| ATOM | 2975 | C | GLY | A2089 | 22.315 | 29.325 | 86.481 | 1.00 | 11.53 |
| ATOM | 2976 | O | GLY | A2089 | 21.438 | 28.469 | 86.678 | 1.00 | 11.02 |
| ATOM | 2977 | N | PHE | A2090 | 22.068 | 30.632 | 86.465 | 1.00 | 9.48 |
| ATOM | 2978 | CA | PHE | A2090 | 20.750 | 31.174 | 86.766 | 1.00 | 8.96 |
| ATOM | 2979 | CB | PHE | A2090 | 20.828 | 32.698 | 86.938 | 1.00 | 9.27 |
| ATOM | 2980 | CG | PHE | A2090 | 19.521 | 33.332 | 87.332 | 1.00 | 8.68 |
| ATOM | 2981 | CD1 | PHE | A2090 | 18.565 | 33.651 | 86.368 | 1.00 | 9.28 |
| ATOM | 2982 | CE1 | PHE | A2090 | 17.350 | 34.242 | 86.727 | 1.00 | 8.45 |
| ATOM | 2983 | CZ | PHE | A2090 | 17.084 | 34.516 | 88.062 | 1.00 | 7.33 |
| ATOM | 2984 | CE2 | PHE | A2090 | 18.032 | 34.210 | 89.036 | 1.00 | 9.57 |
| ATOM | 2985 | CD2 | PHE | A2090 | 19.247 | 33.614 | 88.668 | 1.00 | 9.31 |
| ATOM | 2986 | C | PHE | A2090 | 19.711 | 30.815 | 85.702 | 1.00 | 8.85 |
| ATOM | 2987 | O | PHE | A2090 | 18.604 | 30.389 | 86.032 | 1.00 | 7.64 |
| ATOM | 2988 | N | PHE | A2091 | 20.066 | 30.985 | 84.432 | 1.00 | 7.75 |
| ATOM | 2989 | CA | PHE | A2091 | 19.104 | 30.793 | 83.351 | 1.00 | 7.84 |
| ATOM | 2990 | CB | PHE | A2091 | 19.366 | 31.784 | 82.219 | 1.00 | 8.45 |
| ATOM | 2991 | CG | PHE | A2091 | 19.047 | 33.195 | 82.597 | 1.00 | 8.31 |
| ATOM | 2992 | CD1 | PHE | A2091 | 20.064 | 34.105 | 82.863 | 1.00 | 8.45 |
| ATOM | 2993 | CE1 | PHE | A2091 | 19.763 | 35.412 | 83.236 | 1.00 | 7.75 |
| ATOM | 2994 | CZ | PHE | A2091 | 18.436 | 35.807 | 83.358 | 1.00 | 7.29 |
| ATOM | 2995 | CE2 | PHE | A2091 | 17.413 | 34.895 | 83.110 | 1.00 | 8.23 |
| ATOM | 2996 | CD2 | PHE | A2091 | 17.722 | 33.603 | 82.732 | 1.00 | 6.30 |
| ATOM | 2997 | C | PHE | A2091 | 19.024 | 29.359 | 82.842 | 1.00 | 10.17 |
| ATOM | 2998 | O | PHE | A2091 | 19.827 | 28.500 | 83.234 | 1.00 | 8.08 |
| ATOM | 2999 | N | ASP | A2092 | 18.025 | 29.106 | 81.996 | 1.00 | 10.86 |
| ATOM | 3000 | CA | ASP | A2092 | 17.843 | 27.798 | 81.382 | 1.00 | 11.00 |

FIGURE 3BG

| | A | B | C | D | E | F | G | H | I | J |
|---|---|---|---|---|---|---|---|---|---|---|
| ATOM | 3001 | CB | ASP | A2092 | 16.663 | 27.810 | 80.411 | 1.00 | 11.56 |
| ATOM | 3002 | CG | ASP | A2092 | 15.338 | 28.114 | 81.090 | 1.00 | 11.67 |
| ATOM | 3003 | OD1 | ASP | A2092 | 15.283 | 28.213 | 82.337 | 1.00 | 12.62 |
| ATOM | 3004 | OD2 | ASP | A2092 | 14.293 | 28.275 | 80.438 | 1.00 | 11.35 |
| ATOM | 3005 | C | ASP | A2092 | 19.104 | 27.445 | 80.625 | 1.00 | 10.91 |
| ATOM | 3006 | O | ASP | A2092 | 19.654 | 28.279 | 79.898 | 1.00 | 9.03 |
| ATOM | 3007 | N | HIS | A2093 | 19.557 | 26.208 | 80.803 | 1.00 | 11.68 |
| ATOM | 3008 | CA | HIS | A2093 | 20.769 | 25.730 | 80.153 | 1.00 | 12.85 |
| ATOM | 3009 | CB | HIS | A2093 | 20.930 | 24.224 | 80.361 | 1.00 | 14.55 |
| ATOM | 3010 | CG | HIS | A2093 | 22.208 | 23.682 | 79.808 | 1.00 | 16.84 |
| ATOM | 3011 | ND1 | HIS | A2093 | 23.438 | 23.986 | 80.349 | 1.00 | 18.15 |
| ATOM | 3012 | CE1 | HIS | A2093 | 24.384 | 23.381 | 79.654 | 1.00 | 18.27 |
| ATOM | 3013 | NE2 | HIS | A2093 | 23.811 | 22.700 | 78.678 | 1.00 | 20.07 |
| ATOM | 3014 | CD2 | HIS | A2093 | 22.450 | 22.877 | 78.748 | 1.00 | 19.00 |
| ATOM | 3015 | C | HIS | A2093 | 20.770 | 26.054 | 78.661 | 1.00 | 12.39 |
| ATOM | 3016 | O | HIS | A2093 | 19.798 | 25.778 | 77.953 | 1.00 | 12.30 |
| ATOM | 3017 | N | GLY | A2094 | 21.859 | 26.663 | 78.201 | 1.00 | 11.93 |
| ATOM | 3018 | CA | GLY | A2094 | 22.042 | 26.974 | 76.793 | 1.00 | 12.22 |
| ATOM | 3019 | C | GLY | A2094 | 21.180 | 28.091 | 76.223 | 1.00 | 11.18 |
| ATOM | 3020 | O | GLY | A2094 | 21.170 | 28.300 | 75.010 | 1.00 | 10.56 |
| ATOM | 3021 | N | SER | A2095 | 20.450 | 28.802 | 77.079 | 1.00 | 11.22 |
| ATOM | 3022 | CA | SER | A2095 | 19.509 | 29.822 | 76.611 | 1.00 | 9.81 |
| ATOM | 3023 | CB | SER | A2095 | 18.287 | 29.881 | 77.525 | 1.00 | 11.22 |
| ATOM | 3024 | OG | SER | A2095 | 18.623 | 30.515 | 78.746 | 1.00 | 8.73 |
| ATOM | 3025 | C | SER | A2095 | 20.132 | 31.207 | 76.534 | 1.00 | 10.30 |
| ATOM | 3026 | O | SER | A2095 | 19.592 | 32.094 | 75.863 | 1.00 | 11.08 |
| ATOM | 3027 | N | PHE | A2096 | 21.247 | 31.412 | 77.229 | 1.00 | 9.05 |
| ATOM | 3028 | CA | PHE | A2096 | 21.876 | 32.722 | 77.215 | 1.00 | 10.94 |
| ATOM | 3029 | CB | PHE | A2096 | 22.810 | 32.956 | 78.408 | 1.00 | 10.72 |
| ATOM | 3030 | CG | PHE | A2096 | 23.522 | 34.284 | 78.341 | 1.00 | 11.64 |
| ATOM | 3031 | CD1 | PHE | A2096 | 24.895 | 34.349 | 78.109 | 1.00 | 11.80 |
| ATOM | 3032 | CE1 | PHE | A2096 | 25.546 | 35.581 | 78.022 | 1.00 | 10.72 |
| ATOM | 3033 | CZ | PHE | A2096 | 24.820 | 36.761 | 78.138 | 1.00 | 10.93 |
| ATOM | 3034 | CE2 | PHE | A2096 | 23.440 | 36.706 | 78.353 | 1.00 | 11.90 |
| ATOM | 3035 | CD2 | PHE | A2096 | 22.804 | 35.474 | 78.443 | 1.00 | 10.52 |
| ATOM | 3036 | C | PHE | A2096 | 22.641 | 32.948 | 75.920 | 1.00 | 12.42 |
| ATOM | 3037 | O | PHE | A2096 | 23.552 | 32.189 | 75.592 | 1.00 | 11.58 |
| ATOM | 3038 | N | LYS | A2097 | 22.262 | 33.998 | 75.195 | 1.00 | 11.01 |
| ATOM | 3039 | CA | LYS | A2097 | 22.966 | 34.386 | 73.978 | 1.00 | 11.90 |
| ATOM | 3040 | CB | LYS | A2097 | 22.114 | 34.106 | 72.738 | 1.00 | 14.24 |
| ATOM | 3041 | CG | LYS | A2097 | 22.364 | 32.743 | 72.126 | 1.00 | 18.81 |
| ATOM | 3042 | CD | LYS | A2097 | 21.441 | 31.706 | 72.693 | 1.00 | 21.01 |
| ATOM | 3043 | CE | LYS | A2097 | 21.300 | 30.491 | 71.764 | 1.00 | 22.50 |
| ATOM | 3044 | NZ | LYS | A2097 | 22.564 | 29.725 | 71.585 | 1.00 | 20.96 |
| ATOM | 3045 | C | LYS | A2097 | 23.328 | 35.857 | 74.063 | 1.00 | 9.67 |
| ATOM | 3046 | O | LYS | A2097 | 22.448 | 36.714 | 74.126 | 1.00 | 7.86 |
| ATOM | 3047 | N | GLU | A2098 | 24.631 | 36.124 | 74.068 | 1.00 | 10.19 |
| ATOM | 3048 | CA | GLU | A2098 | 25.181 | 37.453 | 74.280 | 1.00 | 10.14 |
| ATOM | 3049 | CB | GLU | A2098 | 26.639 | 37.327 | 74.751 | 1.00 | 11.38 |
| ATOM | 3050 | CG | GLU | A2098 | 27.244 | 38.615 | 75.297 | 1.00 | 10.69 |
| ATOM | 3051 | CD | GLU | A2098 | 28.638 | 38.440 | 75.889 | 1.00 | 11.21 |
| ATOM | 3052 | OE1 | GLU | A2098 | 29.139 | 37.298 | 75.940 | 1.00 | 8.82 |

FIGURE 3BH

| | A | B | C | D | E | F | G | H | I | J |
|---|---|---|---|---|---|---|---|---|---|---|
| ATOM | 3053 | OE2 | GLU | A2098 | | 29.231 | 39.458 | 76.313 | 1.00 | 9.51 |
| ATOM | 3054 | C | GLU | A2098 | | 25.116 | 38.293 | 73.010 | 1.00 | 9.93 |
| ATOM | 3055 | O | GLU | A2098 | | 25.189 | 37.762 | 71.899 | 1.00 | 9.91 |
| ATOM | 3056 | N | ILE | A2099 | | 24.965 | 39.602 | 73.177 | 1.00 | 8.70 |
| ATOM | 3057 | CA | ILE | A2099 | | 25.139 | 40.538 | 72.070 | 1.00 | 8.38 |
| ATOM | 3058 | CB | ILE | A2099 | | 23.795 | 41.184 | 71.614 | 1.00 | 8.55 |
| ATOM | 3059 | CG1 | ILE | A2099 | | 23.122 | 41.973 | 72.756 | 1.00 | 8.37 |
| ATOM | 3060 | CD1 | ILE | A2099 | | 21.839 | 42.730 | 72.334 | 1.00 | 7.65 |
| ATOM | 3061 | CG2 | ILE | A2099 | | 22.879 | 40.141 | 70.958 | 1.00 | 7.59 |
| ATOM | 3062 | C | ILE | A2099 | | 26.152 | 41.617 | 72.448 | 1.00 | 10.00 |
| ATOM | 3063 | O | ILE | A2099 | | 26.417 | 41.845 | 73.637 | 1.00 | 10.37 |
| ATOM | 3064 | N | MET | A2100 | | 26.710 | 42.271 | 71.430 | 1.00 | 7.47 |
| ATOM | 3065 | CA | MET | A2100 | | 27.687 | 43.346 | 71.617 | 1.00 | 8.80 |
| ATOM | 3066 | CB | MET | A2100 | | 26.989 | 44.622 | 72.114 | 1.00 | 7.49 |
| ATOM | 3067 | CG | MET | A2100 | | 25.959 | 45.194 | 71.137 | 1.00 | 8.34 |
| ATOM | 3068 | SD | MET | A2100 | | 25.170 | 46.710 | 71.765 | 1.00 | 9.69 |
| ATOM | 3069 | CE | MET | A2100 | | 23.995 | 46.028 | 72.946 | 1.00 | 7.98 |
| ATOM | 3070 | C | MET | A2100 | | 28.826 | 42.942 | 72.563 | 1.00 | 9.50 |
| ATOM | 3071 | O | MET | A2100 | | 29.325 | 43.771 | 73.321 | 1.00 | 8.59 |
| ATOM | 3072 | N | ALA | A2101 | | 29.240 | 41.672 | 72.485 | 1.00 | 7.29 |
| ATOM | 3073 | CA | ALA | A2101 | | 30.203 | 41.077 | 73.418 | 1.00 | 8.39 |
| ATOM | 3074 | CB | ALA | A2101 | | 30.432 | 39.575 | 73.088 | 1.00 | 8.18 |
| ATOM | 3075 | C | ALA | A2101 | | 31.546 | 41.804 | 73.566 | 1.00 | 8.20 |
| ATOM | 3076 | O | ALA | A2101 | | 31.942 | 42.088 | 74.684 | 1.00 | 11.09 |
| ATOM | 3077 | N | PRO | A2102 | | 32.249 | 42.100 | 72.467 | 1.00 | 8.97 |
| ATOM | 3078 | CA | PRO | A2102 | | 33.582 | 42.716 | 72.555 | 1.00 | 8.40 |
| ATOM | 3079 | CB | PRO | A2102 | | 34.172 | 42.468 | 71.164 | 1.00 | 8.04 |
| ATOM | 3080 | CG | PRO | A2102 | | 33.201 | 41.590 | 70.468 | 1.00 | 11.24 |
| ATOM | 3081 | CD | PRO | A2102 | | 31.864 | 41.878 | 71.063 | 1.00 | 8.21 |
| ATOM | 3082 | C | PRO | A2102 | | 33.572 | 44.220 | 72.831 | 1.00 | 8.33 |
| ATOM | 3083 | O | PRO | A2102 | | 34.633 | 44.801 | 73.079 | 1.00 | 9.01 |
| ATOM | 3084 | N | TRP | A2103 | | 32.405 | 44.849 | 72.773 | 1.00 | 7.69 |
| ATOM | 3085 | CA | TRP | A2103 | | 32.323 | 46.284 | 73.033 | 1.00 | 6.92 |
| ATOM | 3086 | CB | TRP | A2103 | | 31.269 | 46.938 | 72.134 | 1.00 | 7.15 |
| ATOM | 3087 | CG | TRP | A2103 | | 31.073 | 48.401 | 72.423 | 1.00 | 7.27 |
| ATOM | 3088 | CD1 | TRP | A2103 | | 32.047 | 49.348 | 72.573 | 1.00 | 7.30 |
| ATOM | 3089 | NE1 | TRP | A2103 | | 31.481 | 50.573 | 72.835 | 1.00 | 8.11 |
| ATOM | 3090 | CE2 | TRP | A2103 | | 30.120 | 50.439 | 72.857 | 1.00 | 7.82 |
| ATOM | 3091 | CD2 | TRP | A2103 | | 29.827 | 49.079 | 72.611 | 1.00 | 7.78 |
| ATOM | 3092 | CE3 | TRP | A2103 | | 28.486 | 48.679 | 72.587 | 1.00 | 6.21 |
| ATOM | 3093 | CZ3 | TRP | A2103 | | 27.499 | 49.634 | 72.804 | 1.00 | 7.55 |
| ATOM | 3094 | CH2 | TRP | A2103 | | 27.829 | 50.973 | 73.053 | 1.00 | 6.59 |
| ATOM | 3095 | CZ2 | TRP | A2103 | | 29.125 | 51.394 | 73.086 | 1.00 | 8.27 |
| ATOM | 3096 | C | TRP | A2103 | | 31.983 | 46.525 | 74.490 | 1.00 | 6.86 |
| ATOM | 3097 | O | TRP | A2103 | | 31.078 | 45.883 | 75.027 | 1.00 | 7.05 |
| ATOM | 3098 | N | ALA | A2104 | | 32.706 | 47.443 | 75.133 | 1.00 | 7.98 |
| ATOM | 3099 | CA | ALA | A2104 | | 32.357 | 47.872 | 76.492 | 1.00 | 7.26 |
| ATOM | 3100 | CB | ALA | A2104 | | 31.081 | 48.709 | 76.459 | 1.00 | 7.35 |
| ATOM | 3101 | C | ALA | A2104 | | 32.175 | 46.645 | 77.394 | 1.00 | 8.04 |
| ATOM | 3102 | O | ALA | A2104 | | 31.084 | 46.381 | 77.913 | 1.00 | 7.33 |
| ATOM | 3103 | N | GLN | A2105 | | 33.262 | 45.905 | 77.573 | 1.00 | 9.89 |
| ATOM | 3104 | CA | GLN | A2105 | | 33.228 | 44.577 | 78.185 | 1.00 | 9.25 |

FIGURE 3BI

| | A | B | C | D E | F | G | H | I | J |
|---|---|---|---|---|---|---|---|---|---|
| ATOM | 3105 | CB | GLN | A2105 | 34.484 | 43.795 | 77.797 | 1.00 | 9.43 |
| ATOM | 3106 | CG | GLN | A2105 | 34.563 | 43.498 | 76.311 | 1.00 | 11.71 |
| ATOM | 3107 | CD | GLN | A2105 | 35.849 | 42.801 | 75.923 | 1.00 | 13.30 |
| ATOM | 3108 | OE1 | GLN | A2105 | 36.303 | 41.892 | 76.619 | 1.00 | 15.31 |
| ATOM | 3109 | NE2 | GLN | A2105 | 36.429 | 43.212 | 74.803 | 1.00 | 12.92 |
| ATOM | 3110 | C | GLN | A2105 | 33.038 | 44.545 | 79.698 | 1.00 | 8.13 |
| ATOM | 3111 | O | GLN | A2105 | 32.974 | 43.462 | 80.292 | 1.00 | 9.47 |
| ATOM | 3112 | N | THR | A2106 | 32.936 | 45.712 | 80.326 | 1.00 | 7.43 |
| ATOM | 3113 | CA | THR | A2106 | 32.600 | 45.745 | 81.755 | 1.00 | 7.77 |
| ATOM | 3114 | CB | THR | A2106 | 32.998 | 47.064 | 82.439 | 1.00 | 7.23 |
| ATOM | 3115 | OG1 | THR | A2106 | 32.464 | 48.173 | 81.711 | 1.00 | 8.80 |
| ATOM | 3116 | CG2 | THR | A2106 | 34.510 | 47.260 | 82.381 | 1.00 | 6.92 |
| ATOM | 3117 | C | THR | A2106 | 31.130 | 45.456 | 81.981 | 1.00 | 7.81 |
| ATOM | 3118 | O | THR | A2106 | 30.705 | 45.245 | 83.113 | 1.00 | 9.35 |
| ATOM | 3119 | N | VAL | A2107 | 30.357 | 45.438 | 80.902 | 1.00 | 6.51 |
| ATOM | 3120 | CA | VAL | A2107 | 28.955 | 45.049 | 80.996 | 1.00 | 7.26 |
| ATOM | 3121 | CB | VAL | A2107 | 27.997 | 46.268 | 80.784 | 1.00 | 8.71 |
| ATOM | 3122 | CG1 | VAL | A2107 | 27.996 | 46.728 | 79.334 | 1.00 | 5.06 |
| ATOM | 3123 | CG2 | VAL | A2107 | 26.578 | 45.936 | 81.242 | 1.00 | 7.22 |
| ATOM | 3124 | C | VAL | A2107 | 28.666 | 43.920 | 80.013 | 1.00 | 7.97 |
| ATOM | 3125 | O | VAL | A2107 | 29.269 | 43.845 | 78.934 | 1.00 | 7.71 |
| ATOM | 3126 | N | VAL | A2108 | 27.768 | 43.028 | 80.415 | 1.00 | 8.13 |
| ATOM | 3127 | CA | VAL | A2108 | 27.361 | 41.912 | 79.581 | 1.00 | 9.14 |
| ATOM | 3128 | CB | VAL | A2108 | 27.623 | 40.558 | 80.280 | 1.00 | 9.59 |
| ATOM | 3129 | CG1 | VAL | A2108 | 27.128 | 39.386 | 79.422 | 1.00 | 10.57 |
| ATOM | 3130 | CG2 | VAL | A2108 | 29.107 | 40.408 | 80.590 | 1.00 | 10.60 |
| ATOM | 3131 | C | VAL | A2108 | 25.882 | 42.062 | 79.263 | 1.00 | 9.21 |
| ATOM | 3132 | O | VAL | A2108 | 25.058 | 42.191 | 80.170 | 1.00 | 10.73 |
| ATOM | 3133 | N | THR | A2109 | 25.558 | 42.059 | 77.973 | 1.00 | 7.31 |
| ATOM | 3134 | CA | THR | A2109 | 24.175 | 42.158 | 77.520 | 1.00 | 9.34 |
| ATOM | 3135 | CB | THR | A2109 | 23.947 | 43.432 | 76.692 | 1.00 | 9.03 |
| ATOM | 3136 | OG1 | THR | A2109 | 24.937 | 43.510 | 75.655 | 1.00 | 8.68 |
| ATOM | 3137 | CG2 | THR | A2109 | 24.186 | 44.694 | 77.540 | 1.00 | 6.75 |
| ATOM | 3138 | C | THR | A2109 | 23.821 | 40.950 | 76.669 | 1.00 | 9.86 |
| ATOM | 3139 | O | THR | A2109 | 24.622 | 40.497 | 75.850 | 1.00 | 9.38 |
| ATOM | 3140 | N | GLY | A2110 | 22.617 | 40.431 | 76.862 | 1.00 | 8.21 |
| ATOM | 3141 | CA | GLY | A2110 | 22.136 | 39.370 | 76.007 | 1.00 | 7.96 |
| ATOM | 3142 | C | GLY | A2110 | 20.708 | 39.009 | 76.311 | 1.00 | 8.78 |
| ATOM | 3143 | O | GLY | A2110 | 19.998 | 39.758 | 76.978 | 1.00 | 9.49 |
| ATOM | 3144 | N | ARG | A2111 | 20.297 | 37.851 | 75.813 | 1.00 | 8.45 |
| ATOM | 3145 | CA | ARG | A2111 | 18.937 | 37.365 | 75.987 | 1.00 | 9.50 |
| ATOM | 3146 | CB | ARG | A2111 | 18.211 | 37.303 | 74.641 | 1.00 | 7.82 |
| ATOM | 3147 | CG | ARG | A2111 | 18.026 | 38.669 | 73.972 | 1.00 | 7.41 |
| ATOM | 3148 | CD | ARG | A2111 | 17.296 | 38.595 | 72.629 | 1.00 | 7.38 |
| ATOM | 3149 | NE | ARG | A2111 | 17.249 | 39.898 | 71.965 | 1.00 | 6.74 |
| ATOM | 3150 | CZ | ARG | A2111 | 18.206 | 40.359 | 71.168 | 1.00 | 8.45 |
| ATOM | 3151 | NH1 | ARG | A2111 | 19.294 | 39.623 | 70.924 | 1.00 | 5.25 |
| ATOM | 3152 | NH2 | ARG | A2111 | 18.080 | 41.557 | 70.613 | 1.00 | 6.39 |
| ATOM | 3153 | C | ARG | A2111 | 19.043 | 35.980 | 76.569 | 1.00 | 9.01 |
| ATOM | 3154 | O | ARG | A2111 | 20.031 | 35.298 | 76.349 | 1.00 | 8.85 |
| ATOM | 3155 | N | ALA | A2112 | 18.029 | 35.566 | 77.315 | 1.00 | 10.27 |
| ATOM | 3156 | CA | ALA | A2112 | 18.047 | 34.247 | 77.941 | 1.00 | 9.92 |

FIGURE 3BJ

| | A | B | C | D | E | F | G | H | I | J |
|---|---|---|---|---|---|---|---|---|---|---|
| ATOM | 3157 | CB | ALA | A2112 | | 18.845 | 34.277 | 79.235 | 1.00 | 8.54 |
| ATOM | 3158 | C | ALA | A2112 | | 16.626 | 33.814 | 78.201 | 1.00 | 10.03 |
| ATOM | 3159 | O | ALA | A2112 | | 15.685 | 34.553 | 77.895 | 1.00 | 9.36 |
| ATOM | 3160 | N | ARG | A2113 | | 16.474 | 32.612 | 78.747 | 1.00 | 9.58 |
| ATOM | 3161 | CA | ARG | A2113 | | 15.173 | 32.116 | 79.150 | 1.00 | 10.76 |
| ATOM | 3162 | CB | ARG | A2113 | | 14.734 | 30.938 | 78.270 | 1.00 | 12.05 |
| ATOM | 3163 | CG | ARG | A2113 | | 14.210 | 31.369 | 76.911 | 1.00 | 13.39 |
| ATOM | 3164 | CD | ARG | A2113 | | 13.335 | 30.344 | 76.207 | 1.00 | 14.77 |
| ATOM | 3165 | NE | ARG | A2113 | | 12.200 | 30.994 | 75.561 | 1.00 | 16.16 |
| ATOM | 3166 | CZ | ARG | A2113 | | 12.193 | 31.451 | 74.311 | 1.00 | 17.53 |
| ATOM | 3167 | NH1 | ARG | A2113 | | 13.268 | 31.310 | 73.533 | 1.00 | 17.21 |
| ATOM | 3168 | NH2 | ARG | A2113 | | 11.105 | 32.057 | 73.838 | 1.00 | 15.15 |
| ATOM | 3169 | C | ARG | A2113 | | 15.217 | 31.699 | 80.610 | 1.00 | 10.77 |
| ATOM | 3170 | O | ARG | A2113 | | 16.184 | 31.089 | 81.063 | 1.00 | 8.53 |
| ATOM | 3171 | N | LEU | A2114 | | 14.164 | 32.052 | 81.337 | 1.00 | 10.09 |
| ATOM | 3172 | CA | LEU | A2114 | | 14.005 | 31.653 | 82.723 | 1.00 | 10.01 |
| ATOM | 3173 | CB | LEU | A2114 | | 13.945 | 32.876 | 83.637 | 1.00 | 9.10 |
| ATOM | 3174 | CG | LEU | A2114 | | 13.641 | 32.617 | 85.117 | 1.00 | 9.52 |
| ATOM | 3175 | CD1 | LEU | A2114 | | 14.730 | 31.753 | 85.783 | 1.00 | 9.15 |
| ATOM | 3176 | CD2 | LEU | A2114 | | 13.470 | 33.950 | 85.850 | 1.00 | 7.75 |
| ATOM | 3177 | C | LEU | A2114 | | 12.733 | 30.832 | 82.832 | 1.00 | 10.09 |
| ATOM | 3178 | O | LEU | A2114 | | 11.624 | 31.368 | 82.743 | 1.00 | 9.70 |
| ATOM | 3179 | N | GLY | A2115 | | 12.902 | 29.526 | 83.006 | 1.00 | 9.31 |
| ATOM | 3180 | CA | GLY | A2115 | | 11.790 | 28.594 | 82.948 | 1.00 | 7.02 |
| ATOM | 3181 | C | GLY | A2115 | | 10.982 | 28.738 | 81.674 | 1.00 | 7.76 |
| ATOM | 3182 | O | GLY | A2115 | | 9.762 | 28.636 | 81.705 | 1.00 | 9.78 |
| ATOM | 3183 | N | GLY | A2116 | | 11.657 | 28.992 | 80.552 | 1.00 | 8.17 |
| ATOM | 3184 | CA | GLY | A2116 | | 10.974 | 29.171 | 79.280 | 1.00 | 8.28 |
| ATOM | 3185 | C | GLY | A2116 | | 10.565 | 30.595 | 78.934 | 1.00 | 8.26 |
| ATOM | 3186 | O | GLY | A2116 | | 10.186 | 30.860 | 77.792 | 1.00 | 9.46 |
| ATOM | 3187 | N | ILE | A2117 | | 10.642 | 31.508 | 79.902 | 1.00 | 8.50 |
| ATOM | 3188 | CA | ILE | A2117 | | 10.321 | 32.921 | 79.660 | 1.00 | 7.53 |
| ATOM | 3189 | CB | ILE | A2117 | | 9.884 | 33.635 | 80.954 | 1.00 | 6.70 |
| ATOM | 3190 | CG1 | ILE | A2117 | | 8.841 | 32.825 | 81.727 | 1.00 | 8.34 |
| ATOM | 3191 | CD1 | ILE | A2117 | | 8.715 | 33.295 | 83.176 | 1.00 | 8.97 |
| ATOM | 3192 | CG2 | ILE | A2117 | | 9.387 | 35.058 | 80.640 | 1.00 | 6.26 |
| ATOM | 3193 | C | ILE | A2117 | | 11.529 | 33.665 | 79.098 | 1.00 | 7.89 |
| ATOM | 3194 | O | ILE | A2117 | | 12.561 | 33.756 | 79.764 | 1.00 | 7.95 |
| ATOM | 3195 | N | PRO | A2118 | | 11.400 | 34.230 | 77.901 | 1.00 | 8.68 |
| ATOM | 3196 | CA | PRO | A2118 | | 12.496 | 35.010 | 77.321 | 1.00 | 8.80 |
| ATOM | 3197 | CB | PRO | A2118 | | 12.080 | 35.180 | 75.862 | 1.00 | 8.98 |
| ATOM | 3198 | CG | PRO | A2118 | | 10.579 | 35.069 | 75.866 | 1.00 | 9.31 |
| ATOM | 3199 | CD | PRO | A2118 | | 10.213 | 34.185 | 77.023 | 1.00 | 8.87 |
| ATOM | 3200 | C | PRO | A2118 | | 12.628 | 36.366 | 78.007 | 1.00 | 10.41 |
| ATOM | 3201 | O | PRO | A2118 | | 11.621 | 37.035 | 78.267 | 1.00 | 9.21 |
| ATOM | 3202 | N | VAL | A2119 | | 13.865 | 36.748 | 78.314 | 1.00 | 9.37 |
| ATOM | 3203 | CA | VAL | A2119 | | 14.147 | 38.023 | 78.967 | 1.00 | 8.72 |
| ATOM | 3204 | CB | VAL | A2119 | | 14.422 | 37.861 | 80.499 | 1.00 | 8.83 |
| ATOM | 3205 | CG1 | VAL | A2119 | | 13.241 | 37.222 | 81.219 | 1.00 | 7.67 |
| ATOM | 3206 | CG2 | VAL | A2119 | | 15.714 | 37.065 | 80.763 | 1.00 | 9.09 |
| ATOM | 3207 | C | VAL | A2119 | | 15.380 | 38.657 | 78.341 | 1.00 | 9.76 |
| ATOM | 3208 | O | VAL | A2119 | | 16.235 | 37.955 | 77.802 | 1.00 | 7.95 |

FIGURE 3BK

|      | A    | B    | C   | D   | E     | F      | G      | H      | I    | J     |
|------|------|------|-----|-----|-------|--------|--------|--------|------|-------|
| ATOM | 3209 | N    | GLY | A2120 | 15.469 | 39.981 | 78.420 | 1.00 | 8.76  |
| ATOM | 3210 | CA   | GLY | A2120 | 16.733 | 40.665 | 78.194 | 1.00 | 9.28  |
| ATOM | 3211 | C    | GLY | A2120 | 17.551 | 40.547 | 79.471 | 1.00 | 8.59  |
| ATOM | 3212 | O    | GLY | A2120 | 16.991 | 40.468 | 80.570 | 1.00 | 7.23  |
| ATOM | 3213 | N    | VAL | A2121 | 18.871 | 40.525 | 79.328 | 1.00 | 9.19  |
| ATOM | 3214 | CA   | VAL | A2121 | 19.780 | 40.293 | 80.452 | 1.00 | 7.88  |
| ATOM | 3215 | CB   | VAL | A2121 | 20.465 | 38.904 | 80.351 | 1.00 | 8.97  |
| ATOM | 3216 | CG1  | VAL | A2121 | 21.451 | 38.701 | 81.500 | 1.00 | 7.19  |
| ATOM | 3217 | CG2  | VAL | A2121 | 19.428 | 37.773 | 80.316 | 1.00 | 8.77  |
| ATOM | 3218 | C    | VAL | A2121 | 20.889 | 41.336 | 80.467 | 1.00 | 8.52  |
| ATOM | 3219 | O    | VAL | A2121 | 21.527 | 41.576 | 79.441 | 1.00 | 7.51  |
| ATOM | 3220 | N    | ILE | A2122 | 21.123 | 41.933 | 81.636 | 1.00 | 8.35  |
| ATOM | 3221 | CA   | ILE | A2122 | 22.271 | 42.804 | 81.853 | 1.00 | 8.65  |
| ATOM | 3222 | CB   | ILE | A2122 | 21.842 | 44.278 | 82.030 | 1.00 | 9.57  |
| ATOM | 3223 | CG1  | ILE | A2122 | 21.222 | 44.812 | 80.734 | 1.00 | 11.98 |
| ATOM | 3224 | CD1  | ILE | A2122 | 20.415 | 46.082 | 80.917 | 1.00 | 14.61 |
| ATOM | 3225 | CG2  | ILE | A2122 | 23.051 | 45.151 | 82.400 | 1.00 | 8.78  |
| ATOM | 3226 | C    | ILE | A2122 | 23.037 | 42.307 | 83.076 | 1.00 | 9.78  |
| ATOM | 3227 | O    | ILE | A2122 | 22.467 | 42.173 | 84.160 | 1.00 | 11.34 |
| ATOM | 3228 | N    | ALA | A2123 | 24.322 | 42.008 | 82.892 | 1.00 | 7.80  |
| ATOM | 3229 | CA   | ALA | A2123 | 25.166 | 41.573 | 84.004 | 1.00 | 8.60  |
| ATOM | 3230 | CB   | ALA | A2123 | 25.416 | 40.051 | 83.957 | 1.00 | 6.18  |
| ATOM | 3231 | C    | ALA | A2123 | 26.470 | 42.336 | 83.947 | 1.00 | 8.88  |
| ATOM | 3232 | O    | ALA | A2123 | 26.755 | 42.997 | 82.950 | 1.00 | 8.63  |
| ATOM | 3233 | N    | VAL | A2124 | 27.255 | 42.240 | 85.018 | 1.00 | 10.23 |
| ATOM | 3234 | CA   | VAL | A2124 | 28.453 | 43.065 | 85.171 | 1.00 | 9.79  |
| ATOM | 3235 | CB   | VAL | A2124 | 28.361 | 44.017 | 86.400 | 1.00 | 9.10  |
| ATOM | 3236 | CG1  | VAL | A2124 | 29.405 | 45.141 | 86.307 | 1.00 | 8.44  |
| ATOM | 3237 | CG2  | VAL | A2124 | 26.950 | 44.610 | 86.526 | 1.00 | 10.00 |
| ATOM | 3238 | C    | VAL | A2124 | 29.701 | 42.215 | 85.293 | 1.00 | 10.38 |
| ATOM | 3239 | O    | VAL | A2124 | 29.747 | 41.243 | 86.064 | 1.00 | 7.86  |
| ATOM | 3240 | N    | GLU | A2125 | 30.715 | 42.601 | 84.524 | 1.00 | 10.48 |
| ATOM | 3241 | CA   | GLU | A2125 | 32.032 | 41.987 | 84.613 | 1.00 | 11.27 |
| ATOM | 3242 | CB   | GLU | A2125 | 32.914 | 42.508 | 83.470 | 1.00 | 10.91 |
| ATOM | 3243 | CG   | GLU | A2125 | 34.291 | 41.871 | 83.336 | 1.00 | 9.38  |
| ATOM | 3244 | CD   | GLU | A2125 | 34.241 | 40.366 | 83.390 | 1.00 | 10.03 |
| ATOM | 3245 | OE1  | GLU | A2125 | 34.446 | 39.814 | 84.490 | 1.00 | 11.71 |
| ATOM | 3246 | OE2  | GLU | A2125 | 33.980 | 39.740 | 82.338 | 1.00 | 12.46 |
| ATOM | 3247 | C    | GLU | A2125 | 32.617 | 42.352 | 85.973 | 1.00 | 11.30 |
| ATOM | 3248 | O    | GLU | A2125 | 32.463 | 43.492 | 86.421 | 1.00 | 13.41 |
| ATOM | 3249 | N    | THR | A2126 | 33.234 | 41.381 | 86.648 | 1.00 | 12.08 |
| ATOM | 3250 | CA   | THR | A2126 | 33.950 | 41.657 | 87.898 | 1.00 | 12.32 |
| ATOM | 3251 | CB   | THR | A2126 | 33.546 | 40.687 | 89.043 | 1.00 | 12.67 |
| ATOM | 3252 | OG1  | THR | A2126 | 33.697 | 39.326 | 88.613 | 1.00 | 11.32 |
| ATOM | 3253 | CG2  | THR | A2126 | 32.058 | 40.831 | 89.389 | 1.00 | 11.70 |
| ATOM | 3254 | C    | THR | A2126 | 35.464 | 41.604 | 87.707 | 1.00 | 13.30 |
| ATOM | 3255 | O    | THR | A2126 | 36.212 | 42.122 | 88.536 | 1.00 | 14.37 |
| ATOM | 3256 | N    | ARG | A2127 | 35.907 | 40.975 | 86.622 | 1.00 | 12.46 |
| ATOM | 3257 | CA   | ARG | A2127 | 37.328 | 40.915 | 86.296 | 1.00 | 13.94 |
| ATOM | 3258 | CB   | ARG | A2127 | 37.622 | 39.716 | 85.397 | 1.00 | 12.86 |
| ATOM | 3259 | CG   | ARG | A2127 | 37.303 | 38.368 | 86.026 | 1.00 | 11.75 |
| ATOM | 3260 | CD   | ARG | A2127 | 37.126 | 37.245 | 85.022 | 1.00 | 12.98 |

FIGURE 3BL

|      | A    | B    | C   | D E     | F      | G      | H      | I    | J     |
|------|------|------|-----|---------|--------|--------|--------|------|-------|
| ATOM | 3261 | NE   | ARG | A2127   | 36.139 | 37.560 | 83.984 | 1.00 | 13.10 |
| ATOM | 3262 | CZ   | ARG | A2127   | 36.079 | 36.950 | 82.805 | 1.00 | 13.38 |
| ATOM | 3263 | NH1  | ARG | A2127   | 36.945 | 35.991 | 82.503 | 1.00 | 13.13 |
| ATOM | 3264 | NH2  | ARG | A2127   | 35.155 | 37.295 | 81.919 | 1.00 | 12.04 |
| ATOM | 3265 | C    | ARG | A2127   | 37.761 | 42.200 | 85.604 | 1.00 | 15.91 |
| ATOM | 3266 | O    | ARG | A2127   | 36.947 | 42.865 | 84.948 | 1.00 | 15.60 |
| ATOM | 3267 | N    | THR | A2128   | 39.035 | 42.557 | 85.754 | 1.00 | 14.97 |
| ATOM | 3268 | CA   | THR | A2128   | 39.575 | 43.716 | 85.055 | 1.00 | 16.44 |
| ATOM | 3269 | CB   | THR | A2128   | 40.989 | 44.078 | 85.566 | 1.00 | 17.39 |
| ATOM | 3270 | OG1  | THR | A2128   | 40.897 | 44.542 | 86.919 | 1.00 | 17.43 |
| ATOM | 3271 | CG2  | THR | A2128   | 41.533 | 45.303 | 84.827 | 1.00 | 16.91 |
| ATOM | 3272 | C    | THR | A2128   | 39.578 | 43.454 | 83.554 | 1.00 | 16.03 |
| ATOM | 3273 | O    | THR | A2128   | 40.032 | 42.405 | 83.089 | 1.00 | 14.77 |
| ATOM | 3274 | N    | VAL | A2129   | 39.037 | 44.410 | 82.808 | 1.00 | 17.26 |
| ATOM | 3275 | CA   | VAL | A2129   | 38.982 | 44.308 | 81.358 | 1.00 | 17.44 |
| ATOM | 3276 | CB   | VAL | A2129   | 37.702 | 44.986 | 80.797 | 1.00 | 16.65 |
| ATOM | 3277 | CG1  | VAL | A2129   | 37.805 | 45.211 | 79.278 | 1.00 | 15.20 |
| ATOM | 3278 | CG2  | VAL | A2129   | 36.476 | 44.146 | 81.137 | 1.00 | 16.42 |
| ATOM | 3279 | C    | VAL | A2129   | 40.235 | 44.910 | 80.737 | 1.00 | 18.26 |
| ATOM | 3280 | O    | VAL | A2129   | 40.607 | 46.044 | 81.041 | 1.00 | 16.80 |
| ATOM | 3281 | N    | GLU | A2130   | 40.886 | 44.128 | 79.884 | 1.00 | 22.70 |
| ATOM | 3282 | CA   | GLU | A2130   | 41.961 | 44.631 | 79.039 | 1.00 | 27.51 |
| ATOM | 3283 | CB   | GLU | A2130   | 43.107 | 43.624 | 78.955 | 1.00 | 30.09 |
| ATOM | 3284 | CG   | GLU | A2130   | 44.355 | 44.047 | 79.704 | 1.00 | 33.19 |
| ATOM | 3285 | CD   | GLU | A2130   | 44.511 | 43.307 | 81.012 | 1.00 | 35.19 |
| ATOM | 3286 | OE1  | GLU | A2130   | 44.190 | 43.894 | 82.070 | 1.00 | 36.58 |
| ATOM | 3287 | OE2  | GLU | A2130   | 44.945 | 42.135 | 80.979 | 1.00 | 36.11 |
| ATOM | 3288 | C    | GLU | A2130   | 41.387 | 44.877 | 77.657 | 1.00 | 29.46 |
| ATOM | 3289 | O    | GLU | A2130   | 41.067 | 43.934 | 76.931 | 1.00 | 30.36 |
| ATOM | 3290 | N    | VAL | A2131   | 41.231 | 46.149 | 77.306 | 1.00 | 30.63 |
| ATOM | 3291 | CA   | VAL | A2131   | 40.713 | 46.510 | 75.992 | 1.00 | 32.55 |
| ATOM | 3292 | CB   | VAL | A2131   | 39.490 | 47.484 | 76.079 | 1.00 | 33.13 |
| ATOM | 3293 | CG1  | VAL | A2131   | 39.606 | 48.413 | 77.271 | 1.00 | 33.58 |
| ATOM | 3294 | CG2  | VAL | A2131   | 39.299 | 48.273 | 74.785 | 1.00 | 33.99 |
| ATOM | 3295 | C    | VAL | A2131   | 41.832 | 47.036 | 75.090 | 1.00 | 32.52 |
| ATOM | 3296 | O    | VAL | A2131   | 42.535 | 47.989 | 75.440 | 1.00 | 33.44 |
| ATOM | 3297 | N    | ALA | A2132   | 41.997 | 46.388 | 73.940 | 1.00 | 32.72 |
| ATOM | 3298 | CA   | ALA | A2132   | 42.948 | 46.828 | 72.925 | 1.00 | 32.92 |
| ATOM | 3299 | CB   | ALA | A2132   | 43.257 | 45.693 | 71.963 | 1.00 | 32.38 |
| ATOM | 3300 | C    | ALA | A2132   | 42.386 | 48.031 | 72.175 | 1.00 | 32.97 |
| ATOM | 3301 | O    | ALA | A2132   | 41.337 | 47.934 | 71.531 | 1.00 | 33.50 |
| ATOM | 3302 | N    | VAL | A2133   | 43.072 | 49.167 | 72.293 | 1.00 | 31.71 |
| ATOM | 3303 | CA   | VAL | A2133   | 42.706 | 50.380 | 71.567 | 1.00 | 31.93 |
| ATOM | 3304 | CB   | VAL | A2133   | 42.875 | 51.659 | 72.425 | 1.00 | 32.76 |
| ATOM | 3305 | CG1  | VAL | A2133   | 42.430 | 52.895 | 71.650 | 1.00 | 33.18 |
| ATOM | 3306 | CG2  | VAL | A2133   | 42.096 | 51.547 | 73.732 | 1.00 | 33.06 |
| ATOM | 3307 | C    | VAL | A2133   | 43.565 | 50.466 | 70.304 | 1.00 | 31.87 |
| ATOM | 3308 | O    | VAL | A2133   | 44.768 | 50.754 | 70.378 | 1.00 | 31.22 |
| ATOM | 3309 | N    | PRO | A2134   | 42.947 | 50.204 | 69.152 | 1.00 | 31.24 |
| ATOM | 3310 | CA   | PRO | A2134   | 43.674 | 50.140 | 67.879 | 1.00 | 30.14 |
| ATOM | 3311 | CB   | PRO | A2134   | 42.602 | 49.686 | 66.887 | 1.00 | 30.50 |
| ATOM | 3312 | CG   | PRO | A2134   | 41.314 | 50.098 | 67.506 | 1.00 | 31.44 |

FIGURE 3BM

|   | A | B | C | D E | F | G | H | I | J |
|---|---|---|---|---|---|---|---|---|---|
| ATOM | 3313 | CD | PRO | A2134 | 41.505 | 49.952 | 68.978 | 1.00 | 31.27 |
| ATOM | 3314 | C | PRO | A2134 | 44.241 | 51.491 | 67.470 | 1.00 | 28.63 |
| ATOM | 3315 | O | PRO | A2134 | 43.695 | 52.534 | 67.834 | 1.00 | 27.07 |
| ATOM | 3316 | N | ALA | A2135 | 45.347 | 51.460 | 66.732 | 1.00 | 27.15 |
| ATOM | 3317 | CA | ALA | A2135 | 45.967 | 52.674 | 66.225 | 1.00 | 25.19 |
| ATOM | 3318 | CB | ALA | A2135 | 47.366 | 52.375 | 65.685 | 1.00 | 25.25 |
| ATOM | 3319 | C | ALA | A2135 | 45.096 | 53.282 | 65.140 | 1.00 | 23.23 |
| ATOM | 3320 | O | ALA | A2135 | 44.374 | 52.573 | 64.439 | 1.00 | 21.38 |
| ATOM | 3321 | N | ASP | A2136 | 45.161 | 54.603 | 65.029 | 1.00 | 21.67 |
| ATOM | 3322 | CA | ASP | A2136 | 44.569 | 55.332 | 63.922 | 1.00 | 21.49 |
| ATOM | 3323 | CB | ASP | A2136 | 44.172 | 56.736 | 64.399 | 1.00 | 20.93 |
| ATOM | 3324 | CG | ASP | A2136 | 43.636 | 57.615 | 63.287 | 1.00 | 21.25 |
| ATOM | 3325 | OD1 | ASP | A2136 | 43.466 | 57.130 | 62.146 | 1.00 | 21.70 |
| ATOM | 3326 | OD2 | ASP | A2136 | 43.351 | 58.821 | 63.471 | 1.00 | 22.59 |
| ATOM | 3327 | C | ASP | A2136 | 45.592 | 55.394 | 62.770 | 1.00 | 22.14 |
| ATOM | 3328 | O | ASP | A2136 | 46.603 | 56.088 | 62.880 | 1.00 | 21.37 |
| ATOM | 3329 | N | PRO | A2137 | 45.326 | 54.678 | 61.672 | 1.00 | 22.96 |
| ATOM | 3330 | CA | PRO | A2137 | 46.261 | 54.597 | 60.537 | 1.00 | 23.43 |
| ATOM | 3331 | CB | PRO | A2137 | 45.554 | 53.644 | 59.567 | 1.00 | 23.22 |
| ATOM | 3332 | CG | PRO | A2137 | 44.571 | 52.908 | 60.406 | 1.00 | 23.92 |
| ATOM | 3333 | CD | PRO | A2137 | 44.103 | 53.895 | 61.423 | 1.00 | 22.25 |
| ATOM | 3334 | C | PRO | A2137 | 46.497 | 55.940 | 59.851 | 1.00 | 23.76 |
| ATOM | 3335 | O | PRO | A2137 | 47.514 | 56.095 | 59.169 | 1.00 | 23.34 |
| ATOM | 3336 | N | ALA | A2138 | 45.572 | 56.881 | 60.033 | 1.00 | 22.76 |
| ATOM | 3337 | CA | ALA | A2138 | 45.661 | 58.209 | 59.427 | 1.00 | 24.47 |
| ATOM | 3338 | CB | ALA | A2138 | 44.266 | 58.765 | 59.176 | 1.00 | 24.28 |
| ATOM | 3339 | C | ALA | A2138 | 46.477 | 59.193 | 60.264 | 1.00 | 25.70 |
| ATOM | 3340 | O | ALA | A2138 | 46.722 | 60.324 | 59.841 | 1.00 | 26.68 |
| ATOM | 3341 | N | ASN | A2139 | 46.889 | 58.755 | 61.448 | 1.00 | 27.34 |
| ATOM | 3342 | CA | ASN | A2139 | 47.586 | 59.608 | 62.401 | 1.00 | 29.16 |
| ATOM | 3343 | CB | ASN | A2139 | 46.726 | 59.794 | 63.664 | 1.00 | 29.94 |
| ATOM | 3344 | CG | ASN | A2139 | 47.302 | 60.815 | 64.643 | 1.00 | 30.51 |
| ATOM | 3345 | OD1 | ASN | A2139 | 47.038 | 60.741 | 65.844 | 1.00 | 31.22 |
| ATOM | 3346 | ND2 | ASN | A2139 | 48.075 | 61.773 | 64.139 | 1.00 | 30.44 |
| ATOM | 3347 | C | ASN | A2139 | 48.942 | 59.000 | 62.731 | 1.00 | 30.39 |
| ATOM | 3348 | O | ASN | A2139 | 49.023 | 57.955 | 63.381 | 1.00 | 29.70 |
| ATOM | 3349 | N | LEU | A2140 | 50.000 | 59.661 | 62.265 | 1.00 | 32.42 |
| ATOM | 3350 | CA | LEU | A2140 | 51.370 | 59.164 | 62.391 | 1.00 | 34.84 |
| ATOM | 3351 | CB | LEU | A2140 | 52.359 | 60.172 | 61.781 | 1.00 | 35.77 |
| ATOM | 3352 | CG | LEU | A2140 | 53.876 | 59.959 | 61.877 | 1.00 | 36.44 |
| ATOM | 3353 | CD1 | LEU | A2140 | 54.315 | 58.624 | 61.270 | 1.00 | 37.23 |
| ATOM | 3354 | CD2 | LEU | A2140 | 54.610 | 61.118 | 61.212 | 1.00 | 36.94 |
| ATOM | 3355 | C | LEU | A2140 | 51.761 | 58.805 | 63.828 | 1.00 | 35.88 |
| ATOM | 3356 | O | LEU | A2140 | 52.321 | 57.731 | 64.070 | 1.00 | 36.49 |
| ATOM | 3357 | N | ASP | A2141 | 51.453 | 59.692 | 64.773 | 1.00 | 36.95 |
| ATOM | 3358 | CA | ASP | A2141 | 51.816 | 59.475 | 66.173 | 1.00 | 38.79 |
| ATOM | 3359 | CB | ASP | A2141 | 52.077 | 60.815 | 66.882 | 1.00 | 40.91 |
| ATOM | 3360 | CG | ASP | A2141 | 50.811 | 61.612 | 67.118 | 1.00 | 43.08 |
| ATOM | 3361 | OD1 | ASP | A2141 | 50.201 | 62.073 | 66.130 | 1.00 | 44.09 |
| ATOM | 3362 | OD2 | ASP | A2141 | 50.352 | 61.830 | 68.261 | 1.00 | 44.70 |
| ATOM | 3363 | C | ASP | A2141 | 50.807 | 58.615 | 66.950 | 1.00 | 38.03 |
| ATOM | 3364 | O | ASP | A2141 | 50.933 | 58.446 | 68.166 | 1.00 | 39.19 |

FIGURE 3BN

|      | A    | B    | C   | D   | E     | F      | G      | H      | I    | J     |
|------|------|------|-----|-----|-------|--------|--------|--------|------|-------|
| ATOM | 3365 | N    | SER | A2142 | 49.817 | 58.067 | 66.247 | 1.00 | 36.39 |
| ATOM | 3366 | CA   | SER | A2142 | 48.875 | 57.133 | 66.855 | 1.00 | 34.01 |
| ATOM | 3367 | CB   | SER | A2142 | 47.533 | 57.137 | 66.117 | 1.00 | 33.67 |
| ATOM | 3368 | OG   | SER | A2142 | 46.593 | 56.294 | 66.764 | 1.00 | 31.65 |
| ATOM | 3369 | C    | SER | A2142 | 49.457 | 55.722 | 66.897 | 1.00 | 33.79 |
| ATOM | 3370 | O    | SER | A2142 | 49.734 | 55.120 | 65.858 | 1.00 | 33.06 |
| ATOM | 3371 | N    | GLU | A2143 | 49.651 | 55.214 | 68.110 | 1.00 | 33.88 |
| ATOM | 3372 | CA   | GLU | A2143 | 50.130 | 53.852 | 68.326 | 1.00 | 34.85 |
| ATOM | 3373 | CB   | GLU | A2143 | 51.410 | 53.862 | 69.165 | 1.00 | 36.40 |
| ATOM | 3374 | CG   | GLU | A2143 | 52.669 | 54.220 | 68.389 | 1.00 | 38.18 |
| ATOM | 3375 | CD   | GLU | A2143 | 53.930 | 53.624 | 68.994 | 1.00 | 40.00 |
| ATOM | 3376 | OE1  | GLU | A2143 | 54.054 | 53.604 | 70.240 | 1.00 | 40.43 |
| ATOM | 3377 | OE2  | GLU | A2143 | 54.805 | 53.177 | 68.219 | 1.00 | 40.50 |
| ATOM | 3378 | C    | GLU | A2143 | 49.061 | 53.038 | 69.040 | 1.00 | 34.22 |
| ATOM | 3379 | O    | GLU | A2143 | 48.277 | 53.587 | 69.816 | 1.00 | 32.78 |
| ATOM | 3380 | N    | ALA | A2144 | 49.031 | 51.732 | 68.778 | 1.00 | 34.86 |
| ATOM | 3381 | CA   | ALA | A2144 | 48.101 | 50.835 | 69.463 | 1.00 | 35.84 |
| ATOM | 3382 | CB   | ALA | A2144 | 48.141 | 49.440 | 68.854 | 1.00 | 35.23 |
| ATOM | 3383 | C    | ALA | A2144 | 48.409 | 50.785 | 70.958 | 1.00 | 36.20 |
| ATOM | 3384 | O    | ALA | A2144 | 49.562 | 50.615 | 71.362 | 1.00 | 37.14 |
| ATOM | 3385 | N    | LYS | A2145 | 47.369 | 50.960 | 71.767 | 1.00 | 37.17 |
| ATOM | 3386 | CA   | LYS | A2145 | 47.495 | 50.942 | 73.221 | 1.00 | 37.44 |
| ATOM | 3387 | CB   | LYS | A2145 | 47.178 | 52.323 | 73.816 | 1.00 | 38.13 |
| ATOM | 3388 | CG   | LYS | A2145 | 47.914 | 53.497 | 73.174 | 1.00 | 39.25 |
| ATOM | 3389 | CD   | LYS | A2145 | 49.192 | 53.843 | 73.925 | 1.00 | 40.55 |
| ATOM | 3390 | CE   | LYS | A2145 | 49.965 | 54.950 | 73.223 | 1.00 | 41.19 |
| ATOM | 3391 | NZ   | LYS | A2145 | 51.347 | 54.520 | 72.850 | 1.00 | 42.41 |
| ATOM | 3392 | C    | LYS | A2145 | 46.558 | 49.901 | 73.821 | 1.00 | 37.75 |
| ATOM | 3393 | O    | LYS | A2145 | 45.549 | 49.535 | 73.213 | 1.00 | 38.81 |
| ATOM | 3394 | N    | ILE | A2146 | 46.900 | 49.422 | 75.013 | 1.00 | 37.29 |
| ATOM | 3395 | CA   | ILE | A2146 | 45.999 | 48.577 | 75.792 | 1.00 | 37.13 |
| ATOM | 3396 | CB   | ILE | A2146 | 46.632 | 47.184 | 76.068 | 1.00 | 37.80 |
| ATOM | 3397 | CG1  | ILE | A2146 | 46.647 | 46.339 | 74.790 | 1.00 | 38.35 |
| ATOM | 3398 | CD1  | ILE | A2146 | 47.879 | 45.466 | 74.638 | 1.00 | 39.11 |
| ATOM | 3399 | CG2  | ILE | A2146 | 45.877 | 46.443 | 77.172 | 1.00 | 37.55 |
| ATOM | 3400 | C    | ILE | A2146 | 45.659 | 49.312 | 77.085 | 1.00 | 35.91 |
| ATOM | 3401 | O    | ILE | A2146 | 46.552 | 49.697 | 77.845 | 1.00 | 36.41 |
| ATOM | 3402 | N    | ILE | A2147 | 44.367 | 49.531 | 77.313 | 1.00 | 35.28 |
| ATOM | 3403 | CA   | ILE | A2147 | 43.911 | 50.181 | 78.541 | 1.00 | 34.19 |
| ATOM | 3404 | CB   | ILE | A2147 | 43.124 | 51.501 | 78.259 | 1.00 | 35.84 |
| ATOM | 3405 | CG1  | ILE | A2147 | 41.885 | 51.244 | 77.402 | 1.00 | 37.20 |
| ATOM | 3406 | CD1  | ILE | A2147 | 40.642 | 51.959 | 77.902 | 1.00 | 38.62 |
| ATOM | 3407 | CG2  | ILE | A2147 | 44.034 | 52.558 | 77.624 | 1.00 | 36.54 |
| ATOM | 3408 | C    | ILE | A2147 | 43.102 | 49.230 | 79.415 | 1.00 | 30.83 |
| ATOM | 3409 | O    | ILE | A2147 | 42.475 | 48.287 | 78.923 | 1.00 | 30.14 |
| ATOM | 3410 | N    | GLN | A2148 | 43.145 | 49.477 | 80.718 | 1.00 | 27.39 |
| ATOM | 3411 | CA   | GLN | A2148 | 42.445 | 48.651 | 81.690 | 1.00 | 24.11 |
| ATOM | 3412 | CB   | GLN | A2148 | 43.316 | 48.420 | 82.925 | 1.00 | 26.00 |
| ATOM | 3413 | CG   | GLN | A2148 | 44.598 | 47.631 | 82.648 | 1.00 | 27.84 |
| ATOM | 3414 | CD   | GLN | A2148 | 45.090 | 46.877 | 83.866 | 1.00 | 30.15 |
| ATOM | 3415 | OE1  | GLN | A2148 | 45.147 | 47.430 | 84.969 | 1.00 | 30.97 |
| ATOM | 3416 | NE2  | GLN | A2148 | 45.444 | 45.612 | 83.675 | 1.00 | 31.79 |

FIGURE 3BO

|  | A | B | C | D | E | F | G | H | I | J |
|---|---|---|---|---|---|---|---|---|---|---|
| ATOM | 3417 | C | GLN | A2148 | | 41.142 | 49.319 | 82.093 | 1.00 | 21.48 |
| ATOM | 3418 | O | GLN | A2148 | | 41.089 | 50.535 | 82.276 | 1.00 | 20.75 |
| ATOM | 3419 | N | GLN | A2149 | | 40.093 | 48.512 | 82.208 | 1.00 | 17.56 |
| ATOM | 3420 | CA | GLN | A2149 | | 38.806 | 48.981 | 82.691 | 1.00 | 15.95 |
| ATOM | 3421 | CB | GLN | A2149 | | 37.735 | 48.870 | 81.607 | 1.00 | 14.37 |
| ATOM | 3422 | CG | GLN | A2149 | | 37.934 | 49.786 | 80.408 | 1.00 | 14.29 |
| ATOM | 3423 | CD | GLN | A2149 | | 36.815 | 49.659 | 79.397 | 1.00 | 15.22 |
| ATOM | 3424 | OE1 | GLN | A2149 | | 36.340 | 48.549 | 79.116 | 1.00 | 16.10 |
| ATOM | 3425 | NE2 | GLN | A2149 | | 36.377 | 50.791 | 78.851 | 1.00 | 14.40 |
| ATOM | 3426 | C | GLN | A2149 | | 38.427 | 48.123 | 83.886 | 1.00 | 15.01 |
| ATOM | 3427 | O | GLN | A2149 | | 38.254 | 46.908 | 83.754 | 1.00 | 15.44 |
| ATOM | 3428 | N | ALA | A2150 | | 38.308 | 48.759 | 85.046 | 1.00 | 12.53 |
| ATOM | 3429 | CA | ALA | A2150 | | 37.988 | 48.057 | 86.283 | 1.00 | 13.72 |
| ATOM | 3430 | CB | ALA | A2150 | | 38.089 | 49.001 | 87.473 | 1.00 | 13.64 |
| ATOM | 3431 | C | ALA | A2150 | | 36.594 | 47.441 | 86.200 | 1.00 | 12.18 |
| ATOM | 3432 | O | ALA | A2150 | | 35.694 | 48.006 | 85.572 | 1.00 | 10.82 |
| ATOM | 3433 | N | GLY | A2151 | | 36.438 | 46.271 | 86.815 | 1.00 | 11.69 |
| ATOM | 3434 | CA | GLY | A2151 | | 35.147 | 45.609 | 86.904 | 1.00 | 12.00 |
| ATOM | 3435 | C | GLY | A2151 | | 34.180 | 46.389 | 87.773 | 1.00 | 10.44 |
| ATOM | 3436 | O | GLY | A2151 | | 34.596 | 47.256 | 88.539 | 1.00 | 11.19 |
| ATOM | 3437 | N | GLN | A2152 | | 32.887 | 46.096 | 87.633 | 1.00 | 11.23 |
| ATOM | 3438 | CA | GLN | A2152 | | 31.830 | 46.709 | 88.453 | 1.00 | 11.91 |
| ATOM | 3439 | CB | GLN | A2152 | | 32.003 | 46.341 | 89.932 | 1.00 | 12.77 |
| ATOM | 3440 | CG | GLN | A2152 | | 31.913 | 44.859 | 90.218 | 1.00 | 13.45 |
| ATOM | 3441 | CD | GLN | A2152 | | 32.454 | 44.519 | 91.592 | 1.00 | 16.26 |
| ATOM | 3442 | OE1 | GLN | A2152 | | 33.654 | 44.280 | 91.747 | 1.00 | 18.70 |
| ATOM | 3443 | NE2 | GLN | A2152 | | 31.580 | 44.507 | 92.591 | 1.00 | 13.59 |
| ATOM | 3444 | C | GLN | A2152 | | 31.724 | 48.228 | 88.293 | 1.00 | 12.95 |
| ATOM | 3445 | O | GLN | A2152 | | 31.275 | 48.933 | 89.204 | 1.00 | 13.14 |
| ATOM | 3446 | N | VAL | A2153 | | 32.136 | 48.729 | 87.133 | 1.00 | 12.11 |
| ATOM | 3447 | CA | VAL | A2153 | | 32.101 | 50.159 | 86.869 | 1.00 | 10.88 |
| ATOM | 3448 | CB | VAL | A2153 | | 33.533 | 50.776 | 86.900 | 1.00 | 10.41 |
| ATOM | 3449 | CG1 | VAL | A2153 | | 33.524 | 52.226 | 86.440 | 1.00 | 11.30 |
| ATOM | 3450 | CG2 | VAL | A2153 | | 34.137 | 50.675 | 88.311 | 1.00 | 11.64 |
| ATOM | 3451 | C | VAL | A2153 | | 31.412 | 50.417 | 85.530 | 1.00 | 10.63 |
| ATOM | 3452 | O | VAL | A2153 | | 31.586 | 49.656 | 84.577 | 1.00 | 9.55 |
| ATOM | 3453 | N | TRP | A2154 | | 30.599 | 51.468 | 85.483 | 1.00 | 9.13 |
| ATOM | 3454 | CA | TRP | A2154 | | 30.050 | 51.964 | 84.229 | 1.00 | 8.39 |
| ATOM | 3455 | CB | TRP | A2154 | | 28.677 | 52.594 | 84.441 | 1.00 | 9.18 |
| ATOM | 3456 | CG | TRP | A2154 | | 27.522 | 51.680 | 84.173 | 1.00 | 9.77 |
| ATOM | 3457 | CD1 | TRP | A2154 | | 27.421 | 50.737 | 83.183 | 1.00 | 9.11 |
| ATOM | 3458 | NE1 | TRP | A2154 | | 26.204 | 50.107 | 83.255 | 1.00 | 9.69 |
| ATOM | 3459 | CE2 | TRP | A2154 | | 25.490 | 50.639 | 84.296 | 1.00 | 10.21 |
| ATOM | 3460 | CD2 | TRP | A2154 | | 26.295 | 51.631 | 84.896 | 1.00 | 9.97 |
| ATOM | 3461 | CE3 | TRP | A2154 | | 25.783 | 52.335 | 85.994 | 1.00 | 8.40 |
| ATOM | 3462 | CZ3 | TRP | A2154 | | 24.511 | 52.020 | 86.455 | 1.00 | 10.78 |
| ATOM | 3463 | CH2 | TRP | A2154 | | 23.738 | 51.021 | 85.839 | 1.00 | 9.10 |
| ATOM | 3464 | CZ2 | TRP | A2154 | | 24.206 | 50.326 | 84.763 | 1.00 | 10.80 |
| ATOM | 3465 | C | TRP | A2154 | | 30.998 | 53.018 | 83.675 | 1.00 | 10.27 |
| ATOM | 3466 | O | TRP | A2154 | | 31.218 | 54.061 | 84.289 | 1.00 | 11.81 |
| ATOM | 3467 | N | PHE | A2155 | | 31.577 | 52.718 | 82.522 | 1.00 | 9.67 |
| ATOM | 3468 | CA | PHE | A2155 | | 32.365 | 53.682 | 81.781 | 1.00 | 9.67 |

FIGURE 3BP

| | A | B | C | D | E | F | G | H | I | J |
|---|---|---|---|---|---|---|---|---|---|---|
| ATOM | 3469 | CB | PHE | | A2155 | 33.567 | 52.971 | 81.159 | 1.00 | 9.88 |
| ATOM | 3470 | CG | PHE | | A2155 | 34.555 | 52.474 | 82.184 | 1.00 | 10.34 |
| ATOM | 3471 | CD1 | PHE | | A2155 | 34.444 | 51.191 | 82.714 | 1.00 | 9.16 |
| ATOM | 3472 | CE1 | PHE | | A2155 | 35.341 | 50.737 | 83.681 | 1.00 | 11.19 |
| ATOM | 3473 | CZ | PHE | | A2155 | 36.366 | 51.573 | 84.130 | 1.00 | 9.33 |
| ATOM | 3474 | CE2 | PHE | | A2155 | 36.482 | 52.857 | 83.607 | 1.00 | 11.38 |
| ATOM | 3475 | CD2 | PHE | | A2155 | 35.574 | 53.302 | 82.641 | 1.00 | 10.51 |
| ATOM | 3476 | C | PHE | | A2155 | 31.435 | 54.293 | 80.736 | 1.00 | 10.36 |
| ATOM | 3477 | O | PHE | | A2155 | 30.292 | 53.844 | 80.603 | 1.00 | 10.56 |
| ATOM | 3478 | N | PRO | | A2156 | 31.872 | 55.329 | 80.023 | 1.00 | 10.52 |
| ATOM | 3479 | CA | PRO | | A2156 | 31.050 | 55.868 | 78.935 | 1.00 | 9.91 |
| ATOM | 3480 | CB | PRO | | A2156 | 31.997 | 56.834 | 78.228 | 1.00 | 9.89 |
| ATOM | 3481 | CG | PRO | | A2156 | 32.904 | 57.295 | 79.311 | 1.00 | 11.49 |
| ATOM | 3482 | CD | PRO | | A2156 | 33.134 | 56.080 | 80.186 | 1.00 | 10.10 |
| ATOM | 3483 | C | PRO | | A2156 | 30.609 | 54.743 | 77.997 | 1.00 | 9.19 |
| ATOM | 3484 | O | PRO | | A2156 | 29.430 | 54.686 | 77.651 | 1.00 | 8.19 |
| ATOM | 3485 | N | ASP | | A2157 | 31.520 | 53.837 | 77.642 | 1.00 | 7.51 |
| ATOM | 3486 | CA | ASP | | A2157 | 31.175 | 52.773 | 76.702 | 1.00 | 8.41 |
| ATOM | 3487 | CB | ASP | | A2157 | 32.422 | 52.074 | 76.096 | 1.00 | 9.10 |
| ATOM | 3488 | CG | ASP | | A2157 | 33.308 | 51.362 | 77.131 | 1.00 | 12.11 |
| ATOM | 3489 | OD1 | ASP | | A2157 | 32.956 | 51.252 | 78.328 | 1.00 | 11.89 |
| ATOM | 3490 | OD2 | ASP | | A2157 | 34.410 | 50.862 | 76.813 | 1.00 | 14.78 |
| ATOM | 3491 | C | ASP | | A2157 | 30.134 | 51.811 | 77.290 | 1.00 | 7.73 |
| ATOM | 3492 | O | ASP | | A2157 | 29.112 | 51.536 | 76.649 | 1.00 | 7.75 |
| ATOM | 3493 | N | SER | | A2158 | 30.357 | 51.345 | 78.519 | 1.00 | 6.42 |
| ATOM | 3494 | CA | SER | | A2158 | 29.428 | 50.391 | 79.134 | 1.00 | 8.33 |
| ATOM | 3495 | CB | SER | | A2158 | 30.093 | 49.571 | 80.256 | 1.00 | 7.51 |
| ATOM | 3496 | OG | SER | | A2158 | 30.733 | 50.388 | 81.224 | 1.00 | 9.07 |
| ATOM | 3497 | C | SER | | A2158 | 28.106 | 51.015 | 79.593 | 1.00 | 8.01 |
| ATOM | 3498 | O | SER | | A2158 | 27.076 | 50.333 | 79.627 | 1.00 | 8.05 |
| ATOM | 3499 | N | ALA | | A2159 | 28.129 | 52.302 | 79.944 | 1.00 | 7.64 |
| ATOM | 3500 | CA | ALA | | A2159 | 26.885 | 53.032 | 80.211 | 1.00 | 7.69 |
| ATOM | 3501 | CB | ALA | | A2159 | 27.159 | 54.445 | 80.755 | 1.00 | 3.74 |
| ATOM | 3502 | C | ALA | | A2159 | 26.042 | 53.100 | 78.940 | 1.00 | 7.02 |
| ATOM | 3503 | O | ALA | | A2159 | 24.838 | 52.828 | 78.968 | 1.00 | 6.26 |
| ATOM | 3504 | N | TYR | | A2160 | 26.688 | 53.466 | 77.834 | 1.00 | 7.98 |
| ATOM | 3505 | CA | TYR | | A2160 | 26.048 | 53.509 | 76.516 | 1.00 | 7.17 |
| ATOM | 3506 | CB | TYR | | A2160 | 27.058 | 53.966 | 75.458 | 1.00 | 6.26 |
| ATOM | 3507 | CG | TYR | | A2160 | 26.468 | 54.450 | 74.145 | 1.00 | 6.75 |
| ATOM | 3508 | CD1 | TYR | | A2160 | 27.310 | 54.797 | 73.093 | 1.00 | 6.80 |
| ATOM | 3509 | CE1 | TYR | | A2160 | 26.812 | 55.246 | 71.890 | 1.00 | 7.89 |
| ATOM | 3510 | CZ | TYR | | A2160 | 25.446 | 55.379 | 71.715 | 1.00 | 9.05 |
| ATOM | 3511 | OH | TYR | | A2160 | 24.989 | 55.852 | 70.505 | 1.00 | 8.56 |
| ATOM | 3512 | CE2 | TYR | | A2160 | 24.567 | 55.047 | 72.739 | 1.00 | 8.35 |
| ATOM | 3513 | CD2 | TYR | | A2160 | 25.088 | 54.586 | 73.959 | 1.00 | 7.53 |
| ATOM | 3514 | C | TYR | | A2160 | 25.486 | 52.144 | 76.120 | 1.00 | 5.67 |
| ATOM | 3515 | O | TYR | | A2160 | 24.336 | 52.043 | 75.693 | 1.00 | 7.62 |
| ATOM | 3516 | N | LYS | | A2161 | 26.309 | 51.104 | 76.256 | 1.00 | 7.38 |
| ATOM | 3517 | CA | LYS | | A2161 | 25.919 | 49.735 | 75.915 | 1.00 | 7.14 |
| ATOM | 3518 | CB | LYS | | A2161 | 27.094 | 48.778 | 76.147 | 1.00 | 7.55 |
| ATOM | 3519 | CG | LYS | | A2161 | 26.849 | 47.352 | 75.675 | 1.00 | 8.04 |
| ATOM | 3520 | CD | LYS | | A2161 | 28.134 | 46.530 | 75.768 | 1.00 | 7.74 |

FIGURE 3BQ

|      | A    | B   | C   | D    | E     | F      | G      | H      | I    | J     |
|------|------|-----|-----|------|-------|--------|--------|--------|------|-------|
| ATOM | 3521 | CE  | LYS | A2161 | 27.861 | 45.039 | 75.892 | 1.00 | 7.56  |
| ATOM | 3522 | NZ  | LYS | A2161 | 29.118 | 44.237 | 76.197 | 1.00 | 6.18  |
| ATOM | 3523 | C   | LYS | A2161 | 24.706 | 49.282 | 76.720 | 1.00 | 8.30  |
| ATOM | 3524 | O   | LYS | A2161 | 23.777 | 48.667 | 76.180 | 1.00 | 7.91  |
| ATOM | 3525 | N   | THR | A2162 | 24.729 | 49.591 | 78.015 | 1.00 | 7.56  |
| ATOM | 3526 | CA  | THR | A2162 | 23.620 | 49.295 | 78.915 | 1.00 | 8.14  |
| ATOM | 3527 | CB  | THR | A2162 | 23.991 | 49.713 | 80.355 | 1.00 | 6.94  |
| ATOM | 3528 | OG1 | THR | A2162 | 25.160 | 48.985 | 80.765 | 1.00 | 7.75  |
| ATOM | 3529 | CG2 | THR | A2162 | 22.913 | 49.289 | 81.346 | 1.00 | 6.60  |
| ATOM | 3530 | C   | THR | A2162 | 22.348 | 50.005 | 78.457 | 1.00 | 8.29  |
| ATOM | 3531 | O   | THR | A2162 | 21.307 | 49.382 | 78.290 | 1.00 | 6.32  |
| ATOM | 3532 | N   | ALA | A2163 | 22.442 | 51.313 | 78.252 | 1.00 | 9.22  |
| ATOM | 3533 | CA  | ALA | A2163 | 21.309 | 52.094 | 77.776 | 1.00 | 8.72  |
| ATOM | 3534 | CB  | ALA | A2163 | 21.684 | 53.570 | 77.695 | 1.00 | 6.60  |
| ATOM | 3535 | C   | ALA | A2163 | 20.802 | 51.587 | 76.421 | 1.00 | 7.67  |
| ATOM | 3536 | O   | ALA | A2163 | 19.599 | 51.496 | 76.203 | 1.00 | 8.47  |
| ATOM | 3537 | N   | GLN | A2164 | 21.724 | 51.250 | 75.521 | 1.00 | 8.13  |
| ATOM | 3538 | CA  | GLN | A2164 | 21.354 | 50.729 | 74.212 | 1.00 | 8.27  |
| ATOM | 3539 | CB  | GLN | A2164 | 22.593 | 50.489 | 73.349 | 1.00 | 9.62  |
| ATOM | 3540 | CG  | GLN | A2164 | 22.260 | 50.060 | 71.933 | 1.00 | 10.44 |
| ATOM | 3541 | CD  | GLN | A2164 | 21.691 | 51.200 | 71.124 | 1.00 | 12.00 |
| ATOM | 3542 | OE1 | GLN | A2164 | 22.415 | 52.140 | 70.792 | 1.00 | 12.02 |
| ATOM | 3543 | NE2 | GLN | A2164 | 20.390 | 51.135 | 70.818 | 1.00 | 9.43  |
| ATOM | 3544 | C   | GLN | A2164 | 20.551 | 49.436 | 74.331 | 1.00 | 8.43  |
| ATOM | 3545 | O   | GLN | A2164 | 19.487 | 49.295 | 73.718 | 1.00 | 9.15  |
| ATOM | 3546 | N   | ALA | A2165 | 21.066 | 48.501 | 75.129 | 1.00 | 8.10  |
| ATOM | 3547 | CA  | ALA | A2165 | 20.420 | 47.198 | 75.309 | 1.00 | 6.40  |
| ATOM | 3548 | CB  | ALA | A2165 | 21.264 | 46.310 | 76.191 | 1.00 | 6.46  |
| ATOM | 3549 | C   | ALA | A2165 | 19.029 | 47.373 | 75.908 | 1.00 | 7.93  |
| ATOM | 3550 | O   | ALA | A2165 | 18.076 | 46.715 | 75.471 | 1.00 | 6.17  |
| ATOM | 3551 | N   | ILE | A2166 | 18.912 | 48.267 | 76.893 | 1.00 | 6.93  |
| ATOM | 3552 | CA  | ILE | A2166 | 17.613 | 48.551 | 77.507 | 1.00 | 9.72  |
| ATOM | 3553 | CB  | ILE | A2166 | 17.723 | 49.608 | 78.644 | 1.00 | 9.50  |
| ATOM | 3554 | CG1 | ILE | A2166 | 18.444 | 49.006 | 79.849 | 1.00 | 11.02 |
| ATOM | 3555 | CD1 | ILE | A2166 | 19.088 | 50.022 | 80.766 | 1.00 | 9.89  |
| ATOM | 3556 | CG2 | ILE | A2166 | 16.336 | 50.061 | 79.097 | 1.00 | 7.99  |
| ATOM | 3557 | C   | ILE | A2166 | 16.624 | 48.999 | 76.432 | 1.00 | 10.84 |
| ATOM | 3558 | O   | ILE | A2166 | 15.513 | 48.484 | 76.371 | 1.00 | 10.97 |
| ATOM | 3559 | N   | LYS | A2167 | 17.047 | 49.937 | 75.578 | 1.00 | 9.48  |
| ATOM | 3560 | CA  | LYS | A2167 | 16.202 | 50.432 | 74.498 | 1.00 | 10.18 |
| ATOM | 3561 | CB  | LYS | A2167 | 16.892 | 51.567 | 73.737 | 1.00 | 12.43 |
| ATOM | 3562 | CG  | LYS | A2167 | 16.993 | 52.867 | 74.532 | 1.00 | 18.03 |
| ATOM | 3563 | CD  | LYS | A2167 | 17.351 | 54.048 | 73.640 | 1.00 | 22.39 |
| ATOM | 3564 | CE  | LYS | A2167 | 16.680 | 55.329 | 74.133 | 1.00 | 26.16 |
| ATOM | 3565 | NZ  | LYS | A2167 | 16.278 | 56.227 | 73.001 | 1.00 | 28.11 |
| ATOM | 3566 | C   | LYS | A2167 | 15.808 | 49.326 | 73.525 | 1.00 | 8.19  |
| ATOM | 3567 | O   | LYS | A2167 | 14.641 | 49.217 | 73.157 | 1.00 | 6.84  |
| ATOM | 3568 | N   | ASP | A2168 | 16.789 | 48.536 | 73.091 | 1.00 | 8.52  |
| ATOM | 3569 | CA  | ASP | A2168 | 16.563 | 47.462 | 72.120 | 1.00 | 8.38  |
| ATOM | 3570 | CB  | ASP | A2168 | 17.886 | 46.806 | 71.695 | 1.00 | 9.63  |
| ATOM | 3571 | CG  | ASP | A2168 | 18.811 | 47.751 | 70.918 | 1.00 | 10.79 |
| ATOM | 3572 | OD1 | ASP | A2168 | 18.405 | 48.876 | 70.526 | 1.00 | 9.19  |

FIGURE 3BR

| | A | B | C | D | E | F | G | H | I | J |
|---|---|---|---|---|---|---|---|---|---|---|
| ATOM | 3573 | OD2 | ASP | A2168 | | 19.988 | 47.436 | 70.653 | 1.00 | 10.66 |
| ATOM | 3574 | C | ASP | A2168 | | 15.624 | 46.394 | 72.676 | 1.00 | 9.15 |
| ATOM | 3575 | O | ASP | A2168 | | 14.695 | 45.954 | 71.979 | 1.00 | 7.66 |
| ATOM | 3576 | N | PHE | A2169 | | 15.869 | 45.980 | 73.923 | 1.00 | 6.85 |
| ATOM | 3577 | CA | PHE | A2169 | | 15.020 | 44.984 | 74.588 | 1.00 | 8.07 |
| ATOM | 3578 | CB | PHE | A2169 | | 15.640 | 44.499 | 75.911 | 1.00 | 7.25 |
| ATOM | 3579 | CG | PHE | A2169 | | 16.968 | 43.803 | 75.753 | 1.00 | 7.53 |
| ATOM | 3580 | CD1 | PHE | A2169 | | 17.879 | 43.790 | 76.805 | 1.00 | 8.31 |
| ATOM | 3581 | CE1 | PHE | A2169 | | 19.115 | 43.148 | 76.681 | 1.00 | 8.18 |
| ATOM | 3582 | CZ | PHE | A2169 | | 19.448 | 42.507 | 75.489 | 1.00 | 8.78 |
| ATOM | 3583 | CE2 | PHE | A2169 | | 18.549 | 42.517 | 74.425 | 1.00 | 9.66 |
| ATOM | 3584 | CD2 | PHE | A2169 | | 17.312 | 43.163 | 74.561 | 1.00 | 7.01 |
| ATOM | 3585 | C | PHE | A2169 | | 13.612 | 45.518 | 74.835 | 1.00 | 8.47 |
| ATOM | 3586 | O | PHE | A2169 | | 12.631 | 44.778 | 74.707 | 1.00 | 9.35 |
| ATOM | 3587 | N | ASN | A2170 | | 13.503 | 46.801 | 75.182 | 1.00 | 8.38 |
| ATOM | 3588 | CA | ASN | A2170 | | 12.183 | 47.412 | 75.322 | 1.00 | 9.89 |
| ATOM | 3589 | CB | ASN | A2170 | | 12.258 | 48.873 | 75.776 | 1.00 | 9.06 |
| ATOM | 3590 | CG | ASN | A2170 | | 10.937 | 49.366 | 76.327 | 1.00 | 10.09 |
| ATOM | 3591 | OD1 | ASN | A2170 | | 10.131 | 48.573 | 76.801 | 1.00 | 10.59 |
| ATOM | 3592 | ND2 | ASN | A2170 | | 10.699 | 50.673 | 76.256 | 1.00 | 9.32 |
| ATOM | 3593 | C | ASN | A2170 | | 11.369 | 47.319 | 74.032 | 1.00 | 10.97 |
| ATOM | 3594 | O | ASN | A2170 | | 10.170 | 47.020 | 74.053 | 1.00 | 8.61 |
| ATOM | 3595 | N | ARG | A2171 | | 12.036 | 47.559 | 72.913 | 1.00 | 11.85 |
| ATOM | 3596 | CA | ARG | A2171 | | 11.382 | 47.514 | 71.611 | 1.00 | 12.75 |
| ATOM | 3597 | CB | ARG | A2171 | | 12.189 | 48.314 | 70.603 | 1.00 | 12.68 |
| ATOM | 3598 | CG | ARG | A2171 | | 11.893 | 49.794 | 70.678 | 1.00 | 13.60 |
| ATOM | 3599 | CD | ARG | A2171 | | 13.102 | 50.654 | 70.480 | 1.00 | 14.08 |
| ATOM | 3600 | NE | ARG | A2171 | | 12.813 | 52.055 | 70.737 | 1.00 | 14.26 |
| ATOM | 3601 | CZ | ARG | A2171 | | 12.945 | 52.637 | 71.922 | 1.00 | 16.35 |
| ATOM | 3602 | NH1 | ARG | A2171 | | 12.641 | 53.925 | 72.064 | 1.00 | 15.44 |
| ATOM | 3603 | NH2 | ARG | A2171 | | 13.377 | 51.934 | 72.966 | 1.00 | 12.68 |
| ATOM | 3604 | C | ARG | A2171 | | 11.117 | 46.097 | 71.105 | 1.00 | 12.75 |
| ATOM | 3605 | O | ARG | A2171 | | 10.327 | 45.899 | 70.185 | 1.00 | 13.31 |
| ATOM | 3606 | N | GLU | A2172 | | 11.777 | 45.113 | 71.702 | 1.00 | 11.90 |
| ATOM | 3607 | CA | GLU | A2172 | | 11.440 | 43.718 | 71.438 | 1.00 | 12.86 |
| ATOM | 3608 | CB | GLU | A2172 | | 12.651 | 42.812 | 71.672 | 1.00 | 10.04 |
| ATOM | 3609 | CG | GLU | A2172 | | 13.783 | 43.002 | 70.684 | 1.00 | 11.57 |
| ATOM | 3610 | CD | GLU | A2172 | | 15.125 | 42.591 | 71.256 | 1.00 | 12.51 |
| ATOM | 3611 | OE1 | GLU | A2172 | | 16.128 | 43.246 | 70.922 | 1.00 | 14.85 |
| ATOM | 3612 | OE2 | GLU | A2172 | | 15.183 | 41.622 | 72.047 | 1.00 | 12.98 |
| ATOM | 3613 | C | GLU | A2172 | | 10.299 | 43.294 | 72.356 | 1.00 | 14.00 |
| ATOM | 3614 | O | GLU | A2172 | | 9.742 | 42.201 | 72.208 | 1.00 | 15.89 |
| ATOM | 3615 | N | LYS | A2173 | | 9.978 | 44.164 | 73.315 | 1.00 | 13.80 |
| ATOM | 3616 | CA | LYS | A2173 | | 8.952 | 43.925 | 74.335 | 1.00 | 14.43 |
| ATOM | 3617 | CB | LYS | A2173 | | 7.555 | 43.819 | 73.701 | 1.00 | 17.94 |
| ATOM | 3618 | CG | LYS | A2173 | | 7.173 | 45.108 | 72.939 | 1.00 | 22.71 |
| ATOM | 3619 | CD | LYS | A2173 | | 5.761 | 45.076 | 72.376 | 1.00 | 25.39 |
| ATOM | 3620 | CE | LYS | A2173 | | 5.004 | 46.344 | 72.722 | 1.00 | 28.55 |
| ATOM | 3621 | NZ | LYS | A2173 | | 4.828 | 47.235 | 71.528 | 1.00 | 29.85 |
| ATOM | 3622 | C | LYS | A2173 | | 9.295 | 42.764 | 75.282 | 1.00 | 13.86 |
| ATOM | 3623 | O | LYS | A2173 | | 8.434 | 41.993 | 75.712 | 1.00 | 12.57 |
| ATOM | 3624 | N | LEU | A2174 | | 10.577 | 42.669 | 75.610 | 1.00 | 11.90 |

FIGURE 3BS

|  | A | B | C | D | E | F | G | H | I | J |
|---|---|---|---|---|---|---|---|---|---|---|
| ATOM | 3625 | CA | LEU | A2174 | | 11.074 | 41.684 | 76.557 | 1.00 | 10.63 |
| ATOM | 3626 | CB | LEU | A2174 | | 12.526 | 41.337 | 76.238 | 1.00 | 11.40 |
| ATOM | 3627 | CG | LEU | A2174 | | 12.873 | 40.666 | 74.915 | 1.00 | 13.29 |
| ATOM | 3628 | CD1 | LEU | A2174 | | 14.364 | 40.398 | 74.880 | 1.00 | 13.41 |
| ATOM | 3629 | CD2 | LEU | A2174 | | 12.080 | 39.369 | 74.768 | 1.00 | 14.90 |
| ATOM | 3630 | C | LEU | A2174 | | 11.044 | 42.231 | 77.975 | 1.00 | 9.80 |
| ATOM | 3631 | O | LEU | A2174 | | 11.335 | 43.407 | 78.189 | 1.00 | 9.60 |
| ATOM | 3632 | N | PRO | A2175 | | 10.736 | 41.366 | 78.943 | 1.00 | 10.46 |
| ATOM | 3633 | CA | PRO | A2175 | | 11.040 | 41.658 | 80.347 | 1.00 | 9.81 |
| ATOM | 3634 | CB | PRO | A2175 | | 10.571 | 40.404 | 81.091 | 1.00 | 9.36 |
| ATOM | 3635 | CG | PRO | A2175 | | 9.655 | 39.700 | 80.145 | 1.00 | 10.62 |
| ATOM | 3636 | CD | PRO | A2175 | | 10.105 | 40.044 | 78.770 | 1.00 | 7.96 |
| ATOM | 3637 | C | PRO | A2175 | | 12.547 | 41.771 | 80.459 | 1.00 | 9.85 |
| ATOM | 3638 | O | PRO | A2175 | | 13.265 | 41.228 | 79.610 | 1.00 | 9.49 |
| ATOM | 3639 | N | LEU | A2176 | | 13.019 | 42.443 | 81.497 | 1.00 | 9.38 |
| ATOM | 3640 | CA | LEU | A2176 | | 14.437 | 42.718 | 81.637 | 1.00 | 9.41 |
| ATOM | 3641 | CB | LEU | A2176 | | 14.709 | 44.221 | 81.482 | 1.00 | 9.28 |
| ATOM | 3642 | CG | LEU | A2176 | | 16.151 | 44.743 | 81.591 | 1.00 | 11.07 |
| ATOM | 3643 | CD1 | LEU | A2176 | | 17.040 | 44.185 | 80.479 | 1.00 | 10.80 |
| ATOM | 3644 | CD2 | LEU | A2176 | | 16.159 | 46.272 | 81.543 | 1.00 | 10.22 |
| ATOM | 3645 | C | LEU | A2176 | | 14.921 | 42.226 | 82.987 | 1.00 | 10.05 |
| ATOM | 3646 | O | LEU | A2176 | | 14.298 | 42.494 | 84.017 | 1.00 | 10.39 |
| ATOM | 3647 | N | MET | A2177 | | 16.026 | 41.489 | 82.973 | 1.00 | 7.81 |
| ATOM | 3648 | CA | MET | A2177 | | 16.648 | 41.054 | 84.212 | 1.00 | 9.50 |
| ATOM | 3649 | CB | MET | A2177 | | 16.657 | 39.523 | 84.299 | 1.00 | 7.89 |
| ATOM | 3650 | CG | MET | A2177 | | 15.233 | 38.976 | 84.369 | 1.00 | 10.31 |
| ATOM | 3651 | SD | MET | A2177 | | 15.098 | 37.293 | 84.905 | 1.00 | 11.10 |
| ATOM | 3652 | CE | MET | A2177 | | 15.462 | 37.485 | 86.662 | 1.00 | 9.51 |
| ATOM | 3653 | C | MET | A2177 | | 18.038 | 41.653 | 84.336 | 1.00 | 8.16 |
| ATOM | 3654 | O | MET | A2177 | | 18.902 | 41.434 | 83.487 | 1.00 | 9.69 |
| ATOM | 3655 | N | ILE | A2178 | | 18.222 | 42.446 | 85.386 | 1.00 | 8.05 |
| ATOM | 3656 | CA | ILE | A2178 | | 19.478 | 43.141 | 85.622 | 1.00 | 7.78 |
| ATOM | 3657 | CB | ILE | A2178 | | 19.241 | 44.665 | 85.841 | 1.00 | 8.85 |
| ATOM | 3658 | CG1 | ILE | A2178 | | 18.519 | 45.290 | 84.632 | 1.00 | 6.23 |
| ATOM | 3659 | CD1 | ILE | A2178 | | 18.240 | 46.806 | 84.753 | 1.00 | 8.86 |
| ATOM | 3660 | CG2 | ILE | A2178 | | 20.573 | 45.359 | 86.187 | 1.00 | 7.54 |
| ATOM | 3661 | C | ILE | A2178 | | 20.139 | 42.549 | 86.850 | 1.00 | 9.97 |
| ATOM | 3662 | O | ILE | A2178 | | 19.581 | 42.605 | 87.954 | 1.00 | 10.00 |
| ATOM | 3663 | N | PHE | A2179 | | 21.332 | 41.992 | 86.660 | 1.00 | 8.90 |
| ATOM | 3664 | CA | PHE | A2179 | | 22.092 | 41.447 | 87.771 | 1.00 | 8.71 |
| ATOM | 3665 | CB | PHE | A2179 | | 22.746 | 40.118 | 87.374 | 1.00 | 8.49 |
| ATOM | 3666 | CG | PHE | A2179 | | 21.745 | 39.067 | 87.019 | 1.00 | 8.88 |
| ATOM | 3667 | CD1 | PHE | A2179 | | 21.160 | 39.047 | 85.757 | 1.00 | 8.26 |
| ATOM | 3668 | CE1 | PHE | A2179 | | 20.199 | 38.095 | 85.431 | 1.00 | 9.33 |
| ATOM | 3669 | CZ | PHE | A2179 | | 19.812 | 37.148 | 86.376 | 1.00 | 10.10 |
| ATOM | 3670 | CE2 | PHE | A2179 | | 20.379 | 37.165 | 87.644 | 1.00 | 11.63 |
| ATOM | 3671 | CD2 | PHE | A2179 | | 21.336 | 38.131 | 87.964 | 1.00 | 10.70 |
| ATOM | 3672 | C | PHE | A2179 | | 23.055 | 42.515 | 88.234 | 1.00 | 8.79 |
| ATOM | 3673 | O | PHE | A2179 | | 24.230 | 42.548 | 87.853 | 1.00 | 9.91 |
| ATOM | 3674 | N | ALA | A2180 | | 22.512 | 43.417 | 89.043 | 1.00 | 8.03 |
| ATOM | 3675 | CA | ALA | A2180 | | 23.189 | 44.655 | 89.388 | 1.00 | 9.29 |
| ATOM | 3676 | CB | ALA | A2180 | | 22.234 | 45.606 | 90.074 | 1.00 | 7.55 |

FIGURE 3BT

|      |      | A    | B    | C    | D | E     | F      | G      | H      | I    | J     |
|------|------|------|------|------|---|-------|--------|--------|--------|------|-------|
| ATOM | 3677 | C    | ALA  | A2180 |   |       | 24.422 | 44.416 | 90.246 | 1.00 | 9.74  |
| ATOM | 3678 | O    | ALA  | A2180 |   |       | 24.371 | 43.731 | 91.267 | 1.00 | 10.16 |
| ATOM | 3679 | N    | ASN  | A2181 |   |       | 25.537 | 44.979 | 89.804 | 1.00 | 9.77  |
| ATOM | 3680 | CA   | ASN  | A2181 |   |       | 26.797 | 44.842 | 90.509 | 1.00 | 8.94  |
| ATOM | 3681 | CB   | ASN  | A2181 |   |       | 27.452 | 43.492 | 90.209 | 1.00 | 9.88  |
| ATOM | 3682 | CG   | ASN  | A2181 |   |       | 28.603 | 43.195 | 91.135 | 1.00 | 10.38 |
| ATOM | 3683 | OD1  | ASN  | A2181 |   |       | 28.837 | 43.931 | 92.095 | 1.00 | 12.46 |
| ATOM | 3684 | ND2  | ASN  | A2181 |   |       | 29.332 | 42.113 | 90.861 | 1.00 | 8.47  |
| ATOM | 3685 | C    | ASN  | A2181 |   |       | 27.719 | 45.985 | 90.125 | 1.00 | 10.08 |
| ATOM | 3686 | O    | ASN  | A2181 |   |       | 28.758 | 45.775 | 89.500 | 1.00 | 8.61  |
| ATOM | 3687 | N    | TRP  | A2182 |   |       | 27.325 | 47.197 | 90.500 | 1.00 | 8.28  |
| ATOM | 3688 | CA   | TRP  | A2182 |   |       | 28.093 | 48.383 | 90.137 | 1.00 | 10.09 |
| ATOM | 3689 | CB   | TRP  | A2182 |   |       | 27.280 | 49.282 | 89.212 | 1.00 | 7.96  |
| ATOM | 3690 | CG   | TRP  | A2182 |   |       | 27.100 | 48.744 | 87.819 | 1.00 | 9.73  |
| ATOM | 3691 | CD1  | TRP  | A2182 |   |       | 28.029 | 48.736 | 86.803 | 1.00 | 7.53  |
| ATOM | 3692 | NE1  | TRP  | A2182 |   |       | 27.484 | 48.176 | 85.671 | 1.00 | 8.06  |
| ATOM | 3693 | CE2  | TRP  | A2182 |   |       | 26.185 | 47.817 | 85.934 | 1.00 | 9.51  |
| ATOM | 3694 | CD2  | TRP  | A2182 |   |       | 25.914 | 48.159 | 87.281 | 1.00 | 7.38  |
| ATOM | 3695 | CE3  | TRP  | A2182 |   |       | 24.637 | 47.890 | 87.801 | 1.00 | 9.16  |
| ATOM | 3696 | CZ3  | TRP  | A2182 |   |       | 23.690 | 47.291 | 86.977 | 1.00 | 8.91  |
| ATOM | 3697 | CH2  | TRP  | A2182 |   |       | 23.998 | 46.952 | 85.642 | 1.00 | 9.16  |
| ATOM | 3698 | CZ2  | TRP  | A2182 |   |       | 25.231 | 47.208 | 85.104 | 1.00 | 9.12  |
| ATOM | 3699 | C    | TRP  | A2182 |   |       | 28.538 | 49.188 | 91.345 | 1.00 | 10.09 |
| ATOM | 3700 | O    | TRP  | A2182 |   |       | 27.733 | 49.526 | 92.211 | 1.00 | 10.27 |
| ATOM | 3701 | N    | ARG  | A2183 |   |       | 29.827 | 49.506 | 91.377 | 1.00 | 12.13 |
| ATOM | 3702 | CA   | ARG  | A2183 |   |       | 30.395 | 50.384 | 92.398 | 1.00 | 14.84 |
| ATOM | 3703 | CB   | ARG  | A2183 |   |       | 31.890 | 50.112 | 92.550 | 1.00 | 16.66 |
| ATOM | 3704 | CG   | ARG  | A2183 |   |       | 32.207 | 48.751 | 93.154 | 1.00 | 18.73 |
| ATOM | 3705 | CD   | BARG | A2183 |   |       | 33.684 | 48.351 | 93.117 | 0.50 | 20.92 |
| ATOM | 3706 | CD   | AARG | A2183 |   |       | 33.681 | 48.521 | 93.417 | 0.50 | 19.19 |
| ATOM | 3707 | NE   | BARG | A2183 |   |       | 34.589 | 49.446 | 93.472 | 0.50 | 23.17 |
| ATOM | 3708 | NE   | AARG | A2183 |   |       | 33.914 | 47.285 | 94.159 | 0.50 | 20.50 |
| ATOM | 3709 | CZ   | BARG | A2183 |   |       | 35.602 | 49.349 | 94.330 | 0.50 | 24.91 |
| ATOM | 3710 | CZ   | AARG | A2183 |   |       | 34.847 | 46.388 | 93.858 | 0.50 | 20.49 |
| ATOM | 3711 | NH1B | ARG  | A2183 |   |       | 35.856 | 48.205 | 94.956 | 0.50 | 25.89 |
| ATOM | 3712 | NH1A | ARG  | A2183 |   |       | 35.654 | 46.574 | 92.818 | 0.50 | 21.28 |
| ATOM | 3713 | NH2B | ARG  | A2183 |   |       | 36.362 | 50.409 | 94.575 | 0.50 | 25.03 |
| ATOM | 3714 | NH2A | ARG  | A2183 |   |       | 34.975 | 45.298 | 94.600 | 0.50 | 19.77 |
| ATOM | 3715 | C    | ARG  | A2183 |   |       | 30.161 | 51.853 | 92.056 | 1.00 | 14.95 |
| ATOM | 3716 | O    | ARG  | A2183 |   |       | 30.349 | 52.730 | 92.895 | 1.00 | 14.93 |
| ATOM | 3717 | N    | GLY  | A2184 |   |       | 29.753 | 52.115 | 90.816 | 1.00 | 14.45 |
| ATOM | 3718 | CA   | GLY  | A2184 |   |       | 29.473 | 53.466 | 90.367 | 1.00 | 13.56 |
| ATOM | 3719 | C    | GLY  | A2184 |   |       | 29.855 | 53.706 | 88.918 | 1.00 | 14.22 |
| ATOM | 3720 | O    | GLY  | A2184 |   |       | 30.193 | 52.768 | 88.185 | 1.00 | 13.80 |
| ATOM | 3721 | N    | PHE  | A2185 |   |       | 29.770 | 54.969 | 88.504 | 1.00 | 14.23 |
| ATOM | 3722 | CA   | PHE  | A2185 |   |       | 30.297 | 55.409 | 87.219 | 1.00 | 13.56 |
| ATOM | 3723 | CB   | PHE  | A2185 |   |       | 29.506 | 56.606 | 86.693 | 1.00 | 12.41 |
| ATOM | 3724 | CG   | PHE  | A2185 |   |       | 28.127 | 56.268 | 86.236 | 1.00 | 12.15 |
| ATOM | 3725 | CD1  | PHE  | A2185 |   |       | 27.890 | 55.911 | 84.911 | 1.00 | 10.18 |
| ATOM | 3726 | CE1  | PHE  | A2185 |   |       | 26.613 | 55.596 | 84.481 | 1.00 | 10.10 |
| ATOM | 3727 | CZ   | PHE  | A2185 |   |       | 25.548 | 55.641 | 85.372 | 1.00 | 10.01 |
| ATOM | 3728 | CE2  | PHE  | A2185 |   |       | 25.765 | 55.991 | 86.696 | 1.00 | 13.21 |

FIGURE 3BU

|      | A    | B   | C   | D  | E     | F      | G      | H      | I    | J     |
|------|------|-----|-----|----|-------|--------|--------|--------|------|-------|
| ATOM | 3729 | CD2 |     | PHE | A2185 | 27.054 | 56.309 | 87.124 | 1.00 | 13.24 |
| ATOM | 3730 | C   |     | PHE | A2185 | 31.740 | 55.837 | 87.393 | 1.00 | 14.34 |
| ATOM | 3731 | O   |     | PHE | A2185 | 32.128 | 56.307 | 88.467 | 1.00 | 13.69 |
| ATOM | 3732 | N   |     | SER | A2186 | 32.532 | 55.673 | 86.339 | 1.00 | 13.45 |
| ATOM | 3733 | CA  |     | SER | A2186 | 33.890 | 56.201 | 86.322 | 1.00 | 14.84 |
| ATOM | 3734 | CB  |     | SER | A2186 | 34.675 | 55.632 | 85.141 | 1.00 | 14.68 |
| ATOM | 3735 | OG  |     | SER | A2186 | 36.031 | 56.058 | 85.183 | 1.00 | 20.00 |
| ATOM | 3736 | C   |     | SER | A2186 | 33.808 | 57.721 | 86.239 | 1.00 | 14.18 |
| ATOM | 3737 | O   |     | SER | A2186 | 33.229 | 58.274 | 85.292 | 1.00 | 14.67 |
| ATOM | 3738 | N   |     | GLY | A2187 | 34.369 | 58.387 | 87.244 | 1.00 | 13.22 |
| ATOM | 3739 | CA  |     | GLY | A2187 | 34.274 | 59.832 | 87.367 | 1.00 | 11.28 |
| ATOM | 3740 | C   |     | GLY | A2187 | 35.578 | 60.581 | 87.171 | 1.00 | 12.11 |
| ATOM | 3741 | O   |     | GLY | A2187 | 35.647 | 61.779 | 87.448 | 1.00 | 11.76 |
| ATOM | 3742 | N   |     | GLY | A2188 | 36.609 | 59.881 | 86.701 | 1.00 | 11.55 |
| ATOM | 3743 | CA  |     | GLY | A2188 | 37.880 | 60.507 | 86.371 | 1.00 | 12.38 |
| ATOM | 3744 | C   |     | GLY | A2188 | 37.778 | 61.490 | 85.216 | 1.00 | 12.83 |
| ATOM | 3745 | O   |     | GLY | A2188 | 36.783 | 61.489 | 84.475 | 1.00 | 12.25 |
| ATOM | 3746 | N   |     | MET | A2189 | 38.810 | 62.320 | 85.062 | 1.00 | 10.85 |
| ATOM | 3747 | CA  |     | MET | A2189 | 38.846 | 63.368 | 84.035 | 1.00 | 11.05 |
| ATOM | 3748 | CB  |     | MET | A2189 | 40.217 | 64.076 | 84.017 | 1.00 | 10.06 |
| ATOM | 3749 | CG  | B   | MET | A2189 | 40.587 | 64.695 | 82.683 | 0.35 | 11.84 |
| ATOM | 3750 | CG  | A   | MET | A2189 | 40.430 | 65.077 | 82.863 | 0.65 | 9.83  |
| ATOM | 3751 | SD  | B   | MET | A2189 | 41.463 | 66.236 | 82.836 | 0.35 | 13.20 |
| ATOM | 3752 | SD  | A   | MET | A2189 | 41.016 | 64.340 | 81.292 | 0.65 | 9.78  |
| ATOM | 3753 | CE  | B   | MET | A2189 | 41.589 | 66.686 | 81.120 | 0.35 | 13.22 |
| ATOM | 3754 | CE  | A   | MET | A2189 | 40.999 | 65.719 | 80.267 | 0.65 | 11.30 |
| ATOM | 3755 | C   |     | MET | A2189 | 38.514 | 62.837 | 82.644 | 1.00 | 11.47 |
| ATOM | 3756 | O   |     | MET | A2189 | 37.667 | 63.403 | 81.948 | 1.00 | 12.90 |
| ATOM | 3757 | N   |     | LYS | A2190 | 39.196 | 61.770 | 82.240 | 1.00 | 11.35 |
| ATOM | 3758 | CA  |     | LYS | A2190 | 39.049 | 61.240 | 80.891 | 1.00 | 12.35 |
| ATOM | 3759 | CB  |     | LYS | A2190 | 40.046 | 60.107 | 80.625 | 1.00 | 14.04 |
| ATOM | 3760 | CG  |     | LYS | A2190 | 39.704 | 59.284 | 79.384 | 1.00 | 16.52 |
| ATOM | 3761 | CD  |     | LYS | A2190 | 40.923 | 58.619 | 78.779 | 1.00 | 18.84 |
| ATOM | 3762 | CE  |     | LYS | A2190 | 40.546 | 57.883 | 77.500 | 1.00 | 21.50 |
| ATOM | 3763 | NZ  |     | LYS | A2190 | 40.306 | 58.833 | 76.379 | 1.00 | 22.72 |
| ATOM | 3764 | C   |     | LYS | A2190 | 37.616 | 60.777 | 80.623 | 1.00 | 11.18 |
| ATOM | 3765 | O   |     | LYS | A2190 | 37.045 | 61.096 | 79.581 | 1.00 | 9.97  |
| ATOM | 3766 | N   |     | ASP | A2191 | 37.039 | 60.035 | 81.564 | 1.00 | 10.25 |
| ATOM | 3767 | CA  |     | ASP | A2191 | 35.695 | 59.502 | 81.367 | 1.00 | 12.56 |
| ATOM | 3768 | CB  |     | ASP | A2191 | 35.416 | 58.334 | 82.308 | 1.00 | 13.09 |
| ATOM | 3769 | CG  |     | ASP | A2191 | 36.323 | 57.145 | 82.029 | 1.00 | 16.03 |
| ATOM | 3770 | OD1 |     | ASP | A2191 | 36.565 | 56.830 | 80.843 | 1.00 | 15.79 |
| ATOM | 3771 | OD2 |     | ASP | A2191 | 36.854 | 56.478 | 82.932 | 1.00 | 17.50 |
| ATOM | 3772 | C   |     | ASP | A2191 | 34.632 | 60.585 | 81.470 | 1.00 | 11.19 |
| ATOM | 3773 | O   |     | ASP | A2191 | 33.595 | 60.478 | 80.836 | 1.00 | 11.17 |
| ATOM | 3774 | N   |     | MET | A2192 | 34.913 | 61.634 | 82.243 | 1.00 | 10.21 |
| ATOM | 3775 | CA  |     | MET | A2192 | 34.049 | 62.810 | 82.290 | 1.00 | 10.01 |
| ATOM | 3776 | CB  |     | MET | A2192 | 34.374 | 63.683 | 83.504 | 1.00 | 9.96  |
| ATOM | 3777 | CG  |     | MET | A2192 | 33.955 | 63.055 | 84.837 | 1.00 | 10.68 |
| ATOM | 3778 | SD  |     | MET | A2192 | 32.163 | 62.907 | 85.021 | 1.00 | 12.92 |
| ATOM | 3779 | CE  |     | MET | A2192 | 31.820 | 64.346 | 85.980 | 1.00 | 15.10 |
| ATOM | 3780 | C   |     | MET | A2192 | 34.127 | 63.616 | 80.994 | 1.00 | 10.07 |

FIGURE 3BV

|      | A    | B    | C   | D   | E     | F      | G      | H      | I    | J     |
|------|------|------|-----|-----|-------|--------|--------|--------|------|-------|
| ATOM | 3781 | O    |     | MET | A2192 | 33.096 | 64.018 | 80.446 | 1.00 | 12.68 |
| ATOM | 3782 | N    |     | TYR | A2193 | 35.346 | 63.840 | 80.508 | 1.00 | 10.83 |
| ATOM | 3783 | CA   |     | TYR | A2193 | 35.571 | 64.452 | 79.200 | 1.00 | 11.32 |
| ATOM | 3784 | CB   |     | TYR | A2193 | 37.071 | 64.544 | 78.896 | 1.00 | 14.92 |
| ATOM | 3785 | CG   |     | TYR | A2193 | 37.399 | 65.173 | 77.559 | 1.00 | 17.05 |
| ATOM | 3786 | CD1  |     | TYR | A2193 | 37.461 | 66.552 | 77.420 | 1.00 | 19.59 |
| ATOM | 3787 | CE1  |     | TYR | A2193 | 37.759 | 67.144 | 76.191 | 1.00 | 21.82 |
| ATOM | 3788 | CZ   |     | TYR | A2193 | 38.012 | 66.350 | 75.093 | 1.00 | 22.64 |
| ATOM | 3789 | OH   |     | TYR | A2193 | 38.308 | 66.953 | 73.887 | 1.00 | 26.14 |
| ATOM | 3790 | CE2  |     | TYR | A2193 | 37.966 | 64.969 | 75.203 | 1.00 | 21.87 |
| ATOM | 3791 | CD2  |     | TYR | A2193 | 37.653 | 64.387 | 76.437 | 1.00 | 19.75 |
| ATOM | 3792 | C    |     | TYR | A2193 | 34.856 | 63.652 | 78.112 | 1.00 | 11.40 |
| ATOM | 3793 | O    |     | TYR | A2193 | 34.217 | 64.235 | 77.237 | 1.00 | 11.17 |
| ATOM | 3794 | N    |     | ASP | A2194 | 34.951 | 62.322 | 78.194 | 1.00 | 11.18 |
| ATOM | 3795 | CA   |     | ASP | A2194 | 34.279 | 61.407 | 77.263 | 1.00 | 12.13 |
| ATOM | 3796 | CB   |     | ASP | A2194 | 34.993 | 60.043 | 77.214 | 1.00 | 14.05 |
| ATOM | 3797 | CG   |     | ASP | A2194 | 36.414 | 60.133 | 76.647 | 1.00 | 18.01 |
| ATOM | 3798 | OD1  |     | ASP | A2194 | 36.779 | 61.176 | 76.057 | 1.00 | 18.34 |
| ATOM | 3799 | OD2  |     | ASP | A2194 | 37.245 | 59.203 | 76.753 | 1.00 | 18.95 |
| ATOM | 3800 | C    |     | ASP | A2194 | 32.785 | 61.226 | 77.567 | 1.00 | 11.96 |
| ATOM | 3801 | O    |     | ASP | A2194 | 32.145 | 60.292 | 77.068 | 1.00 | 12.90 |
| ATOM | 3802 | N    |     | GLN | A2195 | 32.238 | 62.119 | 78.394 | 1.00 | 10.22 |
| ATOM | 3803 | CA   |     | GLN | A2195 | 30.792 | 62.320 | 78.483 | 1.00 | 9.56  |
| ATOM | 3804 | CB   |     | GLN | A2195 | 30.207 | 62.590 | 77.083 | 1.00 | 10.88 |
| ATOM | 3805 | CG   |     | GLN | A2195 | 30.888 | 63.739 | 76.327 | 1.00 | 9.28  |
| ATOM | 3806 | CD   |     | GLN | A2195 | 30.712 | 63.654 | 74.819 | 1.00 | 12.24 |
| ATOM | 3807 | OE1  |     | GLN | A2195 | 29.598 | 63.498 | 74.331 | 1.00 | 11.21 |
| ATOM | 3808 | NE2  |     | GLN | A2195 | 31.817 | 63.759 | 74.080 | 1.00 | 13.42 |
| ATOM | 3809 | C    |     | GLN | A2195 | 30.047 | 61.173 | 79.170 | 1.00 | 9.68  |
| ATOM | 3810 | O    |     | GLN | A2195 | 28.921 | 60.860 | 78.798 | 1.00 | 9.11  |
| ATOM | 3811 | N    |     | VAL | A2196 | 30.669 | 60.563 | 80.181 | 1.00 | 9.86  |
| ATOM | 3812 | CA   |     | VAL | A2196 | 30.019 | 59.500 | 80.952 | 1.00 | 9.33  |
| ATOM | 3813 | CB   |     | VAL | A2196 | 30.923 | 58.960 | 82.109 | 1.00 | 11.43 |
| ATOM | 3814 | CG1  |     | VAL | A2196 | 31.127 | 60.010 | 83.222 | 1.00 | 7.90  |
| ATOM | 3815 | CG2  |     | VAL | A2196 | 30.366 | 57.635 | 82.676 | 1.00 | 9.70  |
| ATOM | 3816 | C    |     | VAL | A2196 | 28.637 | 59.940 | 81.472 | 1.00 | 10.15 |
| ATOM | 3817 | O    |     | VAL | A2196 | 27.691 | 59.145 | 81.495 | 1.00 | 10.25 |
| ATOM | 3818 | N    |     | LEU | A2197 | 28.530 | 61.213 | 81.855 | 1.00 | 8.45  |
| ATOM | 3819 | CA   |     | LEU | A2197 | 27.285 | 61.781 | 82.369 | 1.00 | 10.49 |
| ATOM | 3820 | CB   |     | LEU | A2197 | 27.493 | 63.248 | 82.737 | 1.00 | 13.41 |
| ATOM | 3821 | CG   |     | LEU | A2197 | 26.788 | 63.832 | 83.954 | 1.00 | 18.64 |
| ATOM | 3822 | CD1  |     | LEU | A2197 | 26.995 | 62.983 | 85.216 | 1.00 | 18.18 |
| ATOM | 3823 | CD2  |     | LEU | A2197 | 27.277 | 65.257 | 84.175 | 1.00 | 20.03 |
| ATOM | 3824 | C    |     | LEU | A2197 | 26.107 | 61.646 | 81.395 | 1.00 | 9.56  |
| ATOM | 3825 | O    |     | LEU | A2197 | 24.987 | 61.356 | 81.807 | 1.00 | 11.66 |
| ATOM | 3826 | N    |     | LYS | A2198 | 26.366 | 61.857 | 80.109 | 1.00 | 8.75  |
| ATOM | 3827 | CA   |     | LYS | A2198 | 25.323 | 61.763 | 79.082 | 1.00 | 6.70  |
| ATOM | 3828 | CB   |     | LYS | A2198 | 25.873 | 62.176 | 77.714 | 1.00 | 6.19  |
| ATOM | 3829 | CG   |     | LYS | A2198 | 26.540 | 63.546 | 77.679 | 1.00 | 6.64  |
| ATOM | 3830 | CD   |     | LYS | A2198 | 26.730 | 63.988 | 76.228 | 1.00 | 8.38  |
| ATOM | 3831 | CE   |     | LYS | A2198 | 27.410 | 65.343 | 76.133 | 1.00 | 7.38  |
| ATOM | 3832 | NZ   |     | LYS | A2198 | 27.757 | 65.636 | 74.709 | 1.00 | 5.54  |

FIGURE 3BW

|  | A | B | C | D | E | F | G | H | I | J |
|---|---|---|---|---|---|---|---|---|---|---|
| ATOM | 3833 | C | | LYS | A2198 | 24.765 | 60.355 | 78.973 | 1.00 | 7.72 |
| ATOM | 3834 | O | | LYS | A2198 | 23.555 | 60.167 | 78.836 | 1.00 | 8.58 |
| ATOM | 3835 | N | | PHE | A2199 | 25.662 | 59.374 | 79.012 | 1.00 | 8.73 |
| ATOM | 3836 | CA | | PHE | A2199 | 25.305 | 57.971 | 78.803 | 1.00 | 9.95 |
| ATOM | 3837 | CB | | PHE | A2199 | 26.514 | 57.183 | 78.278 | 1.00 | 8.56 |
| ATOM | 3838 | CG | | PHE | A2199 | 27.031 | 57.725 | 76.979 | 1.00 | 10.68 |
| ATOM | 3839 | CD1 | | PHE | A2199 | 28.167 | 58.522 | 76.946 | 1.00 | 10.43 |
| ATOM | 3840 | CE1 | | PHE | A2199 | 28.624 | 59.059 | 75.752 | 1.00 | 11.89 |
| ATOM | 3841 | CZ | | PHE | A2199 | 27.927 | 58.818 | 74.571 | 1.00 | 13.48 |
| ATOM | 3842 | CE2 | | PHE | A2199 | 26.777 | 58.034 | 74.593 | 1.00 | 12.41 |
| ATOM | 3843 | CD2 | | PHE | A2199 | 26.328 | 57.506 | 75.798 | 1.00 | 11.54 |
| ATOM | 3844 | C | | PHE | A2199 | 24.709 | 57.361 | 80.045 | 1.00 | 7.85 |
| ATOM | 3845 | O | | PHE | A2199 | 23.838 | 56.512 | 79.954 | 1.00 | 9.71 |
| ATOM | 3846 | N | | GLY | A2200 | 25.156 | 57.822 | 81.209 | 1.00 | 11.01 |
| ATOM | 3847 | CA | | GLY | A2200 | 24.489 | 57.485 | 82.456 | 1.00 | 9.83 |
| ATOM | 3848 | C | | GLY | A2200 | 23.045 | 57.958 | 82.443 | 1.00 | 10.29 |
| ATOM | 3849 | O | | GLY | A2200 | 22.141 | 57.232 | 82.864 | 1.00 | 9.09 |
| ATOM | 3850 | N | | ALA | A2201 | 22.822 | 59.178 | 81.952 | 1.00 | 8.23 |
| ATOM | 3851 | CA | | ALA | A2201 | 21.466 | 59.720 | 81.863 | 1.00 | 7.13 |
| ATOM | 3852 | CB | | ALA | A2201 | 21.491 | 61.197 | 81.443 | 1.00 | 4.86 |
| ATOM | 3853 | C | | ALA | A2201 | 20.556 | 58.888 | 80.945 | 1.00 | 8.70 |
| ATOM | 3854 | O | | ALA | A2201 | 19.370 | 58.743 | 81.225 | 1.00 | 9.25 |
| ATOM | 3855 | N | | TYR | A2202 | 21.113 | 58.321 | 79.870 | 1.00 | 9.44 |
| ATOM | 3856 | CA | | TYR | A2202 | 20.347 | 57.432 | 78.973 | 1.00 | 10.03 |
| ATOM | 3857 | CB | | TYR | A2202 | 21.170 | 57.059 | 77.731 | 1.00 | 10.05 |
| ATOM | 3858 | CG | | TYR | A2202 | 21.509 | 58.235 | 76.835 | 1.00 | 11.33 |
| ATOM | 3859 | CD1 | | TYR | A2202 | 20.647 | 59.337 | 76.724 | 1.00 | 11.34 |
| ATOM | 3860 | CE1 | | TYR | A2202 | 20.960 | 60.422 | 75.888 | 1.00 | 10.30 |
| ATOM | 3861 | CZ | | TYR | A2202 | 22.140 | 60.400 | 75.158 | 1.00 | 11.02 |
| ATOM | 3862 | OH | | TYR | A2202 | 22.459 | 61.457 | 74.331 | 1.00 | 12.00 |
| ATOM | 3863 | CE2 | | TYR | A2202 | 23.005 | 59.321 | 75.251 | 1.00 | 11.21 |
| ATOM | 3864 | CD2 | | TYR | A2202 | 22.681 | 58.239 | 76.083 | 1.00 | 9.95 |
| ATOM | 3865 | C | | TYR | A2202 | 19.850 | 56.150 | 79.638 | 1.00 | 8.13 |
| ATOM | 3866 | O | | TYR | A2202 | 18.854 | 55.563 | 79.207 | 1.00 | 9.28 |
| ATOM | 3867 | N | | ILE | A2203 | 20.546 | 55.704 | 80.678 | 1.00 | 8.78 |
| ATOM | 3868 | CA | | ILE | A2203 | 20.093 | 54.534 | 81.424 | 1.00 | 7.54 |
| ATOM | 3869 | CB | | ILE | A2203 | 21.157 | 54.056 | 82.421 | 1.00 | 6.35 |
| ATOM | 3870 | CG1 | | ILE | A2203 | 22.384 | 53.534 | 81.665 | 1.00 | 7.70 |
| ATOM | 3871 | CD1 | | ILE | A2203 | 23.637 | 53.378 | 82.548 | 1.00 | 8.02 |
| ATOM | 3872 | CG2 | | ILE | A2203 | 20.578 | 52.967 | 83.337 | 1.00 | 6.85 |
| ATOM | 3873 | C | | ILE | A2203 | 18.784 | 54.879 | 82.131 | 1.00 | 7.99 |
| ATOM | 3874 | O | | ILE | A2203 | 17.841 | 54.096 | 82.092 | 1.00 | 7.50 |
| ATOM | 3875 | N | | VAL | A2204 | 18.731 | 56.059 | 82.749 | 1.00 | 7.42 |
| ATOM | 3876 | CA | | VAL | A2204 | 17.490 | 56.559 | 83.349 | 1.00 | 8.75 |
| ATOM | 3877 | CB | | VAL | A2204 | 17.666 | 57.963 | 84.008 | 1.00 | 8.14 |
| ATOM | 3878 | CG1 | | VAL | A2204 | 16.361 | 58.432 | 84.665 | 1.00 | 8.35 |
| ATOM | 3879 | CG2 | | VAL | A2204 | 18.783 | 57.944 | 85.039 | 1.00 | 6.37 |
| ATOM | 3880 | C | | VAL | A2204 | 16.367 | 56.615 | 82.306 | 1.00 | 9.35 |
| ATOM | 3881 | O | | VAL | A2204 | 15.286 | 56.062 | 82.537 | 1.00 | 8.63 |
| ATOM | 3882 | N | | ASP | A2205 | 16.625 | 57.288 | 81.176 | 1.00 | 8.20 |
| ATOM | 3883 | CA | | ASP | A2205 | 15.650 | 57.421 | 80.085 | 1.00 | 10.16 |
| ATOM | 3884 | CB | | ASP | A2205 | 16.281 | 58.084 | 78.846 | 1.00 | 10.55 |

FIGURE 3BX

| | A | B | C | D | E | F | G | H | I | J |
|---|---|---|---|---|---|---|---|---|---|---|
| ATOM | 3885 | CG | ASP | A2205 | | 16.661 | 59.540 | 79.066 | 1.00 | 12.00 |
| ATOM | 3886 | OD1 | ASP | A2205 | | 17.531 | 60.032 | 78.325 | 1.00 | 10.82 |
| ATOM | 3887 | OD2 | ASP | A2205 | | 16.154 | 60.277 | 79.935 | 1.00 | 14.25 |
| ATOM | 3888 | C | ASP | A2205 | | 15.116 | 56.057 | 79.662 | 1.00 | 9.61 |
| ATOM | 3889 | O | ASP | A2205 | | 13.912 | 55.847 | 79.579 | 1.00 | 9.99 |
| ATOM | 3890 | N | GLY | A2206 | | 16.037 | 55.136 | 79.391 | 1.00 | 10.64 |
| ATOM | 3891 | CA | GLY | A2206 | | 15.691 | 53.810 | 78.914 | 1.00 | 9.46 |
| ATOM | 3892 | C | GLY | A2206 | | 14.839 | 53.037 | 79.896 | 1.00 | 8.75 |
| ATOM | 3893 | O | GLY | A2206 | | 13.860 | 52.419 | 79.499 | 1.00 | 8.33 |
| ATOM | 3894 | N | LEU | A2207 | | 15.202 | 53.074 | 81.176 | 1.00 | 8.71 |
| ATOM | 3895 | CA | LEU | A2207 | | 14.417 | 52.374 | 82.198 | 1.00 | 9.30 |
| ATOM | 3896 | CB | LEU | A2207 | | 15.218 | 52.201 | 83.488 | 1.00 | 7.97 |
| ATOM | 3897 | CG | LEU | A2207 | | 16.429 | 51.262 | 83.359 | 1.00 | 8.21 |
| ATOM | 3898 | CD1 | LEU | A2207 | | 17.232 | 51.232 | 84.645 | 1.00 | 9.20 |
| ATOM | 3899 | CD2 | LEU | A2207 | | 16.010 | 49.845 | 82.965 | 1.00 | 9.08 |
| ATOM | 3900 | C | LEU | A2207 | | 13.071 | 53.045 | 82.467 | 1.00 | 8.76 |
| ATOM | 3901 | O | LEU | A2207 | | 12.067 | 52.361 | 82.683 | 1.00 | 9.94 |
| ATOM | 3902 | N | ARG | A2208 | | 13.049 | 54.379 | 82.438 | 1.00 | 7.39 |
| ATOM | 3903 | CA | ARG | A2208 | | 11.807 | 55.132 | 82.613 | 1.00 | 7.75 |
| ATOM | 3904 | CB | ARG | A2208 | | 12.075 | 56.641 | 82.585 | 1.00 | 9.37 |
| ATOM | 3905 | CG | ARG | A2208 | | 10.925 | 57.469 | 83.164 | 1.00 | 10.46 |
| ATOM | 3906 | CD | ARG | A2208 | | 11.028 | 58.973 | 82.925 | 1.00 | 11.56 |
| ATOM | 3907 | NE | ARG | A2208 | | 11.233 | 59.302 | 81.513 | 1.00 | 12.18 |
| ATOM | 3908 | CZ | ARG | A2208 | | 10.277 | 59.267 | 80.583 | 1.00 | 15.12 |
| ATOM | 3909 | NH1 | ARG | A2208 | | 9.030 | 58.923 | 80.900 | 1.00 | 15.55 |
| ATOM | 3910 | NH2 | ARG | A2208 | | 10.572 | 59.576 | 79.330 | 1.00 | 14.54 |
| ATOM | 3911 | C | ARG | A2208 | | 10.792 | 54.763 | 81.533 | 1.00 | 8.85 |
| ATOM | 3912 | O | ARG | A2208 | | 9.598 | 54.629 | 81.809 | 1.00 | 9.32 |
| ATOM | 3913 | N | GLN | A2209 | | 11.284 | 54.575 | 80.309 | 1.00 | 8.82 |
| ATOM | 3914 | CA | GLN | A2209 | | 10.427 | 54.279 | 79.161 | 1.00 | 10.90 |
| ATOM | 3915 | CB | GLN | A2209 | | 11.120 | 54.709 | 77.861 | 1.00 | 14.07 |
| ATOM | 3916 | CG | GLN | A2209 | | 11.223 | 56.215 | 77.669 | 1.00 | 19.02 |
| ATOM | 3917 | CD | GLN | A2209 | | 12.364 | 56.607 | 76.730 | 1.00 | 21.71 |
| ATOM | 3918 | OE1 | GLN | A2209 | | 12.873 | 55.780 | 75.977 | 1.00 | 25.84 |
| ATOM | 3919 | NE2 | GLN | A2209 | | 12.761 | 57.864 | 76.778 | 1.00 | 24.13 |
| ATOM | 3920 | C | GLN | A2209 | | 10.045 | 52.809 | 79.043 | 1.00 | 9.70 |
| ATOM | 3921 | O | GLN | A2209 | | 9.255 | 52.442 | 78.166 | 1.00 | 7.63 |
| ATOM | 3922 | N | TYR | A2210 | | 10.626 | 51.964 | 79.890 | 1.00 | 9.42 |
| ATOM | 3923 | CA | TYR | A2210 | | 10.393 | 50.517 | 79.808 | 1.00 | 9.25 |
| ATOM | 3924 | CB | TYR | A2210 | | 11.300 | 49.754 | 80.779 | 1.00 | 7.98 |
| ATOM | 3925 | CG | TYR | A2210 | | 11.874 | 48.508 | 80.161 | 1.00 | 9.33 |
| ATOM | 3926 | CD1 | TYR | A2210 | | 12.962 | 48.583 | 79.292 | 1.00 | 9.41 |
| ATOM | 3927 | CE1 | TYR | A2210 | | 13.488 | 47.442 | 78.702 | 1.00 | 8.85 |
| ATOM | 3928 | CZ | TYR | A2210 | | 12.914 | 46.209 | 78.974 | 1.00 | 9.37 |
| ATOM | 3929 | OH | TYR | A2210 | | 13.430 | 45.079 | 78.385 | 1.00 | 8.40 |
| ATOM | 3930 | CE2 | TYR | A2210 | | 11.830 | 46.108 | 79.836 | 1.00 | 9.37 |
| ATOM | 3931 | CD2 | TYR | A2210 | | 11.309 | 47.256 | 80.413 | 1.00 | 8.63 |
| ATOM | 3932 | C | TYR | A2210 | | 8.940 | 50.151 | 80.063 | 1.00 | 10.02 |
| ATOM | 3933 | O | TYR | A2210 | | 8.284 | 50.761 | 80.915 | 1.00 | 8.09 |
| ATOM | 3934 | N | LYS | A2211 | | 8.444 | 49.147 | 79.337 | 1.00 | 10.14 |
| ATOM | 3935 | CA | LYS | A2211 | | 7.028 | 48.775 | 79.424 | 1.00 | 11.42 |
| ATOM | 3936 | CB | LYS | A2211 | | 6.309 | 49.051 | 78.094 | 1.00 | 12.38 |

FIGURE 3BY

|  | A | B | C | D E | F | G | H | I | J |
|---|---|---|---|---|---|---|---|---|---|
| ATOM | 3937 | CG | BLYS | A2211 | 6.260 | 50.533 | 77.707 | 0.50 | 13.69 |
| ATOM | 3938 | CG | ALYS | A2211 | 6.260 | 50.523 | 77.676 | 0.50 | 14.96 |
| ATOM | 3939 | CD | BLYS | A2211 | 5.331 | 51.335 | 78.621 | 0.50 | 14.72 |
| ATOM | 3940 | CD | ALYS | A2211 | 5.367 | 50.725 | 76.453 | 0.50 | 16.70 |
| ATOM | 3941 | CE | BLYS | A2211 | 5.236 | 52.794 | 78.191 | 0.50 | 16.16 |
| ATOM | 3942 | CE | ALYS | A2211 | 6.182 | 50.734 | 75.159 | 0.50 | 19.88 |
| ATOM | 3943 | NZ | BLYS | A2211 | 4.940 | 52.941 | 76.735 | 0.50 | 16.22 |
| ATOM | 3944 | NZ | ALYS | A2211 | 5.818 | 49.604 | 74.253 | 0.50 | 20.42 |
| ATOM | 3945 | C | LYS | A2211 | 6.761 | 47.332 | 79.891 | 1.00 | 12.07 |
| ATOM | 3946 | O | LYS | A2211 | 5.606 | 46.910 | 79.982 | 1.00 | 11.55 |
| ATOM | 3947 | N | GLN | A2212 | 7.826 | 46.582 | 80.170 | 1.00 | 10.34 |
| ATOM | 3948 | CA | GLN | A2212 | 7.705 | 45.203 | 80.637 | 1.00 | 9.02 |
| ATOM | 3949 | CB | GLN | A2212 | 8.422 | 44.248 | 79.675 | 1.00 | 10.28 |
| ATOM | 3950 | CG | GLN | A2212 | 7.839 | 44.196 | 78.272 | 1.00 | 9.45 |
| ATOM | 3951 | CD | GLN | A2212 | 8.198 | 45.420 | 77.448 | 1.00 | 11.02 |
| ATOM | 3952 | OE1 | GLN | A2212 | 7.314 | 46.087 | 76.915 | 1.00 | 10.41 |
| ATOM | 3953 | NE2 | GLN | A2212 | 9.493 | 45.721 | 77.346 | 1.00 | 11.57 |
| ATOM | 3954 | C | GLN | A2212 | 8.319 | 45.109 | 82.028 | 1.00 | 8.68 |
| ATOM | 3955 | O | GLN | A2212 | 9.043 | 46.024 | 82.430 | 1.00 | 8.46 |
| ATOM | 3956 | N | PRO | A2213 | 8.049 | 44.026 | 82.770 | 1.00 | 8.50 |
| ATOM | 3957 | CA | PRO | A2213 | 8.658 | 43.851 | 84.093 | 1.00 | 9.05 |
| ATOM | 3958 | CB | PRO | A2213 | 8.211 | 42.442 | 84.502 | 1.00 | 9.25 |
| ATOM | 3959 | CG | PRO | A2213 | 6.903 | 42.265 | 83.788 | 1.00 | 7.43 |
| ATOM | 3960 | CD | PRO | A2213 | 7.151 | 42.900 | 82.441 | 1.00 | 8.88 |
| ATOM | 3961 | C | PRO | A2213 | 10.174 | 43.930 | 84.022 | 1.00 | 8.96 |
| ATOM | 3962 | O | PRO | A2213 | 10.787 | 43.437 | 83.073 | 1.00 | 8.39 |
| ATOM | 3963 | N | ILE | A2214 | 10.758 | 44.579 | 85.019 | 1.00 | 7.54 |
| ATOM | 3964 | CA | ILE | A2214 | 12.190 | 44.662 | 85.164 | 1.00 | 8.37 |
| ATOM | 3965 | CB | ILE | A2214 | 12.670 | 46.127 | 85.064 | 1.00 | 9.50 |
| ATOM | 3966 | CG1 | ILE | A2214 | 12.410 | 46.701 | 83.670 | 1.00 | 10.27 |
| ATOM | 3967 | CD1 | ILE | A2214 | 12.629 | 48.223 | 83.583 | 1.00 | 11.99 |
| ATOM | 3968 | CG2 | ILE | A2214 | 14.157 | 46.237 | 85.447 | 1.00 | 8.96 |
| ATOM | 3969 | C | ILE | A2214 | 12.519 | 44.102 | 86.538 | 1.00 | 10.13 |
| ATOM | 3970 | O | ILE | A2214 | 11.995 | 44.578 | 87.554 | 1.00 | 9.14 |
| ATOM | 3971 | N | LEU | A2215 | 13.372 | 43.081 | 86.567 | 1.00 | 7.73 |
| ATOM | 3972 | CA | LEU | A2215 | 13.788 | 42.476 | 87.824 | 1.00 | 7.16 |
| ATOM | 3973 | CB | LEU | A2215 | 13.536 | 40.959 | 87.822 | 1.00 | 7.05 |
| ATOM | 3974 | CG | LEU | A2215 | 12.061 | 40.568 | 87.660 | 1.00 | 8.10 |
| ATOM | 3975 | CD1 | LEU | A2215 | 11.899 | 39.054 | 87.597 | 1.00 | 6.30 |
| ATOM | 3976 | CD2 | LEU | A2215 | 11.190 | 41.159 | 88.774 | 1.00 | 7.87 |
| ATOM | 3977 | C | LEU | A2215 | 15.251 | 42.783 | 88.030 | 1.00 | 7.27 |
| ATOM | 3978 | O | LEU | A2215 | 16.098 | 42.387 | 87.224 | 1.00 | 8.35 |
| ATOM | 3979 | N | ILE | A2216 | 15.536 | 43.521 | 89.095 | 1.00 | 8.13 |
| ATOM | 3980 | CA | ILE | A2216 | 16.902 | 43.882 | 89.436 | 1.00 | 8.54 |
| ATOM | 3981 | CB | ILE | A2216 | 17.040 | 45.393 | 89.730 | 1.00 | 9.02 |
| ATOM | 3982 | CG1 | ILE | A2216 | 16.510 | 46.200 | 88.545 | 1.00 | 8.83 |
| ATOM | 3983 | CD1 | ILE | A2216 | 16.826 | 47.686 | 88.590 | 1.00 | 10.61 |
| ATOM | 3984 | CG2 | ILE | A2216 | 18.517 | 45.735 | 90.040 | 1.00 | 7.78 |
| ATOM | 3985 | C | ILE | A2216 | 17.309 | 43.070 | 90.644 | 1.00 | 9.36 |
| ATOM | 3986 | O | ILE | A2216 | 16.638 | 43.095 | 91.672 | 1.00 | 7.51 |
| ATOM | 3987 | N | TYR | A2217 | 18.407 | 42.341 | 90.502 | 1.00 | 8.07 |
| ATOM | 3988 | CA | TYR | A2217 | 18.858 | 41.458 | 91.555 | 1.00 | 9.48 |

FIGURE 3BZ

|  | A | B | C | D | E | F | G | H | I | J |
|---|---|---|---|---|---|---|---|---|---|---|
| ATOM | 3989 | CB  | TYR | A2217 | 18.537 | 40.007 | 91.167 | 1.00 | 9.22 |
| ATOM | 3990 | CG  | TYR | A2217 | 19.009 | 38.929 | 92.125 | 1.00 | 10.63 |
| ATOM | 3991 | CD1 | TYR | A2217 | 19.268 | 37.645 | 91.649 | 1.00 | 9.44 |
| ATOM | 3992 | CE1 | TYR | A2217 | 19.688 | 36.643 | 92.489 | 1.00 | 12.50 |
| ATOM | 3993 | CZ  | TYR | A2217 | 19.864 | 36.905 | 93.839 | 1.00 | 11.58 |
| ATOM | 3994 | OH  | TYR | A2217 | 20.291 | 35.885 | 94.648 | 1.00 | 11.60 |
| ATOM | 3995 | CE2 | TYR | A2217 | 19.620 | 38.173 | 94.355 | 1.00 | 9.29 |
| ATOM | 3996 | CD2 | TYR | A2217 | 19.182 | 39.179 | 93.495 | 1.00 | 8.54 |
| ATOM | 3997 | C   | TYR | A2217 | 20.344 | 41.693 | 91.768 | 1.00 | 9.98 |
| ATOM | 3998 | O   | TYR | A2217 | 21.130 | 41.549 | 90.837 | 1.00 | 11.75 |
| ATOM | 3999 | N   | ILE | A2218 | 20.712 | 42.109 | 92.980 | 1.00 | 9.28 |
| ATOM | 4000 | CA  | ILE | A2218 | 22.114 | 42.211 | 93.367 | 1.00 | 8.54 |
| ATOM | 4001 | CB  | ILE | A2218 | 22.329 | 43.273 | 94.481 | 1.00 | 8.36 |
| ATOM | 4002 | CG1 | ILE | A2218 | 21.557 | 44.565 | 94.175 | 1.00 | 8.34 |
| ATOM | 4003 | CD1 | ILE | A2218 | 21.345 | 45.477 | 95.392 | 1.00 | 10.36 |
| ATOM | 4004 | CG2 | ILE | A2218 | 23.821 | 43.583 | 94.645 | 1.00 | 8.41 |
| ATOM | 4005 | C   | ILE | A2218 | 22.520 | 40.832 | 93.869 | 1.00 | 9.80 |
| ATOM | 4006 | O   | ILE | A2218 | 22.076 | 40.418 | 94.932 | 1.00 | 10.66 |
| ATOM | 4007 | N   | PRO | A2219 | 23.339 | 40.113 | 93.099 | 1.00 | 11.15 |
| ATOM | 4008 | CA  | PRO | A2219 | 23.714 | 38.730 | 93.429 | 1.00 | 10.99 |
| ATOM | 4009 | CB  | PRO | A2219 | 24.448 | 38.262 | 92.162 | 1.00 | 12.12 |
| ATOM | 4010 | CG  | PRO | A2219 | 24.074 | 39.242 | 91.112 | 1.00 | 12.83 |
| ATOM | 4011 | CD  | PRO | A2219 | 23.950 | 40.551 | 91.834 | 1.00 | 10.86 |
| ATOM | 4012 | C   | PRO | A2219 | 24.643 | 38.632 | 94.655 | 1.00 | 10.85 |
| ATOM | 4013 | O   | PRO | A2219 | 25.047 | 39.676 | 95.179 | 1.00 | 12.25 |
| ATOM | 4014 | N   | PRO | A2220 | 24.956 | 37.419 | 95.119 | 1.00 | 10.04 |
| ATOM | 4015 | CA  | PRO | A2220 | 25.907 | 37.238 | 96.228 | 1.00 | 10.51 |
| ATOM | 4016 | CB  | PRO | A2220 | 26.164 | 35.722 | 96.244 | 1.00 | 10.79 |
| ATOM | 4017 | CG  | PRO | A2220 | 24.994 | 35.117 | 95.598 | 1.00 | 11.13 |
| ATOM | 4018 | CD  | PRO | A2220 | 24.437 | 36.133 | 94.618 | 1.00 | 9.62 |
| ATOM | 4019 | C   | PRO | A2220 | 27.224 | 37.955 | 95.938 | 1.00 | 11.22 |
| ATOM | 4020 | O   | PRO | A2220 | 27.734 | 37.842 | 94.819 | 1.00 | 9.22 |
| ATOM | 4021 | N   | TYR | A2221 | 27.738 | 38.688 | 96.927 | 1.00 | 11.34 |
| ATOM | 4022 | CA  | TYR | A2221 | 29.032 | 39.382 | 96.853 | 1.00 | 12.88 |
| ATOM | 4023 | CB  | TYR | A2221 | 30.195 | 38.385 | 96.697 | 1.00 | 14.78 |
| ATOM | 4024 | CG  | TYR | A2221 | 30.112 | 37.261 | 97.712 | 1.00 | 17.18 |
| ATOM | 4025 | CD1 | TYR | A2221 | 29.687 | 35.989 | 97.339 | 1.00 | 18.04 |
| ATOM | 4026 | CE1 | TYR | A2221 | 29.588 | 34.959 | 98.274 | 1.00 | 20.10 |
| ATOM | 4027 | CZ  | TYR | A2221 | 29.907 | 35.206 | 99.599 | 1.00 | 21.53 |
| ATOM | 4028 | OH  | TYR | A2221 | 29.810 | 34.195 | 100.529 | 1.00 | 25.74 |
| ATOM | 4029 | CE2 | TYR | A2221 | 30.321 | 36.464 | 99.999 | 1.00 | 21.06 |
| ATOM | 4030 | CD2 | TYR | A2221 | 30.417 | 37.487 | 99.056 | 1.00 | 19.39 |
| ATOM | 4031 | C   | TYR | A2221 | 29.066 | 40.509 | 95.818 | 1.00 | 11.68 |
| ATOM | 4032 | O   | TYR | A2221 | 30.115 | 41.085 | 95.524 | 1.00 | 12.50 |
| ATOM | 4033 | N   | ALA | A2222 | 27.895 | 40.839 | 95.293 | 1.00 | 11.49 |
| ATOM | 4034 | CA  | ALA | A2222 | 27.753 | 42.005 | 94.442 | 1.00 | 10.18 |
| ATOM | 4035 | CB  | ALA | A2222 | 26.731 | 41.740 | 93.357 | 1.00 | 7.16 |
| ATOM | 4036 | C   | ALA | A2222 | 27.349 | 43.212 | 95.277 | 1.00 | 10.41 |
| ATOM | 4037 | O   | ALA | A2222 | 26.979 | 43.087 | 96.445 | 1.00 | 9.27 |
| ATOM | 4038 | N   | GLU | A2223 | 27.404 | 44.387 | 94.663 | 1.00 | 12.11 |
| ATOM | 4039 | CA  | GLU | A2223 | 27.013 | 45.607 | 95.346 | 1.00 | 12.96 |
| ATOM | 4040 | CB  | GLU | A2223 | 28.210 | 46.234 | 96.071 | 1.00 | 14.54 |

FIGURE 3CA

|      | A    | B   | C   | D E    | F      | G      | H       | I    | J     |
|------|------|-----|-----|--------|--------|--------|---------|------|-------|
| ATOM | 4041 | CG  | GLU | A2223  | 29.384 | 46.598 | 95.176  | 1.00 | 18.33 |
| ATOM | 4042 | CD  | GLU | A2223  | 30.629 | 46.928 | 95.976  | 1.00 | 21.01 |
| ATOM | 4043 | OE1 | GLU | A2223  | 31.623 | 46.168 | 95.883  | 1.00 | 22.21 |
| ATOM | 4044 | OE2 | GLU | A2223  | 30.605 | 47.944 | 96.707  | 1.00 | 20.56 |
| ATOM | 4045 | C   | GLU | A2223  | 26.400 | 46.597 | 94.374  | 1.00 | 12.35 |
| ATOM | 4046 | O   | GLU | A2223  | 26.668 | 46.557 | 93.175  | 1.00 | 11.77 |
| ATOM | 4047 | N   | LEU | A2224  | 25.582 | 47.493 | 94.907  | 1.00 | 10.91 |
| ATOM | 4048 | CA  | LEU | A2224  | 25.035 | 48.572 | 94.121  | 1.00 | 10.08 |
| ATOM | 4049 | CB  | LEU | A2224  | 23.566 | 48.308 | 93.810  | 1.00 | 9.70  |
| ATOM | 4050 | CG  | LEU | A2224  | 22.876 | 49.231 | 92.802  | 1.00 | 9.56  |
| ATOM | 4051 | CD1 | LEU | A2224  | 23.632 | 49.285 | 91.469  | 1.00 | 8.16  |
| ATOM | 4052 | CD2 | LEU | A2224  | 21.437 | 48.781 | 92.612  | 1.00 | 10.38 |
| ATOM | 4053 | C   | LEU | A2224  | 25.238 | 49.869 | 94.898  | 1.00 | 11.33 |
| ATOM | 4054 | O   | LEU | A2224  | 24.725 | 50.029 | 96.007  | 1.00 | 9.39  |
| ATOM | 4055 | N   | ARG | A2225  | 26.013 | 50.780 | 94.313  | 1.00 | 10.70 |
| ATOM | 4056 | CA  | ARG | A2225  | 26.441 | 51.987 | 95.009  | 1.00 | 10.87 |
| ATOM | 4057 | CB  | ARG | A2225  | 27.958 | 51.968 | 95.229  | 1.00 | 10.44 |
| ATOM | 4058 | CG  | ARG | A2225  | 28.481 | 50.721 | 95.907  | 1.00 | 10.05 |
| ATOM | 4059 | CD  | ARG | A2225  | 28.341 | 50.747 | 97.409  | 1.00 | 10.26 |
| ATOM | 4060 | NE  | ARG | A2225  | 28.865 | 49.521 | 97.998  | 1.00 | 11.46 |
| ATOM | 4061 | CZ  | ARG | A2225  | 28.806 | 49.227 | 99.290  | 1.00 | 11.53 |
| ATOM | 4062 | NH1 | ARG | A2225  | 28.242 | 50.076 | 100.150 | 1.00 | 11.96 |
| ATOM | 4063 | NH2 | ARG | A2225  | 29.314 | 48.084 | 99.724  | 1.00 | 9.68  |
| ATOM | 4064 | C   | ARG | A2225  | 26.102 | 53.267 | 94.281  | 1.00 | 11.00 |
| ATOM | 4065 | O   | ARG | A2225  | 26.034 | 53.292 | 93.052  | 1.00 | 11.56 |
| ATOM | 4066 | N   | GLY | A2226  | 25.926 | 54.331 | 95.063  | 1.00 | 11.18 |
| ATOM | 4067 | CA  | GLY | A2226  | 25.945 | 55.697 | 94.566  | 1.00 | 10.96 |
| ATOM | 4068 | C   | GLY | A2226  | 25.147 | 55.936 | 93.308  | 1.00 | 11.97 |
| ATOM | 4069 | O   | GLY | A2226  | 23.973 | 55.580 | 93.242  | 1.00 | 10.22 |
| ATOM | 4070 | N   | GLY | A2227  | 25.798 | 56.534 | 92.312  | 1.00 | 11.68 |
| ATOM | 4071 | CA  | GLY | A2227  | 25.149 | 56.876 | 91.059  | 1.00 | 12.11 |
| ATOM | 4072 | C   | GLY | A2227  | 24.584 | 55.682 | 90.318  | 1.00 | 11.11 |
| ATOM | 4073 | O   | GLY | A2227  | 23.606 | 55.813 | 89.583  | 1.00 | 11.84 |
| ATOM | 4074 | N   | SER | A2228  | 25.186 | 54.511 | 90.525  | 1.00 | 9.06  |
| ATOM | 4075 | CA  | SER | A2228  | 24.725 | 53.307 | 89.852  | 1.00 | 10.27 |
| ATOM | 4076 | CB  | SER | A2228  | 25.760 | 52.189 | 89.947  | 1.00 | 10.95 |
| ATOM | 4077 | OG  | SER | A2228  | 26.849 | 52.490 | 89.102  | 1.00 | 11.51 |
| ATOM | 4078 | C   | SER | A2228  | 23.376 | 52.860 | 90.387  | 1.00 | 10.84 |
| ATOM | 4079 | O   | SER | A2228  | 22.521 | 52.444 | 89.611  | 1.00 | 12.03 |
| ATOM | 4080 | N   | TRP | A2229  | 23.183 | 52.953 | 91.704  | 1.00 | 10.67 |
| ATOM | 4081 | CA  | TRP | A2229  | 21.861 | 52.718 | 92.282  | 1.00 | 8.61  |
| ATOM | 4082 | CB  | TRP | A2229  | 21.864 | 52.822 | 93.820  | 1.00 | 9.05  |
| ATOM | 4083 | CG  | TRP | A2229  | 20.572 | 52.327 | 94.401  | 1.00 | 9.68  |
| ATOM | 4084 | CD1 | TRP | A2229  | 19.322 | 52.849 | 94.183  | 1.00 | 11.71 |
| ATOM | 4085 | NE1 | TRP | A2229  | 18.373 | 52.110 | 94.846  | 1.00 | 12.46 |
| ATOM | 4086 | CE2 | TRP | A2229  | 18.994 | 51.086 | 95.512  | 1.00 | 10.66 |
| ATOM | 4087 | CD2 | TRP | A2229  | 20.383 | 51.191 | 95.249  | 1.00 | 10.25 |
| ATOM | 4088 | CE3 | TRP | A2229  | 21.246 | 50.249 | 95.826  | 1.00 | 9.55  |
| ATOM | 4089 | CZ3 | TRP | A2229  | 20.710 | 49.249 | 96.627  | 1.00 | 9.26  |
| ATOM | 4090 | CH2 | TRP | A2229  | 19.324 | 49.168 | 96.863  | 1.00 | 9.79  |
| ATOM | 4091 | CZ2 | TRP | A2229  | 18.452 | 50.081 | 96.322  | 1.00 | 9.85  |
| ATOM | 4092 | C   | TRP | A2229  | 20.860 | 53.706 | 91.698  | 1.00 | 9.60  |

FIGURE 3CB

| | A | B | C | D | E | F | G | H | I | J |
|---|---|---|---|---|---|---|---|---|---|---|
| ATOM | 4093 | O | | TRP | A2229 | 19.800 | 53.319 | 91.209 | 1.00 | 9.19 |
| ATOM | 4094 | N | | VAL | A2230 | 21.216 | 54.982 | 91.749 | 1.00 | 7.59 |
| ATOM | 4095 | CA | | VAL | A2230 | 20.327 | 56.060 | 91.328 | 1.00 | 8.67 |
| ATOM | 4096 | CB | | VAL | A2230 | 21.086 | 57.401 | 91.339 | 1.00 | 9.52 |
| ATOM | 4097 | CG1 | | VAL | A2230 | 20.276 | 58.501 | 90.667 | 1.00 | 8.37 |
| ATOM | 4098 | CG2 | | VAL | A2230 | 21.436 | 57.780 | 92.774 | 1.00 | 9.81 |
| ATOM | 4099 | C | | VAL | A2230 | 19.675 | 55.822 | 89.959 | 1.00 | 9.86 |
| ATOM | 4100 | O | | VAL | A2230 | 18.445 | 55.911 | 89.818 | 1.00 | 11.39 |
| ATOM | 4101 | N | | VAL | A2231 | 20.492 | 55.497 | 88.962 | 1.00 | 8.46 |
| ATOM | 4102 | CA | | VAL | A2231 | 20.009 | 55.430 | 87.588 | 1.00 | 8.68 |
| ATOM | 4103 | CB | | VAL | A2231 | 21.148 | 55.596 | 86.558 | 1.00 | 6.62 |
| ATOM | 4104 | CG1 | | VAL | A2231 | 21.897 | 56.926 | 86.776 | 1.00 | 4.13 |
| ATOM | 4105 | CG2 | | VAL | A2231 | 22.079 | 54.398 | 86.589 | 1.00 | 4.87 |
| ATOM | 4106 | C | | VAL | A2231 | 19.200 | 54.167 | 87.276 | 1.00 | 8.67 |
| ATOM | 4107 | O | | VAL | A2231 | 18.642 | 54.050 | 86.187 | 1.00 | 7.88 |
| ATOM | 4108 | N | | ILE | A2232 | 19.146 | 53.220 | 88.213 | 1.00 | 9.89 |
| ATOM | 4109 | CA | | ILE | A2232 | 18.317 | 52.015 | 88.018 | 1.00 | 8.91 |
| ATOM | 4110 | CB | | ILE | A2232 | 19.189 | 50.741 | 87.795 | 1.00 | 9.88 |
| ATOM | 4111 | CG1 | | ILE | A2232 | 19.827 | 50.253 | 89.111 | 1.00 | 8.21 |
| ATOM | 4112 | CD1 | | ILE | A2232 | 20.585 | 48.913 | 88.978 | 1.00 | 9.78 |
| ATOM | 4113 | CG2 | | ILE | A2232 | 20.234 | 50.992 | 86.706 | 1.00 | 8.99 |
| ATOM | 4114 | C | | ILE | A2232 | 17.280 | 51.788 | 89.121 | 1.00 | 10.63 |
| ATOM | 4115 | O | | ILE | A2232 | 16.632 | 50.740 | 89.175 | 1.00 | 10.60 |
| ATOM | 4116 | N | | ASP | A2233 | 17.102 | 52.772 | 89.992 | 1.00 | 8.99 |
| ATOM | 4117 | CA | | ASP | A2233 | 16.154 | 52.604 | 91.084 | 1.00 | 9.97 |
| ATOM | 4118 | CB | | ASP | A2233 | 16.184 | 53.795 | 92.028 | 1.00 | 8.74 |
| ATOM | 4119 | CG | | ASP | A2233 | 15.320 | 53.568 | 93.235 | 1.00 | 9.96 |
| ATOM | 4120 | OD1 | | ASP | A2233 | 15.725 | 52.766 | 94.099 | 1.00 | 8.63 |
| ATOM | 4121 | OD2 | | ASP | A2233 | 14.214 | 54.123 | 93.385 | 1.00 | 9.41 |
| ATOM | 4122 | C | | ASP | A2233 | 14.706 | 52.352 | 90.627 | 1.00 | 8.94 |
| ATOM | 4123 | O | | ASP | A2233 | 14.242 | 52.923 | 89.648 | 1.00 | 9.46 |
| ATOM | 4124 | N | | ALA | A2234 | 14.009 | 51.497 | 91.367 | 1.00 | 7.63 |
| ATOM | 4125 | CA | | ALA | A2234 | 12.591 | 51.215 | 91.142 | 1.00 | 6.88 |
| ATOM | 4126 | CB | | ALA | A2234 | 12.027 | 50.420 | 92.313 | 1.00 | 6.62 |
| ATOM | 4127 | C | | ALA | A2234 | 11.720 | 52.442 | 90.881 | 1.00 | 7.97 |
| ATOM | 4128 | O | | ALA | A2234 | 10.823 | 52.386 | 90.046 | 1.00 | 7.16 |
| ATOM | 4129 | N | | THR | A2235 | 11.980 | 53.552 | 91.575 | 1.00 | 7.58 |
| ATOM | 4130 | CA | | THR | A2235 | 11.122 | 54.735 | 91.434 | 1.00 | 8.85 |
| ATOM | 4131 | CB | | THR | A2235 | 11.399 | 55.782 | 92.530 | 1.00 | 9.04 |
| ATOM | 4132 | OG1 | | THR | A2235 | 12.793 | 56.085 | 92.550 | 1.00 | 7.94 |
| ATOM | 4133 | CG2 | | THR | A2235 | 11.100 | 55.236 | 93.918 | 1.00 | 9.31 |
| ATOM | 4134 | C | | THR | A2235 | 11.248 | 55.419 | 90.081 | 1.00 | 9.59 |
| ATOM | 4135 | O | | THR | A2235 | 10.468 | 56.313 | 89.768 | 1.00 | 11.20 |
| ATOM | 4136 | N | | ILE | A2236 | 12.234 | 55.017 | 89.281 | 1.00 | 10.70 |
| ATOM | 4137 | CA | | ILE | A2236 | 12.304 | 55.494 | 87.902 | 1.00 | 10.37 |
| ATOM | 4138 | CB | | ILE | A2236 | 13.665 | 55.134 | 87.267 | 1.00 | 11.05 |
| ATOM | 4139 | CG1 | | ILE | A2236 | 14.768 | 56.010 | 87.875 | 1.00 | 10.10 |
| ATOM | 4140 | CD1 | | ILE | A2236 | 16.114 | 55.411 | 87.751 | 1.00 | 9.45 |
| ATOM | 4141 | CG2 | | ILE | A2236 | 13.654 | 55.326 | 85.743 | 1.00 | 10.38 |
| ATOM | 4142 | C | | ILE | A2236 | 11.130 | 54.937 | 87.097 | 1.00 | 10.68 |
| ATOM | 4143 | O | | ILE | A2236 | 10.616 | 55.593 | 86.193 | 1.00 | 11.47 |
| ATOM | 4144 | N | | ASN | A2237 | 10.708 | 53.724 | 87.441 | 1.00 | 9.38 |

FIGURE 3CC

|      | A    | B   | C   | D   | E     | F      | G      | H      | I    | J     |
|------|------|-----|-----|-----|-------|--------|--------|--------|------|-------|
| ATOM | 4145 | CA  | ASN | A2237 |      | 9.587  | 53.075 | 86.766 | 1.00 | 8.88  |
| ATOM | 4146 | CB  | ASN | A2237 |      | 10.083 | 52.339 | 85.508 | 1.00 | 8.65  |
| ATOM | 4147 | CG  | ASN | A2237 |      | 8.941  | 51.892 | 84.583 | 1.00 | 10.15 |
| ATOM | 4148 | OD1 | ASN | A2237 |      | 7.793  | 51.735 | 85.005 | 1.00 | 9.79  |
| ATOM | 4149 | ND2 | ASN | A2237 |      | 9.269  | 51.661 | 83.322 | 1.00 | 9.36  |
| ATOM | 4150 | C   | ASN | A2237 |      | 8.929  | 52.112 | 87.765 | 1.00 | 9.94  |
| ATOM | 4151 | O   | ASN | A2237 |      | 9.138  | 50.897 | 87.698 | 1.00 | 9.58  |
| ATOM | 4152 | N   | PRO | A2238 |      | 8.181  | 52.662 | 88.728 | 1.00 | 11.43 |
| ATOM | 4153 | CA  | PRO | A2238 |      | 7.624  | 51.853 | 89.821 | 1.00 | 11.82 |
| ATOM | 4154 | CB  | PRO | A2238 |      | 7.001  | 52.899 | 90.755 | 1.00 | 12.63 |
| ATOM | 4155 | CG  | PRO | A2238 |      | 6.737  | 54.084 | 89.879 | 1.00 | 13.21 |
| ATOM | 4156 | CD  | PRO | A2238 |      | 7.841  | 54.092 | 88.868 | 1.00 | 12.21 |
| ATOM | 4157 | C   | PRO | A2238 |      | 6.583  | 50.833 | 89.344 | 1.00 | 12.58 |
| ATOM | 4158 | O   | PRO | A2238 |      | 6.291  | 49.890 | 90.073 | 1.00 | 14.23 |
| ATOM | 4159 | N   | LEU | A2239 |      | 6.056  | 51.003 | 88.135 | 1.00 | 12.33 |
| ATOM | 4160 | CA  | LEU | A2239 |      | 5.121  | 50.026 | 87.576 | 1.00 | 15.57 |
| ATOM | 4161 | CB  | LEU | A2239 |      | 4.257  | 50.648 | 86.474 | 1.00 | 18.06 |
| ATOM | 4162 | CG  | LEU | A2239 |      | 3.428  | 51.884 | 86.834 | 1.00 | 21.93 |
| ATOM | 4163 | CD1 | LEU | A2239 |      | 2.728  | 52.457 | 85.605 | 1.00 | 21.97 |
| ATOM | 4164 | CD2 | LEU | A2239 |      | 2.430  | 51.553 | 87.922 | 1.00 | 23.82 |
| ATOM | 4165 | C   | LEU | A2239 |      | 5.842  | 48.793 | 87.030 | 1.00 | 14.03 |
| ATOM | 4166 | O   | LEU | A2239 |      | 5.234  | 47.736 | 86.898 | 1.00 | 15.30 |
| ATOM | 4167 | N   | CYS | A2240 |      | 7.127  | 48.933 | 86.709 | 1.00 | 11.22 |
| ATOM | 4168 | CA  | CYS | A2240 |      | 7.870  | 47.845 | 86.067 | 1.00 | 10.09 |
| ATOM | 4169 | CB  | CYS | A2240 |      | 8.485  | 48.316 | 84.749 | 1.00 | 10.78 |
| ATOM | 4170 | SG  | CYS | A2240 |      | 7.265  | 48.714 | 83.485 | 1.00 | 13.90 |
| ATOM | 4171 | C   | CYS | A2240 |      | 8.963  | 47.238 | 86.925 | 1.00 | 9.74  |
| ATOM | 4172 | O   | CYS | A2240 |      | 9.152  | 46.019 | 86.921 | 1.00 | 8.47  |
| ATOM | 4173 | N   | ILE | A2241 |      | 9.699  | 48.088 | 87.637 | 1.00 | 7.84  |
| ATOM | 4174 | CA  | ILE | A2241 |      | 10.906 | 47.646 | 88.318 | 1.00 | 9.39  |
| ATOM | 4175 | CB  | ILE | A2241 |      | 11.930 | 48.804 | 88.434 | 1.00 | 9.38  |
| ATOM | 4176 | CG1 | ILE | A2241 |      | 12.290 | 49.372 | 87.047 | 1.00 | 9.96  |
| ATOM | 4177 | CD1 | ILE | A2241 |      | 13.043 | 50.724 | 87.093 | 1.00 | 7.97  |
| ATOM | 4178 | CG2 | ILE | A2241 |      | 13.169 | 48.342 | 89.214 | 1.00 | 7.34  |
| ATOM | 4179 | C   | ILE | A2241 |      | 10.619 | 47.091 | 89.705 | 1.00 | 11.33 |
| ATOM | 4180 | O   | ILE | A2241 |      | 9.927  | 47.726 | 90.496 | 1.00 | 10.55 |
| ATOM | 4181 | N   | GLU | A2242 |      | 11.167 | 45.909 | 89.983 | 1.00 | 9.90  |
| ATOM | 4182 | CA  | GLU | A2242 |      | 11.284 | 45.396 | 91.345 | 1.00 | 9.18  |
| ATOM | 4183 | CB  | GLU | A2242 |      | 10.416 | 44.144 | 91.558 | 1.00 | 8.28  |
| ATOM | 4184 | CG  | GLU | A2242 |      | 8.924  | 44.426 | 91.379 | 1.00 | 11.74 |
| ATOM | 4185 | CD  | GLU | A2242 |      | 8.014  | 43.256 | 91.711 | 1.00 | 10.48 |
| ATOM | 4186 | OE1 | GLU | A2242 |      | 6.785  | 43.477 | 91.733 | 1.00 | 12.27 |
| ATOM | 4187 | OE2 | GLU | A2242 |      | 8.504  | 42.125 | 91.939 | 1.00 | 10.38 |
| ATOM | 4188 | C   | GLU | A2242 |      | 12.751 | 45.110 | 91.625 | 1.00 | 9.49  |
| ATOM | 4189 | O   | GLU | A2242 |      | 13.465 | 44.548 | 90.786 | 1.00 | 10.78 |
| ATOM | 4190 | N   | MET | A2243 |      | 13.208 | 45.533 | 92.794 | 1.00 | 8.01  |
| ATOM | 4191 | CA  | MET | A2243 |      | 14.590 | 45.319 | 93.192 | 1.00 | 8.92  |
| ATOM | 4192 | CB  | MET | A2243 |      | 15.209 | 46.624 | 93.681 | 1.00 | 8.35  |
| ATOM | 4193 | CG  | MET | A2243 |      | 15.122 | 47.739 | 92.641 | 1.00 | 9.82  |
| ATOM | 4194 | SD  | MET | A2243 |      | 15.779 | 49.290 | 93.277 | 1.00 | 10.87 |
| ATOM | 4195 | CE  | MET | A2243 |      | 17.468 | 49.196 | 92.708 | 1.00 | 8.60  |
| ATOM | 4196 | C   | MET | A2243 |      | 14.673 | 44.251 | 94.266 | 1.00 | 9.82  |

FIGURE 3CD

|      | A    | B   | C   | D   | E     | F      | G      | H       | I    | J     |
|------|------|-----|-----|-----|-------|--------|--------|---------|------|-------|
| ATOM | 4197 | O   |     | MET | A2243 | 13.842 | 44.208 | 95.176  | 1.00 | 8.30  |
| ATOM | 4198 | N   |     | TYR | A2244 | 15.673 | 43.387 | 94.128  | 1.00 | 9.52  |
| ATOM | 4199 | CA  |     | TYR | A2244 | 15.938 | 42.296 | 95.055  | 1.00 | 10.07 |
| ATOM | 4200 | CB  |     | TYR | A2244 | 15.560 | 40.949 | 94.423  | 1.00 | 9.72  |
| ATOM | 4201 | CG  |     | TYR | A2244 | 14.084 | 40.871 | 94.144  | 1.00 | 12.12 |
| ATOM | 4202 | CD1 |     | TYR | A2244 | 13.563 | 41.277 | 92.911  | 1.00 | 12.20 |
| ATOM | 4203 | CE1 |     | TYR | A2244 | 12.197 | 41.232 | 92.666  | 1.00 | 11.85 |
| ATOM | 4204 | CZ  |     | TYR | A2244 | 11.345 | 40.794 | 93.661  | 1.00 | 11.74 |
| ATOM | 4205 | OH  |     | TYR | A2244 | 9.996  | 40.747 | 93.439  | 1.00 | 12.58 |
| ATOM | 4206 | CE2 |     | TYR | A2244 | 11.839 | 40.395 | 94.892  | 1.00 | 12.14 |
| ATOM | 4207 | CD2 |     | TYR | A2244 | 13.201 | 40.442 | 95.127  | 1.00 | 10.79 |
| ATOM | 4208 | C   |     | TYR | A2244 | 17.412 | 42.313 | 95.383  | 1.00 | 11.37 |
| ATOM | 4209 | O   |     | TYR | A2244 | 18.239 | 42.632 | 94.529  | 1.00 | 11.96 |
| ATOM | 4210 | N   |     | ALA | A2245 | 17.742 | 41.982 | 96.625  | 1.00 | 10.94 |
| ATOM | 4211 | CA  |     | ALA | A2245 | 19.133 | 41.937 | 97.040  | 1.00 | 11.45 |
| ATOM | 4212 | CB  |     | ALA | A2245 | 19.427 | 43.028 | 98.060  | 1.00 | 9.74  |
| ATOM | 4213 | C   |     | ALA | A2245 | 19.440 | 40.573 | 97.612  | 1.00 | 10.44 |
| ATOM | 4214 | O   |     | ALA | A2245 | 18.667 | 40.044 | 98.409  | 1.00 | 11.44 |
| ATOM | 4215 | N   |     | ASP | A2246 | 20.561 | 39.992 | 97.196  | 1.00 | 10.01 |
| ATOM | 4216 | CA  |     | ASP | A2246 | 20.995 | 38.741 | 97.795  | 1.00 | 10.06 |
| ATOM | 4217 | CB  |     | ASP | A2246 | 22.199 | 38.141 | 97.073  | 1.00 | 8.75  |
| ATOM | 4218 | CG  |     | ASP | A2246 | 22.417 | 36.692 | 97.442  | 1.00 | 10.09 |
| ATOM | 4219 | OD1 |     | ASP | A2246 | 21.759 | 35.825 | 96.831  | 1.00 | 9.53  |
| ATOM | 4220 | OD2 |     | ASP | A2246 | 23.208 | 36.326 | 98.340  | 1.00 | 10.28 |
| ATOM | 4221 | C   |     | ASP | A2246 | 21.340 | 38.958 | 99.260  | 1.00 | 10.16 |
| ATOM | 4222 | O   |     | ASP | A2246 | 21.731 | 40.054 | 99.652  | 1.00 | 8.10  |
| ATOM | 4223 | N   |     | LYS | A2247 | 21.160 | 37.907 | 100.054 | 1.00 | 11.12 |
| ATOM | 4224 | CA  |     | LYS | A2247 | 21.593 | 37.863 | 101.450 | 1.00 | 13.70 |
| ATOM | 4225 | CB  |     | LYS | A2247 | 21.460 | 36.433 | 101.979 | 1.00 | 14.87 |
| ATOM | 4226 | CG  |     | LYS | A2247 | 20.759 | 36.315 | 103.316 | 1.00 | 20.46 |
| ATOM | 4227 | CD  |     | LYS | A2247 | 20.826 | 34.874 | 103.844 | 1.00 | 23.03 |
| ATOM | 4228 | CE  |     | LYS | A2247 | 19.507 | 34.437 | 104.483 | 1.00 | 27.61 |
| ATOM | 4229 | NZ  |     | LYS | A2247 | 18.313 | 34.706 | 103.609 | 1.00 | 30.63 |
| ATOM | 4230 | C   |     | LYS | A2247 | 23.041 | 38.319 | 101.609 | 1.00 | 13.41 |
| ATOM | 4231 | O   |     | LYS | A2247 | 23.393 | 38.939 | 102.612 | 1.00 | 12.79 |
| ATOM | 4232 | N   |     | GLU | A2248 | 23.875 | 37.994 | 100.618 | 1.00 | 12.49 |
| ATOM | 4233 | CA  |     | GLU | A2248 | 25.295 | 38.328 | 100.665 | 1.00 | 13.53 |
| ATOM | 4234 | CB  |     | GLU | A2248 | 26.156 | 37.116 | 100.270 | 1.00 | 15.19 |
| ATOM | 4235 | CG  |     | GLU | A2248 | 25.765 | 35.798 | 100.936 | 1.00 | 19.19 |
| ATOM | 4236 | CD  |     | GLU | A2248 | 25.811 | 35.832 | 102.460 | 1.00 | 21.84 |
| ATOM | 4237 | OE1 |     | GLU | A2248 | 26.562 | 36.649 | 103.047 | 1.00 | 22.03 |
| ATOM | 4238 | OE2 |     | GLU | A2248 | 25.094 | 35.015 | 103.080 | 1.00 | 24.65 |
| ATOM | 4239 | C   |     | GLU | A2248 | 25.645 | 39.534 | 99.798  | 1.00 | 13.64 |
| ATOM | 4240 | O   |     | GLU | A2248 | 26.779 | 39.670 | 99.348  | 1.00 | 14.92 |
| ATOM | 4241 | N   |     | SER | A2249 | 24.673 | 40.408 | 99.570  | 1.00 | 11.97 |
| ATOM | 4242 | CA  |     | SER | A2249 | 24.911 | 41.612 | 98.784  | 1.00 | 11.99 |
| ATOM | 4243 | CB  |     | SER | A2249 | 23.772 | 41.834 | 97.789  | 1.00 | 10.94 |
| ATOM | 4244 | OG  |     | SER | A2249 | 22.570 | 42.148 | 98.469  | 1.00 | 10.70 |
| ATOM | 4245 | C   |     | SER | A2249 | 25.083 | 42.841 | 99.680  | 1.00 | 11.75 |
| ATOM | 4246 | O   |     | SER | A2249 | 24.873 | 42.778 | 100.901 | 1.00 | 10.83 |
| ATOM | 4247 | N   |     | ARG | A2250 | 25.478 | 43.950 | 99.064  | 1.00 | 10.57 |
| ATOM | 4248 | CA  |     | ARG | A2250 | 25.617 | 45.224 | 99.754  | 1.00 | 10.25 |

FIGURE 3CE

| | A | B | C | D | E | F | G | H | I | J |
|---|---|---|---|---|---|---|---|---|---|---|
| ATOM | 4249 | CB | | ARG | A2250 | 27.092 | 45.516 | 100.045 | 1.00 | 10.93 |
| ATOM | 4250 | CG | | ARG | A2250 | 27.688 | 44.719 | 101.219 | 1.00 | 10.50 |
| ATOM | 4251 | CD | | ARG | A2250 | 27.044 | 45.028 | 102.562 | 1.00 | 11.32 |
| ATOM | 4252 | NE | | ARG | A2250 | 27.695 | 44.337 | 103.669 | 1.00 | 12.27 |
| ATOM | 4253 | CZ | | ARG | A2250 | 27.330 | 43.153 | 104.152 | 1.00 | 14.82 |
| ATOM | 4254 | NH1 | | ARG | A2250 | 26.313 | 42.482 | 103.619 | 1.00 | 14.30 |
| ATOM | 4255 | NH2 | | ARG | A2250 | 27.992 | 42.631 | 105.179 | 1.00 | 14.56 |
| ATOM | 4256 | C | | ARG | A2250 | 25.035 | 46.349 | 98.909 | 1.00 | 11.36 |
| ATOM | 4257 | O | | ARG | A2250 | 24.942 | 46.232 | 97.687 | 1.00 | 11.58 |
| ATOM | 4258 | N | | GLY | A2251 | 24.653 | 47.440 | 99.560 | 1.00 | 10.19 |
| ATOM | 4259 | CA | | GLY | A2251 | 24.167 | 48.611 | 98.853 | 1.00 | 10.83 |
| ATOM | 4260 | C | | GLY | A2251 | 24.253 | 49.840 | 99.731 | 1.00 | 12.27 |
| ATOM | 4261 | O | | GLY | A2251 | 23.952 | 49.774 | 100.924 | 1.00 | 12.79 |
| ATOM | 4262 | N | | GLY | A2252 | 24.638 | 50.967 | 99.142 | 1.00 | 11.74 |
| ATOM | 4263 | CA | | GLY | A2252 | 24.747 | 52.207 | 99.888 | 1.00 | 11.92 |
| ATOM | 4264 | C | | GLY | A2252 | 25.296 | 53.342 | 99.055 | 1.00 | 11.65 |
| ATOM | 4265 | O | | GLY | A2252 | 25.762 | 53.132 | 97.933 | 1.00 | 10.25 |
| ATOM | 4266 | N | | VAL | A2253 | 25.254 | 54.549 | 99.609 | 1.00 | 10.02 |
| ATOM | 4267 | CA | | VAL | A2253 | 25.671 | 55.734 | 98.864 | 1.00 | 11.12 |
| ATOM | 4268 | CB | | VAL | A2253 | 25.397 | 57.041 | 99.636 | 1.00 | 11.24 |
| ATOM | 4269 | CG1 | | VAL | A2253 | 25.832 | 58.266 | 98.812 | 1.00 | 8.34 |
| ATOM | 4270 | CG2 | | VAL | A2253 | 23.910 | 57.128 | 99.989 | 1.00 | 8.09 |
| ATOM | 4271 | C | | VAL | A2253 | 27.133 | 55.596 | 98.464 | 1.00 | 11.77 |
| ATOM | 4272 | O | | VAL | A2253 | 27.462 | 55.664 | 97.277 | 1.00 | 11.41 |
| ATOM | 4273 | N | | LEU | A2254 | 27.997 | 55.361 | 99.444 | 1.00 | 10.99 |
| ATOM | 4274 | CA | | LEU | A2254 | 29.410 | 55.139 | 99.158 | 1.00 | 13.61 |
| ATOM | 4275 | CB | | LEU | A2254 | 30.283 | 56.166 | 99.901 | 1.00 | 12.77 |
| ATOM | 4276 | CG | | LEU | A2254 | 30.088 | 57.658 | 99.599 | 1.00 | 13.75 |
| ATOM | 4277 | CD1 | | LEU | A2254 | 31.002 | 58.499 | 100.475 | 1.00 | 13.24 |
| ATOM | 4278 | CD2 | | LEU | A2254 | 30.315 | 57.994 | 98.103 | 1.00 | 13.50 |
| ATOM | 4279 | C | | LEU | A2254 | 29.808 | 53.724 | 99.559 | 1.00 | 13.07 |
| ATOM | 4280 | O | | LEU | A2254 | 29.045 | 53.027 | 100.223 | 1.00 | 14.05 |
| ATOM | 4281 | N | | GLU | A2255 | 31.001 | 53.304 | 99.148 | 1.00 | 13.81 |
| ATOM | 4282 | CA | | GLU | A2255 | 31.638 | 52.131 | 99.729 | 1.00 | 15.13 |
| ATOM | 4283 | CB | | GLU | A2255 | 32.872 | 51.736 | 98.913 | 1.00 | 18.78 |
| ATOM | 4284 | CG | | GLU | A2255 | 32.574 | 50.690 | 97.849 | 1.00 | 25.02 |
| ATOM | 4285 | CD | | GLU | A2255 | 33.503 | 50.779 | 96.659 | 1.00 | 28.34 |
| ATOM | 4286 | OE1 | | GLU | A2255 | 33.003 | 50.976 | 95.539 | 1.00 | 31.16 |
| ATOM | 4287 | OE2 | | GLU | A2255 | 34.736 | 50.650 | 96.838 | 1.00 | 31.52 |
| ATOM | 4288 | C | | GLU | A2255 | 32.017 | 52.454 | 101.186 | 1.00 | 14.02 |
| ATOM | 4289 | O | | GLU | A2255 | 32.241 | 53.621 | 101.505 | 1.00 | 13.00 |
| ATOM | 4290 | N | | PRO | A2256 | 32.073 | 51.443 | 102.060 | 1.00 | 12.45 |
| ATOM | 4291 | CA | | PRO | A2256 | 32.319 | 51.662 | 103.498 | 1.00 | 14.32 |
| ATOM | 4292 | CB | | PRO | A2256 | 32.567 | 50.250 | 104.042 | 1.00 | 15.14 |
| ATOM | 4293 | CG | | PRO | A2256 | 31.981 | 49.324 | 103.073 | 1.00 | 15.81 |
| ATOM | 4294 | CD | | PRO | A2256 | 31.897 | 50.017 | 101.741 | 1.00 | 13.97 |
| ATOM | 4295 | C | | PRO | A2256 | 33.549 | 52.534 | 103.776 | 1.00 | 13.90 |
| ATOM | 4296 | O | | PRO | A2256 | 33.537 | 53.354 | 104.698 | 1.00 | 13.45 |
| ATOM | 4297 | N | | GLU | A2257 | 34.595 | 52.346 | 102.979 | 1.00 | 14.89 |
| ATOM | 4298 | CA | | GLU | A2257 | 35.823 | 53.133 | 103.088 | 1.00 | 15.26 |
| ATOM | 4299 | CB | | GLU | A2257 | 36.893 | 52.581 | 102.134 | 1.00 | 16.17 |
| ATOM | 4300 | CG | B | GLU | A2257 | 37.266 | 51.117 | 102.377 | 0.50 | 16.69 |

FIGURE 3CF

|      | A    | B    | C   | D    | E     | F      | G      | H       | I    | J     |
|------|------|------|-----|------|-------|--------|--------|---------|------|-------|
| ATOM | 4301 | CG   | AGLU | A2257 | 37.567 | 51.303 | 102.622 | 0.50 | 16.07 |
| ATOM | 4302 | CD   | BGLU | A2257 | 36.323 | 50.110 | 101.717 | 0.50 | 16.88 |
| ATOM | 4303 | CD   | AGLU | A2257 | 38.725 | 51.548 | 103.580 | 0.50 | 15.77 |
| ATOM | 4304 | OE1  | BGLU | A2257 | 35.301 | 50.508 | 101.118 | 0.50 | 15.32 |
| ATOM | 4305 | OE1  | AGLU | A2257 | 39.183 | 52.705 | 103.719 | 0.50 | 16.17 |
| ATOM | 4306 | OE2  | BGLU | A2257 | 36.607 | 48.896 | 101.800 | 0.50 | 18.84 |
| ATOM | 4307 | OE2  | AGLU | A2257 | 39.189 | 50.566 | 104.194 | 0.50 | 16.41 |
| ATOM | 4308 | C    | GLU | A2257 | 35.530 | 54.611 | 102.797 | 1.00 | 14.72 |
| ATOM | 4309 | O    | GLU | A2257 | 36.009 | 55.497 | 103.504 | 1.00 | 13.61 |
| ATOM | 4310 | N    | GLY | A2258 | 34.716 | 54.868 | 101.774 | 1.00 | 13.21 |
| ATOM | 4311 | CA   | GLY | A2258 | 34.296 | 56.219 | 101.442 | 1.00 | 13.43 |
| ATOM | 4312 | C    | GLY | A2258 | 33.440 | 56.850 | 102.530 | 1.00 | 13.93 |
| ATOM | 4313 | O    | GLY | A2258 | 33.669 | 58.003 | 102.915 | 1.00 | 12.58 |
| ATOM | 4314 | N    | THR | A2259 | 32.456 | 56.091 | 103.022 | 1.00 | 11.76 |
| ATOM | 4315 | CA   | THR | A2259 | 31.566 | 56.539 | 104.100 | 1.00 | 12.34 |
| ATOM | 4316 | CB   | THR | A2259 | 30.597 | 55.403 | 104.493 | 1.00 | 13.22 |
| ATOM | 4317 | OG1  | THR | A2259 | 29.818 | 55.026 | 103.353 | 1.00 | 12.53 |
| ATOM | 4318 | CG2  | THR | A2259 | 29.547 | 55.897 | 105.504 | 1.00 | 12.80 |
| ATOM | 4319 | C    | THR | A2259 | 32.363 | 56.984 | 105.328 | 1.00 | 13.27 |
| ATOM | 4320 | O    | THR | A2259 | 32.098 | 58.039 | 105.910 | 1.00 | 12.51 |
| ATOM | 4321 | N    | VAL | A2260 | 33.342 | 56.166 | 105.702 | 1.00 | 12.73 |
| ATOM | 4322 | CA   | VAL | A2260 | 34.221 | 56.450 | 106.828 | 1.00 | 14.65 |
| ATOM | 4323 | CB   | VAL | A2260 | 35.135 | 55.235 | 107.122 | 1.00 | 14.48 |
| ATOM | 4324 | CG1  | VAL | A2260 | 36.325 | 55.620 | 108.001 | 1.00 | 15.80 |
| ATOM | 4325 | CG2  | VAL | A2260 | 34.323 | 54.132 | 107.792 | 1.00 | 13.57 |
| ATOM | 4326 | C    | VAL | A2260 | 35.023 | 57.731 | 106.585 | 1.00 | 16.49 |
| ATOM | 4327 | O    | VAL | A2260 | 35.149 | 58.565 | 107.484 | 1.00 | 17.42 |
| ATOM | 4328 | N    | GLU | A2261 | 35.527 | 57.894 | 105.361 | 1.00 | 17.87 |
| ATOM | 4329 | CA   | GLU | A2261 | 36.283 | 59.085 | 104.974 | 1.00 | 20.27 |
| ATOM | 4330 | CB   | GLU | A2261 | 36.755 | 58.974 | 103.517 | 1.00 | 23.52 |
| ATOM | 4331 | CG   | GLU | A2261 | 37.895 | 59.914 | 103.140 | 1.00 | 28.01 |
| ATOM | 4332 | CD   | GLU | A2261 | 39.190 | 59.636 | 103.897 | 1.00 | 30.86 |
| ATOM | 4333 | OE1  | GLU | A2261 | 39.660 | 58.473 | 103.903 | 1.00 | 30.70 |
| ATOM | 4334 | OE2  | GLU | A2261 | 39.747 | 60.595 | 104.481 | 1.00 | 33.49 |
| ATOM | 4335 | C    | GLU | A2261 | 35.475 | 60.366 | 105.176 | 1.00 | 18.95 |
| ATOM | 4336 | O    | GLU | A2261 | 36.037 | 61.424 | 105.444 | 1.00 | 20.77 |
| ATOM | 4337 | N    | ILE | A2262 | 34.157 | 60.256 | 105.059 | 1.00 | 18.44 |
| ATOM | 4338 | CA   | ILE | A2262 | 33.260 | 61.390 | 105.249 | 1.00 | 19.18 |
| ATOM | 4339 | CB   | ILE | A2262 | 32.042 | 61.293 | 104.267 | 1.00 | 19.68 |
| ATOM | 4340 | CG1  | ILE | A2262 | 32.505 | 61.203 | 102.803 | 1.00 | 21.48 |
| ATOM | 4341 | CD1  | ILE | A2262 | 33.264 | 62.433 | 102.289 | 1.00 | 22.76 |
| ATOM | 4342 | CG2  | ILE | A2262 | 31.057 | 62.447 | 104.475 | 1.00 | 20.65 |
| ATOM | 4343 | C    | ILE | A2262 | 32.776 | 61.489 | 106.699 | 1.00 | 18.71 |
| ATOM | 4344 | O    | ILE | A2262 | 32.751 | 62.577 | 107.274 | 1.00 | 21.10 |
| ATOM | 4345 | N    | LYS | A2263 | 32.420 | 60.351 | 107.288 | 1.00 | 17.76 |
| ATOM | 4346 | CA   | LYS | A2263 | 31.632 | 60.336 | 108.522 | 1.00 | 18.14 |
| ATOM | 4347 | CB   | LYS | A2263 | 30.300 | 59.613 | 108.288 | 1.00 | 17.20 |
| ATOM | 4348 | CG   | LYS | A2263 | 29.482 | 60.128 | 107.098 | 1.00 | 20.64 |
| ATOM | 4349 | CD   | LYS | A2263 | 28.858 | 61.494 | 107.363 | 1.00 | 22.28 |
| ATOM | 4350 | CE   | LYS | A2263 | 27.687 | 61.417 | 108.329 | 1.00 | 24.51 |
| ATOM | 4351 | NZ   | LYS | A2263 | 27.008 | 62.741 | 108.447 | 1.00 | 27.41 |
| ATOM | 4352 | C    | LYS | A2263 | 32.317 | 59.736 | 109.751 | 1.00 | 17.31 |

FIGURE 3CG

|      | A    | B   | C   | D  | E     | F      | G      | H       | I    | J     |
|------|------|-----|-----|----|-------|--------|--------|---------|------|-------|
| ATOM | 4353 | O   | LYS | A2263 | 31.775 | 59.809 | 110.851 | 1.00 | 18.43 |
| ATOM | 4354 | N   | PHE | A2264 | 33.482 | 59.122 | 109.570 | 1.00 | 16.28 |
| ATOM | 4355 | CA  | PHE | A2264 | 34.174 | 58.481 | 110.686 | 1.00 | 15.75 |
| ATOM | 4356 | CB  | PHE | A2264 | 33.889 | 56.972 | 110.705 | 1.00 | 14.76 |
| ATOM | 4357 | CG  | PHE | A2264 | 33.807 | 56.371 | 112.090 | 1.00 | 15.46 |
| ATOM | 4358 | CD1 | PHE | A2264 | 32.726 | 55.570 | 112.447 | 1.00 | 13.95 |
| ATOM | 4359 | CE1 | PHE | A2264 | 32.651 | 54.996 | 113.718 | 1.00 | 14.15 |
| ATOM | 4360 | CZ  | PHE | A2264 | 33.666 | 55.220 | 114.644 | 1.00 | 15.22 |
| ATOM | 4361 | CE2 | PHE | A2264 | 34.753 | 56.009 | 114.296 | 1.00 | 15.17 |
| ATOM | 4362 | CD2 | PHE | A2264 | 34.822 | 56.574 | 113.024 | 1.00 | 15.00 |
| ATOM | 4363 | C   | PHE | A2264 | 35.666 | 58.776 | 110.598 | 1.00 | 15.12 |
| ATOM | 4364 | O   | PHE | A2264 | 36.493 | 57.872 | 110.447 | 1.00 | 12.62 |
| ATOM | 4365 | N   | ARG | A2265 | 35.985 | 60.064 | 110.710 | 1.00 | 16.49 |
| ATOM | 4366 | CA  | ARG | A2265 | 37.336 | 60.577 | 110.526 | 1.00 | 17.79 |
| ATOM | 4367 | CB  | ARG | A2265 | 37.283 | 62.058 | 110.122 | 1.00 | 19.39 |
| ATOM | 4368 | CG  | ARG | A2265 | 36.865 | 62.271 | 108.669 | 1.00 | 19.89 |
| ATOM | 4369 | CD  | ARG | A2265 | 36.150 | 63.586 | 108.378 | 1.00 | 21.33 |
| ATOM | 4370 | NE  | ARG | A2265 | 35.845 | 63.706 | 106.948 | 1.00 | 21.99 |
| ATOM | 4371 | CZ  | ARG | A2265 | 35.446 | 64.821 | 106.341 | 1.00 | 22.67 |
| ATOM | 4372 | NH1 | ARG | A2265 | 35.282 | 65.950 | 107.029 | 1.00 | 21.83 |
| ATOM | 4373 | NH2 | ARG | A2265 | 35.204 | 64.805 | 105.033 | 1.00 | 21.73 |
| ATOM | 4374 | C   | ARG | A2265 | 38.185 | 60.372 | 111.778 | 1.00 | 18.53 |
| ATOM | 4375 | O   | ARG | A2265 | 37.692 | 59.860 | 112.788 | 1.00 | 17.24 |
| ATOM | 4376 | N   | LYS | A2266 | 39.457 | 60.770 | 111.700 | 1.00 | 20.36 |
| ATOM | 4377 | CA  | LYS | A2266 | 40.434 | 60.573 | 112.782 | 1.00 | 21.59 |
| ATOM | 4378 | CB  | LYS | A2266 | 41.739 | 61.321 | 112.471 | 1.00 | 23.28 |
| ATOM | 4379 | CG  | LYS | A2266 | 42.875 | 61.047 | 113.451 | 1.00 | 25.16 |
| ATOM | 4380 | CD  | LYS | A2266 | 44.227 | 61.422 | 112.858 | 1.00 | 27.79 |
| ATOM | 4381 | CE  | LYS | A2266 | 45.286 | 61.571 | 113.943 | 1.00 | 29.41 |
| ATOM | 4382 | NZ  | LYS | A2266 | 46.656 | 61.722 | 113.363 | 1.00 | 31.16 |
| ATOM | 4383 | C   | LYS | A2266 | 39.912 | 60.962 | 114.170 | 1.00 | 21.11 |
| ATOM | 4384 | O   | LYS | A2266 | 40.099 | 60.219 | 115.137 | 1.00 | 22.01 |
| ATOM | 4385 | N   | LYS | A2267 | 39.256 | 62.118 | 114.253 | 1.00 | 21.12 |
| ATOM | 4386 | CA  | LYS | A2267 | 38.695 | 62.624 | 115.505 | 1.00 | 21.07 |
| ATOM | 4387 | CB  | LYS | A2267 | 38.053 | 63.996 | 115.284 | 1.00 | 24.29 |
| ATOM | 4388 | CG  | LYS | A2267 | 38.328 | 64.997 | 116.397 | 1.00 | 27.95 |
| ATOM | 4389 | CD  | LYS | A2267 | 37.030 | 65.501 | 117.023 | 1.00 | 30.14 |
| ATOM | 4390 | CE  | LYS | A2267 | 37.261 | 66.030 | 118.430 | 1.00 | 31.74 |
| ATOM | 4391 | NZ  | LYS | A2267 | 36.870 | 65.033 | 119.471 | 1.00 | 32.84 |
| ATOM | 4392 | C   | LYS | A2267 | 37.676 | 61.661 | 116.111 | 1.00 | 19.65 |
| ATOM | 4393 | O   | LYS | A2267 | 37.599 | 61.512 | 117.331 | 1.00 | 18.08 |
| ATOM | 4394 | N   | ASP | A2268 | 36.896 | 61.011 | 115.253 | 1.00 | 18.25 |
| ATOM | 4395 | CA  | ASP | A2268 | 35.944 | 60.005 | 115.701 | 1.00 | 18.32 |
| ATOM | 4396 | CB  | ASP | A2268 | 34.856 | 59.788 | 114.651 | 1.00 | 20.20 |
| ATOM | 4397 | CG  | ASP | A2268 | 33.705 | 60.760 | 114.807 | 1.00 | 21.61 |
| ATOM | 4398 | OD1 | ASP | A2268 | 33.121 | 61.162 | 113.781 | 1.00 | 23.16 |
| ATOM | 4399 | OD2 | ASP | A2268 | 33.318 | 61.181 | 115.919 | 1.00 | 23.51 |
| ATOM | 4400 | C   | ASP | A2268 | 36.620 | 58.688 | 116.063 | 1.00 | 16.54 |
| ATOM | 4401 | O   | ASP | A2268 | 36.162 | 57.982 | 116.964 | 1.00 | 17.90 |
| ATOM | 4402 | N   | LEU | A2269 | 37.701 | 58.361 | 115.357 | 1.00 | 14.67 |
| ATOM | 4403 | CA  | LEU | A2269 | 38.502 | 57.179 | 115.666 | 1.00 | 13.85 |
| ATOM | 4404 | CB  | LEU | A2269 | 39.556 | 56.938 | 114.578 | 1.00 | 13.03 |

FIGURE 3CH

| | A | B | C | D | E | F | G | H | I | J |
|---|---|---|---|---|---|---|---|---|---|---|
| ATOM | 4405 | CG | LEU | A2269 | 39.086 | 56.582 | 113.159 | 1.00 | 13.74 |
| ATOM | 4406 | CD1 | LEU | A2269 | 40.281 | 56.370 | 112.248 | 1.00 | 13.15 |
| ATOM | 4407 | CD2 | LEU | A2269 | 38.182 | 55.347 | 113.153 | 1.00 | 11.75 |
| ATOM | 4408 | C | LEU | A2269 | 39.159 | 57.312 | 117.045 | 1.00 | 14.58 |
| ATOM | 4409 | O | LEU | A2269 | 39.170 | 56.362 | 117.833 | 1.00 | 16.42 |
| ATOM | 4410 | N | ILE | A2270 | 39.688 | 58.500 | 117.332 | 1.00 | 14.34 |
| ATOM | 4411 | CA | ILE | A2270 | 40.266 | 58.803 | 118.638 | 1.00 | 14.96 |
| ATOM | 4412 | CB | ILE | A2270 | 40.950 | 60.191 | 118.615 | 1.00 | 15.69 |
| ATOM | 4413 | CG1 | ILE | A2270 | 42.211 | 60.140 | 117.746 | 1.00 | 16.18 |
| ATOM | 4414 | CD1 | ILE | A2270 | 42.594 | 61.472 | 117.141 | 1.00 | 19.16 |
| ATOM | 4415 | CG2 | ILE | A2270 | 41.277 | 60.675 | 120.040 | 1.00 | 15.24 |
| ATOM | 4416 | C | ILE | A2270 | 39.187 | 58.727 | 119.720 | 1.00 | 15.36 |
| ATOM | 4417 | O | ILE | A2270 | 39.404 | 58.136 | 120.782 | 1.00 | 15.73 |
| ATOM | 4418 | N | LYS | A2271 | 38.026 | 59.315 | 119.433 | 1.00 | 15.21 |
| ATOM | 4419 | CA | LYS | A2271 | 36.860 | 59.242 | 120.313 | 1.00 | 17.17 |
| ATOM | 4420 | CB | LYS | A2271 | 35.673 | 59.966 | 119.677 | 1.00 | 20.30 |
| ATOM | 4421 | CG | LYS | A2271 | 35.083 | 61.082 | 120.520 | 1.00 | 24.62 |
| ATOM | 4422 | CD | LYS | A2271 | 33.635 | 61.360 | 120.122 | 1.00 | 26.63 |
| ATOM | 4423 | CE | LYS | A2271 | 32.699 | 61.299 | 121.331 | 1.00 | 28.57 |
| ATOM | 4424 | NZ | LYS | A2271 | 31.267 | 61.537 | 120.953 | 1.00 | 30.45 |
| ATOM | 4425 | C | LYS | A2271 | 36.488 | 57.789 | 120.625 | 1.00 | 15.76 |
| ATOM | 4426 | O | LYS | A2271 | 36.137 | 57.461 | 121.761 | 1.00 | 15.50 |
| ATOM | 4427 | N | SER | A2272 | 36.576 | 56.923 | 119.616 | 1.00 | 14.52 |
| ATOM | 4428 | CA | SER | A2272 | 36.333 | 55.491 | 119.803 | 1.00 | 13.35 |
| ATOM | 4429 | CB | SER | A2272 | 36.235 | 54.771 | 118.457 | 1.00 | 12.72 |
| ATOM | 4430 | OG | SER | A2272 | 35.140 | 55.262 | 117.711 | 1.00 | 15.08 |
| ATOM | 4431 | C | SER | A2272 | 37.414 | 54.847 | 120.676 | 1.00 | 12.64 |
| ATOM | 4432 | O | SER | A2272 | 37.097 | 54.077 | 121.580 | 1.00 | 11.55 |
| ATOM | 4433 | N | MET | A2273 | 38.678 | 55.174 | 120.404 | 1.00 | 13.01 |
| ATOM | 4434 | CA | MET | A2273 | 39.805 | 54.707 | 121.217 | 1.00 | 14.93 |
| ATOM | 4435 | CB | MET | A2273 | 41.112 | 55.300 | 120.712 | 1.00 | 15.78 |
| ATOM | 4436 | CG | MET | A2273 | 41.672 | 54.643 | 119.487 | 1.00 | 17.17 |
| ATOM | 4437 | SD | MET | A2273 | 43.093 | 55.589 | 118.958 | 1.00 | 17.38 |
| ATOM | 4438 | CE | MET | A2273 | 42.898 | 55.497 | 117.193 | 1.00 | 15.78 |
| ATOM | 4439 | C | MET | A2273 | 39.643 | 55.084 | 122.682 | 1.00 | 14.98 |
| ATOM | 4440 | O | MET | A2273 | 39.829 | 54.249 | 123.565 | 1.00 | 13.61 |
| ATOM | 4441 | N | ARG | A2274 | 39.293 | 56.347 | 122.926 | 1.00 | 17.12 |
| ATOM | 4442 | CA | ARG | A2274 | 39.108 | 56.869 | 124.280 | 1.00 | 19.31 |
| ATOM | 4443 | CB | ARG | A2274 | 38.797 | 58.367 | 124.237 | 1.00 | 20.65 |
| ATOM | 4444 | CG | ARG | A2274 | 39.420 | 59.164 | 125.368 | 1.00 | 23.56 |
| ATOM | 4445 | CD | ARG | A2274 | 38.415 | 59.868 | 126.264 | 1.00 | 24.96 |
| ATOM | 4446 | NE | ARG | A2274 | 39.070 | 60.642 | 127.318 | 1.00 | 26.53 |
| ATOM | 4447 | CZ | ARG | A2274 | 39.326 | 61.946 | 127.253 | 1.00 | 27.16 |
| ATOM | 4448 | NH1 | ARG | A2274 | 38.981 | 62.653 | 126.182 | 1.00 | 28.22 |
| ATOM | 4449 | NH2 | ARG | A2274 | 39.929 | 62.549 | 128.268 | 1.00 | 27.69 |
| ATOM | 4450 | C | ARG | A2274 | 38.005 | 56.128 | 125.027 | 1.00 | 19.33 |
| ATOM | 4451 | O | ARG | A2274 | 38.071 | 55.974 | 126.248 | 1.00 | 20.71 |
| ATOM | 4452 | N | ARG | A2275 | 37.005 | 55.666 | 124.279 | 1.00 | 18.83 |
| ATOM | 4453 | CA | ARG | A2275 | 35.848 | 54.983 | 124.844 | 1.00 | 18.20 |
| ATOM | 4454 | CB | ARG | A2275 | 34.630 | 55.161 | 123.925 | 1.00 | 18.82 |
| ATOM | 4455 | CG | ARG | A2275 | 33.343 | 54.527 | 124.440 | 1.00 | 17.93 |
| ATOM | 4456 | CD | ARG | A2275 | 32.118 | 54.813 | 123.592 | 1.00 | 17.15 |

FIGURE 3CI

|      | A    | B   | C D E    | F      | G      | H       | I    | J     |
|------|------|-----|----------|--------|--------|---------|------|-------|
| ATOM | 4457 | NE  | ARG A2275 | 32.253 | 54.337 | 122.213 | 1.00 | 16.94 |
| ATOM | 4458 | CZ  | ARG A2275 | 31.960 | 53.107 | 121.804 | 1.00 | 14.73 |
| ATOM | 4459 | NH1 | ARG A2275 | 31.507 | 52.201 | 122.663 | 1.00 | 13.78 |
| ATOM | 4460 | NH2 | ARG A2275 | 32.119 | 52.780 | 120.529 | 1.00 | 14.20 |
| ATOM | 4461 | C   | ARG A2275 | 36.113 | 53.500 | 125.128 | 1.00 | 19.46 |
| ATOM | 4462 | O   | ARG A2275 | 35.794 | 53.013 | 126.214 | 1.00 | 21.25 |
| ATOM | 4463 | N   | ILE A2276 | 36.701 | 52.784 | 124.172 | 1.00 | 18.60 |
| ATOM | 4464 | CA  | ILE A2276 | 36.797 | 51.323 | 124.291 | 1.00 | 18.03 |
| ATOM | 4465 | CB  | ILE A2276 | 35.984 | 50.607 | 123.165 | 1.00 | 17.86 |
| ATOM | 4466 | CG1 | ILE A2276 | 36.558 | 50.920 | 121.781 | 1.00 | 17.45 |
| ATOM | 4467 | CD1 | ILE A2276 | 36.264 | 49.857 | 120.735 | 1.00 | 18.97 |
| ATOM | 4468 | CG2 | ILE A2276 | 34.503 | 50.968 | 123.251 | 1.00 | 17.61 |
| ATOM | 4469 | C   | ILE A2276 | 38.207 | 50.719 | 124.408 | 1.00 | 17.71 |
| ATOM | 4470 | O   | ILE A2276 | 38.334 | 49.509 | 124.591 | 1.00 | 18.61 |
| ATOM | 4471 | N   | ASP A2277 | 39.253 | 51.535 | 124.295 | 1.00 | 16.66 |
| ATOM | 4472 | CA  | ASP A2277 | 40.606 | 51.039 | 124.565 | 1.00 | 18.58 |
| ATOM | 4473 | CB  | ASP A2277 | 41.633 | 51.534 | 123.544 | 1.00 | 17.00 |
| ATOM | 4474 | CG  | ASP A2277 | 43.010 | 50.923 | 123.773 | 1.00 | 18.22 |
| ATOM | 4475 | OD1 | ASP A2277 | 43.949 | 51.661 | 124.145 | 1.00 | 16.90 |
| ATOM | 4476 | OD2 | ASP A2277 | 43.241 | 49.706 | 123.620 | 1.00 | 18.56 |
| ATOM | 4477 | C   | ASP A2277 | 41.051 | 51.402 | 125.980 | 1.00 | 18.91 |
| ATOM | 4478 | O   | ASP A2277 | 41.239 | 52.582 | 126.287 | 1.00 | 19.34 |
| ATOM | 4479 | N   | PRO A2278 | 41.220 | 50.386 | 126.829 | 1.00 | 19.20 |
| ATOM | 4480 | CA  | PRO A2278 | 41.581 | 50.588 | 128.240 | 1.00 | 18.81 |
| ATOM | 4481 | CB  | PRO A2278 | 41.790 | 49.159 | 128.754 | 1.00 | 19.12 |
| ATOM | 4482 | CG  | PRO A2278 | 40.951 | 48.315 | 127.851 | 1.00 | 19.61 |
| ATOM | 4483 | CD  | PRO A2278 | 41.071 | 48.954 | 126.500 | 1.00 | 19.02 |
| ATOM | 4484 | C   | PRO A2278 | 42.856 | 51.413 | 128.440 | 1.00 | 18.93 |
| ATOM | 4485 | O   | PRO A2278 | 42.872 | 52.290 | 129.310 | 1.00 | 19.69 |
| ATOM | 4486 | N   | ALA A2279 | 43.892 | 51.135 | 127.650 | 1.00 | 18.05 |
| ATOM | 4487 | CA  | ALA A2279 | 45.158 | 51.860 | 127.741 | 1.00 | 18.51 |
| ATOM | 4488 | CB  | ALA A2279 | 46.217 | 51.201 | 126.869 | 1.00 | 18.74 |
| ATOM | 4489 | C   | ALA A2279 | 44.990 | 53.334 | 127.371 | 1.00 | 19.41 |
| ATOM | 4490 | O   | ALA A2279 | 45.428 | 54.213 | 128.116 | 1.00 | 17.91 |
| ATOM | 4491 | N   | TYR A2280 | 44.348 | 53.593 | 126.231 | 1.00 | 19.31 |
| ATOM | 4492 | CA  | TYR A2280 | 44.038 | 54.956 | 125.802 | 1.00 | 21.31 |
| ATOM | 4493 | CB  | TYR A2280 | 43.348 | 54.963 | 124.433 | 1.00 | 21.40 |
| ATOM | 4494 | CG  | TYR A2280 | 43.540 | 56.251 | 123.660 | 1.00 | 21.94 |
| ATOM | 4495 | CD1 | TYR A2280 | 42.715 | 57.355 | 123.882 | 1.00 | 22.02 |
| ATOM | 4496 | CE1 | TYR A2280 | 42.893 | 58.545 | 123.173 | 1.00 | 22.48 |
| ATOM | 4497 | CZ  | TYR A2280 | 43.905 | 58.635 | 122.231 | 1.00 | 23.13 |
| ATOM | 4498 | OH  | TYR A2280 | 44.091 | 59.803 | 121.525 | 1.00 | 24.10 |
| ATOM | 4499 | CE2 | TYR A2280 | 44.737 | 57.554 | 121.992 | 1.00 | 23.23 |
| ATOM | 4500 | CD2 | TYR A2280 | 44.553 | 56.369 | 122.708 | 1.00 | 23.12 |
| ATOM | 4501 | C   | TYR A2280 | 43.169 | 55.681 | 126.827 | 1.00 | 22.26 |
| ATOM | 4502 | O   | TYR A2280 | 43.442 | 56.833 | 127.172 | 1.00 | 21.94 |
| ATOM | 4503 | N   | LYS A2281 | 42.129 | 55.000 | 127.307 | 1.00 | 24.25 |
| ATOM | 4504 | CA  | LYS A2281 | 41.244 | 55.545 | 128.334 | 1.00 | 26.32 |
| ATOM | 4505 | CB  | LYS A2281 | 40.179 | 54.518 | 128.732 | 1.00 | 27.81 |
| ATOM | 4506 | CG  | LYS A2281 | 38.971 | 55.109 | 129.445 | 1.00 | 29.24 |
| ATOM | 4507 | CD  | LYS A2281 | 37.881 | 54.064 | 129.632 | 1.00 | 30.72 |
| ATOM | 4508 | CE  | LYS A2281 | 36.935 | 54.454 | 130.754 | 1.00 | 32.10 |

FIGURE 3CJ

| | A | B | C | D E | F | G | H | I | J |
|---|---|---|---|---|---|---|---|---|---|
| ATOM | 4509 | NZ | LYS | A2281 | 36.334 | 53.259 | 131.412 | 1.00 | 33.00 |
| ATOM | 4510 | C | LYS | A2281 | 42.044 | 55.980 | 129.562 | 1.00 | 27.07 |
| ATOM | 4511 | O | LYS | A2281 | 41.931 | 57.124 | 130.008 | 1.00 | 26.36 |
| ATOM | 4512 | N | LYS | A2282 | 42.858 | 55.065 | 130.087 | 1.00 | 28.10 |
| ATOM | 4513 | CA | LYS | A2282 | 43.678 | 55.329 | 131.267 | 1.00 | 29.02 |
| ATOM | 4514 | CB | LYS | A2282 | 44.442 | 54.066 | 131.689 | 1.00 | 29.95 |
| ATOM | 4515 | CG | LYS | A2282 | 45.160 | 54.172 | 133.029 | 1.00 | 31.43 |
| ATOM | 4516 | CD | LYS | A2282 | 44.330 | 53.587 | 134.161 | 1.00 | 33.14 |
| ATOM | 4517 | CE | LYS | A2282 | 44.979 | 53.852 | 135.515 | 1.00 | 34.29 |
| ATOM | 4518 | NZ | LYS | A2282 | 44.579 | 55.176 | 136.078 | 1.00 | 34.87 |
| ATOM | 4519 | C | LYS | A2282 | 44.635 | 56.500 | 131.045 | 1.00 | 28.83 |
| ATOM | 4520 | O | LYS | A2282 | 44.685 | 57.420 | 131.865 | 1.00 | 30.15 |
| ATOM | 4521 | N | LEU | A2283 | 45.370 | 56.472 | 129.933 | 1.00 | 28.37 |
| ATOM | 4522 | CA | LEU | A2283 | 46.344 | 57.518 | 129.613 | 1.00 | 29.11 |
| ATOM | 4523 | CB | LEU | A2283 | 47.079 | 57.216 | 128.301 | 1.00 | 27.23 |
| ATOM | 4524 | CG | LEU | A2283 | 48.072 | 56.044 | 128.259 | 1.00 | 26.72 |
| ATOM | 4525 | CD1 | LEU | A2283 | 48.447 | 55.714 | 126.822 | 1.00 | 25.40 |
| ATOM | 4526 | CD2 | LEU | A2283 | 49.326 | 56.317 | 129.087 | 1.00 | 26.52 |
| ATOM | 4527 | C | LEU | A2283 | 45.721 | 58.918 | 129.565 | 1.00 | 31.28 |
| ATOM | 4528 | O | LEU | A2283 | 46.317 | 59.881 | 130.060 | 1.00 | 30.53 |
| ATOM | 4529 | N | MET | A2284 | 44.525 | 59.016 | 128.981 | 1.00 | 32.36 |
| ATOM | 4530 | CA | MET | A2284 | 43.797 | 60.281 | 128.892 | 1.00 | 34.77 |
| ATOM | 4531 | CB | MET | A2284 | 42.585 | 60.152 | 127.964 | 1.00 | 35.89 |
| ATOM | 4532 | CG | MET | A2284 | 42.903 | 60.288 | 126.482 | 1.00 | 37.29 |
| ATOM | 4533 | SD | MET | A2284 | 43.356 | 61.962 | 125.985 | 1.00 | 39.49 |
| ATOM | 4534 | CE | MET | A2284 | 42.630 | 62.047 | 124.328 | 1.00 | 40.86 |
| ATOM | 4535 | C | MET | A2284 | 43.347 | 60.767 | 130.267 | 1.00 | 35.70 |
| ATOM | 4536 | O | MET | A2284 | 43.341 | 61.971 | 130.532 | 1.00 | 35.58 |
| ATOM | 4537 | N | GLU | A2285 | 42.971 | 59.824 | 131.128 | 1.00 | 36.90 |
| ATOM | 4538 | CA | GLU | A2285 | 42.554 | 60.126 | 132.496 | 1.00 | 39.20 |
| ATOM | 4539 | CB | GLU | A2285 | 41.899 | 58.903 | 133.142 | 1.00 | 39.31 |
| ATOM | 4540 | CG | GLU | A2285 | 40.486 | 58.624 | 132.654 | 1.00 | 40.19 |
| ATOM | 4541 | CD | GLU | A2285 | 39.930 | 57.303 | 133.156 | 1.00 | 40.40 |
| ATOM | 4542 | OE1 | GLU | A2285 | 38.690 | 57.146 | 133.157 | 1.00 | 40.81 |
| ATOM | 4543 | OE2 | GLU | A2285 | 40.723 | 56.420 | 133.546 | 1.00 | 40.84 |
| ATOM | 4544 | C | GLU | A2285 | 43.726 | 60.614 | 133.351 | 1.00 | 40.48 |
| ATOM | 4545 | O | GLU | A2285 | 43.582 | 61.562 | 134.128 | 1.00 | 41.31 |
| ATOM | 4546 | N | GLN | A2286 | 44.879 | 59.961 | 133.198 | 1.00 | 41.36 |
| ATOM | 4547 | CA | GLN | A2286 | 46.111 | 60.360 | 133.879 | 1.00 | 41.90 |
| ATOM | 4548 | CB | GLN | A2286 | 47.217 | 59.327 | 133.648 | 1.00 | 41.44 |
| ATOM | 4549 | CG | GLN | A2286 | 47.026 | 58.015 | 134.391 | 1.00 | 41.54 |
| ATOM | 4550 | CD | GLN | A2286 | 48.042 | 56.958 | 133.986 | 1.00 | 41.57 |
| ATOM | 4551 | OE1 | GLN | A2286 | 48.958 | 56.651 | 134.746 | 1.00 | 41.50 |
| ATOM | 4552 | NE2 | GLN | A2286 | 47.880 | 56.399 | 132.790 | 1.00 | 41.79 |
| ATOM | 4553 | C | GLN | A2286 | 46.587 | 61.735 | 133.410 | 1.00 | 42.75 |
| ATOM | 4554 | O | GLN | A2286 | 47.212 | 62.473 | 134.171 | 1.00 | 42.44 |
| ATOM | 4555 | N | LEU | A2287 | 46.285 | 62.067 | 132.155 | 1.00 | 43.88 |
| ATOM | 4556 | CA | LEU | A2287 | 46.636 | 63.364 | 131.578 | 1.00 | 45.62 |
| ATOM | 4557 | CB | LEU | A2287 | 46.672 | 63.282 | 130.048 | 1.00 | 44.66 |
| ATOM | 4558 | CG | LEU | A2287 | 47.977 | 62.809 | 129.400 | 1.00 | 44.62 |
| ATOM | 4559 | CD1 | LEU | A2287 | 47.706 | 62.270 | 128.005 | 1.00 | 44.20 |
| ATOM | 4560 | CD2 | LEU | A2287 | 49.020 | 63.923 | 129.353 | 1.00 | 44.23 |

FIGURE 3CK

|      | A    | B   | C   | D E       | F      | G      | H       | I    | J     |
|------|------|-----|-----|-----------|--------|--------|---------|------|-------|
| ATOM | 4561 | C   | LEU | A2287     | 45.693 | 64.487 | 132.024 | 1.00 | 47.37 |
| ATOM | 4562 | O   | LEU | A2287     | 45.985 | 65.669 | 131.821 | 1.00 | 47.66 |
| ATOM | 4563 | N   | GLY | A2288     | 44.568 | 64.109 | 132.630 | 1.00 | 49.35 |
| ATOM | 4564 | CA  | GLY | A2288     | 43.589 | 65.064 | 133.124 | 1.00 | 51.40 |
| ATOM | 4565 | C   | GLY | A2288     | 43.862 | 65.550 | 134.538 | 1.00 | 52.89 |
| ATOM | 4566 | O   | GLY | A2288     | 43.173 | 66.444 | 135.031 | 1.00 | 53.20 |
| ATOM | 4567 | N   | GLU | A2289     | 44.863 | 64.957 | 135.188 | 1.00 | 53.94 |
| ATOM | 4568 | CA  | GLU | A2289     | 45.255 | 65.341 | 136.542 | 1.00 | 55.66 |
| ATOM | 4569 | CB  | GLU | A2289     | 46.152 | 64.269 | 137.167 | 1.00 | 56.35 |
| ATOM | 4570 | CG  | GLU | A2289     | 45.545 | 63.572 | 138.375 | 1.00 | 57.55 |
| ATOM | 4571 | CD  | GLU | A2289     | 44.664 | 62.397 | 137.994 | 1.00 | 58.09 |
| ATOM | 4572 | OE1 | GLU | A2289     | 43.427 | 62.572 | 137.953 | 1.00 | 58.32 |
| ATOM | 4573 | OE2 | GLU | A2289     | 45.206 | 61.299 | 137.737 | 1.00 | 58.38 |
| ATOM | 4574 | C   | GLU | A2289     | 45.966 | 66.697 | 136.547 | 1.00 | 56.28 |
| ATOM | 4575 | O   | GLU | A2289     | 46.905 | 66.908 | 135.775 | 1.00 | 56.42 |
| ATOM | 4576 | N   | PRO | A2290     | 45.513 | 67.613 | 137.406 | 1.00 | 56.85 |
| ATOM | 4577 | CA  | PRO | A2290     | 46.098 | 68.959 | 137.487 | 1.00 | 56.99 |
| ATOM | 4578 | CB  | PRO | A2290     | 45.054 | 69.746 | 138.287 | 1.00 | 57.25 |
| ATOM | 4579 | CG  | PRO | A2290     | 44.367 | 68.721 | 139.134 | 1.00 | 57.24 |
| ATOM | 4580 | CD  | PRO | A2290     | 44.400 | 67.433 | 138.359 | 1.00 | 56.99 |
| ATOM | 4581 | C   | PRO | A2290     | 47.455 | 68.996 | 138.198 | 1.00 | 56.75 |
| ATOM | 4582 | O   | PRO | A2290     | 48.236 | 69.921 | 137.965 | 1.00 | 56.85 |
| ATOM | 4583 | N   | ASP | A2291     | 47.722 | 67.999 | 139.041 | 1.00 | 56.63 |
| ATOM | 4584 | CA  | ASP | A2291     | 48.960 | 67.919 | 139.822 | 1.00 | 56.34 |
| ATOM | 4585 | CB  | ASP | A2291     | 48.708 | 67.160 | 141.130 | 1.00 | 56.98 |
| ATOM | 4586 | CG  | ASP | A2291     | 47.976 | 65.844 | 140.912 | 1.00 | 57.66 |
| ATOM | 4587 | OD1 | ASP | A2291     | 48.611 | 64.776 | 141.054 | 1.00 | 58.11 |
| ATOM | 4588 | OD2 | ASP | A2291     | 46.768 | 65.781 | 140.593 | 1.00 | 57.58 |
| ATOM | 4589 | C   | ASP | A2291     | 50.112 | 67.269 | 139.044 | 1.00 | 55.49 |
| ATOM | 4590 | O   | ASP | A2291     | 51.192 | 67.035 | 139.595 | 1.00 | 55.57 |
| ATOM | 4591 | N   | LEU | A2292     | 49.870 | 66.994 | 137.764 | 1.00 | 54.13 |
| ATOM | 4592 | CA  | LEU | A2292     | 50.832 | 66.326 | 136.891 | 1.00 | 52.29 |
| ATOM | 4593 | CB  | LEU | A2292     | 50.142 | 65.911 | 135.586 | 1.00 | 52.42 |
| ATOM | 4594 | CG  | LEU | A2292     | 49.969 | 64.434 | 135.206 | 1.00 | 52.52 |
| ATOM | 4595 | CD1 | LEU | A2292     | 51.109 | 63.998 | 134.308 | 1.00 | 52.60 |
| ATOM | 4596 | CD2 | LEU | A2292     | 49.836 | 63.502 | 136.412 | 1.00 | 52.73 |
| ATOM | 4597 | C   | LEU | A2292     | 52.045 | 67.202 | 136.583 | 1.00 | 50.71 |
| ATOM | 4598 | O   | LEU | A2292     | 51.898 | 68.341 | 136.131 | 1.00 | 50.69 |
| ATOM | 4599 | N   | SER | A2293     | 53.237 | 66.660 | 136.832 | 1.00 | 48.80 |
| ATOM | 4600 | CA  | SER | A2293     | 54.492 | 67.361 | 136.556 | 1.00 | 46.57 |
| ATOM | 4601 | CB  | SER | A2293     | 55.658 | 66.706 | 137.307 | 1.00 | 46.27 |
| ATOM | 4602 | OG  | SER | A2293     | 55.957 | 65.422 | 136.789 | 1.00 | 45.56 |
| ATOM | 4603 | C   | SER | A2293     | 54.780 | 67.419 | 135.055 | 1.00 | 45.37 |
| ATOM | 4604 | O   | SER | A2293     | 54.231 | 66.631 | 134.282 | 1.00 | 44.92 |
| ATOM | 4605 | N   | ASP | A2294     | 55.640 | 68.355 | 134.655 | 1.00 | 43.88 |
| ATOM | 4606 | CA  | ASP | A2294     | 55.996 | 68.549 | 133.247 | 1.00 | 42.83 |
| ATOM | 4607 | CB  | ASP | A2294     | 56.886 | 69.784 | 133.083 | 1.00 | 43.72 |
| ATOM | 4608 | CG  | ASP | A2294     | 56.114 | 71.082 | 133.232 | 1.00 | 44.48 |
| ATOM | 4609 | OD1 | ASP | A2294     | 55.702 | 71.652 | 132.199 | 1.00 | 44.43 |
| ATOM | 4610 | OD2 | ASP | A2294     | 55.873 | 71.608 | 134.340 | 1.00 | 44.86 |
| ATOM | 4611 | C   | ASP | A2294     | 56.684 | 67.323 | 132.645 | 1.00 | 41.26 |
| ATOM | 4612 | O   | ASP | A2294     | 56.527 | 67.034 | 131.455 | 1.00 | 41.28 |

FIGURE 3CL

| | A | B | C | D | E | F | G | H | I | J |
|---|---|---|---|---|---|---|---|---|---|---|
| ATOM | 4613 | N | LYS | A2295 | | 57.436 | 66.611 | 133.481 | 1.00 | 39.12 |
| ATOM | 4614 | CA | LYS | A2295 | | 58.140 | 65.395 | 133.084 | 1.00 | 37.28 |
| ATOM | 4615 | CB | LYS | A2295 | | 59.175 | 65.026 | 134.148 | 1.00 | 36.25 |
| ATOM | 4616 | CG | LYS | A2295 | | 60.122 | 63.911 | 133.755 | 1.00 | 35.53 |
| ATOM | 4617 | CD | LYS | A2295 | | 60.766 | 63.305 | 134.988 | 1.00 | 34.76 |
| ATOM | 4618 | CE | LYS | A2295 | | 61.994 | 62.508 | 134.621 | 1.00 | 34.07 |
| ATOM | 4619 | NZ | LYS | A2295 | | 63.122 | 62.808 | 135.537 | 1.00 | 33.57 |
| ATOM | 4620 | C | LYS | A2295 | | 57.177 | 64.227 | 132.854 | 1.00 | 36.25 |
| ATOM | 4621 | O | LYS | A2295 | | 57.311 | 63.487 | 131.876 | 1.00 | 34.68 |
| ATOM | 4622 | N | ASP | A2296 | | 56.220 | 64.068 | 133.766 | 1.00 | 35.82 |
| ATOM | 4623 | CA | ASP | A2296 | | 55.213 | 63.015 | 133.671 | 1.00 | 36.20 |
| ATOM | 4624 | CB | ASP | A2296 | | 54.467 | 62.860 | 135.000 | 1.00 | 37.14 |
| ATOM | 4625 | CG | ASP | A2296 | | 55.240 | 62.034 | 136.018 | 1.00 | 38.42 |
| ATOM | 4626 | OD1 | ASP | A2296 | | 55.376 | 62.494 | 137.172 | 1.00 | 38.89 |
| ATOM | 4627 | OD2 | ASP | A2296 | | 55.739 | 60.915 | 135.764 | 1.00 | 38.89 |
| ATOM | 4628 | C | ASP | A2296 | | 54.225 | 63.281 | 132.529 | 1.00 | 35.71 |
| ATOM | 4629 | O | ASP | A2296 | | 53.719 | 62.342 | 131.912 | 1.00 | 34.86 |
| ATOM | 4630 | N | ARG | A2297 | | 53.969 | 64.561 | 132.257 | 1.00 | 34.89 |
| ATOM | 4631 | CA | ARG | A2297 | | 53.099 | 64.985 | 131.161 | 1.00 | 34.46 |
| ATOM | 4632 | CB | ARG | A2297 | | 52.871 | 66.504 | 131.211 | 1.00 | 35.41 |
| ATOM | 4633 | CG | ARG | A2297 | | 51.908 | 67.047 | 130.155 | 1.00 | 37.01 |
| ATOM | 4634 | CD | ARG | A2297 | | 51.036 | 68.196 | 130.635 | 1.00 | 38.16 |
| ATOM | 4635 | NE | ARG | A2297 | | 49.840 | 67.718 | 131.326 | 1.00 | 39.31 |
| ATOM | 4636 | CZ | ARG | A2297 | | 49.480 | 68.075 | 132.556 | 1.00 | 39.65 |
| ATOM | 4637 | NH1 | ARG | A2297 | | 50.218 | 68.928 | 133.258 | 1.00 | 40.09 |
| ATOM | 4638 | NH2 | ARG | A2297 | | 48.372 | 67.576 | 133.088 | 1.00 | 40.11 |
| ATOM | 4639 | C | ARG | A2297 | | 53.666 | 64.574 | 129.802 | 1.00 | 33.34 |
| ATOM | 4640 | O | ARG | A2297 | | 52.957 | 63.987 | 128.983 | 1.00 | 32.91 |
| ATOM | 4641 | N | LYS | A2298 | | 54.945 | 64.878 | 129.580 | 1.00 | 32.14 |
| ATOM | 4642 | CA | LYS | A2298 | | 55.619 | 64.576 | 128.319 | 1.00 | 31.59 |
| ATOM | 4643 | CB | LYS | A2298 | | 57.012 | 65.212 | 128.288 | 1.00 | 33.24 |
| ATOM | 4644 | CG | LYS | A2298 | | 57.538 | 65.512 | 126.891 | 1.00 | 34.27 |
| ATOM | 4645 | CD | LYS | A2298 | | 58.840 | 64.766 | 126.623 | 1.00 | 35.33 |
| ATOM | 4646 | CE | LYS | A2298 | | 60.044 | 65.693 | 126.713 | 1.00 | 35.67 |
| ATOM | 4647 | NZ | LYS | A2298 | | 60.551 | 66.075 | 125.365 | 1.00 | 36.14 |
| ATOM | 4648 | C | LYS | A2298 | | 55.709 | 63.073 | 128.053 | 1.00 | 30.19 |
| ATOM | 4649 | O | LYS | A2298 | | 55.604 | 62.635 | 126.903 | 1.00 | 29.63 |
| ATOM | 4650 | N | ASP | A2299 | | 55.898 | 62.294 | 129.117 | 1.00 | 27.39 |
| ATOM | 4651 | CA | ASP | A2299 | | 55.918 | 60.837 | 129.020 | 1.00 | 25.73 |
| ATOM | 4652 | CB | ASP | A2299 | | 56.415 | 60.211 | 130.328 | 1.00 | 24.69 |
| ATOM | 4653 | CG | ASP | A2299 | | 56.103 | 58.724 | 130.426 | 1.00 | 23.89 |
| ATOM | 4654 | OD1 | ASP | A2299 | | 56.618 | 57.945 | 129.596 | 1.00 | 23.39 |
| ATOM | 4655 | OD2 | ASP | A2299 | | 55.352 | 58.242 | 131.300 | 1.00 | 24.24 |
| ATOM | 4656 | C | ASP | A2299 | | 54.542 | 60.276 | 128.654 | 1.00 | 25.59 |
| ATOM | 4657 | O | ASP | A2299 | | 54.430 | 59.446 | 127.750 | 1.00 | 24.81 |
| ATOM | 4658 | N | LEU | A2300 | | 53.510 | 60.732 | 129.361 | 1.00 | 25.78 |
| ATOM | 4659 | CA | LEU | A2300 | | 52.146 | 60.255 | 129.148 | 1.00 | 27.37 |
| ATOM | 4660 | CB | LEU | A2300 | | 51.206 | 60.770 | 130.243 | 1.00 | 27.00 |
| ATOM | 4661 | CG | LEU | A2300 | | 51.297 | 60.094 | 131.615 | 1.00 | 26.75 |
| ATOM | 4662 | CD1 | LEU | A2300 | | 50.513 | 60.889 | 132.639 | 1.00 | 27.13 |
| ATOM | 4663 | CD2 | LEU | A2300 | | 50.812 | 58.652 | 131.582 | 1.00 | 27.15 |
| ATOM | 4664 | C | LEU | A2300 | | 51.606 | 60.608 | 127.765 | 1.00 | 27.93 |

FIGURE 3CM

|      | A    | B   | C D  | E     | F      | G      | H       | I    | J     |
|------|------|-----|------|-------|--------|--------|---------|------|-------|
| ATOM | 4665 | O   | LEU  | A2300 | 50.964 | 59.777 | 127.122 | 1.00 | 28.58 |
| ATOM | 4666 | N   | GLU  | A2301 | 51.877 | 61.830 | 127.306 | 1.00 | 29.47 |
| ATOM | 4667 | CA  | GLU  | A2301 | 51.451 | 62.259 | 125.972 | 1.00 | 31.39 |
| ATOM | 4668 | CB  | GLU  | A2301 | 51.478 | 63.787 | 125.830 | 1.00 | 32.59 |
| ATOM | 4669 | CG  | GLU  | A2301 | 52.855 | 64.407 | 125.652 | 1.00 | 35.17 |
| ATOM | 4670 | CD  | GLU  | A2301 | 52.830 | 65.925 | 125.701 | 1.00 | 36.42 |
| ATOM | 4671 | OE1 | GLU  | A2301 | 52.155 | 66.491 | 126.591 | 1.00 | 37.24 |
| ATOM | 4672 | OE2 | GLU  | A2301 | 53.493 | 66.553 | 124.849 | 1.00 | 36.69 |
| ATOM | 4673 | C   | GLU  | A2301 | 52.255 | 61.562 | 124.867 | 1.00 | 31.13 |
| ATOM | 4674 | O   | GLU  | A2301 | 51.758 | 61.367 | 123.758 | 1.00 | 31.22 |
| ATOM | 4675 | N   | GLY  | A2302 | 53.493 | 61.188 | 125.183 | 1.00 | 30.79 |
| ATOM | 4676 | CA  | GLY  | A2302 | 54.298 | 60.365 | 124.299 | 1.00 | 29.86 |
| ATOM | 4677 | C   | GLY  | A2302 | 53.694 | 58.979 | 124.167 | 1.00 | 29.08 |
| ATOM | 4678 | O   | GLY  | A2302 | 53.626 | 58.426 | 123.067 | 1.00 | 29.52 |
| ATOM | 4679 | N   | ARG  | A2303 | 53.245 | 58.432 | 125.296 | 1.00 | 27.99 |
| ATOM | 4680 | CA  | ARG  | A2303 | 52.582 | 57.129 | 125.340 | 1.00 | 27.74 |
| ATOM | 4681 | CB  | ARG  | A2303 | 52.455 | 56.644 | 126.785 | 1.00 | 27.44 |
| ATOM | 4682 | CG  | ARG  | A2303 | 53.737 | 56.068 | 127.374 | 1.00 | 27.96 |
| ATOM | 4683 | CD  | ARG  | A2303 | 53.740 | 55.998 | 128.891 | 1.00 | 28.51 |
| ATOM | 4684 | NE  | ARG  | A2303 | 52.711 | 55.093 | 129.405 | 1.00 | 29.70 |
| ATOM | 4685 | CZ  | ARG  | A2303 | 52.326 | 55.026 | 130.677 | 1.00 | 30.12 |
| ATOM | 4686 | NH1 | ARG  | A2303 | 51.380 | 54.167 | 131.037 | 1.00 | 30.28 |
| ATOM | 4687 | NH2 | ARG  | A2303 | 52.878 | 55.815 | 131.592 | 1.00 | 30.63 |
| ATOM | 4688 | C   | ARG  | A2303 | 51.198 | 57.150 | 124.679 | 1.00 | 27.50 |
| ATOM | 4689 | O   | ARG  | A2303 | 50.769 | 56.151 | 124.097 | 1.00 | 25.56 |
| ATOM | 4690 | N   | LEU  | A2304 | 50.505 | 58.283 | 124.784 | 1.00 | 27.70 |
| ATOM | 4691 | CA  | LEU  | A2304 | 49.192 | 58.451 | 124.162 | 1.00 | 28.70 |
| ATOM | 4692 | CB  | LEU  | A2304 | 48.475 | 59.695 | 124.702 | 1.00 | 29.27 |
| ATOM | 4693 | CG  | LEU  | A2304 | 46.996 | 59.860 | 124.327 | 1.00 | 29.79 |
| ATOM | 4694 | CD1 | LEU  | A2304 | 46.090 | 58.970 | 125.171 | 1.00 | 29.37 |
| ATOM | 4695 | CD2 | LEU  | A2304 | 46.573 | 61.317 | 124.439 | 1.00 | 30.53 |
| ATOM | 4696 | C   | LEU  | A2304 | 49.306 | 58.504 | 122.639 | 1.00 | 28.49 |
| ATOM | 4697 | O   | LEU  | A2304 | 48.560 | 57.820 | 121.940 | 1.00 | 28.49 |
| ATOM | 4698 | N   | LYS  | A2305 | 50.244 | 59.310 | 122.142 | 1.00 | 28.89 |
| ATOM | 4699 | CA  | LYS  | A2305 | 50.547 | 59.386 | 120.712 | 1.00 | 30.43 |
| ATOM | 4700 | CB  | LYS  | A2305 | 51.631 | 60.433 | 120.439 | 1.00 | 32.19 |
| ATOM | 4701 | CG  | LYS  | A2305 | 51.186 | 61.568 | 119.525 | 1.00 | 33.99 |
| ATOM | 4702 | CD  | LYS  | A2305 | 51.637 | 61.349 | 118.089 | 1.00 | 35.30 |
| ATOM | 4703 | CE  | LYS  | A2305 | 50.556 | 61.769 | 117.105 | 1.00 | 36.30 |
| ATOM | 4704 | NZ  | LYS  | A2305 | 51.025 | 61.698 | 115.693 | 1.00 | 37.08 |
| ATOM | 4705 | C   | LYS  | A2305 | 50.974 | 58.032 | 120.143 | 1.00 | 30.32 |
| ATOM | 4706 | O   | LYS  | A2305 | 50.571 | 57.668 | 119.035 | 1.00 | 30.56 |
| ATOM | 4707 | N   | ALA  | A2306 | 51.778 | 57.293 | 120.907 | 1.00 | 29.04 |
| ATOM | 4708 | CA  | ALA  | A2306 | 52.220 | 55.958 | 120.510 | 1.00 | 28.59 |
| ATOM | 4709 | CB  | ALA  | A2306 | 53.265 | 55.425 | 121.480 | 1.00 | 27.61 |
| ATOM | 4710 | C   | ALA  | A2306 | 51.044 | 54.987 | 120.390 | 1.00 | 28.67 |
| ATOM | 4711 | O   | ALA  | A2306 | 50.928 | 54.272 | 119.392 | 1.00 | 28.14 |
| ATOM | 4712 | N   | ARG  | A2307 | 50.174 | 54.975 | 121.400 | 1.00 | 28.43 |
| ATOM | 4713 | CA  | ARG  | A2307 | 48.987 | 54.122 | 121.395 | 1.00 | 29.01 |
| ATOM | 4714 | CB  | ARG  | A2307 | 48.265 | 54.182 | 122.746 | 1.00 | 28.73 |
| ATOM | 4715 | CG  | ARG  | A2307 | 47.166 | 53.140 | 122.920 | 1.00 | 28.13 |
| ATOM | 4716 | CD  | ARG  | A2307 | 47.666 | 51.769 | 123.338 | 1.00 | 28.27 |

FIGURE 3CN

| | A | B | C | D | E | F | G | H | I | J |
|---|---|---|---|---|---|---|---|---|---|---|
| ATOM | 4717 | NE | ARG | A2307 | | 46.603 | 50.766 | 123.312 | 1.00 | 28.84 |
| ATOM | 4718 | CZ | ARG | A2307 | | 46.767 | 49.501 | 122.936 | 1.00 | 29.33 |
| ATOM | 4719 | NH1 | ARG | A2307 | | 47.956 | 49.058 | 122.542 | 1.00 | 28.58 |
| ATOM | 4720 | NH2 | ARG | A2307 | | 45.733 | 48.671 | 122.952 | 1.00 | 29.55 |
| ATOM | 4721 | C | ARG | A2307 | | 48.036 | 54.505 | 120.264 | 1.00 | 29.50 |
| ATOM | 4722 | O | ARG | A2307 | | 47.471 | 53.634 | 119.602 | 1.00 | 28.49 |
| ATOM | 4723 | N | GLU | A2308 | | 47.881 | 55.809 | 120.052 | 1.00 | 30.95 |
| ATOM | 4724 | CA | GLU | A2308 | | 47.054 | 56.356 | 118.981 | 1.00 | 33.40 |
| ATOM | 4725 | CB | GLU | A2308 | | 47.010 | 57.882 | 119.082 | 1.00 | 34.23 |
| ATOM | 4726 | CG | GLU | A2308 | | 45.836 | 58.541 | 118.377 | 1.00 | 35.56 |
| ATOM | 4727 | CD | GLU | A2308 | | 45.931 | 60.053 | 118.413 | 1.00 | 36.62 |
| ATOM | 4728 | OE1 | GLU | A2308 | | 46.487 | 60.642 | 117.458 | 1.00 | 36.72 |
| ATOM | 4729 | OE2 | GLU | A2308 | | 45.464 | 60.651 | 119.407 | 1.00 | 37.18 |
| ATOM | 4730 | C | GLU | A2308 | | 47.554 | 55.935 | 117.599 | 1.00 | 34.47 |
| ATOM | 4731 | O | GLU | A2308 | | 46.760 | 55.535 | 116.748 | 1.00 | 34.48 |
| ATOM | 4732 | N | ASP | A2309 | | 48.867 | 56.021 | 117.387 | 1.00 | 35.50 |
| ATOM | 4733 | CA | ASP | A2309 | | 49.475 | 55.679 | 116.101 | 1.00 | 36.46 |
| ATOM | 4734 | CB | ASP | A2309 | | 50.911 | 56.206 | 116.021 | 1.00 | 37.68 |
| ATOM | 4735 | CG | ASP | A2309 | | 50.971 | 57.719 | 115.851 | 1.00 | 39.06 |
| ATOM | 4736 | OD1 | ASP | A2309 | | 51.981 | 58.327 | 116.270 | 1.00 | 39.89 |
| ATOM | 4737 | OD2 | ASP | A2309 | | 50.063 | 58.387 | 115.312 | 1.00 | 39.76 |
| ATOM | 4738 | C | ASP | A2309 | | 49.434 | 54.177 | 115.817 | 1.00 | 36.23 |
| ATOM | 4739 | O | ASP | A2309 | | 49.382 | 53.758 | 114.656 | 1.00 | 35.74 |
| ATOM | 4740 | N | LEU | A2310 | | 49.450 | 53.376 | 116.880 | 1.00 | 35.16 |
| ATOM | 4741 | CA | LEU | A2310 | | 49.322 | 51.927 | 116.760 | 1.00 | 34.92 |
| ATOM | 4742 | CB | LEU | A2310 | | 49.811 | 51.240 | 118.038 | 1.00 | 35.89 |
| ATOM | 4743 | CG | LEU | A2310 | | 49.929 | 49.713 | 118.028 | 1.00 | 36.87 |
| ATOM | 4744 | CD1 | LEU | A2310 | | 51.337 | 49.269 | 117.638 | 1.00 | 37.61 |
| ATOM | 4745 | CD2 | LEU | A2310 | | 49.538 | 49.143 | 119.384 | 1.00 | 37.49 |
| ATOM | 4746 | C | LEU | A2310 | | 47.882 | 51.509 | 116.438 | 1.00 | 33.72 |
| ATOM | 4747 | O | LEU | A2310 | | 47.655 | 50.669 | 115.564 | 1.00 | 34.00 |
| ATOM | 4748 | N | LEU | A2311 | | 46.920 | 52.108 | 117.138 | 1.00 | 31.41 |
| ATOM | 4749 | CA | LEU | A2311 | | 45.511 | 51.722 | 117.029 | 1.00 | 29.12 |
| ATOM | 4750 | CB | LEU | A2311 | | 44.749 | 52.088 | 118.308 | 1.00 | 26.03 |
| ATOM | 4751 | CG | LEU | A2311 | | 45.048 | 51.349 | 119.615 | 1.00 | 24.13 |
| ATOM | 4752 | CD1 | LEU | A2311 | | 44.127 | 51.871 | 120.697 | 1.00 | 22.70 |
| ATOM | 4753 | CD2 | LEU | A2311 | | 44.908 | 49.841 | 119.473 | 1.00 | 23.26 |
| ATOM | 4754 | C | LEU | A2311 | | 44.777 | 52.311 | 115.825 | 1.00 | 28.93 |
| ATOM | 4755 | O | LEU | A2311 | | 43.749 | 51.772 | 115.406 | 1.00 | 29.83 |
| ATOM | 4756 | N | LEU | A2312 | | 45.294 | 53.414 | 115.285 | 1.00 | 28.91 |
| ATOM | 4757 | CA | LEU | A2312 | | 44.636 | 54.131 | 114.190 | 1.00 | 29.30 |
| ATOM | 4758 | CB | LEU | A2312 | | 45.450 | 55.353 | 113.743 | 1.00 | 31.18 |
| ATOM | 4759 | CG | LEU | A2312 | | 44.789 | 56.722 | 113.938 | 1.00 | 32.47 |
| ATOM | 4760 | CD1 | LEU | A2312 | | 45.826 | 57.780 | 114.291 | 1.00 | 33.02 |
| ATOM | 4761 | CD2 | LEU | A2312 | | 44.011 | 57.138 | 112.698 | 1.00 | 33.69 |
| ATOM | 4762 | C | LEU | A2312 | | 44.263 | 53.247 | 112.990 | 1.00 | 28.65 |
| ATOM | 4763 | O | LEU | A2312 | | 43.115 | 53.288 | 112.554 | 1.00 | 27.20 |
| ATOM | 4764 | N | PRO | A2313 | | 45.205 | 52.458 | 112.459 | 1.00 | 28.48 |
| ATOM | 4765 | CA | PRO | A2313 | | 44.900 | 51.566 | 111.333 | 1.00 | 27.60 |
| ATOM | 4766 | CB | PRO | A2313 | | 46.220 | 50.817 | 111.112 | 1.00 | 28.36 |
| ATOM | 4767 | CG | PRO | A2313 | | 47.252 | 51.735 | 111.635 | 1.00 | 28.90 |
| ATOM | 4768 | CD | PRO | A2313 | | 46.625 | 52.358 | 112.845 | 1.00 | 28.56 |

FIGURE 3CO

| | A | B | C | D | E | F | G | H | I | J |
|---|---|---|---|---|---|---|---|---|---|---|
| ATOM | 4769 | C | | PRO | A2313 | 43.775 | 50.576 | 111.629 | 1.00 | 25.63 |
| ATOM | 4770 | O | | PRO | A2313 | 42.913 | 50.394 | 110.773 | 1.00 | 24.63 |
| ATOM | 4771 | N | | ILE | A2314 | 43.778 | 49.958 | 112.809 | 1.00 | 24.94 |
| ATOM | 4772 | CA | | ILE | A2314 | 42.776 | 48.934 | 113.115 | 1.00 | 24.12 |
| ATOM | 4773 | CB | | ILE | A2314 | 43.304 | 47.873 | 114.128 | 1.00 | 25.17 |
| ATOM | 4774 | CG1 | | ILE | A2314 | 42.491 | 46.575 | 114.018 | 1.00 | 26.31 |
| ATOM | 4775 | CD1 | | ILE | A2314 | 42.835 | 45.711 | 112.808 | 1.00 | 27.12 |
| ATOM | 4776 | CG2 | | ILE | A2314 | 43.284 | 48.400 | 115.561 | 1.00 | 25.30 |
| ATOM | 4777 | C | | ILE | A2314 | 41.406 | 49.490 | 113.521 | 1.00 | 21.06 |
| ATOM | 4778 | O | | ILE | A2314 | 40.380 | 48.880 | 113.215 | 1.00 | 21.16 |
| ATOM | 4779 | N | | TYR | A2315 | 41.389 | 50.638 | 114.198 | 1.00 | 17.44 |
| ATOM | 4780 | CA | | TYR | A2315 | 40.127 | 51.299 | 114.535 | 1.00 | 14.81 |
| ATOM | 4781 | CB | | TYR | A2315 | 40.330 | 52.384 | 115.596 | 1.00 | 13.58 |
| ATOM | 4782 | CG | | TYR | A2315 | 40.187 | 51.854 | 117.009 | 1.00 | 12.81 |
| ATOM | 4783 | CD1 | | TYR | A2315 | 41.111 | 50.948 | 117.529 | 1.00 | 11.94 |
| ATOM | 4784 | CE1 | | TYR | A2315 | 40.979 | 50.443 | 118.815 | 1.00 | 11.51 |
| ATOM | 4785 | CZ | | TYR | A2315 | 39.915 | 50.840 | 119.601 | 1.00 | 11.26 |
| ATOM | 4786 | OH | | TYR | A2315 | 39.795 | 50.336 | 120.874 | 1.00 | 11.60 |
| ATOM | 4787 | CE2 | | TYR | A2315 | 38.978 | 51.738 | 119.113 | 1.00 | 12.15 |
| ATOM | 4788 | CD2 | | TYR | A2315 | 39.114 | 52.235 | 117.815 | 1.00 | 12.66 |
| ATOM | 4789 | C | | TYR | A2315 | 39.461 | 51.856 | 113.279 | 1.00 | 14.47 |
| ATOM | 4790 | O | | TYR | A2315 | 38.232 | 51.946 | 113.197 | 1.00 | 12.15 |
| ATOM | 4791 | N | | HIS | A2316 | 40.280 | 52.209 | 112.293 | 1.00 | 14.95 |
| ATOM | 4792 | CA | | HIS | A2316 | 39.769 | 52.606 | 110.989 | 1.00 | 16.10 |
| ATOM | 4793 | CB | | HIS | A2316 | 40.906 | 53.049 | 110.068 | 1.00 | 16.47 |
| ATOM | 4794 | CG | | HIS | A2316 | 40.470 | 53.292 | 108.658 | 1.00 | 17.19 |
| ATOM | 4795 | ND1 | | HIS | A2316 | 39.877 | 54.469 | 108.259 | 1.00 | 18.41 |
| ATOM | 4796 | CE1 | | HIS | A2316 | 39.587 | 54.399 | 106.973 | 1.00 | 18.23 |
| ATOM | 4797 | NE2 | | HIS | A2316 | 39.960 | 53.213 | 106.526 | 1.00 | 17.85 |
| ATOM | 4798 | CD2 | | HIS | A2316 | 40.510 | 52.500 | 107.562 | 1.00 | 17.67 |
| ATOM | 4799 | C | | HIS | A2316 | 39.001 | 51.444 | 110.360 | 1.00 | 14.75 |
| ATOM | 4800 | O | | HIS | A2316 | 37.914 | 51.634 | 109.816 | 1.00 | 15.28 |
| ATOM | 4801 | N | | GLN | A2317 | 39.580 | 50.248 | 110.449 | 1.00 | 15.55 |
| ATOM | 4802 | CA | | GLN | A2317 | 38.952 | 49.025 | 109.958 | 1.00 | 17.04 |
| ATOM | 4803 | CB | B | GLN | A2317 | 39.932 | 47.847 | 109.998 | 0.50 | 17.46 |
| ATOM | 4804 | CB | A | GLN | A2317 | 39.951 | 47.862 | 110.038 | 0.50 | 16.89 |
| ATOM | 4805 | CG | B | GLN | A2317 | 40.848 | 47.750 | 108.774 | 0.50 | 19.74 |
| ATOM | 4806 | CG | A | GLN | A2317 | 39.368 | 46.492 | 109.730 | 0.50 | 18.78 |
| ATOM | 4807 | CD | B | GLN | A2317 | 40.088 | 47.709 | 107.452 | 0.50 | 21.34 |
| ATOM | 4808 | CD | A | GLN | A2317 | 40.298 | 45.601 | 108.928 | 0.50 | 19.56 |
| ATOM | 4809 | OE1 | B | GLN | A2317 | 39.298 | 46.793 | 107.207 | 0.50 | 22.85 |
| ATOM | 4810 | OE1 | A | GLN | A2317 | 39.850 | 44.903 | 108.017 | 0.50 | 19.70 |
| ATOM | 4811 | NE2 | B | GLN | A2317 | 40.327 | 48.700 | 106.599 | 0.50 | 21.05 |
| ATOM | 4812 | NE2 | A | GLN | A2317 | 41.587 | 45.609 | 109.270 | 0.50 | 19.96 |
| ATOM | 4813 | C | | GLN | A2317 | 37.678 | 48.706 | 110.746 | 1.00 | 15.46 |
| ATOM | 4814 | O | | GLN | A2317 | 36.695 | 48.235 | 110.182 | 1.00 | 14.67 |
| ATOM | 4815 | N | | VAL | A2318 | 37.703 | 48.980 | 112.047 | 1.00 | 14.34 |
| ATOM | 4816 | CA | | VAL | A2318 | 36.519 | 48.831 | 112.887 | 1.00 | 12.05 |
| ATOM | 4817 | CB | | VAL | A2318 | 36.828 | 49.134 | 114.375 | 1.00 | 11.04 |
| ATOM | 4818 | CG1 | | VAL | A2318 | 35.539 | 49.261 | 115.183 | 1.00 | 11.03 |
| ATOM | 4819 | CG2 | | VAL | A2318 | 37.715 | 48.049 | 114.966 | 1.00 | 10.93 |
| ATOM | 4820 | C | | VAL | A2318 | 35.401 | 49.741 | 112.376 | 1.00 | 10.77 |

FIGURE 3CP

| | A | B | C | D | E | F | G | H | I | J |
|---|---|---|---|---|---|---|---|---|---|---|
| ATOM | 4821 | O | | VAL | A2318 | 34.254 | 49.310 | 112.265 | 1.00 | 9.97 |
| ATOM | 4822 | N | | ALA | A2319 | 35.756 | 50.990 | 112.061 | 1.00 | 10.36 |
| ATOM | 4823 | CA | | ALA | A2319 | 34.821 | 51.976 | 111.518 | 1.00 | 10.17 |
| ATOM | 4824 | CB | | ALA | A2319 | 35.481 | 53.346 | 111.412 | 1.00 | 9.75 |
| ATOM | 4825 | C | | ALA | A2319 | 34.278 | 51.547 | 110.163 | 1.00 | 10.09 |
| ATOM | 4826 | O | | ALA | A2319 | 33.088 | 51.712 | 109.889 | 1.00 | 9.93 |
| ATOM | 4827 | N | | VAL | A2320 | 35.158 | 51.002 | 109.323 | 1.00 | 10.45 |
| ATOM | 4828 | CA | | VAL | A2320 | 34.772 | 50.468 | 108.015 | 1.00 | 10.97 |
| ATOM | 4829 | CB | | VAL | A2320 | 35.997 | 49.898 | 107.239 | 1.00 | 11.04 |
| ATOM | 4830 | CG1 | | VAL | A2320 | 35.557 | 49.080 | 106.025 | 1.00 | 12.16 |
| ATOM | 4831 | CG2 | | VAL | A2320 | 36.913 | 51.023 | 106.789 | 1.00 | 12.62 |
| ATOM | 4832 | C | | VAL | A2320 | 33.687 | 49.401 | 108.189 | 1.00 | 11.04 |
| ATOM | 4833 | O | | VAL | A2320 | 32.671 | 49.416 | 107.489 | 1.00 | 12.92 |
| ATOM | 4834 | N | | GLN | A2321 | 33.897 | 48.503 | 109.148 | 1.00 | 10.43 |
| ATOM | 4835 | CA | | GLN | A2321 | 32.936 | 47.446 | 109.442 | 1.00 | 10.56 |
| ATOM | 4836 | CB | | GLN | A2321 | 33.523 | 46.424 | 110.417 | 1.00 | 10.44 |
| ATOM | 4837 | CG | | GLN | A2321 | 32.602 | 45.254 | 110.697 | 1.00 | 13.28 |
| ATOM | 4838 | CD | | GLN | A2321 | 32.126 | 44.597 | 109.417 | 1.00 | 14.59 |
| ATOM | 4839 | OE1 | | GLN | A2321 | 32.873 | 43.845 | 108.807 | 1.00 | 17.09 |
| ATOM | 4840 | NE2 | | GLN | A2321 | 30.897 | 44.900 | 108.996 | 1.00 | 12.98 |
| ATOM | 4841 | C | | GLN | A2321 | 31.638 | 48.035 | 109.983 | 1.00 | 10.95 |
| ATOM | 4842 | O | | GLN | A2321 | 30.545 | 47.610 | 109.597 | 1.00 | 10.88 |
| ATOM | 4843 | N | | PHE | A2322 | 31.768 | 49.027 | 110.862 | 1.00 | 11.18 |
| ATOM | 4844 | CA | | PHE | A2322 | 30.614 | 49.771 | 111.357 | 1.00 | 10.37 |
| ATOM | 4845 | CB | | PHE | A2322 | 31.061 | 50.872 | 112.329 | 1.00 | 10.07 |
| ATOM | 4846 | CG | | PHE | A2322 | 29.943 | 51.752 | 112.799 | 1.00 | 10.45 |
| ATOM | 4847 | CD1 | | PHE | A2322 | 29.054 | 51.311 | 113.775 | 1.00 | 9.87 |
| ATOM | 4848 | CE1 | | PHE | A2322 | 28.014 | 52.121 | 114.201 | 1.00 | 10.49 |
| ATOM | 4849 | CZ | | PHE | A2322 | 27.849 | 53.380 | 113.651 | 1.00 | 9.87 |
| ATOM | 4850 | CE2 | | PHE | A2322 | 28.733 | 53.835 | 112.685 | 1.00 | 10.26 |
| ATOM | 4851 | CD2 | | PHE | A2322 | 29.774 | 53.018 | 112.262 | 1.00 | 10.03 |
| ATOM | 4852 | C | | PHE | A2322 | 29.796 | 50.346 | 110.187 | 1.00 | 10.13 |
| ATOM | 4853 | O | | PHE | A2322 | 28.572 | 50.180 | 110.139 | 1.00 | 9.21 |
| ATOM | 4854 | N | | ALA | A2323 | 30.478 | 51.001 | 109.245 | 1.00 | 9.26 |
| ATOM | 4855 | CA | | ALA | A2323 | 29.844 | 51.511 | 108.023 | 1.00 | 9.33 |
| ATOM | 4856 | CB | | ALA | A2323 | 30.867 | 52.255 | 107.152 | 1.00 | 7.90 |
| ATOM | 4857 | C | | ALA | A2323 | 29.177 | 50.383 | 107.229 | 1.00 | 8.89 |
| ATOM | 4858 | O | | ALA | A2323 | 28.033 | 50.510 | 106.800 | 1.00 | 9.74 |
| ATOM | 4859 | N | | ASP | A2324 | 29.899 | 49.277 | 107.067 | 1.00 | 9.64 |
| ATOM | 4860 | CA | | ASP | A2324 | 29.447 | 48.127 | 106.286 | 1.00 | 9.58 |
| ATOM | 4861 | CB | | ASP | A2324 | 30.533 | 47.036 | 106.264 | 1.00 | 9.42 |
| ATOM | 4862 | CG | | ASP | A2324 | 30.123 | 45.820 | 105.445 | 1.00 | 11.92 |
| ATOM | 4863 | OD1 | | ASP | A2324 | 29.964 | 44.722 | 106.032 | 1.00 | 10.60 |
| ATOM | 4864 | OD2 | | ASP | A2324 | 29.909 | 45.879 | 104.211 | 1.00 | 11.49 |
| ATOM | 4865 | C | | ASP | A2324 | 28.113 | 47.549 | 106.765 | 1.00 | 9.79 |
| ATOM | 4866 | O | | ASP | A2324 | 27.281 | 47.152 | 105.948 | 1.00 | 8.75 |
| ATOM | 4867 | N | | PHE | A2325 | 27.907 | 47.513 | 108.082 | 1.00 | 10.23 |
| ATOM | 4868 | CA | | PHE | A2325 | 26.658 | 47.009 | 108.660 | 1.00 | 10.73 |
| ATOM | 4869 | CB | | PHE | A2325 | 26.790 | 46.843 | 110.179 | 1.00 | 12.14 |
| ATOM | 4870 | CG | | PHE | A2325 | 27.571 | 45.627 | 110.601 | 1.00 | 12.20 |
| ATOM | 4871 | CD1 | | PHE | A2325 | 28.503 | 45.714 | 111.634 | 1.00 | 12.35 |
| ATOM | 4872 | CE1 | | PHE | A2325 | 29.228 | 44.594 | 112.040 | 1.00 | 12.61 |

FIGURE 3CQ

| | A | B | C | D E | F | G | H | I | J |
|---|---|---|---|---|---|---|---|---|---|
| ATOM | 4873 | CZ | PHE | A2325 | 29.025 | 43.371 | 111.412 | 1.00 | 12.62 |
| ATOM | 4874 | CE2 | PHE | A2325 | 28.097 | 43.269 | 110.385 | 1.00 | 13.98 |
| ATOM | 4875 | CD2 | PHE | A2325 | 27.371 | 44.396 | 109.985 | 1.00 | 12.99 |
| ATOM | 4876 | C | PHE | A2325 | 25.420 | 47.865 | 108.329 | 1.00 | 12.10 |
| ATOM | 4877 | O | PHE | A2325 | 24.277 | 47.409 | 108.501 | 1.00 | 11.07 |
| ATOM | 4878 | N | HIS | A2326 | 25.649 | 49.099 | 107.870 | 1.00 | 10.90 |
| ATOM | 4879 | CA | HIS | A2326 | 24.575 | 49.960 | 107.372 | 1.00 | 10.73 |
| ATOM | 4880 | CB | HIS | A2326 | 25.001 | 51.437 | 107.355 | 1.00 | 9.69 |
| ATOM | 4881 | CG | HIS | A2326 | 25.258 | 52.039 | 108.702 | 1.00 | 10.59 |
| ATOM | 4882 | ND1 | HIS | A2326 | 26.370 | 51.734 | 109.456 | 1.00 | 11.75 |
| ATOM | 4883 | CE1 | HIS | A2326 | 26.353 | 52.447 | 110.570 | 1.00 | 11.91 |
| ATOM | 4884 | NE2 | HIS | A2326 | 25.282 | 53.219 | 110.553 | 1.00 | 9.86 |
| ATOM | 4885 | CD2 | HIS | A2326 | 24.584 | 52.988 | 109.394 | 1.00 | 9.44 |
| ATOM | 4886 | C | HIS | A2326 | 24.194 | 49.593 | 105.934 | 1.00 | 10.56 |
| ATOM | 4887 | O | HIS | A2326 | 23.158 | 50.036 | 105.425 | 1.00 | 9.76 |
| ATOM | 4888 | N | ASP | A2327 | 25.047 | 48.819 | 105.268 | 1.00 | 10.18 |
| ATOM | 4889 | CA | ASP | A2327 | 24.893 | 48.581 | 103.834 | 1.00 | 10.20 |
| ATOM | 4890 | CB | ASP | A2327 | 26.248 | 48.715 | 103.128 | 1.00 | 12.33 |
| ATOM | 4891 | CG | ASP | A2327 | 26.857 | 50.098 | 103.280 | 1.00 | 11.96 |
| ATOM | 4892 | OD1 | ASP | A2327 | 28.080 | 50.225 | 103.065 | 1.00 | 11.46 |
| ATOM | 4893 | OD2 | ASP | A2327 | 26.201 | 51.109 | 103.617 | 1.00 | 12.41 |
| ATOM | 4894 | C | ASP | A2327 | 24.256 | 47.241 | 103.480 | 1.00 | 11.06 |
| ATOM | 4895 | O | ASP | A2327 | 24.294 | 46.825 | 102.327 | 1.00 | 11.04 |
| ATOM | 4896 | N | THR | A2328 | 23.658 | 46.579 | 104.466 | 1.00 | 10.89 |
| ATOM | 4897 | CA | THR | A2328 | 23.172 | 45.211 | 104.304 | 1.00 | 10.52 |
| ATOM | 4898 | CB | THR | A2328 | 23.036 | 44.529 | 105.685 | 1.00 | 11.86 |
| ATOM | 4899 | OG1 | THR | A2328 | 22.039 | 45.216 | 106.449 | 1.00 | 11.96 |
| ATOM | 4900 | CG2 | THR | A2328 | 24.319 | 44.694 | 106.513 | 1.00 | 9.67 |
| ATOM | 4901 | C | THR | A2328 | 21.830 | 45.136 | 103.579 | 1.00 | 10.75 |
| ATOM | 4902 | O | THR | A2328 | 21.104 | 46.127 | 103.502 | 1.00 | 10.75 |
| ATOM | 4903 | N | PRO | A2329 | 21.506 | 43.957 | 103.049 | 1.00 | 11.10 |
| ATOM | 4904 | CA | PRO | A2329 | 20.162 | 43.674 | 102.534 | 1.00 | 11.21 |
| ATOM | 4905 | CB | PRO | A2329 | 20.229 | 42.185 | 102.174 | 1.00 | 11.46 |
| ATOM | 4906 | CG | PRO | A2329 | 21.650 | 41.919 | 101.938 | 1.00 | 12.35 |
| ATOM | 4907 | CD | PRO | A2329 | 22.414 | 42.812 | 102.865 | 1.00 | 11.17 |
| ATOM | 4908 | C | PRO | A2329 | 19.119 | 43.898 | 103.615 | 1.00 | 10.80 |
| ATOM | 4909 | O | PRO | A2329 | 18.033 | 44.388 | 103.305 | 1.00 | 10.22 |
| ATOM | 4910 | N | GLY | A2330 | 19.459 | 43.560 | 104.860 | 1.00 | 10.43 |
| ATOM | 4911 | CA | GLY | A2330 | 18.596 | 43.820 | 105.997 | 1.00 | 10.76 |
| ATOM | 4912 | C | GLY | A2330 | 18.140 | 45.266 | 106.070 | 1.00 | 10.53 |
| ATOM | 4913 | O | GLY | A2330 | 16.950 | 45.532 | 106.256 | 1.00 | 10.23 |
| ATOM | 4914 | N | ARG | A2331 | 19.072 | 46.204 | 105.917 | 1.00 | 10.69 |
| ATOM | 4915 | CA | ARG | A2331 | 18.699 | 47.618 | 105.933 | 1.00 | 9.97 |
| ATOM | 4916 | CB | ARG | A2331 | 19.899 | 48.556 | 106.114 | 1.00 | 9.65 |
| ATOM | 4917 | CG | ARG | A2331 | 19.443 | 49.969 | 106.479 | 1.00 | 10.40 |
| ATOM | 4918 | CD | ARG | A2331 | 20.528 | 50.998 | 106.796 | 1.00 | 12.22 |
| ATOM | 4919 | NE | ARG | A2331 | 19.881 | 52.240 | 107.223 | 1.00 | 11.99 |
| ATOM | 4920 | CZ | ARG | A2331 | 19.465 | 53.201 | 106.401 | 1.00 | 11.58 |
| ATOM | 4921 | NH1 | ARG | A2331 | 19.663 | 53.107 | 105.089 | 1.00 | 10.57 |
| ATOM | 4922 | NH2 | ARG | A2331 | 18.862 | 54.273 | 106.897 | 1.00 | 10.99 |
| ATOM | 4923 | C | ARG | A2331 | 17.906 | 48.001 | 104.686 | 1.00 | 10.16 |
| ATOM | 4924 | O | ARG | A2331 | 16.932 | 48.735 | 104.778 | 1.00 | 10.49 |

FIGURE 3CR

|  | A | B | C | D | E | F | G | H | I | J |
|---|---|---|---|---|---|---|---|---|---|---|
| ATOM | 4925 | N | MET | | A2332 | 18.321 | 47.485 | 103.532 | 1.00 | 11.19 |
| ATOM | 4926 | CA | MET | | A2332 | 17.627 | 47.744 | 102.278 | 1.00 | 11.59 |
| ATOM | 4927 | CB | MET | | A2332 | 18.245 | 46.937 | 101.130 | 1.00 | 11.96 |
| ATOM | 4928 | CG | MET | | A2332 | 19.631 | 47.385 | 100.724 | 1.00 | 13.91 |
| ATOM | 4929 | SD | MET | | A2332 | 20.157 | 46.464 | 99.277 | 1.00 | 17.28 |
| ATOM | 4930 | CE | MET | | A2332 | 21.688 | 45.769 | 99.829 | 1.00 | 17.15 |
| ATOM | 4931 | C | MET | | A2332 | 16.157 | 47.388 | 102.410 | 1.00 | 10.83 |
| ATOM | 4932 | O | MET | | A2332 | 15.289 | 48.176 | 102.026 | 1.00 | 10.06 |
| ATOM | 4933 | N | LEU | | A2333 | 15.890 | 46.204 | 102.962 | 1.00 | 10.71 |
| ATOM | 4934 | CA | LEU | | A2333 | 14.523 | 45.722 | 103.148 | 1.00 | 12.11 |
| ATOM | 4935 | CB | LEU | | A2333 | 14.525 | 44.260 | 103.625 | 1.00 | 11.97 |
| ATOM | 4936 | CG | LEU | | A2333 | 13.175 | 43.532 | 103.623 | 1.00 | 12.21 |
| ATOM | 4937 | CD1 | LEU | | A2333 | 12.609 | 43.426 | 102.210 | 1.00 | 12.36 |
| ATOM | 4938 | CD2 | LEU | | A2333 | 13.278 | 42.146 | 104.282 | 1.00 | 10.69 |
| ATOM | 4939 | C | LEU | | A2333 | 13.735 | 46.597 | 104.120 | 1.00 | 11.68 |
| ATOM | 4940 | O | LEU | | A2333 | 12.614 | 47.011 | 103.827 | 1.00 | 13.20 |
| ATOM | 4941 | N | GLU | | A2334 | 14.333 | 46.879 | 105.273 | 1.00 | 13.59 |
| ATOM | 4942 | CA | GLU | | A2334 | 13.686 | 47.690 | 106.294 | 1.00 | 13.96 |
| ATOM | 4943 | CB | GLU | | A2334 | 14.566 | 47.774 | 107.552 | 1.00 | 15.96 |
| ATOM | 4944 | CG | B | GLU A2334 | 13.972 | 48.561 | 108.716 | 0.50 | 16.47 |
| ATOM | 4945 | CG | A | GLU A2334 | 13.793 | 48.135 | 108.814 | 0.50 | 18.20 |
| ATOM | 4946 | CD | B | GLU A2334 | 12.602 | 48.071 | 109.157 | 0.50 | 16.36 |
| ATOM | 4947 | CD | A | GLU A2334 | 13.929 | 47.099 | 109.914 | 0.50 | 19.79 |
| ATOM | 4948 | OE1 | B | GLU A2334 | 12.247 | 46.902 | 108.885 | 0.50 | 16.88 |
| ATOM | 4949 | OE1 | A | GLU A2334 | 14.103 | 47.497 | 111.083 | 0.50 | 20.37 |
| ATOM | 4950 | OE2 | B | GLU A2334 | 11.875 | 48.865 | 109.788 | 0.50 | 17.46 |
| ATOM | 4951 | OE2 | A | GLU A2334 | 13.856 | 45.886 | 109.615 | 0.50 | 21.69 |
| ATOM | 4952 | C | GLU | | A2334 | 13.320 | 49.079 | 105.771 | 1.00 | 14.55 |
| ATOM | 4953 | O | GLU | | A2334 | 12.248 | 49.607 | 106.085 | 1.00 | 15.37 |
| ATOM | 4954 | N | LYS | | A2335 | 14.201 | 49.658 | 104.960 | 1.00 | 14.49 |
| ATOM | 4955 | CA | LYS | | A2335 | 13.953 | 50.984 | 104.398 | 1.00 | 15.15 |
| ATOM | 4956 | CB | LYS | | A2335 | 15.275 | 51.705 | 104.086 | 1.00 | 14.27 |
| ATOM | 4957 | CG | LYS | | A2335 | 16.242 | 51.846 | 105.282 | 1.00 | 14.74 |
| ATOM | 4958 | CD | LYS | | A2335 | 15.577 | 52.425 | 106.549 | 1.00 | 14.96 |
| ATOM | 4959 | CE | LYS | | A2335 | 15.365 | 53.931 | 106.439 | 1.00 | 16.10 |
| ATOM | 4960 | NZ | LYS | | A2335 | 14.818 | 54.533 | 107.705 | 1.00 | 16.16 |
| ATOM | 4961 | C | LYS | | A2335 | 13.043 | 50.932 | 103.168 | 1.00 | 15.98 |
| ATOM | 4962 | O | LYS | | A2335 | 12.683 | 51.972 | 102.611 | 1.00 | 17.74 |
| ATOM | 4963 | N | GLY | | A2336 | 12.669 | 49.721 | 102.758 | 1.00 | 14.09 |
| ATOM | 4964 | CA | GLY | | A2336 | 11.762 | 49.525 | 101.644 | 1.00 | 14.16 |
| ATOM | 4965 | C | GLY | | A2336 | 12.302 | 49.838 | 100.257 | 1.00 | 13.86 |
| ATOM | 4966 | O | GLY | | A2336 | 11.518 | 50.148 | 99.358 | 1.00 | 14.72 |
| ATOM | 4967 | N | VAL | | A2337 | 13.620 | 49.756 | 100.064 | 1.00 | 13.53 |
| ATOM | 4968 | CA | VAL | | A2337 | 14.195 | 50.021 | 98.733 | 1.00 | 11.76 |
| ATOM | 4969 | CB | VAL | | A2337 | 15.573 | 50.742 | 98.787 | 1.00 | 10.32 |
| ATOM | 4970 | CG1 | VAL | | A2337 | 15.476 | 52.030 | 99.599 | 1.00 | 7.22 |
| ATOM | 4971 | CG2 | VAL | | A2337 | 16.663 | 49.819 | 99.325 | 1.00 | 9.33 |
| ATOM | 4972 | C | VAL | | A2337 | 14.282 | 48.760 | 97.869 | 1.00 | 12.06 |
| ATOM | 4973 | O | VAL | | A2337 | 14.534 | 48.839 | 96.668 | 1.00 | 13.52 |
| ATOM | 4974 | N | ILE | | A2338 | 14.092 | 47.601 | 98.495 | 1.00 | 11.74 |
| ATOM | 4975 | CA | ILE | | A2338 | 13.998 | 46.332 | 97.780 | 1.00 | 11.31 |
| ATOM | 4976 | CB | ILE | | A2338 | 15.226 | 45.419 | 98.058 | 1.00 | 12.62 |

FIGURE 3CS

| | A | B | C | D | E | F | G | H | I | J |
|---|---|---|---|---|---|---|---|---|---|---|
| ATOM | 4977 | CG1 | ILE | A2338 | | 15.334 | 45.075 | 99.559 | 1.00 | 10.50 |
| ATOM | 4978 | CD1 | ILE | A2338 | | 16.408 | 44.023 | 99.890 | 1.00 | 9.72 |
| ATOM | 4979 | CG2 | ILE | A2338 | | 16.516 | 46.051 | 97.503 | 1.00 | 10.04 |
| ATOM | 4980 | C | ILE | A2338 | | 12.708 | 45.636 | 98.189 | 1.00 | 14.05 |
| ATOM | 4981 | O | ILE | A2338 | | 12.163 | 45.911 | 99.270 | 1.00 | 12.64 |
| ATOM | 4982 | N | SER | A2339 | | 12.223 | 44.746 | 97.326 | 1.00 | 13.34 |
| ATOM | 4983 | CA | SER | A2339 | | 11.004 | 43.982 | 97.589 | 1.00 | 14.64 |
| ATOM | 4984 | CB | SER | A2339 | | 10.379 | 43.503 | 96.274 | 1.00 | 14.79 |
| ATOM | 4985 | OG | SER | A2339 | | 9.980 | 44.597 | 95.467 | 1.00 | 14.61 |
| ATOM | 4986 | C | SER | A2339 | | 11.257 | 42.777 | 98.491 | 1.00 | 14.31 |
| ATOM | 4987 | O | SER | A2339 | | 10.401 | 42.411 | 99.296 | 1.00 | 15.32 |
| ATOM | 4988 | N | ASP | A2340 | | 12.424 | 42.155 | 98.332 | 1.00 | 14.16 |
| ATOM | 4989 | CA | ASP | A2340 | | 12.779 | 40.949 | 99.075 | 1.00 | 15.47 |
| ATOM | 4990 | CB | ASP | A2340 | | 12.177 | 39.705 | 98.410 | 1.00 | 20.19 |
| ATOM | 4991 | CG | ASP | A2340 | | 10.794 | 39.385 | 98.913 | 1.00 | 25.29 |
| ATOM | 4992 | OD1 | ASP | A2340 | | 10.683 | 38.934 | 100.070 | 1.00 | 27.72 |
| ATOM | 4993 | OD2 | ASP | A2340 | | 9.764 | 39.552 | 98.222 | 1.00 | 27.68 |
| ATOM | 4994 | C | ASP | A2340 | | 14.279 | 40.757 | 99.126 | 1.00 | 14.29 |
| ATOM | 4995 | O | ASP | A2340 | | 15.011 | 41.249 | 98.260 | 1.00 | 12.79 |
| ATOM | 4996 | N | ILE | A2341 | | 14.718 | 40.028 | 100.149 | 1.00 | 10.93 |
| ATOM | 4997 | CA | ILE | A2341 | | 16.073 | 39.518 | 100.230 | 1.00 | 10.93 |
| ATOM | 4998 | CB | ILE | A2341 | | 16.579 | 39.519 | 101.691 | 1.00 | 11.64 |
| ATOM | 4999 | CG1 | ILE | A2341 | | 16.641 | 40.946 | 102.252 | 1.00 | 10.30 |
| ATOM | 5000 | CD1 | ILE | A2341 | | 16.887 | 40.997 | 103.766 | 1.00 | 11.76 |
| ATOM | 5001 | CG2 | ILE | A2341 | | 17.944 | 38.818 | 101.793 | 1.00 | 10.84 |
| ATOM | 5002 | C | ILE | A2341 | | 16.028 | 38.093 | 99.692 | 1.00 | 11.91 |
| ATOM | 5003 | O | ILE | A2341 | | 15.231 | 37.273 | 100.150 | 1.00 | 11.66 |
| ATOM | 5004 | N | LEU | A2342 | | 16.878 | 37.803 | 98.717 | 1.00 | 10.95 |
| ATOM | 5005 | CA | LEU | A2342 | | 16.879 | 36.489 | 98.089 | 1.00 | 10.95 |
| ATOM | 5006 | CB | LEU | A2342 | | 16.825 | 36.620 | 96.557 | 1.00 | 10.34 |
| ATOM | 5007 | CG | LEU | A2342 | | 15.663 | 37.425 | 95.943 | 1.00 | 10.98 |
| ATOM | 5008 | CD1 | LEU | A2342 | | 15.677 | 37.298 | 94.427 | 1.00 | 9.71 |
| ATOM | 5009 | CD2 | LEU | A2342 | | 14.293 | 37.005 | 96.500 | 1.00 | 10.62 |
| ATOM | 5010 | C | LEU | A2342 | | 18.087 | 35.681 | 98.520 | 1.00 | 11.13 |
| ATOM | 5011 | O | LEU | A2342 | | 19.049 | 36.216 | 99.072 | 1.00 | 13.53 |
| ATOM | 5012 | N | GLU | A2343 | | 18.014 | 34.376 | 98.300 | 1.00 | 12.88 |
| ATOM | 5013 | CA | GLU | A2343 | | 19.173 | 33.520 | 98.462 | 1.00 | 14.06 |
| ATOM | 5014 | CB | BGLU | A2343 | | 18.909 | 32.422 | 99.487 | 0.50 | 14.75 |
| ATOM | 5015 | CB | AGLU | A2343 | | 18.885 | 32.423 | 99.507 | 0.50 | 15.09 |
| ATOM | 5016 | CG | BGLU | A2343 | | 19.337 | 32.808 | 100.889 | 0.50 | 16.86 |
| ATOM | 5017 | CG | AGLU | A2343 | | 19.418 | 31.030 | 99.184 | 0.50 | 17.16 |
| ATOM | 5018 | CD | BGLU | A2343 | | 19.188 | 31.670 | 101.873 | 0.50 | 17.31 |
| ATOM | 5019 | CD | AGLU | A2343 | | 18.797 | 29.925 | 100.030 | 0.50 | 19.30 |
| ATOM | 5020 | OE1 | BGLU | A2343 | | 20.108 | 30.827 | 101.947 | 0.50 | 18.45 |
| ATOM | 5021 | OE1 | AGLU | A2343 | | 18.057 | 30.236 | 100.990 | 0.50 | 19.55 |
| ATOM | 5022 | OE2 | BGLU | A2343 | | 18.153 | 31.621 | 102.567 | 0.50 | 17.78 |
| ATOM | 5023 | OE2 | AGLU | A2343 | | 19.054 | 28.733 | 99.737 | 0.50 | 19.64 |
| ATOM | 5024 | C | GLU | A2343 | | 19.473 | 32.944 | 97.093 | 1.00 | 12.77 |
| ATOM | 5025 | O | GLU | A2343 | | 18.606 | 32.320 | 96.478 | 1.00 | 11.59 |
| ATOM | 5026 | N | TRP | A2344 | | 20.689 | 33.198 | 96.610 | 1.00 | 12.17 |
| ATOM | 5027 | CA | TRP | A2344 | | 21.114 | 32.821 | 95.259 | 1.00 | 13.46 |
| ATOM | 5028 | CB | TRP | A2344 | | 22.636 | 32.929 | 95.138 | 1.00 | 13.22 |

FIGURE 3CT

| | A | B | C | D E | F | G | H | I | J |
|---|---|---|---|---|---|---|---|---|---|
| ATOM | 5029 | CG | TRP | A2344 | 23.169 | 32.514 | 93.796 | 1.00 | 12.33 |
| ATOM | 5030 | CD1 | TRP | A2344 | 23.912 | 31.400 | 93.521 | 1.00 | 13.45 |
| ATOM | 5031 | NE1 | TRP | A2344 | 24.211 | 31.346 | 92.182 | 1.00 | 12.32 |
| ATOM | 5032 | CE2 | TRP | A2344 | 23.670 | 32.441 | 91.563 | 1.00 | 11.98 |
| ATOM | 5033 | CD2 | TRP | A2344 | 23.003 | 33.199 | 92.552 | 1.00 | 11.87 |
| ATOM | 5034 | CE3 | TRP | A2344 | 22.351 | 34.377 | 92.165 | 1.00 | 10.54 |
| ATOM | 5035 | CZ3 | TRP | A2344 | 22.388 | 34.754 | 90.831 | 1.00 | 11.04 |
| ATOM | 5036 | CH2 | TRP | A2344 | 23.058 | 33.981 | 89.877 | 1.00 | 10.35 |
| ATOM | 5037 | CZ2 | TRP | A2344 | 23.706 | 32.824 | 90.220 | 1.00 | 11.66 |
| ATOM | 5038 | C | TRP | A2344 | 20.667 | 31.428 | 94.825 | 1.00 | 14.84 |
| ATOM | 5039 | O | TRP | A2344 | 20.112 | 31.259 | 93.740 | 1.00 | 14.76 |
| ATOM | 5040 | N | LYS | A2345 | 20.914 | 30.436 | 95.676 | 1.00 | 15.80 |
| ATOM | 5041 | CA | LYS | A2345 | 20.617 | 29.046 | 95.345 | 1.00 | 17.69 |
| ATOM | 5042 | CB | LYS | A2345 | 20.960 | 28.123 | 96.517 | 1.00 | 19.24 |
| ATOM | 5043 | CG | LYS | A2345 | 22.436 | 27.784 | 96.593 | 1.00 | 22.17 |
| ATOM | 5044 | CD | LYS | A2345 | 22.736 | 26.841 | 97.753 | 1.00 | 24.38 |
| ATOM | 5045 | CE | LYS | A2345 | 24.234 | 26.736 | 98.004 | 1.00 | 25.37 |
| ATOM | 5046 | NZ | LYS | A2345 | 24.522 | 25.738 | 99.075 | 1.00 | 27.12 |
| ATOM | 5047 | C | LYS | A2345 | 19.176 | 28.831 | 94.890 | 1.00 | 17.21 |
| ATOM | 5048 | O | LYS | A2345 | 18.943 | 28.091 | 93.938 | 1.00 | 17.56 |
| ATOM | 5049 | N | THR | A2346 | 18.225 | 29.493 | 95.554 | 1.00 | 15.18 |
| ATOM | 5050 | CA | THR | A2346 | 16.800 | 29.328 | 95.243 | 1.00 | 13.87 |
| ATOM | 5051 | CB | THR | A2346 | 15.992 | 29.109 | 96.526 | 1.00 | 13.97 |
| ATOM | 5052 | OG1 | THR | A2346 | 16.148 | 30.249 | 97.376 | 1.00 | 12.31 |
| ATOM | 5053 | CG2 | THR | A2346 | 16.549 | 27.926 | 97.349 | 1.00 | 14.35 |
| ATOM | 5054 | C | THR | A2346 | 16.211 | 30.519 | 94.480 | 1.00 | 12.19 |
| ATOM | 5055 | O | THR | A2346 | 14.986 | 30.614 | 94.310 | 1.00 | 12.54 |
| ATOM | 5056 | N | ALA | A2347 | 17.081 | 31.414 | 94.023 | 1.00 | 9.88 |
| ATOM | 5057 | CA | ALA | A2347 | 16.662 | 32.668 | 93.396 | 1.00 | 10.74 |
| ATOM | 5058 | CB | ALA | A2347 | 17.817 | 33.668 | 93.382 | 1.00 | 10.36 |
| ATOM | 5059 | C | ALA | A2347 | 16.099 | 32.477 | 91.992 | 1.00 | 10.16 |
| ATOM | 5060 | O | ALA | A2347 | 15.242 | 33.244 | 91.557 | 1.00 | 11.00 |
| ATOM | 5061 | N | ARG | A2348 | 16.576 | 31.457 | 91.286 | 1.00 | 10.22 |
| ATOM | 5062 | CA | ARG | A2348 | 16.065 | 31.167 | 89.953 | 1.00 | 11.03 |
| ATOM | 5063 | CB | ARG | A2348 | 16.904 | 30.077 | 89.272 | 1.00 | 9.04 |
| ATOM | 5064 | CG | ARG | A2348 | 16.177 | 29.227 | 88.247 | 1.00 | 8.35 |
| ATOM | 5065 | CD | ARG | A2348 | 16.998 | 28.040 | 87.755 | 1.00 | 7.77 |
| ATOM | 5066 | NE | ARG | A2348 | 16.265 | 27.172 | 86.828 | 1.00 | 6.31 |
| ATOM | 5067 | CZ | ARG | A2348 | 16.076 | 27.425 | 85.533 | 1.00 | 7.97 |
| ATOM | 5068 | NH1 | ARG | A2348 | 16.554 | 28.542 | 84.976 | 1.00 | 6.36 |
| ATOM | 5069 | NH2 | ARG | A2348 | 15.401 | 26.556 | 84.787 | 1.00 | 5.73 |
| ATOM | 5070 | C | ARG | A2348 | 14.590 | 30.778 | 90.048 | 1.00 | 11.28 |
| ATOM | 5071 | O | ARG | A2348 | 13.765 | 31.262 | 89.274 | 1.00 | 12.35 |
| ATOM | 5072 | N | THR | A2349 | 14.280 | 29.924 | 91.021 | 1.00 | 10.19 |
| ATOM | 5073 | CA | THR | A2349 | 12.921 | 29.467 | 91.283 | 1.00 | 11.23 |
| ATOM | 5074 | CB | THR | A2349 | 12.943 | 28.355 | 92.356 | 1.00 | 11.50 |
| ATOM | 5075 | OG1 | THR | A2349 | 13.811 | 27.296 | 91.926 | 1.00 | 13.12 |
| ATOM | 5076 | CG2 | THR | A2349 | 11.576 | 27.675 | 92.481 | 1.00 | 12.79 |
| ATOM | 5077 | C | THR | A2349 | 12.006 | 30.616 | 91.720 | 1.00 | 9.51 |
| ATOM | 5078 | O | THR | A2349 | 10.896 | 30.759 | 91.202 | 1.00 | 10.35 |
| ATOM | 5079 | N | PHE | A2350 | 12.467 | 31.419 | 92.676 | 1.00 | 9.67 |
| ATOM | 5080 | CA | PHE | A2350 | 11.688 | 32.555 | 93.165 | 1.00 | 11.22 |

FIGURE 3CU

| | A | B | C | D | E | F | G | H | I | J |
|---|---|---|---|---|---|---|---|---|---|---|
| ATOM | 5081 | CB | PHE | A2350 | | 12.405 | 33.271 | 94.318 | 1.00 | 12.38 |
| ATOM | 5082 | CG | PHE | A2350 | | 11.722 | 34.545 | 94.756 | 1.00 | 14.90 |
| ATOM | 5083 | CD1 | PHE | A2350 | | 10.894 | 34.554 | 95.875 | 1.00 | 16.65 |
| ATOM | 5084 | CE1 | PHE | A2350 | | 10.253 | 35.726 | 96.276 | 1.00 | 17.16 |
| ATOM | 5085 | CZ | PHE | A2350 | | 10.430 | 36.891 | 95.556 | 1.00 | 15.61 |
| ATOM | 5086 | CE2 | PHE | A2350 | | 11.247 | 36.893 | 94.434 | 1.00 | 15.85 |
| ATOM | 5087 | CD2 | PHE | A2350 | | 11.888 | 35.727 | 94.041 | 1.00 | 13.59 |
| ATOM | 5088 | C | PHE | A2350 | | 11.399 | 33.555 | 92.041 | 1.00 | 10.94 |
| ATOM | 5089 | O | PHE | A2350 | | 10.257 | 33.986 | 91.862 | 1.00 | 10.46 |
| ATOM | 5090 | N | LEU | A2351 | | 12.433 | 33.940 | 91.301 | 1.00 | 10.30 |
| ATOM | 5091 | CA | LEU | A2351 | | 12.259 | 34.969 | 90.279 | 1.00 | 9.85 |
| ATOM | 5092 | CB | LEU | A2351 | | 13.596 | 35.603 | 89.862 | 1.00 | 9.54 |
| ATOM | 5093 | CG | LEU | A2351 | | 14.231 | 36.501 | 90.931 | 1.00 | 9.89 |
| ATOM | 5094 | CD1 | LEU | A2351 | | 15.694 | 36.775 | 90.604 | 1.00 | 11.99 |
| ATOM | 5095 | CD2 | LEU | A2351 | | 13.442 | 37.818 | 91.115 | 1.00 | 10.50 |
| ATOM | 5096 | C | LEU | A2351 | | 11.464 | 34.453 | 89.085 | 1.00 | 10.09 |
| ATOM | 5097 | O | LEU | A2351 | | 10.758 | 35.216 | 88.440 | 1.00 | 9.99 |
| ATOM | 5098 | N | TYR | A2352 | | 11.547 | 33.152 | 88.815 | 1.00 | 13.49 |
| ATOM | 5099 | CA | TYR | A2352 | | 10.707 | 32.568 | 87.774 | 1.00 | 14.26 |
| ATOM | 5100 | CB | TYR | A2352 | | 10.959 | 31.069 | 87.586 | 1.00 | 13.39 |
| ATOM | 5101 | CG | TYR | A2352 | | 9.848 | 30.426 | 86.803 | 1.00 | 12.72 |
| ATOM | 5102 | CD1 | TYR | A2352 | | 9.805 | 30.526 | 85.411 | 1.00 | 11.08 |
| ATOM | 5103 | CE1 | TYR | A2352 | | 8.764 | 29.961 | 84.688 | 1.00 | 9.99 |
| ATOM | 5104 | CZ | TYR | A2352 | | 7.746 | 29.302 | 85.358 | 1.00 | 10.65 |
| ATOM | 5105 | OH | TYR | A2352 | | 6.710 | 28.739 | 84.647 | 1.00 | 9.97 |
| ATOM | 5106 | CE2 | TYR | A2352 | | 7.762 | 29.201 | 86.739 | 1.00 | 10.21 |
| ATOM | 5107 | CD2 | TYR | A2352 | | 8.800 | 29.769 | 87.453 | 1.00 | 11.52 |
| ATOM | 5108 | C | TYR | A2352 | | 9.229 | 32.815 | 88.079 | 1.00 | 15.23 |
| ATOM | 5109 | O | TYR | A2352 | | 8.490 | 33.327 | 87.232 | 1.00 | 15.24 |
| ATOM | 5110 | N | TRP | A2353 | | 8.813 | 32.451 | 89.291 | 1.00 | 15.50 |
| ATOM | 5111 | CA | TRP | A2353 | | 7.415 | 32.560 | 89.691 | 1.00 | 14.36 |
| ATOM | 5112 | CB | TRP | A2353 | | 7.154 | 31.783 | 90.982 | 1.00 | 14.04 |
| ATOM | 5113 | CG | TRP | A2353 | | 7.150 | 30.299 | 90.761 | 1.00 | 14.49 |
| ATOM | 5114 | CD1 | TRP | A2353 | | 8.055 | 29.395 | 91.242 | 1.00 | 14.19 |
| ATOM | 5115 | NE1 | TRP | A2353 | | 7.732 | 28.129 | 90.822 | 1.00 | 14.83 |
| ATOM | 5116 | CE2 | TRP | A2353 | | 6.597 | 28.187 | 90.056 | 1.00 | 16.00 |
| ATOM | 5117 | CD2 | TRP | A2353 | | 6.204 | 29.544 | 89.990 | 1.00 | 15.34 |
| ATOM | 5118 | CE3 | TRP | A2353 | | 5.056 | 29.874 | 89.255 | 1.00 | 15.97 |
| ATOM | 5119 | CZ3 | TRP | A2353 | | 4.352 | 28.852 | 88.608 | 1.00 | 15.93 |
| ATOM | 5120 | CH2 | TRP | A2353 | | 4.773 | 27.513 | 88.694 | 1.00 | 17.26 |
| ATOM | 5121 | CZ2 | TRP | A2353 | | 5.886 | 27.160 | 89.412 | 1.00 | 16.60 |
| ATOM | 5122 | C | TRP | A2353 | | 6.971 | 34.008 | 89.824 | 1.00 | 13.80 |
| ATOM | 5123 | O | TRP | A2353 | | 5.824 | 34.343 | 89.516 | 1.00 | 12.09 |
| ATOM | 5124 | N | ARG | A2354 | | 7.885 | 34.860 | 90.279 | 1.00 | 12.95 |
| ATOM | 5125 | CA | ARG | A2354 | | 7.608 | 36.279 | 90.367 | 1.00 | 12.87 |
| ATOM | 5126 | CB | ARG | A2354 | | 8.730 | 37.024 | 91.098 | 1.00 | 12.32 |
| ATOM | 5127 | CG | ARG | A2354 | | 8.392 | 38.485 | 91.410 | 1.00 | 13.07 |
| ATOM | 5128 | CD | ARG | A2354 | | 7.171 | 38.654 | 92.305 | 1.00 | 12.33 |
| ATOM | 5129 | NE | ARG | A2354 | | 6.774 | 40.052 | 92.462 | 1.00 | 12.59 |
| ATOM | 5130 | CZ | ARG | A2354 | | 5.636 | 40.451 | 93.027 | 1.00 | 12.57 |
| ATOM | 5131 | NH1 | ARG | A2354 | | 4.764 | 39.560 | 93.493 | 1.00 | 13.47 |
| ATOM | 5132 | NH2 | ARG | A2354 | | 5.362 | 41.742 | 93.122 | 1.00 | 11.20 |

FIGURE 3CV

|      | A    | B    | C   | D E       | F       | G      | H      | I    | J     |
|------|------|------|-----|-----------|---------|--------|--------|------|-------|
| ATOM | 5133 | C    |     | ARG A2354 | 7.408   | 36.857 | 88.969 | 1.00 | 12.03 |
| ATOM | 5134 | O    |     | ARG A2354 | 6.471   | 37.614 | 88.749 | 1.00 | 14.29 |
| ATOM | 5135 | N    |     | LEU A2355 | 8.287   | 36.493 | 88.038 | 1.00 | 11.29 |
| ATOM | 5136 | CA   |     | LEU A2355 | 8.192   | 36.966 | 86.657 | 1.00 | 10.52 |
| ATOM | 5137 | CB   |     | LEU A2355 | 9.445   | 36.585 | 85.853 | 1.00 | 10.94 |
| ATOM | 5138 | CG   |     | LEU A2355 | 9.557   | 37.078 | 84.402 | 1.00 | 10.50 |
| ATOM | 5139 | CD1  |     | LEU A2355 | 9.470   | 38.588 | 84.293 | 1.00 | 11.58 |
| ATOM | 5140 | CD2  |     | LEU A2355 | 10.840  | 36.575 | 83.773 | 1.00 | 11.64 |
| ATOM | 5141 | C    |     | LEU A2355 | 6.920   | 36.453 | 85.980 | 1.00 | 10.92 |
| ATOM | 5142 | O    |     | LEU A2355 | 6.199   | 37.225 | 85.333 | 1.00 | 7.73  |
| ATOM | 5143 | N    |     | ARG A2356 | 6.636   | 35.162 | 86.149 | 1.00 | 11.10 |
| ATOM | 5144 | CA   |     | ARG A2356 | 5.420   | 34.568 | 85.599 | 1.00 | 11.63 |
| ATOM | 5145 | CB   |     | ARG A2356 | 5.267   | 33.113 | 86.049 | 1.00 | 13.49 |
| ATOM | 5146 | CG   |     | ARG A2356 | 5.944   | 32.067 | 85.190 | 1.00 | 16.00 |
| ATOM | 5147 | CD   |     | ARG A2356 | 5.604   | 32.071 | 83.701 | 1.00 | 18.28 |
| ATOM | 5148 | NE   |     | ARG A2356 | 4.176   | 32.005 | 83.401 | 1.00 | 20.30 |
| ATOM | 5149 | CZ   |     | ARG A2356 | 3.384   | 30.968 | 83.661 | 1.00 | 21.99 |
| ATOM | 5150 | NH1  |     | ARG A2356 | 3.856   | 29.878 | 84.260 | 1.00 | 20.15 |
| ATOM | 5151 | NH2  |     | ARG A2356 | 2.101   | 31.031 | 83.331 | 1.00 | 21.78 |
| ATOM | 5152 | C    |     | ARG A2356 | 4.200   | 35.354 | 86.057 | 1.00 | 10.78 |
| ATOM | 5153 | O    |     | ARG A2356 | 3.340   | 35.709 | 85.255 | 1.00 | 11.67 |
| ATOM | 5154 | N    |     | ARG A2357 | 4.149   | 35.622 | 87.359 | 1.00 | 10.97 |
| ATOM | 5155 | CA   |     | ARG A2357 | 3.056   | 36.360 | 87.983 | 1.00 | 11.85 |
| ATOM | 5156 | CB   |     | ARG A2357 | 3.215   | 36.343 | 89.502 | 1.00 | 14.02 |
| ATOM | 5157 | CG   |     | ARG A2357 | 2.055   | 36.960 | 90.242 | 1.00 | 16.75 |
| ATOM | 5158 | CD   |     | ARG A2357 | 2.475   | 37.839 | 91.377 | 1.00 | 18.32 |
| ATOM | 5159 | NE   |     | ARG A2357 | 1.319   | 38.401 | 92.060 | 1.00 | 18.79 |
| ATOM | 5160 | CZ   |     | ARG A2357 | 0.976   | 38.135 | 93.309 | 1.00 | 18.16 |
| ATOM | 5161 | NH1  |     | ARG A2357 | 1.700   | 37.300 | 94.050 | 1.00 | 18.45 |
| ATOM | 5162 | NH2  |     | ARG A2357 | -0.099  | 38.713 | 93.825 | 1.00 | 18.70 |
| ATOM | 5163 | C    |     | ARG A2357 | 2.940   | 37.800 | 87.487 | 1.00 | 11.92 |
| ATOM | 5164 | O    |     | ARG A2357 | 1.828   | 38.288 | 87.249 | 1.00 | 10.74 |
| ATOM | 5165 | N    |     | LEU A2358 | 4.080   | 38.481 | 87.352 | 1.00 | 9.73  |
| ATOM | 5166 | CA   |     | LEU A2358 | 4.083   | 39.852 | 86.860 | 1.00 | 9.18  |
| ATOM | 5167 | CB   |     | LEU A2358 | 5.468   | 40.503 | 87.014 | 1.00 | 10.31 |
| ATOM | 5168 | CG   |     | LEU A2358 | 5.982   | 40.778 | 88.433 | 1.00 | 11.83 |
| ATOM | 5169 | CD1  |     | LEU A2358 | 7.430   | 41.267 | 88.389 | 1.00 | 10.15 |
| ATOM | 5170 | CD2  |     | LEU A2358 | 5.097   | 41.790 | 89.157 | 1.00 | 12.21 |
| ATOM | 5171 | C    |     | LEU A2358 | 3.606   | 39.933 | 85.413 | 1.00 | 9.18  |
| ATOM | 5172 | O    |     | LEU A2358 | 2.871   | 40.856 | 85.049 | 1.00 | 10.75 |
| ATOM | 5173 | N    |     | LEU A2359 | 4.030   | 38.977 | 84.590 | 1.00 | 8.35  |
| ATOM | 5174 | CA   |     | LEU A2359 | 3.620   | 38.940 | 83.187 | 1.00 | 9.94  |
| ATOM | 5175 | CB   |     | LEU A2359 | 4.426   | 37.897 | 82.405 | 1.00 | 7.73  |
| ATOM | 5176 | CG   |     | LEU A2359 | 5.890   | 38.249 | 82.108 | 1.00 | 6.77  |
| ATOM | 5177 | CD1  |     | LEU A2359 | 6.652   | 37.053 | 81.534 | 1.00 | 5.45  |
| ATOM | 5178 | CD2  |     | LEU A2359 | 5.988   | 39.459 | 81.173 | 1.00 | 4.53  |
| ATOM | 5179 | C    |     | LEU A2359 | 2.114   | 38.691 | 83.053 | 1.00 | 12.81 |
| ATOM | 5180 | O    |     | LEU A2359 | 1.441   | 39.352 | 82.257 | 1.00 | 13.49 |
| ATOM | 5181 | N    |     | LEU A2360 | 1.590   | 37.751 | 83.843 | 1.00 | 13.10 |
| ATOM | 5182 | CA   |     | LEU A2360 | 0.161   | 37.436 | 83.818 | 1.00 | 15.02 |
| ATOM | 5183 | CB   |     | LEU A2360 | -0.139  | 36.151 | 84.589 | 1.00 | 15.29 |
| ATOM | 5184 | CG   |     | LEU A2360 | -0.174  | 34.854 | 83.788 | 1.00 | 14.51 |

FIGURE 3CW

| | A | B | C | D E | F | G | H | I | J |
|---|---|---|---|---|---|---|---|---|---|
| ATOM | 5185 | CD1 | LEU | A2360 | -0.260 | 33.686 | 84.748 | 1.00 | 16.52 |
| ATOM | 5186 | CD2 | LEU | A2360 | -1.337 | 34.831 | 82.795 | 1.00 | 14.85 |
| ATOM | 5187 | C | LEU | A2360 | -0.674 | 38.577 | 84.379 | 1.00 | 17.25 |
| ATOM | 5188 | O | LEU | A2360 | -1.683 | 38.964 | 83.785 | 1.00 | 16.30 |
| ATOM | 5189 | N | GLU | A2361 | -0.240 | 39.120 | 85.515 | 1.00 | 18.38 |
| ATOM | 5190 | CA | GLU | A2361 | -0.916 | 40.256 | 86.125 | 1.00 | 21.75 |
| ATOM | 5191 | CB | GLU | A2361 | -0.237 | 40.657 | 87.432 | 1.00 | 22.50 |
| ATOM | 5192 | CG | GLU | A2361 | -0.832 | 39.969 | 88.648 | 1.00 | 24.00 |
| ATOM | 5193 | CD | GLU | A2361 | -0.340 | 40.553 | 89.955 | 1.00 | 24.20 |
| ATOM | 5194 | OE1 | GLU | A2361 | -0.596 | 39.939 | 91.003 | 1.00 | 25.14 |
| ATOM | 5195 | OE2 | GLU | A2361 | 0.297 | 41.624 | 89.941 | 1.00 | 27.08 |
| ATOM | 5196 | C | GLU | A2361 | -0.992 | 41.450 | 85.180 | 1.00 | 22.64 |
| ATOM | 5197 | O | GLU | A2361 | -2.015 | 42.133 | 85.139 | 1.00 | 24.45 |
| ATOM | 5198 | N | ASP | A2362 | 0.078 | 41.686 | 84.421 | 1.00 | 21.87 |
| ATOM | 5199 | CA | ASP | A2362 | 0.111 | 42.780 | 83.448 | 1.00 | 24.49 |
| ATOM | 5200 | CB | ASP | A2362 | 1.529 | 43.005 | 82.915 | 1.00 | 24.23 |
| ATOM | 5201 | CG | ASP | A2362 | 1.582 | 44.056 | 81.814 | 1.00 | 26.45 |
| ATOM | 5202 | OD1 | ASP | A2362 | 1.605 | 43.672 | 80.623 | 1.00 | 27.03 |
| ATOM | 5203 | OD2 | ASP | A2362 | 1.595 | 45.286 | 82.042 | 1.00 | 27.43 |
| ATOM | 5204 | C | ASP | A2362 | -0.873 | 42.576 | 82.286 | 1.00 | 25.08 |
| ATOM | 5205 | O | ASP | A2362 | -1.477 | 43.538 | 81.810 | 1.00 | 25.79 |
| ATOM | 5206 | N | GLN | A2363 | -1.020 | 41.333 | 81.833 | 1.00 | 26.24 |
| ATOM | 5207 | CA | GLN | A2363 | -1.996 | 40.993 | 80.795 | 1.00 | 28.91 |
| ATOM | 5208 | CB | GLN | A2363 | -1.916 | 39.508 | 80.435 | 1.00 | 27.99 |
| ATOM | 5209 | CG | GLN | A2363 | -0.706 | 39.126 | 79.604 | 1.00 | 28.07 |
| ATOM | 5210 | CD | GLN | A2363 | -0.720 | 37.663 | 79.195 | 1.00 | 29.32 |
| ATOM | 5211 | OE1 | GLN | A2363 | -1.156 | 37.325 | 78.094 | 1.00 | 30.23 |
| ATOM | 5212 | NE2 | GLN | A2363 | -0.249 | 36.794 | 80.081 | 1.00 | 29.58 |
| ATOM | 5213 | C | GLN | A2363 | -3.417 | 41.355 | 81.236 | 1.00 | 30.15 |
| ATOM | 5214 | O | GLN | A2363 | -4.208 | 41.869 | 80.445 | 1.00 | 31.75 |
| ATOM | 5215 | N | VAL | A2364 | -3.724 | 41.091 | 82.505 | 1.00 | 31.33 |
| ATOM | 5216 | CA | VAL | A2364 | -5.018 | 41.436 | 83.092 | 1.00 | 31.80 |
| ATOM | 5217 | CB | VAL | A2364 | -5.253 | 40.689 | 84.429 | 1.00 | 31.36 |
| ATOM | 5218 | CG1 | VAL | A2364 | -6.647 | 40.972 | 84.979 | 1.00 | 30.99 |
| ATOM | 5219 | CG2 | VAL | A2364 | -5.045 | 39.191 | 84.249 | 1.00 | 30.80 |
| ATOM | 5220 | C | VAL | A2364 | -5.133 | 42.948 | 83.306 | 1.00 | 33.65 |
| ATOM | 5221 | O | VAL | A2364 | -6.173 | 43.542 | 83.007 | 1.00 | 34.17 |
| ATOM | 5222 | N | LYS | A2365 | -4.060 | 43.559 | 83.810 | 1.00 | 34.90 |
| ATOM | 5223 | CA | LYS | A2365 | -4.019 | 45.000 | 84.070 | 1.00 | 36.81 |
| ATOM | 5224 | CB | LYS | A2365 | -2.701 | 45.396 | 84.742 | 1.00 | 37.67 |
| ATOM | 5225 | CG | LYS | A2365 | -2.642 | 45.097 | 86.233 | 1.00 | 38.75 |
| ATOM | 5226 | CD | LYS | A2365 | -1.213 | 45.171 | 86.760 | 1.00 | 39.36 |
| ATOM | 5227 | CE | LYS | A2365 | -1.140 | 44.729 | 88.211 | 1.00 | 39.64 |
| ATOM | 5228 | NZ | LYS | A2365 | -0.241 | 45.597 | 89.023 | 1.00 | 40.28 |
| ATOM | 5229 | C | LYS | A2365 | -4.223 | 45.830 | 82.804 | 1.00 | 38.00 |
| ATOM | 5230 | O | LYS | A2365 | -4.826 | 46.904 | 82.857 | 1.00 | 37.15 |
| ATOM | 5231 | N | GLN | A2366 | -3.721 | 45.327 | 81.675 | 1.00 | 39.47 |
| ATOM | 5232 | CA | GLN | A2366 | -3.879 | 46.008 | 80.388 | 1.00 | 41.06 |
| ATOM | 5233 | CB | BGLN | A2366 | -2.843 | 45.504 | 79.378 | 0.50 | 40.76 |
| ATOM | 5234 | CB | AGLN | A2366 | -2.807 | 45.558 | 79.379 | 0.50 | 40.58 |
| ATOM | 5235 | CG | BGLN | A2366 | -1.424 | 46.003 | 79.628 | 0.50 | 40.86 |
| ATOM | 5236 | CG | AGLN | A2366 | -3.067 | 44.219 | 78.696 | 0.50 | 40.46 |

FIGURE 3CX

|      | A    | B    | C    | D | E     | F       | G      | H      | I    | J     |
|------|------|------|------|---|-------|---------|--------|--------|------|-------|
| ATOM | 5237 | CD   | BGLN | A | 2366  | -1.162  | 47.359 | 79.005 | 0.50 | 41.05 |
| ATOM | 5238 | CD   | AGLN | A | 2366  | -2.237  | 44.025 | 77.440 | 0.50 | 40.59 |
| ATOM | 5239 | OE1  | BGLN | A | 2366  | -1.485  | 48.390 | 79.595 | 0.50 | 41.12 |
| ATOM | 5240 | OE1  | AGLN | A | 2366  | -1.171  | 43.409 | 77.483 | 0.50 | 40.07 |
| ATOM | 5241 | NE2  | BGLN | A | 2366  | -0.576  | 47.363 | 77.813 | 0.50 | 40.94 |
| ATOM | 5242 | NE2  | AGLN | A | 2366  | -2.726  | 44.543 | 76.318 | 0.50 | 40.31 |
| ATOM | 5243 | C    | GLN  | A | 2366  | -5.297  | 45.849 | 79.821 | 1.00 | 42.04 |
| ATOM | 5244 | O    | GLN  | A | 2366  | -5.723  | 46.632 | 78.973 | 1.00 | 42.14 |
| ATOM | 5245 | N    | GLU  | A | 2367  | -6.013  | 44.832 | 80.300 | 1.00 | 44.16 |
| ATOM | 5246 | CA   | GLU  | A | 2367  | -7.413  | 44.611 | 79.942 | 1.00 | 45.38 |
| ATOM | 5247 | CB   | GLU  | A | 2367  | -7.809  | 43.157 | 80.201 | 1.00 | 46.99 |
| ATOM | 5248 | CG   | GLU  | A | 2367  | -8.971  | 42.672 | 79.353 | 1.00 | 49.18 |
| ATOM | 5249 | CD   | GLU  | A | 2367  | -8.544  | 41.734 | 78.241 | 1.00 | 50.82 |
| ATOM | 5250 | OE1  | GLU  | A | 2367  | -9.368  | 40.883 | 77.846 | 1.00 | 52.05 |
| ATOM | 5251 | OE2  | GLU  | A | 2367  | -7.395  | 41.845 | 77.757 | 1.00 | 51.58 |
| ATOM | 5252 | C    | GLU  | A | 2367  | -8.335  | 45.552 | 80.718 | 1.00 | 45.01 |
| ATOM | 5253 | O    | GLU  | A | 2367  | -9.319  | 46.058 | 80.173 | 1.00 | 44.95 |
| ATOM | 5254 | N    | ILE  | A | 2368  | -8.013  | 45.770 | 81.991 | 1.00 | 44.54 |
| ATOM | 5255 | CA   | ILE  | A | 2368  | -8.741  | 46.715 | 82.837 | 1.00 | 44.87 |
| ATOM | 5256 | CB   | ILE  | A | 2368  | -8.322  | 46.554 | 84.330 | 1.00 | 44.59 |
| ATOM | 5257 | CG1  | ILE  | A | 2368  | -8.825  | 45.220 | 84.893 | 1.00 | 44.68 |
| ATOM | 5258 | CD1  | ILE  | A | 2368  | -7.957  | 44.640 | 85.997 | 1.00 | 43.90 |
| ATOM | 5259 | CG2  | ILE  | A | 2368  | -8.846  | 47.706 | 85.187 | 1.00 | 44.53 |
| ATOM | 5260 | C    | ILE  | A | 2368  | -8.514  | 48.149 | 82.347 | 1.00 | 45.22 |
| ATOM | 5261 | O    | ILE  | A | 2368  | -9.429  | 48.975 | 82.375 | 1.00 | 45.11 |
| ATOM | 5262 | N    | LEU  | A | 2369  | -7.293  | 48.423 | 81.889 | 1.00 | 45.80 |
| ATOM | 5263 | CA   | LEU  | A | 2369  | -6.903  | 49.747 | 81.413 | 1.00 | 46.61 |
| ATOM | 5264 | CB   | LEU  | A | 2369  | -5.386  | 49.825 | 81.237 | 1.00 | 47.27 |
| ATOM | 5265 | CG   | LEU  | A | 2369  | -4.650  | 50.900 | 82.038 | 1.00 | 48.03 |
| ATOM | 5266 | CD1  | LEU  | A | 2369  | -3.396  | 50.317 | 82.678 | 1.00 | 48.66 |
| ATOM | 5267 | CD2  | LEU  | A | 2369  | -4.302  | 52.098 | 81.156 | 1.00 | 48.54 |
| ATOM | 5268 | C    | LEU  | A | 2369  | -7.597  | 50.144 | 80.112 | 1.00 | 47.07 |
| ATOM | 5269 | O    | LEU  | A | 2369  | -7.928  | 51.312 | 79.919 | 1.00 | 47.81 |
| ATOM | 5270 | N    | GLN  | A | 2370  | -7.810  | 49.178 | 79.220 | 1.00 | 47.28 |
| ATOM | 5271 | CA   | GLN  | A | 2370  | -8.490  | 49.450 | 77.952 | 1.00 | 48.06 |
| ATOM | 5272 | CB   | GLN  | A | 2370  | -8.107  | 48.425 | 76.874 | 1.00 | 49.09 |
| ATOM | 5273 | CG   | GLN  | A | 2370  | -8.565  | 46.993 | 77.138 | 1.00 | 50.22 |
| ATOM | 5274 | CD   | GLN  | A | 2370  | -8.210  | 46.035 | 76.009 | 1.00 | 50.74 |
| ATOM | 5275 | OE1  | GLN  | A | 2370  | -7.270  | 46.277 | 75.247 | 1.00 | 51.45 |
| ATOM | 5276 | NE2  | GLN  | A | 2370  | -8.960  | 44.943 | 75.904 | 1.00 | 50.62 |
| ATOM | 5277 | C    | GLN  | A | 2370  | -10.013 | 49.558 | 78.118 | 1.00 | 47.94 |
| ATOM | 5278 | O    | GLN  | A | 2370  | -10.704 | 50.103 | 77.251 | 1.00 | 47.58 |
| ATOM | 5279 | N    | ALA  | A | 2371  | -10.520 | 49.037 | 79.235 | 1.00 | 47.14 |
| ATOM | 5280 | CA   | ALA  | A | 2371  | -11.935 | 49.145 | 79.581 | 1.00 | 46.73 |
| ATOM | 5281 | CB   | ALA  | A | 2371  | -12.436 | 47.840 | 80.168 | 1.00 | 46.13 |
| ATOM | 5282 | C    | ALA  | A | 2371  | -12.190 | 50.300 | 80.548 | 1.00 | 46.76 |
| ATOM | 5283 | O    | ALA  | A | 2371  | -13.335 | 50.720 | 80.735 | 1.00 | 46.91 |
| ATOM | 5284 | N    | SER  | A | 2372  | -11.118 | 50.795 | 81.165 | 1.00 | 46.20 |
| ATOM | 5285 | CA   | SER  | A | 2372  | -11.168 | 51.932 | 82.082 | 1.00 | 46.40 |
| ATOM | 5286 | CB   | SER  | A | 2372  | -11.658 | 51.496 | 83.466 | 1.00 | 46.75 |
| ATOM | 5287 | OG   | SER  | A | 2372  | -12.691 | 52.346 | 83.931 | 1.00 | 46.80 |
| ATOM | 5288 | C    | SER  | A | 2372  | -9.785  | 52.574 | 82.176 | 1.00 | 46.93 |

FIGURE 3CY

|      | A    | B    | C    | D | E     | F       | G      | H      | I    | J     |
|------|------|------|------|---|-------|---------|--------|--------|------|-------|
| ATOM | 5289 | O    |      | SER | A2372 | -8.958  | 52.186 | 83.007 | 1.00 | 46.08 |
| ATOM | 5290 | N    |      | GLY | A2373 | -9.543  | 53.556 | 81.310 | 1.00 | 48.01 |
| ATOM | 5291 | CA   |      | GLY | A2373 | -8.235  | 54.178 | 81.174 | 1.00 | 49.66 |
| ATOM | 5292 | C    |      | GLY | A2373 | -7.806  | 55.087 | 82.308 | 1.00 | 50.93 |
| ATOM | 5293 | O    |      | GLY | A2373 | -6.608  | 55.294 | 82.515 | 1.00 | 51.70 |
| ATOM | 5294 | N    |      | GLU | A2374 | -8.777  | 55.627 | 83.040 | 1.00 | 52.17 |
| ATOM | 5295 | CA   |      | GLU | A2374 | -8.510  | 56.599 | 84.100 | 1.00 | 53.66 |
| ATOM | 5296 | CB   |      | GLU | A2374 | -9.700  | 57.547 | 84.265 | 1.00 | 54.66 |
| ATOM | 5297 | CG   |      | GLU | A2374 | -9.858  | 58.562 | 83.145 | 1.00 | 55.67 |
| ATOM | 5298 | CD   |      | GLU | A2374 | -10.704 | 59.752 | 83.557 | 1.00 | 56.44 |
| ATOM | 5299 | OE1  |      | GLU | A2374 | -11.924 | 59.574 | 83.770 | 1.00 | 56.75 |
| ATOM | 5300 | OE2  |      | GLU | A2374 | -10.146 | 60.866 | 83.667 | 1.00 | 56.58 |
| ATOM | 5301 | C    |      | GLU | A2374 | -8.172  | 55.954 | 85.445 | 1.00 | 54.08 |
| ATOM | 5302 | O    |      | GLU | A2374 | -7.675  | 56.626 | 86.352 | 1.00 | 54.68 |
| ATOM | 5303 | N    |      | LEU | A2375 | -8.436  | 54.653 | 85.560 | 1.00 | 54.09 |
| ATOM | 5304 | CA   |      | LEU | A2375 | -8.248  | 53.915 | 86.809 | 1.00 | 54.05 |
| ATOM | 5305 | CB   |      | LEU | A2375 | -8.814  | 52.498 | 86.677 | 1.00 | 54.66 |
| ATOM | 5306 | CG   |      | LEU | A2375 | -10.046 | 52.153 | 87.518 | 1.00 | 55.09 |
| ATOM | 5307 | CD1  |      | LEU | A2375 | -11.290 | 52.900 | 87.041 | 1.00 | 55.54 |
| ATOM | 5308 | CD2  |      | LEU | A2375 | -10.283 | 50.653 | 87.492 | 1.00 | 55.68 |
| ATOM | 5309 | C    |      | LEU | A2375 | -6.788  | 53.862 | 87.250 | 1.00 | 53.61 |
| ATOM | 5310 | O    |      | LEU | A2375 | -5.905  | 53.498 | 86.470 | 1.00 | 53.90 |
| ATOM | 5311 | N    |      | SER | A2376 | -6.550  | 54.232 | 88.507 | 1.00 | 52.99 |
| ATOM | 5312 | CA   |      | SER | A2376 | -5.203  | 54.277 | 89.071 | 1.00 | 52.36 |
| ATOM | 5313 | CB   |      | SER | A2376 | -5.196  | 55.059 | 90.391 | 1.00 | 52.63 |
| ATOM | 5314 | OG   |      | SER | A2376 | -5.060  | 54.202 | 91.512 | 1.00 | 52.67 |
| ATOM | 5315 | C    |      | SER | A2376 | -4.615  | 52.880 | 89.260 | 1.00 | 51.75 |
| ATOM | 5316 | O    |      | SER | A2376 | -5.342  | 51.885 | 89.290 | 1.00 | 51.51 |
| ATOM | 5317 | N    |      | HIS | A2377 | -3.293  | 52.823 | 89.391 | 1.00 | 50.77 |
| ATOM | 5318 | CA   |      | HIS | A2377 | -2.568  | 51.559 | 89.498 | 1.00 | 49.87 |
| ATOM | 5319 | CB   | B    | HIS | A2377 | -1.082  | 51.792 | 89.219 | 0.50 | 49.72 |
| ATOM | 5320 | CB   | A    | HIS | A2377 | -1.068  | 51.770 | 89.266 | 0.50 | 49.94 |
| ATOM | 5321 | CG   | B    | HIS | A2377 | -0.826  | 52.741 | 88.087 | 0.50 | 49.34 |
| ATOM | 5322 | CG   | A    | HIS | A2377 | -0.213  | 50.665 | 89.808 | 0.50 | 49.74 |
| ATOM | 5323 | ND1  | B    | HIS | A2377 | -0.470  | 54.058 | 88.285 | 0.50 | 49.21 |
| ATOM | 5324 | ND1  | A    | HIS | A2377 | -0.110  | 49.435 | 89.195 | 0.50 | 49.78 |
| ATOM | 5325 | CE1  | B    | HIS | A2377 | -0.318  | 54.652 | 87.115 | 0.50 | 48.90 |
| ATOM | 5326 | CE1  | A    | HIS | A2377 |  0.705  | 48.664 | 89.892 | 0.50 | 49.58 |
| ATOM | 5327 | NE2  | B    | HIS | A2377 | -0.567  | 53.770 | 86.164 | 0.50 | 48.87 |
| ATOM | 5328 | NE2  | A    | HIS | A2377 |  1.133  | 49.349 | 90.938 | 0.50 | 49.53 |
| ATOM | 5329 | CD2  | B    | HIS | A2377 | -0.891  | 52.567 | 86.746 | 0.50 | 49.13 |
| ATOM | 5330 | CD2  | A    | HIS | A2377 |  0.573  | 50.603 | 90.909 | 0.50 | 49.55 |
| ATOM | 5331 | C    |      | HIS | A2377 | -2.791  | 50.862 | 90.844 | 1.00 | 49.32 |
| ATOM | 5332 | O    |      | HIS | A2377 | -2.902  | 49.632 | 90.898 | 1.00 | 48.79 |
| ATOM | 5333 | N    |      | VAL | A2378 | -2.857  | 51.648 | 91.919 | 1.00 | 48.35 |
| ATOM | 5334 | CA   |      | VAL | A2378 | -3.162  | 51.117 | 93.249 | 1.00 | 47.61 |
| ATOM | 5335 | CB   |      | VAL | A2378 | -2.794  | 52.127 | 94.386 | 1.00 | 47.84 |
| ATOM | 5336 | CG1  |      | VAL | A2378 | -3.719  | 53.348 | 94.394 | 1.00 | 47.61 |
| ATOM | 5337 | CG2  |      | VAL | A2378 | -2.772  | 51.442 | 95.752 | 1.00 | 48.14 |
| ATOM | 5338 | C    |      | VAL | A2378 | -4.624  | 50.645 | 93.329 | 1.00 | 46.74 |
| ATOM | 5339 | O    |      | VAL | A2378 | -4.944  | 49.708 | 94.068 | 1.00 | 46.28 |
| ATOM | 5340 | N    |      | HIS | A2379 | -5.488  | 51.290 | 92.544 | 1.00 | 45.68 |

FIGURE 3CZ

|  | A | B | C | D | E | F | G | H | I | J |
|---|---|---|---|---|---|---|---|---|---|---|
| ATOM | 5341 | CA | | HIS | A2379 | -6.894 | 50.912 | 92.412 | 1.00 | 44.69 |
| ATOM | 5342 | CB | B | HIS | A2379 | -7.650 | 52.001 | 91.640 | 0.35 | 44.33 |
| ATOM | 5343 | CB | A | HIS | A2379 | -7.690 | 52.005 | 91.688 | 0.65 | 45.19 |
| ATOM | 5344 | CG | B | HIS | A2379 | -9.141 | 51.859 | 91.672 | 0.35 | 44.14 |
| ATOM | 5345 | CG | A | HIS | A2379 | -8.164 | 53.107 | 92.587 | 0.65 | 45.82 |
| ATOM | 5346 | ND1 | B | HIS | A2379 | -9.814 | 50.881 | 90.972 | 0.35 | 44.04 |
| ATOM | 5347 | ND1 | A | HIS | A2379 | -9.448 | 53.607 | 92.537 | 0.65 | 45.92 |
| ATOM | 5348 | CE1 | B | HIS | A2379 | -11.112 | 51.007 | 91.180 | 0.35 | 43.89 |
| ATOM | 5349 | CE1 | A | HIS | A2379 | -9.581 | 54.565 | 93.437 | 0.65 | 46.04 |
| ATOM | 5350 | NE2 | B | HIS | A2379 | -11.307 | 52.038 | 91.981 | 0.35 | 44.08 |
| ATOM | 5351 | NE2 | A | HIS | A2379 | -8.430 | 54.704 | 94.070 | 0.65 | 46.06 |
| ATOM | 5352 | CD2 | B | HIS | A2379 | -10.090 | 52.590 | 92.303 | 0.35 | 44.06 |
| ATOM | 5353 | CD2 | A | HIS | A2379 | -7.526 | 53.806 | 93.557 | 0.65 | 45.87 |
| ATOM | 5354 | C | | HIS | A2379 | -7.037 | 49.562 | 91.701 | 1.00 | 43.46 |
| ATOM | 5355 | O | | HIS | A2379 | -7.822 | 48.715 | 92.128 | 1.00 | 42.78 |
| ATOM | 5356 | N | | ILE | A2380 | -6.270 | 49.369 | 90.627 | 1.00 | 42.63 |
| ATOM | 5357 | CA | | ILE | A2380 | -6.271 | 48.107 | 89.881 | 1.00 | 41.70 |
| ATOM | 5358 | CB | | ILE | A2380 | -5.588 | 48.272 | 88.496 | 1.00 | 41.56 |
| ATOM | 5359 | CG1 | | ILE | A2380 | -6.366 | 49.264 | 87.627 | 1.00 | 41.18 |
| ATOM | 5360 | CD1 | | ILE | A2380 | -5.527 | 49.952 | 86.567 | 1.00 | 41.60 |
| ATOM | 5361 | CG2 | | ILE | A2380 | -5.480 | 46.925 | 87.778 | 1.00 | 41.07 |
| ATOM | 5362 | C | | ILE | A2380 | -5.617 | 46.980 | 90.687 | 1.00 | 40.58 |
| ATOM | 5363 | O | | ILE | A2380 | -6.104 | 45.847 | 90.685 | 1.00 | 40.30 |
| ATOM | 5364 | N | | GLN | A2381 | -4.523 | 47.304 | 91.375 | 1.00 | 40.50 |
| ATOM | 5365 | CA | | GLN | A2381 | -3.825 | 46.350 | 92.239 | 1.00 | 40.20 |
| ATOM | 5366 | CB | | GLN | A2381 | -2.582 | 46.990 | 92.861 | 1.00 | 41.30 |
| ATOM | 5367 | CG | | GLN | A2381 | -1.546 | 45.991 | 93.353 | 1.00 | 42.71 |
| ATOM | 5368 | CD | | GLN | A2381 | -0.632 | 45.510 | 92.242 | 1.00 | 43.45 |
| ATOM | 5369 | OE1 | | GLN | A2381 | -0.955 | 44.551 | 91.539 | 1.00 | 43.30 |
| ATOM | 5370 | NE2 | | GLN | A2381 | 0.507 | 46.177 | 92.077 | 1.00 | 43.85 |
| ATOM | 5371 | C | | GLN | A2381 | -4.737 | 45.810 | 93.337 | 1.00 | 40.05 |
| ATOM | 5372 | O | | GLN | A2381 | -4.753 | 44.605 | 93.597 | 1.00 | 40.07 |
| ATOM | 5373 | N | | SER | A2382 | -5.492 | 46.708 | 93.971 | 1.00 | 39.24 |
| ATOM | 5374 | CA | | SER | A2382 | -6.449 | 46.328 | 95.009 | 1.00 | 38.77 |
| ATOM | 5375 | CB | | SER | A2382 | -6.938 | 47.555 | 95.783 | 1.00 | 38.59 |
| ATOM | 5376 | OG | | SER | A2382 | -7.385 | 48.571 | 94.905 | 1.00 | 39.53 |
| ATOM | 5377 | C | | SER | A2382 | -7.630 | 45.576 | 94.407 | 1.00 | 38.01 |
| ATOM | 5378 | O | | SER | A2382 | -8.223 | 44.715 | 95.059 | 1.00 | 38.04 |
| ATOM | 5379 | N | | MET | A2383 | -7.954 | 45.908 | 93.159 | 1.00 | 37.64 |
| ATOM | 5380 | CA | | MET | A2383 | -9.036 | 45.266 | 92.420 | 1.00 | 37.50 |
| ATOM | 5381 | CB | | MET | A2383 | -9.286 | 46.012 | 91.106 | 1.00 | 38.03 |
| ATOM | 5382 | CG | | MET | A2383 | -10.629 | 45.746 | 90.467 | 1.00 | 38.43 |
| ATOM | 5383 | SD | | MET | A2383 | -10.837 | 46.708 | 88.962 | 1.00 | 38.85 |
| ATOM | 5384 | CE | | MET | A2383 | -11.967 | 47.961 | 89.539 | 1.00 | 39.49 |
| ATOM | 5385 | C | | MET | A2383 | -8.735 | 43.793 | 92.145 | 1.00 | 36.78 |
| ATOM | 5386 | O | | MET | A2383 | -9.603 | 42.936 | 92.325 | 1.00 | 36.79 |
| ATOM | 5387 | N | | LEU | A2384 | -7.506 | 43.511 | 91.715 | 1.00 | 36.72 |
| ATOM | 5388 | CA | | LEU | A2384 | -7.067 | 42.146 | 91.428 | 1.00 | 36.19 |
| ATOM | 5389 | CB | | LEU | A2384 | -5.693 | 42.148 | 90.752 | 1.00 | 36.67 |
| ATOM | 5390 | CG | | LEU | A2384 | -5.661 | 42.151 | 89.222 | 1.00 | 36.73 |
| ATOM | 5391 | CD1 | | LEU | A2384 | -4.319 | 42.671 | 88.728 | 1.00 | 36.68 |
| ATOM | 5392 | CD2 | | LEU | A2384 | -5.938 | 40.762 | 88.662 | 1.00 | 36.48 |

FIGURE 3DA

| | A | B | C | D | E | F | G | H | I | J |
|---|---|---|---|---|---|---|---|---|---|---|
| ATOM | 5393 | C | | LEU | A2384 | -7.026 | 41.290 | 92.688 | 1.00 | 35.84 |
| ATOM | 5394 | O | | LEU | A2384 | -7.398 | 40.115 | 92.657 | 1.00 | 36.15 |
| ATOM | 5395 | N | | ARG | A2385 | -6.574 | 41.887 | 93.790 | 1.00 | 35.38 |
| ATOM | 5396 | CA | | ARG | A2385 | -6.578 | 41.233 | 95.096 | 1.00 | 35.08 |
| ATOM | 5397 | CB | | ARG | A2385 | -5.868 | 42.104 | 96.139 | 1.00 | 35.68 |
| ATOM | 5398 | CG | | ARG | A2385 | -5.348 | 41.335 | 97.349 | 1.00 | 35.34 |
| ATOM | 5399 | CD | | ARG | A2385 | -4.976 | 42.215 | 98.535 | 1.00 | 35.78 |
| ATOM | 5400 | NE | | ARG | A2385 | -4.740 | 41.440 | 99.755 | 1.00 | 36.06 |
| ATOM | 5401 | CZ | | ARG | A2385 | -5.685 | 41.088 | 100.626 | 1.00 | 36.93 |
| ATOM | 5402 | NH1 | | ARG | A2385 | -6.953 | 41.428 | 100.427 | 1.00 | 35.81 |
| ATOM | 5403 | NH2 | | ARG | A2385 | -5.362 | 40.386 | 101.704 | 1.00 | 36.96 |
| ATOM | 5404 | C | | ARG | A2385 | -8.003 | 40.914 | 95.549 | 1.00 | 35.20 |
| ATOM | 5405 | O | | ARG | A2385 | -8.262 | 39.822 | 96.060 | 1.00 | 35.32 |
| ATOM | 5406 | N | | ARG | A2386 | -8.917 | 41.867 | 95.350 | 1.00 | 34.35 |
| ATOM | 5407 | CA | | ARG | A2386 | -10.327 | 41.697 | 95.708 | 1.00 | 34.24 |
| ATOM | 5408 | CB | | ARG | A2386 | -11.125 | 42.965 | 95.388 | 1.00 | 35.27 |
| ATOM | 5409 | CG | | ARG | A2386 | -11.170 | 43.979 | 96.515 | 1.00 | 36.24 |
| ATOM | 5410 | CD | | ARG | A2386 | -12.295 | 45.004 | 96.410 | 1.00 | 36.72 |
| ATOM | 5411 | NE | | ARG | A2386 | -12.407 | 45.622 | 95.084 | 1.00 | 37.47 |
| ATOM | 5412 | CZ | | ARG | A2386 | -11.655 | 46.628 | 94.643 | 1.00 | 37.58 |
| ATOM | 5413 | NH1 | | ARG | A2386 | -11.853 | 47.110 | 93.424 | 1.00 | 37.89 |
| ATOM | 5414 | NH2 | | ARG | A2386 | -10.703 | 47.153 | 95.407 | 1.00 | 38.02 |
| ATOM | 5415 | C | | ARG | A2386 | -10.941 | 40.515 | 94.973 | 1.00 | 32.60 |
| ATOM | 5416 | O | | ARG | A2386 | -11.587 | 39.663 | 95.583 | 1.00 | 31.53 |
| ATOM | 5417 | N | | TRP | A2387 | -10.720 | 40.473 | 93.661 | 1.00 | 32.03 |
| ATOM | 5418 | CA | | TRP | A2387 | -11.215 | 39.396 | 92.812 | 1.00 | 32.58 |
| ATOM | 5419 | CB | | TRP | A2387 | -10.859 | 39.667 | 91.343 | 1.00 | 34.75 |
| ATOM | 5420 | CG | | TRP | A2387 | -11.538 | 40.899 | 90.743 | 1.00 | 36.51 |
| ATOM | 5421 | CD1 | | TRP | A2387 | -12.530 | 41.660 | 91.311 | 1.00 | 36.60 |
| ATOM | 5422 | NE1 | | TRP | A2387 | -12.887 | 42.685 | 90.467 | 1.00 | 37.13 |
| ATOM | 5423 | CE2 | | TRP | A2387 | -12.132 | 42.608 | 89.326 | 1.00 | 37.19 |
| ATOM | 5424 | CD2 | | TRP | A2387 | -11.269 | 41.495 | 89.464 | 1.00 | 37.14 |
| ATOM | 5425 | CE3 | | TRP | A2387 | -10.386 | 41.201 | 88.415 | 1.00 | 37.40 |
| ATOM | 5426 | CZ3 | | TRP | A2387 | -10.390 | 42.014 | 87.282 | 1.00 | 38.14 |
| ATOM | 5427 | CH2 | | TRP | A2387 | -11.259 | 43.111 | 87.180 | 1.00 | 37.94 |
| ATOM | 5428 | CZ2 | | TRP | A2387 | -12.136 | 43.423 | 88.187 | 1.00 | 37.85 |
| ATOM | 5429 | C | | TRP | A2387 | -10.683 | 38.036 | 93.274 | 1.00 | 31.57 |
| ATOM | 5430 | O | | TRP | A2387 | -11.405 | 37.041 | 93.239 | 1.00 | 31.41 |
| ATOM | 5431 | N | | PHE | A2388 | -9.430 | 38.011 | 93.730 | 1.00 | 30.93 |
| ATOM | 5432 | CA | | PHE | A2388 | -8.813 | 36.804 | 94.289 | 1.00 | 30.53 |
| ATOM | 5433 | CB | | PHE | A2388 | -7.300 | 36.999 | 94.454 | 1.00 | 28.40 |
| ATOM | 5434 | CG | | PHE | A2388 | -6.602 | 35.843 | 95.121 | 1.00 | 26.17 |
| ATOM | 5435 | CD1 | | PHE | A2388 | -6.403 | 35.834 | 96.499 | 1.00 | 25.26 |
| ATOM | 5436 | CE1 | | PHE | A2388 | -5.759 | 34.770 | 97.120 | 1.00 | 25.39 |
| ATOM | 5437 | CZ | | PHE | A2388 | -5.296 | 33.700 | 96.357 | 1.00 | 25.84 |
| ATOM | 5438 | CE2 | | PHE | A2388 | -5.486 | 33.701 | 94.979 | 1.00 | 25.61 |
| ATOM | 5439 | CD2 | | PHE | A2388 | -6.135 | 34.770 | 94.370 | 1.00 | 25.41 |
| ATOM | 5440 | C | | PHE | A2388 | -9.435 | 36.380 | 95.622 | 1.00 | 31.91 |
| ATOM | 5441 | O | | PHE | A2388 | -9.662 | 35.192 | 95.855 | 1.00 | 31.45 |
| ATOM | 5442 | N | | VAL | A2389 | -9.686 | 37.353 | 96.494 | 1.00 | 33.83 |
| ATOM | 5443 | CA | | VAL | A2389 | -10.314 | 37.100 | 97.793 | 1.00 | 35.88 |
| ATOM | 5444 | CB | | VAL | A2389 | -10.236 | 38.347 | 98.718 | 1.00 | 35.65 |

FIGURE 3DB

|      | A    | B    | C   | D   | E     | F       | G      | H       | I    | J     |
|------|------|------|-----|-----|-------|---------|--------|---------|------|-------|
| ATOM | 5445 | CG1  | VAL | A2389 | -11.056 | 38.155 | 99.994  | 1.00 | 35.33 |
| ATOM | 5446 | CG2  | VAL | A2389 | -8.783  | 38.662 | 99.067  | 1.00 | 35.12 |
| ATOM | 5447 | C    | VAL | A2389 | -11.763 | 36.642 | 97.608  | 1.00 | 37.59 |
| ATOM | 5448 | O    | VAL | A2389 | -12.235 | 35.757 | 98.321  | 1.00 | 37.60 |
| ATOM | 5449 | N    | GLU | A2390 | -12.447 | 37.235 | 96.631  | 1.00 | 40.15 |
| ATOM | 5450 | CA   | GLU | A2390 | -13.834 | 36.892 | 96.318  | 1.00 | 42.43 |
| ATOM | 5451 | CB   | GLU | A2390 | -14.361 | 37.780 | 95.188  | 1.00 | 43.04 |
| ATOM | 5452 | CG   | GLU | A2390 | -15.742 | 38.355 | 95.448  | 1.00 | 43.89 |
| ATOM | 5453 | CD   | GLU | A2390 | -16.530 | 38.577 | 94.171  | 1.00 | 44.24 |
| ATOM | 5454 | OE1  | GLU | A2390 | -16.276 | 39.591 | 93.484  | 1.00 | 44.63 |
| ATOM | 5455 | OE2  | GLU | A2390 | -17.404 | 37.739 | 93.858  | 1.00 | 43.77 |
| ATOM | 5456 | C    | GLU | A2390 | -14.024 | 35.414 | 95.959  | 1.00 | 43.37 |
| ATOM | 5457 | O    | GLU | A2390 | -14.985 | 34.787 | 96.403  | 1.00 | 43.38 |
| ATOM | 5458 | N    | THR | A2391 | -13.103 | 34.865 | 95.169  | 1.00 | 44.50 |
| ATOM | 5459 | CA   | THR | A2391 | -13.222 | 33.486 | 94.684  | 1.00 | 45.28 |
| ATOM | 5460 | CB   | THR | A2391 | -12.704 | 33.355 | 93.230  | 1.00 | 45.55 |
| ATOM | 5461 | OG1  | THR | A2391 | -11.739 | 34.380 | 92.957  | 1.00 | 46.22 |
| ATOM | 5462 | CG2  | THR | A2391 | -13.822 | 33.647 | 92.240  | 1.00 | 45.86 |
| ATOM | 5463 | C    | THR | A2391 | -12.557 | 32.436 | 95.574  | 1.00 | 45.22 |
| ATOM | 5464 | O    | THR | A2391 | -12.929 | 31.261 | 95.529  | 1.00 | 45.37 |
| ATOM | 5465 | N    | GLU | A2392 | -11.586 | 32.856 | 96.381  | 1.00 | 45.34 |
| ATOM | 5466 | CA   | GLU | A2392 | -10.831 | 31.921 | 97.219  | 1.00 | 45.16 |
| ATOM | 5467 | CB   | GLU | A2392 | -9.319  | 32.128 | 97.045  | 1.00 | 45.50 |
| ATOM | 5468 | CG   | GLU | A2392 | -8.795  | 31.853 | 95.641  | 1.00 | 45.59 |
| ATOM | 5469 | CD   | GLU | A2392 | -8.778  | 30.375 | 95.293  | 1.00 | 45.99 |
| ATOM | 5470 | OE1  | GLU | A2392 | -7.773  | 29.698 | 95.599  | 1.00 | 45.87 |
| ATOM | 5471 | OE2  | GLU | A2392 | -9.771  | 29.889 | 94.711  | 1.00 | 45.87 |
| ATOM | 5472 | C    | GLU | A2392 | -11.209 | 31.981 | 98.701  | 1.00 | 45.09 |
| ATOM | 5473 | O    | GLU | A2392 | -11.008 | 31.011 | 99.439  | 1.00 | 44.98 |
| ATOM | 5474 | N    | GLY | A2393 | -11.752 | 33.118 | 99.129  | 1.00 | 44.75 |
| ATOM | 5475 | CA   | GLY | A2393 | -12.145 | 33.307 | 100.516 | 1.00 | 44.44 |
| ATOM | 5476 | C    | GLY | A2393 | -11.181 | 34.182 | 101.295 | 1.00 | 44.43 |
| ATOM | 5477 | O    | GLY | A2393 | -10.026 | 34.362 | 100.896 | 1.00 | 43.89 |
| ATOM | 5478 | N    | ALA | A2394 | -11.664 | 34.723 | 102.412 | 1.00 | 44.05 |
| ATOM | 5479 | CA   | ALA | A2394 | -10.873 | 35.599 | 103.275 | 1.00 | 43.59 |
| ATOM | 5480 | CB   | ALA | A2394 | -11.779 | 36.318 | 104.268 | 1.00 | 44.14 |
| ATOM | 5481 | C    | ALA | A2394 | -9.770  | 34.840 | 104.010 | 1.00 | 43.52 |
| ATOM | 5482 | O    | ALA | A2394 | -8.739  | 35.418 | 104.365 | 1.00 | 43.14 |
| ATOM | 5483 | N    | VAL | A2395 | -10.000 | 33.548 | 104.238 | 1.00 | 43.11 |
| ATOM | 5484 | CA   | VAL | A2395 | -9.021  | 32.672 | 104.881 | 1.00 | 42.99 |
| ATOM | 5485 | CB   | VAL | A2395 | -9.664  | 31.309 | 105.312 | 1.00 | 43.85 |
| ATOM | 5486 | CG1  | VAL | A2395 | -10.314 | 30.585 | 104.126 | 1.00 | 44.42 |
| ATOM | 5487 | CG2  | VAL | A2395 | -8.653  | 30.409 | 106.022 | 1.00 | 43.82 |
| ATOM | 5488 | C    | VAL | A2395 | -7.789  | 32.457 | 103.991 | 1.00 | 42.04 |
| ATOM | 5489 | O    | VAL | A2395 | -6.676  | 32.285 | 104.491 | 1.00 | 41.89 |
| ATOM | 5490 | N    | LYS | A2396 | -8.001  | 32.495 | 102.675 | 1.00 | 40.56 |
| ATOM | 5491 | CA   | LYS | A2396 | -6.936  | 32.267 | 101.701 | 1.00 | 39.22 |
| ATOM | 5492 | CB   | LYS | A2396 | -7.457  | 31.405 | 100.547 | 1.00 | 39.42 |
| ATOM | 5493 | CG   | LYS | A2396 | -7.518  | 29.919 | 100.867 | 1.00 | 40.06 |
| ATOM | 5494 | CD   | LYS | A2396 | -7.564  | 29.081 | 99.601  | 1.00 | 41.14 |
| ATOM | 5495 | CE   | LYS | A2396 | -8.318  | 27.782 | 99.830  | 1.00 | 41.76 |
| ATOM | 5496 | NZ   | LYS | A2396 | -7.390  | 26.647 | 100.074 | 1.00 | 42.73 |

FIGURE 3DC

|  | A | B | C | D E | F | G | H | I | J |
|---|---|---|---|---|---|---|---|---|---|
| ATOM | 5497 | C |  | LYS A2396 | -6.330 | 33.571 | 101.170 | 1.00 | 38.00 |
| ATOM | 5498 | O |  | LYS A2396 | -5.486 | 33.548 | 100.270 | 1.00 | 38.01 |
| ATOM | 5499 | N |  | ALA A2397 | -6.756 | 34.696 | 101.743 | 1.00 | 36.61 |
| ATOM | 5500 | CA |  | ALA A2397 | -6.311 | 36.027 | 101.325 | 1.00 | 34.87 |
| ATOM | 5501 | CB |  | ALA A2397 | -7.040 | 37.100 | 102.116 | 1.00 | 34.73 |
| ATOM | 5502 | C |  | ALA A2397 | -4.796 | 36.228 | 101.427 | 1.00 | 34.22 |
| ATOM | 5503 | O |  | ALA A2397 | -4.220 | 37.011 | 100.668 | 1.00 | 33.94 |
| ATOM | 5504 | N |  | TYR A2398 | -4.164 | 35.515 | 102.358 | 1.00 | 33.15 |
| ATOM | 5505 | CA |  | TYR A2398 | -2.716 | 35.583 | 102.559 | 1.00 | 32.57 |
| ATOM | 5506 | CB |  | TYR A2398 | -2.329 | 34.937 | 103.896 | 1.00 | 33.70 |
| ATOM | 5507 | CG |  | TYR A2398 | -2.130 | 33.434 | 103.847 | 1.00 | 34.62 |
| ATOM | 5508 | CD1 |  | TYR A2398 | -3.219 | 32.559 | 103.905 | 1.00 | 34.96 |
| ATOM | 5509 | CE1 |  | TYR A2398 | -3.032 | 31.174 | 103.864 | 1.00 | 35.62 |
| ATOM | 5510 | CZ |  | TYR A2398 | -1.746 | 30.660 | 103.765 | 1.00 | 35.54 |
| ATOM | 5511 | OH |  | TYR A2398 | -1.541 | 29.299 | 103.725 | 1.00 | 35.96 |
| ATOM | 5512 | CE2 |  | TYR A2398 | -0.655 | 31.510 | 103.707 | 1.00 | 35.47 |
| ATOM | 5513 | CD2 |  | TYR A2398 | -0.851 | 32.887 | 103.750 | 1.00 | 34.94 |
| ATOM | 5514 | C |  | TYR A2398 | -1.913 | 34.966 | 101.405 | 1.00 | 31.59 |
| ATOM | 5515 | O |  | TYR A2398 | -0.747 | 35.310 | 101.204 | 1.00 | 31.68 |
| ATOM | 5516 | N |  | LEU A2399 | -2.543 | 34.063 | 100.654 | 1.00 | 30.28 |
| ATOM | 5517 | CA |  | LEU A2399 | -1.894 | 33.396 | 99.523 | 1.00 | 28.70 |
| ATOM | 5518 | CB |  | LEU A2399 | -2.680 | 32.150 | 99.098 | 1.00 | 28.12 |
| ATOM | 5519 | CG |  | LEU A2399 | -2.728 | 30.971 | 100.076 | 1.00 | 28.46 |
| ATOM | 5520 | CD1 |  | LEU A2399 | -3.875 | 30.043 | 99.717 | 1.00 | 27.92 |
| ATOM | 5521 | CD2 |  | LEU A2399 | -1.407 | 30.207 | 100.102 | 1.00 | 27.51 |
| ATOM | 5522 | C |  | LEU A2399 | -1.683 | 34.328 | 98.326 | 1.00 | 27.78 |
| ATOM | 5523 | O |  | LEU A2399 | -1.080 | 33.932 | 97.330 | 1.00 | 27.19 |
| ATOM | 5524 | N |  | TRP A2400 | -2.188 | 35.557 | 98.429 | 1.00 | 27.33 |
| ATOM | 5525 | CA |  | TRP A2400 | -1.944 | 36.593 | 97.425 | 1.00 | 26.24 |
| ATOM | 5526 | CB |  | TRP A2400 | -2.782 | 37.846 | 97.711 | 1.00 | 25.23 |
| ATOM | 5527 | CG |  | TRP A2400 | -2.647 | 38.908 | 96.655 | 1.00 | 24.34 |
| ATOM | 5528 | CD1 |  | TRP A2400 | -2.078 | 40.143 | 96.802 | 1.00 | 24.41 |
| ATOM | 5529 | NE1 |  | TRP A2400 | -2.131 | 40.835 | 95.615 | 1.00 | 24.00 |
| ATOM | 5530 | CE2 |  | TRP A2400 | -2.736 | 40.053 | 94.667 | 1.00 | 23.47 |
| ATOM | 5531 | CD2 |  | TRP A2400 | -3.072 | 38.826 | 95.286 | 1.00 | 24.11 |
| ATOM | 5532 | CE3 |  | TRP A2400 | -3.710 | 37.841 | 94.516 | 1.00 | 24.08 |
| ATOM | 5533 | CZ3 |  | TRP A2400 | -3.982 | 38.106 | 93.176 | 1.00 | 23.97 |
| ATOM | 5534 | CH2 |  | TRP A2400 | -3.631 | 39.334 | 92.594 | 1.00 | 23.84 |
| ATOM | 5535 | CZ2 |  | TRP A2400 | -3.010 | 40.318 | 93.320 | 1.00 | 23.32 |
| ATOM | 5536 | C |  | TRP A2400 | -0.456 | 36.951 | 97.328 | 1.00 | 25.02 |
| ATOM | 5537 | O |  | TRP A2400 | 0.015 | 37.387 | 96.276 | 1.00 | 25.39 |
| ATOM | 5538 | N |  | ASP A2401 | 0.270 | 36.759 | 98.428 | 1.00 | 23.95 |
| ATOM | 5539 | CA |  | ASP A2401 | 1.713 | 36.975 | 98.467 | 1.00 | 25.03 |
| ATOM | 5540 | CB |  | ASP A2401 | 2.176 | 37.240 | 99.904 | 1.00 | 28.14 |
| ATOM | 5541 | CG |  | ASP A2401 | 1.945 | 38.680 | 100.346 | 1.00 | 30.45 |
| ATOM | 5542 | OD1 |  | ASP A2401 | 1.366 | 39.473 | 99.572 | 1.00 | 31.74 |
| ATOM | 5543 | OD2 |  | ASP A2401 | 2.311 | 39.108 | 101.462 | 1.00 | 32.30 |
| ATOM | 5544 | C |  | ASP A2401 | 2.491 | 35.793 | 97.883 | 1.00 | 23.26 |
| ATOM | 5545 | O |  | ASP A2401 | 3.693 | 35.899 | 97.652 | 1.00 | 23.96 |
| ATOM | 5546 | N |  | ASN A2402 | 1.804 | 34.673 | 97.663 | 1.00 | 20.73 |
| ATOM | 5547 | CA |  | ASN A2402 | 2.408 | 33.475 | 97.085 | 1.00 | 19.85 |
| ATOM | 5548 | CB |  | ASN A2402 | 1.724 | 32.216 | 97.638 | 1.00 | 20.48 |

FIGURE 3DD

| | A | B | C | D | E | F | G | H | I | J |
|---|---|---|---|---|---|---|---|---|---|---|
| ATOM | 5549 | CG | ASN | A2402 | | 2.504 | 30.942 | 97.359 | 1.00 | 21.10 |
| ATOM | 5550 | OD1 | ASN | A2402 | | 2.802 | 30.176 | 98.278 | 1.00 | 22.52 |
| ATOM | 5551 | ND2 | ASN | A2402 | | 2.815 | 30.693 | 96.092 | 1.00 | 19.08 |
| ATOM | 5552 | C | ASN | A2402 | | 2.339 | 33.511 | 95.556 | 1.00 | 19.31 |
| ATOM | 5553 | O | ASN | A2402 | | 1.273 | 33.320 | 94.969 | 1.00 | 19.31 |
| ATOM | 5554 | N | ASN | A2403 | | 3.489 | 33.746 | 94.927 | 1.00 | 18.40 |
| ATOM | 5555 | CA | ASN | A2403 | | 3.578 | 33.946 | 93.480 | 1.00 | 17.78 |
| ATOM | 5556 | CB | ASN | A2403 | | 5.007 | 34.330 | 93.073 | 1.00 | 16.40 |
| ATOM | 5557 | CG | ASN | A2403 | | 5.421 | 35.688 | 93.606 | 1.00 | 15.34 |
| ATOM | 5558 | OD1 | ASN | A2403 | | 4.664 | 36.648 | 93.527 | 1.00 | 15.14 |
| ATOM | 5559 | ND2 | ASN | A2403 | | 6.630 | 35.771 | 94.158 | 1.00 | 15.67 |
| ATOM | 5560 | C | ASN | A2403 | | 3.105 | 32.752 | 92.662 | 1.00 | 18.30 |
| ATOM | 5561 | O | ASN | A2403 | | 2.368 | 32.916 | 91.688 | 1.00 | 15.19 |
| ATOM | 5562 | N | GLN | A2404 | | 3.532 | 31.558 | 93.064 | 1.00 | 18.16 |
| ATOM | 5563 | CA | GLN | A2404 | | 3.141 | 30.331 | 92.375 | 1.00 | 21.15 |
| ATOM | 5564 | CB | GLN | A2404 | | 3.925 | 29.129 | 92.916 | 1.00 | 22.59 |
| ATOM | 5565 | CG | GLN | A2404 | | 3.620 | 27.814 | 92.192 | 1.00 | 25.56 |
| ATOM | 5566 | CD | GLN | A2404 | | 4.466 | 26.644 | 92.673 | 1.00 | 27.31 |
| ATOM | 5567 | OE1 | GLN | A2404 | | 5.338 | 26.804 | 93.532 | 1.00 | 28.95 |
| ATOM | 5568 | NE2 | GLN | A2404 | | 4.209 | 25.466 | 92.117 | 1.00 | 27.47 |
| ATOM | 5569 | C | GLN | A2404 | | 1.632 | 30.093 | 92.461 | 1.00 | 20.49 |
| ATOM | 5570 | O | GLN | A2404 | | 0.997 | 29.712 | 91.475 | 1.00 | 20.57 |
| ATOM | 5571 | N | VAL | A2405 | | 1.060 | 30.331 | 93.639 | 1.00 | 21.13 |
| ATOM | 5572 | CA | VAL | A2405 | | -0.379 | 30.180 | 93.835 | 1.00 | 20.07 |
| ATOM | 5573 | CB | VAL | A2405 | | -0.765 | 30.265 | 95.341 | 1.00 | 20.90 |
| ATOM | 5574 | CG1 | VAL | A2405 | | -2.273 | 30.393 | 95.527 | 1.00 | 20.40 |
| ATOM | 5575 | CG2 | VAL | A2405 | | -0.249 | 29.035 | 96.087 | 1.00 | 19.49 |
| ATOM | 5576 | C | VAL | A2405 | | -1.154 | 31.185 | 92.977 | 1.00 | 20.11 |
| ATOM | 5577 | O | VAL | A2405 | | -2.153 | 30.830 | 92.346 | 1.00 | 19.47 |
| ATOM | 5578 | N | VAL | A2406 | | -0.671 | 32.426 | 92.928 | 1.00 | 19.89 |
| ATOM | 5579 | CA | VAL | A2406 | | -1.330 | 33.477 | 92.149 | 1.00 | 20.05 |
| ATOM | 5580 | CB | VAL | A2406 | | -0.806 | 34.896 | 92.509 | 1.00 | 20.78 |
| ATOM | 5581 | CG1 | VAL | A2406 | | -1.423 | 35.954 | 91.603 | 1.00 | 20.49 |
| ATOM | 5582 | CG2 | VAL | A2406 | | -1.129 | 35.224 | 93.958 | 1.00 | 21.40 |
| ATOM | 5583 | C | VAL | A2406 | | -1.252 | 33.208 | 90.640 | 1.00 | 19.62 |
| ATOM | 5584 | O | VAL | A2406 | | -2.220 | 33.464 | 89.918 | 1.00 | 18.67 |
| ATOM | 5585 | N | VAL | A2407 | | -0.116 | 32.684 | 90.174 | 1.00 | 18.67 |
| ATOM | 5586 | CA | VAL | A2407 | | 0.022 | 32.265 | 88.776 | 1.00 | 19.87 |
| ATOM | 5587 | CB | VAL | A2407 | | 1.434 | 31.705 | 88.465 | 1.00 | 19.45 |
| ATOM | 5588 | CG1 | VAL | A2407 | | 1.462 | 30.987 | 87.113 | 1.00 | 17.66 |
| ATOM | 5589 | CG2 | VAL | A2407 | | 2.462 | 32.812 | 88.484 | 1.00 | 18.62 |
| ATOM | 5590 | C | VAL | A2407 | | -1.042 | 31.216 | 88.438 | 1.00 | 21.48 |
| ATOM | 5591 | O | VAL | A2407 | | -1.755 | 31.345 | 87.442 | 1.00 | 22.62 |
| ATOM | 5592 | N | GLN | A2408 | | -1.149 | 30.197 | 89.287 | 1.00 | 23.92 |
| ATOM | 5593 | CA | GLN | A2408 | | -2.123 | 29.124 | 89.105 | 1.00 | 26.72 |
| ATOM | 5594 | CB | GLN | A2408 | | -1.940 | 28.046 | 90.180 | 1.00 | 29.15 |
| ATOM | 5595 | CG | GLN | A2408 | | -0.669 | 27.195 | 89.999 | 1.00 | 32.76 |
| ATOM | 5596 | CD | GLN | A2408 | | -0.256 | 26.395 | 91.247 | 1.00 | 34.99 |
| ATOM | 5597 | OE1 | GLN | A2408 | | 0.793 | 25.740 | 91.244 | 1.00 | 35.25 |
| ATOM | 5598 | NE2 | GLN | A2408 | | -1.071 | 26.444 | 92.300 | 1.00 | 35.49 |
| ATOM | 5599 | C | GLN | A2408 | | -3.557 | 29.665 | 89.085 | 1.00 | 27.59 |
| ATOM | 5600 | O | GLN | A2408 | | -4.367 | 29.243 | 88.259 | 1.00 | 28.12 |

FIGURE 3DE

| | A | B | C | D | E | F | G | H | I | J |
|---|---|---|---|---|---|---|---|---|---|---|
| ATOM | 5601 | N | TRP | A2409 | | -3.849 | 30.619 | 89.970 | 1.00 | 28.27 |
| ATOM | 5602 | CA | TRP | A2409 | | -5.154 | 31.287 | 90.015 | 1.00 | 28.20 |
| ATOM | 5603 | CB | TRP | A2409 | | -5.289 | 32.152 | 91.278 | 1.00 | 28.59 |
| ATOM | 5604 | CG | TRP | A2409 | | -6.599 | 32.898 | 91.357 | 1.00 | 27.88 |
| ATOM | 5605 | CD1 | TRP | A2409 | | -7.788 | 32.421 | 91.838 | 1.00 | 28.45 |
| ATOM | 5606 | NE1 | TRP | A2409 | | -8.762 | 33.387 | 91.741 | 1.00 | 28.16 |
| ATOM | 5607 | CE2 | TRP | A2409 | | -8.216 | 34.518 | 91.190 | 1.00 | 27.82 |
| ATOM | 5608 | CD2 | TRP | A2409 | | -6.852 | 34.245 | 90.934 | 1.00 | 27.84 |
| ATOM | 5609 | CE3 | TRP | A2409 | | -6.063 | 35.257 | 90.363 | 1.00 | 28.38 |
| ATOM | 5610 | CZ3 | TRP | A2409 | | -6.651 | 36.489 | 90.072 | 1.00 | 28.97 |
| ATOM | 5611 | CH2 | TRP | A2409 | | -8.012 | 36.724 | 90.339 | 1.00 | 28.81 |
| ATOM | 5612 | CZ2 | TRP | A2409 | | -8.808 | 35.754 | 90.895 | 1.00 | 28.35 |
| ATOM | 5613 | C | TRP | A2409 | | -5.425 | 32.142 | 88.779 | 1.00 | 28.54 |
| ATOM | 5614 | O | TRP | A2409 | | -6.541 | 32.149 | 88.261 | 1.00 | 29.05 |
| ATOM | 5615 | N | LEU | A2410 | | -4.416 | 32.877 | 88.318 | 1.00 | 28.54 |
| ATOM | 5616 | CA | LEU | A2410 | | -4.577 | 33.699 | 87.122 | 1.00 | 28.81 |
| ATOM | 5617 | CB | LEU | A2410 | | -3.393 | 34.656 | 86.930 | 1.00 | 28.86 |
| ATOM | 5618 | CG | LEU | A2410 | | -3.293 | 35.861 | 87.874 | 1.00 | 30.10 |
| ATOM | 5619 | CD1 | LEU | A2410 | | -1.850 | 36.312 | 88.005 | 1.00 | 30.08 |
| ATOM | 5620 | CD2 | LEU | A2410 | | -4.163 | 37.020 | 87.408 | 1.00 | 30.71 |
| ATOM | 5621 | C | LEU | A2410 | | -4.788 | 32.821 | 85.887 | 1.00 | 29.12 |
| ATOM | 5622 | O | LEU | A2410 | | -5.597 | 33.153 | 85.023 | 1.00 | 29.14 |
| ATOM | 5623 | N | GLU | A2411 | | -4.078 | 31.696 | 85.824 | 1.00 | 29.05 |
| ATOM | 5624 | CA | GLU | A2411 | | -4.210 | 30.751 | 84.715 | 1.00 | 31.85 |
| ATOM | 5625 | CB | GLU | A2411 | | -3.125 | 29.674 | 84.791 | 1.00 | 32.09 |
| ATOM | 5626 | CG | GLU | A2411 | | -1.769 | 30.098 | 84.248 | 1.00 | 32.78 |
| ATOM | 5627 | CD | GLU | A2411 | | -0.684 | 29.062 | 84.496 | 1.00 | 33.62 |
| ATOM | 5628 | OE1 | GLU | A2411 | | 0.393 | 29.172 | 83.874 | 1.00 | 33.44 |
| ATOM | 5629 | OE2 | GLU | A2411 | | -0.900 | 28.137 | 85.312 | 1.00 | 33.75 |
| ATOM | 5630 | C | GLU | A2411 | | -5.591 | 30.092 | 84.683 | 1.00 | 33.13 |
| ATOM | 5631 | O | GLU | A2411 | | -6.176 | 29.919 | 83.613 | 1.00 | 33.90 |
| ATOM | 5632 | N | GLN | A2412 | | -6.102 | 29.735 | 85.861 | 1.00 | 34.48 |
| ATOM | 5633 | CA | GLN | A2412 | | -7.402 | 29.077 | 85.991 | 1.00 | 36.25 |
| ATOM | 5634 | CB | GLN | A2412 | | -7.539 | 28.430 | 87.371 | 1.00 | 37.15 |
| ATOM | 5635 | CG | GLN | A2412 | | -6.866 | 27.070 | 87.494 | 1.00 | 38.70 |
| ATOM | 5636 | CD | GLN | A2412 | | -7.164 | 26.385 | 88.819 | 1.00 | 39.96 |
| ATOM | 5637 | OE1 | GLN | A2412 | | -6.694 | 26.824 | 89.873 | 1.00 | 40.50 |
| ATOM | 5638 | NE2 | GLN | A2412 | | -7.944 | 25.310 | 88.770 | 1.00 | 39.49 |
| ATOM | 5639 | C | GLN | A2412 | | -8.579 | 30.020 | 85.738 | 1.00 | 36.79 |
| ATOM | 5640 | O | GLN | A2412 | | -9.668 | 29.571 | 85.380 | 1.00 | 37.97 |
| ATOM | 5641 | N | HIS | A2413 | | -8.358 | 31.319 | 85.924 | 1.00 | 37.45 |
| ATOM | 5642 | CA | HIS | A2413 | | -9.404 | 32.321 | 85.710 | 1.00 | 37.44 |
| ATOM | 5643 | CB | HIS | A2413 | | -9.610 | 33.154 | 86.980 | 1.00 | 36.96 |
| ATOM | 5644 | CG | HIS | A2413 | | -10.095 | 32.351 | 88.148 | 1.00 | 36.47 |
| ATOM | 5645 | ND1 | HIS | A2413 | | -11.423 | 32.298 | 88.515 | 1.00 | 36.62 |
| ATOM | 5646 | CE1 | HIS | A2413 | | -11.555 | 31.509 | 89.567 | 1.00 | 36.46 |
| ATOM | 5647 | NE2 | HIS | A2413 | | -10.362 | 31.043 | 89.892 | 1.00 | 36.25 |
| ATOM | 5648 | CD2 | HIS | A2413 | | -9.433 | 31.552 | 89.018 | 1.00 | 36.17 |
| ATOM | 5649 | C | HIS | A2413 | | -9.130 | 33.206 | 84.488 | 1.00 | 38.33 |
| ATOM | 5650 | O | HIS | A2413 | | -9.671 | 34.310 | 84.372 | 1.00 | 37.62 |
| ATOM | 5651 | N | TRP | A2414 | | -8.300 | 32.695 | 83.577 | 1.00 | 40.41 |
| ATOM | 5652 | CA | TRP | A2414 | | -7.962 | 33.368 | 82.322 | 1.00 | 41.70 |

FIGURE 3DF

|      | A    | B   | C   | D   | E     | F       | G      | H      | I    | J     |
|------|------|-----|-----|-----|-------|---------|--------|--------|------|-------|
| ATOM | 5653 | CB  | TRP | A2414 |     | -6.875  | 34.413 | 82.554 | 1.00 | 43.49 |
| ATOM | 5654 | CG  | TRP | A2414 |     | -7.362  | 35.816 | 82.477 | 1.00 | 44.82 |
| ATOM | 5655 | CD1 | TRP | A2414 |     | -7.543  | 36.679 | 83.519 | 1.00 | 45.25 |
| ATOM | 5656 | NE1 | TRP | A2414 |     | -7.999  | 37.891 | 83.055 | 1.00 | 45.98 |
| ATOM | 5657 | CE2 | TRP | A2414 |     | -8.120  | 37.829 | 81.691 | 1.00 | 45.77 |
| ATOM | 5658 | CD2 | TRP | A2414 |     | -7.726  | 36.532 | 81.293 | 1.00 | 45.56 |
| ATOM | 5659 | CE3 | TRP | A2414 |     | -7.762  | 36.210 | 79.926 | 1.00 | 46.28 |
| ATOM | 5660 | CZ3 | TRP | A2414 |     | -8.184  | 37.176 | 79.018 | 1.00 | 46.89 |
| ATOM | 5661 | CH2 | TRP | A2414 |     | -8.569  | 38.456 | 79.450 | 1.00 | 46.89 |
| ATOM | 5662 | CZ2 | TRP | A2414 |     | -8.545  | 38.801 | 80.778 | 1.00 | 46.20 |
| ATOM | 5663 | C   | TRP | A2414 |     | -7.482  | 32.372 | 81.267 | 1.00 | 42.25 |
| ATOM | 5664 | O   | TRP | A2414 |     | -8.160  | 31.387 | 80.963 | 1.00 | 41.84 |
| TER  | 5664 |     | TRP | A2414 |     |         |        |        |      |       |
| ATOM | 5665 | N   | ASN | A2427 |     | -16.369 | 40.700 | 84.639 | 1.00 | 42.37 |
| ATOM | 5666 | CA  | ASN | A2427 |     | -15.927 | 41.681 | 85.629 | 1.00 | 42.75 |
| ATOM | 5667 | CB  | ASN | A2427 |     | -14.819 | 41.097 | 86.517 | 1.00 | 43.44 |
| ATOM | 5668 | CG  | ASN | A2427 |     | -15.316 | 39.984 | 87.431 | 1.00 | 44.20 |
| ATOM | 5669 | OD1 | ASN | A2427 |     | -16.382 | 40.088 | 88.043 | 1.00 | 43.18 |
| ATOM | 5670 | ND2 | ASN | A2427 |     | -14.537 | 38.913 | 87.528 | 1.00 | 44.44 |
| ATOM | 5671 | C   | ASN | A2427 |     | -15.442 | 42.979 | 84.981 | 1.00 | 42.52 |
| ATOM | 5672 | O   | ASN | A2427 |     | -15.857 | 44.078 | 85.364 | 1.00 | 41.88 |
| ATOM | 5673 | N   | ILE | A2428 |     | -14.562 | 42.835 | 83.996 | 1.00 | 41.22 |
| ATOM | 5674 | CA  | ILE | A2428 |     | -14.008 | 43.965 | 83.263 | 1.00 | 40.44 |
| ATOM | 5675 | CB  | ILE | A2428 |     | -12.805 | 43.489 | 82.401 | 1.00 | 40.57 |
| ATOM | 5676 | CG1 | ILE | A2428 |     | -11.563 | 43.323 | 83.285 | 1.00 | 40.55 |
| ATOM | 5677 | CD1 | ILE | A2428 |     | -10.617 | 42.217 | 82.850 | 1.00 | 40.34 |
| ATOM | 5678 | CG2 | ILE | A2428 |     | -12.513 | 44.446 | 81.247 | 1.00 | 41.14 |
| ATOM | 5679 | C   | ILE | A2428 |     | -15.107 | 44.649 | 82.439 | 1.00 | 39.50 |
| ATOM | 5680 | O   | ILE | A2428 |     | -15.081 | 45.867 | 82.237 | 1.00 | 38.16 |
| ATOM | 5681 | N   | THR | A2429 |     | -16.090 | 43.855 | 82.015 | 1.00 | 38.57 |
| ATOM | 5682 | CA  | THR | A2429 |     | -17.242 | 44.325 | 81.243 | 1.00 | 37.85 |
| ATOM | 5683 | CB  | THR | A2429 |     | -18.155 | 43.122 | 80.851 | 1.00 | 38.81 |
| ATOM | 5684 | OG1 | THR | A2429 |     | -19.283 | 43.585 | 80.101 | 1.00 | 40.35 |
| ATOM | 5685 | CG2 | THR | A2429 |     | -18.792 | 42.468 | 82.082 | 1.00 | 39.20 |
| ATOM | 5686 | C   | THR | A2429 |     | -18.049 | 45.441 | 81.930 | 1.00 | 36.84 |
| ATOM | 5687 | O   | THR | A2429 |     | -18.643 | 46.288 | 81.256 | 1.00 | 35.96 |
| ATOM | 5688 | N   | TYR | A2430 |     | -18.058 | 45.439 | 83.261 | 1.00 | 35.49 |
| ATOM | 5689 | CA  | TYR | A2430 |     | -18.786 | 46.444 | 84.033 | 1.00 | 34.84 |
| ATOM | 5690 | CB  | TYR | A2430 |     | -19.039 | 45.951 | 85.462 | 1.00 | 36.24 |
| ATOM | 5691 | CG  | TYR | A2430 |     | -19.833 | 44.660 | 85.542 | 1.00 | 36.90 |
| ATOM | 5692 | CD1 | TYR | A2430 |     | -21.181 | 44.619 | 85.174 | 1.00 | 37.01 |
| ATOM | 5693 | CE1 | TYR | A2430 |     | -21.911 | 43.432 | 85.248 | 1.00 | 37.30 |
| ATOM | 5694 | CZ  | TYR | A2430 |     | -21.289 | 42.274 | 85.694 | 1.00 | 37.65 |
| ATOM | 5695 | OH  | TYR | A2430 |     | -21.997 | 41.098 | 85.773 | 1.00 | 38.00 |
| ATOM | 5696 | CE2 | TYR | A2430 |     | -19.953 | 42.291 | 86.067 | 1.00 | 37.84 |
| ATOM | 5697 | CD2 | TYR | A2430 |     | -19.234 | 43.481 | 85.988 | 1.00 | 37.47 |
| ATOM | 5698 | C   | TYR | A2430 |     | -18.066 | 47.791 | 84.053 | 1.00 | 33.32 |
| ATOM | 5699 | O   | TYR | A2430 |     | -18.709 | 48.841 | 84.072 | 1.00 | 32.74 |
| ATOM | 5700 | N   | LEU | A2431 |     | -16.736 | 47.755 | 84.048 | 1.00 | 33.50 |
| ATOM | 5701 | CA  | LEU | A2431 |     | -15.926 | 48.971 | 83.974 | 1.00 | 33.24 |
| ATOM | 5702 | CB  | LEU | A2431 |     | -14.452 | 48.661 | 84.240 | 1.00 | 33.57 |
| ATOM | 5703 | CG  | LEU | A2431 |     | -14.029 | 48.210 | 85.642 | 1.00 | 34.26 |

FIGURE 3DG

| | A | B | C | D | E | F | G | H | I | J |
|---|---|---|---|---|---|---|---|---|---|---|
| ATOM | 5704 | CD1 | LEU | A2431 | -12.644 | 47.585 | 85.582 | 1.00 | 33.44 |
| ATOM | 5705 | CD2 | LEU | A2431 | -14.050 | 49.373 | 86.628 | 1.00 | 34.55 |
| ATOM | 5706 | C | LEU | A2431 | -16.071 | 49.646 | 82.611 | 1.00 | 32.86 |
| ATOM | 5707 | O | LEU | A2431 | -16.080 | 50.875 | 82.518 | 1.00 | 32.18 |
| ATOM | 5708 | N | LYS | A2432 | -16.187 | 48.824 | 81.568 | 1.00 | 32.74 |
| ATOM | 5709 | CA | LYS | A2432 | -16.310 | 49.288 | 80.185 | 1.00 | 32.81 |
| ATOM | 5710 | CB | LYS | A2432 | -16.230 | 48.096 | 79.220 | 1.00 | 32.53 |
| ATOM | 5711 | CG | LYS | A2432 | -16.241 | 48.459 | 77.737 | 1.00 | 33.67 |
| ATOM | 5712 | CD | LYS | A2432 | -14.846 | 48.790 | 77.229 | 1.00 | 33.24 |
| ATOM | 5713 | CE | LYS | A2432 | -14.898 | 49.450 | 75.861 | 1.00 | 34.05 |
| ATOM | 5714 | NZ | LYS | A2432 | -14.053 | 50.676 | 75.812 | 1.00 | 34.46 |
| ATOM | 5715 | C | LYS | A2432 | -17.599 | 50.082 | 79.955 | 1.00 | 33.04 |
| ATOM | 5716 | O | LYS | A2432 | -17.590 | 51.096 | 79.258 | 1.00 | 33.56 |
| ATOM | 5717 | N | HIS | A2433 | -18.694 | 49.616 | 80.553 | 1.00 | 32.51 |
| ATOM | 5718 | CA | HIS | A2433 | -20.004 | 50.266 | 80.448 | 1.00 | 31.62 |
| ATOM | 5719 | CB | HIS | A2433 | -21.051 | 49.429 | 81.198 | 1.00 | 32.15 |
| ATOM | 5720 | CG | HIS | A2433 | -22.385 | 50.095 | 81.354 | 1.00 | 33.12 |
| ATOM | 5721 | ND1 | HIS | A2433 | -22.743 | 50.787 | 82.491 | 1.00 | 33.85 |
| ATOM | 5722 | CE1 | HIS | A2433 | -23.974 | 51.248 | 82.356 | 1.00 | 33.88 |
| ATOM | 5723 | NE2 | HIS | A2433 | -24.432 | 50.871 | 81.176 | 1.00 | 33.88 |
| ATOM | 5724 | CD2 | HIS | A2433 | -23.460 | 50.145 | 80.531 | 1.00 | 33.54 |
| ATOM | 5725 | C | HIS | A2433 | -19.967 | 51.710 | 80.962 | 1.00 | 30.20 |
| ATOM | 5726 | O | HIS | A2433 | -20.461 | 52.622 | 80.299 | 1.00 | 30.02 |
| ATOM | 5727 | N | ASP | A2434 | -19.360 | 51.907 | 82.130 | 1.00 | 29.62 |
| ATOM | 5728 | CA | ASP | A2434 | -19.298 | 53.218 | 82.771 | 1.00 | 28.39 |
| ATOM | 5729 | CB | ASP | A2434 | -18.949 | 53.079 | 84.256 | 1.00 | 27.90 |
| ATOM | 5730 | CG | ASP | A2434 | -20.157 | 52.729 | 85.112 | 1.00 | 28.64 |
| ATOM | 5731 | OD1 | ASP | A2434 | -19.967 | 52.065 | 86.156 | 1.00 | 27.49 |
| ATOM | 5732 | OD2 | ASP | A2434 | -21.328 | 53.071 | 84.826 | 1.00 | 27.49 |
| ATOM | 5733 | C | ASP | A2434 | -18.310 | 54.160 | 82.091 | 1.00 | 28.48 |
| ATOM | 5734 | O | ASP | A2434 | -18.541 | 55.366 | 82.035 | 1.00 | 28.53 |
| ATOM | 5735 | N | SER | A2435 | -17.211 | 53.608 | 81.582 | 1.00 | 28.08 |
| ATOM | 5736 | CA | SER | A2435 | -16.182 | 54.410 | 80.929 | 1.00 | 27.81 |
| ATOM | 5737 | CB | SER | A2435 | -14.870 | 53.630 | 80.824 | 1.00 | 28.09 |
| ATOM | 5738 | OG | SER | A2435 | -14.979 | 52.574 | 79.887 | 1.00 | 28.94 |
| ATOM | 5739 | C | SER | A2435 | -16.639 | 54.897 | 79.554 | 1.00 | 28.13 |
| ATOM | 5740 | O | SER | A2435 | -16.366 | 56.037 | 79.175 | 1.00 | 26.51 |
| ATOM | 5741 | N | VAL | A2436 | -17.341 | 54.029 | 78.823 | 1.00 | 29.13 |
| ATOM | 5742 | CA | VAL | A2436 | -17.900 | 54.372 | 77.518 | 1.00 | 30.64 |
| ATOM | 5743 | CB | VAL | A2436 | -18.429 | 53.119 | 76.766 | 1.00 | 30.35 |
| ATOM | 5744 | CG1 | VAL | A2436 | -19.398 | 53.500 | 75.650 | 1.00 | 30.10 |
| ATOM | 5745 | CG2 | VAL | A2436 | -17.275 | 52.328 | 76.187 | 1.00 | 29.99 |
| ATOM | 5746 | C | VAL | A2436 | -18.996 | 55.428 | 77.672 | 1.00 | 32.56 |
| ATOM | 5747 | O | VAL | A2436 | -19.037 | 56.403 | 76.915 | 1.00 | 33.40 |
| ATOM | 5748 | N | LEU | A2437 | -19.865 | 55.227 | 78.661 | 1.00 | 34.05 |
| ATOM | 5749 | CA | LEU | A2437 | -20.926 | 56.177 | 78.983 | 1.00 | 35.10 |
| ATOM | 5750 | CB | LEU | A2437 | -21.823 | 55.628 | 80.096 | 1.00 | 36.60 |
| ATOM | 5751 | CG | LEU | A2437 | -23.264 | 55.295 | 79.717 | 1.00 | 38.22 |
| ATOM | 5752 | CD1 | LEU | A2437 | -23.360 | 53.890 | 79.143 | 1.00 | 39.34 |
| ATOM | 5753 | CD2 | LEU | A2437 | -24.180 | 55.443 | 80.926 | 1.00 | 38.84 |
| ATOM | 5754 | C | LEU | A2437 | -20.355 | 57.530 | 79.390 | 1.00 | 34.67 |
| ATOM | 5755 | O | LEU | A2437 | -20.880 | 58.567 | 78.992 | 1.00 | 35.23 |

FIGURE 3DH

| | A | B | C | D | E | F | G | H | I | J |
|---|---|---|---|---|---|---|---|---|---|---|
| ATOM | 5756 | N | LYS | A2438 | -19.278 | 57.507 | 80.176 | 1.00 | 33.99 |
| ATOM | 5757 | CA | LYS | A2438 | -18.574 | 58.723 | 80.577 | 1.00 | 33.81 |
| ATOM | 5758 | CB | LYS | A2438 | -17.455 | 58.397 | 81.569 | 1.00 | 34.25 |
| ATOM | 5759 | CG | LYS | A2438 | -17.193 | 59.486 | 82.594 | 1.00 | 35.65 |
| ATOM | 5760 | CD | LYS | A2438 | -15.718 | 59.849 | 82.654 | 1.00 | 36.34 |
| ATOM | 5761 | CE | LYS | A2438 | -15.498 | 61.142 | 83.424 | 1.00 | 36.75 |
| ATOM | 5762 | NZ | LYS | A2438 | -15.308 | 60.890 | 84.880 | 1.00 | 36.83 |
| ATOM | 5763 | C | LYS | A2438 | -18.006 | 59.464 | 79.363 | 1.00 | 33.06 |
| ATOM | 5764 | O | LYS | A2438 | -18.072 | 60.694 | 79.295 | 1.00 | 32.70 |
| ATOM | 5765 | N | THR | A2439 | -17.460 | 58.701 | 78.414 | 1.00 | 32.26 |
| ATOM | 5766 | CA | THR | A2439 | -16.904 | 59.239 | 77.173 | 1.00 | 31.57 |
| ATOM | 5767 | CB | THR | A2439 | -16.201 | 58.119 | 76.376 | 1.00 | 30.00 |
| ATOM | 5768 | OG1 | THR | A2439 | -15.117 | 57.588 | 77.146 | 1.00 | 28.19 |
| ATOM | 5769 | CG2 | THR | A2439 | -15.522 | 58.676 | 75.130 | 1.00 | 28.99 |
| ATOM | 5770 | C | THR | A2439 | -17.985 | 59.899 | 76.317 | 1.00 | 32.51 |
| ATOM | 5771 | O | THR | A2439 | -17.839 | 61.055 | 75.911 | 1.00 | 32.77 |
| ATOM | 5772 | N | ILE | A2440 | -19.059 | 59.158 | 76.048 | 1.00 | 33.41 |
| ATOM | 5773 | CA | ILE | A2440 | -20.184 | 59.666 | 75.261 | 1.00 | 36.00 |
| ATOM | 5774 | CB | ILE | A2440 | -21.211 | 58.534 | 74.962 | 1.00 | 35.32 |
| ATOM | 5775 | CG1 | ILE | A2440 | -20.657 | 57.588 | 73.893 | 1.00 | 34.62 |
| ATOM | 5776 | CD1 | ILE | A2440 | -21.254 | 56.196 | 73.916 | 1.00 | 34.55 |
| ATOM | 5777 | CG2 | ILE | A2440 | -22.558 | 59.107 | 74.505 | 1.00 | 35.92 |
| ATOM | 5778 | C | ILE | A2440 | -20.837 | 60.881 | 75.935 | 1.00 | 38.05 |
| ATOM | 5779 | O | ILE | A2440 | -21.167 | 61.862 | 75.263 | 1.00 | 38.27 |
| ATOM | 5780 | N | ARG | A2441 | -20.990 | 60.817 | 77.258 | 1.00 | 39.84 |
| ATOM | 5781 | CA | ARG | A2441 | -21.539 | 61.921 | 78.047 | 1.00 | 42.87 |
| ATOM | 5782 | CB | ARG | A2441 | -21.654 | 61.523 | 79.521 | 1.00 | 44.47 |
| ATOM | 5783 | CG | ARG | A2441 | -22.824 | 62.149 | 80.263 | 1.00 | 47.05 |
| ATOM | 5784 | CD | ARG | A2441 | -22.725 | 62.038 | 81.782 | 1.00 | 48.85 |
| ATOM | 5785 | NE | ARG | A2441 | -21.783 | 63.009 | 82.341 | 1.00 | 50.48 |
| ATOM | 5786 | CZ | ARG | A2441 | -21.619 | 63.248 | 83.639 | 1.00 | 51.15 |
| ATOM | 5787 | NH1 | ARG | A2441 | -20.734 | 64.154 | 84.036 | 1.00 | 51.43 |
| ATOM | 5788 | NH2 | ARG | A2441 | -22.333 | 62.589 | 84.545 | 1.00 | 51.15 |
| ATOM | 5789 | C | ARG | A2441 | -20.695 | 63.189 | 77.913 | 1.00 | 43.63 |
| ATOM | 5790 | O | ARG | A2441 | -21.234 | 64.282 | 77.733 | 1.00 | 43.43 |
| ATOM | 5791 | N | GLY | A2442 | -19.376 | 63.028 | 77.999 | 1.00 | 44.11 |
| ATOM | 5792 | CA | GLY | A2442 | -18.443 | 64.135 | 77.878 | 1.00 | 45.90 |
| ATOM | 5793 | C | GLY | A2442 | -18.454 | 64.776 | 76.503 | 1.00 | 47.05 |
| ATOM | 5794 | O | GLY | A2442 | -18.320 | 65.994 | 76.386 | 1.00 | 46.80 |
| ATOM | 5795 | N | LEU | A2443 | -18.625 | 63.953 | 75.470 | 1.00 | 48.75 |
| ATOM | 5796 | CA | LEU | A2443 | -18.648 | 64.424 | 74.085 | 1.00 | 50.99 |
| ATOM | 5797 | CB | LEU | A2443 | -18.449 | 63.259 | 73.109 | 1.00 | 50.19 |
| ATOM | 5798 | CG | LEU | A2443 | -17.050 | 62.636 | 73.023 | 1.00 | 49.84 |
| ATOM | 5799 | CD1 | LEU | A2443 | -17.115 | 61.270 | 72.359 | 1.00 | 49.42 |
| ATOM | 5800 | CD2 | LEU | A2443 | -16.063 | 63.540 | 72.290 | 1.00 | 49.77 |
| ATOM | 5801 | C | LEU | A2443 | -19.920 | 65.205 | 73.739 | 1.00 | 53.30 |
| ATOM | 5802 | O | LEU | A2443 | -19.906 | 66.050 | 72.845 | 1.00 | 53.18 |
| ATOM | 5803 | N | VAL | A2444 | -21.012 | 64.911 | 74.442 | 1.00 | 56.79 |
| ATOM | 5804 | CA | VAL | A2444 | -22.262 | 65.658 | 74.288 | 1.00 | 60.13 |
| ATOM | 5805 | CB | VAL | A2444 | -23.512 | 64.778 | 74.589 | 1.00 | 59.73 |
| ATOM | 5806 | CG1 | VAL | A2444 | -24.807 | 65.572 | 74.420 | 1.00 | 59.87 |
| ATOM | 5807 | CG2 | VAL | A2444 | -23.538 | 63.551 | 73.685 | 1.00 | 59.37 |

FIGURE 3DI

|  | A | B | C | D | E | F | G | H | I | J |
|---|---|---|---|---|---|---|---|---|---|---|
| ATOM | 5808 | C | VAL | A2444 | -22.238 | 66.909 | 75.176 | 1.00 | 63.19 |
| ATOM | 5809 | O | VAL | A2444 | -22.781 | 67.953 | 74.806 | 1.00 | 63.56 |
| ATOM | 5810 | N | GLU | A2445 | -21.590 | 66.797 | 76.337 | 1.00 | 66.71 |
| ATOM | 5811 | CA | GLU | A2445 | -21.401 | 67.925 | 77.252 | 1.00 | 70.16 |
| ATOM | 5812 | CB | GLU | A2445 | -20.879 | 67.434 | 78.606 | 1.00 | 69.95 |
| ATOM | 5813 | CG | GLU | A2445 | -21.763 | 67.796 | 79.790 | 1.00 | 69.82 |
| ATOM | 5814 | CD | GLU | A2445 | -21.493 | 66.929 | 81.008 | 1.00 | 69.80 |
| ATOM | 5815 | OE1 | GLU | A2445 | -22.319 | 66.038 | 81.299 | 1.00 | 69.82 |
| ATOM | 5816 | OE2 | GLU | A2445 | -20.458 | 67.139 | 81.675 | 1.00 | 69.48 |
| ATOM | 5817 | C | GLU | A2445 | -20.453 | 68.987 | 76.684 | 1.00 | 72.96 |
| ATOM | 5818 | O | GLU | A2445 | -20.430 | 70.125 | 77.160 | 1.00 | 73.36 |
| ATOM | 5819 | N | GLU | A2446 | -19.675 | 68.608 | 75.672 | 1.00 | 76.09 |
| ATOM | 5820 | CA | GLU | A2446 | -18.747 | 69.529 | 75.018 | 1.00 | 79.58 |
| ATOM | 5821 | CB | GLU | A2446 | -17.337 | 68.933 | 74.969 | 1.00 | 80.88 |
| ATOM | 5822 | CG | GLU | A2446 | -16.571 | 69.032 | 76.283 | 1.00 | 82.87 |
| ATOM | 5823 | CD | GLU | A2446 | -16.701 | 70.393 | 76.950 | 1.00 | 84.05 |
| ATOM | 5824 | OE1 | GLU | A2446 | -17.424 | 70.493 | 77.966 | 1.00 | 84.45 |
| ATOM | 5825 | OE2 | GLU | A2446 | -16.082 | 71.362 | 76.457 | 1.00 | 84.57 |
| ATOM | 5826 | C | GLU | A2446 | -19.218 | 69.938 | 73.622 | 1.00 | 81.05 |
| ATOM | 5827 | O | GLU | A2446 | -18.766 | 70.949 | 73.077 | 1.00 | 81.66 |
| ATOM | 5828 | N | ASN | A2447 | -20.119 | 69.140 | 73.053 | 1.00 | 82.57 |
| ATOM | 5829 | CA | ASN | A2447 | -20.791 | 69.467 | 71.798 | 1.00 | 83.95 |
| ATOM | 5830 | CB | ASN | A2447 | -20.336 | 68.533 | 70.671 | 1.00 | 84.08 |
| ATOM | 5831 | CG | ASN | A2447 | -18.826 | 68.512 | 70.500 | 1.00 | 84.51 |
| ATOM | 5832 | OD1 | ASN | A2447 | -18.257 | 69.350 | 69.801 | 1.00 | 84.79 |
| ATOM | 5833 | ND2 | ASN | A2447 | -18.171 | 67.551 | 71.143 | 1.00 | 84.44 |
| ATOM | 5834 | C | ASN | A2447 | -22.306 | 69.388 | 72.004 | 1.00 | 84.91 |
| ATOM | 5835 | O | ASN | A2447 | -22.924 | 68.358 | 71.717 | 1.00 | 85.14 |
| ATOM | 5836 | N | PRO | A2448 | -22.896 | 70.481 | 72.499 | 1.00 | 85.83 |
| ATOM | 5837 | CA | PRO | A2448 | -24.284 | 70.491 | 72.995 | 1.00 | 86.41 |
| ATOM | 5838 | CB | PRO | A2448 | -24.499 | 71.953 | 73.399 | 1.00 | 86.58 |
| ATOM | 5839 | CG | PRO | A2448 | -23.129 | 72.470 | 73.655 | 1.00 | 86.70 |
| ATOM | 5840 | CD | PRO | A2448 | -22.269 | 71.811 | 72.620 | 1.00 | 86.29 |
| ATOM | 5841 | C | PRO | A2448 | -25.359 | 70.053 | 71.994 | 1.00 | 86.93 |
| ATOM | 5842 | O | PRO | A2448 | -26.457 | 69.696 | 72.429 | 1.00 | 87.19 |
| ATOM | 5843 | N | GLU | A2449 | -25.057 | 70.064 | 70.697 | 1.00 | 87.39 |
| ATOM | 5844 | CA | GLU | A2449 | -25.957 | 69.534 | 69.682 | 1.00 | 87.57 |
| ATOM | 5845 | CB | GLU | A2449 | -25.708 | 70.164 | 68.302 | 1.00 | 87.20 |
| ATOM | 5846 | CG | GLU | A2449 | -24.293 | 70.676 | 68.068 | 1.00 | 87.27 |
| ATOM | 5847 | CD | GLU | A2449 | -23.856 | 70.545 | 66.621 | 1.00 | 87.47 |
| ATOM | 5848 | OE1 | GLU | A2449 | -24.345 | 71.324 | 65.771 | 1.00 | 87.38 |
| ATOM | 5849 | OE2 | GLU | A2449 | -23.020 | 69.662 | 66.332 | 1.00 | 87.42 |
| ATOM | 5850 | C | GLU | A2449 | -25.817 | 68.008 | 69.642 | 1.00 | 88.20 |
| ATOM | 5851 | O | GLU | A2449 | -26.092 | 67.340 | 70.642 | 1.00 | 87.61 |
| ATOM | 5852 | N | VAL | A2450 | -25.395 | 67.470 | 68.494 | 1.00 | 89.41 |
| ATOM | 5853 | CA | VAL | A2450 | -25.106 | 66.037 | 68.315 | 1.00 | 90.50 |
| ATOM | 5854 | CB | VAL | A2450 | -23.903 | 65.570 | 69.204 | 1.00 | 90.95 |
| ATOM | 5855 | CG1 | VAL | A2450 | -23.788 | 64.045 | 69.252 | 1.00 | 91.12 |
| ATOM | 5856 | CG2 | VAL | A2450 | -22.602 | 66.191 | 68.708 | 1.00 | 90.87 |
| ATOM | 5857 | C | VAL | A2450 | -26.335 | 65.120 | 68.477 | 1.00 | 91.05 |
| ATOM | 5858 | O | VAL | A2450 | -26.628 | 64.312 | 67.591 | 1.00 | 91.25 |
| ATOM | 5859 | N | ALA | A2451 | -27.039 | 65.250 | 69.601 | 1.00 | 91.42 |

FIGURE 3DJ

|      | A    | B     | C   | D   | E     | F       | G      | H      | I    | J     |
|------|------|-------|-----|-----|-------|---------|--------|--------|------|-------|
| ATOM | 5860 | CA    |     | ALA | A2451 | -28.247 | 64.472 | 69.868 | 1.00 | 91.56 |
| ATOM | 5861 | CB    |     | ALA | A2451 | -28.502 | 64.386 | 71.365 | 1.00 | 91.47 |
| ATOM | 5862 | C     |     | ALA | A2451 | -29.454 | 65.071 | 69.154 | 1.00 | 91.60 |
| ATOM | 5863 | O     |     | ALA | A2451 | -29.670 | 64.829 | 67.966 | 1.00 | 91.29 |
| TER  | 5863 |       |     | ALA | A2451 |         |        |        |      |       |
| HETATM | 5864 | AO7  |    | ACO | A3003 | 32.530  | 51.286 | 34.512 | 1.00 | 29.25 |
| HETATM | 5865 | AP3* |    | ACO | A3003 | 31.269  | 50.478 | 34.717 | 1.00 | 28.44 |
| HETATM | 5866 | AO9  |    | ACO | A3003 | 31.507  | 49.007 | 34.974 | 1.00 | 27.73 |
| HETATM | 5867 | AO8  |    | ACO | A3003 | 30.158  | 50.761 | 33.737 | 1.00 | 28.88 |
| HETATM | 5868 | AO3* |    | ACO | A3003 | 30.643  | 51.049 | 36.079 | 1.00 | 28.19 |
| HETATM | 5869 | AC3* |    | ACO | A3003 | 31.252  | 50.862 | 37.349 | 1.00 | 28.30 |
| HETATM | 5870 | AC2* |    | ACO | A3003 | 30.822  | 51.998 | 38.256 | 1.00 | 27.77 |
| HETATM | 5871 | AO2* |    | ACO | A3003 | 30.636  | 53.219 | 37.563 | 1.00 | 27.91 |
| HETATM | 5872 | AC1* |    | ACO | A3003 | 29.502  | 51.470 | 38.784 | 1.00 | 27.48 |
| HETATM | 5873 | AN9  |    | ACO | A3003 | 29.185  | 51.980 | 40.123 | 1.00 | 27.37 |
| HETATM | 5874 | AC8  |    | ACO | A3003 | 29.964  | 51.958 | 41.234 | 1.00 | 26.62 |
| HETATM | 5875 | AN7  |    | ACO | A3003 | 29.332  | 52.502 | 42.321 | 1.00 | 25.72 |
| HETATM | 5876 | AC5  |    | ACO | A3003 | 28.116  | 52.877 | 41.894 | 1.00 | 26.09 |
| HETATM | 5877 | AC6  |    | ACO | A3003 | 26.886  | 53.504 | 42.425 | 1.00 | 24.95 |
| HETATM | 5878 | AN6  |    | ACO | A3003 | 26.843  | 53.862 | 43.729 | 1.00 | 24.23 |
| HETATM | 5879 | AN1  |    | ACO | A3003 | 25.830  | 53.704 | 41.595 | 1.00 | 25.33 |
| HETATM | 5880 | AC2  |    | ACO | A3003 | 25.821  | 53.360 | 40.291 | 1.00 | 26.24 |
| HETATM | 5881 | AC4  |    | ACO | A3003 | 28.046  | 52.525 | 40.492 | 1.00 | 26.50 |
| HETATM | 5882 | AN3  |    | ACO | A3003 | 26.872  | 52.780 | 39.689 | 1.00 | 26.41 |
| HETATM | 5883 | AO4* |    | ACO | A3003 | 29.642  | 50.050 | 38.888 | 1.00 | 28.44 |
| HETATM | 5884 | AC4* |    | ACO | A3003 | 30.674  | 49.608 | 38.000 | 1.00 | 28.40 |
| HETATM | 5885 | AC5* |    | ACO | A3003 | 31.726  | 48.833 | 38.788 | 1.00 | 28.91 |
| HETATM | 5886 | AO5* |    | ACO | A3003 | 32.354  | 49.714 | 39.725 | 1.00 | 30.05 |
| HETATM | 5887 | AP1  |    | ACO | A3003 | 33.842  | 49.424 | 40.259 | 1.00 | 30.69 |
| HETATM | 5888 | AO1  |    | ACO | A3003 | 34.254  | 50.524 | 41.205 | 1.00 | 30.23 |
| HETATM | 5889 | AO2  |    | ACO | A3003 | 34.734  | 49.114 | 39.080 | 1.00 | 29.51 |
| HETATM | 5890 | AO3  |    | ACO | A3003 | 33.547  | 48.067 | 41.076 | 1.00 | 29.70 |
| HETATM | 5891 | AP2  |    | ACO | A3003 | 34.365  | 47.616 | 42.383 | 1.00 | 29.74 |
| HETATM | 5892 | AO4  |    | ACO | A3003 | 35.832  | 47.911 | 42.178 | 1.00 | 29.96 |
| HETATM | 5893 | AO5  |    | ACO | A3003 | 33.913  | 46.217 | 42.714 | 1.00 | 29.22 |
| HETATM | 5894 | AO6  |    | ACO | A3003 | 33.810  | 48.609 | 43.518 | 1.00 | 29.19 |
| HETATM | 5895 | PC12 |    | ACO | A3003 | 32.444  | 48.601 | 43.930 | 1.00 | 27.85 |
| HETATM | 5896 | PC11 |    | ACO | A3003 | 32.205  | 49.777 | 44.875 | 1.00 | 28.14 |
| HETATM | 5897 | PC13 |    | ACO | A3003 | 30.705  | 49.911 | 45.121 | 1.00 | 26.46 |
| HETATM | 5898 | PC14 |    | ACO | A3003 | 32.886  | 49.436 | 46.198 | 1.00 | 27.63 |
| HETATM | 5899 | PC10 |    | ACO | A3003 | 32.809  | 51.055 | 44.264 | 1.00 | 28.57 |
| HETATM | 5900 | PO10 |    | ACO | A3003 | 32.418  | 51.218 | 42.903 | 1.00 | 28.06 |
| HETATM | 5901 | PC9  |    | ACO | A3003 | 32.430  | 52.303 | 45.016 | 1.00 | 29.62 |
| HETATM | 5902 | PO9  |    | ACO | A3003 | 32.992  | 52.591 | 46.061 | 1.00 | 30.91 |
| HETATM | 5903 | PN8  |    | ACO | A3003 | 31.470  | 53.048 | 44.467 | 1.00 | 29.63 |
| HETATM | 5904 | PC7  |    | ACO | A3003 | 30.888  | 54.185 | 45.144 | 1.00 | 30.01 |
| HETATM | 5905 | PC6  |    | ACO | A3003 | 29.851  | 53.757 | 46.174 | 1.00 | 30.18 |
| HETATM | 5906 | PC5  |    | ACO | A3003 | 29.241  | 55.001 | 46.766 | 1.00 | 30.59 |
| HETATM | 5907 | PO5  |    | ACO | A3003 | 29.953  | 55.965 | 47.022 | 1.00 | 30.45 |
| HETATM | 5908 | PN4  |    | ACO | A3003 | 27.924  | 54.955 | 46.974 | 1.00 | 28.76 |
| HETATM | 5909 | PC3  |    | ACO | A3003 | 27.155  | 56.107 | 47.410 | 1.00 | 31.55 |
| HETATM | 5910 | PC2  |    | ACO | A3003 | 27.400  | 56.415 | 48.882 | 1.00 | 31.19 |

FIGURE 3DK

| | A | B | C | D | E | F | G | H | I | J |
|---|---|---|---|---|---|---|---|---|---|---|
| HETATM | 5911 | PS1 | | ACO | A3003 | 26.521 | 57.876 | 49.335 | 1.00 | 35.60 |
| HETATM | 5912 | C | | ACO | A3003 | 25.066 | 57.408 | 50.006 | 1.00 | 30.94 |
| HETATM | 5913 | O | | ACO | A3003 | 24.714 | 56.241 | 49.932 | 1.00 | 27.32 |
| HETATM | 5914 | CH3 | | ACO | A3003 | 24.224 | 58.434 | 50.687 | 1.00 | 31.30 |
| ATOM | 5915 | O | | HOH | A4000 | 28.729 | 60.559 | 54.050 | 1.00 | 20.23 |
| ATOM | 5916 | O | | HOH | A4003 | 34.018 | 55.135 | 48.344 | 1.00 | 61.38 |
| ATOM | 5917 | O | | HOH | A4004 | 33.750 | 54.661 | 55.884 | 1.00 | 24.16 |
| ATOM | 5918 | O | | HOH | A4005 | 33.019 | 42.726 | 50.863 | 1.00 | 40.20 |
| ATOM | 5919 | O | | HOH | A4006 | 34.838 | 46.278 | 48.072 | 1.00 | 46.47 |
| ATOM | 5920 | O | | HOH | A4007 | 34.824 | 42.088 | 58.521 | 1.00 | 27.75 |
| ATOM | 5921 | O | | HOH | A4008 | 30.211 | 38.637 | 53.563 | 1.00 | 32.78 |
| ATOM | 5922 | O | | HOH | A4010 | 31.861 | 34.880 | 63.418 | 1.00 | 35.56 |
| ATOM | 5923 | O | | HOH | A4011 | 34.287 | 37.947 | 64.412 | 1.00 | 41.35 |
| ATOM | 5924 | O | | HOH | A4012 | 20.532 | 41.817 | 69.042 | 1.00 | 22.86 |
| ATOM | 5925 | O | | HOH | A4013 | 23.681 | 48.929 | 65.355 | 1.00 | 19.68 |
| ATOM | 5926 | O | | HOH | A4014 | 21.698 | 48.650 | 69.153 | 1.00 | 18.99 |
| ATOM | 5927 | O | | HOH | A4015 | 17.449 | 53.605 | 65.481 | 1.00 | 19.08 |
| ATOM | 5928 | O | | HOH | A4016 | 15.034 | 55.022 | 65.593 | 1.00 | 19.51 |
| ATOM | 5929 | O | | HOH | A4017 | 19.122 | 55.704 | 66.011 | 1.00 | 21.98 |
| ATOM | 5930 | O | | HOH | A4018 | 17.714 | 55.077 | 69.026 | 1.00 | 46.59 |
| ATOM | 5931 | O | | HOH | A4019 | 19.388 | 46.543 | 61.899 | 1.00 | 22.00 |
| ATOM | 5932 | O | | HOH | A4020 | 21.981 | 55.444 | 66.518 | 1.00 | 18.15 |
| ATOM | 5933 | O | | HOH | A4025 | 12.814 | 47.627 | 67.388 | 1.00 | 19.77 |
| ATOM | 5934 | O | | HOH | A4026 | 7.416 | 41.332 | 67.526 | 1.00 | 22.46 |
| ATOM | 5935 | O | | HOH | A4027 | 7.476 | 42.808 | 69.897 | 1.00 | 28.51 |
| ATOM | 5936 | O | | HOH | A4028 | 7.605 | 43.100 | 65.524 | 1.00 | 25.65 |
| ATOM | 5937 | O | | HOH | A4029 | 8.219 | 49.353 | 70.518 | 1.00 | 41.35 |
| ATOM | 5938 | O | | HOH | A4031 | 9.355 | 53.073 | 70.528 | 1.00 | 35.77 |
| ATOM | 5939 | O | | HOH | A4032 | 5.213 | 55.253 | 66.493 | 1.00 | 42.95 |
| ATOM | 5940 | O | | HOH | A4033 | 7.426 | 56.068 | 56.277 | 1.00 | 50.10 |
| ATOM | 5941 | O | | HOH | A4034 | 18.569 | 56.109 | 46.877 | 1.00 | 28.67 |
| ATOM | 5942 | O | | HOH | A4035 | 14.077 | 66.304 | 49.174 | 1.00 | 26.13 |
| ATOM | 5943 | O | | HOH | A4036 | 21.748 | 65.868 | 41.280 | 1.00 | 26.13 |
| ATOM | 5944 | O | | HOH | A4037 | 24.249 | 64.920 | 40.690 | 1.00 | 28.67 |
| ATOM | 5945 | O | | HOH | A4038 | 24.709 | 63.113 | 42.435 | 1.00 | 33.11 |
| ATOM | 5946 | O | | HOH | A4039 | 20.330 | 55.356 | 35.073 | 1.00 | 40.76 |
| ATOM | 5947 | O | | HOH | A4040 | 13.596 | 61.664 | 34.692 | 1.00 | 44.52 |
| ATOM | 5948 | O | | HOH | A4041 | 17.209 | 62.894 | 35.538 | 1.00 | 25.49 |
| ATOM | 5949 | O | | HOH | A4042 | 21.842 | 58.816 | 31.984 | 1.00 | 25.30 |
| ATOM | 5950 | O | | HOH | A4043 | 21.195 | 75.999 | 38.756 | 1.00 | 32.27 |
| ATOM | 5951 | O | | HOH | A4044 | 25.492 | 76.693 | 36.354 | 1.00 | 39.11 |
| ATOM | 5952 | O | | HOH | A4045 | 29.099 | 75.620 | 30.433 | 1.00 | 29.08 |
| ATOM | 5953 | O | | HOH | A4046 | 28.442 | 75.284 | 17.768 | 1.00 | 46.29 |
| ATOM | 5954 | O | | HOH | A4048 | 25.400 | 82.416 | 14.444 | 1.00 | 60.82 |
| ATOM | 5955 | O | | HOH | A4049 | 15.321 | 73.944 | 37.282 | 1.00 | 33.37 |
| ATOM | 5956 | O | | HOH | A4050 | 17.177 | 69.082 | 26.794 | 1.00 | 36.00 |
| ATOM | 5957 | O | | HOH | A4051 | 35.084 | 70.880 | 21.975 | 1.00 | 39.76 |
| ATOM | 5958 | O | | HOH | A4053 | 39.707 | 82.802 | 25.904 | 1.00 | 47.09 |
| ATOM | 5959 | O | | HOH | A4054 | 33.407 | 60.940 | 23.826 | 1.00 | 41.51 |
| ATOM | 5960 | O | | HOH | A4055 | 32.913 | 63.225 | 25.986 | 1.00 | 38.97 |
| ATOM | 5961 | O | | HOH | A4057 | 19.453 | 47.959 | 46.124 | 1.00 | 32.15 |
| ATOM | 5962 | O | | HOH | A4058 | 3.438 | 36.965 | 63.399 | 1.00 | 29.20 |

FIGURE 3DL

|      | A    | B | C | D   | E     | F      | G      | H      | I    | J     |
|------|------|---|---|-----|-------|--------|--------|--------|------|-------|
| ATOM | 5963 | O |   | HOH | A4059 | 7.418  | 37.098 | 63.855 | 1.00 | 24.62 |
| ATOM | 5964 | O |   | HOH | A4060 | 1.025  | 39.134 | 59.571 | 1.00 | 46.34 |
| ATOM | 5965 | O |   | HOH | A4061 | 3.119  | 48.839 | 52.109 | 1.00 | 27.61 |
| ATOM | 5966 | O |   | HOH | A4062 | 2.414  | 51.211 | 57.857 | 1.00 | 33.85 |
| ATOM | 5967 | O |   | HOH | A4063 | 1.755  | 48.601 | 49.660 | 1.00 | 29.57 |
| ATOM | 5968 | O |   | HOH | A4064 | 14.435 | 49.875 | 60.800 | 1.00 | 22.99 |
| ATOM | 5969 | O |   | HOH | A4065 | 16.712 | 48.825 | 59.106 | 1.00 | 38.04 |
| ATOM | 5970 | O |   | HOH | A4066 | 14.847 | 52.927 | 40.299 | 1.00 | 37.06 |
| ATOM | 5971 | O |   | HOH | A4067 | 23.506 | 51.852 | 38.319 | 1.00 | 40.18 |
| ATOM | 5972 | O |   | HOH | A4068 | 22.985 | 44.981 | 36.781 | 1.00 | 39.08 |
| ATOM | 5973 | O |   | HOH | A4069 | 22.013 | 40.630 | 47.337 | 1.00 | 31.11 |
| ATOM | 5974 | O |   | HOH | A4070 | 21.463 | 38.974 | 45.213 | 1.00 | 29.91 |
| ATOM | 5975 | O |   | HOH | A4071 | 23.278 | 38.983 | 49.120 | 1.00 | 29.31 |
| ATOM | 5976 | O |   | HOH | A4072 | 1.675  | 29.203 | 66.961 | 1.00 | 32.69 |
| ATOM | 5977 | O |   | HOH | A4073 | 4.895  | 30.800 | 72.565 | 1.00 | 44.56 |
| ATOM | 5978 | O |   | HOH | A4074 | 5.931  | 26.948 | 72.722 | 1.00 | 47.92 |
| ATOM | 5979 | O |   | HOH | A4075 | 10.458 | 41.656 | 45.478 | 1.00 | 26.36 |
| ATOM | 5980 | O |   | HOH | A4076 | 9.773  | 43.184 | 40.414 | 1.00 | 44.33 |
| ATOM | 5981 | O |   | HOH | A4077 | 11.958 | 35.472 | 36.053 | 1.00 | 60.93 |
| ATOM | 5982 | O |   | HOH | A4078 | 9.573  | 35.985 | 37.641 | 1.00 | 43.36 |
| ATOM | 5983 | O |   | HOH | A4079 | -1.206 | 41.135 | 47.645 | 1.00 | 51.33 |
| ATOM | 5984 | O |   | HOH | A4080 | 1.475  | 31.730 | 50.864 | 1.00 | 61.06 |
| ATOM | 5985 | O |   | HOH | A4081 | 15.202 | 30.348 | 48.077 | 1.00 | 32.82 |
| ATOM | 5986 | O |   | HOH | A4082 | 12.193 | 32.887 | 45.748 | 1.00 | 63.53 |
| ATOM | 5987 | O |   | HOH | A4083 | 15.104 | 27.989 | 69.260 | 1.00 | 39.31 |
| ATOM | 5988 | O |   | HOH | A4084 | 24.023 | 26.555 | 63.013 | 1.00 | 59.91 |
| ATOM | 5989 | O |   | HOH | A4086 | 22.722 | 29.478 | 48.597 | 1.00 | 53.44 |
| ATOM | 5990 | O |   | HOH | A4088 | 47.055 | 51.290 | 57.458 | 1.00 | 49.67 |
| ATOM | 5991 | O |   | HOH | A4089 | 41.255 | 57.224 | 60.917 | 1.00 | 34.18 |
| ATOM | 5992 | O |   | HOH | A4090 | 40.605 | 59.156 | 57.734 | 1.00 | 48.52 |
| ATOM | 5993 | O |   | HOH | A4091 | 38.964 | 46.469 | 50.904 | 1.00 | 51.39 |
| ATOM | 5994 | O |   | HOH | A4093 | 39.272 | 44.862 | 66.917 | 1.00 | 41.75 |
| ATOM | 5995 | O |   | HOH | A4094 | 29.366 | 45.066 | 69.340 | 1.00 | 25.13 |
| ATOM | 5996 | O |   | HOH | A4095 | 28.539 | 39.814 | 70.238 | 1.00 | 23.88 |
| ATOM | 5997 | O |   | HOH | A4096 | 35.883 | 47.267 | 72.084 | 1.00 | 35.69 |
| ATOM | 5998 | O |   | HOH | A4097 | 34.764 | 39.975 | 65.953 | 1.00 | 32.62 |
| ATOM | 5999 | O |   | HOH | A4098 | 25.187 | 51.574 | 70.980 | 1.00 | 21.07 |
| ATOM | 6000 | O |   | HOH | A4099 | 24.421 | 49.391 | 69.393 | 1.00 | 24.15 |
| ATOM | 6001 | O |   | HOH | A4100 | 30.488 | 37.027 | 67.117 | 1.00 | 31.88 |
| ATOM | 6002 | O |   | HOH | A4101 | 27.810 | 33.896 | 65.772 | 1.00 | 33.87 |
| ATOM | 6003 | O |   | HOH | A4102 | 32.960 | 35.125 | 55.143 | 1.00 | 57.29 |
| ATOM | 6004 | O |   | HOH | A4103 | 28.748 | 36.224 | 53.127 | 1.00 | 43.05 |
| ATOM | 6005 | O |   | HOH | A4104 | 27.698 | 31.622 | 64.223 | 1.00 | 37.89 |
| ATOM | 6006 | O |   | HOH | A4105 | 12.912 | 28.684 | 67.770 | 1.00 | 31.16 |
| ATOM | 6007 | O |   | HOH | A4106 | 10.230 | 31.633 | 67.005 | 1.00 | 27.21 |
| ATOM | 6008 | O |   | HOH | A4107 | 23.055 | 36.665 | 70.232 | 1.00 | 25.87 |
| ATOM | 6009 | O |   | HOH | A4108 | 20.682 | 37.294 | 71.851 | 1.00 | 22.00 |
| ATOM | 6010 | O |   | HOH | A4109 | 1.158  | 34.176 | 62.644 | 1.00 | 58.20 |
| ATOM | 6011 | O |   | HOH | A4110 | 0.198  | 41.898 | 73.963 | 1.00 | 49.07 |
| ATOM | 6012 | O |   | HOH | A4111 | 0.243  | 40.977 | 76.426 | 1.00 | 61.50 |
| ATOM | 6013 | O |   | HOH | A4112 | 4.712  | 39.094 | 77.648 | 1.00 | 34.97 |
| ATOM | 6014 | O |   | HOH | A4113 | 3.372  | 32.470 | 76.025 | 1.00 | 48.04 |

FIGURE 3DM

|      | A    | B | C D E    | F       | G      | H      | I    | J     |
|------|------|---|----------|---------|--------|--------|------|-------|
| ATOM | 6015 | O | HOH A4114 | -0.161  | 34.747 | 76.911 | 1.00 | 56.14 |
| ATOM | 6016 | O | HOH A4115 | 14.082  | 27.358 | 77.978 | 1.00 | 29.48 |
| ATOM | 6017 | O | HOH A4116 | 10.239  | 22.867 | 85.441 | 1.00 | 47.97 |
| ATOM | 6018 | O | HOH A4117 | 16.880  | 28.449 | 92.108 | 1.00 | 32.92 |
| ATOM | 6019 | O | HOH A4118 | 30.902  | 40.679 | 92.868 | 1.00 | 25.36 |
| ATOM | 6020 | O | HOH A4119 | 28.901  | 38.917 | 92.539 | 1.00 | 28.92 |
| ATOM | 6021 | O | HOH A4120 | 33.800  | 30.256 | 79.881 | 1.00 | 34.20 |
| ATOM | 6022 | O | HOH A4121 | 29.946  | 31.384 | 78.870 | 1.00 | 30.60 |
| ATOM | 6023 | O | HOH A4122 | 31.176  | 42.006 | 77.488 | 1.00 | 25.78 |
| ATOM | 6024 | O | HOH A4123 | 31.682  | 37.097 | 75.219 | 1.00 | 43.96 |
| ATOM | 6025 | O | HOH A4124 | 22.371  | 28.496 | 83.347 | 1.00 | 28.18 |
| ATOM | 6026 | O | HOH A4125 | 26.443  | 30.540 | 76.884 | 1.00 | 52.45 |
| ATOM | 6027 | O | HOH A4126 | 17.331  | 24.350 | 78.639 | 1.00 | 36.15 |
| ATOM | 6028 | O | HOH A4127 | 17.935  | 21.756 | 79.195 | 1.00 | 51.05 |
| ATOM | 6029 | O | HOH A4128 | 23.423  | 25.811 | 82.839 | 1.00 | 34.72 |
| ATOM | 6030 | O | HOH A4129 | 23.775  | 29.755 | 77.509 | 1.00 | 38.85 |
| ATOM | 6031 | O | HOH A4130 | 24.117  | 27.457 | 79.392 | 1.00 | 28.52 |
| ATOM | 6032 | O | HOH A4131 | 27.891  | 41.805 | 76.065 | 1.00 | 22.47 |
| ATOM | 6033 | O | HOH A4132 | 28.497  | 34.637 | 75.677 | 1.00 | 36.10 |
| ATOM | 6034 | O | HOH A4133 | 30.829  | 33.439 | 75.071 | 1.00 | 41.48 |
| ATOM | 6035 | O | HOH A4134 | 26.663  | 34.002 | 73.778 | 1.00 | 29.63 |
| ATOM | 6036 | O | HOH A4135 | 26.147  | 33.909 | 71.159 | 1.00 | 62.42 |
| ATOM | 6037 | O | HOH A4136 | 28.030  | 37.442 | 71.432 | 1.00 | 35.14 |
| ATOM | 6038 | O | HOH A4137 | 33.800  | 52.589 | 72.809 | 1.00 | 47.40 |
| ATOM | 6039 | O | HOH A4138 | 33.638  | 48.764 | 79.446 | 1.00 | 24.61 |
| ATOM | 6040 | O | HOH A4139 | 29.591  | 47.978 | 83.695 | 1.00 | 23.48 |
| ATOM | 6041 | O | HOH A4140 | 17.600  | 29.989 | 72.338 | 1.00 | 42.50 |
| ATOM | 6042 | O | HOH A4141 | 26.350  | 41.074 | 87.295 | 1.00 | 20.43 |
| ATOM | 6043 | O | HOH A4142 | 28.673  | 40.380 | 88.440 | 1.00 | 24.49 |
| ATOM | 6044 | O | HOH A4143 | 40.528  | 41.024 | 87.966 | 1.00 | 46.79 |
| ATOM | 6045 | O | HOH A4144 | 38.903  | 34.306 | 84.420 | 1.00 | 54.75 |
| ATOM | 6046 | O | HOH A4145 | 37.248  | 40.668 | 79.698 | 1.00 | 52.83 |
| ATOM | 6047 | O | HOH A4146 | 38.644  | 54.614 | 72.557 | 1.00 | 70.26 |
| ATOM | 6048 | O | HOH A4148 | 48.565  | 52.321 | 62.247 | 1.00 | 45.73 |
| ATOM | 6049 | O | HOH A4152 | 39.462  | 51.369 | 85.284 | 1.00 | 35.29 |
| ATOM | 6050 | O | HOH A4153 | 37.043  | 53.484 | 79.166 | 1.00 | 60.45 |
| ATOM | 6051 | O | HOH A4154 | 34.369  | 54.210 | 77.688 | 1.00 | 27.30 |
| ATOM | 6052 | O | HOH A4156 | 32.399  | 59.625 | 74.513 | 1.00 | 39.31 |
| ATOM | 6053 | O | HOH A4157 | 13.669  | 51.778 | 76.885 | 1.00 | 22.43 |
| ATOM | 6054 | O | HOH A4158 | 7.782   | 47.906 | 74.824 | 1.00 | 34.95 |
| ATOM | 6055 | O | HOH A4159 | 6.248   | 41.154 | 78.385 | 1.00 | 33.13 |
| ATOM | 6056 | O | HOH A4160 | 29.496  | 55.976 | 95.560 | 1.00 | 44.38 |
| ATOM | 6057 | O | HOH A4161 | 30.712  | 63.527 | 81.749 | 1.00 | 25.59 |
| ATOM | 6058 | O | HOH A4162 | 35.609  | 62.351 | 73.890 | 1.00 | 51.56 |
| ATOM | 6059 | O | HOH A4163 | 20.983  | 63.412 | 74.276 | 1.00 | 37.80 |
| ATOM | 6060 | O | HOH A4164 | 13.134  | 60.046 | 78.306 | 1.00 | 31.85 |
| ATOM | 6061 | O | HOH A4165 | 8.391   | 55.328 | 84.201 | 1.00 | 29.07 |
| ATOM | 6062 | O | HOH A4166 | 7.732   | 58.203 | 83.289 | 1.00 | 36.54 |
| ATOM | 6063 | O | HOH A4167 | 8.770   | 59.551 | 85.686 | 1.00 | 37.60 |
| ATOM | 6064 | O | HOH A4168 | 10.287  | 58.313 | 87.133 | 1.00 | 51.28 |
| ATOM | 6065 | O | HOH A4169 | 7.231   | 53.467 | 80.832 | 1.00 | 36.78 |
| ATOM | 6066 | O | HOH A4170 | 6.493   | 55.796 | 79.403 | 1.00 | 71.61 |

FIGURE 3DN

|      | A    | B | C | D | E     | F      | G      | H       | I    | J     |
|------|------|---|---|---|-------|--------|--------|---------|------|-------|
| ATOM | 6067 | O |   | HOH | A4171 | 7.765  | 53.875 | 76.478  | 1.00 | 45.75 |
| ATOM | 6068 | O |   | HOH | A4172 | 6.128  | 53.328 | 86.238  | 1.00 | 32.68 |
| ATOM | 6069 | O |   | HOH | A4173 | 4.905  | 44.786 | 85.617  | 1.00 | 38.61 |
| ATOM | 6070 | O |   | HOH | A4174 | 2.527  | 40.967 | 80.338  | 1.00 | 34.81 |
| ATOM | 6071 | O |   | HOH | A4175 | 6.926  | 44.418 | 87.198  | 1.00 | 27.80 |
| ATOM | 6072 | O |   | HOH | A4176 | 29.319 | 47.820 | 102.443 | 1.00 | 23.70 |
| ATOM | 6073 | O |   | HOH | A4177 | 8.497  | 57.326 | 90.959  | 1.00 | 34.30 |
| ATOM | 6074 | O |   | HOH | A4178 | 5.951  | 45.048 | 89.739  | 1.00 | 29.88 |
| ATOM | 6075 | O |   | HOH | A4179 | 8.263  | 40.360 | 95.528  | 1.00 | 29.32 |
| ATOM | 6076 | O |   | HOH | A4180 | 6.727  | 42.345 | 96.500  | 1.00 | 45.05 |
| ATOM | 6077 | O |   | HOH | A4181 | 7.264  | 44.867 | 95.978  | 1.00 | 47.71 |
| ATOM | 6078 | O |   | HOH | A4182 | 11.493 | 46.784 | 94.664  | 1.00 | 25.25 |
| ATOM | 6079 | O |   | HOH | A4184 | 21.757 | 49.276 | 102.648 | 1.00 | 28.52 |
| ATOM | 6080 | O |   | HOH | A4186 | 39.204 | 64.265 | 111.922 | 1.00 | 47.33 |
| ATOM | 6081 | O |   | HOH | A4190 | 27.559 | 52.981 | 105.796 | 1.00 | 36.57 |
| ATOM | 6082 | O |   | HOH | A4191 | 25.468 | 54.565 | 106.092 | 1.00 | 29.73 |
| ATOM | 6083 | O |   | HOH | A4192 | 16.156 | 41.127 | 107.312 | 1.00 | 38.80 |
| ATOM | 6084 | O |   | HOH | A4194 | 9.790  | 51.113 | 104.711 | 1.00 | 51.51 |
| ATOM | 6085 | O |   | HOH | A4195 | 8.598  | 49.010 | 103.375 | 1.00 | 54.85 |
| ATOM | 6086 | O |   | HOH | A4196 | 12.679 | 39.186 | 101.921 | 1.00 | 37.90 |
| ATOM | 6087 | O |   | HOH | A4197 | 15.806 | 33.070 | 96.865  | 1.00 | 29.66 |
| ATOM | 6088 | O |   | HOH | A4198 | 13.851 | 33.382 | 98.660  | 1.00 | 49.07 |
| ATOM | 6089 | O |   | HOH | A4199 | 12.834 | 29.940 | 95.825  | 1.00 | 41.79 |
| ATOM | 6090 | O |   | HOH | A4200 | 8.793  | 31.008 | 95.038  | 1.00 | 44.88 |
| ATOM | 6091 | O |   | HOH | A4202 | 22.533 | 31.262 | 98.298  | 1.00 | 32.24 |
| ATOM | 6092 | O |   | HOH | A4204 | 8.304  | 33.622 | 93.716  | 1.00 | 31.86 |
| ATOM | 6093 | O |   | HOH | A4205 | 9.090  | 25.612 | 91.067  | 1.00 | 35.09 |
| ATOM | 6094 | O |   | HOH | A4206 | 2.368  | 40.633 | 94.868  | 1.00 | 53.16 |
| ATOM | 6095 | O |   | HOH | A4207 | 3.151  | 44.960 | 89.747  | 1.00 | 43.33 |
| ATOM | 6096 | O |   | HOH | A4208 | 2.746  | 43.320 | 86.219  | 1.00 | 38.66 |
| ATOM | 6097 | O |   | HOH | A4209 | 5.796  | 33.572 | 96.494  | 1.00 | 39.68 |
| ATOM | 6098 | O |   | HOH | A4211 | 4.832  | 42.436 | 79.894  | 1.00 | 32.61 |
| ATOM | 6099 | O |   | HOH | A4212 | 5.584  | 42.114 | 75.690  | 1.00 | 50.86 |
| ATOM | 6100 | O |   | HOH | A4214 | -1.988 | 39.261 | 76.405  | 1.00 | 44.73 |
| ATOM | 6101 | O |   | HOH | A4215 | 2.671  | 43.870 | 73.125  | 1.00 | 37.87 |
| ATOM | 6102 | O |   | HOH | A4216 | 4.513  | 42.310 | 71.423  | 1.00 | 27.13 |
| ATOM | 6103 | O |   | HOH | A4218 | 7.890  | 45.281 | 69.018  | 1.00 | 35.33 |
| ATOM | 6104 | O |   | HOH | A4219 | 9.552  | 48.011 | 68.625  | 1.00 | 47.71 |
| ATOM | 6105 | O |   | HOH | A4220 | 34.323 | 41.992 | 95.519  | 1.00 | 61.79 |
| ATOM | 6106 | O |   | HOH | A4221 | 33.388 | 39.489 | 92.433  | 1.00 | 32.01 |
| ATOM | 6107 | O |   | HOH | A4222 | 36.304 | 48.011 | 90.502  | 1.00 | 45.37 |
| ATOM | 6108 | O |   | HOH | A4223 | 35.742 | 44.123 | 90.210  | 1.00 | 55.64 |
| ATOM | 6109 | O |   | HOH | A4224 | 38.675 | 45.116 | 88.300  | 1.00 | 40.56 |
| ATOM | 6110 | O |   | HOH | A4230 | 45.545 | 53.972 | 70.133  | 1.00 | 49.29 |
| ATOM | 6111 | O |   | HOH | A4232 | 51.522 | 50.514 | 73.728  | 1.00 | 67.06 |
| ATOM | 6112 | O |   | HOH | A4233 | 42.864 | 57.134 | 72.135  | 1.00 | 62.96 |
| ATOM | 6113 | O |   | HOH | A4234 | 46.232 | 58.575 | 69.289  | 1.00 | 53.39 |
| ATOM | 6114 | O |   | HOH | A4239 | 50.981 | 50.572 | 66.787  | 1.00 | 60.93 |
| ATOM | 6115 | O |   | HOH | A4240 | 44.804 | 50.101 | 63.563  | 1.00 | 58.86 |
| ATOM | 6116 | O |   | HOH | A4242 | 15.101 | 26.283 | 94.223  | 1.00 | 40.69 |
| ATOM | 6117 | O |   | HOH | A4243 | 18.029 | 20.015 | 87.761  | 1.00 | 51.54 |
| ATOM | 6118 | O |   | HOH | A4244 | 11.309 | 20.915 | 83.505  | 1.00 | 57.21 |

FIGURE 3DO

|  | A | B | C | D | E | F | G | H | I | J |
|---|---|---|---|---|---|---|---|---|---|---|
| ATOM | 6119 | O |  | HOH | A4245 | 5.237 | 26.028 | 84.880 | 1.00 | 77.86 |
| ATOM | 6120 | O |  | HOH | A4246 | 3.238 | 34.472 | 82.767 | 1.00 | 38.76 |
| ATOM | 6121 | O |  | HOH | A4247 | 1.220 | 32.419 | 80.780 | 1.00 | 60.92 |
| ATOM | 6122 | O |  | HOH | A4248 | 2.965 | 30.156 | 79.971 | 1.00 | 44.80 |
| ATOM | 6123 | O |  | HOH | A4249 | 7.141 | 24.979 | 74.075 | 1.00 | 44.93 |
| ATOM | 6124 | O |  | HOH | A4250 | 6.083 | 24.231 | 70.247 | 1.00 | 45.81 |
| ATOM | 6125 | O |  | HOH | A4252 | 23.847 | 34.151 | 69.236 | 1.00 | 35.21 |
| ATOM | 6126 | O |  | HOH | A4253 | 25.266 | 33.665 | 66.485 | 1.00 | 44.03 |
| ATOM | 6127 | O |  | HOH | A4255 | 12.576 | 31.443 | 65.798 | 1.00 | 28.95 |
| ATOM | 6128 | O |  | HOH | A4256 | 15.767 | 27.821 | 75.928 | 1.00 | 27.08 |
| ATOM | 6129 | O |  | HOH | A4257 | 32.217 | 28.221 | 80.133 | 1.00 | 52.36 |
| ATOM | 6130 | O |  | HOH | A4259 | 35.762 | 47.033 | 76.760 | 1.00 | 26.19 |
| ATOM | 6131 | O |  | HOH | A4260 | 33.239 | 40.847 | 80.002 | 1.00 | 30.96 |
| ATOM | 6132 | O |  | HOH | A4261 | 30.849 | 55.466 | 74.449 | 1.00 | 37.70 |
| ATOM | 6133 | O |  | HOH | A4262 | 34.623 | 56.208 | 74.937 | 1.00 | 65.34 |
| ATOM | 6134 | O |  | HOH | A4264 | 35.344 | 42.923 | 98.902 | 1.00 | 72.31 |
| ATOM | 6135 | O |  | HOH | A4265 | 40.900 | 57.507 | 74.106 | 1.00 | 51.94 |
| ATOM | 6136 | O |  | HOH | A4266 | 24.843 | 30.444 | 97.443 | 1.00 | 50.14 |
| ATOM | 6137 | O |  | HOH | A4267 | 25.168 | 60.702 | 110.353 | 1.00 | 28.62 |
| ATOM | 6138 | O |  | HOH | A4268 | 24.835 | 63.410 | 109.797 | 1.00 | 41.85 |
| ATOM | 6139 | O |  | HOH | A4269 | 36.260 | 48.676 | 127.438 | 1.00 | 68.53 |
| ATOM | 6140 | O |  | HOH | A4271 | 38.921 | 57.321 | 109.303 | 1.00 | 52.05 |
| ATOM | 6141 | O |  | HOH | A4273 | 38.603 | 67.041 | 96.128 | 1.00 | 44.74 |
| ATOM | 6142 | O |  | HOH | A4274 | 36.932 | 63.804 | 96.937 | 1.00 | 56.48 |
| ATOM | 6143 | O |  | HOH | A4275 | 36.543 | 62.054 | 100.516 | 1.00 | 45.82 |
| ATOM | 6144 | O |  | HOH | A4276 | 42.550 | 67.721 | 95.527 | 1.00 | 65.78 |
| ATOM | 6145 | O |  | HOH | A4278 | 38.683 | 58.682 | 83.656 | 1.00 | 38.34 |
| ATOM | 6146 | O |  | HOH | A4279 | 36.608 | 57.131 | 78.027 | 1.00 | 40.37 |
| ATOM | 6147 | O |  | HOH | A4280 | 44.164 | 57.819 | 78.772 | 1.00 | 48.18 |
| ATOM | 6148 | O |  | HOH | A4281 | 35.611 | 51.356 | 74.545 | 1.00 | 40.17 |
| ATOM | 6149 | O |  | HOH | A4282 | 35.060 | 48.626 | 74.485 | 1.00 | 28.91 |
| ATOM | 6150 | O |  | HOH | A4283 | 34.630 | 53.002 | 70.131 | 1.00 | 37.16 |
| ATOM | 6151 | O |  | HOH | A4284 | 37.521 | 52.869 | 75.602 | 1.00 | 83.56 |
| ATOM | 6152 | O |  | HOH | A4285 | 40.238 | 53.842 | 133.358 | 1.00 | 83.49 |
| ATOM | 6153 | O |  | HOH | A4286 | 37.709 | 52.680 | 87.758 | 1.00 | 55.12 |
| ATOM | 6154 | O |  | HOH | A4291 | 30.580 | 45.498 | 99.035 | 1.00 | 45.03 |
| ATOM | 6155 | O |  | HOH | A4292 | 28.807 | 42.597 | 98.380 | 1.00 | 34.73 |
| ATOM | 6156 | O |  | HOH | A4293 | 29.736 | 39.503 | 102.505 | 1.00 | 63.04 |
| ATOM | 6157 | O |  | HOH | A4294 | 27.169 | 32.163 | 96.627 | 1.00 | 55.24 |
| ATOM | 6158 | O |  | HOH | A4295 | 22.971 | 33.716 | 98.980 | 1.00 | 30.22 |
| ATOM | 6159 | O |  | HOH | A4297 | 35.814 | 34.406 | 96.802 | 1.00 | 51.13 |
| ATOM | 6160 | O |  | HOH | A4298 | 37.036 | 33.043 | 89.606 | 1.00 | 56.75 |
| ATOM | 6161 | O |  | HOH | A4299 | 39.309 | 35.259 | 90.479 | 1.00 | 46.79 |
| ATOM | 6162 | O |  | HOH | A4301 | 17.768 | 39.251 | 40.241 | 1.00 | 30.94 |
| ATOM | 6163 | O |  | HOH | A4302 | 16.065 | 40.703 | 37.568 | 1.00 | 42.67 |
| ATOM | 6164 | O |  | HOH | A4303 | 11.292 | 43.619 | 43.593 | 1.00 | 31.68 |
| ATOM | 6165 | O |  | HOH | A4304 | 9.011 | 45.259 | 42.943 | 1.00 | 42.78 |
| ATOM | 6166 | O |  | HOH | A4305 | 25.280 | 44.442 | 39.080 | 1.00 | 36.73 |
| ATOM | 6167 | O |  | HOH | A4306 | 16.282 | 50.756 | 39.514 | 1.00 | 34.25 |
| ATOM | 6168 | O |  | HOH | A4308 | 20.413 | 58.532 | 28.843 | 1.00 | 36.13 |
| ATOM | 6169 | O |  | HOH | A4309 | 20.053 | 60.782 | 31.417 | 1.00 | 35.07 |
| ATOM | 6170 | O |  | HOH | A4310 | 22.211 | 54.419 | 30.971 | 1.00 | 47.02 |

FIGURE 3DP

| | A | B | C | D | E | F | G | H | I | J |
|---|---|---|---|---|---|---|---|---|---|---|
| ATOM | 6171 | O | HOH | A | 4311 | 18.071 | 54.707 | 38.155 | 1.00 | 42.25 |
| ATOM | 6172 | O | HOH | A | 4312 | 15.475 | 54.816 | 38.331 | 1.00 | 45.02 |
| ATOM | 6173 | O | HOH | A | 4313 | 13.224 | 56.193 | 38.490 | 1.00 | 45.33 |
| ATOM | 6174 | O | HOH | A | 4314 | 23.814 | 32.344 | 45.924 | 1.00 | 37.75 |
| ATOM | 6175 | O | HOH | A | 4315 | 24.863 | 28.263 | 44.925 | 1.00 | 57.65 |
| ATOM | 6176 | O | HOH | A | 4317 | 18.778 | 22.177 | 57.584 | 1.00 | 45.82 |
| ATOM | 6177 | O | HOH | A | 4319 | 5.492 | 29.081 | 50.002 | 1.00 | 36.87 |
| ATOM | 6178 | O | HOH | A | 4320 | 7.393 | 33.677 | 45.280 | 1.00 | 57.78 |
| ATOM | 6179 | O | HOH | A | 4321 | 4.339 | 28.233 | 57.570 | 1.00 | 42.04 |
| ATOM | 6180 | O | HOH | A | 4322 | 0.788 | 31.200 | 65.532 | 1.00 | 37.09 |
| ATOM | 6181 | O | HOH | A | 4323 | 0.054 | 32.543 | 67.766 | 1.00 | 52.03 |
| ATOM | 6182 | O | HOH | A | 4324 | 2.787 | 32.855 | 73.099 | 1.00 | 44.97 |
| ATOM | 6183 | O | HOH | A | 4325 | 2.970 | 35.323 | 71.830 | 1.00 | 31.32 |
| ATOM | 6184 | O | HOH | A | 4326 | -1.375 | 38.700 | 66.937 | 1.00 | 43.61 |
| ATOM | 6185 | O | HOH | A | 4327 | 1.231 | 38.274 | 63.638 | 1.00 | 30.58 |
| ATOM | 6186 | O | HOH | A | 4328 | 30.049 | 27.867 | 62.515 | 1.00 | 61.65 |
| ATOM | 6187 | O | HOH | A | 4329 | 15.440 | 29.790 | 73.918 | 1.00 | 46.07 |
| ATOM | 6188 | O | HOH | A | 4330 | 7.091 | 28.336 | 82.269 | 1.00 | 41.51 |
| ATOM | 6189 | O | HOH | A | 4331 | 38.745 | 54.953 | 81.831 | 1.00 | 50.17 |
| ATOM | 6190 | O | HOH | A | 4332 | 44.380 | 51.823 | 84.900 | 1.00 | 66.43 |
| ATOM | 6191 | O | HOH | A | 4334 | 39.968 | 41.489 | 79.391 | 1.00 | 43.08 |
| ATOM | 6192 | O | HOH | A | 4335 | 37.529 | 40.888 | 65.079 | 1.00 | 41.77 |
| ATOM | 6193 | O | HOH | A | 4336 | 27.869 | 32.966 | 52.710 | 1.00 | 53.64 |
| ATOM | 6194 | O | HOH | A | 4337 | 3.240 | 34.396 | 53.617 | 1.00 | 52.86 |
| ATOM | 6195 | O | HOH | A | 4338 | 31.808 | 43.512 | 95.250 | 1.00 | 35.93 |
| ATOM | 6196 | O | HOH | A | 4339 | 29.217 | 55.195 | 93.139 | 1.00 | 43.07 |
| ATOM | 6197 | O | HOH | A | 4349 | 33.191 | 44.099 | 48.332 | 1.00 | 40.15 |
| ATOM | 6198 | O | HOH | A | 4350 | 37.474 | 40.595 | 58.835 | 1.00 | 55.51 |
| ATOM | 6199 | O | HOH | A | 4352 | 31.819 | 38.504 | 51.758 | 1.00 | 49.18 |
| ATOM | 6200 | O | HOH | A | 4353 | 15.155 | 45.831 | 59.702 | 1.00 | 31.59 |
| ATOM | 6201 | O | HOH | A | 4354 | 3.381 | 47.867 | 76.113 | 1.00 | 60.73 |
| ATOM | 6202 | O | HOH | A | 4355 | 4.726 | 45.638 | 76.659 | 1.00 | 29.17 |
| ATOM | 6203 | O | HOH | A | 4356 | 3.409 | 43.234 | 75.686 | 1.00 | 37.87 |
| ATOM | 6204 | O | HOH | A | 4357 | 9.393 | 51.631 | 72.959 | 1.00 | 39.27 |
| ATOM | 6205 | O | HOH | A | 4358 | 3.221 | 55.162 | 63.032 | 1.00 | 39.66 |
| ATOM | 6206 | O | HOH | A | 4359 | 4.213 | 56.541 | 52.335 | 1.00 | 52.70 |
| ATOM | 6207 | O | HOH | A | 4360 | 6.056 | 58.319 | 51.953 | 1.00 | 48.56 |
| ATOM | 6208 | O | HOH | A | 4361 | 2.443 | 53.877 | 56.433 | 1.00 | 72.21 |
| ATOM | 6209 | O | HOH | A | 4362 | 6.507 | 57.740 | 47.697 | 1.00 | 51.72 |
| ATOM | 6210 | O | HOH | A | 4363 | 27.595 | 61.952 | 42.470 | 1.00 | 29.01 |
| ATOM | 6211 | O | HOH | A | 4364 | 21.934 | 56.271 | 37.482 | 1.00 | 36.34 |
| ATOM | 6212 | O | HOH | A | 4365 | 23.945 | 54.478 | 37.558 | 1.00 | 32.97 |
| ATOM | 6213 | O | HOH | A | 4366 | 14.674 | 64.601 | 32.880 | 1.00 | 46.72 |
| ATOM | 6214 | O | HOH | A | 4367 | 13.376 | 64.966 | 35.462 | 1.00 | 45.02 |
| ATOM | 6215 | O | HOH | A | 4368 | 13.727 | 57.416 | 33.690 | 1.00 | 40.65 |
| ATOM | 6216 | O | HOH | A | 4369 | 18.574 | 76.532 | 35.223 | 1.00 | 66.47 |
| ATOM | 6217 | O | HOH | A | 4371 | 25.281 | 77.727 | 40.563 | 1.00 | 42.21 |
| ATOM | 6218 | O | HOH | A | 4372 | 27.556 | 78.067 | 32.550 | 1.00 | 40.98 |
| ATOM | 6219 | O | HOH | A | 4373 | 30.351 | 77.999 | 32.662 | 1.00 | 54.24 |
| ATOM | 6220 | O | HOH | A | 4374 | 12.682 | 73.312 | 37.273 | 1.00 | 44.52 |
| ATOM | 6221 | O | HOH | A | 4375 | 12.693 | 29.012 | 47.695 | 1.00 | 55.07 |
| ATOM | 6222 | O | HOH | A | 4376 | 16.901 | 28.425 | 46.574 | 1.00 | 52.00 |

FIGURE 3DQ

|  | A | B | C D E | F | G | H | I | J |
|---|---|---|---|---|---|---|---|---|
| ATOM | 6223 | O | HOH A4377 | 35.142 | 58.592 | 21.151 | 1.00 | 54.62 |
| ATOM | 6224 | O | HOH A4378 | 32.057 | 59.247 | 21.856 | 1.00 | 65.92 |
| ATOM | 6225 | O | HOH A4379 | 20.209 | 48.180 | 42.527 | 1.00 | 32.90 |
| ATOM | 6226 | O | HOH A4380 | -0.293 | 36.080 | 63.386 | 1.00 | 48.77 |
| ATOM | 6227 | O | HOH A4381 | 0.035 | 40.710 | 62.018 | 1.00 | 43.50 |
| ATOM | 6228 | O | HOH A4382 | 2.351 | 51.456 | 52.363 | 1.00 | 42.66 |
| ATOM | 6229 | O | HOH A4383 | 1.278 | 48.653 | 54.024 | 1.00 | 41.86 |
| ATOM | 6230 | O | HOH A4384 | 0.518 | 50.800 | 55.595 | 1.00 | 50.03 |
| ATOM | 6231 | O | HOH A4385 | -0.095 | 46.747 | 49.670 | 1.00 | 56.98 |
| ATOM | 6232 | O | HOH A4386 | 1.104 | 51.429 | 60.180 | 1.00 | 43.45 |
| ATOM | 6233 | O | HOH A4387 | -1.543 | 50.910 | 59.900 | 1.00 | 52.20 |
| ATOM | 6234 | O | HOH A4388 | 12.426 | 51.908 | 39.071 | 1.00 | 48.73 |
| ATOM | 6235 | O | HOH A4389 | 10.114 | 54.778 | 41.743 | 1.00 | 56.20 |
| ATOM | 6236 | O | HOH A4390 | 11.001 | 56.443 | 45.685 | 1.00 | 34.25 |
| ATOM | 6237 | O | HOH A4391 | 13.575 | 60.079 | 44.719 | 1.00 | 45.75 |
| ATOM | 6238 | O | HOH A4392 | 11.965 | 58.776 | 46.278 | 1.00 | 64.78 |
| ATOM | 6239 | O | HOH A4393 | 10.359 | 60.727 | 47.275 | 1.00 | 48.45 |
| ATOM | 6240 | O | HOH A4394 | 9.200 | 66.122 | 51.152 | 1.00 | 49.26 |
| ATOM | 6241 | O | HOH A4395 | 7.538 | 61.200 | 51.451 | 1.00 | 54.78 |
| ATOM | 6242 | O | HOH A4396 | 6.154 | 60.115 | 56.352 | 1.00 | 44.99 |
| ATOM | 6243 | O | HOH A4397 | 2.640 | 55.155 | 60.074 | 1.00 | 43.15 |
| ATOM | 6244 | O | HOH A4398 | 4.337 | 57.322 | 58.994 | 1.00 | 61.91 |
| ATOM | 6245 | O | HOH A4400 | 19.657 | 45.735 | 35.174 | 1.00 | 59.54 |
| ATOM | 6246 | O | HOH A4401 | 24.820 | 46.954 | 35.440 | 1.00 | 66.52 |
| ATOM | 6247 | O | HOH A4402 | 27.020 | 42.937 | 40.997 | 1.00 | 46.08 |
| ATOM | 6248 | O | HOH A4403 | 29.909 | 39.515 | 40.724 | 1.00 | 49.87 |
| ATOM | 6249 | O | HOH A4404 | 29.653 | 43.508 | 41.186 | 1.00 | 55.65 |
| ATOM | 6250 | O | HOH A4405 | 30.630 | 45.339 | 42.980 | 1.00 | 51.83 |
| ATOM | 6251 | O | HOH A4406 | 32.764 | 44.648 | 44.310 | 1.00 | 54.98 |
| ATOM | 6252 | O | HOH A4407 | 10.860 | 36.883 | 41.119 | 1.00 | 42.13 |
| ATOM | 6253 | O | HOH A4408 | 9.046 | 34.977 | 43.619 | 1.00 | 45.66 |
| ATOM | 6254 | O | HOH A4409 | 7.838 | 42.988 | 38.533 | 1.00 | 54.96 |
| ATOM | 6255 | O | HOH A4410 | 9.929 | 40.447 | 35.904 | 1.00 | 47.08 |
| ATOM | 6256 | O | HOH A4411 | 8.319 | 24.567 | 53.909 | 1.00 | 44.18 |
| ATOM | 6257 | O | HOH A4412 | 13.287 | 27.932 | 71.462 | 1.00 | 43.38 |
| ATOM | 6258 | O | HOH A4413 | 12.031 | 26.367 | 66.431 | 1.00 | 45.87 |
| ATOM | 6259 | O | HOH A4416 | 40.626 | 48.572 | 61.687 | 1.00 | 46.18 |
| ATOM | 6260 | O | HOH A4417 | 44.459 | 46.918 | 60.172 | 1.00 | 67.93 |
| ATOM | 6261 | O | HOH A4418 | 40.850 | 42.506 | 55.971 | 1.00 | 49.15 |
| ATOM | 6262 | O | HOH A4419 | 37.603 | 44.493 | 52.350 | 1.00 | 56.24 |
| ATOM | 6263 | O | HOH A4420 | 40.092 | 43.230 | 52.464 | 1.00 | 60.59 |
| ATOM | 6264 | O | HOH A4421 | 39.586 | 42.269 | 66.098 | 1.00 | 50.37 |
| ATOM | 6265 | O | HOH A4422 | 33.369 | 38.044 | 71.159 | 1.00 | 45.71 |
| ATOM | 6266 | O | HOH A4423 | 29.577 | 34.589 | 67.750 | 1.00 | 58.82 |
| ATOM | 6267 | O | HOH A4424 | -2.624 | 33.546 | 65.099 | 1.00 | 68.04 |
| ATOM | 6268 | O | HOH A4425 | 3.610 | 36.511 | 78.346 | 1.00 | 57.30 |
| ATOM | 6269 | O | HOH A4426 | 2.220 | 35.559 | 80.436 | 1.00 | 39.27 |
| ATOM | 6270 | O | HOH A4427 | 2.699 | 30.298 | 77.198 | 1.00 | 45.38 |
| ATOM | 6271 | O | HOH A4428 | 14.939 | 24.643 | 79.008 | 1.00 | 39.96 |
| ATOM | 6272 | O | HOH A4429 | 29.657 | 29.163 | 80.235 | 1.00 | 36.55 |
| ATOM | 6273 | O | HOH A4430 | 32.294 | 32.600 | 79.264 | 1.00 | 40.39 |
| ATOM | 6274 | O | HOH A4431 | 32.806 | 33.606 | 76.837 | 1.00 | 51.32 |

FIGURE 3DR

| | A | B | C | D | E | F | G | H | I | J |
|---|---|---|---|---|---|---|---|---|---|---|
| ATOM | 6275 | O | HOH | A | 4432 | 35.496 | 37.406 | 78.669 | 1.00 | 47.32 |
| ATOM | 6276 | O | HOH | A | 4433 | 27.950 | 32.746 | 77.779 | 1.00 | 37.73 |
| ATOM | 6277 | O | HOH | A | 4434 | 33.503 | 39.694 | 75.559 | 1.00 | 46.07 |
| ATOM | 6278 | O | HOH | A | 4435 | 21.384 | 24.374 | 83.812 | 1.00 | 29.93 |
| ATOM | 6279 | O | HOH | A | 4436 | 28.318 | 28.311 | 78.002 | 1.00 | 45.93 |
| ATOM | 6280 | O | HOH | A | 4437 | 19.520 | 21.375 | 84.540 | 1.00 | 45.80 |
| ATOM | 6281 | O | HOH | A | 4438 | 24.849 | 19.565 | 80.638 | 1.00 | 70.16 |
| ATOM | 6282 | O | HOH | A | 4439 | 17.067 | 29.679 | 69.676 | 1.00 | 49.98 |
| ATOM | 6283 | O | HOH | A | 4440 | 43.326 | 44.458 | 87.967 | 1.00 | 49.33 |
| ATOM | 6284 | O | HOH | A | 4441 | 41.320 | 37.734 | 85.046 | 1.00 | 78.26 |
| ATOM | 6285 | O | HOH | A | 4442 | 40.522 | 38.400 | 87.496 | 1.00 | 53.42 |
| ATOM | 6286 | O | HOH | A | 4443 | 34.947 | 39.980 | 78.032 | 1.00 | 40.83 |
| ATOM | 6287 | O | HOH | A | 4444 | 39.004 | 41.480 | 76.417 | 1.00 | 59.05 |
| ATOM | 6288 | O | HOH | A | 4447 | 3.979 | 44.884 | 79.404 | 1.00 | 37.38 |
| ATOM | 6289 | O | HOH | A | 4448 | 5.061 | 45.645 | 83.299 | 1.00 | 43.75 |
| ATOM | 6290 | O | HOH | A | 4449 | 2.244 | 47.147 | 87.474 | 1.00 | 53.81 |
| ATOM | 6291 | O | HOH | A | 4451 | 1.227 | 41.807 | 92.478 | 1.00 | 49.02 |
| ATOM | 6292 | O | HOH | A | 4452 | 5.952 | 45.455 | 93.417 | 1.00 | 57.15 |
| ATOM | 6293 | O | HOH | A | 4453 | 4.694 | 38.178 | 97.029 | 1.00 | 41.14 |
| ATOM | 6294 | O | HOH | A | 4455 | 7.213 | 37.968 | 95.813 | 1.00 | 33.83 |
| ATOM | 6295 | O | HOH | A | 4456 | 34.104 | 61.960 | 111.599 | 1.00 | 37.70 |
| ATOM | 6296 | O | HOH | A | 4458 | 29.052 | 52.554 | 103.377 | 1.00 | 37.83 |
| ATOM | 6297 | O | HOH | A | 4459 | 6.249 | 30.783 | 94.939 | 1.00 | 44.81 |
| ATOM | 6298 | O | HOH | A | 4460 | 0.577 | 46.636 | 72.108 | 1.00 | 68.77 |
| ATOM | 6299 | O | HOH | A | 4461 | 35.344 | 41.646 | 92.768 | 1.00 | 58.90 |
| ATOM | 6300 | O | HOH | A | 4467 | 18.274 | 54.583 | 76.950 | 1.00 | 60.46 |
| ATOM | 6301 | O | HOH | A | 4468 | 30.636 | 56.946 | 72.610 | 1.00 | 42.54 |
| ATOM | 6302 | O | HOH | A | 4471 | 38.441 | 52.027 | 73.263 | 1.00 | 66.66 |
| ATOM | 6303 | O | HOH | A | 4472 | 23.502 | 33.131 | 101.603 | 1.00 | 49.57 |
| ATOM | 6304 | O | HOH | A | 4473 | 34.973 | 31.433 | 90.084 | 1.00 | 53.13 |
| ATOM | 6305 | O | HOH | A | 4476 | -1.111 | 37.141 | 69.960 | 1.00 | 50.14 |
| ATOM | 6306 | O | HOH | A | 4477 | 0.423 | 35.209 | 70.974 | 1.00 | 48.71 |
| ATOM | 6307 | O | HOH | A | 4478 | 5.781 | 27.128 | 80.450 | 1.00 | 42.18 |
| ATOM | 6308 | O | HOH | A | 4479 | 26.254 | 30.479 | 54.009 | 1.00 | 42.16 |
| ATOM | 6309 | O | HOH | A | 4481 | 40.952 | 50.479 | 44.034 | 1.00 | 75.04 |
| ATOM | 6310 | O | HOH | A | 4482 | 18.267 | 52.910 | 70.583 | 1.00 | 37.40 |
| ATOM | 6311 | O | HOH | A | 4483 | 12.769 | 53.379 | 75.146 | 1.00 | 46.40 |
| ATOM | 6312 | O | HOH | A | 4484 | 15.161 | 55.566 | 69.087 | 1.00 | 52.68 |
| ATOM | 6313 | O | HOH | A | 4485 | 9.546 | 59.481 | 76.540 | 1.00 | 51.04 |
| ATOM | 6314 | O | HOH | A | 4486 | 7.615 | 60.671 | 77.637 | 1.00 | 51.16 |
| ATOM | 6315 | O | HOH | A | 4487 | 5.643 | 52.611 | 82.834 | 1.00 | 54.36 |
| ATOM | 6316 | O | HOH | A | 4488 | 2.253 | 39.759 | 78.045 | 1.00 | 46.31 |
| ATOM | 6317 | O | HOH | A | 4489 | 2.937 | 48.694 | 64.336 | 1.00 | 50.48 |
| ATOM | 6318 | O | HOH | A | 4490 | -1.902 | 48.627 | 61.434 | 1.00 | 49.08 |
| ATOM | 6319 | O | HOH | A | 4491 | -0.883 | 44.277 | 55.296 | 1.00 | 51.70 |
| ATOM | 6320 | O | HOH | A | 4492 | -2.589 | 48.795 | 52.175 | 1.00 | 67.04 |
| ATOM | 6321 | O | HOH | A | 4493 | -2.262 | 40.624 | 63.779 | 1.00 | 41.28 |
| ATOM | 6322 | O | HOH | A | 4494 | 13.657 | 46.928 | 35.401 | 1.00 | 43.48 |
| ATOM | 6323 | O | HOH | A | 4495 | 17.374 | 49.736 | 36.263 | 1.00 | 46.27 |
| ATOM | 6324 | O | HOH | A | 4496 | 36.864 | 63.759 | 103.027 | 1.00 | 56.77 |
| ATOM | 6325 | O | HOH | A | 4497 | 40.809 | 61.606 | 109.126 | 1.00 | 52.00 |
| ATOM | 6326 | O | HOH | A | 4498 | 32.624 | 63.707 | 109.900 | 1.00 | 38.98 |

FIGURE 3DS

| | A | B | C | D | E | F | G | H | I | J |
|---|---|---|---|---|---|---|---|---|---|---|
| ATOM | 6327 | O | | HOH | A4499 | 38.412 | 55.421 | 104.409 | 1.00 | 39.53 |
| ATOM | 6328 | O | | HOH | A4500 | 33.799 | 55.608 | 98.027 | 1.00 | 44.75 |
| ATOM | 6329 | O | | HOH | A4501 | 31.890 | 54.968 | 96.488 | 1.00 | 39.22 |
| ATOM | 6330 | O | | HOH | A4502 | 30.151 | 62.720 | 111.177 | 1.00 | 42.55 |
| ATOM | 6331 | O | | HOH | A4503 | 28.978 | 60.466 | 111.607 | 1.00 | 51.64 |
| ATOM | 6332 | O | | HOH | A4504 | 38.801 | 62.994 | 119.316 | 1.00 | 52.60 |
| ATOM | 6333 | O | | HOH | A4505 | 38.536 | 66.517 | 121.547 | 1.00 | 71.66 |
| ATOM | 6334 | O | | HOH | A4506 | 41.568 | 48.462 | 121.607 | 1.00 | 34.68 |
| ATOM | 6335 | O | | HOH | A4507 | 37.772 | 47.048 | 123.154 | 1.00 | 40.36 |
| ATOM | 6336 | O | | HOH | A4508 | 42.143 | 46.213 | 122.754 | 1.00 | 54.36 |
| ATOM | 6337 | O | | HOH | A4509 | 47.686 | 52.951 | 129.785 | 1.00 | 58.47 |
| ATOM | 6338 | O | | HOH | A4510 | 44.343 | 48.600 | 125.866 | 1.00 | 67.25 |
| ATOM | 6339 | O | | HOH | A4511 | 47.245 | 48.060 | 126.180 | 1.00 | 57.97 |
| ATOM | 6340 | O | | HOH | A4512 | 45.706 | 48.817 | 129.840 | 1.00 | 70.14 |
| ATOM | 6341 | O | | HOH | A4513 | 41.731 | 57.668 | 106.623 | 1.00 | 58.42 |
| ATOM | 6342 | O | | HOH | A4514 | 43.435 | 50.603 | 108.118 | 1.00 | 46.30 |
| ATOM | 6343 | O | | HOH | A4515 | 18.692 | 40.483 | 106.836 | 1.00 | 43.44 |
| ATOM | 6344 | O | | HOH | A4516 | 9.986 | 46.106 | 100.747 | 1.00 | 49.46 |
| ATOM | 6345 | O | | HOH | A4517 | 13.100 | 56.009 | 104.125 | 1.00 | 46.53 |
| ATOM | 6346 | O | | HOH | A4518 | 11.539 | 53.928 | 104.624 | 1.00 | 54.05 |
| ATOM | 6347 | O | | HOH | A4519 | 8.554 | 50.147 | 99.047 | 1.00 | 78.42 |
| ATOM | 6348 | O | | HOH | A4520 | 12.300 | 54.142 | 100.873 | 1.00 | 58.50 |
| ATOM | 6349 | O | | HOH | A4521 | 9.849 | 52.954 | 100.465 | 1.00 | 62.10 |
| ATOM | 6350 | O | | HOH | A4522 | 12.181 | 35.127 | 99.667 | 1.00 | 47.92 |
| ATOM | 6351 | O | | HOH | A4523 | 12.743 | 36.445 | 101.983 | 1.00 | 57.39 |
| ATOM | 6352 | O | | HOH | A4524 | 9.297 | 33.742 | 99.685 | 1.00 | 60.18 |
| ATOM | 6353 | O | | HOH | A4525 | 16.308 | 35.257 | 101.875 | 1.00 | 45.93 |
| ATOM | 6354 | O | | HOH | A4526 | 23.726 | 27.369 | 101.239 | 1.00 | 70.51 |
| ATOM | 6355 | O | | HOH | A4527 | 15.617 | 29.890 | 100.022 | 1.00 | 51.59 |
| ATOM | 6356 | O | | HOH | A4528 | 23.953 | 25.207 | 94.956 | 1.00 | 51.83 |
| ATOM | 6357 | O | | HOH | A4529 | 27.614 | 24.622 | 94.114 | 1.00 | 51.02 |
| ATOM | 6358 | O | | HOH | A4530 | 16.827 | 24.531 | 97.912 | 1.00 | 65.19 |
| ATOM | 6359 | O | | HOH | A4531 | 13.131 | 26.921 | 96.006 | 1.00 | 43.58 |
| ATOM | 6360 | O | | HOH | A4532 | -11.046 | 44.931 | 77.950 | 1.00 | 67.31 |
| ATOM | 6361 | O | | HOH | A4533 | -9.315 | 42.181 | 99.143 | 1.00 | 71.71 |
| ATOM | 6362 | O | | HOH | A4534 | -2.014 | 40.030 | 100.880 | 1.00 | 68.38 |
| ATOM | 6363 | O | | HOH | A4535 | -14.409 | 44.187 | 93.016 | 1.00 | 53.23 |
| ATOM | 6364 | O | | HOH | A4536 | -8.252 | 44.422 | 98.021 | 1.00 | 60.16 |
| ATOM | 6365 | O | | HOH | A4537 | -5.187 | 27.907 | 96.596 | 1.00 | 68.86 |
| ATOM | 6366 | O | | HOH | A4538 | -4.691 | 26.735 | 100.751 | 1.00 | 79.25 |
| ATOM | 6367 | O | | HOH | A4539 | 1.909 | 33.694 | 100.967 | 1.00 | 56.50 |
| ATOM | 6368 | O | | HOH | A4540 | -4.414 | 29.421 | 93.036 | 1.00 | 56.48 |
| ATOM | 6369 | O | | HOH | A4541 | -15.868 | 44.165 | 88.075 | 1.00 | 57.14 |
| ATOM | 6370 | O | | HOH | A4542 | -13.929 | 52.900 | 77.510 | 1.00 | 45.73 |
| ATOM | 6371 | O | | HOH | A4543 | -14.251 | 57.368 | 80.047 | 1.00 | 51.26 |
| ATOM | 6372 | O | | HOH | A4544 | -14.655 | 55.153 | 76.122 | 1.00 | 54.50 |
| ATOM | 6373 | O | | HOH | A4545 | -12.602 | 59.185 | 76.857 | 1.00 | 61.48 |
| ATOM | 6374 | O | | HOH | A4546 | 36.093 | 51.048 | 43.142 | 1.00 | 59.51 |
| ATOM | 6375 | O | | HOH | A4547 | 33.444 | 48.267 | 49.152 | 1.00 | 42.45 |
| ATOM | 6376 | O | | HOH | A4548 | 34.895 | 50.873 | 48.650 | 1.00 | 56.48 |
| ATOM | 6377 | O | | HOH | A4549 | 35.276 | 43.482 | 53.838 | 1.00 | 38.83 |
| ATOM | 6378 | O | | HOH | A4550 | 35.030 | 40.916 | 51.069 | 1.00 | 54.75 |

FIGURE 3DT

|      | A    | B    | C | D   | E     | F      | G      | H      | I    | J     |
|------|------|------|---|-----|-------|--------|--------|--------|------|-------|
| ATOM | 6379 | O | HOH | A4551 | 38.498 | 39.533 | 81.659 | 1.00 | 61.10 |
| ATOM | 6380 | O | HOH | A4552 | 26.450 | 32.841 | 98.986 | 1.00 | 57.87 |
| ATOM | 6381 | O | HOH | A4553 | 16.792 | 16.453 | 38.850 | 1.00 | 42.15 |
| ATOM | 6382 | O | HOH | A4554 | 28.083 | 35.843 | 36.134 | 1.00 | 50.58 |
| ATOM | 6383 | O | HOH | A4555 | 13.006 | 42.142 | 34.791 | 1.00 | 72.71 |
| ATOM | 6384 | O | HOH | A4556 | 18.683 | 41.286 | 37.482 | 1.00 | 62.83 |
| ATOM | 6385 | O | HOH | A4557 | 20.757 | 26.777 | 46.031 | 1.00 | 70.69 |
| ATOM | 6386 | O | HOH | A4558 | 18.054 | 25.541 | 43.451 | 1.00 | 60.78 |
| ATOM | 6387 | O | HOH | A4559 | 20.406 | 28.521 | 49.567 | 1.00 | 64.56 |
| ATOM | 6388 | O | HOH | A4560 | 35.148 | 35.801 | 52.870 | 1.00 | 67.79 |
| ATOM | 6389 | O | HOH | A4561 | 25.147 | 31.072 | 49.756 | 1.00 | 64.41 |
| ATOM | 6390 | O | HOH | A4562 | 12.672 | 29.037 | 44.645 | 1.00 | 63.08 |
| ATOM | 6391 | O | HOH | A4563 | 26.141 | 26.665 | 54.809 | 1.00 | 50.39 |
| ATOM | 6392 | O | HOH | A4564 | 23.235 | 27.156 | 52.909 | 1.00 | 53.78 |
| ATOM | 6393 | O | HOH | A4565 | 25.999 | 22.088 | 63.724 | 1.00 | 76.66 |
| ATOM | 6394 | O | HOH | A4566 | 16.010 | 25.437 | 68.994 | 1.00 | 58.15 |
| ATOM | 6395 | O | HOH | A4567 | 7.157  | 45.507 | 39.706 | 1.00 | 43.66 |
| ATOM | 6396 | O | HOH | A4568 | 6.284  | 51.033 | 40.982 | 1.00 | 56.93 |
| ATOM | 6397 | O | HOH | A4569 | 4.408  | 48.351 | 37.475 | 1.00 | 80.10 |
| ATOM | 6398 | O | HOH | A4570 | 3.287  | 54.913 | 45.258 | 1.00 | 44.17 |
| ATOM | 6399 | O | HOH | A4571 | -0.723 | 54.531 | 45.238 | 1.00 | 57.75 |
| ATOM | 6400 | O | HOH | A4572 | 0.456  | 52.734 | 50.822 | 1.00 | 56.85 |
| ATOM | 6401 | O | HOH | A4573 | 0.958  | 35.683 | 52.895 | 1.00 | 51.11 |
| ATOM | 6402 | O | HOH | A4574 | 1.143  | 35.316 | 41.984 | 1.00 | 51.98 |
| ATOM | 6403 | O | HOH | A4576 | 3.553  | 22.665 | 64.027 | 1.00 | 54.64 |
| ATOM | 6404 | O | HOH | A4577 | 4.749  | 55.905 | 56.166 | 1.00 | 59.98 |
| ATOM | 6405 | O | HOH | A4578 | 0.067  | 46.442 | 54.013 | 1.00 | 68.97 |
| ATOM | 6406 | O | HOH | A4579 | -3.555 | 47.559 | 57.781 | 1.00 | 62.59 |
| ATOM | 6407 | O | HOH | A4580 | -0.553 | 45.705 | 63.821 | 1.00 | 55.62 |
| ATOM | 6408 | O | HOH | A4581 | 18.460 | 55.091 | 28.869 | 1.00 | 43.41 |
| ATOM | 6409 | O | HOH | A4582 | 20.787 | 56.321 | 32.235 | 1.00 | 47.05 |
| ATOM | 6410 | O | HOH | A4583 | 25.663 | 61.700 | 41.010 | 1.00 | 40.94 |
| ATOM | 6411 | O | HOH | A4584 | 27.298 | 57.747 | 27.503 | 1.00 | 57.83 |
| ATOM | 6412 | O | HOH | A4585 | 26.372 | 61.144 | 25.001 | 1.00 | 45.48 |
| ATOM | 6413 | O | HOH | A4586 | 22.594 | 61.738 | 22.932 | 1.00 | 45.46 |
| ATOM | 6414 | O | HOH | A4587 | 21.284 | 57.262 | 26.576 | 1.00 | 53.16 |
| ATOM | 6415 | O | HOH | A4588 | 30.210 | 65.406 | 19.126 | 1.00 | 49.99 |
| ATOM | 6416 | O | HOH | A4589 | 27.503 | 69.242 | 20.813 | 1.00 | 36.24 |
| ATOM | 6417 | O | HOH | A4590 | 37.313 | 75.937 | 21.711 | 1.00 | 49.17 |
| ATOM | 6418 | O | HOH | A4591 | 42.895 | 76.496 | 26.689 | 1.00 | 48.90 |
| ATOM | 6419 | O | HOH | A4592 | 44.646 | 80.412 | 31.837 | 1.00 | 54.33 |
| ATOM | 6420 | O | HOH | A4593 | 27.361 | 68.590 | 16.253 | 1.00 | 61.34 |
| ATOM | 6421 | O | HOH | A4594 | 26.007 | 72.640 | 14.705 | 1.00 | 47.07 |
| ATOM | 6422 | O | HOH | A4595 | 28.073 | 74.453 | 15.196 | 1.00 | 55.83 |
| ATOM | 6423 | O | HOH | A4596 | 17.508 | 74.996 | 27.862 | 1.00 | 45.00 |
| ATOM | 6424 | O | HOH | A4597 | 12.771 | 62.899 | 31.386 | 1.00 | 65.48 |
| ATOM | 6425 | O | HOH | A4598 | 10.932 | 65.269 | 32.019 | 1.00 | 52.75 |
| ATOM | 6426 | O | HOH | A4599 | 17.939 | 77.596 | 24.990 | 1.00 | 73.64 |
| ATOM | 6427 | O | HOH | A4600 | 19.052 | 81.047 | 25.576 | 1.00 | 57.99 |
| ATOM | 6428 | O | HOH | A4601 | 19.538 | 83.907 | 28.080 | 1.00 | 64.74 |
| ATOM | 6429 | O | HOH | A4602 | 26.442 | 85.487 | 23.026 | 1.00 | 47.90 |
| ATOM | 6430 | O | HOH | A4603 | 26.558 | 78.772 | 13.985 | 1.00 | 58.23 |

FIGURE 3DU

| | A | B | C | D | E | F | G | H | I | J |
|---|---|---|---|---|---|---|---|---|---|---|
| ATOM | 6431 | O | HOH | A4604 | | 35.821 | 79.554 | 18.875 | 1.00 | 58.44 |
| ATOM | 6432 | O | HOH | A4605 | | 20.147 | 78.201 | 31.489 | 1.00 | 44.54 |
| ATOM | 6433 | O | HOH | A4606 | | 20.825 | 77.926 | 35.712 | 1.00 | 60.62 |
| ATOM | 6434 | O | HOH | A4607 | | 12.466 | 59.704 | 42.150 | 1.00 | 59.52 |
| ATOM | 6435 | O | HOH | A4609 | | 10.078 | 58.175 | 55.369 | 1.00 | 42.70 |
| ATOM | 6436 | O | HOH | A4610 | | 7.363 | 54.828 | 71.008 | 1.00 | 59.82 |
| ATOM | 6437 | O | HOH | A4611 | | 6.501 | 47.599 | 69.530 | 1.00 | 50.04 |
| ATOM | 6438 | O | HOH | A4612 | | 17.187 | 46.542 | 60.033 | 1.00 | 43.22 |
| ATOM | 6439 | O | HOH | A4613 | | 44.503 | 53.404 | 47.592 | 1.00 | 45.93 |
| ATOM | 6440 | O | HOH | A4614 | | 45.711 | 57.543 | 46.742 | 1.00 | 58.82 |
| ATOM | 6441 | O | HOH | A4615 | | 48.134 | 63.847 | 46.739 | 1.00 | 68.88 |
| ATOM | 6442 | O | HOH | A4616 | | 41.641 | 44.440 | 50.542 | 1.00 | 54.08 |
| ATOM | 6443 | O | HOH | A4617 | | 40.642 | 47.851 | 64.358 | 1.00 | 78.03 |
| ATOM | 6444 | O | HOH | A4618 | | 41.964 | 45.162 | 64.880 | 1.00 | 58.52 |
| ATOM | 6445 | O | HOH | A4619 | | 37.556 | 43.336 | 60.330 | 1.00 | 35.93 |
| ATOM | 6446 | O | HOH | A4620 | | 39.583 | 40.786 | 71.241 | 1.00 | 62.16 |
| ATOM | 6447 | O | HOH | A4621 | | 36.972 | 39.783 | 72.184 | 1.00 | 53.62 |
| ATOM | 6448 | O | HOH | A4622 | | 34.649 | 39.375 | 73.376 | 1.00 | 44.74 |
| ATOM | 6449 | O | HOH | A4623 | | 34.088 | 33.129 | 57.536 | 1.00 | 59.73 |
| ATOM | 6450 | O | HOH | A4624 | | 31.304 | 28.399 | 57.943 | 1.00 | 57.41 |
| ATOM | 6451 | O | HOH | A4625 | | 19.511 | 27.996 | 69.262 | 1.00 | 48.77 |
| ATOM | 6452 | O | HOH | A4626 | | 19.112 | 27.497 | 72.963 | 1.00 | 55.39 |
| ATOM | 6453 | O | HOH | A4627 | | 1.601 | 47.522 | 69.706 | 1.00 | 57.28 |
| ATOM | 6454 | O | HOH | A4628 | | -2.139 | 46.246 | 67.640 | 1.00 | 59.00 |
| ATOM | 6455 | O | HOH | A4629 | | -2.518 | 39.430 | 69.662 | 1.00 | 54.91 |
| ATOM | 6456 | O | HOH | A4630 | | 11.670 | 18.294 | 80.121 | 1.00 | 71.03 |
| ATOM | 6457 | O | HOH | A4631 | | 12.659 | 18.704 | 82.661 | 1.00 | 63.11 |
| ATOM | 6458 | O | HOH | A4632 | | 19.222 | 20.801 | 81.315 | 1.00 | 62.79 |
| ATOM | 6459 | O | HOH | A4633 | | 15.970 | 17.374 | 85.033 | 1.00 | 71.54 |
| ATOM | 6460 | O | HOH | A4634 | | 18.640 | 21.521 | 92.640 | 1.00 | 44.73 |
| ATOM | 6461 | O | HOH | A4635 | | 23.176 | 23.375 | 98.364 | 1.00 | 49.15 |
| ATOM | 6462 | O | HOH | A4636 | | 21.395 | 22.602 | 89.474 | 1.00 | 50.80 |
| ATOM | 6463 | O | HOH | A4637 | | 27.521 | 21.399 | 90.319 | 1.00 | 75.88 |
| ATOM | 6464 | O | HOH | A4638 | | 28.779 | 22.662 | 92.154 | 1.00 | 53.38 |
| ATOM | 6465 | O | HOH | A4639 | | 30.785 | 27.906 | 92.099 | 1.00 | 49.37 |
| ATOM | 6466 | O | HOH | A4640 | | 31.314 | 26.810 | 97.173 | 1.00 | 59.84 |
| ATOM | 6467 | O | HOH | A4641 | | 31.209 | 38.637 | 87.400 | 1.00 | 43.55 |
| ATOM | 6468 | O | HOH | A4642 | | 35.664 | 33.323 | 80.887 | 1.00 | 49.91 |
| ATOM | 6469 | O | HOH | A4643 | | 37.922 | 32.259 | 81.962 | 1.00 | 61.50 |
| ATOM | 6470 | O | HOH | A4644 | | 26.160 | 26.745 | 77.786 | 1.00 | 53.20 |
| ATOM | 6471 | O | HOH | A4645 | | 25.529 | 27.595 | 74.877 | 1.00 | 54.09 |
| ATOM | 6472 | O | HOH | A4646 | | 18.282 | 26.776 | 75.712 | 1.00 | 40.47 |
| ATOM | 6473 | O | HOH | A4647 | | 24.068 | 30.764 | 69.495 | 1.00 | 61.89 |
| ATOM | 6474 | O | HOH | A4648 | | 23.088 | 18.551 | 84.091 | 1.00 | 58.08 |
| ATOM | 6475 | O | HOH | A4649 | | 21.021 | 23.371 | 75.236 | 1.00 | 68.15 |
| ATOM | 6476 | O | HOH | A4650 | | 23.407 | 24.239 | 74.503 | 1.00 | 62.08 |
| ATOM | 6477 | O | HOH | A4651 | | 23.579 | 29.565 | 74.203 | 1.00 | 57.81 |
| ATOM | 6478 | O | HOH | A4652 | | 38.594 | 42.646 | 89.294 | 1.00 | 44.92 |
| ATOM | 6479 | O | HOH | A4653 | | 42.504 | 39.854 | 80.929 | 1.00 | 70.24 |
| ATOM | 6480 | O | HOH | A4654 | | 43.284 | 41.825 | 88.332 | 1.00 | 62.62 |
| ATOM | 6481 | O | HOH | A4655 | | 41.701 | 50.133 | 86.964 | 1.00 | 59.19 |
| ATOM | 6482 | O | HOH | A4656 | | 41.971 | 45.054 | 91.989 | 1.00 | 64.87 |

FIGURE 3DV

| | A | B | C | D | E | F | G | H | I | J |
|---|---|---|---|---|---|---|---|---|---|---|
| ATOM | 6483 | O | HOH | A4657 | 46.121 | 44.398 | 91.223 | 1.00 | 54.76 |
| ATOM | 6484 | O | HOH | A4658 | 40.552 | 43.359 | 72.526 | 1.00 | 71.63 |
| ATOM | 6485 | O | HOH | A4659 | 41.998 | 55.555 | 66.880 | 1.00 | 44.64 |
| ATOM | 6486 | O | HOH | A4660 | 49.777 | 62.195 | 60.931 | 1.00 | 62.73 |
| ATOM | 6487 | O | HOH | A4661 | 55.014 | 57.257 | 67.904 | 1.00 | 73.72 |
| ATOM | 6488 | O | HOH | A4662 | 48.362 | 59.885 | 70.269 | 1.00 | 75.89 |
| ATOM | 6489 | O | HOH | A4663 | 51.947 | 59.938 | 70.200 | 1.00 | 69.16 |
| ATOM | 6490 | O | HOH | A4664 | 46.274 | 47.236 | 71.506 | 1.00 | 69.82 |
| ATOM | 6491 | O | HOH | A4665 | 37.304 | 51.288 | 90.525 | 1.00 | 47.85 |
| ATOM | 6492 | O | HOH | A4666 | 17.441 | 58.717 | 75.884 | 1.00 | 33.28 |
| ATOM | 6493 | O | HOH | A4667 | 15.071 | 58.689 | 74.889 | 1.00 | 41.90 |
| ATOM | 6494 | O | HOH | A4669 | 31.682 | 52.902 | 95.031 | 1.00 | 44.74 |
| ATOM | 6495 | O | HOH | A4670 | 39.404 | 61.272 | 75.342 | 1.00 | 67.85 |
| ATOM | 6496 | O | HOH | A4671 | 7.043 | 58.547 | 79.128 | 1.00 | 45.66 |
| ATOM | 6497 | O | HOH | A4672 | 13.449 | 56.202 | 73.391 | 1.00 | 49.54 |
| ATOM | 6498 | O | HOH | A4673 | 3.435 | 48.991 | 80.480 | 1.00 | 56.43 |
| ATOM | 6499 | O | HOH | A4674 | 28.966 | 41.086 | 100.645 | 1.00 | 56.30 |
| ATOM | 6500 | O | HOH | A4675 | 6.995 | 47.367 | 90.131 | 1.00 | 45.59 |
| ATOM | 6501 | O | HOH | A4676 | 37.835 | 55.840 | 100.002 | 1.00 | 75.71 |
| ATOM | 6502 | O | HOH | A4677 | 37.263 | 59.093 | 99.865 | 1.00 | 61.66 |
| ATOM | 6503 | O | HOH | A4678 | 30.839 | 62.012 | 116.301 | 1.00 | 60.29 |
| ATOM | 6504 | O | HOH | A4679 | 35.717 | 61.757 | 123.969 | 1.00 | 48.45 |
| ATOM | 6505 | O | HOH | A4680 | 34.675 | 54.287 | 128.297 | 1.00 | 62.80 |
| ATOM | 6506 | O | HOH | A4681 | 34.885 | 57.792 | 126.354 | 1.00 | 63.23 |
| ATOM | 6507 | O | HOH | A4682 | 49.900 | 52.416 | 128.486 | 1.00 | 65.94 |
| ATOM | 6508 | O | HOH | A4683 | 51.812 | 53.778 | 124.513 | 1.00 | 52.69 |
| ATOM | 6509 | O | HOH | A4684 | 51.334 | 51.499 | 122.651 | 1.00 | 54.74 |
| ATOM | 6510 | O | HOH | A4685 | 52.976 | 53.435 | 118.011 | 1.00 | 61.55 |
| ATOM | 6511 | O | HOH | A4686 | 47.371 | 56.111 | 110.225 | 1.00 | 56.99 |
| ATOM | 6512 | O | HOH | A4687 | 42.983 | 56.603 | 109.582 | 1.00 | 82.67 |
| ATOM | 6513 | O | HOH | A4688 | 31.404 | 44.671 | 102.189 | 1.00 | 52.99 |
| ATOM | 6514 | O | HOH | A4689 | 9.373 | 48.022 | 110.393 | 1.00 | 81.68 |
| ATOM | 6515 | O | HOH | A4690 | 7.529 | 50.881 | 111.922 | 1.00 | 74.23 |
| ATOM | 6516 | O | HOH | A4691 | 10.538 | 48.551 | 96.059 | 1.00 | 40.15 |
| ATOM | 6517 | O | HOH | A4692 | 19.098 | 30.414 | 105.019 | 1.00 | 76.55 |
| ATOM | 6518 | O | HOH | A4693 | 22.079 | 29.596 | 100.341 | 1.00 | 51.08 |
| ATOM | 6519 | O | HOH | A4694 | 16.777 | 21.299 | 94.840 | 1.00 | 75.43 |
| ATOM | 6520 | O | HOH | A4695 | 6.492 | 24.397 | 86.631 | 1.00 | 51.06 |
| ATOM | 6521 | O | HOH | A4696 | 3.138 | 22.865 | 83.911 | 1.00 | 62.28 |
| ATOM | 6522 | O | HOH | A4697 | 0.255 | 26.350 | 86.866 | 1.00 | 81.92 |
| ATOM | 6523 | O | HOH | A4698 | -0.862 | 43.812 | 96.131 | 1.00 | 63.40 |
| ATOM | 6524 | O | HOH | A4699 | -3.986 | 35.904 | 79.454 | 1.00 | 55.00 |
| ATOM | 6525 | O | HOH | A4700 | -1.231 | 49.120 | 85.847 | 1.00 | 80.87 |
| ATOM | 6526 | O | HOH | A4701 | -11.744 | 54.905 | 83.994 | 1.00 | 73.20 |
| ATOM | 6527 | O | HOH | A4702 | -15.286 | 52.460 | 84.480 | 1.00 | 67.69 |
| ATOM | 6528 | O | HOH | A4703 | 26.250 | 51.488 | 36.870 | 1.00 | 51.30 |
| ATOM | 6529 | O | HOH | A4704 | 25.092 | 49.297 | 37.381 | 1.00 | 48.49 |
| ATOM | 6530 | O | HOH | A4705 | 28.229 | 46.688 | 37.199 | 1.00 | 50.91 |
| ATOM | 6531 | O | HOH | A4706 | 30.532 | 58.709 | 50.019 | 1.00 | 50.70 |
| ATOM | 6532 | O | HOH | A4707 | 7.940 | 37.662 | 98.383 | 1.00 | 57.69 |
| ATOM | 6533 | O | HOH | A4708 | -3.962 | 28.444 | 81.329 | 1.00 | 62.91 |
| ATOM | 6534 | O | HOH | A4709 | -0.192 | 28.864 | 80.830 | 1.00 | 63.67 |

FIGURE 3DW

| | A | B | C | D | E | F | G | H | I | J |
|---|---|---|---|---|---|---|---|---|---|---|
| ATOM | 6535 | O | | HOH | A4710 | -4.208 | 26.200 | 91.250 | 1.00 | 67.72 |
| ATOM | 6536 | O | | HOH | A4711 | -3.318 | 26.121 | 87.132 | 1.00 | 72.22 |
| ATOM | 6537 | O | | HOH | A4712 | 19.515 | 20.409 | 64.490 | 1.00 | 63.99 |
| ATOM | 6538 | O | | HOH | A4713 | 22.224 | 17.041 | 66.591 | 1.00 | 67.42 |
| ATOM | 6539 | O | | HOH | A4714 | 12.260 | 13.141 | 57.656 | 1.00 | 59.66 |
| ATOM | 6540 | O | | HOH | A4715 | -2.080 | 45.786 | 41.951 | 1.00 | 60.11 |
| ATOM | 6541 | O | | HOH | A4716 | 2.978 | 43.551 | 39.837 | 1.00 | 64.58 |
| ATOM | 6542 | O | | HOH | A4717 | -0.192 | 46.776 | 38.248 | 1.00 | 61.68 |
| ATOM | 6543 | O | | HOH | A4718 | -2.534 | 47.992 | 38.811 | 1.00 | 62.60 |
| ATOM | 6544 | O | | HOH | A4719 | -0.396 | 43.325 | 50.037 | 1.00 | 60.72 |
| ATOM | 6545 | O | | HOH | A4720 | 6.522 | 31.637 | 46.491 | 1.00 | 52.30 |
| ATOM | 6546 | O | | HOH | A4721 | 8.868 | 49.583 | 39.877 | 1.00 | 51.44 |
| ATOM | 6547 | O | | HOH | A4722 | 0.244 | 25.502 | 57.697 | 1.00 | 60.29 |
| ATOM | 6548 | O | | HOH | A4724 | 22.724 | 40.515 | 36.979 | 1.00 | 56.68 |
| ATOM | 6549 | O | | HOH | A4725 | 29.920 | 45.156 | 38.572 | 1.00 | 54.50 |
| ATOM | 6550 | O | | HOH | A4726 | 32.868 | 52.818 | 48.567 | 1.00 | 58.26 |
| ATOM | 6551 | O | | HOH | A4729 | 35.716 | 60.924 | 55.306 | 1.00 | 45.65 |
| ATOM | 6552 | O | | HOH | A4730 | 27.038 | 58.099 | 53.411 | 1.00 | 61.58 |
| ATOM | 6553 | O | | HOH | A4731 | 35.122 | 63.546 | 54.902 | 1.00 | 51.96 |
| ATOM | 6554 | O | | HOH | A4732 | 21.884 | 29.626 | 79.403 | 1.00 | 52.84 |
| ATOM | 6555 | O | | HOH | A4733 | 35.758 | 27.830 | 82.343 | 1.00 | 69.26 |
| ATOM | 6556 | O | | HOH | A4734 | 32.981 | 30.066 | 75.096 | 1.00 | 67.46 |
| ATOM | 6557 | O | | HOH | A4735 | 31.213 | 36.265 | 71.962 | 1.00 | 51.16 |
| ATOM | 6558 | O | | HOH | A4736 | 34.701 | 34.881 | 72.301 | 1.00 | 60.24 |
| ATOM | 6559 | O | | HOH | A4737 | 37.984 | 37.087 | 57.768 | 1.00 | 69.00 |
| ATOM | 6560 | O | | HOH | A4738 | 41.525 | 43.928 | 58.188 | 1.00 | 66.90 |
| ATOM | 6561 | O | | HOH | A4739 | 35.396 | 68.030 | 77.908 | 1.00 | 58.42 |
| ATOM | 6562 | O | | HOH | A4740 | 38.300 | 69.586 | 73.841 | 1.00 | 56.02 |
| ATOM | 6563 | O | | HOH | A4741 | 20.203 | 55.762 | 74.440 | 1.00 | 41.94 |
| ATOM | 6564 | O | | HOH | A4742 | 33.451 | 34.676 | 100.642 | 1.00 | 66.73 |
| ATOM | 6565 | O | | HOH | A4743 | 19.088 | 57.961 | 73.335 | 1.00 | 55.70 |
| ATOM | 6566 | O | | HOH | A4744 | 12.021 | 57.733 | 70.752 | 1.00 | 52.33 |
| ATOM | 6567 | O | | HOH | A4745 | 32.201 | 59.377 | 54.696 | 1.00 | 49.66 |
| ATOM | 6568 | O | | HOH | A4746 | 33.022 | 63.491 | 53.577 | 1.00 | 52.27 |
| ATOM | 6569 | O | | HOH | A4747 | 28.777 | 57.006 | 51.763 | 1.00 | 57.72 |
| ATOM | 6570 | O | | HOH | A4748 | 29.033 | 53.334 | 35.349 | 1.00 | 64.59 |
| ATOM | 6571 | O | | HOH | A4749 | 18.014 | 47.738 | 34.869 | 1.00 | 61.44 |
| ATOM | 6572 | O | | HOH | A4750 | 21.478 | 47.781 | 34.073 | 1.00 | 64.56 |
| ATOM | 6573 | O | | HOH | A4751 | 36.698 | 45.756 | 49.988 | 1.00 | 45.87 |
| ATOM | 6574 | O | | HOH | A4752 | 41.615 | 53.899 | 68.559 | 1.00 | 55.70 |
| ATOM | 6575 | O | | HOH | A4753 | 46.445 | 49.171 | 65.922 | 1.00 | 66.32 |
| ATOM | 6576 | O | | HOH | A4754 | -14.870 | 44.985 | 78.661 | 1.00 | 53.29 |
| ATOM | 6577 | O | | HOH | A4755 | -13.633 | 59.963 | 79.999 | 1.00 | 62.43 |
| ATOM | 6578 | O | | HOH | A4756 | -11.564 | 53.685 | 78.540 | 1.00 | 60.36 |
| ATOM | 6579 | O | | HOH | A4757 | -5.916 | 45.838 | 98.411 | 1.00 | 63.40 |
| ATOM | 6580 | O | | HOH | A4758 | -3.707 | 48.185 | 96.490 | 1.00 | 66.05 |
| ATOM | 6581 | O | | HOH | A4759 | -0.964 | 24.131 | 87.829 | 1.00 | 61.77 |
| ATOM | 6582 | O | | HOH | A4760 | 14.121 | 24.289 | 74.985 | 1.00 | 49.49 |
| ATOM | 6583 | O | | HOH | A4761 | 21.321 | 27.062 | 71.509 | 1.00 | 59.08 |
| ATOM | 6584 | O | | HOH | A4762 | 38.405 | 41.426 | 73.704 | 1.00 | 52.47 |
| ATOM | 6585 | O | | HOH | A4763 | 43.319 | 45.896 | 68.282 | 1.00 | 62.33 |
| ATOM | 6586 | O | | HOH | A4764 | 45.041 | 43.011 | 70.400 | 1.00 | 55.80 |

> US 7,534,592 B1

CRYSTALLIZATION OF CARBOXYLTRANSFERASE DOMAIN OF ACETYL-COENZYME A CARBOXYLASE 2 WITH A LIGAND

FIELD OF THE INVENTION

The present invention relates to a member of a family of Acetyl-Coenzyme A Carboxylases (ACC) and more specifically to a particular ACC known as the carboxyltransferase domain of Acetyl-Coenzyme A Carboxylase 2 (ACC2). Provided are ACC2 in crystalline form, methods of forming crystals comprising ACC2, methods of using crystals comprising ACC2, a crystal structure of ACC2, and methods of using the crystal structure.

BACKGROUND OF THE INVENTION

A general approach to designing inhibitors that are selective for a given protein is to determine how a putative inhibitor interacts with a three dimensional structure of that protein. For this reason it is useful to obtain the protein in crystalline form and perform X-ray diffraction techniques to determine the protein's three-dimensional structure coordinates. Various methods for preparing crystalline proteins are known in the art.

Once protein crystals are produced, crystallographic data can be generated using the crystals to provide useful structural information that assists in the design of small molecules that bind to the active site of the protein and inhibit the protein's activity in vivo. If the protein is crystallized as a complex with a ligand, one can determine both the shape of the protein's binding pocket when bound to the ligand, as well as the amino acid residues that are capable of close contact with the ligand. By knowing the shape and amino acid residues comprised in the binding pocket, one may design new ligands that will interact favorably with the protein. With such structural information, available computational methods may be used to predict how strong the ligand binding interaction will be. Such methods aid in the design of inhibitors that bind strongly, as well as selectively to the protein. A need thus exists for proteins in crystalline form.

SUMMARY OF THE INVENTION

The present invention is directed to crystals comprising ACC2 and particularly crystals comprising ACC2 that have sufficient size and quality to obtain useful information about the structural properties of ACC2 and molecules or complexes that may associate with ACC2.

In one embodiment, a composition is provided that comprises a protein in crystalline form wherein at least a portion of the protein has 55%, 65%, 75%, 85%, 90%, 95%, 97%, 99% or greater identity with residues 1715-2483 of SEQ. ID No. 1.

In one variation, the protein has activity characteristic of ACC2. For example, the protein may optionally be inhibited by inhibitors of wild type ACC2. The protein crystal may also diffract X-rays for a determination of structure coordinates to a resolution of 4 Å, 3.5 Å, 3.0 Å or less.

In one variation, the protein crystal has a crystal lattice in a $C222_1$ space group. The protein crystal may also have a crystal lattice having unit cell dimensions, +/−5%, of a=112.181 Å, b=117.698 Å and c=144.754 Å, $\alpha=\beta=\gamma=90$ degrees.

The present invention is also directed to crystallizing ACC2. The present invention is also directed to the conditions useful for crystallizing ACC2. It should be recognized that a wide variety of crystallization methods can be used in combination with the crystallization conditions to form crystals comprising ACC2 including, but not limited to, vapor diffusion, batch, dialysis, and other methods of contacting the protein solution for the purpose of crystallization.

In one embodiment, a method is provided for forming crystals of a protein comprising: forming a crystallization volume comprising: a protein wherein at least a portion of the protein has 55%, 65%, 75%, 85%, 90%, 95%, 97%, 99% or greater identity with residues 1715-2483 of SEQ. ID No. 1; and storing the crystallization volume under conditions suitable for crystal formation.

In one variation, the crystallization volume comprises the protein in a concentration between 1 mg/mil and 200 mg/ml, and 2-50% w/v of precipitant wherein the precipitant comprises one or more members of the group consisting of PEG having a molecular weight range between 200-20000 and wherein the crystallization volume has a pH between pH 4 and pH10.

The method may optionally further comprise forming a protein crystal that has a crystal lattice in a C222, space group. The method also optionally further comprises forming a protein crystal that has a crystal lattice having unit cell dimensions, +/−5%, of a=112.181 Å, b=117.698 Å and c=144.754 Å, $\alpha=\beta=\gamma=90$ degrees. The invention also relates to protein crystals formed by these methods.

The present invention is also directed to a composition comprising an isolated protein that comprises or consists of one or more of the protein sequence(s) of ACC2 taught herein for crystallizing ACC2. The present invention is also directed to a composition comprising an isolated nucleic acid molecule that comprises or consists of the nucleotides for expressing the protein sequence of ACC2 taught herein for crystallizing ACC2.

The present invention is also directed to an expression vector that may be used to express the isolated proteins taught herein for crystallizing ACC2. In one variation, the expression vector comprises a promoter that promotes expression of the isolated protein.

The present invention is also directed to a cell line transformed or transfected by an isolated nucleic acid molecule or expression vector of the present invention.

The present invention is also directed to structure coordinates for ACC2 as well as structure coordinates that are comparatively similar to these structure coordinates. It is noted that these comparatively similar structure coordinates may encompass proteins with similar sequences and/or structures, such as other ACC. For example, machine-readable data storage media is provided having data storage material encoded with machine-readable data that comprises structure coordinates that are comparatively similar to the structure coordinates of ACC2. The present invention is also directed to a machine readable data storage medium having data storage material encoded with machine readable data, which, when read by an appropriate machine, can display a three dimensional representation of all or a portion of a structure of ACC2 or a model that is comparatively similar to the structure of all or a portion of ACC2.

Various embodiments of machine readable data storage medium are provided that comprise data storage material encoded with machine readable data. The machine readable data comprises: structure coordinates that have a root mean square deviation equal to or less than the RMSD value specified in Columns 3, 4 or 5 of Table 1A or Table 1B when compared to the structure coordinates of FIG. 3, the root mean square deviation being calculated such that the portion of amino acid residues specified in Column 2 of Table 1A or Table 1B of each set of structure coordinates are superimposed and the root mean square deviation is based only on those amino acid residues in the structure coordinates that are also present in the portion of the protein specified in Column 1 of Table 1A or Table 1B. The amino acids being overlayed and compared need not be identical when the RMSD calculation is performed on alpha carbons and main chain atoms but the amino acids being overlayed and compared must have identical side chains when the RMSD calculation is performed on all non-hydrogen atoms.

For example, in one embodiment where the comparison is based on the 4 Angstrom set of amino acid residues (Column 1) and is based on superimposing alpha-carbon atoms (Column 2), the structure coordinates may have a root mean square deviation equal to or less than 0.568 Angstrom for the Acetyl-CoEnzyme A binding site (Table 1A) or 0.688 Angstrom the Biotin binding site (Table 1B), when compared to the structure coordinates of FIG. 3.

TABLE 1A

| AA RESIDUES TO USE TO PERFORM RMSD COMPARISON | PORTION OF EACH AA RESIDUE USED TO PERFORM RMSD COMPARISON | RMSD VALUE LESS THAN OR EQUAL TO | | |
|---|---|---|---|---|
| Table 2A (4 Angstrom set) | alpha-carbon atoms[1] | 0.568 | 0.46 | 0.28 |
| | main-chain atoms[1] | 0.585 | 0.39 | 0.29 |
| | all non-hydrogen[2] | 1.106 | 0.74 | 0.55 |
| Table 3A (7 Angstrom set) | alpha-carbon atoms[1] | 0.544 | 0.36 | 0.27 |
| | main-chain atoms[1] | 0.563 | 0.38 | 0.28 |
| | all non-hydrogen[2] | 0.951 | 0.64 | 0.48 |
| Table 4A (10 Angstrom set) | alpha-carbon atoms[1] | 0.566 | 0.38 | 0.28 |
| | main-chain atoms[1] | 0.590 | 0.40 | 0.30 |
| | all non-hydrogen[2] | 0.976 | 0.65 | 0.49 |
| 1715-2483 of SEQ. ID No. 1 | alpha-carbon atoms[1] | 1.37 | 0.92 | 0.69 |
| | main-chain atoms[1] | 1.45 | 0.97 | 0.73 |
| | all non-hydrogen[2] | 1.84 | 1.23 | 0.92 |

[1] the RMSD computed between the atoms of all amino acids that are common to both the target and the reference in the aligned and superposed structure. The amino acids need not be identical.
[2] the RMSD computed only between identical amino acids, which are common to both the target and the reference in the aligned and superposed structure.

TABLE 1B

| AA RESIDUES TO USE TO PERFORM RMSD COMPARISON | PORTION OF EACH AA RESIDUE USED TO PERFORM RMSD COMPARISON | RMSD VALUE LESS THAN OR EQUAL TO | | |
|---|---|---|---|---|
| Table 2B (4 Angstrom set) | alpha-carbon atoms[1] | 0.688 | 0.46 | 0.34 |
| | main-chain atoms[1] | 0.685 | 0.46 | 0.34 |
| | all non-hydrogen[2] | 1.107 | 0.74 | 0.55 |
| Table 3B (7 Angstrom set) | alpha-carbon atoms[1] | 0.678 | 0.47 | 0.34 |
| | main-chain atoms[1] | 0.721 | 0.48 | 0.36 |
| | all non-hydrogen[2] | 1.089 | 0.73 | 0.54 |
| Table 4B (10 Angstrom set) | alpha-carbon atoms[1] | 0.716 | 0.48 | 0.36 |
| | main-chain atoms[1] | 0.733 | 0.49 | 0.37 |
| | all non-hydrogen[2] | 1.162 | 0.78 | 0.58 |
| 1715-2483 of SEQ. ID No. 1 | alpha-carbon atoms[1] | 1.29 | 0.86 | 0.65 |
| | main-chain atoms[1] | 1.36 | 0.91 | 0.68 |
| | all non-hydrogen[2] | 1.69 | 1.13 | 0.85 |

[1] the RMSD computed between the atoms of all amino acids that are common to both the target and the reference in the aligned and superposed structure. The amino acids need not be identical.
[2] the RMSD computed only between identical amino acids, which are common to both the target and the reference in the aligned and superposed structure.

The present invention is also directed to a three-dimensional structure of all or a portion of ACC2. This three-dimensional structure may be used to identify binding sites, to provide mutants having desirable binding properties, and ultimately, to design, characterize, or identify ligands capable of interacting with ACC2. Ligands that interact with ACC2 may be any type of atom, compound, protein or chemical group that binds to or otherwise associates with the protein. Examples of types of ligands include natural substrates for ACC2, inhibitors of ACC2, and heavy atoms. The inhibitors of ACC2 may optionally be used as drugs to treat therapeutic indications by modifying the in vivo activity of ACC2.

In various embodiments, methods are provided for displaying a three dimensional representation of a structure of a protein comprising:

taking machine readable data comprising structure coordinates that have a root mean square deviation equal to or less than the RMSD value specified in Columns 3, 4 or 5 of Table 1A or Table 1B when compared to the structure coordinates of FIG. 3, the root mean square deviation being calculated such that the portion of amino acid residues specified in Column 2 of Table 1A or Table 1B of each set of structure coordinates are superimposed and the root mean square deviation is based only on those amino acid residues in the structure coordinates that are also present in the portion of the protein specified in Column 1 of Table 1A or Table 1B;

computing a three dimensional representation of a structure based on the structure coordinates; and displaying the three dimensional representation.

The present invention is also directed to a method for solving a three-dimensional crystal structure of a target protein using the structure of ACC2.

In various embodiments, computational methods are provided comprising:

taking machine readable data comprising structure coordinates that have a root mean square deviation equal to or less than the RMSD value specified in Columns 3, 4 or 5 of Table 1A or Table 1B when compared to the structure coordinates of FIG. 3, the root mean square deviation being calculated such that the portion of amino acid residues specified in Column 2 of Table 1A or Table 1B of each set of structure coordinates are superimposed and the root mean square deviation is based only on those amino acid residues in the structure coordinates that are also present in the portion of the protein specified in Column 1 of Table 1A or Table 1B;

computing phases based on the structural coordinates;

computing an electron density map based on the computed phases; and determining a three-dimensional crystal structure based on the computed electron density map.

In various embodiments, computational methods are provided comprising: taking an X-ray diffraction pattern of a crystal of the target protein; and computing a three-dimensional electron density map from the X-ray diffraction pattern by molecular replacement, wherein structure coordinates used as a molecular replacement model comprise structure coordinates that have a root mean square deviation equal to or less than the RMSD value specified in Columns 3, 4 or 5 of Table 1A or Table 1B when compared to the structure coordinates of FIG. 3, the root mean square deviation being calculated such that the portion of amino acid residues specified in Column 2 of Table 1A or Table 1B of each set of structure coordinates are superimposed and the root mean square deviation is based only on those amino acid residues in the structure coordinates that are also present in the portion of the protein specified in Column 1 of Table 1A or Table 1B.

These methods may optionally further comprise determining a three-dimensional crystal structure based upon the computed three-dimensional electron density map.

The present invention is also directed to using a crystal structure of ACC2, in particular the structure coordinates of ACC2 and the surface contour defined by them, in methods for screening, designing, or optimizing molecules or other chemical entities that interact with and preferably inhibit ACC2.

One skilled in the art will appreciate the numerous uses of the inventions described herein, particularly in the areas of drug design, screening and optimization of drug candidates, as well as in determining additional unknown crystal structures. For example, a further aspect of the present invention relates to using a three-dimensional crystal structure of all or a portion of ACC2 and/or its structure coordinates to evaluate the ability of entities to associate with ACC2. The entities may be any entity that may function as a ligand and thus may be any type of atom, compound, protein (such as antibodies) or chemical group that can bind to or otherwise associate with a protein.

In various embodiments, methods are provided for evaluating a potential of an entity to associate with a protein comprising:

creating a computer model of a protein structure using structure coordinates that comprise structure coordinates that have a root mean square deviation equal to or less than the RMSD value specified in Columns 3, 4 or 5 of Table 1A or Table 1B when compared to the structure coordinates of FIG. 3, the root mean square deviation being calculated such that the portion of amino acid residues specified in Column 2 of Table 1A or Table 1B of each set of structure coordinates are superimposed and the root mean square deviation is based only on those amino acid residues in the structure coordinates that are also present in the portion of the protein specified in Column 1 of Table 1A or Table 1B;

performing a fitting operation between the entity and the computer model; and analyzing results of the fitting operation to quantify an association between the entity and the model.

In other embodiments, methods are provided for identifying entities that can associate with a protein comprising:

generating a three-dimensional structure of a protein using structure coordinates that comprise structure coordinates that have a root mean square deviation equal to or less than the RMSD value specified in Columns 3, 4 or 5 of Table 1A or Table 1B when compared to the structure coordinates of FIG. 3, the root mean square deviation being calculated such that the portion of amino acid residues specified in Column 2 of Table 1A or Table 1B of each set of structure coordinates are superimposed and the root mean square deviation is based only on those amino acid residues in the structure coordinates that are also present in the portion of the protein specified in Column 1 of Table 1A or Table 1B;

employing the three-dimensional structure to design or select an entity that can associate with the protein; and contacting the entity with a protein wherein at least a portion of the protein has 55%, 65%, 75%, 85%, 90%, 95%, 97%, 99% or greater identity with residues 1715-2483 of SEQ. ID No. 1.

In other embodiments, methods are provided for identifying entities that can associate with a protein comprising:

generating a three-dimensional structure of a protein using structure coordinates that comprise structure coordinates that have a root mean square deviation equal to or less than the RMSD value specified in Columns 3, 4 or 5 of Table 1A or Table 1B when compared to the structure coordinates of FIG. 3, the root mean square deviation being calculated such that the portion of amino acid residues specified in Column 2 of Table 1A or Table 1B of each set of structure coordinates are superimposed and the root mean square deviation is based only on those amino acid residues in the structure coordinates that are also present in the portion of the protein specified in Column 1 of Table 1A or Table 1B; and employing the three-dimensional structure to design or select an entity that can associate with the protein.

In other embodiments, methods are provided for identifying entities that can associate with a protein comprising:

computing a computer model for a protein binding pocket, at least a portion of the computer model having a surface contour that has a root mean square deviation equal to or less than a given RMSD value specified in Columns 3, 4 or 5 of Table 1A or Table 1B when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1A or Table 1B (specified in Column 2 of Table 1A or Table 1B) are superimposed according to the RMSD calculation, and (c) the root mean square deviation is calculated based only on those amino acid residues present in both the protein being modeled and the portion of the protein associated with the given RMSD in Table 1A or Table 1B (specified in Column 1 of Table 1A or Table 1B);

employing the computer model to design or select an entity that can associate with the protein; and contacting the entity with a protein wherein at least a portion of the protein has 55%, 65%, 75%, 85%, 90%, 95%, 97%, 99% or greater identity with residues 1715-2483 of SEQ. ID No. 1.

In other embodiments, methods are provided for identifying entities that can associate with a protein comprising:

computing a computer model for a protein binding pocket, at least a portion of the computer model having a surface contour that has a root mean square deviation equal to or less than a given RMSD value specified in Columns 3, 4 or 5 of Table 1A or Table 1B when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1A or Table 1B (specified in Column 2 of Table 1A or Table 1B) are superimposed according to the RMSD calculation, and (c) the root mean square deviation is calculated based only on those amino acid residues present in both the protein being modeled and the portion of the protein associated with the given RMSD in Table 1A or Table 1B (specified in Column 1 of Table 1A or Table 1B); and employing the computer model to design or select an entity that can associate with the protein.

In other embodiments, methods are provided for evaluating the ability of an entity to associate with a protein, the method comprising:

constructing a computer model defined by structure coordinates that have a root mean square deviation equal to or less than the RMSD value specified in Columns 3, 4 or 5 of Table 1A or Table 1B when compared to the structure coordinates of FIG. 3, the root mean square deviation being calculated such that the portion of amino acid residues specified in Column 2 of Table 1A or Table 1B of each set of structure coordinates are superimposed and the root mean square deviation is based only on those amino acid residues in the structure coordinates that are also present in the portion of the protein specified in Column 1 of Table 1A or Table 1B;

selecting an entity to be evaluated by a method selected from the group consisting of (i) assembling molecular fragments into the entity, (ii) selecting an entity from a small molecule database, (iii) de novo ligand design of the entity, and (iv) modifying a known ligand for ACC2, or a portion thereof;

performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the binding pocket.

In other embodiments, methods are provided for evaluating the ability of an entity to associate with a protein, the method comprising:

computing a computer model for a protein binding pocket, at least a portion of the computer model having a surface contour that has a root mean square deviation equal to or less than a given RMSD value specified in Columns 3, 4 or 5 of Table 1A or Table 1B when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1A or Table 1B (specified in Column 2 of Table 1A or Table 1B) are superimposed according to the RMSD calculation, and (c) the root mean square deviation is calculated based only on those amino acid residues present in both the protein being modeled and the portion of the protein associated with the given RMSD in Table 1A or Table 1B (specified in Column 1 of Table 1);

selecting an entity to be evaluated by a method selected from the group consisting of (i) assembling molecular fragments into the entity, (ii) selecting an entity from a small molecule database, (iii) de novo ligand design of the entity, and (iv) modifying a known ligand for ACC2, or a portion thereof;

performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the binding pocket.

In regard to each of these embodiments, the protein may optionally have activity characteristic of ACC2. For example, the protein may optionally be inhibited by inhibitors of wild type ACC2.

In another embodiment, a method is provided for identifying an entity that associates with a protein comprising: taking structure coordinates from diffraction data obtained from a crystal of a protein wherein at least a portion of the protein has 55%, 65%, 75%, 85%, 90%, 95%, 97%, 99% or greater identity with residues 1715-2483 of SEQ. ID No. 1; and performing rational drug design using a three dimensional structure that is based on the obtained structure coordinates.

The protein crystals may optionally have a crystal lattice with a C222, space group and unit cell dimensions, +/−5%, of a=112.181 Å, b=117.698 Å, c=144.754 Å and $\alpha=\beta=\gamma=90$ degrees.

The method may optionally further comprise selecting one or more entities based on the rational drug design and contacting the selected entities with the protein. The method may also optionally further comprise measuring an activity of the protein when contacted with the one or more entities. The method also may optionally further comprise comparing activity of the protein in a presence of and in the absence of the one or more entities; and selecting entities where activity of the protein changes depending whether a particular entity is present. The method also may optionally further comprise contacting cells expressing the protein with the one or more entities and detecting a change in a phenotype of the cells when a particular entity is present.

BRIEF DESCRIPTION OF THE FIGURES

FIG. 1 illustrates SEQ. ID Nos. 1, 2, and 3, referred to in this application.

FIG. 3 lists a set of atomic structure coordinates for ACC2 as derived by X-ray crystallography from a crystal that comprises the protein. The following abbreviations are used in FIG. 3: "X, Y, Z" crystallographically define the atomic position of the element measured; "B" is a thermal factor that measures movement of the atom around its atomic center; "Occ" is an occupancy factor that refers to the fraction of the molecules in which each atom occupies the position specified by the coordinates (a value of "1" indicates that each atom has the same conformation, i.e., the same position, in all molecules of the crystal).

DETAILED DESCRIPTION OF THE INVENTION

Figure 2:
FIG. 2 illustrates a crystal of ACC2 corresponding to SEQ. ID No. 3, having a crystal lattice in a C222$_1$ space group and unit cell dimensions, +/−5%, of a=112.181 Å, b=117.698 Å and c=144.754 Å, $\alpha=\beta=\gamma=90$ degrees.

The present invention relates to a member of a family of Acetyl-Coenzyme A Carboxylases (ACCs) and more specifically to a particular portion of an ACC known as the Carboxyltransferase domain of human Acetyl-Coenzyme A Carboxylase 2 (ACC2). Provided is ACC2 in crystalline form, methods of forming crystals comprising ACC2, methods of using crystals comprising ACC2, a crystal structure of ACC2, and methods of using the crystal structure.

In describing protein structure and function herein, reference is made to amino acids comprising the protein. The amino acids may also be referred to by their conventional abbreviations; A=Ala=Alanine; T=Thr=Threonine; V=Val=Valine; C=Cys=Cysteine; L=Leu=Leucine; Y=Tyr=Tyrosine; I=Ile=Isoleucine; N=Asn=Asparagine; P=Pro=Proline; Q=Gln=Glutamine; F=Phe=Phenylalanine; D=Asp=Aspartic Acid; W=Trp=Tryptophan; E=Glu=Glutamic Acid; M=Met=Methionine; K=Lys=Lysine; G=Gly=Glycine; R=Arg=Arginine; S=Ser=Serine; and H=His=Histidine.

1. ACC2

Acetyl CoEnzyme A Carboxylases (ACCs) are enzymes that perform the first committed step in fatty acid biosynthesis and are central to a set of cardiovascular risk factors termed the Metabolic Syndrome. This syndrome is characterized by a number of symptoms including, but not limited to, abdominal obesity, hyperinsulinemia and hypertension, that together lead to an increased risk of developing heart disease and type 2 diabetes (reviewed in Harwood, *Curr. Op. Invest. Drugs*

5:283-289, 2004). ACC forms malonyl-CoA from acetyl-CoA through a two-step, ATP-dependent reaction. The first step carboxylates biotin, while the second step transfers this carboxyl group from carboxybiotin to acetyl-CoA to from malonyl CoA. It is this second carboxyltransferase reaction that is the target of the present work. The malonyl-coA produced by ACC is a critical metabolic regulator of fatty acid oxidation as it acts as an allosteric inhibitor of carnitine palmitoyltransferase 1, the enzyme that performs the first committed step in fatty acid oxidation in mitochondria (Mc-Garry, J. D., & Brown, N. F., *Eur. J. Biochem.*, 244:1-14, 1997).

In humans, ACCs occur as two isoenzymes. ACC1 is present in liver and adipose tissue and is located in the cytosol. ACC2 is a slightly larger enzyme present in oxidative tissue such as liver, heart and muscle, and is located in the mitochondria. Due to this compartmentalization, the malonyl-CoA formed by ACC1 in the cytosol is used primarily for fatty acid synthesis, while that produced by ACC2 functions mostly to regulate fatty acid oxidation. Studies with gene knock-outs show that mice lacking ACC2, but with a functional ACC1 enzyme, have a reduced fat content while still retaining normal growth rates, life expectancy and breeding ability when compared to normal siblings (Abu-Elheiga, L., Matzuk, M. M., Abo-Hashema, K. A. H., & Wakil, S. J., *Science* 291:2613-2616, 2001). These mice lacking ACC2 were further shown to be protected against obesity and diabetes when fed unhealthful diets (Abu-Elheiga, L., Oh, W., Kordari, P. & Wakil S. J., *Proc. Natl. Acad. Sci. USA,* 100: 10207-10212, 2003), indicating that potential ACC enzyme inhibitors could have broad therapeutic value in the treatment of Metabolic Syndrome.

Work on developing effective ACC inhibitors has been limited primarily to non-selective compounds, while attempts to understand the structural basis of the binding mode of these compounds have been restricted to the carboxyltransferase domain of yeast ACC2, which shares only 52% amino acid identity with the carboxyltransferase domain of human ACC2. The structural results for yeast ACC2 complexed with the non-selective inhibitor CP-640186 (Zhang, H., Tweel, B., Li, J., & Tong, L., Structure, 12:1683-1691, 2004) and the herbicides haloxyfop and diclofop (Zhang, H., Tweel, B., & Tong, L., *Proc. Natl. Acad. Sci. USA,* 101:5910-5915, 2004) have demonstrated that these compounds bind to sites distinct from the acetyl-CoA substrate site, with CP-640186 in particular binding to the proposed binding site for carboxybiotin.

In one embodiment, ACC2 comprises the wild-type form of full length ACC2, set forth herein as SEQ. ID No. 1 (GenBank Accession Number U89344; (Abu-Elheiga, L., Almarza-Ortega, D. B., Baldini, A. and Wakil, S. J. Human acetyl-CoA carboxylase 2. Molecular cloning, characterization, chromosomal mapping, and evidence for two isoforms, *J. Biol. Chem.* 272 (16), 10669-10677 (1997))

In another embodiment, ACC2 comprises residues 1715-2483 of SEQ. ID No. 1 which comprises the active site domain of wild-type ACC2 that is represented in the set of structural coordinates shown in FIG. 3.

It should be recognized that the invention may be readily extended to various variants of wild-type ACC2 and variants of fragments thereof. In another embodiment, ACC2 comprises a sequence wherein at least a portion of the sequence has 55%, 65%, 75%, 85%, 90%, 95%, 97%, 99% or greater identity with SEQ. ID No. 1.

It is also noted that the above sequences of ACC2 are also intended to encompass isoforms, mutants and fusion proteins of these sequences. An example of a fusion protein is provided by SEQ. ID No. 3, which includes a 6 residue C-terminal tag (6 residues are histidine) that may be used to facilitate purification of the protein.

With the crystal structure provided herein, it is now known where amino acid residues are positioned in the structure. As a result, the impact of different substitutions can be more easily predicted and understood.

For example, based on the crystal structure, applicants have determined that the ACC2 amino acids shown in Tables 2A and 2B encompass a 4-Angstrom radius around the ACC2 Acetyl-CoEnzyme A and Biotin active sites, respectively, and thus are likely to interact with any active site inhibitor of ACC2. Applicants have also determined that the amino acids of Tables 3A and 3B encompass a 7-Angstrom radius around the ACC2 Acetyl-CoEnzyme A and Biotin active sites, respectively. Further it has been determined that the amino acids of Tables 4A and 4B encompass a 10-Angstrom radius around the ACC2 Acetyl-CoEnzyme A and Biotin active sites, respectively. It is noted that there is one ACC2 molecule in the asymmetric unit, referred to as chain A. Structural coordinates appear in FIG. 3. It is noted that the sequence and structure of the residues in one or both of the active sites may also be conserved and hence pertinent to other ACC2 variants and homologs.

One or more of the sets of amino acids set forth in the tables is preferably conserved in a variant of ACC2. Hence, ACC2 may optionally comprise a sequence wherein at least a portion of the sequence has 55%, 65%, 75%, 85%, 90%, 95%, 97%, 99% or greater identity with any one of the above sequences (e.g., all of SEQ. ID No. 1 or residues 1715-2483 of SEQ. ID No. 1) where at least the residues shown in Tables 2A, 2B, 3A, 3B, 4A and/or 4B are conserved with the exception of 0, 1, 2, 3, or 4 residues. It should be recognized that one might optionally vary some of the binding site residues in order to determine the effect such changes have on structure or activity.

TABLE 2A

Amino Acids encompassed by a
4-Angstrom radius around the ACC2 Acetyl-CoEnzyme A binding
site ("S" denotes residues from the (x, -y, -z) symmetry-related molecule).

| ILE A1824 | SER A1826 | SER A1856 |
| GLY A1857 | ALA A1858 | ARG A1859 |
| ILE A1860 | LEU A1933 | ARG A1959 |
| GLY A1962 | ILE A1963 | GLY S2226 |
| GLY S2227 | VAL S2230 | VAL S2253 |
| LEU S2254 | ILE S2262 | LYS S2263 |
| ARG S2265 | | |

TABLE 2B

Amino Acids encompassed by a
4-Angstrom radius around the ACC2 Biotin binding site binding
site ("S" denotes residues from the (x, -y, -z) symmetry-related molecule).

| ARG A2183 | GLY A2184 | PHE A2185 |
| SER A2186 | GLY A2187 | GLY A2188 |
| LEU A2254 | GLU A2255 | GLU A2257 |
| GLY A2258 | GLU A2261 | LEU A2262 |
| THR S1985 | ALA S1989 | LEU S1990 |
| LYS S1992 | VAL S1993 | |

TABLE 3A

Amino Acids encompassed by a
7-Angstrom radius around the ACC2 Acetyl-CoEnzyme A binding
site ("S" denotes residues from the (x, -y, -z) symmetry-related molecule).

| | | |
|---|---|---|
| ILE A1824 | SER A1826 | SER A1856 |
| GLY A1857 | ALA A1858 | ARG A1859 |
| ILE A1860 | LEU A1933 | ARG A1959 |
| GLY A1962 | ILE A1963 | GLY A2226 |
| GLY S2227 | VAL S2230 | VAL S2253 |
| LEU S2254 | ILE S2262 | LYS S2263 |
| ARG S2265 | | |
| LEU A1737 | ARG A1823 | PHE A1827 |
| ASN A1855 | GLY A1861 | ASN A1932 |
| SER A1936 | ILE A1961 | GLY A1964 |
| TYR A1966 | HIS A1981 | ILE A1983 |
| LEU A1984 | THR A1985 | GLY A1986 |
| SER A1988 | ALA A1989 | ASN A2002 |
| ARG S2225 | SER S2228 | TRP S2229 |
| THR S2259 | GLU S2261 | PHE S2264 |
| ASP S2268 | | |

TABLE 3B

Amino Acids encompassed by a
7-Angstrom radius around the ACC2 Biotin binding
site ("S" denotes residues from the (x, -y, -z) symmetry-related molecule).

| | | |
|---|---|---|
| ALA A2150 | GLN A2152 | VAL A2153 |
| TRP A2154 | PHE A2155 | TRP A2182 |
| ARG A2183 | GLY A2184 | PHE A2185 |
| SER A2186 | GLY A2187 | GLY A2188 |
| MET A2189 | ASP A2191 | ARG A2225 |
| GLY A2226 | SER A2228 | VAL A2253 |
| LEU A2254 | GLU A2255 | PRO A2256 |
| GLU A2257 | GLY A2258 | THR A2259 |
| VAL A2260 | GLU A2261 | LEU A2262 |
| ARG A2265 | ILE S1860 | LEU S1984 |
| THR S1985 | GLY S1986 | SER S1988 |
| ALA S1989 | LEU S1990 | ASN S1991 |
| LYS S1992 | VAL S1993 | LEU S1994 |
| GLY S1995 | VAL S1998 | TYR S1999 |
| ALA S2138 | | |

TABLE 4A

Amino Acids encompassed by a
10-Angstrom radius around the ACC2 Acetyl-CoEnzyme A binding
site ("S" denotes residues from the (x, -y, -z) symmetry-related molecule).

| | | |
|---|---|---|
| ILE A1824 | SER A1826 | SER A1856 |
| GLY A1857 | ALA A1858 | ARG A1859 |
| ILE A1860 | LEU A1933 | ARG A1959 |
| GLY A1962 | ILE A1963 | GLY A2226 |
| GLY S2227 | VAL S2230 | VAL S2253 |
| LEU S2254 | ILE S2262 | LYS S2263 |
| ARG S2265 | LYS S2266 | LYS S2267 |
| LEU A1737 | ARG A1823 | PHE A1827 |
| ASN A1855 | GLY A1861 | ASN A1932 |
| SER A1936 | ILE A1961 | GLY A1964 |
| TYR A1966 | HIS A1981 | ILE A1983 |
| LEU A1984 | THR A1985 | GLY A1986 |
| SER A1988 | ALA A1989 | ASN A2002 |
| ARG S2225 | SER S2228 | TRP S2229 |
| THR S2259 | GLU S2261 | PHE S2264 |
| ASP S2268 | VAL S2260 | GLY S2258 |
| GLU S2255 | GLY S2252 | ASP S2233 |
| ILE S2232 | VAL S2231 | LEU S2224 |
| LEU S2197 | PHE S2185 | GLY S2184 |
| ARG S2183 | GLN A1733 | THR A1736 |
| ILE A1820 | THR A1821 | PHE A1822 |
| GLY A1825 | GLY A1828 | GLU A1831 |
| ASP A1832 | ALA A1854 | MET A1862 |
| GLU A1864 | LYS A1867 | GLY A1927 |
| LEU A1928 | GLY A1929 | VAL A1930 |

TABLE 4A-continued

Amino Acids encompassed by a
10-Angstrom radius around the ACC2 Acetyl-CoEnzyme A binding
site ("S" denotes residues from the (x, -y, -z) symmetry-related molecule).

| | | |
|---|---|---|
| GLU A1931 | ARG A1934 | GLY A1935 |
| GLY A1937 | ILE A1939 | ALA A1940 |
| CYS A1958 | ALA A1960 | ALA A1965 |
| LEU A1967 | ALA A1987 | ILE A1990 |
| LYS A1992 | LEU A2005 | |

TABLE 4B

Amino Acids encompassed by a
10-Angstrom radius around the ACC2 Biotin binding
site ("S" denotes residues from the (x, -y, -z) symmetry-related molecule).

| | | |
|---|---|---|
| THR A2128 | GLN A2148 | GLN A2149 |
| ALA A2150 | GLY A2151 | GLN A2152 |
| VAL A2153 | TRP A2154 | PHE A2155 |
| PRO A2156 | ASN A2181 | TRP A2182 |
| ARG A2183 | GLY A2184 | PHE A2185 |
| SER A2186 | GLY A2187 | GLY A2188 |
| MET A2189 | LYS A2190 | ASP A2191 |
| MET A2192 | VAL A2196 | GLU A2223 |
| LEU A2224 | ARG A2225 | GLY A2226 |
| GLY A2227 | SER A2228 | TRP A2229 |
| GLY A2252 | VAL A2253 | LEU A2254 |
| GLU A2255 | PRO A2256 | GLU A2257 |
| GLY A2258 | THR A2259 | VAL A2260 |
| GLU A2261 | ILE A2262 | LYS A2263 |
| PHE A2264 | ARG A2265 | HIS A2316 |
| GLN A2317 | VAL A2320 | ALA A2323 |
| ASP A2327 | ILE S1860 | ILE S1961 |
| ILE S1983 | LEU S1984 | THR S1985 |
| GLY S1986 | ALA S1987 | SER S1988 |
| ALA S1989 | LEU S1990 | ASN S1991 |
| LYS S1992 | VAL S1993 | LEU S1994 |
| GLY S1995 | ARG S1996 | VAL S1998 |
| TYR S1999 | LEU S2005 | ASP S2136 |
| PRO S2137 | ALA S2138 | ASN S2139 |

With the benefit of the crystal structure and guidance provided by Tables 2A, 2B, 3A, 3B, 4A and 4B, a wide variety of ACC2 variants (e.g., insertions, deletions, substitutions, etc.) that fall within the above specified identity ranges may be designed and manufactured utilizing recombinant DNA techniques well known to those skilled in the art, particularly in view of the knowledge of the crystal structure provided herein. These modifications can be used in a number of combinations to produce the variants. The present invention is useful for crystallizing and then solving the structure of the range of variants of ACC2.

Variants of ACC2 may be insertional variants in which one or more amino acid residues are introduced into a predetermined site in the ACC2 sequence. For instance, insertional variants can be fusions of heterologous proteins or polypeptides to the amino or carboxyl terminus of the subunits.

Variants of ACC2 also may be substitutional variants in which at least one residue has been removed and a different residue inserted in its place. Non-natural amino acids (i.e., amino acids not normally found in native proteins), as well as isosteric analogs (amino acid or otherwise), may optionally be employed in substitutional variants. Examples of suitable substitutions are well known in the art, such as Glu→Asp, Asp→Glu, Ser→Cys, and Cys→Ser for example.

Another class of variants is deletional variants, which are characterized by the removal of one or more amino acid residues from the ACC2 sequence.

Other variants may be produced by chemically modifying amino acids of the native protein (e.g., diethylpyrocarbonate treatment that modifies histidine residues). Preferred are chemical modifications that are specific for certain amino acid side chains. Specificity may also be achieved by blocking other side chains with antibodies directed to the side chains to be protected. Chemical modification includes such reactions as oxidation, reduction, amidation, deamidation, or substitution of bulky groups such as polysaccharides or polyethylene glycol.

Exemplary modifications include the modification of lysinyl and amino terminal residues by reaction with succinic or other carboxylic acid anhydrides. Modification with these agents has the effect of reversing the charge of the lysinyl residues. Other suitable reagents for modifying amino-containing residues include imidoesters such as methyl picolinimidate; pyridoxal phosphate; pyridoxal chloroborohydride; trinitrobenzenesulfonic acid; O-methylisourea; 2,4-pentanedione; transaminase catalyzed reaction with glyoxylate; and N-hydroxysuccinamide esters of polyethylene glycol or other bulky substitutions.

Arginyl residues may be modified by reaction with a number of reagents, including phenylglyoxal; 2,3-butanedione; 1,2-cyclohexanedione; and ninhydrin. Modification of arginine residues requires that the reaction be performed in alkaline conditions because of the high $pK_a$ of the guanidine functional group. Furthermore, these reagents may react with the groups of lysine as well as the arginine epsilon-amino group.

Tyrosyl residues may also be modified to introduce spectral labels into tyrosyl residues by reaction with aromatic diazonium compounds or tetranitromethane, forming O-acetyl tyrosyl species and 3-nitro derivatives, respectively. Tyrosyl residues may also be iodinated using $^{125}I$ or $^{131}I$ to prepare labeled proteins for use in radioimmunoassays.

Carboxyl side groups (aspartyl or glutamyl) may be selectively modified by reaction with carbodiimides or they may be converted to asparaginyl and glutaminyl residues by reaction with ammonium ions. Conversely, asparaginyl and glutaminyl residues may be deamidated to the corresponding aspartyl or glutamyl residues, respectively, under mildly acidic conditions. Either form of these residues falls within the scope of this invention.

Other modifications that may be formed include the hydroxylation of proline and lysine, phosphorylation of hydroxyl groups of seryl or threonyl groups of lysine, arginine and histidine side chains (T. E. Creighton, *Proteins: Structure and Molecular Properties*, W.H. Freeman & Co., San Francisco, pp. 79-86, 1983), acetylation of the N-terminal amine and amidation of any C-terminal carboxyl group.

As can be seen, modifications of the nucleic sequence encoding ACC2 may be accomplished by a variety of well-known techniques, such as site-directed mutagenesis (see, Gillman and Smith, *Gene* 8:81-97 (1979) and Roberts, S. et al., *Nature* 328:731-734 (1987)). When modifications are made, these modifications may optionally be evaluated for their affect on a variety of different properties including, for example, solubility, crystallizability and a modification to the protein's structure and activity.

In one variation, the variant and/or fragment of wild-type ACC2 is functional in the sense that the resulting protein is capable of associating with at least one same chemical entity that is also capable of selectively associating with a protein comprising the wild-type ACC2 (e.g., residues 1715-2483 of SEQ. ID No. 1) since this common associative ability evidences that at least a portion of the native structure has been conserved.

It is noted that the activity of the native protein need not necessarily be conserved. Rather, amino acid substitutions, additions or deletions that interfere with native activity but which do not significantly alter the three-dimensional structure of the domain are specifically contemplated by the invention. Crystals comprising such variants of ACC2, and the atomic structure coordinates obtained therefrom, can be used to identify compounds that bind to the native domain. These compounds may affect the activity of the native domain.

Amino acid substitutions, deletions and additions that do not significantly interfere with the three-dimensional structure of ACC2 will depend, in part, on the region where the substitution, addition or deletion occurs in the crystal structure. These modifications to the protein can now be made far more intelligently with the crystal structure information provided herein. In highly variable regions of the molecule, non-conservative substitutions as well as conservative substitutions may be tolerated without significantly disrupting the three-dimensional structure of the molecule. In highly conserved regions, or regions containing significant secondary structure, conservative amino acid substitutions are preferred.

Conservative amino acid substitutions are well known in the art, and include substitutions made on the basis of similarity in polarity, charge, solubility, hydrophobicity, hydrophilicity and/or the amphipathic nature of the amino acid residues involved. For example, negatively charged amino acids include aspartic acid and glutamic acid; positively charged amino acids include lysine and arginine; amino acids with uncharged polar head groups having similar hydrophilicity values include the following: leucine; isoleucine; valine; glycine; alanine; asparagine; glutamine; serine; threonine; phenylalanine; and tyrosine. Other conservative amino acid substitutions are well known in the art.

It should be understood that the protein may be produced in whole or in part by chemical synthesis. As a result, the selection of amino acids available for substitution or addition is not limited to the genetically encoded amino acids. Indeed, mutants may optionally contain non-genetically encoded amino acids. Conservative amino acid substitutions for many of the commonly known non-genetically encoded amino acids are well known in the art. Conservative substitutions for other amino acids can be determined based on their physical properties as compared to the properties of the genetically encoded amino acids.

In some instances, it may be particularly advantageous or convenient to substitute, delete and/or add amino acid residues in order to provide convenient cloning sites in cDNA encoding the polypeptide, to aid in purification of the polypeptide, etc. Such substitutions, deletions and/or additions which do not substantially alter the three dimensional structure of ACC2 will be apparent to those having skills in the art, particularly in view of the three dimensional structure of ACC2 provided herein.

2. Cloning, Expression and Purification of ACC2

The gene encoding ACC2 can be isolated from RNA, cDNA or cDNA libraries. In this case, the portion of the gene encoding amino acid residues 1715-2483 of SEQ. ID No. 1 corresponding to carboxyltransferase domain of ACC2, was isolated and is shown as SEQ. ID No. 2.

Construction of expression vectors and recombinant proteins from the DNA sequence encoding ACC2 may be performed by various methods well known in the art. For example, these techniques may be performed according to Sambrook et al., Molecular Cloning-A Laboratory Manual, Cold Spring Harbor, N.Y. (1989), and Kriegler, M., Gene Transfer and Expression, A Laboratory Manual, Stockton Press, New York (1990).

A variety of expression systems and hosts may be used for the expression of ACC2. Example 1 provides one such expression system.

Once expressed, purification steps are employed to produce ACC2 in a relatively homogeneous state. In general, a higher purity solution of a protein increases the likelihood that the protein will crystallize. Typical purification methods include the use of centrifugation, partial fractionation, using salt or organic compounds, dialysis, conventional column chromatography (such as ion exchange, molecular sizing chromatography, etc.), high performance liquid chromatography (HPLC), and gel electrophoresis methods (see, e.g., Deutcher, "Guide to Protein Purification" in Methods in Enzymology (1990), Academic Press, Berkeley, Calif.).

ACC2 may optionally be affinity labeled during cloning, preferably with a C-terminal six-histidine tag to facilitate purification. With the use of an affinity label, it is possible to perform a one-step purification process on a purification column that has a unique affinity for the label. These and other purification methods are known and will be apparent to one of skill in the art.

3. Crystallization & Crystals Comprising ACC2

One aspect of the present invention relates to methods for forming crystals comprising ACC2 as well as crystals comprising ACC2.

In one embodiment, a method for forming crystals comprising ACC2 is provided comprising forming a crystallization volume comprising ACC2, one or more precipitants, optionally a buffer, optionally a monovalent and/or divalent salt and optionally an organic solvent; and storing the crystallization volume under conditions suitable for crystal formation.

In yet another embodiment, a method for forming crystals comprising ACC2 is provided comprising forming a crystallization volume comprising ACC2 in solution comprising the components shown in Table 5; and storing the crystallization volume under conditions suitable for crystal formation.

TABLE 5

Precipitant 5-50% w/v of precipitant wherein the precipitant comprises one or more members of the group consisting of PEG MME having a molecular weight range between 1000-10000, PEG having a molecular weight range between 100-10000, and 0.2-4.0 M Ammonium formate or Sodium, potassium or ammonium phosphate.

pH pH 4-10. Buffers that may be used include, but are not limited to tris, bicine, phosphate, cacodylate, acetate, citrate, HEPES, PIPES, MES and combinations thereof.

Additives

Optionally 0.05 to 2.5 M additives wherein the additives comprise a monovalent and/or divalent salt (for example, sodium, lithium, magnesium, calcium, and the like)

Protein Concentration 1 mg/ml-200 mg/ml

Temperature

1° C.-25° C.

In yet another embodiment, a method for forming crystals comprising ACC2 is provided comprising forming a crystallization volume comprising ACC2; introducing crystals comprising ACC2 as nucleation sites; and storing the crystallization volume under conditions suitable for crystal formation.

Crystallization experiments may optionally be performed in volumes commonly used in the art, for example typically 15, 10, 5, 2 microliters or less. It is noted that the crystallization volume optionally has a volume of less than 1 microliter, optionally 500, 250, 150, 100, 50 or less nanoliters.

It is also noted that crystallization may be performed by any crystallization method including, but not limited to batch, dialysis and vapor diffusion (e.g., sitting drop and hanging drop) methods. Micro, macro and/or streak seeding of crystals may also be performed to facilitate crystallization.

It should be understood that forming crystals comprising ACC2 and crystals comprising ACC2 according to the invention are not intended to be limited to the wild type, full length ACC2 shown in SEQ. ID No. 1 and fragments comprising residues 1715-2483 of SEQ. ID No. 1. Rather, it should be recognized that the invention may be extended to various other fragments and variants of wild-type ACC2 as described above.

It should also be understood that forming crystals comprising ACC2 and crystals comprising ACC2 according to the invention may be such that ACC2 is optionally complexed with one or more ligands and one or more copies of the same ligand. The ligand used to form the complex may be any ligand capable of binding to ACC2. In one variation, the ligand is a natural substrate. In another variation, the ligand is an inhibitor.

In one particular embodiment, ACC2 crystals have a crystal lattice in the $C222_1$ space group. ACC2 crystals may also optionally have unit cell dimensions, +/−5%, of a=112.181 Å, b=117.698 Å and c=144.754 Å, $\alpha=\beta=\gamma=90°$. ACC2 crystals also preferably are capable of diffracting X-rays for determination of atomic coordinates to a resolution of 4 Å, 3.5 Å, 3.0 Å or better.

Crystals comprising ACC2 may be formed by a variety of different methods known in the art. For example, crystallizations may be performed by batch, dialysis, and vapor diffusion (sitting drop and hanging drop) methods. A detailed description of basic protein crystallization setups may be found in McRee, D., *Practical Protein Crystallography*, $2^{nd}$ Ed. (1999), Academic Press Inc. Further descriptions regarding performing crystallization experiments are provided in Stevens et al. (2000) *Curr. Opin. Struct. Biol.:* 10(5):558-63, and U.S. Pat. Nos. 6,296,673; 5,419,278; and 5,096,676.

In one variation, crystals comprising ACC2 are formed by mixing substantially pure ACC2 with an aqueous buffer containing a precipitant at a concentration just below a concentration necessary to precipitate the protein. One suitable precipitant for crystallizing ACC2 is polyethylene glycol (PEG), which combines some of the characteristics of the salts and other organic precipitants (see, for example, Ward et al., J. Mol. Biol. 98:161, 1975, and McPherson, J. Biol. Chem. 251:6300, 1976).

During a crystallization experiment, water is removed by diffusion or evaporation to increase the concentration of the precipitant, thus creating precipitating conditions for the protein. In one particular variation, crystals are grown by vapor diffusion in hanging drops or sitting drops. According to these methods, a protein/precipitant solution is formed and then allowed to equilibrate in a closed container with a larger aqueous reservoir having a precipitant concentration for producing crystals. The protein/precipitant solution continues to equilibrate until crystals grow.

By performing submicroliter volume sized crystallization experiments, as detailed in U.S. Pat. No. 6,296,673, effective crystallization conditions for forming crystals of a ACC2 complex were obtained. In order to accomplish this, systematic broad screen crystallization trials were performed on an ACC2 complex using the sitting drop technique. In each experiment, a 100 nL mixture of ACC2 complex and precipitant was placed on a platform positioned over a well containing 100 µL of the precipitating solution. Precipitate and crystal formation was detected in the sitting drops. Fine screening was then carried out for those crystallization conditions that appeared to produce precipitate and/or crystal in the drops.

Based on the crystallization experiments that were performed, a thorough understanding of how different crystallization conditions affect ACC2 crystallization was obtained. Based on this understanding, a series of crystallization conditions were identified that may be used to form crystals comprising ACC2. These conditions are summarized in Table 5. A particular example of crystallization conditions that may be used to form diffraction quality crystals of the ACC2 complex is detailed in Example 2. FIG. 2 illustrates crystals of the ACC2 complex formed using the crystallization conditions provided in Table 5.

One skilled in the art will recognize that the crystallization conditions provided in Table 5 and Example 2 can be varied and still yield protein crystals comprising ACC2. For example, it is noted that variations on the crystallization conditions described herein can be readily determined by taking the conditions provided in Table 5 and performing fine screens around those conditions by varying the type and concentration of the components in order to determine additional suitable conditions for crystallizing ACC2, variants of ACC2, and ligand complexes thereof.

Crystals comprising ACC2 have a wide range of uses. For example, now that crystals comprising ACC2 have been produced, it is noted that crystallizations may be performed using such crystals as a nucleation site within a concentrated protein solution. According to this variation, a concentrated protein solution is prepared and crystalline material (microcrystals) is used to 'seed' the protein solution to assist nucleation for crystal growth. If the concentrations of the protein and any precipitants are optimal for crystal growth, the seed crystal will provide a nucleation site around which a larger crystal forms. Given the ability to form crystals comprising ACC2 according to the present invention, the crystals so formed can be used by this crystallization technique to initiate crystal growth of other ACC2 comprising crystals, including ACC2 complexed to other ligands.

As will be described herein in greater detail, crystals may also be used to perform X-ray or neutron diffraction analysis in order to determine the three-dimensional structure of ACC2 and, in particular, to assist in the identification of its active site. Knowledge of the binding site region allows rational design and construction of ligands including inhibitors. Crystallization and structural determination of ACC2 mutants having altered bioactivity allows the evaluation of whether such changes are caused by general structure deformation or by side chain alterations at the substitution site.

4. X-Ray Data Collection and Structure Determination

Crystals comprising ACC2 may be obtained as described above in Section 3. As described herein, these crystals may then be used to perform X-ray data collection and for structure determination.

In one embodiment, described in Example 2, crystals of ACC2 were obtained where ACC2 has the sequence of residues shown in SEQ. ID No. 3. These particular crystals were used to determine the three dimensional structure of ACC2. However, it is noted that other crystals comprising ACC2 including different ACC2 variants, fragments, and complexes thereof may also be used.

Diffraction data were collected from cryocooled crystals (100K) of ACC2 at the Advanced Light Source (ALS) beamline 5.0.3 using an ADSC Quantum CCD detector. The diffraction pattern of the ACC2 crystals displayed symmetry consistent with space group C222, with unit cell dimensions a=112.181 Å, b=117.698 Å and c=144.754 Å, $\alpha=\beta=\gamma=90°$ (+/−5%). Data were collected and integrated to 2.0 Å with the HKL2000 program package (Otwinowski, Z. and Minor, W., *Meth. Enzymol.* 276:307 (1997)).

The structure solution for ACC2 in the space group $C222_1$ with unit cell dimensions a=112.181 Å, b=117.698 Å and c=144.754 Å, $\alpha=\beta=\gamma=90°$ (+/−5%) was obtained by the molecular replacement method using the CCP4 program package (Collaborative Computational Project, N. The CCP4 Suite: Programs for Protein Crystallography. *Acta Crystallogr.* D50, 760-763 (1994)), with the coordinates for *Saccharomyces cerevisiae* ACC2 (Zhang, H., Tweel, B., & Tong, L. *Proc. Natl. Acad. Sci. USA* 101:5910 (2004); PDB code 1UYT) used as a search model. Using data in the resolution range 45.0 to 3.5 Å, the correct solutions were obtained yielding a correlation coefficient of 0.328 and an R-value of 0.506. The molecular replacement solutions were subjected to rigid body refinement followed by restrained least-squares refinement using the maximum likelihood method as implemented in REFMAC (Murshudov, G. N., Vagin, A. A. and Dodson E. J. *Acta Crystallogr* D53:240 (1997)). The initial refinement resulted in an R-value of 0.280 and an $R_{free}$ value of 0.330 from which differences between the ACC2 structure and the molecular replacement model could be discerned. Multiple rounds of manual fitting of the ACC2 sequence and ordered regions not present in the initial model were performed with Xfit (McRee, D. E., *J. Struct. Biol.* 125:156 (1999)). Manual fitting was interspersed with restrained least-squares refinement in REFMAC against data from 20.0 to 2.0 Å. All stages of refinement were carried with bulk solvent corrections, and excluded 5% of $R_{free}$ reflections for cross-validation. The data collection and data refinement statistics are given in Table 6.

TABLE 6

| Crystal data | | |
|---|---|---|
| Space group | | $C222_1$ |
| Unit cell dimensions | | a = 112.181 Å |
| | | b = 117.698 Å |
| | | c = 144.754 Å |
| | | $\alpha = \beta = \gamma = 90°$ |
| Data collection | | |
| X-ray source | | ALS BL 5.0.3 |
| Wavelength [Å] | | 1.00 |
| Resolution [Å] | | 2.03 |
| Observations (unique) | | 56715 |
| Redundancy | | 3.9 |
| Completeness | overall (outer shell) | 91.3 (91.8)% |
| I/σ(I) | overall (outer shell) | 10.2 (2.7) |
| $R_{symm}^1$ | overall (outer shell) | 0.070 (.517) |
| Refinement | | |
| Reflections used | | 53793 |
| R-factor | | 17.20% |
| $R_{free}$ | | 21.13% |
| r.m.s bonds | | 0.007 Å |
| r.m.s angles | | 1.04° |

During structure determination, where the unit cell dimensions were a=112.181 Å, b=117.698 Å and c=144.754 Å, $\alpha=\beta=\gamma=90°$, it was realized that the asymmetric unit comprised one ACC2 molecule bound to acetyl-coenzyme A, with the biological dimer of ACC2 completed via a crystallographic (x, −y, −z) symmetry transformation. Structure coordinates were determined for this complex and the resultant set of structural coordinates from the refinement are presented in FIG. 3. For the purposes of structural comparisons the (x, −y, −z) symmetry-related dimer residues are indicated by the segment identifier "S".

It is noted that the sequence of the structure coordinates presented in FIG. 3 differ in some regards from the sequence shown in SEQ. ID No. 3. Structure coordinates are not reported for residues 1715-1718, 2415-2426, and 2452-2483 as well as the C-terminal six His tag because the electron density obtained was insufficient to identify their position.

Those of skill in the art understand that a set of structure coordinates (such as those in FIG. 3) for a protein or a protein-complex or a portion thereof, is a relative set of points that define a shape in three dimensions. Thus, it is possible that an entirely different set of structure coordinates could define a similar or identical shape. Moreover, slight variations in the individual coordinates may have little effect on overall shape. In terms of binding pockets, these variations would not be expected to significantly alter the nature of ligands that could associate with those pockets. The term "binding pocket" as used herein refers to a region of the protein that, as a result of its shape, favorably associates with a ligand.

These variations in coordinates may be generated because of mathematical manipulations of the ACC2 structure coordinates. For example, the sets of structure coordinates shown in FIG. 3 could be manipulated by crystallographic permutations of the structure coordinates, fractionalization of the structure coordinates, application of a rotation matrix, integer additions or subtractions to sets of the structure coordinates, inversion of the structure coordinates or any combination of the above.

Alternatively, modifications in the crystal structure due to mutations, additions, substitutions, and/or deletions of amino acids or other changes in any of the components that make up the crystal could also account for variations in structure coordinates. If such variations are within an acceptable standard error as compared to the original coordinates, the resulting three-dimensional shape should be considered to be the same. Thus, for example, a ligand that binds to the active site binding pocket of ACC2 would also be expected to bind to another binding pocket whose structure coordinates defined a shape that fell within the acceptable error.

Various computational methods may be used to determine whether a particular protein or a portion thereof (referred to here as the "target protein"), typically the binding pocket, has a high degree of three-dimensional spatial similarity to another protein (referred to here as the "reference protein") against which the target protein is being compared.

The process of comparing a target protein structure to a reference protein structure may generally be divided into three steps: 1) defining the equivalent residues and/or atoms for the target and reference proteins, 2) performing a fitting operation between the proteins; and 3) analyzing the results. These steps are described in more detail below. All structure comparisons reported herein and the structure comparisons claimed are intended to be based on the particular comparison procedure described below.

Equivalent residues or atoms can be determined based upon an alignment of primary sequences of the proteins, an alignment of their structural domains or as a combination of both. Sequence alignments generally implement the dynamic programming algorithm of Needleman and Wunsch [*J. Mol. Biol.* 48: 442-453, 1970]. For the purpose of this invention the sequence alignment was performed using the publicly available software program MOE (Chemical Computing Group Inc.) package version 2002.3. When using the MOE program, alignment was performed in the sequence editor window using the ALIGN option utilizing the following program parameters: Initial pairwise Build-up: ON, Substitution Matrix: Blosum62, Round Robin: ON, Gap Start: 7, Gap Extend: 1, Iterative Refinement: ON, Build-up: TREE-BASED, Secondary Structure: NONE, Structural Alignment: ENABLED, Gap Start: 1, Gap Extend: 0.1

Once aligned, a rigid body fitting operation is performed where the structure for the target protein is translated and rotated to obtain an optimum fit relative to the structure of the reference protein. The fitting operation uses an algorithm that computes the optimum translation and rotation to be applied to the moving structure, such that the root mean square deviation of the fit over the specified pairs of equivalent atoms is an absolute minimum. For the purpose of fitting operations made herein, the publicly available software program MOE (Chemical Computing Group Inc.) v. 2002.3 was used.

The results from this process are typically reported as an RMSD value between two sets of atoms. The term "root mean square deviation" means the square root of the arithmetic mean of the squares of deviations. It is a way to express the deviation or variation from a trend or object. As used herein, an RMSD value refers to a calculated value based on variations in the atomic coordinates of a target protein from the atomic coordinates of a reference protein or portions of thereof. The structure coordinates for ACC2, provided in FIG. 3, are used as the reference protein in these calculations.

The same set of atoms was used for initial fitting of the structures and for computing root mean square deviation values. For example, if a root mean square deviation (RMSD) between $C\alpha$ atoms of two proteins is needed, the proteins in question should be superposed only on the $C\alpha$ atoms and not on any other set of atoms. Similarly, if an RMSD calculation for all atoms is required, the superposition of two structures should be performed on all atoms.

Based on a review of protein structures deposited in the Protein Databank (PDB), 1OD2 AND 1W2X were identified as having the smallest RMSD values relative to the structure coordinates provided herein for the Acetyl-CoEnzyme A and Biotin active sites, respectively. Table 7A below provides a series of RMSD values that were calculated by the above described process, for the Acetyl-CoEnzyme A binding site using the structure coordinates in FIG. 3 as the reference protein and the structure coordinates from PDB code 1OD2 (*S. cerevisiae* ACC2 carboxyltransferase domain in complex with Acetyl Coenzyme A) as the target protein. Similarly, Table 7B provides a series of RMSD values that were calculated by the above described process, for the biotin competitive inhibitor binding site using the structure coordinates in FIG. 3 as the reference protein and the structure coordinates from PDB code 1W2X (*S. cerevisiae* ACC2 carboxyltransferase domain in complex with CP-640186, Zhang, H., Tweel, B., Li, J. & Tong. L, *Structure* 12:1683 (2004)).

TABLE 7A

| AA RESIDUES USED TO PERFORM RMSD COMPARISON WITH PDB:1OD2 | PORTION OF EACH AA RESIDUE USED TO PERFORM RMSD COMPARISON WITH PDB:1OD2 | RMSD [Å] |
|---|---|---|
| Table 2A (4 Angstrom set) | alpha-carbon atoms[1] | 0.56 |
| | main-chain atoms[1] | 0.58 |
| | all non-hydrogen[2] | 1.10 |
| Table 3A (7 Angstrom set) | alpha-carbon atoms[1] | 0.54 |
| | main-chain atoms[1] | 0.56 |
| | all non-hydrogen[2] | 0.95 |
| Table 4A (10 Angstrom set) | alpha-carbon atoms[1] | 0.57 |
| | main-chain atoms[1] | 0.59 |
| | all non-hydrogen[2] | 0.98 |

TABLE 7A-continued

| AA RESIDUES USED TO PERFORM RMSD COMPARISON WITH PDB:1OD2 | PORTION OF EACH AA RESIDUE USED TO PERFORM RMSD COMPARISON WITH PDB:1OD2 | RMSD [Å] |
|---|---|---|
| 1715-2483 of SEQ. ID No. 1 | alpha-carbon atoms[1] | 1.37 |
| | main-chain atoms[1] | 1.45 |
| | all non-hydrogen[2] | 1.83 |

[1] the RMSD computed between the atoms of all amino acids that are common to both the target and the reference in the aligned and superposed structure. The amino acids need not be identical.
[2] the RMSD computed only between identical amino acids, which are common to both the target and the reference in the aligned and superposed structure.

TABLE 7B

| AA RESIDUES USED TO PERFORM RMSD COMPARISON WITH PDB:1W2X | PORTION OF EACH AA RESIDUE USED TO PERFORM RMSD COMPARISON WITH PDB:1W2X | RMSD [Å] |
|---|---|---|
| Table 2B (4 Angstrom set) | alpha-carbon atoms[1] | 0.69 |
| | main-chain atoms[1] | 0.69 |
| | all non-hydrogen[2] | 1.11 |
| Table 3B (7 Angstrom set) | alpha-carbon atoms[1] | 0.68 |
| | main-chain atoms[1] | 0.72 |
| | all non-hydrogen[2] | 1.09 |
| Table 4B (10 Angstrom set) | alpha-carbon atoms[1] | 0.72 |
| | main-chain atoms[1] | 0.73 |
| | all non-hydrogen[2] | 1.16 |
| 1715-2483 of SEQ. ID No. 1 | alpha-carbon atoms[1] | 1.29 |
| | main-chain atoms[1] | 1.36 |
| | all non-hydrogen[2] | 1.69 |

[1] the RMSD computed between the atoms of all amino acids that are common to both the target and the reference in the aligned and superposed structure. The amino acids need not be identical.
[2] the RMSD computed only between identical amino acids, which are common to both the target and the reference in the aligned and superposed structure.

It is noted that mutants and variants of ACC2, as well as other ACC, are likely to have similar structures despite having different sequences. For example, the binding pockets of these related proteins are likely to have similar contours. Accordingly, it should be recognized that the structure coordinates and binding pocket models provided herein have utility for these other related proteins.

Accordingly, in one embodiment, the invention relates to data, computer readable media comprising data, and uses of the data where the data comprises all or a portion of the structure coordinates shown in FIG. 3 or structure coordinates having a root mean square deviation (RMSD) equal to or less than the RMSD value specified in Columns 3, 4 or 5 of Table 1A and/or Table 1B when compared to the structure coordinates of FIG. 3, the root mean square deviation being calculated such that the portion of amino acid residues specified in Column 2 of Table 1A and Table 1B of each set of structure coordinates are superimposed and the root mean square deviation is based only on those amino acid residues in the structure coordinates that are also present in the portion of the protein specified in Column 1 of Table 1A or Table 1B.

As noted, there are many different ways to express the surface contours of the ACC2 structure other than by using the structure coordinates provided in FIG. 3. Accordingly, it is noted that the present invention is also directed to any data, computer readable media comprising data, and uses of the data where the data defines a computer model for a protein binding pocket, at least a portion of the computer model having a surface contour that has a root mean square deviation equal to or less than a given RMSD value specified in Columns 3, 4 or 5 of Table 1A or Table 1B when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1A or Table 1B (specified in Column 2 of Table 1A or Table 1B) are superimposed according to the RMSD calculation, and (c) the root mean square deviation is calculated based only on those amino acid residues present in both the protein being modeled and the portion of the protein associated with the given RMSD in Table 1A or Table 1B (specified in Column 1 of Table 1A or Table 1B).

5. ACC2 Structure

The present invention is also directed to a three-dimensional crystal structure of ACC2. This crystal structure may be used to identify binding sites, to provide mutants having desirable binding properties, and ultimately, to design, characterize, or identify ligands that interact with ACC2 as well as other structurally similar proteins.

The three-dimensional crystal structure of ACC2 may be generated, as is known in the art, from the structure coordinates shown in FIG. 3 and similar such coordinates.

During the course of structure solution it became evident that the crystals of ACC2 of the present invention contained only one ACC2 molecule in the asymmetric unit, with the other half of the biological dimmer completed by the (x, -y, -z) symmetry-related molecule. The final refined coordinates include amino acid residues 1719-2414 and 2427-2451 (FIG. 3). Structure coordinates are not reported for residues 1715-1718, 2415-2426, and 2452-2483 as well as the C-terminal six His tag. The final coordinate set additionally includes 672 solvent molecules modeled as water, and one acetyl-coenzyme A molecule.

Figure 4:
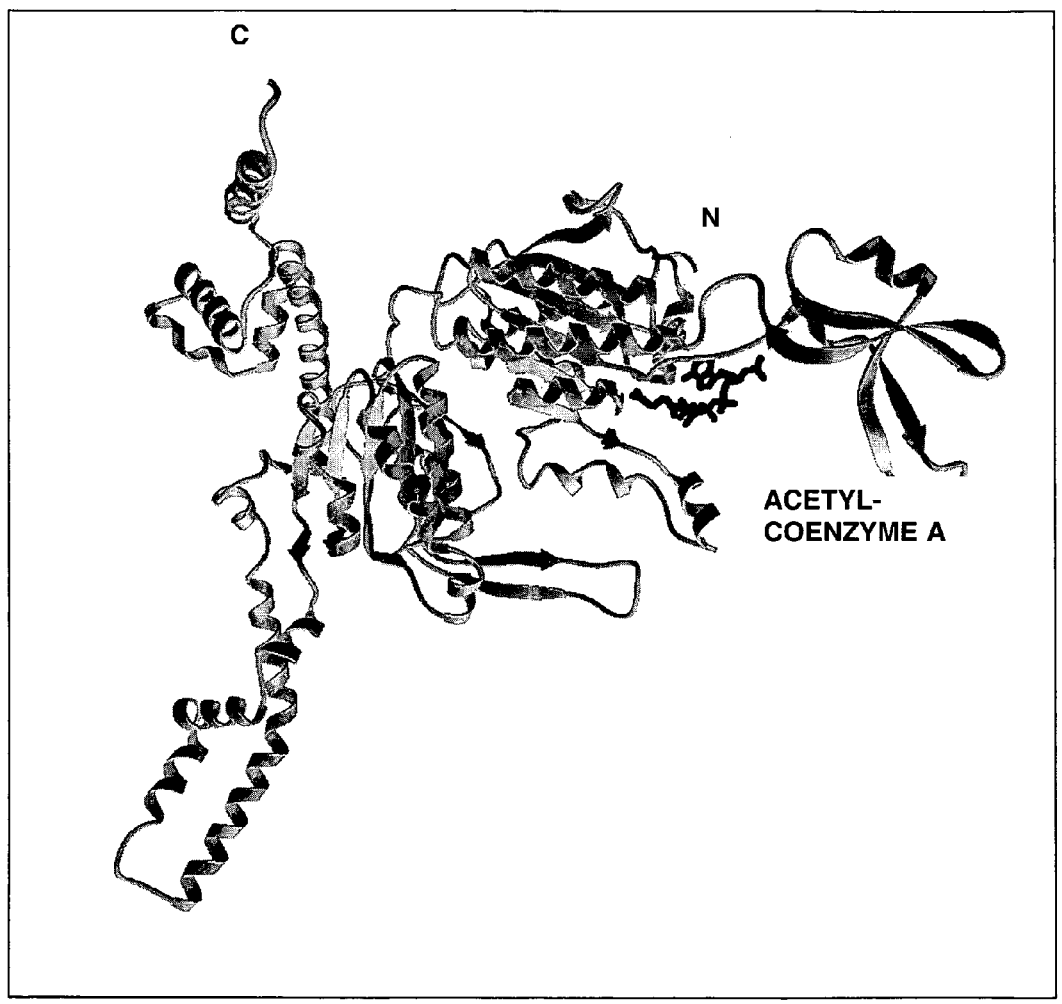
FIG. 4 illustrates a ribbon diagram overview of the structure of ACC2 corresponding to SEQ. ID No. 3, highlighting secondary structural elements of the protein.

FIG. 4 illustrates a ribbon diagram overview of the structure of ACC2, highlighting the secondary structural elements of the protein.

Figure 5:
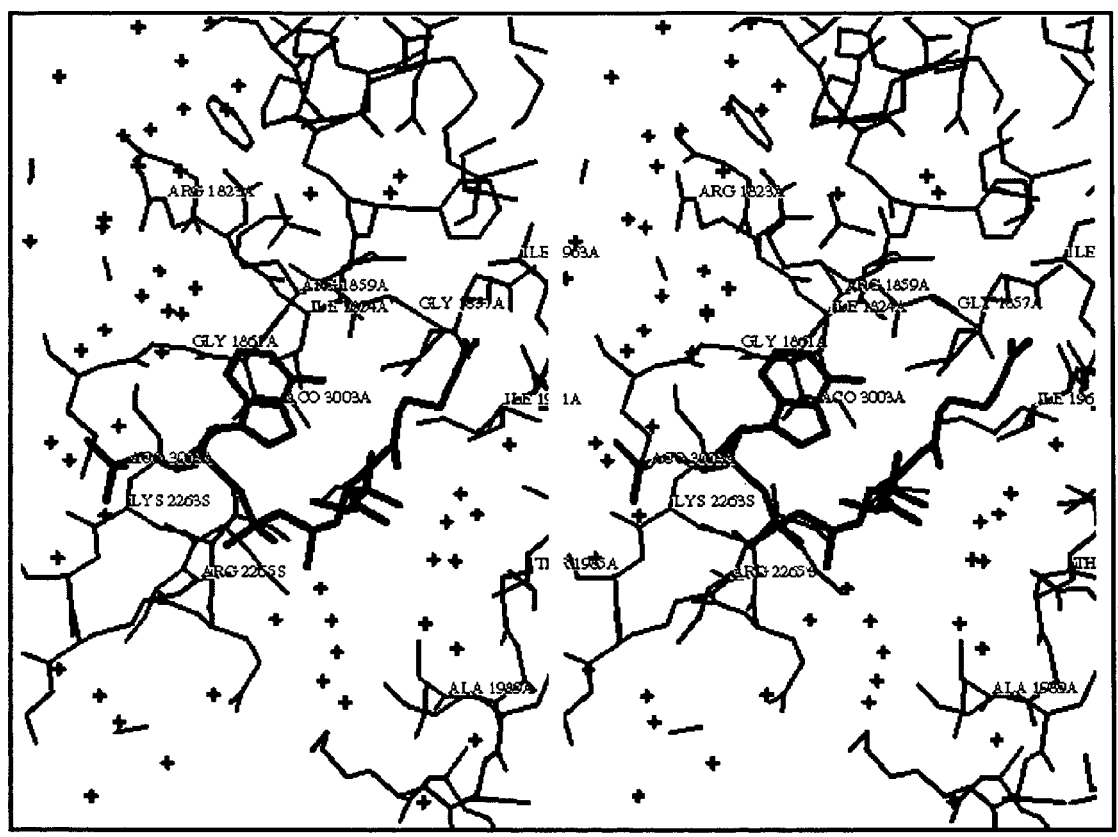
FIG. 5 illustrates the Acetyl-CoEnzyme A binding site of ACC2 based on the determined crystal structure for the molecule in the asymmetric unit corresponding to the coordinates shown in FIG. 3.

FIG. 5 illustrates the acetyl-coenzyme A binding site of human ACC2 based on the determined crystal structure corresponding to the coordinates shown in FIG. 3.

6. ACC2 Active Site and Ligand Interaction

The terms "binding site" or "binding pocket", as used herein, refer to a region of a protein that, as a result of its shape, favorably associates with a ligand or substrate. The term "ACC2-like binding pocket" refers to a portion of a molecule or molecular complex whose shape is sufficiently similar to the ACC2 binding pockets as to bind common ligands. This commonality of shape may be quantitatively defined based on a comparison to a reference point, that reference point being the structure coordinates provided herein. For example, the commonality of shape may be quantitatively defined based on a root mean square deviation (RMSD) from the structure coordinates of the backbone atoms of the amino acids that make up the binding pockets in ACC2 (as set forth in FIG. 3).

The "active site binding pockets" or "active site" of ACC2 refers to the area on the surface of ACC2 where the substrate binds.

FIG. 5 illustrates the acetyl-coenzyme A binding site of ACC2 based on the determined crystal structure for the molecule in the asymmetric unit corresponding to the structure coordinates shown in FIG. 3. The binding site for acetyl-coenzyme A is located at the interface of the biological dimmer between the ACC2 molecule and a symmetry-related molecule (FIG. 5).

The putative biotin binding site of ACCs is a primary target for the design of small molecule inhibitors and is delineated by the binding of the inhibitor CP-640186 to the *S. cerevisiae* ACC2 enzyme (Zhang, H., Tweel, B., Li, J. & Tong. L, *Structure* 12:1683 (2004). This binding site appears well conserved among ACC enzymes and involves residues at the interface of the biological dimer. This biotin binding cleft shows subtle differences in site architecture that may be explored to confer specificity of inhibition.

In resolving the crystal structure of ACC2, Applicants determined that ACC2 amino acids shown in Tables 2A and 2B (above) are encompassed within a 4-Angstrom radius around the ACC2 Acetyl-CoEnzyme A and Biotin active sites, respectively, and therefore are likely close enough to interact with an active site inhibitor of ACC2. Applicants have also determined that the amino acids shown in Tables 3A and 3B (above) are encompassed within a 7-Angstrom radius around the ACC2 Acetyl-CoEnzyme A and Biotin active sites, respectively. Further, the amino acids shown in Tables 4A and 4B (above) are encompassed within a 10-Angstrom radius around the ACC2 Acetyl-CoEnzyme A and Biotin active sites, respectively. Due to their proximity to the active site, the amino acids in the 4, 7, and/or 10 Angstrom sets are preferably conserved in variants of ACC2. While it is desirable to largely conserve these residues, it should be recognized however that variants may also involve varying 1, 2, 3, 4 or more of the residues set forth in Tables 2A, 2B, 3A, 3B, 4A and 4B in order, for example, to evaluate the roles these amino acids play in the binding pocket.

With the knowledge of the ACC2 crystal structure provided herein, Applicants are able to know the contour of an ACC2 binding pocket based on the relative positioning of the 4, 7, and/or 10 Angstroms sets of amino acids. Again, it is noted that it may be desirable to form variants where 1, 2, 3, 4 or more of the residues set forth in Tables 2A, 2B, 3A, 3B, 4A and 4B are varied in order to evaluate the roles these amino acids play in the binding pocket. Accordingly, any set of structure coordinates for a protein from any source shall be considered within the scope of the present invention if the structure coordinates have a root mean square deviation equal to or less than the RMSD value specified in Columns 3, 4 or 5 of Table 1A or Table 1B when compared to the structure coordinates of FIG. 3, the root mean square deviation being calculated such that the portion of amino acid residues specified in Column 2 of Table 1A or Table 1B of each set of structure coordinates are superimposed and the root mean square deviation is based only on those amino acid residues in the structure coordinates that are also present in the portion of the protein specified in Column 1 of Table 1A or Table 1B.

Accordingly, in various embodiments, the invention relates to data, computer readable media comprising data, and uses of the data where the data comprises structure coordinates that have a root mean square deviation equal to or less than the RMSD value specified in Columns 3, 4 or 5 of Table 1A or Table 1B when compared to the structure coordinates of FIG. 3, the root mean square deviation being calculated such that the portion of amino acid residues specified in Column 2 of Table 1A or Table 1B of each set of structure coordinates are superimposed and the root mean square deviation is based only on those amino acid residues in the structure coordinates that are also present in the portion of the protein specified in Column 1 of Table 1A or Table 1B.

As noted above, there are many different ways to express the surface contours of the ACC2 structure other than by using the structure coordinates provided in FIG. 3. Accordingly, it is noted that the present invention is also directed to any data, computer readable media comprising data, and uses of the data where the data defines a computer model for a protein binding pocket, at least a portion of the computer model having a surface contour that has a root mean square deviation equal to or less than a given RMSD value specified in Columns 3, 4 or 5 of Table 1A or Table 1B when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1A or Table 1B (specified in Column 2 of Table 1A or Table 1B) are superimposed according to the RMSD calculation, and (c) the root mean square deviation is calculated based only on those amino acid residues present in both the protein being modeled and the portion of the protein associated with the given RMSD in Table 1A or Table 1B (specified in Column 1 of Table 1A or Table 1B).

It will be readily apparent to those of skill in the art that the numbering of amino acids in other isoforms of ACC2 may be different than that set forth for ACC2. Corresponding amino acids in other isoforms of ACC2 are easily identified by visual inspection of the amino acid sequences or by using commercially available homology software programs, as further described below.

7. System for Displaying the Three Dimensional Structure of ACC2

The present invention is also directed to machine-readable data storage media having data storage material encoded with machine-readable data that comprises structure coordinates for ACC2. The present invention is also directed to a machine readable data storage media having data storage material encoded with machine readable data, which, when read by an appropriate machine, can display a three dimensional representation of a structure of ACC2.

All or a portion of the ACC2 coordinate data shown in FIG. 3, when used in conjunction with a computer programmed with software to translate those coordinates into the three-dimensional structure of ACC2 may be used for a variety of purposes, especially for purposes relating to drug discovery. Software for generating three-dimensional graphical representations are known and commercially available. The ready use of the coordinate data requires that it be stored in a computer-readable format. Thus, in accordance with the present invention, data capable of being displayed as the three-dimensional structure of ACC2 and/or portions thereof and/or their structurally similar variants may be stored in a machine-readable storage medium, which is capable of displaying a graphical three-dimensional representation of the structure.

For example, in various embodiments, a computer is provided for producing a three-dimensional representation of at least an ACC2-like binding pocket, the computer comprising:

machine readable data storage medium comprising a data storage material encoded with machine-readable data, the machine readable data comprising structure coordinates that have a root mean square deviation equal to or less than the RMSD value specified in Columns 3, 4 or 5 of Table 1A or Table 1B when compared to the structure coordinates of FIG. 3, the root mean square deviation being calculated such that the portion of amino acid residues specified in Column 2 of Table 1A or Table 1B of each set of structure coordinates are superimposed and the root mean square deviation is based only on those amino acid residues in the structure coordinates that are also present in the portion of the protein specified in Column 1 of Table 1A or Table 1B;

a working memory for storing instructions for processing the machine-readable data;

a central-processing unit coupled to the working memory and to the machine-readable data storage medium, for processing the machine-readable data into the three-dimensional representation; and an output hardware coupled to the central processing unit, for receiving the three dimensional representation.

Another embodiment of this invention provides a machine-readable data storage medium, comprising a data storage material encoded with machine readable data which, when used by a machine programmed with instructions for using said data, displays a graphical three-dimensional representation comprising ACC2 or a portion or variant thereof.

In various variations, the machine readable data comprises data for representing a protein based on structure coordinates where the structure coordinates have a root mean square deviation equal to or less than the RMSD value specified in Columns 3, 4 or 5 of Table 1A or Table 1B when compared to the structure coordinates of FIG. 3, the root mean square deviation being calculated such that the portion of amino acid residues specified in Column 2 of Table 1A or Table 1B of each set of structure coordinates are superimposed and the root mean square deviation is based only on those amino acid residues in the structure coordinates that are also present in the portion of the protein specified in Column 1 of Table 1A or Table 1B.

According to another embodiment, the machine-readable data storage medium comprises a data storage material encoded with a first set of machine readable data which comprises the Fourier transform of structure coordinates that have a root mean square deviation equal to or less than the RMSD value specified in Columns 3, 4 or 5 of Table 1A or Table 1B when compared to the structure coordinates of FIG. 3, the root mean square deviation being calculated such that the portion of amino acid residues specified in Column 2 of Table 1A or Table 1B of each set of structure coordinates are superimposed and the root mean square deviation is based only on those amino acid residues in the structure coordinates that are also present in the portion of the protein specified in Column 1 of Table 1A or Table 1B, and which, when using a machine programmed with instructions for using said data, can be combined with a second set of machine readable data comprising the X-ray diffraction pattern of another molecule or molecular complex to determine at least a portion of the structure coordinates corresponding to the second set of machine readable data. For example, the Fourier transform of the structure coordinates set forth in FIG. 3 may be used to determine at least a portion of the structure coordinates of other ACC2-like enzymes, and isoforms of ACC2.

Optionally, a computer system is provided in combination with the machine-readable data storage medium provided herein. In one embodiment, the computer system comprises a working memory for storing instructions for processing the machine-readable data; a processing unit coupled to the working memory and to the machine-readable data storage medium, for processing the machine-readable data into the three-dimensional representation; and an output hardware coupled to the processing unit, for receiving the three-dimensional representation.

Figure 6:
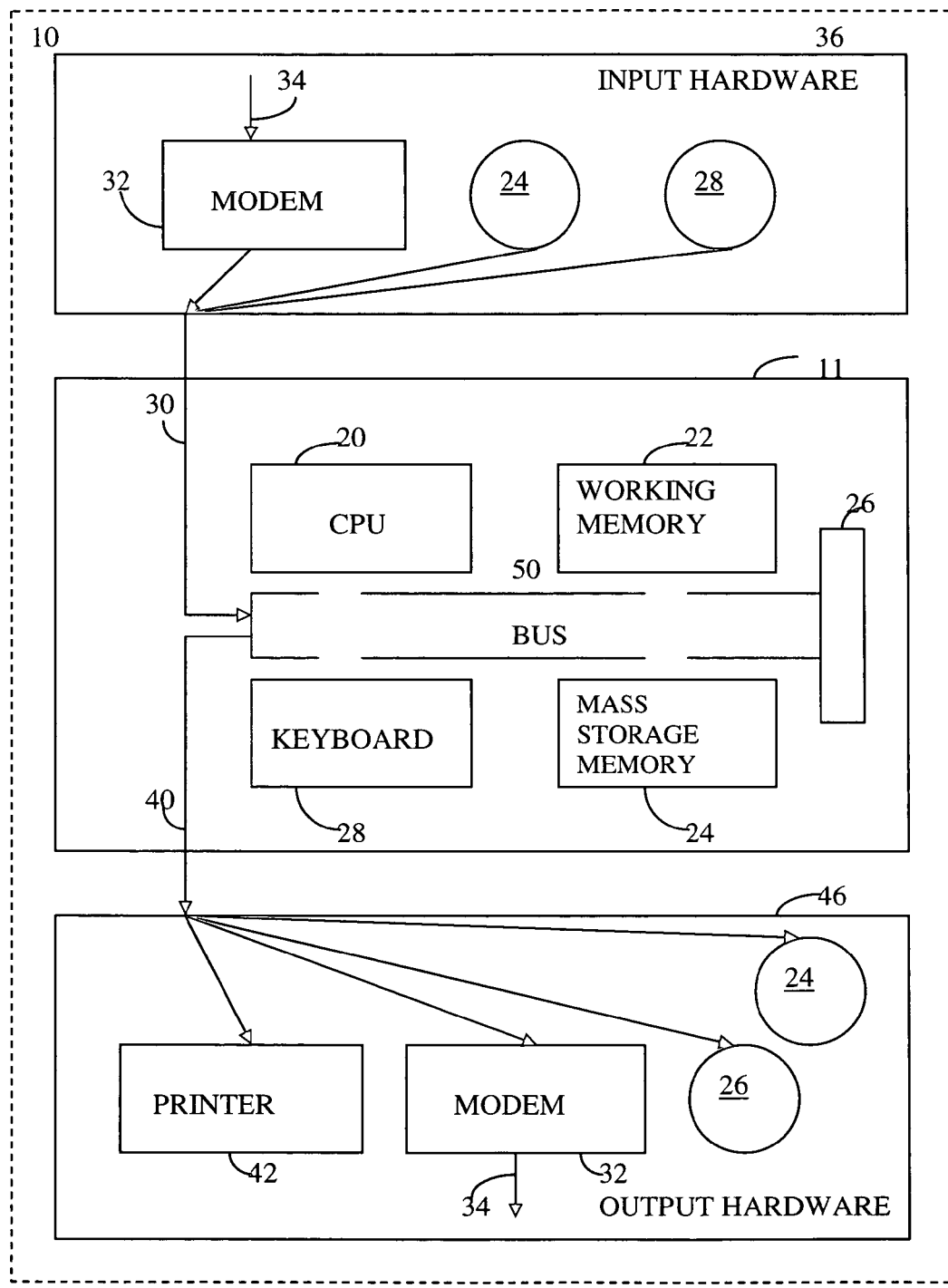
FIG. 6 illustrates a system that may be used to carry out instructions for displaying a crystal structure of ACC2 encoded on a storage medium.

FIG. 6 illustrates an example of a computer system that may be used in combination with storage media according to the present invention. As illustrated, the computer system 10 includes a computer 11 comprising a central processing unit ("CPU") 20, a working memory 22 which may be, e.g., RAM (random-access memory) or "core" memory, mass storage memory 24 (such as one or more disk drives or CD-ROM drives), one or more cathode-ray tube ("CRT") display terminals 26, one or more keyboards 28, one or more input lines 30, and one or more output lines 40, all of which are interconnected by a conventional bi-directional system bus 50.

Input hardware 36, coupled to computer 11 by input lines 30, may be implemented in a variety of ways. For example, machine-readable data of this invention may be inputted via the use of a modem or modems 32 connected by a telephone line or dedicated data line 34. Alternatively or additionally, the input hardware 36 may comprise CD-ROM drives or disk drives 24. In conjunction with display terminal 26, keyboard 28 may also be used as an input device.

Conventional devices, coupled to computer 11 by output lines 40, may similarly implement output hardware 46. By way of example, output hardware 46 may include CRT display terminal 26 for displaying a graphical representation of a binding pocket of this invention using a program such as MOE as described herein. Output hardware might also include a printer 42, so that hard copy output may be produced, or a disk drive 24, to store system output for later use.

In operation, CPU 20 coordinates the use of the various input and output devices 36, 46; coordinates data accesses from mass storage 24 and accesses to and from working memory 22; and determines the sequence of data processing steps. A number of programs may be used to process the machine-readable data of this invention. Such programs are discussed in reference to using the three dimensional structure of ACC2 described herein.

The storage medium encoded with machine-readable data according to the present invention can be any conventional data storage device known in the art. For example, the storage medium can be a conventional floppy diskette or hard disk. The storage medium can also be an optically readable data storage medium, such as a CD-ROM or a DVD-ROM, or a rewritable medium such as a magneto-optical disk that is optically readable and magneto-optically writable.

8. Uses of the Three Dimensional Structure of ACC2

The three-dimensional crystal structure of the present invention may be used to identify ACC2 binding sites, be used as a molecular replacement model to solve the structure of unknown crystallized proteins, to design mutants having desirable binding properties, and ultimately, to design, characterize, and identify entities capable of interacting with ACC2 and other structurally similar proteins as well as other uses that would be recognized by one of ordinary skill in the art. Such entities may be chemical entities or proteins. The term "chemical entity," as used herein, refers to chemical compounds, complexes of at least two chemical compounds, and fragments of such compounds.

The ACC2 structure coordinates provided herein are useful for screening and identifying drugs that inhibit ACC2 and other structurally similar proteins. For example, the structure encoded by the data may be computationally evaluated for its ability to associate with putative substrates or ligands. Such compounds that associate with ACC2 may inhibit ACC2, and are potential drug candidates. Additionally or alternatively, the structure encoded by the data may be displayed in a graphical three-dimensional representation on a computer screen. This allows visual inspection of the structure, as well as visual inspection of the structure's association with the compounds.

Thus, according to another embodiment of the present invention, a method is provided for evaluating the potential of an entity to associate with ACC2 or a fragment or variant thereof by using all or a portion of the structure coordinates provided in FIG. 3 or functional equivalents thereof. A method is also provided for evaluating the potential of an entity to associate with ACC2 or a fragment or variant thereof by using structure coordinates similar to all or a portion of the structure coordinates provided in FIG. 3 or functional equivalents thereof.

The method may optionally comprise the steps of: creating a computer model of all or a portion of a protein structure (e.g., a binding pocket) using structure coordinates according to the present invention; performing a fitting operation between the entity and the computer model; and analyzing the results of the fitting operation to quantify the association between the entity and the model. The portion of the protein structure used optionally comprises all of the amino acids listed in Tables 2A, 2B, 3A, 3B, 4A and 4B that are present in the structure coordinates being used.

It is noted that the computer model may not necessarily directly use the structure coordinates. Rather, a computer model can be formed that defines a surface contour that is the same or similar to the surface contour defined by the structure coordinates.

The structure coordinates provided herein can also be utilized in a method for identifying a ligand (e.g., entities capable of associating with a protein) of a protein comprising an ACC2-like binding pocket. One embodiment of the method comprises: using all or a portion of the structure coordinates provided herein to generate a three-dimensional structure of an ACC2-like binding pocket; employing the three-dimensional structure to design or select a potential ligand; synthesizing the potential ligand; and contacting the synthesized potential ligand with a protein comprising an ACC2-like binding pocket to determine the ability of the potential ligand to interact with the protein. According to this method, the structure coordinates used may have a root mean square deviation equal to or less than the RMSD values specified in Columns 3, 4 or 5 of Table 1A or Table 1B when compared to the structure coordinates of FIG. 3 according to the RMSD calculation method set forth herein, provided that the portion of amino acid residues specified in Column 2 of Table 1A or Table 1B of each set of structure coordinates are superimposed and the root mean square deviation is calculated based only on those amino acid residues in the structure coordinates that are also present in the portion of the protein specified in Column 1 of Table 1A or Table 1B. The portion of the protein structure used optionally comprises all of the amino acids listed in Tables 2A, 2B, 3A, 3B, 4A and/or 4B that are present.

As noted previously, the three-dimensional structure of an ACC2-like binding pocket need not be generated directly from structure coordinates. Rather, a computer model can be formed that defines a surface contour that is the same or similar to the surface contour defined by the structure coordinates.

A method is also provided for evaluating the ability of an entity, such as a compound or a protein to associate with an ACC2-like binding pocket, the method comprising: constructing a computer model of a binding pocket defined by structure coordinates that have a root mean square deviation equal to or less than the RMSD value specified in Columns 3, 4 or 5 of Table 1A or Table 1B when compared to the structure coordinates of FIG. 3, the root mean square deviation being calculated such that the portion of amino acid residues specified in Column 2 of Table 1A or Table 1B of each set of structure coordinates are superimposed and the root mean square deviation is based only on those amino acid residues in the structure coordinates that are also present in the portion of the protein specified in Column 1 of Table 1A or Table 1B; selecting an entity to be evaluated by a method selected from the group consisting of (i) assembling molecular fragments into the entity, (ii) selecting an entity from a small molecule database, (iii) de novo ligand design of the entity, and (iv) modifying a known ligand for ACC2, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the binding pocket.

The computer model of a binding pocket used in this embodiment need not be generated directly from structure coordinates. Rather, a computer model can be formed that defines a surface contour that is the same or similar to the surface contour defined by the structure coordinates.

Also according to the method, the method may further include synthesizing the entity and contacting a protein having an ACC2-like binding pocket with the synthesized entity.

With the structure provided herein, the present invention for the first time permits the use of molecular design techniques to identify, select or design potential inhibitors of ACC2, based on the structure of an ACC2-like binding pocket. Such a predictive model is valuable in light of the high costs associated with the preparation and testing of the many diverse compounds that may possibly bind to the ACC2 protein.

According to this invention, a potential ACC2 inhibitor may now be evaluated for its ability to bind an ACC2-like binding pocket prior to its actual synthesis and testing. If a proposed entity is predicted to have insufficient interaction or association with the binding pocket, preparation and testing of the entity can be obviated. However, if the computer modeling indicates a strong interaction, the entity may then be obtained and tested for its ability to bind.

A potential inhibitor of an ACC2-like binding pocket may be computationally evaluated using a series of steps in which chemical entities or fragments are screened and selected for their ability to associate with the ACC2-like binding pockets.

One skilled in the art may use one of several methods to screen entities (whether chemical or protein) for their ability to associate with an ACC2-like binding pocket. This process may begin by visual inspection of, for example, an ACC2-like binding pocket on a computer screen based on the ACC2 structure coordinates in FIG. 3 or other coordinates which define a similar shape generated from the machine-readable storage medium. Selected fragments or chemical entities may then be positioned in a variety of orientations, or docked, within that binding pocket as defined above. Docking may be accomplished using software such as Quanta and Sybyl, followed by energy minimization and molecular dynamics with standard molecular mechanics force fields, such as CHARMM and AMBER.

Specialized computer programs may also assist in the process of selecting entities. These include: GRID (P. J. Goodford, "A Computational Procedure for Determining Energetically Favorable Binding Sites on Biologically Important Macromolecules", J. Med. Chem., 28, pp. 849-857 (1985)) available from Oxford University, Oxford, UK; MCSS (A. Miranker et al., "Functionality Maps of Binding Sites: A Multiple Copy Simultaneous Search Method." Proteins: Structure, Function and Genetics, 11, pp. 29-34 (1991)) available from Molecular Simulations, San Diego, Calif.; AUTODOCK (D. S. Goodsell et al., "Automated Docking of Substrates to Proteins by Simulated Annealing", Proteins: Structure, Function, and Genetics, 8, pp. 195-202 (1990)) available from Scripps Research Institute, La Jolla, Calif.; and DOCK (I. D. Kuntz et al., "A Geometric Approach to Macromolecule-Ligand Interactions", J. Mol. Biol., 161, pp. 269-288 (1982)) available from University of California, San Francisco, Calif.

Once suitable entities have been selected, they can be designed or assembled. Assembly may be preceded by visual inspection of the relationship of the fragments to each other on the three-dimensional image displayed on a computer screen in relation to the structure coordinates of ACC2. This may then be followed by manual model building using software such as MOE, QUANTA or Sybyl [Tripos Associates, St. Louis, Mo.].

Useful programs to aid one of skill in the art in connecting the individual chemical entities or fragments include: CAVEAT (P. A. Bartlett et al, "CAVEAT: A Program to Facilitate the Structure-Derived Design of Biologically Active Molecules", in "Molecular Recognition in Chemical and Biological Problems", Special Pub., Royal Chem. Soc., 78, pp. 182-196 (1989); G. Lauri and P. A. Bartlett, "CAVEAT: a Program to Facilitate the Design of Organic Molecules", J. Comput. Aided Mol. Des., 8, pp. 51-66 (1994)) available from the University of California, Berkeley, Calif.; 3D Database systems such as ISIS (MDL Information Systems, San Leandro, Calif.) reviewed in Y. C. Martin, "3D Database Searching in Drug Design", J. Med. Chem., 35, pp. 2145-2154 (1992); and HOOK (M. B. Eisen et al, "HOOK: A Program for Finding Novel Molecular Architectures that Satisfy the Chemical and Steric Requirements of a Macromolecule Binding Site", Proteins: Struct., Funct., Genet., 19, pp. 199-221 (1994)) available from Molecular Simulations, San Diego, Calif.

Instead of proceeding to build an inhibitor of an ACC2-like binding pocket in a step-wise fashion one fragment or entity at a time as described above, inhibitory or other ACC2 binding compounds may be designed as a whole or "de novo" using either an empty binding site or optionally including some portion(s) of a known inhibitor(s). There are many de novo ligand design methods including: LUDI (H.-J. Bohm, "The Computer Program LUDI: A New Method for the De Novo Design of Enzyme Inhibitors", J. Comp. Aid. Molec. Design, 6, pp. 61-78 (1992)) available from Molecular Simulations Incorporated, San Diego, Calif.; LEGEND (Y. Nishibata et al., Tetrahedron, 47, p. 8985 (1991)) available from Molecular Simulations Incorporated, San Diego, Calif.; LEAPFROG available from Tripos Associates, St. Louis, Mo.; and SPROUT (V. Gillet et al, "SPROUT: A Program for Structure Generation)", J. Comput. Aided Mol. Design, 7, pp. 127-153 (1993)) available from the University of Leeds, UK.

Other molecular modeling techniques may also be employed in accordance with this invention (see, e.g., Cohen et al., "Molecular Modeling Software and Methods for Medicinal Chemistry, J. Med. Chem., 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modern Methods in Computer-Aided Drug Design", in Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", Curr. Opin. Struct. Biology, 4, pp. 777-781 (1994)).

Once an entity has been designed or selected, for example, by the above methods, the efficiency with which that entity may bind to an ACC2 binding pocket may be tested and optimized by computational evaluation. For example, an effective ACC2 binding pocket inhibitor preferably demonstrates a relatively small difference in energy between its bound and free states (i.e., a small deformation energy of binding). Thus, the most efficient ACC2 binding pocket inhibitors should preferably be designed with deformation energy of binding of not greater than about 10 kcal/mole, and more preferably, not greater than 7 kcal/mole. ACC2 binding pocket inhibitors may interact with the binding pocket in more than one of multiple conformations that are similar in overall binding energy. In those cases, the deformation energy of binding is taken to be the difference between the energy of the free entity and the average energy of the conformations observed when the inhibitor binds to the protein.

An entity designed or selected as binding to an ACC2 binding pocket may be further computationally optimized so that in its bound state it would preferably lack repulsive electrostatic interaction with the target enzyme and with the surrounding water molecules. Such non-complementary electrostatic interactions include repulsive charge-charge, dipole-dipole and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. COPYRGT. 1995); AMBER, version 4.1 (P. A. Kollman, University of California at San Francisco, COPYRGT 1995); QUANTA/CHARMM (Molecular Simulations, Inc., San Diego, Calif. COPYRGT. 1995); Insight II/Discover (Molecular Simulations, Inc., San Diego, Calif. COPYRGT. 1995); DelPhi (Molecular Simulations, Inc., San Diego, Calif. COPYRGT. 1995); and AMSOL (Quantum Chemistry Program Exchange, Indiana University). These programs may be implemented, for instance, using a Silicon Graphics workstation such as an Indigo.sup.2 with "IMPACT" graphics. Other hardware systems and software packages will be known to those skilled in the art.

Another approach provided by this invention, is the computational screening of small molecule databases for chemical entities or compounds that can bind in whole, or in part, to an ACC2 binding pocket. In this screening, the quality of fit of such entities to the binding site may be judged either by shape complementarities or by estimated interaction energy [E. C. Meng et al., J. Comp. Chem., 13, 505-524 (1992)].

According to another embodiment, the invention provides compounds that associate with an ACC2-like binding pocket produced or identified by various methods set forth above.

The structure coordinates set forth in FIG. 3 can also be used to aid in obtaining structural information about another crystallized molecule or molecular complex. This may be achieved by any of a number of well-known techniques, including molecular replacement.

For example, a method is also provided for utilizing molecular replacement to obtain structural information about a protein whose structure is unknown comprising the steps of: generating an X-ray diffraction pattern of a crystal of the protein whose structure is unknown; generating a three-dimensional electron density map of the protein whose structure is unknown from the X-ray diffraction pattern by using at least a portion of the structure coordinates set forth in FIG. 3 as a molecular replacement model.

By using molecular replacement, all or part of the structure coordinates of the ACC2 provided by this invention (and set forth in FIG. 3) can be used to determine the structure of another crystallized molecule or molecular complex more quickly and efficiently than attempting an ab initio structure determination. One particular use includes use with other structurally similar proteins. Molecular replacement provides an accurate estimation of the phases for an unknown structure. Phases are a factor in equations used to solve crystal structures that cannot be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of ACC2 according to FIG. 3 within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex [E. Lattman, "Use of the Rotation and Translation Functions", in Meth. Enzymol., 115, pp. 55-77 (1985); M. G. Rossmann, ed., "The Molecular Replacement Method", Int. Sci. Rev. Ser., No. 13, Gordon & Breach, New York (1972)].

The structure of any portion of any crystallized molecule or molecular complex that is sufficiently homologous to any portion of ACC2 can be resolved by this method.

In one embodiment, the method of molecular replacement is utilized to obtain structural information about the present invention and any other ACC2-like molecule. The structure coordinates of ACC2, as provided by this invention, are particularly useful in solving the structure of other isoforms of ACC2 or ACC2 complexes.

The structure coordinates of ACC2 as provided by this invention are useful in solving the structure of ACC2 variants that have amino acid substitutions, additions and/or deletions (referred to collectively as "ACC2 mutants", as compared to naturally occurring ACC2). These ACC2 mutants may optionally be crystallized in co-complex with a ligand, such as an inhibitor, substrate analogue or a suicide substrate. The crystal structures of a series of such complexes may then be solved by molecular replacement and compared with that of ACC2. Potential sites for modification within the various binding sites of the enzyme may thus be identified. This information provides an additional tool for determining the most efficient binding interactions such as, for example, increased hydrophobic interactions, between ACC2 and a ligand. It is noted that the ligand may be the protein's natural ligand or may be a potential agonist or antagonist of a protein.

All of the complexes referred to above may be studied using well-known X-ray diffraction techniques and may be refined versus 1.5-3 Å resolution X-ray data to an R value of about 0.22 or less using computer software, such as X-PLOR [Yale University, COPYRIGHT. 1992, distributed by Molecular Simulations, Inc.; see, e.g., Blundell & Johnson, supra; Meth. Enzymol., Vol. 114 & 115, H. W. Wyckoff et al., eds., Academic Press (1985)]. This information may thus be used to optimize known ACC2 inhibitors, and more importantly, to design new ACC2 inhibitors.

The structure coordinates described above may also be used to derive the dihedral angles, phi and psi, that define the conformation of the amino acids in the protein backbone. As will be understood by those skilled in the art, the $phi_n$ angle refers to the rotation around the bond between the alpha-carbon and the nitrogen, and the $psi_n$ angle refers to the rotation around the bond between the carbonyl carbon and the alpha-carbon. The subscript "n" identifies the amino acid whose conformation is being described [for a general reference, see Blundell and Johnson, Protein Crystallography, Academic Press, London, 1976].

9. Uses of the Crystal and Diffraction Pattern of ACC2

Crystals, crystallization conditions and the diffraction pattern of ACC2 that can be generated from the crystals also have a range of uses. One particular use relates to screening entities that are not known ligands of ACC2 for their ability to bind to ACC2. For example, with the availability of crystallization conditions, crystals and diffraction patterns of ACC2 provided according to the present invention, it is possible to take a crystal of ACC2; expose the crystal to one or more entities that may be a ligand of ACC2; and determine whether a ligand/ACC2 complex is formed. The crystals of ACC2 may be exposed to potential ligands by various methods, including but not limited to, soaking a crystal in a solution of one or more potential ligands or co-crystallizing ACC2 in the presence of one or more potential ligands. Given the structure coordinates provided herein, once a ligand complex is formed, the structure coordinates can be used as a model in molecular replacement in order to determine the structure of the ligand complex.

Once one or more ligands are identified, structural information from the ligand/ACC2 complex(es) may be used to design new ligands that bind tighter, bind more specifically, have better biological activity or have better safety profiles than known ligands.

In one embodiment, a method is provided for identifying a ligand that binds to ACC2 comprising: (a) attempting to crystallize a protein that comprises a sequence wherein at least a portion of the sequence has 55%, 65%, 75%, 85%, 90%, 95%, 97%, 99% or greater identity with SEQ. ID No. 3 in the presence of one or more entities; (b) if crystals of the protein are obtained in step (a), obtaining an X-ray diffraction pattern of the protein crystal; and (c) determining whether a ligand/protein complex was formed by comparing an X-ray diffraction pattern of a crystal of the protein formed in the absence of the one or more entities to the crystal formed in the presence of the one or more entities.

In another embodiment, a method is provided for identifying a ligand that binds to ACC2 comprising: soaking a crystal of a protein wherein at least a portion of the protein has 55%, 65%, 75%, 85%, 90%, 95%, 97%, 99% or greater identity with SEQ. ID No. 3 with one or more entities; determining whether a ligand/protein complex was formed by comparing an X-ray diffraction pattern of a crystal of the protein that has not been soaked with the one or more entities to the crystal that has been soaked with the one or more entities.

Optionally, the method may further comprise converting the diffraction patterns into electron density maps using phases of the protein crystal and comparing the electron density maps.

Libraries of "shape-diverse" compounds may optionally be used to allow direct identification of the ligand-receptor complex even when the ligand is exposed as part of a mixture. According to this variation, the need for time-consuming de-convolution of a hit from the mixture is avoided. More specifically, the calculated electron density function reveals the binding event, identifies the bound compound and provides a detailed 3-D structure of the ligand-receptor complex. Once a hit is found, one may optionally also screen a number of analogs or derivatives of the hit for tighter binding or better biological activity by traditional screening methods. The hit and information about the structure of the target may also be used to develop analogs or derivatives with tighter binding or better biological activity. It is noted that the ligand-ACC2 complex may optionally be exposed to additional iterations of potential ligands so that two or more hits can be linked together to make a more potent ligand. Screening for potential ligands by co-crystallization and/or soaking is further described in U.S. Pat. No. 6,297,021, which is incorporated herein by reference.

EXAMPLES

Example 1

Expression and Purification of ACC2

This example describes cloning, expression and purification of ACC2. It should be noted that a variety of other expression systems and hosts are also suitable for the expression of ACC2, as would be readily appreciated by one of skill in the art.

The portion of the gene encoding residues 1715-2483 (from SEQ. ID No. 1), which corresponds to the catalytic domain of human ACC2, was cloned into a modified pFast-Bac1 vector at the RsrII and XbaI sites. Expression from this vector produced the recombinant ACC2 catalytic domain with a 6×-histidine tag at the C-terminus. Recombinant baculovirus genomic DNAs incorporating the ACC2 catalytic domain cDNA sequences were generated by transposition using the Bac-to-Bac system (Invitrogen). Infectious viral particles were obtained by transfection of a 2 ml adherent culture of Spodoptera frugiperda Sf9 insect cells with the recombinant viral genomic DNA. Growth in ESF 921 protein free medium (Expression Systems) was for 3 days at 27° C. The resulting Passage 0 viral supernatant was used to obtain Passage 1 high titer viral stock (HTS) by infection of a 30 ml adherent culture of Spodoptera frugiperda Sf9 insect cells grown under similar conditions. 10 ml of Passage 1 HTS was used in turn to infect a 300 ml suspension culture of Spodoptera frugiperda Sf9 insect cells in order to generate Passage 2 HTS.

Passage 2 HTS was used to infect a 6-liter culture of Spodoptera frugiperda Sf9 insect cells (at a density of approx. $3 \times 10^6$ cells/ml) in shake flasks grown in ESF-921 serum-free medium at a multiplicity of infection (moi) of approximately 8 (empirical value based on usual HTS viral counts). Cell growth/infection proceeded for three days after which time the cells were pelleted by centrifugation and the cell pellet stored at −80° C. until required. Frozen cell pellets from such 6-liter cultures were removed from the −80° C. freezer and each suspended in 150 ml of Lysis Buffer (25 mM Tris-HCl, pH 7.9, 1 M NaCl, 20 mM imidazole, 0.25 mM TCEP, and 2 'Complete-EDTA' Roche Protease Inhibitor tablets). The suspensions were homogenized at 4° C. followed by centrifugation at 16,000 rpm for 30 minutes. To each supernatant were added 8 ml of a 50% slurry of ProBond (InVitrogen) resin that had been equilibrated in Lysis Buffer without protease inhibitors. The suspensions were mixed for 90 min followed by centrifugation at 640 g for 5 min. The supernatants were discarded and the resin pellets washed three times with Lysis Buffer without protease inhibitors. Each resin sample was transferred to an OMNI chromatography column (10 cm×1.5 cm diameter) at 4° C. and washed with 1 liter of 25 mM Tris-HCl, pH 7.9, 1 M NaCl, 0.25 mM TCEP and 20 mM imidazole. Target elution was effected by the addition of 25 mM Tris-HCl, pH 8.8, 5 mM NaCl, 200 mM imidazole-HCl, pH 7.9, 0.25 mM TCEP. The eluates were pooled (the yield at this stage was 175 mg total protein in 50 ml) and further purified through Mono Q chromatography in 25 mM This pH 8.5 and gradient NaCl. The protein peak was concentrated and buffer-adjusted to 25 mM Tris-HCl buffer, pH 8.5, 50 mM NaCl, 1 mM Benzamidine. The purified ACC2 was concentrated to 110 mg/ml with a total volume of 1.5 ml (165 mg purified ACC2). The purified protein had the correct molecular mass as determined by Mass Spectrograph (MS) analysis (86.482 KDa expected and 86.518 (with one acetylation) observed), was dimer by analytical size-exclusion chromatography (SEC) and exhibited a major band by both isoelectric focusing (IEF) and by sodium-dodecyl-sulfate polyacrylamide gel electrophoresis (SDS-PAGE) analyses.

Example 2

Crystallization of ACC2

This example describes the crystallization of ACC2. It is noted that the precise crystallization conditions used may be further varied, for example by performing a fine screen based on these crystallization conditions.

ACC2 protein samples (corresponding to SEQ. ID No. 3) were incubated with 5 mM Acetyl-CoA before setting crystallization trials. Crystals were obtained after an extensive and broad screen of conditions, followed by optimization. Diffraction quality crystals were grown in 100 nl sitting droplets using the vapor diffusion method. 50 nl comprising the ACC2-Acetyl-CoA complex (25 mg/ml) was mixed with 50 nL from a reservoir solution (100 µl) comprising: 5% PEGMME 5000; and 0.1M MES buffer pH=6.1. The resulting solution was incubated over a period of 5-6 weeks at 4° C. Crystals typically appeared after 5-7 days and grew to a maximum size within 4-6 weeks. Single crystals were transferred, briefly, into a cryoprotecting solution containing the reservoir solution supplemented with 25% v/v ethylene glycol. Crystals were then flash frozen by immersion in liquid nitrogen and then stored under liquid nitrogen. A crystal of the ACC2-Acetyl CoA complex produced as described is illustrated in FIG. 2.

While the present invention is disclosed with reference to certain embodiments and examples detailed above, it is to be understood that these embodiments and examples are intended to be illustrative rather than limiting, as it is contemplated that modifications will readily occur to those skilled in the art, which modifications are intended to be within the scope of the invention and the appended claims. All patents, patent applications, papers, and books cited in this application are incorporated herein in their entirety.

What is claimed is:

1. A composition comprising a protein-ligand complex in crystalline form wherein the protein of the complex consists of SEQ ID NO:3, wherein said protein is in complex with acetyl CoA, and wherein the protein crystal has a crystal lattice in a C222₁ space group and unit cell dimensions, +/−5%, of a=112.181 Å, b=117.698 Å and c=144.754 Å, α=β=γ=90°.

2. The composition according to claim 1 wherein the protein crystal diffracts X-rays for a determination of structure coordinates to a resolution of a number equal to or greater than 3.0 Angstroms.

3. A method for forming a crystal of a protein comprising:
forming a crystallization volume comprising: a precipitant solution and a protein that consists of SEQ ID NO:3, wherein said protein is in complex with acetyl CoA, and wherein the protein crystal has a crystal lattice in a C222₁ space group and unit cell dimensions, +/−5%, of a=112.181 Å, b=117.698 Å and c=144.754 Å, α=β=γ=90°; and
storing the crystallization volume under conditions suitable for crystal formation of the protein.

4. A method according to claim 3 wherein the protein crystal that is formed diffracts X-rays for a determination of structure coordinates to a resolution of a number equal to or greater than 3.0 Angstroms.

5. The method according to claim 3, further comprising diffracting the protein crystal that is formed to produce a series of diffraction patterns and solving the structure of the protein from the diffraction patterns.

6. An isolated non-crystalline protein consisting of amino acids 1715-2483 of SEQ ID NO:1.

7. A non-crystalline protein consisting of SEQ ID NO:3.

* * * * *

SEQUENCE LISTING

<160> NUMBER OF SEQ ID NOS: 3

<210> SEQ ID NO 1
<211> LENGTH: 2483
<212> TYPE: PRT
<213> ORGANISM: Homo sapien

```
<220> FEATURE:
<221> NAME/KEY: MISC_FEATURE
<222> LOCATION: (1)..(2483)
<223> OTHER INFORMATION: Amino acid sequence for full-length human wild
      type ACC2

<400> SEQUENCE: 1

Met Val Leu Leu Leu Cys Leu Ser Cys Leu Ile Phe Ser Cys Leu Thr
1               5                   10                  15

Phe Ser Trp Leu Lys Ile Trp Glu Lys Met Thr Asp Ser Lys Pro Ile
            20                  25                  30

Thr Lys Ser Lys Ser Glu Ala Asn Leu Ile Pro Ser Gln Glu Pro Phe
        35                  40                  45

Pro Ala Ser Asp Asn Ser Gly Glu Thr Pro Gln Arg Asn Gly Glu Gly
    50                  55                  60

His Thr Leu His Lys Asp Thr Gln Pro Gly Arg Ala Gln Pro Pro Thr
65                  70                  75                  80

Lys Ala Gln Arg Ser Gly Arg Arg Asn Ser Leu Pro Pro Ser Arg
                85                  90                  95

Gln Lys Pro Pro Arg Asn Pro Leu Ser Ser Ser Asp Ala Ala Pro Ser
                100                 105                 110

Pro Glu Leu Gln Ala Asn Gly Thr Gly Thr Gln Gly Leu Glu Ala Thr
            115                 120                 125

Asp Thr Asn Gly Leu Ser Ser Ser Ala Arg Pro Gln Gly Ser Lys Leu
    130                 135                 140

Val Pro Ser Lys Glu Asp Lys Lys Gln Ala Asn Ile Lys Arg Gln Leu
145                 150                 155                 160

Met Thr Asn Phe Ile Leu Gly Ser Phe Asp Asp Tyr Ser Ser Asp Glu
                165                 170                 175

Asp Ser Val Ala Gly Ser Ser Arg Glu Ser Thr Arg Lys Gly Ser Arg
                180                 185                 190

Ala Ser Leu Gly Ala Leu Ser Leu Glu Ala Tyr Leu Thr Thr Gly Glu
            195                 200                 205

Ala Glu Thr Arg Val Pro Thr Met Arg Pro Ser Met Ser Gly Leu His
    210                 215                 220

Leu Val Lys Arg Gly Arg Glu His Lys Lys Leu Asp Leu His Arg Asp
225                 230                 235                 240

Phe Thr Val Ala Ser Pro Ala Glu Phe Val Thr Arg Phe Gly Gly Asp
                245                 250                 255

Arg Val Ile Glu Lys Val Leu Ile Ala Asn Asn Gly Ile Ala Ala Val
                260                 265                 270

Lys Cys Met Arg Ser Ile Arg Arg Trp Ala Tyr Glu Met Phe Arg Asn
            275                 280                 285

Glu Arg Ala Ile Arg Phe Val Arg Met Val Thr Pro Glu Asp Leu Lys
    290                 295                 300

Ala Asn Ala Glu Tyr Ile Lys Met Ala Asp His Tyr Gly Pro Ala Pro
305                 310                 315                 320

Gly Gly Pro Asn Asn Asn Tyr Ala Asn Val Glu Leu Ile Val Asp
                325                 330                 335

Ile Ala Lys Arg Ile Pro Leu Gln Ala Val Trp Ala Gly Trp Gly His
                340                 345                 350

Ala Leu Glu Asn Pro Lys Leu Pro Glu Leu Leu Cys Lys Asn Gly Val
            355                 360                 365

Ala Phe Leu Gly Pro Pro Arg Leu Arg Pro Met Val Gly Leu Gly Asp
    370                 375                 380
```

```
Lys Ile Ala Ser Thr Val Ala Gln Thr Leu Gln Val Pro Thr Leu
385                 390                 395                 400

Pro Arg Ser Gly Ser Ala Leu Thr Val Glu Trp Thr Glu Asp Leu
                405                 410                 415

Gln Gln Gly Lys Arg Ile Ser Val Pro Glu Asp Val Tyr Asp Lys Gly
                420                 425                 430

Cys Val Lys Asp Val Asp Glu Gly Leu Glu Ala Ala Glu Arg Ile Gly
                435                 440                 445

Phe Pro Leu Met Ile Lys Ala Ser Glu Gly Gly Gly Lys Gly Ile
                450                 455                 460

Arg Glu Thr Glu Ser Ala Glu Asp Phe Pro Ile Leu Phe Arg Gln Val
465                 470                 475                 480

Gln Ser Glu Ile Pro Gly Ser Pro Ile Phe Leu Met Lys Leu Ala Gln
                485                 490                 495

His Ala Arg His Leu Glu Val Gln Ile Leu Ala Asp Gln Tyr Gly Asn
                500                 505                 510

Ala Val Ser Leu Phe Gly Arg Asp Cys Ser Ile Gln Arg Arg His Gln
                515                 520                 525

Lys Ile Val Glu Glu Ala Pro Ala Thr Ile Ala Pro Leu Ala Ile Phe
530                 535                 540

Glu Phe Met Glu Gln Cys Ala Ile Arg Leu Ala Lys Thr Val Gly Tyr
545                 550                 555                 560

Val Ser Ala Gly Thr Val Glu Tyr Leu Tyr Ser Gln Asp Gly Ser Phe
                565                 570                 575

His Phe Leu Glu Leu Asn Pro Arg Leu Gln Val Glu His Pro Cys Thr
                580                 585                 590

Glu Met Ile Ala Asp Val Asn Leu Pro Ala Ala Gln Leu Gln Ile Ala
                595                 600                 605

Met Gly Ala Pro Leu His Arg Leu Lys Asp Ile Arg Leu Leu Tyr Gly
                610                 615                 620

Glu Ser Pro Trp Gly Asp Ser Pro Ile Ser Phe Glu Asn Ser Ala His
625                 630                 635                 640

Leu Pro Cys Pro Arg Gly His Val Ile Ala Thr Arg Ile Thr Ser Glu
                645                 650                 655

Asn Pro Asp Glu Gly Phe Lys Pro Ser Ser Gly Thr Val Gln Glu Leu
                660                 665                 670

Asn Phe Arg Ser Ser Lys Asn Val Trp Gly Tyr Phe Thr Val Ala Ala
                675                 680                 685

Thr Gly Gly Leu His Glu Phe Ala Ile Ser Gln Phe Gly His Cys Phe
                690                 695                 700

Ser Trp Gly Glu Asn Arg Lys Glu Ala Ile Ser Asn Met Val Val Ala
705                 710                 715                 720

Leu Lys Glu Leu Ser Leu Arg Gly Asp Phe Arg Thr Thr Val Glu Tyr
                725                 730                 735

Leu Ile Asn Leu Leu Glu Thr Glu Ser Phe Gln Asn Asn Tyr Ile Asp
                740                 745                 750

Thr Gly Trp Leu Asp Tyr Leu Ile Ala Glu Lys Val Gln Lys Lys Pro
                755                 760                 765

Asn Ile Met Leu Gly Val Val Cys Gly Ala Leu Glu Arg Gly Asp Ala
                770                 775                 780

Met Phe Arg Thr Cys Met Thr Asp Phe Leu His Ser Leu Glu Arg Gly
785                 790                 795                 800
```

-continued

```
Gln Val Leu Pro Ala Asp Ser Leu Leu Asn Leu Val Asp Val Glu Leu
            805                 810                 815

Ile Tyr Glu Gly Val Lys Tyr Ile Leu Lys Val Thr Arg Gln Ser Leu
            820                 825                 830

Thr Met Phe Val Leu Ile Met Asn Gly Cys His Ile Glu Ile Asp Ala
            835                 840                 845

His Arg Leu Asn Asp Gly Gly Leu Leu Ser Tyr Asn Gly Asn Ser
850                 855                 860

Tyr Thr Thr Tyr Met Lys Glu Val Asp Ser Tyr Arg Thr Ile Gly
865                 870                 875                 880

Asn Lys Thr Cys Val Phe Glu Lys Glu Asn Asp Pro Thr Val Leu Arg
            885                 890                 895

Ser Pro Ser Ala Gly Lys Leu Thr Gln Ile Thr Val Glu Asp Gly Gly
            900                 905                 910

His Val Glu Ala Gly Arg Arg Tyr Ala Glu Met Glu Val Met Lys Met
            915                 920                 925

Ile Met Thr Leu Asn Val Gln Glu Arg Gly Arg Val Lys Tyr Ile Lys
            930                 935                 940

Arg Pro Gly Ala Val Leu Glu Ala Gly Cys Val Val Ala Arg Leu Glu
945                 950                 955                 960

Leu Asp Asp Pro Ser Lys Val His Pro Ala Glu Pro Phe Thr Gly Glu
            965                 970                 975

Leu Pro Ala Gln Gln Asn Thr Ala Asp Leu Gly Lys Lys Leu His Arg
            980                 985                 990

Val Phe His Ser Val Leu Gly Ser Leu Thr Asn Val Met Ser Gly Phe
            995                 1000                1005

Cys Leu Pro Glu Pro Phe Phe Ser Ile Lys Leu Lys Glu Trp Val
    1010                1015                1020

Gln Lys Leu Met Met Thr Leu Arg His Pro Ser Leu Leu Leu Asp
    1025                1030                1035

Val Gln Glu Ile Met Thr Ser Arg Ala Gly Arg Ile Pro Pro Pro
    1040                1045                1050

Val Glu Lys Ser Val Arg Lys Val Met Ala Gln Tyr Ala Ser Asn
    1055                1060                1065

Ile Thr Ser Val Leu Cys Gln Phe Pro Ser Gln Gln Ile Ala Thr
    1070                1075                1080

Ile Leu Asp Cys His Ala Ala Thr Leu Gln Arg Lys Ala Asp Arg
    1085                1090                1095

Glu Val Phe Phe Ile Asn Thr Gln Ser Met Val Gln Leu Val Gln
    1100                1105                1110

Arg Tyr Arg Ser Gly Ile Arg Gly His Met Lys Thr Val Val Ile
    1115                1120                1125

Asp Leu Leu Arg Arg Tyr Leu Arg Val Glu Thr Ile Phe Gly Lys
    1130                1135                1140

Ala Arg Asp Ala Asp Ala Asn Ser Ser Gly Met Val Gly Gly Val
    1145                1150                1155

Arg Ser Leu Ser Phe Thr Ser Val Trp Val Val Leu Ser Pro Pro
    1160                1165                1170

Ala His Tyr Asp Lys Cys Val Ile Asn Leu Arg Glu Gln Phe Lys
    1175                1180                1185

Pro Asp Met Ser Gln Val Leu Asp Cys Ile Phe Ser His Ala Gln
    1190                1195                1200

Val Thr Lys Lys Asn Gln Leu Val Ile Met Leu Ile Asp Glu Leu
```

-continued

```
            1205                1210                1215
Cys Gly Pro Asp Pro Ser Leu Ser Asp Glu Leu Ile Ser Ile Leu
        1220                1225                1230
Asn Glu Leu Thr Gln Leu Ser Lys Ser Glu His Cys Lys Val Ala
        1235                1240                1245
Leu Arg Ala Arg Gln Ile Leu Ile Ala Ser Pro Ser Tyr Glu Leu
        1250                1255                1260
Arg His Asn Gln Val Glu Ser Ile Phe Leu Ser Ala Ile Asp Met
        1265                1270                1275
Tyr Gly His Gln Phe Cys Pro Glu Asn Leu Gln Lys Leu Ile Leu
        1280                1285                1290
Ser Glu Thr Thr Ile Phe Asp Val Leu Asn Thr Phe Phe Tyr His
        1295                1300                1305
Ala Asn Lys Val Val Cys Met Ala Ser Leu Glu Val Tyr Val Gly
        1310                1315                1320
Gly Ala Tyr Ile Ala Tyr Val Leu Asn Ser Leu Gln His Arg Gln
        1325                1330                1335
Leu Pro Asp Gly Thr Cys Val Val Glu Phe Gln Phe Met Leu Pro
        1340                1345                1350
Ser Ser His Pro Asn Arg Met Thr Val Pro Ile Ser Ile Thr Asn
        1355                1360                1365
Pro Asp Leu Leu Arg His Thr Thr Glu Leu Phe Met Asp Ser Gly
        1370                1375                1380
Phe Ser Pro Leu Cys Gln Arg Met Gly Ala Met Val Ala Phe Arg
        1385                1390                1395
Arg Phe Glu Asp Phe Thr Arg Asn Phe Asp Glu Val Ile Ser Cys
        1400                1405                1410
Phe Ala Asn Val Pro Lys Asp Pro Pro Leu Phe Ser Glu Ala Arg
        1415                1420                1425
Thr Ser Leu Tyr Ser Glu Asp Asp Cys Lys Ser Leu Arg Glu Glu
        1430                1435                1440
Pro Ile His Ile Leu Asn Val Ser Ile Gln Cys Ala Asp His Leu
        1445                1450                1455
Glu Asp Glu Ala Leu Val Pro Ile Leu Arg Thr Phe Val Gln Ser
        1460                1465                1470
Lys Lys Asn Ile Leu Val Asp Tyr Gly Leu Arg Arg Ile Pro Phe
        1475                1480                1485
Leu Ile Ala Gln Glu Lys Glu Phe Pro Lys Phe Phe Thr Phe Arg
        1490                1495                1500
Ala Arg Asp Glu Phe Ala Glu Asp Arg Ile Tyr Arg His Leu Glu
        1505                1510                1515
Pro Ala Leu Ala Phe Gln Leu Glu Leu Asn Arg Met Arg Asn Phe
        1520                1525                1530
Asp Leu Thr Ala Val Pro Cys Ala Asn His Lys Met His Leu Tyr
        1535                1540                1545
Leu Gly Ala Ala Lys Val Glu Gly Arg Tyr Glu Val Thr Asp His
        1550                1555                1560
Arg Phe Phe Ile Arg Ala Ile Ile Arg His Ser Asp Leu Ile Thr
        1565                1570                1575
Lys Glu Ala Ser Phe Glu Tyr Leu Gln Asn Glu Gly Glu Arg Leu
        1580                1585                1590
Leu Leu Glu Ala Met Asp Glu Leu Glu Val Ala Phe Asn Asn Thr
        1595                1600                1605
```

-continued

```
Asn Val Arg Thr Asp Cys Asn His Ile Phe Leu Asn Phe Val Pro
    1610            1615                1620

Thr Val Ile Met Asp Pro Asn Lys Ile Glu Glu Ser Val Arg Tyr
    1625            1630                1635

Met Val Met Arg Tyr Gly Ser Arg Leu Trp Lys Leu Arg Val Leu
    1640            1645                1650

Gln Ala Glu Val Lys Ile Asn Ile Arg Gln Thr Thr Thr Gly Ser
    1655            1660                1665

Ala Val Pro Ile Arg Leu Phe Ile Thr Asn Glu Ser Gly Tyr Tyr
    1670            1675                1680

Leu Asp Ile Ser Leu Tyr Lys Glu Val Thr Asp Ser Arg Ser Gly
    1685            1690                1695

Asn Ile Met Phe His Ser Phe Gly Asn Lys Gln Gly Pro Gln His
    1700            1705                1710

Gly Met Leu Ile Asn Thr Pro Tyr Val Thr Lys Asp Leu Leu Gln
    1715            1720                1725

Ala Lys Arg Phe Gln Ala Gln Thr Leu Gly Thr Thr Tyr Ile Tyr
    1730            1735                1740

Asp Phe Pro Glu Met Phe Arg Gln Ala Leu Phe Lys Leu Trp Gly
    1745            1750                1755

Ser Pro Asp Lys Tyr Pro Lys Asp Ile Leu Thr Tyr Thr Glu Leu
    1760            1765                1770

Val Leu Asp Ser Gln Gly Gln Leu Val Glu Met Asn Arg Leu Pro
    1775            1780                1785

Gly Gly Asn Glu Val Gly Met Val Ala Phe Lys Met Arg Phe Lys
    1790            1795                1800

Thr Gln Glu Tyr Pro Glu Gly Arg Asp Val Ile Val Ile Gly Asn
    1805            1810                1815

Asp Ile Thr Phe Arg Ile Gly Ser Phe Gly Pro Gly Glu Asp Leu
    1820            1825                1830

Leu Tyr Leu Arg Ala Ser Glu Met Ala Arg Ala Glu Ala Ile Pro
    1835            1840                1845

Lys Ile Tyr Val Ala Ala Asn Ser Gly Ala Arg Ile Gly Met Ala
    1850            1855                1860

Glu Glu Ile Lys His Met Phe His Val Ala Trp Val Asp Pro Glu
    1865            1870                1875

Asp Pro His Lys Gly Phe Lys Tyr Leu Tyr Leu Thr Pro Gln Asp
    1880            1885                1890

Tyr Thr Arg Ile Ser Ser Leu Asn Ser Val His Cys Lys His Ile
    1895            1900                1905

Glu Glu Gly Gly Glu Ser Arg Tyr Met Ile Thr Asp Ile Ile Gly
    1910            1915                1920

Lys Asp Asp Gly Leu Gly Val Glu Asn Leu Arg Gly Ser Gly Met
    1925            1930                1935

Ile Ala Gly Glu Ser Ser Leu Ala Tyr Glu Glu Ile Val Thr Ile
    1940            1945                1950

Ser Leu Val Thr Cys Arg Ala Ile Gly Ile Gly Ala Tyr Leu Val
    1955            1960                1965

Arg Leu Gly Gln Arg Val Ile Gln Val Glu Asn Ser His Ile Ile
    1970            1975                1980

Leu Thr Gly Ala Ser Ala Leu Asn Lys Val Leu Gly Arg Glu Val
    1985            1990                1995
```

-continued

```
Tyr Thr Ser Asn Asn Gln Leu Gly Gly Val Gln Ile Met His Tyr
2000                2005                2010
Asn Gly Val Ser His Ile Thr Val Pro Asp Asp Phe Glu Gly Val
    2015                2020                2025
Tyr Thr Ile Leu Glu Trp Leu Ser Tyr Met Pro Lys Asp Asn His
    2030                2035                2040
Ser Pro Val Pro Ile Ile Thr Pro Thr Asp Pro Ile Asp Arg Glu
    2045                2050                2055
Ile Glu Phe Leu Pro Ser Arg Ala Pro Tyr Asp Pro Arg Trp Met
    2060                2065                2070
Leu Ala Gly Arg Pro His Pro Thr Leu Lys Gly Thr Trp Gln Ser
    2075                2080                2085
Gly Phe Phe Asp His Gly Ser Phe Lys Glu Ile Met Ala Pro Trp
    2090                2095                2100
Ala Gln Thr Val Val Thr Gly Arg Ala Arg Leu Gly Gly Ile Pro
    2105                2110                2115
Val Gly Val Ile Ala Val Glu Thr Arg Thr Val Glu Val Ala Val
    2120                2125                2130
Pro Ala Asp Pro Ala Asn Leu Asp Ser Glu Ala Lys Ile Ile Gln
    2135                2140                2145
Gln Ala Gly Gln Val Trp Phe Pro Asp Ser Ala Tyr Lys Thr Ala
    2150                2155                2160
Gln Ala Ile Lys Asp Phe Asn Arg Glu Lys Leu Pro Leu Met Ile
    2165                2170                2175
Phe Ala Asn Trp Arg Gly Phe Ser Gly Gly Met Lys Asp Met Tyr
    2180                2185                2190
Asp Gln Val Leu Lys Phe Gly Ala Tyr Ile Val Asp Gly Leu Arg
    2195                2200                2205
Gln Tyr Lys Gln Pro Ile Leu Ile Tyr Ile Arg Pro Met Arg Glu
    2210                2215                2220
Leu Arg Gly Gly Ser Trp Val Val Ile Asp Ala Thr Ile Asn Pro
    2225                2230                2235
Leu Cys Ile Glu Met Tyr Ala Asp Lys Glu Ser Arg Gly Gly Val
    2240                2245                2250
Leu Glu Pro Glu Gly Thr Val Glu Ile Lys Phe Arg Lys Glu Asp
    2255                2260                2265
Leu Ile Lys Ser Met Arg Arg Ile Asp Pro Ala Tyr Lys Lys Leu
    2270                2275                2280
Met Glu Gln Leu Gly Glu Pro Asp Leu Ser Asp Lys Asp Arg Lys
    2285                2290                2295
Asp Leu Glu Gly Arg Leu Lys Ala Arg Glu Asp Leu Leu Leu Pro
    2300                2305                2310
Ile Tyr His Gln Val Ala Val Gln Phe Ala Asp Phe His Asp Thr
    2315                2320                2325
Pro Gly Arg Met Leu Glu Lys Gly Val Ile Ser Asp Ile Leu Glu
    2330                2335                2340
Trp Lys Thr Ala Arg Thr Phe Leu Tyr Trp Arg Leu Arg Arg Leu
    2345                2350                2355
Leu Leu Glu Asp Gln Val Lys Gln Glu Ile Leu Gln Ala Ser Gly
    2360                2365                2370
Glu Leu Ser His Val His Ile Gln Ser Met Leu Arg Arg Trp Phe
    2375                2380                2385
Val Glu Thr Glu Gly Ala Val Lys Ala Tyr Leu Trp Asp Asn Asn
```

```
              2390                2395                2400
Gln Val Val Gln Trp Leu Glu Gln His Trp Gln Ala Gly Asp
    2405                2410                2415

Gly Pro Arg Ser Thr Ile Arg Glu Asn Ile Thr Tyr Leu Lys His
    2420                2425                2430

Asp Ser Val Leu Lys Thr Ile Arg Gly Leu Val Glu Glu Asn Pro
    2435                2440                2445

Glu Val Ala Val Asp Cys Val Ile Tyr Leu Ser Gln His Ile Ser
    2450                2455                2460

Pro Ala Glu Arg Ala Gln Val Val His Leu Leu Ser Thr Met Asp
    2465                2470                2475

Ser Pro Ala Ser Thr
    2480

<210> SEQ ID NO 2
<211> LENGTH: 2307
<212> TYPE: DNA
<213> ORGANISM: Homo sapien
<220> FEATURE:
<221> NAME/KEY: misc_feature
<222> LOCATION: (1)..(2307)
<223> OTHER INFORMATION: Human cDNA sequence encoding residues 1715-2483
      of ACC2

<400> SEQUENCE: 2
atgctgatca atactcccta cgtcaccaag gatctgctcc aggccaagcg attccaggcc      60
cagaccctgg gaaccaccta catctatgac ttcccggaaa tgttcaggca ggctctcttt     120
aaactgtggg gctccccaga caagtatccc aaagacatcc tgacatacac tgaattagtg     180
ttggactctc agggccagct ggtggagatg aaccgacttc ctggtggaaa tgaggtgggc     240
atggtggcct tcaaaatgag gtttaagacc caggagtacc cggaaggacg ggatgtgatc     300
gtcatcggca tgacatcac ctttcgcatt ggatcctttg ccctggaga ggaccttctg       360 tacctgcggg catccgagat ggcccgggca gagggcattc caaaattta cgtggcagcc     420 aacagtggcg cccgtattgg catggcagag gagatcaaac acatgttcca cgtggcttgg    480
gtggacccag aagaccccca caaaggattt aaatacctgt acctgactcc caagactac    540 accagaatca gctccctgaa ctccgtccac tgtaaacaca tcgaggaagg aggagagtcc    600
agatacatga tcacggatat catcgggaag gatgatggct gggcgtgga gaatctgagg     660 ggctcaggca tgattgctgg ggagtcctct ctggcttacg aagagatcgt caccattagc    720
ttggtgacct gccgagccat tgggattggg gcctacttgg tgaggctggg ccagcgagtg    780
atccaggtgg agaattccca catcatcctc acaggagcaa gtgctctcaa caaggtcctg    840
ggaagagagg tctacacatc caacaaccag ctgggtggcg ttcagatcat gcattacaat    900
ggtgtctccc acatcaccgt gccagatgac tttgaggggg tttataccat cctggagtgg    960
ctgtcctata tgccaaagga taatcacagc cctgtcccta tcatcacacc cactgaccc   1020 attgacagag aaattgaatt cctcccatcc agagctccct cgacccccg gtggatgctt    1080 gcaggaaggc ctcacccaac tctgaaggga acgtggcaga gcggattctt tgaccatggc    1140
agtttcaagg aaatcatggc accctgggcg cagaccgtgg tgacaggacg agcaaggctt    1200 gggggggattc ccgtgggagt gattgctgtg gagacacgga ctgtggaggt ggcagtccct    1260
gcagaccctg ccaacctgga ttctgaggcc aagataattc agcaggcagg acaggtgtgg    1320
ttcccagact cagcctacaa aaccgcccag gccatcaagg acttcaaccg ggagaagttg    1380
```

-continued

```
cccctgatga tctttgccaa ctggaggggg ttctccggtg gcatgaaaga catgtatgac    1440
caggtgctga agtttggagc ctacatcgtg gacggcctta caatacaa acagcccatc     1500 ctgatctata tcccgcccta tgcggagctc cggggaggct cctgggtggt catagatgcc    1560
accatcaacc cgctgtgcat agaaatgtat gcagacaaag agagcagggg tggtgttctg    1620
gaaccagagg ggacagtgga gattaagttc cgaaagaaag atctgataaa gtccatgaga    1680
aggatcgatc cagcttacaa gaagctcatg aacagctag gggaacctga tctctccgac    1740
aaggaccgaa aggacctgga gggccggcta aaggctcgcg aggacctgct gctccccatc    1800
taccaccagg tggcggtgca gttcgccgac ttccatgaca cacccggccg gatgctggag    1860
aagggcgtca tatctgacat cctggagtgg aagaccgcac gcaccttcct gtattggcgt    1920
ctgcgccgcc tcctcctgga ggaccaggtc aagcaggaga tcctgcaggc cagcggggag    1980
ctgagtcacg tgcatatcca gtccatgctg cgtcgctggt tcgtggagac ggaggggct     2040 gtcaaggcct acttgtggga caacaaccag gtggttgtgc agtggctgga acagcactgg    2100
caggcagggg atggcccgcg ctccaccatc cgtgagaaca tcacgtacct gaagcacgac    2160
tctgtcctca agaccatccg aggcctggtt gaagaaaacc ccgaggtggc cgtggactgt    2220
gtgatatacc tgagccagca catcagccca gctgagcggg cgcaggtcgt tcacctgctg    2280
tctaccatgg acagcccggc ctccacc                                        2307
```

```
<210> SEQ ID NO 3
<211> LENGTH: 775
<212> TYPE: PRT
<213> ORGANISM: Artificial
<220> FEATURE:
<223> OTHER INFORMATION: Amino acid sequence for residues 1715-2483 of
      ACC2 with a C-terminal 6x histidine tag
<220> FEATURE:
<221> NAME/KEY: MISC_FEATURE
<222> LOCATION: (1)..(775)
<223> OTHER INFORMATION: Amino acid sequence for residues 1715-2483 of
      ACC2 with a C-terminal 6x histidine tag

<400> SEQUENCE: 3

Met Leu Ile Asn Thr Pro Tyr Val Thr Lys Asp Leu Gln Ala Lys
1               5                   10                  15

Arg Phe Gln Ala Gln Thr Leu Gly Thr Thr Tyr Ile Tyr Asp Phe Pro
            20                  25                  30

Glu Met Phe Arg Gln Ala Leu Phe Lys Leu Trp Gly Ser Pro Asp Lys
        35                  40                  45

Tyr Pro Lys Asp Ile Leu Thr Tyr Thr Glu Leu Val Leu Asp Ser Gln
    50                  55                  60

Gly Gln Leu Val Glu Met Asn Arg Leu Pro Gly Gly Asn Glu Val Gly
65                  70                  75                  80

Met Val Ala Phe Lys Met Arg Phe Lys Thr Gln Glu Tyr Pro Glu Gly
                85                  90                  95

Arg Asp Val Ile Val Ile Gly Asn Asp Ile Thr Phe Arg Ile Gly Ser
            100                 105                 110

Phe Gly Pro Gly Glu Asp Leu Leu Tyr Leu Arg Ala Ser Glu Met Ala
        115                 120                 125

Arg Ala Glu Gly Ile Pro Lys Ile Tyr Val Ala Ala Asn Ser Gly Ala
    130                 135                 140

Arg Ile Gly Met Ala Glu Glu Ile Lys His Met Phe His Val Ala Trp
145                 150                 155                 160

Val Asp Pro Glu Asp Pro His Lys Gly Phe Lys Tyr Leu Tyr Leu Thr
```

-continued

```
                165                 170                 175
Pro Gln Asp Tyr Thr Arg Ile Ser Ser Leu Asn Ser Val His Cys Lys
            180                 185                 190
His Ile Glu Glu Gly Gly Glu Ser Arg Tyr Met Ile Thr Asp Ile Ile
        195                 200                 205
Gly Lys Asp Asp Gly Leu Gly Val Glu Asn Leu Arg Gly Ser Gly Met
    210                 215                 220
Ile Ala Gly Glu Ser Ser Leu Ala Tyr Glu Glu Ile Val Thr Ile Ser
225                 230                 235                 240
Leu Val Thr Cys Arg Ala Ile Gly Ile Gly Ala Tyr Leu Val Arg Leu
                245                 250                 255
Gly Gln Arg Val Ile Gln Val Glu Asn Ser His Ile Ile Leu Thr Gly
            260                 265                 270
Ala Ser Ala Leu Asn Lys Val Leu Gly Arg Glu Val Tyr Thr Ser Asn
        275                 280                 285
Asn Gln Leu Gly Gly Val Gln Ile Met His Tyr Asn Gly Val Ser His
    290                 295                 300
Ile Thr Val Pro Asp Asp Phe Glu Gly Val Tyr Thr Ile Leu Glu Trp
305                 310                 315                 320
Leu Ser Tyr Met Pro Lys Asp Asn His Ser Pro Val Pro Ile Ile Thr
                325                 330                 335
Pro Thr Asp Pro Ile Asp Arg Glu Ile Glu Phe Leu Pro Ser Arg Ala
            340                 345                 350
Pro Tyr Asp Pro Arg Trp Met Leu Ala Gly Arg Pro His Pro Thr Leu
        355                 360                 365
Lys Gly Thr Trp Gln Ser Gly Phe Phe Asp His Gly Ser Phe Lys Glu
    370                 375                 380
Ile Met Ala Pro Trp Ala Gln Thr Val Val Thr Gly Arg Ala Arg Leu
385                 390                 395                 400
Gly Gly Ile Pro Val Gly Val Ile Ala Val Glu Thr Arg Thr Val Glu
                405                 410                 415
Val Ala Val Pro Ala Asp Pro Ala Asn Leu Asp Ser Glu Ala Lys Ile
            420                 425                 430
Ile Gln Gln Ala Gly Gln Val Trp Phe Pro Asp Ser Ala Tyr Lys Thr
        435                 440                 445
Ala Gln Ala Ile Lys Asp Phe Asn Arg Glu Lys Leu Pro Leu Met Ile
    450                 455                 460
Phe Ala Asn Trp Arg Gly Phe Ser Gly Gly Met Lys Asp Met Tyr Asp
465                 470                 475                 480
Gln Val Leu Lys Phe Gly Ala Tyr Ile Val Asp Gly Leu Arg Gln Tyr
                485                 490                 495
Lys Gln Pro Ile Leu Ile Tyr Ile Pro Pro Tyr Ala Glu Leu Arg Gly
            500                 505                 510
Gly Ser Trp Val Val Ile Asp Ala Thr Ile Asn Pro Leu Cys Ile Glu
        515                 520                 525
Met Tyr Ala Asp Lys Glu Ser Arg Gly Gly Val Leu Glu Pro Glu Gly
    530                 535                 540
Thr Val Glu Ile Lys Phe Arg Lys Lys Asp Leu Ile Lys Ser Met Arg
545                 550                 555                 560
Arg Ile Asp Pro Ala Tyr Lys Lys Leu Met Glu Gln Leu Gly Glu Pro
                565                 570                 575
Asp Leu Ser Asp Lys Asp Arg Lys Asp Leu Glu Gly Arg Leu Lys Ala
            580                 585                 590
```

-continued

```
Arg Glu Asp Leu Leu Leu Pro Ile Tyr His Gln Val Ala Val Gln Phe
        595             600             605

Ala Asp Phe His Asp Thr Pro Gly Arg Met Leu Glu Lys Gly Val Ile
        610             615             620

Ser Asp Ile Leu Glu Trp Lys Thr Ala Arg Thr Phe Leu Tyr Trp Arg
625             630             635                     640

Leu Arg Arg Leu Leu Leu Glu Asp Gln Val Lys Gln Glu Ile Leu Gln
            645             650             655

Ala Ser Gly Glu Leu Ser His Val His Ile Gln Ser Met Leu Arg Arg
            660             665             670

Trp Phe Val Glu Thr Glu Gly Ala Val Lys Ala Tyr Leu Trp Asp Asn
        675             680             685

Asn Gln Val Val Val Gln Trp Leu Glu Gln His Trp Gln Ala Gly Asp
        690             695             700

Gly Pro Arg Ser Thr Ile Arg Glu Asn Ile Thr Tyr Leu Lys His Asp
705             710             715                     720

Ser Val Leu Lys Thr Ile Arg Gly Leu Val Glu Glu Asn Pro Glu Val
            725             730             735

Ala Val Asp Cys Val Ile Tyr Leu Ser Gln His Ile Ser Pro Ala Glu
            740             745             750

Arg Ala Gln Val Val His Leu Leu Ser Thr Met Asp Ser Pro Ala Ser
            755             760             765

Thr His His His His His His
        770             775
```